US008703148B2

(12) United States Patent
Biemans et al.

(10) Patent No.: US 8,703,148 B2
(45) Date of Patent: Apr. 22, 2014

(54) IMMUNOGENIC COMPOSITION

(75) Inventors: Ralph Leon Biemans, Rixensart (BE); Philippe Denoel, Rixensart (BE); Pierre Duvivier, Rixensart (BE); Tomas Maira-Litran, Boston, MA (US); Jan Poolman, Rixensart (BE)

(73) Assignee: GlaxoSmithKline Biologicals S.A (BE)

( * ) Notice: Subject to any disclaimer, the term of this patent is extended or adjusted under 35 U.S.C. 154(b) by 793 days.

(21) Appl. No.: 12/294,689

(22) PCT Filed: Mar. 29, 2007

(86) PCT No.: PCT/EP2007/053059
§ 371 (c)(1),
(2), (4) Date: Sep. 26, 2008

(87) PCT Pub. No.: WO2007/113223
PCT Pub. Date: Oct. 11, 2007

(65) Prior Publication Data
US 2010/0322959 A1    Dec. 23, 2010

Related U.S. Application Data

(60) Provisional application No. 60/787,249, filed on Mar. 30, 2006, provisional application No. 60/787,587, filed on Mar. 30, 2006.

(30) Foreign Application Priority Data

Mar. 30, 2006  (GB) .................................. 0606416.6
Mar. 30, 2006  (GB) .................................. 0606417.4

(51) Int. Cl.
| | | |
|---|---|---|
| A61K 39/385 | (2006.01) | |
| A61K 39/085 | (2006.01) | |
| A61K 39/02 | (2006.01) | |
| A61K 39/00 | (2006.01) | |
| A61K 39/38 | (2006.01) | |
| A61K 31/70 | (2006.01) | |
| C07H 1/00 | (2006.01) | |

(52) U.S. Cl.
USPC .................. 424/194.1; 424/243.1; 424/237.1; 424/197.11; 424/831; 424/234.1; 424/185.1; 424/184.1; 514/23; 536/123.1

(58) Field of Classification Search
None
See application file for complete search history.

(56) References Cited

U.S. PATENT DOCUMENTS

2005/0118198 A1   6/2005  Pier et al.
2009/0162341 A1*  6/2009  Foster et al. ............... 424/94.63

FOREIGN PATENT DOCUMENTS

WO    WO 03/053462    7/2003
WO    WO 2004/080490  9/2004

OTHER PUBLICATIONS

Fattom, et al., *Effect of conjugation methodology, carrier protein, and adjuvants on the immune response to Staphylococcus aureus capsular polysaccharides*, Vaccine, vol. 13, No. 14, pp. 1288-1293 (1995).
Henderson, *Bioconjugate Techniques*, Academic Press, XP-002473633; pp. 34, 187-188, 218-220, 228-248 (1996).

* cited by examiner

*Primary Examiner* — S. Devi
(74) *Attorney, Agent, or Firm* — Jason C. Fedon; William T. Han

(57) ABSTRACT

The present application relates to immunogenic compositions comprising staphylococcal PNAG which is less than 40% N-acetylated and is conjugated to a carrier protein by a linker bonded to an amine group on PNAG to form a PNAG conjugate. Vaccines, methods of treatment using and processes to make an immunogenic composition comprising PNAG and Type 5 and/or 8 capsular polysaccharides are also described.

10 Claims, 69 Drawing Sheets

FIGURE 1

SEQ ID NO:1 polypeptide sequence
MLQVTDVSLRFGDRKLFEDVNIKFTEGNCYGLIGANGAGKSTFLKILSGELDSQTGHVSLGKNERLAVLKQDHYAYEDER
VLDVVIKGHERLYEVMKEKDEIYMKPDFSDEDGIRAAELEGEFAEMNGWNAEADAANLLSGLGIDPTLHDKKMAELENNQ
KIKVLLAQSLFGEPDVLLLDEPTNGLDIPAISWLEDFLINFDNTVIVVSHDRHFLNNVCTHIADLDFGKIKVYVGNYDFW
YQSSQLAQKMAQEQNKKKEEKMKELQDFIARFSANASKSKQATSRKKQLEKIELDDIQPSSRRYPFVKFTPEREIGNDLL
IVQNLSKTIDGEKVLDNVSFTMNPNDKAILIGDSEIAKTTLLKILAGEMEPDEGSFKWGVTTSLSYFPKDNSEFFEGVNM
NLVDWLRQYAPEDEQTETFLRGFLGRMLFSGEEVKKKASVLSGGEKVRCMLSKMMLSSANVLLLDEPTNHLDLESITAVN
DGLKSFKGSIIFTSYDFEFINTIANRVIDLNKQGGVSKEIPYEEYLQEIGVLK

SEQ ID NO:2 polypeptide sequence
MLQVTDVSLRFGDRKLFEDVNIKFTEGNCYGLIGANGAGKSTFLKILSGEIDSQTGHVSLGKDERLAVLKQDHFAYEDER
VLDVVIKGHERLYQVMKEKDEIYMKPDFSDEDGIRAAELEGEFAEMNGWNAEADAANLLSGLGIEPDLHDKNMSELENNQ
KVKVLLAQSLFGDPDVLLLDEPTNGLDIPAISWLEDFLINFENTVIVVSHDRHFLNNVCTHIADLDFGKIKLYVGNYDFW
YQSSQLAQKMAQEQNKKKEEKMKELQDFIARFSANASKSKQATSRKKQLEKIELDDIQPSSRRYPYVKFTPEREIGNDLL
TVENLSKTIDGEKVLDNVSFTMNPNDKAILVGDSEIAKTTLLKILAGEMEPDEGTFKWGVTTSLSYFPKDNSEFFDGVDM
NLVEWLRQYAPEDEQTETFLRGFLGRMLFSGEEVKKKASVLSGGEKVRCMLSKMMLSSANVLLLDEPTNHLDLESITAVN
DGLKSFKGSIIFTSYDFEFINTIANRVIDLNQAGALSKEVPYEEYLQEIGVLQNN

SEQ ID NO:3 polypeptide sequence
MPIITDVYAREVLDSRGNPTVEVEVLTESGAFGRALVPSGASTGEHEAVELRDGDKSRYLGKGVTKAVENVNEIIAPEII
EGEFSVLDQVSIDKMMIALDGTPNKGKLGANAILGVSIAVARAAADLLGQPLYKYLGGFNGKQLPVPMMNIVNGGSHSDA
PIAFQEFMILPVGATTFKESLRWGTEIFHNLKSILSKRGLETAVGDEGGFAPKFEGTEDAVETIIQAIEAAGYKPGEEVF
LGFDCASSEFYENGVYDYSKFEGEHGAKRTAAEQVDYLEQLVDKYPIITIEDGMDENDWDGWKQLTERIGDRVQLVGDDL
FVTNTEILAKGIENGIGNSILIKVNQIGTLTETFDAIEMAQKAGYTAVVSHRSGETEDTTIADIAVATNAGQIKTGSLSR
TDRIAKYNQLLRIEDELFET
AKYDGIKSFYNLDK

SEQ ID NO:4 polypeptide sequence
MPIITDVYAREVLDSRGNPTVEVEVLTESGAFGRALVPSGASTGEHEAVELRDGDKSRYLGKGVTKAVENVNEMIAPEIV
EGEFSVLDQVSIDKMMIQLDGTHNKGKLGANAILGVSIAVARAAADLLGQPLYKYLGGFNGKQLPVPMMNIVNGGSHSDA
PIAFQEFMILPVGAESFKESLRWGAEIFHNLKSILSERGLETAVGDEGGFAPRFEGTEDAVETIIKAIEKAGYKPGEDVF
LGFDCASSEFYENGVYDYTKFEGEHGAKRSAAEQVDYLEELIGKYPIITIEDGMDENDWEGWKQLTDRIGDKVQLVGDDL
FVTNTEILSKGIEQGIGNSILIKVNQIGTLTETFDAIEMAQKAGYTAVVSHRSGETEDTTIADIAVATNAGQIKTGSLSR
TDRIAKYNQLLRIEDELYETAKFEGIKSFYNLDK

SEQ ID NO:5 polypeptide sequence
MKKIVTATIATAGLATIAFAGHDAQAAEQNNNGYNSNDAQSYSYTYTIDAQGNYHYTWTGNWNPSQLTQNNTYYYNNYNT
YSYNNASYNNYYNHSYQYNNYTNNSQTATNNYYTGGSGASYSTTSNNVHVTTTAAPSSNGRSISNGYASGSNLYTSGQCT
YYVFDRVGGKIGSTWGNASNWANAAASSGYTVNNTPKVGAIMQTTQGYYGHVAYVEGVNSNGSVRVSEMNYGHGAGVVTS
RTISANQAGSYNFIH

SEQ ID NO:6 polypeptide sequence
MKKIATATIATAGFATIAIASGNQAHASEQDNYGYNPNDPTSYSYTYTIDAQGNYHYTWKGNWHPSQLNQDNGYYSYYYY
NGYNNYNNYNNGYSYNNYSRYNNYSNNNQSYNYNNYNSYNTNSYRTGGLGASYSTSSNNVQVTTTMAPSSNGRSISSGYT
SGRNLYTSGQCTYYVFDRVGGKIGSTWGNASNWANAAARAGYTVNNTPKAGAIMQTTQGAYGHVAYVESVNSNGSVRVSE
MNYGYGPGVVTSRTISASQAAGYNFIH

SEQ ID NO:7 polypeptide sequence
MKKIATATIATAGIATFAFAHHDAQAAEQNNDGYNPNDPYSYSYTYTIDAEGNYHYTWKGNWSPDRVNTSYNYNNYNNYN
YYGYNNYSNYNNYSNYNNYNNYQSNNTQSQRTTQPTGGLGASYSTSSSNVHVTTTSAPSSNGVSLSNARSASGNLYTSGQ
CTYYVFDRVGGKIGSTWGNANNWANAAARSGYTVNNSPAKGAILQTSQGAYGHVAYVEGVNSNGSIRVSEMNYGHGAGVV
TSRTISASQAASYNYIH

FIGURE 1 cont.

SEQ ID NO:8 polypeptide sequence
MKKLVPLLLALLLLVAACGTGGKQSSDKSNGKLKVVTTNSILYDMAKNVGGDNVDIHSIVPVGQDPHEYEVKPKDIKKLT
DADVILYNGLNLETGNGWFEKALEQAGKSLKDKKVIAVSKDVKPIYLNGEEGNKDKQDPHAWLSLDNGIKYVKTIQQTFI
DNDKKHKADYEKQGNKYIAQLEKLNNDSKDKFNDIPKEQRAMITSEGAFKYFSKQYGITPGYIWEINTEKQGTPEQMRQA
IEFVKKHKLKHLLVETSVDKKAMESLSEETKKDIFGEVYTDSIGKEGTKGDSYYKMMKSNIETVHGSMK

SEQ ID NO:9 polypeptide sequence
MKKILALAIAFLIILAACGNHSNHEHHSHEGKLKVVTTNSILYDMVKRVGGNKVDVHSIVPVGQDPHEYEVKPKDIKALT
DADVVFYNGLNLETGNGWFEKALDQAGKSTKDKNVIAASNNVKPIYLNGEEGNKNKQDPHAWLSLENGIKYVKTIQKSLE
HHDKKDKSTYEKQGNAYISKLEELNKDSKNKFDDIPKNQRAMMTSEGAFKYFAQQFDVKPGYIWEINTEKQGTPGQMKQA
IKFVKDNHLKHLLVETSVDKKAMQSLSEETKKDIYGEVFTDSIGKEGTKGDSYYKMMKSNIDTIHGSMK

SEQ ID NO:10 polypeptide sequence
MKKTIMASSLAVALGVTGYAAGTGHQAHAAEVNVDQAHLVDLAHNHQDQLNAAPIKDGAYDIHFVKDGFQYNFTSNGTTW
SWSYEAANGQTAGFSNVAGADYTTSYNQGSDVQSVSYNAQSSNSNVEAVSAPTYHNYSTSTTSSSVRLSNGNTAGATGSS
AAQIMAQRTGVSASTWAAIIARESNGQVNAYNPSGASGLFQTMPGWGPTNTVDQQINAAVKAYKAQGLGAWGF

SEQ ID NO:11 polypeptide sequence
MKKTVIASTLAVSLGIAGYGLSGHEAHASETTNVDKAHLVDLAQHNPEELNAKPVQAGAYDIHFVDNGYQYNFTSNGSEW
SWSYAVAGSDADYTESSSNQEVSANTQSSNTNVQAVSAPTSSESRSYSTSTTSYSAPSHNYSSHSSSVRLSNGNTAGSVG
SYAAAQMAARTGVSASTWEHIIARESNGQLHARNASGAAGLFQTMPGWGSTGSVNDQINAAYKAYKAQGLSAWGM

SEQ ID NO:12 polypeptide sequence
MNYRDKIQKFSIRKYTVGTFSTVIATLVFLGFNTSQAHAAETNQPASVVKQKQQSNNEQTENRESQVQNSQNSQNSQSLS
ATHENEQPNNSQANLVNQKVAQSSTTNDEQPASQNVNTKKDSATAATTQPDKEESKHKQNESQSANKNGNDNRAAHVENH
EANVVTASDSSDNGNVQHDRNELQAFFDANYHDYRFIDRENADSGTFNYVKGIFDKINTLLGSNDPINNKDLQLAYKELE
QAVALIRTMPQRQQTSRRSNRIQTRSVESRAAEPRSVSDYQNANSSYYVENANDGSGYPVGTYINASSKGAPYNLPTTPW
NTLKASDSKEIALMTAKQTGDGYQWVIKFNKGHAPHQNMIFWFALPADQVPVGRTDFVTVNSDGTNVQWSHGAGAGANKP
LQQMWEYGVNDPDRSHDFKIRNRSGQVIYSWPTVHVYSLEDLSRASDYFSEAGATPATKAFGRQNFEYINGQKPAESPGV
PKVYTFIGQGDASYTISFKTQGPTVNKLYYAAGGRALEYNQLFMYSQLYVESTQDHQQRLNGLRQVVNRTYRIGTTKRVE
VSQGNVQTKKVLESTNLNIDDFVDDPLSYVKTPSNKVLGFYPTNANTNAFRPGGVQELNEYQLSQLFTDQKLQEAARTRN
PIRLMIGFDYPDGYGNSETLVPVNLTVLPEIQHNIKFFKNDDTQNIAEKPFSKQAGHPVFYVYAGNQGNASVNLGGSVTS
IQPLRINLTSNENFTDKDWQITGIPRTLHIENSTNRTNNARERNIELVGNLLPGDYFGTIRFGRKEQLFEIRVKPHTPTI
TTTAEQLRGTALQKVPVNISGIPLDPSALVYLVAPTNQTTNGGSEADQIPSGYTILATGTPDGVHNTITIRPQDYVVFIP
PVGKQIRAVVYYNKVVASNMSNAVTILPDDIPPTINNPVGINAKYYRGDEVNFTMGVSDRHSGIKNTTITTLPSGWTSNL
TKSDNKNGSLAITGRVSMNQAFNSDITFKVSATDNVNNTTNDSQSKHVSIHVGKISEDAHPIVLGNTEKVVVVNPTAVSN
DEKQSIITAFMNKNQNIRGYLASTDPVTVDNNGNVTLHYRDGSSTTLDATNVMTYEPVVKSEYQTANAAKTATVTIAKGQ
SFNIGDIKQYFTLSNGQAIPNGTFTNITSDRTIPTAQEVSQMNAGTQLYHIVASNAYHKDTEDFYISLKIVDVKQPEGDQ
RVYRTSTYDLTTDEISKVKQAFINANRDVITLAEGDISVTNTPNGANVSTITVNINKGRLTKSFASNLANMNFLRWVNFP
QDYTVTWTNAKIANRPTDGGLSWSDDHKSLIYRYDATLGTQITTNDILTMLKATTTVPGLRNNITGNEKAQAEAGGRPNY
RTTGYSQSNATTDGQRQFTLNGQVIQILDIINPSNGYGGQPVTNSNTRANHSNSTVVNVNEPAANGAGAFTIDHVVKSNS
THNASDAVYKAQLYLTPYGPKQYVEHLNQNTGNTTDAINIYFVPSDLVNPTISVGNYTNHQVFSGETFTNTITANDNFGV
QSVTVPNTSQITGTVDNNHQHVSATAPNVTSATSKTINLLATDTSGNTATTSFNVTVKPLRDKYRVGTSSTAANPVRIAN
ISNNATVSQADQTTIINSLTFTSNAPNRNYATASANEITSKTVSNVSRTGNNANVTVTVTHQDGTTSTVTVPVKHVIPEI
VAHSHYTVQGQDFPAGNGSSAADYFKLSNGSAIPDATITWVSGQAPNKDNTRIGEDITVTAHILIDGETTPITKTATYKV
VRTVPKHVFETARGVLYPGVSDMYDAKQYVKPVNNSWSTNAQHMNFQFVGTYGPNKDVVGISTRLIRVTYDNRQTEDLTI
LSKVKPDPPRIDANSVTYKAGLTNQEIKVNNVLNNSSVKLFKADNTPLNVTNITHGSGFSSVVTVSDALPNGGIKAKSSI
SMNNVTYTTQDEHGQVVTVTRNESVDSNDSASVTVTPQLQATTEGAVFIKGGDGFDFGHVERFIQNPPHGATVAWHDSPD
TWKNTVGNTHKTAVVTLPSGQGTRNVEVPVKVYPVANAKAPSRDVKGQNLTHGTNAIDYITFDPNTNTNGITAAWANRQQ
PNNQQAGVQHLNVDVTYPGISAAKRVPVTVNVYQFEFPQTTYTTTVGGTLASGTQASGYAHMQNASGLPTDGFTYKWNRD
TTGTNDANWAAMNKPNTAQVVNAKYDVIYNGHTFATSLPAKFVVKDVQPAKPTVTETAAGAITIAPGANQTVNTHAGNVT
TYADKLVIKRNGNVVTFTRRNNTSPWVKEASADNVTGIVGTNNGITVAAGTFNPADTIQVVATQGSGETISDEQRSDDF
TVVAPQPNQATTKIWQNGHIDITPNNPSGHLINPTQAMDIAYTEKVGNGAEHSKTINVVRGQNNQWTIANKPDYVTLDAQ
TGKVTFNANTIKPNSSITITPKAGTGHSVSSNPSTLTAPAAHTVNTTEIVKDYGSNVTAAEINNAVQVANKRTATIKNGT
AMPTNLAGGSTTTIPVTVTYNDGSTEEVQESIFTKADKRELITAKNHLDDPVSTEGKKPGTITQYNNAMHNAQQQINTAK

FIGURE 1 cont.
TEAQQVINNERATPQQVSDALTKVRAAQTKIDQAKALLQNKEDNSQLVTSKNNLQSSVNQVPSTAGMTQQSIDNYNAKKR
EAETEITAAQRVIDNGDATAQQISDEKHRVDNALTALNQAKHDLTADTHALEQAVQQLNRTGTTTGKKPASITAYNNSIR
ALQSDLTSAKNSANAIIQKPIRTVQEVQSALTNVNRVNERLTQAINQLVPLADNSALRTAKTKLDEEINKSVTTDGMTQS
SIQAYENAKRAGQTETTNAQNVINNGDATDQQIAAEKTKVEEKYNSLKQAIAGLTPDLAPLQTAKTQLQNDIDQPTSTTG
MTSASVAAFNDKLSAARTKIQEIDRVLASHPDVATIRQNVTAANAAKTALDQARNGLTVDKAPLENAKNQLQHSIDTQTS
TTGMTQDSINAYNAKLTAARNKVQQINQVLAGSPTVDQINTNTSAANQAKSDLDHARQALTPDKAPLQNAKTQLEQSINQ
PTDTTGMTTASLNAYNQKLQAARQKLTEINQVLNGNPTVQNINDKVAEANQAKDQLNTARQGLTLDRQPALTTLHGASNL
NQAQQNNFTQQINAAQNHAALETIKSNITALNTAMTKLKDSVADNNTIKSGQNYTDATPANKQAYDNAVNAAKGVIGETT
NPTMDVNTVNQKAASVKSTKDALDGQQNLQRAKTEATNAITHASDLNQAQKNALTQQVNSAQNVQAVNDIKQTTQSLNTA
MTGLKRGVANHNQVVQSDNYVNADTNKKNDYNNAYNHANDIINGNAQHPVITPSDVNNALSNVTSKEHALNGEAKLNAAK
QEANTALGHLNNLNNVQRQNLQSQINGAHQIDAVNTIKQNATNLNSAMGNLRQAVADKDQVKRTEDYADADTAKQNAYNS
AVSSAETIINQTANPTMSVDDVNRATSAVTTNKNALNGDEKLVQSKTDAARAIDALPHLNNAQKADVKSKINAASNIAGV
NTVKQQGTDLNTAMGNLQGAINDEQTTLNSQNYQDATPSKKTAYTNAVQAAKDILNKSNGQNKTKDQVTEAMNQVNSAKN
NLDGTRLLDQAKQTAKQQLNNMTHLTTAQKTNLTNQINSGTTVAGVHTVQSNANTLDQAMNTLRQSIANNDATKASEDYV
DANNDKQTAYNNAVAAAETIINANSNPEMNPSTITQKAEQVNSSKTALNGDENLATAKQNAKTYLNTLTSITDAQKNNLI
SQISSATRVSGVDTVKQNAQHLDQAMANLQNGINNESQVKSSEKYRDADTNKQQEYDNAITAAKAILNKSTGPNTAQNAV
EAALQRVNTAKDALNGDAKLIAAQNAAKQHLGTLTHITTAQRNDLTNQIS

SEQ ID NO:13 polypeptide sequence
MGNLQTAINDKSGTLASQNFLDADEQKRNAYNQAISAAETILNKQTGPNTAKTAVEQALNNVNSAKHALNGTQNLNNAKQ
AAITAINGASDLNQKQKDALKAQANGAQRVSNANDVQRNATELNTAMGQLQHAIADKTNTLASSKYVNADSTKQNAYTTK
VTNAEHIISGTPTVVTTPSEVTAAANQVNSAKQELNGDERLRVAKQNANTAIDALTQLNTPQKAKLKEQVGQANRLEDVQ
SVQTNGQSLNNAMKGLRDSIANETTVKASQNYTDASPNNQSTYNSAVSNAKGIINQTNNPTMDTSAITQATTQVNNAKNG
LNGAENLRNAQNTAKQNLNTLSHLTNNQKSAISSQIDRAGHVSEVTAAKNAATELNAQMGNLEQAIHDQNTVKQGVNFTD
ADKAKRDAYTNAVSRAETILNKTQGANTSKQDVEAAIQNVTSAKNALNGDQNVTNAKNAAKNALNNLTSINNAQKRDLTT
KIDQATTVAGVEAVSNTGTQLNTAMANLQNGINDKANTLASENYHDADSDKKTAYTQAVTNAENILNKNSGSNLDKAAVE
NALSQVTNAKGALNGNHNLEQAKSNANTTINGLQHLTTAQKDKLKQQVQQAQNVAGVDTVKSSANTLNGAMGTLRNSIQD
NTATKNGQNYLDATERNKTNYNNAVDSANGVINATSNPNMDANAINQIATQVTSTKNALDGTHNLTQAKQTATNAIDGAT
NLNKAQKDALKAQVTSAQRVANVTSIQQTANELNTAMGQLQHGIDDENATKQTQKYRDAEQSKKTAYDQAVAAAKAILNK
QTGSNSDKAAVDRALQQVTSTKDALNGDAKLAEAKAAARQNLGTLNHITNAQRTALEGQINQATTVDGVNTVKTNANTLD
GAMNSLQGAINDKDATLRNQNYLDADESKRNAYTQAVTAAEGILNKQTGGNTSKADVDNALNAVTRAKAALNGAENLRNA
KTSATNTINGLPNLTQLQKDNLKHQVEQAQNVVGVNGVKDKGNTLNTAMGALRTSIQNDNTTKTSQNYLDASDSNKNNYN
TAVNNANGVINATNNPNMDANAINDMANQVNTTKAALNGAQNLAQAKTNATNTINNAQDLNQKQKDALKTQVNNAQRVSD
ANNVQHTATELNGAMTALKAAIADKERTKASGNYVNADQEKRQAYDSKVTNAENIINGTPNATLTVNDVNSAASQVNAAK
TALNGDNNLRVAKEHANNTIDGLAQLNNVQKAKLKEQVQSATTLDGVQTVKNSSQTLNTAMKGLRDSIANEATIKAGQNY
TDASPNNRNEYDSAVTAAKAIINQTSNPTMEPNTITQATSQVTTKEHALNGAQNLAQAKTTAKNNLNNLTSINNAQKDAL
TRNIDGATTVAGVNQETAKATELNNAMHSLQNGINDETQTKQTQKYLDAEPSKKSAYDQAVNAAKAILTKASGQNVDKAA
VEQALQNVNSTKTALNGDAKLNEAKAAAKQTLGTLTHINNAQRNALDNEITQATNVEGVNTVKAKAQQLDGAMGQLETSI
RDKDTTLQSQNYQDADDAKRTAYSQAVNAAATILNKTAGGNTPKADVERAMQAVTQANTALNGIQNLERAKQAANTAITN
ASDLNTKQKEALKAQVTSAGRVSAANGVEHTATELNTAMTALKRAIADKADTKASGNYVNADANKRQAYDEKVTAAEHIV
SGTPTPTLTPSDVTNAATQVTNAKTQLNGNHNLEVAKQNANTAIDGLTSLNGPQKAKLKEQVGQATTLPNVQTVRDNAQT
LNTAMKGLRDSIANEATIKAGQNYTDASQNKQNDYNNAVTAAKAIIGQTTSPSMIAQEINQAKDQVTAKQQALNGQENLR
TAQTNAKQHLNGLSDLTNAQKDAAKRQIEGATHVNEVTQAQNNADALNTAMTNLKNGIQDQNTIKQGVNFTDADEAKRNA
YTNAVTQAEQILNKAQGPNTAKDGVETALQNVQRAKNELNGNQNVANAKTTAKNALNNLTSINNAQKAALKSQIEGATTV
AGVNQVSTMASELNTAMSNLQRGINDEAATKAAQKYTEADRDKQTAYNDAVTAAKTLLDKTAGSNDNKVAVEQALQRVNT
AKTALNGDARLNEAKNTAKQQLATMSHLTNAQKANLTEQIERGTTVAGVQGIQANAGTLNQAMNQLRQSIASKDATKSSE
DYQDANADLQNAYNDAVTNAEGIISATNNPEMNPDTINQKASQVNSAKSALNGDEKLAAVKQTAKSDIGRLTDLNNAQRT
AANAEVDQAPNLAAVTAAKNKATSLNTAMGNLKHALAEKDNTKRSVNYTDADQPKQQAYDTAVTQAEAITNANGSNANET
QVQAALNQLNQAKNDLNGDNKVAQAKETAKRALASYSNLNNAQSTAATSQIDNATTVADVTAAQNTANELNTAMGQLQNG
INDQNTVKQQVNFTDADQGKKDAYTNAVTNAQGILDKANGQNMTKAQVEAALNQVTTAKNALNGDANVRQAKSDAKANLG
TLTHLNNAQKQDLTSQIEGATTVNGVNSVKTKAQDLDGAMQRLESAIANKDQTKASENYIDADPTKKTAFDNAITQAESY
LNKDHGTNKDKQAVEQAIQSVTSTENALNGDANLQCAKTEATQAIDNLTQLNTPQKTALKQQVNAAQRVSGVTDLKNSAT
SLNNAMDQLKQAIGDHDTIVAGGNYTNASPDKQGAYTDAYNAAKNIVNGSPNVITNAADVTAATQRVNNAETSLNGDTNL
ATAKQQAKDALRQMTHLSDAQKQSITGQIDSATQVTGVQSVKDNATNLDNAMNQLRNSIANKDEVKASQPYVDADTDKQN
AYNTAVTSAENIINATSQPTLDPSAVTQAANQVNTNKTALNGAQNLANKKQETTANINRLSHLNNAQKQDLNTQVTNAPN
ISTVNQVKTKAEQLDQAMERLINGIQDKDQVKQSVNFTDADPEKQTAYNNAVTAAENIINQANGTNANQSQVEAALSTVT
TTKQALNGDRKVTDAKNNANQTLSTLDNLNNAQKGAVTGNINQAHTVAEVTQAIQTQAELNTAMGNLKNSLNDKDTTLGS
QNFADADPEKKNAYNEAVRNAENILNKSTGTNVPKDQVEAAMNQVNTTKAALNGTQNLEKAKQHANTAIDGLSHLTNAQK

FIGURE 1 cont.

```
EALKQLVQQSTTVAEAQGNEQKANNVDAAMDKLRQSIADNATTKQNQNYTDASPNKKDAYNNAVTTAQGIIDQTTNPSLD
PTVINQAAGQVSTSKNALNGNENLEAAKQQATQSLGSLDNLNNAQKQAVTNQINGAHTVDEANQIKQNAQNLNTAMGNLK
QAIADKDATKATVNFTDADQAKQQAYNTAVTNAENIISKANGGNATQTEVEQAIQQVNAAKQALNGNANVQHAKDEATAL
INNSNDLNQAQKDALKQQVQNATTVAGVNNVKQTAQELNNAMTQLKQGIADKEQTKADGNFVNADSDKQNAYNQAVAKAE
ALISGTPDVVVTPSEITAALNKVTQAKNDLNGNTNLATAKQNVQHAIDQLPNLNQAQRDEYSKQITQATLVPNVNAIQQA
ATTLNDAMTQLKQGIANKAQIKGSENYHDADTDKQTAYDNAVTKAEELLKQTTNPTMDPNTIQQALTKVNDTNQALNGNQ
KLADAKQDAKTTLGTLDHLNDAQKQALTTQVEQAPDIATVNNVKQNAQNLNNAMTNLNNALQDKTETLNSINFTDADQAK
KDDYTNAVSHAEGILSKANGSNASQTEVEQAMQRVNEAKQALNGNDNVQRAKDAAKQVITNANDLNQAQKDALKQQVDAA
QTVANVNTIKQTAQDLNQAMTQLKQGIADKDQTKANGNFVNADTDKQNAYNNAVAHAEQIISGTPNANVDPQQVAQALQQ
VNQAKGDLNGNHNLQVAKDNANTAIDQLPNLNQPQKTALKDQVSHAELVTGVNAIKQNADALNNAMGTLKQQIQANSQVP
QSVDFTQADQDKQQAYNNAANQAQQIANGTPTPVLAPDTVTKAVTTMNQAKDALNGDEKLAQAKQDALANLDTLRDLNQP
QRDALRNQINQAQALATVEQTKQNAQNVNTAMGNLKQGIANKDTVKASENYHDADVDKQTAYTNAVSQAEGIINQTTNPT
LNPDDITRALTQVTDAKNSLNGEAKLATEKQNAKDAVSGMTHLNDAQKQALKGQIDQSPEIATVNQVKQTATSLDQAMDQ
LSQAINDKDQILADGNYLNADPDKQNAYKQAVAKAEALLNKQSGTNEVQAQVESITNEVNAAKQALNGNDNLANAKQQAK
QQLANLTHLNDAQKQSFESQITQAPLVTDVTTINQKAQTLDHAMELLRNSVADNQTTLASEDYHDATAQRQNDYNKAVTA
ANNIINQTTSPTMNPDDVNGATTQVNNTKVALDGDENLAAAKQQANNRLDQLDHLNNAQKQQLQSQITQSSDIAAVNGHK
QTAESLNTAMGNLINAIADHQAVEQRGNFINADTDKQTAYNTAVNEAAAMINKQTGQNANQTEVEQAITKVQTTLQALNG
DHNLQVAKTNATQAIDVLTSLNDPQKTALKDQVTAATLVTAVHQIEQNANTLNQAMHGLRQSIQDNAATKANSKYINEDQ
PEQQNYDQAVQAANNIINEQTATLDNNAINQVAATVNTTKAALHGDVKLQNDKDHAKQTVSQLAHLNNAQKHMEDTLIDS
ETTRTAVKQDLTEVQALDQLMDALQQSIADKDATRASSAYVNAEPNKKQAYDEAVQNAESIIAGLNNPTINKGNVSSATQ
AVISSKNALDGVERLAQDKQTAGNSLNHLDQLTPAQQQALENQINNATTCDKVAEIIAQAQALNEAMKALKESIKDQPQT
EASSKFINEDQAQKDAYTQAVQHAKDLINKTTDPTLAKSIIDQATQAVTDAKNNLHGDQKLAQDKQRATETLNNLSNLNT
PQRQALENQINNAATRGEVAQKLTEAQALNQAMEALRNSIQDQQQTESGSKFINEDKPQKDAYQAAVQNAKDLINQTGNP
TLDKAQVEQLTHAFKQAKDNLHGDQKLADDKQHAVTDLNQLNGLNNPQRQALESQINNAATRGEVAQKLAEAKALDQAMQ
ALRNSIQDQQQTEAGSKFINEDKPQKDAYQAAVQNAKDLINQTGNPTLDKSQVEQLTQAVTTAKDNLHGDQKLARDQQQA
VTTVNALPNLNHAQQQTLTDAINAAPTRTEVAQHVQTATELDHAMETLKNKVDQVNTDKAQPNYTEASTDKKEAVDQALQ
AAQSITDPTNGSNANKDAVEQALTKLQEKVNELNGNERVAEAKTQAKQTIDQLTHLNADQIATAKQNIDQATKLQPIAEL
VDQATQLNQSMDQLQQAVNEHANVEQTIDYTQADSDKQKAYKQAIADAENVLKQNANKQQVDQALQNILNAKQALNGDER
VALAKTNGKHDIDQLNALNNAQQDGFKGRIDQSNDLNQIQQIVDEAKALNRAMDQLSQEITGNEGRTKGSTNYVNADTQV
KQVYDEAVDKAKQALDKSSGQNLTAEQVIKLNDAVTAAKKALNGEERLNNRKAEALQRLDQLTHLNNAQRQLAIQQINNA
ETLNKASRAINRATKLDNAMGAVQQYIDEQHLGVISSTNYINADDNLKANYDNAIANAAHELDKVQGNAIAKAEAEQLKQ
NIIDAQNALNGDQNLANAKDKANAFVNSLNGLNQQQQDLAHKAINNADTVSDVTDIVNNQIDLNDAMETLKHLVDNEIPN
AEQTVNYQNADDNAKTNFDDAKRLANTLLNSDNTNVNDINGAIQAVNDAIHNLNGDQRLQDAKDKAIQSINQALANKLKE
IEASNATDQDKLIAKNKAEELANSIINNINKATSNQAVSQVQTAGNHAIEQVHANEIPKAKIDANKDVDKQVQALIDEID
RNPNLTDKEKQALKDRINQILQQGHNDINNALTKEEIEQAKAQLAQALQDIKDLVKAKEDAKQDVDKQVQALIDEIDQNP
NLTDKEKQALKDRINQILQQGHNGINNAMTKEEIEQAKAQLAQALKEIKDLVKAKENAKQDVDKQVQALIDEIDQNPNLT
DKEKQALKDRINQILQQGHNDINNAMTKEEIEQAKAQLAQALQDIKDLVKAKEDAKNAIKALANAKRDQINSNPDLTPEQ
KAKALKEIDEAEKRALQNVENAQTIDQLNRGLNLGLDDIRNTHVWEVDEQPAVNEIFEATPEQILVNGELIVHRDDIITE
QDILAHINLIDQLSAEVIDTPSTATISDSLTAKVEVTLLDGSKVIVNVPVKVVEKELSVVKQQAIESIENAAQQKIDEIN
NSVTLTLEQKEAAIAEVNKLKQQAIDHVNNAPDVHSVEEIQQQEQAYIEQFNPEQFTIEQAKSNAIKSIEDAIQHMIDEI
KARTDLTDKEKQEAIAKLNQLKEQAIQAIQRAQSISEITEQLEQFKAQMKAANPTAKELAKRKQEAISRIKDFSNEKINS
IRNSEIGTADEKQAAMNQINEIVLETIRDINNAHTLQQVEAALNNGIARISAVQIVISDRAKQSSSTGNESNSHLTIGYG
TANHPFNSSTIGHKKKLDEDDDIDPLHMRHFSNNFGNVIKNAIGVVGISGLLASFWFFIAKRRRKEDEEEELEIRDNNKD
SIKETLDDTKHLPLLFAKRRRKEDEEDVTVEEKDSLNNGESLDKVKHTPFFLPKRRRKEDEEDVEVTNENTDEKVLKDNE
HSPLLFAKRRRKDKEEDVETTTSIESKDEDVPLLLAKKKNQKDNQSKDKKSASKNTSKKVAAKKKKKKSKKNKK
```

SEQ ID NO:14 polypeptide sequence
```
MNNRDKLQKFSIRKYAIGTFSTVIATLVFMGINTNHASADELNQNQKLIKQLNQTDDDSNTHSQEIENNKQNSSGQTES
LRSSTSQNQANARLSDQFKDTNETSQQLPTNVSDDSINQSHSEANMNNEPLKVDNSTMQAHSKIVSDSDGNASENKHHKL
TENVLAESRASKNDKEKENLQEKDKSQQVHPPLDKNALQAFFDASYHNYRMIDRDRADATEYQKVKSTFDYVNDLLGNNQ
NIPSEQLVSAYQQLEKALELARTLPQQSTTEKRGRRSTRSVVENRSSRSDYLDARTEYYVSKDDDDSGFPPGTFFHASNR
RWPYNLPRSRNILRASDVQGNAYITTKRLKDGYQWDILFNSNHKGHEYMYYWFGLPSDQTPTGPVTFTIINRDGSSTSTG
GVGFGSGAPLPQFWRSAGAINSSVANDFKHGSATNYAFYDGVNNFSDFARGGELYFDREGATQTNKYYGDENFALLNSEK
PDQIRGLDTIYSFKGSGDVSYRISFKTQGAPTARLYYAAGARSGEYKQATNYNQLYVEPYKNYRNRVQSNVQVKNRTLHL
KRTIRQFDPTLQRTTDVPILDSDGSGSIDSVYDPLSYVKNVTGTVLGIYPSYLPYNQERWQGANAMNAYQIEELFSQENL
QNAARSGRPIQFLVGFDVEDSHHNPETLLPVNLYVKPELKHTIELYHDNEKQDRKEFSVSK
```

FIGURE 1 cont.
SEQ ID NO:15 polypeptide sequence

```
MSGTLHNTVGSGILPYQQEIRIKLTSNEPIKDSEWSITGYPNTLTLQNAVGRTNNATEKNLALVGHIDPGNYFITVKFGD
KVEQFEIRSKPTPPRIITTANELRGNPNHKPEIRVTDIPNDTTAKIKLVMGGTDGDHDPEINPYTVPENYTVVAEAYHDN
DPSKNGVLTFRSSDYLKDLPLSGELKAIVYYNQYVQSNFSKSVPFSSDTTPPTINEPAGLVHKYYRGDHVEITLPVTDNT
GGSGLRDVNVNLPQGWTKTFTINPNNNTEGTLKLIGNIPSNEAYNTTYHFNITATDNSGNTTNPAKTFILNVGKLADDLN
PVGLSRDQLQLVTDPSSLSNSEREEVKRKISEANANIRSYLLQNNPILAGVNGDVTFYYRDGSVDVIDAENVITYEPERK
SIFSENGNTNKKEAVITIARGQNYTIGPNLRKYFSLSNGSDLPNRDFTSISAIGSLPSSSEISRLNVGNYNYRVNAKNAY
HKTQQELNLKLKIVEVNAPTGNNRVYRVSTYNLTNDEINKIKQAFKAANSGLNLNDNDITVSNNFDHRNVSSVTVTIRKG
DLIKEFSSNLNNMNFLRWVNIRDDYTISWTSSKIQGRNTDGGLEWSPDHKSLIYKYDATLGRQINTNDVLTLLQATAKNS
NLRSNINSNEKQLAERGSNGYSKSIIRDDGEKSYLLNSNPIQVLDLVEPDNGYGGRQVSHSNVIYNEKNSSIVNGQVPEA
NGASAFNIDKVVKANAANNGIMGVIYKAQLYLAPYSPKGYIEKLGQNLSNTNNVINVYFVPSDKVNPSITVGNYDHHTVY
SGETFKNTINVNDNYGLNTVASTSDSAITMTRNNNELVGQAPNVTNSINKIVKVKATDKSGNESIVSFTVNIKPLNEKYR
ITTSSSNQTPVRISNIQNNANLSIEDQNRVKSSLSMTKILGTRNYVNESNNDVRSQVVSKVNRSGNNATVNVTTTFSDGT
TNTITVPVKHVLLEVVPTTRTTVRGQQFPTGKGTSPNDFFSLRTGGPVDARIVWVNNQGPDINSNQIGRDLTLHAEIFFD
GETTPIRKDTTYKLSQSIPKQIYETTINGRFNSSGDAYPGNFVQAVNQYWPEHMDFRWAQGSGTPSSRNAGSFTKTVTVV
YQNGQTENVNVLFKVKPNKPVIDSNSVISKGQLNGQQILVRNVPQNAQVTLYQSNGTVIPNTNTTIDSNGIATVTIQGTL
PTGNITAKTSMTNNVTYTKQNSSGIASNTTEDISVFSENSDQVNVTAGMQAKNDGIKIIKGTNYNFNDFNSFISNIPAHS
TLTWNEEPNSWKNNIGTTTKTVTVTLPNHQGTRTVDIPITIYPTVTAKNPVRDQKGRNLTNGTDVYNYIIFENNNRLGGT
ASWKDNRQPDKNIAGVQNLIALVNYPGISTPLEVPVKVWVYNFDFTQPIYKIQVGDTFPKGTWAGYYKHLENGEGLPIDG
WKFYWNQQSTGTTSDQWQSLAYTRTPFVKTGTYDVVNPSNWGVWQTSQSAKFIVTNAKPNQPTITQSKTGDVTVTPGAVR
NILISGTNDYIQASADKIVINKNGNKLTTFVKNNDGRWTVETGSPDINGIGPTNNGTAISLSRLAVRPGDSIEAIATEGS
GETISTSATSEIYIVKAPQPEQVATHTYDNGTFDILPDNSRNSLNPTERVEINYTEKLNGNETQKSFTITKNNNGKWTIN
NKPNYVEFNQDNGKVVFSANTIKPNSQITITPKAGQGNTENTNPTVIQAPAQHTLTINEIVKEQGQNVTNDDINNAVQVP
NKNRVAIKQGNALPTNLAGGSTSHIPVVIYYSDGSSEEATETVRTKVNKTELINARRRLDEEISKENKTPSSIRNFDQAM
NRAQSQINTAKSDADQVIGTEFATPQQVNSALSKVQAAQNKINEAKALLQNKADNSQLVRAKEQLQQSIQPAASTDGMTQ
DSTRNYNNKRQAAEQAIQHANSVINNGDATSQQINDAKNTVEQAQRDYVEAKSNLRADKSQLQSAYDTLNRDVLTNDKKP
ASVRRYNEAISNIRKELDTAKADASSTLRNTNPSVEQVRDALNKINTVQPKVNQAIALLQPKENNSELVQAKKRLQDAVN
DIPQTQGMTQQTINNYNDKQREAERALTSAQRVIDNGDATTQEITSEKSKVEQAMQALTNAKSNLRADKNELQTAYNKLI
ENVSTNGKKPASIRQYETAKARIQNQINDAKNEAERILGNDNPQVSQVTQALNKIKAIQPKLTEAINMLQNKENNTELVN
AKNRLENAVNDTDPTHGMTQETINNYNAKKREAQNEIQKANMIINNGDATAQDISSEKSKVEQVLQALQNAKNDLRADKR
ELQTAYNKLIQNVNTNGKKPSSIQNYKSARRNIENQYNTAKNEAHNVLENTNPTVNAVEDALRKINAIQPEVTKAINILQ
DKEDNSELVRAKEKLDQAINSQPSLNGMTQESINNYTTKRREAQNIASSADTIINNGDASIEQITENKIRVEEATNALNE
AKQHLTADTTSLKTEVRKLSRRGDTNNKKPSSVSAYNNTIHSLQSEITQTENRANTIINKPIRSVEEVNNALHEVNQLNQ
RLTDTINLLQPLANKESLKEARNRLESKINETVQTDGMTQQSVENYKQAKIKAQNESSIAQTLINNGDASDQEVSTEIEK
LNQKLSELTNSINHLTVNKEPLETAKNQLQANIDQKPSTDGMTQQSVQSYERKLQEAKDKINSINNVLANNPDVNAIRTN
KVETEQINNELTQAKQGLTVDKQPLINAKTALQQSLDNQPSTTGMTEATIQNYNAKRQKAEQVIQNANKIIENAQPSVQQ
VSDEKSKVEQALSELNNAKSALRADKQELQQAYNQLIQPTDLNNKKPASITAYNQRYQQFSNELNSTKTNTDRILKEQNP
SVADVNNALNKVREVQQKLNEARALLQNKEDNSALVRAKEQLQQAVDQVPSTEGMTQQTKDDYNSKQQAAQQEISKAQQV
IDNGDATTQQISNAKTNVERALEALNNAKTGLRADKEELQNAYNQLTQNIDTSGKTPASIRKYNEAKSRIQTQIDSAKNE
ANSILTNDNPQVSQVTAALNKIKAVQPELDKAIAMLKNKENNNALVQAKQQLQQIVNEVDPTQGMTTDTANNYKSKKREA
EDEIQKAQQIINNGDATEQQITNETNRVNQAINAINKAKNDLRADKSQLENAYNQLIQNVDTNGKKPASIQQYQAARQAI
ETQYNNAKSEAHQILENSNPSVNEVAQALQKVEAVQLKVNDAIHILQNKENNSALVTAKNQLQQSVNDQPLTTGMTQDSI
NNYEAKRNEAQSAIRNAEAVINNGDATAKQISDEKSKVEQALAHLNDAKQQLTADTTELQTAVQQLNRRGDTNNKKPRSI
NAYNKAIQSLETQITSAKDNANAVIQKPIRTVQEVNNALQQVNQLNQQLTEAINQLQPLSNNDALKAARLNLENKINQTV
QTDGMTQQSIEAYQNAKRVAQNESNTALALINNGDADEQQITTETDRVNQQTTNLTQAINGLTVNKEPLETAKTALQNNI
DQVPSTDGMTQQSVANYNQKLQIAKNEINTINNVLANNPDVNAIKTNKAEAERISNDLTQAKNNLQVDTQPLEKIKRQLQ
DEIDQGTNTDGMTQDSVDNYNDSLSAAIIEKGKVNKLLKRNPTVEQVKESVANAQQVIQDLQNARTSLVPDKTQLQEAKN
RLENSINQQTDTDGMTQDSLNNYNDKLAKARQNLEKISKVLGGQPTVAEIRQNTDEANAHKQALDTARSQLTLNREPYIN
HINNESHLNNAQKDNFKAQVNSAPNHNTLETIKNKADTLNQSMTALSESIADYENQKQQENYLDASNNKRQDYDNAVNAA
KGILNQTQSPTMSADVIDQKAEDVKRTKTALDGNQRLEVAKQQALNHLNTLNDLNDAQRQTLTDTINHSPNINSVNQAKE
KANTVNTAMTQLKQTIANYDDELHDGNYINADKDKKDAYNNAVNNAKQLINQSDANQAQLDPAEINKVTQRVNTTKNDLN
GNDKLAEAKRDANTTIDGLTYLNEAQRNKAKENVGKASTKTNITSQLQDYNQLNIAMQALRNSVNDVNNVKANSNYINED
NGPKEAYNQAVTHAQTLINAQSNPEMSRDVVNQKTQAVNTAHQNLHGQQKLEQAQSSANTEIGNLPNLTNTQKAKEKELV
NSKQTRTEVQEQLNQAKSLDSSMGTLKSVAKQPTVQKTSVYINEDQPEQSAYNDSITMGQTIINKTADPVLDKTLVDNA
ISNISTKENALHGEQKLTTAKTEAINALNTLADLNTPQKEAIKTAINTAHTRTDVTAEQSKANQINSAMHTLRQNISDNE
SVTNESNYINAEPEKQHAFTEALNNAKEIVNEQQATLDANSINQKAQAILTTKNALDGEEQLRRAKENADQEINTLNQLT
DAQRNSEKGLVNSSQTRTEVASQLAKAKELNKVMEQLNHLINGKNQMINSSKFINEDANQQQAYSNAIASAEALKNKSQN
PELDKVTIEQAINNINSAINNLNGEAKLTKAKEDAVASINNLSGLTNEQKTKENQAVNGAQTRDVANKLRDAEALDQSM
```

FIGURE 1 cont.
```
QTLRDLVNNQNAIHSTSNYFNEDSTQKNTYDNAIDNGSTYITGQHNPELNKSTIDQTISRINTAKNDLHGVEKLQRDKGT
ANQEIGQLGYLNDPQKSGEESLVNGSNTRSEVEEHLNEAKSLNNAMKQLRDKVAEKTNVKQSSDYINDSTEHQRGYDQAL
QEAENIINEIGNPTLNKSEIEQKLQQLTDAQNALQGSHLLEEAKNNAITGINKLTALNDAQRQKAIENVQAQQTIPAVNQ
QLTLDREINTAMQALRDKVGQQNNVHQQSNYFNEDEQPKHNYDNSVQAGQTIIDKLQDPIMNKNEIEQAINQINTTQTAL
SGENKLHTDQESTNRQIEGLSSLNTAQINAEKDLVNQAKTRTDVAQKLAAAKEINSAMSNLRDGIQNKEDIKRSSAYINA
DPTKVTAYDQALQNAENIINATPNVELNKATIEQALSRVQQAQQDLDGVQQLANAKQQATQTVNGLNSLNDGQKRELNLL
INSANTRTKVQEELNKATELNHAMEALRNSVQNVDQVKQSSNYVNEDQPEQHNYDNAVNEAQATINNNAQPVLDKLAIER
LTQTVNTTKDALHGAQKLTQDQQAAETGIRGLTSLNEPQKNAEVAKVTAATTRDEVRNIRQEATTLDTAMLGLRKSIKDK
NDTKNSSKYINEDHDQQQAYDNAVNNAQQVIDETQATLSSDTINQLANAVTQAKSNLHGDTKLQHDKDSAKQTIAQLQNL
NSAQKHMEDSLIDNESTRTQVQHDLTEAQALDGLMGALKESIKDYTNIVSNGNYINAEPSKKQAYDAAVQNAQNIINGTN
QPTINKGNVTTATQTVKNTKDALDGDHRLEEAKNNANQTIRNLSNLNNAQKDAEKNLVNSASTLEQVQQNLQTAQQLDNA
MGELRQSIAKKDQVKADSKYLNEDPQIKQNYDDAVQRVETIINETQNPELLKANIDQATQSVQNAEQALHGAEKLNQDKQ
TSSTELDGLTDLTDAQREKLREQINTSNSRDDIKQKIEQAKALNDAMKKLKEQVAQKDGVHANSDYTNEDSAQKDAYNNA
LKQAEDIINNSSNPNLNAQDITNALNNIKQAQDNLHGAQKLQQDKNTTNQAIGNLNHLNQPQKDALIQAINGATSRDQVA
EKLKEAEALDEAMKQLEDQVNQDDQISNSSPFINEDSDKQKTYNDKIQAAKEIINQTSNPTLDKQKIADTLQNIKDAVNN
LHGDQKLAQSKQDANNQLNHLDDLTEEQKNHFKPLINNADTRDEVNKQLEIAKQLNGDMSTLHKVINDKDQIQHLSNYIN
ADNDKKQNYDNAIKEAEDLIHNHPDTLDHKALQDLLNKIDQAHNELNGESRFKQALDNALNDIDSLNSLNVPQRQTVKDN
INHVTTLESLAQELQKAKELNDAMKAMRDSIMNQEQIRKNSNYTNEDLAQQNAYNHAVDKINNIIGEDNATMDPQIIKQA
TQDINTAINGLNGDQKLQDAKTDAKQQITNFTGLTEPQKQALENIINQQTSRANVAKQLSHAKFLNGKMEELKVAVAKAS
LVRQNSNYINEDVSEKEAYEQAIAKGQEIINSENNPTISSTDINRTIQEINDAEQNLHGDNKLRQAQEIAKNEIQNLDGL
NSAQITKLIQDIGRTTTKPAVTQKLEEAKAINQAMQQLKQSIADKDATLNSSNYLNEDSEKKLAYDNAVSQAEQLINQLN
DPTMDISNIQAITQKVIQAKDSLHGANKLAQNQADSNLIINQSTNLNDKQKQALNDLINHAQTKQQVAEIIAQANKLNNE
MGTLKTLVEEQSNVHQQSKYINEDPQVQNIYNDSIQKGREILNGTTDDVLNNNKIADAIQNIHLTKNDLHGDQKLQKAQQ
DATNELNYLTNLNNSQRQSEHDEINSAPSRTEVSNDLNHAKALNEAMRQLENEVALENSVKKLSDFINEDEAAQNEYSNA
LQKAKDIINGVPSSTLDKATIEDALLELQNARESLHGEQKLQEAKNQAVAEIDNLQALNPGQVLAEKTLVNQASTKPEVQ
EALQKAKELNEAMKALKTEINKKEQIKADSRYVNADSGLQANYNSALNYGSQIIATTQPPELNKDVINRATQTIKTAENN
LNGQSKLAEAKSDGNQSIEHLQGLTQSQKDKQHDLINQAQTKQQVDDIVNNSKQLDNSMNQLQQIVNNDNTVKQNSDFIN
EDSSQQDAYNHAIQAAKDLITAHPTIMDKNQIDQAIENIKQALNDLHGSNKLSEDKKEASEQLQNLNSLTNGQKDTILNH
IFSAPTRSQVGEKIASAKQLNNTMKALRDSIADNNEILQSSKYFNEDSEQQNAYNQAVNKAKNIINDQPTPVMANDEIQS
VLNEVKQTKDNLHGDQKLANDKTDAQATLNALNYLNDAQRGNLETKVQNSNSRPEVQKVVQLANQLNDAMKKLDDALTGN
DAIKQTSNYINEDTSQQVNFDEYTDRGKNIVAEQTNPNMSPTNINTIADKITEAKNDLHGVQKLKQAQQQSINTINQMTG
LNQAQKEQLNQEIQQTQTRSEVHQVINKAQALNDSMNTLRQSITDEHEVKQTSNYINETVGNQTAYNNAVDRVKQIINQT
SNPTMNPLEVERATSNVKISKDALHGERELNDNKNSKTFAVNHLDNLNQAQKEALTHEIEQATIVSQVNNIYNKAKALNN
DMKKLKDIVAQQDNVRQSNNYINEDSTPQNMYNDTINHAQSIIDQVANPTMSHDEIENAINNIKHAINALDGEHKLQQAK
ENANLLINSLNDLNAPQRDAINRLVNEAQTREKVAEQLQSAQALNDAMKHLRNSIQNQSSVRQESKYINASDAKKEQYNH
AVREVENIINEQHPTLDKEIIKQLTDGVNQANNDLNGVELLDADKQNAHQSIPTLMHLNQAQQNALNEKINNAVTRTEVA
AIIGQAKLLDHAMENLEESIKDKEQVKQSSNYINEDSDVQETYDNAVDHVTEILNQTVNPTLSIEDIEHAINEVNQAKKQ
LRGKQKLYQTIDLADKELSKLDDLTSQQSSSISNQIYTAKTRTEVAQAIEKAKSLNHAMKALNKVYKNADKVLDSSRFIN
EDQPEKKAYQQAINHVDSIIHRQTNPEMDPTVINSITHELETAQNNLHGDQKLAHAQQDAANVINGLIHLNVAQREVMIN
TNTNATTREKVAKNLDNAQALDKAMETLQQVVAHKNNILNDSKYLNEDSKYQQQYDRVIADAEQLLNQTTNPTLEPYKVD
IVKDNVLANEKILFGAEKLSYDKSNANDEIKHMNYLNNAQKQSIKDMISHAALRTEVKQLLQQAKILDEAMKSLEDKTQV
VITDTTLPNYTEASEDKKEKVDQTVSHAQAIIDKINGSNVSLDQVRQALEQLTQASENLDGDQRVEEAKVHANQTIDQLT
HLNSLQQQTAKESVKNATKLEEIATVSNNAQALNKVMGKLEQFINHADSVENSDNYRQADDDKIIAYDEALEHGQDIQKT
NATQNETKQALQQLIYAETSLNGFERLNHARPRALEYIKSLEKINNAQKSALEDKVTQSHDLLELEHIVNEGTNLNDIMG
ELANAIVNNYAPTKASINYINADNLRKDNFTQAINNARDALNKTQGQNLDFNAIDTFKDDIFKTKDALNGIERLTAAKSK
AEKLIDSLKFINKAQFTHANDEIMNTNSIAQLSRIVNQAFDLNDAMKSLRDELNNQAFPVQASSNYINSDEDLKQQFDHA
LSNARKVLAKENGKNLDEKQIQGLKQVIEDTKDALNGIQRLSKAKAKAIQYVQSLSYINDAQRHIAENNIHNSDDLSSLA
NTLSKASDLDNAMKDLRDTIESNSTSVPNSVNYINADKNLQIEFDEALQQASATSSKTSENPATIEEVLGLSQAIYDTKN
ALNGEQRLATEKSKDLKLIKGLKDLNKAQLEDVTNKVNSANTLTELSQLTQSTLELNDKMKLLRDKLKTLVNPVKASLNY
RNADYNLKRQFNKALKEAKGVLNKNSGTNVNINDIQHLLTQIDNAKDQLNGERRLKEHQQKSEVFIIKELDILNNAQKAA
IINQIRASKDIKIINQIVDNAIELNDAMQGLKEHVAQLTATTKDNIEYLNADEDHKLQYDYAINLANNVLDKENGTNKDA
NIIIGMIQNMDDARALLNGIERLKDAQTKAHNDIKDTLKRQLDEIEHANATSNSKAQAKQMVNEEARKALSNINDATSND
LVNQAKDEGQSAIEHIHADELPKAKLDANQMIDQKVEDINHLISQNPNLSNEEKNKLISQINKLVNGIKNEIQQAINKQQ
IENATTKLDEVIETTKKLIIAKAEAKQMIKELSQKKRDAINNNTDLTPSQKAHALADIDKTEKDALQHIENSNSIDDINN
NKEHAFNTLAHIIIWDTDQQPLVFELPELSLQNALVTSEVVVHRDETISLESIIGAMTLTDELKVNIVSLPNTDKVADHL
TAKVKVILADGSYVTVNVPVKVVEKELQIAKKDAIKTIDVLVKQKIKDIDSNNELTSTQREDAKAEIERLKKQAIDKVNH
SKSIKDIETVKRTDFEEIDQFDPKRFTLNKAKKDIITDVNTQIQNGFKEIETIKGLTSNEKTQFDKQLTALQKEFLEKVE
HAHNLVELNQLQQEFNNRYKHILNQAHLLGEKHIAEHKLGYVVVNKTQQILNNQSASYFIKQWALDRIKQIQLETMNSIR
```

FIGURE 1 cont.
GAHTVQDVHKALLQGIEQILKVNVSIINQSFNDSLHNFNYLHSKFDARLREKDVANHIVQTETFKEVLKGTGVEPGKINK
ETQQPKLHKNDNDSLFKHLVDNFGKTVGVITLTGLLSSFWLVLAKRRKKEEEEKQSIKNHHKDIRLSDTDKIDPIVITKR
KIDKEEQIQNDDKHSIPVAKHKKSKEKQLSEEDIHSIPVVKRKQNSDNKDTKQKKVTSKKKKTPQSTKKVVKTKKRSKK

SEQ ID NO:16 polypeptide sequence
MRDKKGPVNKRVDFLSNKLNKYSIRKFTVGTASILIGSLMYLGTQQEAEAAENNIENPTTLKDNVQSKEVKIEEVTNKDT
APQGVEAKSEVTSNKDTIEHEASVKAEDISKKEDTPKEVANVAEVQPKSSVTHNAEAPKVRKARSVDEGSFDITRDSKNV
VESTPITIQGKEHFEGYGSVDIQKNPTDLGVSEVTRFNVGNESNGLIGALQLKNKIDFSKDFNFKVRVANNHQSNTTGAD
GWGFLFSKGNAEEYLTNGGILGDKGLVNSGGFKIDTGYIYTSSMDKTEKQAGQGYRGYGAFVKNDSSGNSQMVGENIDKS
KTNFLNYADNSTNTSDGKFHGQRLNDVILTYVASTGKMRAEYAGKTWETSITDLGLSKNQAYNFLITSSQRWGLNQGINA
NGWMRTDLKGSEFTFTPEAPKTITELEKKVEEIPFKKERKFNPDLAPGTEKVTREGQKGEKTITTPTLKNPLTGEIISKG
ESKEEITKDPINELTEYGPETIAPGHRDEFDPKLPTGEKEEVPGKPGIKNPETGDVVRPPVDSVTKYGPVKGDSIVEKEE
IPFEKERKFNPDLAPGTEKVTREGQKGEKTITTPTLKNPLTGEIISKGESKEEITKDPINELTEYGPETIAPGHRDEFDP
KLPTGEKEEVPGKPGIKNPETGDVVRPPVDSVTKYGPVKGDSIVEKEEIPFKKERKFNPDLAPGTEKVTREGQKGEKTIT
TPTLKNPLTGEIISKGESKEEITKDPINELTEYGPETITPGHRDEFDPKLPTGEKEEVPGKPGIKNPETGDVVRPPVDSV
TKYGPVKGDSIVEKEEIPFEKERKFNPDLAPGTEKVTREGQKGEKTITTPTLKNPLTGEIISKGESKEEITKDPVNELTE
FGGEKIPQGHKDIFDPNLPTDQTEKVPGKPGIKNPDTGKVIEEPVDDVIKHGPKTGTPETKTVEIPFETKREFNPKLQPG
EERVKQEGQPGSKTITTPITVNPLTGEKVGEGQPTEEITKQPVDKIVEFGGEKPKDPKGPENPEKPSRPTHPSGPVNPNN
PGLSKDRAKPNGPVHSMDKNDKVKKSKIAKESVANQEKKRAELPKTGLESTQKGLIFSSIIGIAGLMLLARRRKN

SEQ ID NO:17 polypeptide sequence
MGKRRQGPINKKVDFLPNKLNKYSIRKFTVGTASILLGSTLIFGSSSHEAKAAEEKQVDPITQANQNDSSERSLENTNQP
TVNNEAPQMSSTLQAEEGSNAEAPNVPTIKANSDNDTQTQFSEAPTRNDLARKEDIPAVSKNEELQSSQPNTDSKIEPTT
SEPVNLNYSSPFMSLLSMPADSSSNNTKNTIDIPPTTVKGRDNYDFYGRVDIQSNPTDLNATNLTRYNYGQPPGTTTAGA
VQFKNQVSFDKDFDFNIRVANNRQSNTTGADGWGFMFSKKDGDDFLKNGGILREKGTPSAAGFRIDTGYYNNDPLDKIQK
QAGQGYRGYGTFVKNDSQGNTSKVGSGTPSTDFLNYADNTTNDLDGKFHGQKLNNVNLKYNASNQTFTATYAGKTWTATL
SELGLSPTDSYNFLVTSSQYGNGNSGTYADGVMRADLDGATLTYTPKAVDGDPITSTKEIPFNKKREFDPNLAPGTEKVV
QKGEPGIETTTTPTYVNPNTGEKVGEGTPTTKITKQPVDEIVHYGGEEIKPGHKDEFDPNAPKGSQTTQPGKPGVKNPDT
GEVVTPPVDDVTKYGPVDGDPITSTEEIPFDKKREFNPDLKPGEERVKQKGEPGTKTITTPTTKNPLTGEKVGEGEPTEK
ITKQPVDEITEYGGEEIKPGHKDEFDPNAPKGSQEDVPGKPGVKNPDTGEVVTPPVDDVTKYGPVDGDPITSTEEIPFDK
KREFDPNLAPGTEKVVQKGEPGTKTITTPTTKNPLTGEKVGEGEPTEKITKQPVDEIVHYGGEEIKPGHKDEFDPNAPKG
SQEDVPGKPGVKNPDTGEVVTPPVDDVTKYGPVDGDPITSTEEIPFDKKREFNPDLKPGEERVKQKGEPGTKTITTPTTK
NPLTGEKVGEGEPTEKVTKQPVDEIVHYGGEEIKPGHKDEFDPNAPKGSQEDVPGKPGVKNPDTGEVVTPPVDDVTKYGP
VDGDPITSTEEIPFDKKREFDPNLAPGTEKVVQKGEPGTKTITTPTTKNPLTGEKVGEGEPTEKITKQPVDEIVHYGGEE
IKPGHKDEFDPNAPKGSQTTQPGKPGVKNPDTGEVVTPPVDDVTKYGPVDGDPITSTEEIPFDKKREFDPNLAPGTEKVV
QKGEPGTKTITTPTTKNPLTGEKVGEGEPTEKITKQPVDEIVHYGGEQIPQGHKDEFDPNAPVDSKTEVPGKPGVKNPDT
GEVVTPPVDDVTKYGPKVGNPITSTEEIPFDKKRVFNPDLKPGEERVKQKGEPGTKTITTPILVNPITGEKVGEGKSTEK
VTKQPVDEIVEYGPTKAEPGKPAEPGKPAEPGKPAEPGKPAEPGTPAEPGKPAEPGKPAEPGKPAEPGKPAEPGKPAEPG
TPAEPGKPAEPGKPAEPGKPAEPGTPAEPGKPAEPGTPAEPGKPAEPGTPTQSGAPEQPNRSMHSTDNKNQLPDTGENRQ
ANEGTLVGSLLAIVGSLFIFGRRKKGNEK

SEQ ID NO:18 polypeptide sequence
MKKLYTSYGTYGFLHQIKINNPTHQLFQFSASDTSVIFEETDGETVLKSPSIYEVIKEIGEFSEHHFYCAIFIPSTEDHA
YQLEKKLISVDDNFRNFGGFKSYRLLRPAKGTTYKIYFGFADRHAYEDFKQSDAFNDHFSKDALSHYFGSSGQHSSYFER
YLYPIKE

SEQ ID NO:19 polypeptide sequence
MYLYTSYGTYQFLNQIKLNHQERSLFQFSTNDSSIILEESEGKSILKHPSAYQVIDSTGEFNEHHFYSAIFVPTSEDHRQ
QLEKKLLLVDVPLRNFGGFKSYRLLKPTEGSTYKIYFGFANRTAYEDFKASDIFNENFSKDALSQYFGASGQHSSYFERY
LYPIEDH

SEQ ID NO:20 polypeptide sequence
MINRDNKKAITKKGMISNRLNKFSIRKYTVGTASILVGTTLIFGLGNQEAKAAENTSTENAKQDDATTSDNKEVVSETEN
NSTTENDSTNPIKKETNTDSQPEAKEESTTSSTQQQQNNVTATTETKPQNIEKENVKPSTDKTATEDTSVILEEKKAPNY
TNNDVTTKPSTSEIQTKPTTPQESTNIENSQPQPTPSKVDNQVTDATNPKEPVNVSKEELKNNPEKLKELVRNDNNTDRS
TKPVATAPTSVAPKRLNAKMRFAVAQPAAVASNNVNDLITVTKQTIKVGDGKDNVAAAHDGKDIEYDTEFTIDNKVKKGD

FIGURE 1 cont.
TMTINYDKNVIPSDLTDKNDPIDITDPSGEVIAKGTFDKATKQITYTFTDYVDKYEDIKARLTLYSYIDKQAVPNETSLN
LTFATAGKETSQNVSVDYQDPMVHGDSNIQSIFTKLDENKQTIEQQIYVNPLKKTATNTKVDIAGSQVDDYGNIKLGNGS
TIIDQNTEIKVYKVNPNQQLPQSNRIYDFSQYEDVTSQFDNKKSFSNNVATLDFGDINSAYIIKVVSKYTPTSDGELDIA
QGTSMRTTDKYGYYNYAGYSNFIVTSNDTGGGDGTVKPEEKLYKIGDYVWEDVDKDGVQGTDSKEKPMANVLVTLTYPDG
TTKSVRTDANGHYEFGGLKDGETYTVKFETPAGYLPTKVNGTTDGEKDSNGSSITVKINGKDDMSLDTGFYKEPKYNLGD
YVWEDTNKDGIQDANEPGIKDVKVTLKDSTGKVIGTTTTDASGKYKFTDLDNGNYTVEFETPAGYTPTVKNTTAEDKDSN
GLTTTGVIKDADNMTLDSGFYKTPKYSLGDYVWYDSNKDGKQDSTEKGIKDVKVTLLNEKGEVIGTTKTDENGKYRFDNL
DSGKYKVIFEKPAGLTQTVTNTTEDDKDADGGEVDVTITDHDDFILDNGYFEEDTSDSDSDSDSDSDSDSDSDSDSDSDS
DSDSDSDSDSDSDSDSDSDSDSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDAGKHTPVKPMSTTKDHHNKAKALPETGSENNGSNNATLF
GGLFAALGSLLLFGRRKKQNK

SEQ ID NO:21 polypeptide sequence
MINKKNNLLTKKKPIANKSNKYAIRKFTVGTASIVIGATLLFGLGHNEAKAEENSVQDVKDSNTDDELSDSNDQSSDEEK
NDVINNNQSINTDDNNQIIKKEETNNYDGIEKRSEDRTESTTNVDENEATFLQKTPQDNTHLTEEEVKESSSVESSNSSI
DTAQQPSHTTINREESVQTSDNVEDSHVSDFANSKIKESNTESGKEENTIEQPNKVKEDSTTSQPSGYTNIDEKISNQDE
LLNLPINEYENKARPLSTTSAQPSIKRVTVNQLAAEQGSNVNHLIKVTDQSITEGYDDSEGVIKAHDAENLIYDVTFEVD
DKVKSGDTMTVDIDKNTVPSDLTDSFTIPKIKDNSGEIIATGTYDNKNKQITYTFTDYVDKYENIKAHLKLTSYIDKSKV
PNNNTKLDVEYKTALSSVNKTITVEYQRPNENRTANLQSMFTNIDTKNHTVEQTIYINPLRYSAKETNVNISGNGDEGST
IIDDSTIIKVYKVGDNQNLPDSNRIYDYSEYEDVTNDDYAQLGNNNDVNINFGNIDSPYIIKVISKYDPNKDDYTTIQQT
VTMQTTINEYTGEFRTASYDNTIAFSTSSGQGQGDLPPEKTYKIGDYVWEDVDKDGIQNTNDNEKPLSNVLVTLTYPDGT
SKSVRTDEDGKYQFDGLKNGLTYKITFETPEGYTPTLKHSGTNPALDSEGNSVWVTINGQDDMTIDSGFYQTPKYSLGNY
VWYDTNKDGIQGDDEKGISGVKVTLKDENGNIISTTTTDENGKYQFDNLNSGNYIVHFDKPSGMTQTTTDSGDDDEQDAD
GEEVHVTITDHDDFSIDNGYYDDESDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDSDSDNDSDLGNSSDKSTKDKLPDTGANEDYGSKGTLLGTLFAGL
GALLLGKRRKNRKNKN

SEQ ID NO:22 polypeptide sequence
MSNNFKDDFEKNRQSIDTNSHQDHTEDVEKDQSELEHQDTIENTEQQFPPRNAQRRKRRRDLATNHNKQVHNESQTSEDN
VQNEAGTIDDRQVESSHSTESQEPSHQDSTPQHEEEYYNKNAFAMDKSHPEPIEDNDKHETIKDAENNTEHSTVSDKSIA
EQSQQPKPYFATGANQANTSKDKHDDVTVKQDKDESKDHHSGKKGAAIGAGTAGVAGAAGAMGVSKAKKHSNDAQNKSNS
DKSNNSTEDKASQDKSKDHHNGKKGAAIGAGTAGLAGGAASKSASAASKPHASNNASQNHDEHDNHDRDKERKKGGMAKV
LLPLIAAVLIIGALAIFGGMALNNHNNGTKENKIANTNKNNADESKDKDTSKDASKDKSKSTDSDKSKEDQDKATKDESD
NDQNNANQANNQAQNNQNQQQANQNQQQQQQRQGGGQRHTVNGQENLYRIAIQYYGSGSPENVEKIRRANGLSGNNIRNG
QQIVIP

SEQ ID NO:23 polypeptide sequence
MIELIKMEGMIVVSNNNFKDDFEKNRQSINPDEQQTELKEDDKTNENKKEADSQNSLSNNSNQQFPPRNAQRRKRRRETA
TNQSKQQDDKHQKNSDAKTTEGSLDDRYDEAQLQQQHDKSQQQNKTEKQSQDNRMKDGKDAAIVNGTSESPEHKSKSTQN
RPGPKAQQQKRKSESTQSKPSTNKDKKAATGAGIAGAAGVAGAAETSKRHHNKKDKQDSKHSNHENDEKSVKNDDQKQSK
KGKKAAVGAGAAAGVGAAGVAHHNNQNKHHNEEKNSQNNQYNDQSEGKKKGGFMKILLPLIAAILILGAIAIFGGMALN
NHNDSKSDDQKIANQSKKDSDKKDGAQSEDNKDKKSDSNKDKKSDSDKNADDDSDNSSSNPNATSTNNNDNVANNNSNYT
NQNQQDNANQNSNNQQATQGQQSHTVYGQENLYRIAIQYYGEGTQANVDKIKRANGLSSNNIHNGQTLVIPQ

SEQ ID NO:24 polypeptide sequence
MKNKLIAKSLLTIAAIGITTTTIASTADASEGYGPREKKPVSINHNIVEYNDGTFKYQSRPKFNSTPKYIKFKHDYNILE
FNDGTFEYGARPQFNKPAAKTDATIKKEQKLIQAQNLVREFEKTHTVSAHRKAQKAVNLVSFEYKVKKMVLQERIDNVLK
QGLVR

SEQ ID NO:25 polypeptide sequence
MKTRIVSSVTTTLLLGSILMNPVANAADSDINIKTGTTDIGSNTTVKTGDLVTYDKENGMHKKVFYSFIDDKNHNKKLLV
IRTKGTIAGQYRVYSEEGANKSGLAWPSAFKVQLQLPDNEVAQISDYYPRNSIDTKEYMSTLTYGFNGNVTGDDTGKIGG
LIGANVSIGHTLKYVQPDFKTILESPTDKKVGWKVIFNNMVNQNWGPYDRDSWNPVYGNQLFMKTRNGSMKAAENFLDPN
KASSLLSSGFSPDFATVITMDRKASKQQTNIDVIYERVRDDYQLHWTSTNWKGTNTKDKWTDRSSERYKIDWEKEEMTN

FIGURE 1 cont.
SEQ ID NO:26 polypeptide sequence
MHMKNKYISKLLVGAATITLATMISNGEAKASENTQQTSTKHQTTQNNYVTDQQKAFYQVLHLKGITEEQRNQYIKTLRE
HPERAQEVFSESLKDSKNPDRRVAQQNAFYNVLKNDNLTEQEKNNYIAQIKENPDRSQQVWVESVQSSKAKERQNIENAD
KAIKDFQDNKAPHDKSAAYEANSKLPKDLRDKNNRFVEKVSIEKAIVRHDERVKSANDAISKLNEKDSIENRRLAQREVN
KAPMDVKEHLQKQLDALVAQKDAEKKVAPKVEAPQIQSPQIEKPKAESPKVEVPQSKLLGYYQSLKDSFNYGYKYLTDTY
KSYKEKYDTAKYYYNTYYKYKGAIDQTVLTVLGSGSKSYIQPLKVDDKNGYLAKSYAQVRNYVTESINTGKVLYTFYQNP
TLVKTAIKAQETASSIKNTLSNLLSFWK

SEQ ID NO:27 polypeptide sequence
MTKHYLNSKYQSEQRSSAMKKITMGTASIILGSLVYIGADSQQVNAATEATNATNNQSTQVSQATSQPINFQVQKDGSSE
KSHMDDYMQHPGKVIKQNNKYYFQTVLNNASFWKEYKFYNANNQELATTVVNDNKKADTRTINVAVEPGYKSLTTKVHIV
VPQINYNHRYTTHLEFEKAIPTLADAAKPNNVKPVQPKPAQPKTPTEQTKPVQPKVEKVKPTVTTTSKVEDNHSTKVVST
DTTKDQTKTQTAHTVKTAQTAQEQNKVQTPVKDVATAKSESNNQAVSDNKSQQTNKVTKHNETPKQASKAKELPKTGLTS
VDNFISTVAFATLALLGSLSLLLFKRKESK

SEQ ID NO:28 polypeptide sequence
MNKQQKEFKSFYSIRKSSLGVASVAISTLLLLMSNGEAQAAAEETGGTNTEAQPKTEAVASPTTTSEKAPETKPVANAVS
VSNKEVEAPTSETKEAKEVKEVKAPKETKAVKPAAKATNNTYPILNQELREAIKNPAIKDKDHSAPNSRPIDFEMKKENG
EQQFYHYASSVKPARVIFTDSKPEIELGLQSGQFWRKFEVYEGDKKLPIKLVSYDTVKDYAYIRFSVSNGTKAVKIVSST
HFNNKEEKYDYTLMEFAQPIYNSADKFKTEEDYKAEKLLAPYKKAKTLERQVYELNKIQDKLPEKLKAEYKKKLEDTKKA
LDEQVKSAITEFQNVQPTNEKMTDLQDTKYVVYESVENNESMMDTFVKHPIKTGMLNGKKYMVMETTNDDYWKDFMVEGQ
RVRTISKDAKNNTRTIIFPYVEGKTLYDAIVKVHVKTIDYDGQYHVRIVDKEAFTKANTDKSNKKEQQDNSAKKEATPAT
PSKPTPSPVEKESQKQDSQKDDNKQLPSVEKENDASSESGKDKTPATKPTKGEVESSSTTPTKVVSTTQNVAKPTTASSK
TTKDVVQTSAGSSEAKDSAPLQKANIKNTNDGHTQSQNNKNTQENKAKSLPQTGEESNKDMTLPLMALLALSSIVAFVLP
RKRKN

SEQ ID NO:29 polypeptide sequence
MNNKKTATNRKGMIPNRLNKFSIRKYSVGTASILVGTTLIFGLSGHEAKAAEHTNGELNQSKNETTAPSENKTTEKVDSR
QLKDNTQTATADQPKVTMSDSATVKETSSNMQSPQNATASQSTTQTSNVTTNDKSSTTYSNETDKSNLTQAKNVSTTPKT
TTIKQRALNRMAVNTVAAPQQGTNVNDKVHFTNIDIAIDKGHVNKTTGNTEFWATSSDVLKLKANYTIDDSVKEGDTFTF
KYGQYFRPGSVRLPSQTQNLYNAQGNIIAKGIYDSKTNTTTYTFTNYVDQYTNVSGSFEQVAFAKRENATTDKTAYKMEV
TLGNDTYSKDVIVDYGNQKGQQLISSTNYINNEDLSRNMTVYVNQPKKTYTKETFVTNLTGYKFNPDAKNFKIYEVTDQN
QFVDSFTPDTSKLKDVTGQFDVIYSNDNKTATVDLLNGQSSSDKQYIIQQVAYPDNSSTDNGKIDYTLETQNGKSSWSNS
YSNVNGSSTANGDQKKYNLGDYVWEDTNKDGKQDANEKGIKGVYVILKDSNGKELDRTTTDENGKYQFTGLSNGTYSVEF
STPAGYTPTTANAGTDDAVDSDGLTTTGVIKDADNMTLDSGFYKTPKYSLGDYVWYDSNKDGKQDSTEKGIKGVKVTLQN
EKGEVIGTTETDENGKYRFDNLDSGKYKVIFEKPAGLTQTGTNTTEDDKDADGGEVDVTITDHDDFTLDNGYYEEETSDS
DSDSDSDSDSDSDSDSDSDSDSDSDSDSDSDSDSDSDSDSDSDSDSDSESDSDSDSDSDSDSDSDSDSDSDS
DSDSDSDSDSDSDSDSDSDNDSDSDSDSDSDSDSDSDSDSDSDSDSDSDSDSDSDSDSDSDSDSDSDSDSDS
DSDSDSDSDSDAGKHTPTKPMSTVKDQHKTAKALPETGSENNNSNNGTLFGGLFAALGSLLLFGRRKKQNK

SEQ ID NO:30 polypeptide sequence
MNMKKKEKHAIRKKSIGVASVLVGTLIGFGLLSSKEADASENSVTQSDSASNESKSNDSSSVSAAPKTDDTNVSDTKTSS
NTNNGETSVAQNPAQQETTQSSSTNATTEETPVTGEATTTTTNQANTPATTQSSNTNAEELVNQTSNETTSNDTNTVSSV
NSPQNSTNAENVSTTQDTSTEATPSNNESAPQNTDASNKDVVSQAVNPSTPRMRAFSLAAVAADAPAAGTDITNQLTDVK
VTIDSGTTVYPHQAGYVKLNYGFSVPNSAVKGDTFKITVPKELNLNGVTSTAKVPPIMAGDQVLANGVIDSDGNVIYTFT
DYVDNKENVTANITMPAYIDPENVTKTGNVTLTTGIGTNTASKTVLIDYEKYGQFHNLSIKGTIDQIDKTNNTYRQTIYV
NPSGDNVVLPALTGNLIPNTKSNALIDAKNTDIKVYRVDNANDLSESYYVNPSDFEDVTNQVRISFPNANQYKVEFPTDD
DQITTPYIVVVNGHIDPASTGDLALRSTFYGYDSNFIWRSMSWDNEVAFNNGSGSGDGIDKPVVPEQPDEPGEIEPIPED
SDSDPGSDSGSDSNSDSGSDSGSDSTSDSGSDSASDSDSASDSDSASDSDSASDSDSASDSDSASDSDSASDSDSASDSD
SASDSDSASDSDSASDSDSASDSDSASDSDSDSDSDSDSDSDSDSDSDSDSDSDSDSDSDSDSDSDSDSDSDSDSDSDSD
SDSDSDSDSDSDSDSDSDSDSDSDSDSDSDSDSDSASDSDSDSESDSDSDSDSDSDSDSDSD
SESDSDSDSDSDSESDSDSDSDSDSASDSDSGSDSDSSSDSDSTSDTGSDNDSDSDSNSDSESGSNNNVVPPNSPK
NGTNASNKNEAKDSKEPLPDTGSEDEANTSLIWGLLASLGSLLLFRRKKENKDKK

FIGURE 1 cont.
SEQ ID NO:31 polypeptide sequence
MKNNLRYGIRKHKLGAASVFLGTMIVVGMGQDKEAAASEQKTTTVEENGNSATDNKTSETQTTATNVNHIEETQSYNATV
TEQPSNATQVTTEEAPKAVQAPQTAQPANVETVKEEEKPQVKETTQPQDNSGNQRQVDLTPKKVTQNQGTETQVEVAQPR
TASESKPRVTRSADVAEAKEASDVSEVKGTDVTSKVTVESGSIEAPQGNKVEPHAGQRVVLKYKLKFADGLKRGDYFDFT
LSNNVNTYGVSTARKVPEIKNGSVVMATGEILGNGNIRYTFTNEIEHKVEVTANLEINLFIDPKTVQSNGEQKITSKLNG
EETEKTIPVVYNPGVSNSYTNVNGSIETFNKESNKFTHIAYIKPMNGNQSNTVSVTGTLTEGSNLAGGQPTVKVYEYLGK
KDELPQSVYANTSDTNKFKDVTKEMNGKLSVQDNGSYSLNLDKLDKTYVIHYTGEYLQGSDQVNFRTELYGYPERAYKSY
YVYGGYRLTWDNGLVLYSNKADGNGKNGQIIQDNDFEYKEDTAKGTMSGQYDAKQIIETEENQDNTPLDIDYHTAIDGEG
GYVDGYIETIEETDSSAIDIDYHTAVDSEVGHVGGYTESSEESNPIDFEESTHENSKHHADVVEYEEDTNPGGGQVTTES
NLVEFDEESTKGIVTGAVSDHTTIEDTKEYTTESNLIELVDELPEEHGQAQGPIEEITENNHHISHSGLGTENGHGNYGV
IEEIEENSHVDIKSELGYEGGQNSGNQSFEEDTEEDKPKYEQGGNIVDIDFDSVPQIHGQNKGDQSFEEDTEKDKPKYEH
GGNIIDIDFDSVPQIHGFNKHNEIIEEDTNKDKPNYQFGGHNSVDFEEDTLPKVSGQNEGQQTIEEDTTPPTPPTPEVPS
EPETPMPPTPEVPSEPETPTPPTPEVPSEPETPTPPTPEVPSEPETPTPPTPEVPSEPETPTPPTPEVPAEPGKPVPPAK
EEPKKPSKPVEQGKVVTPVIEINEKVKAVAPTKKAQSKKSELPETGGEESTNKGMLFGGLFSILGLALLRRNKKNNKA

SEQ ID NO:32 polypeptide sequence
MKKRIDYLSNKQNKYSIRRFTVGTTSVIVGATILFGIGNHQAQASEQSNDTTQSSKNNASADSEKNNMIETPQLNTTAND
TSDISANTNSANVDSTTKPMSTQTSNTTTTEPASTNETPQPTAIKNQATAAKMQDQTVPQEANSQVDNKTTNDANSIATN
SELKNSQTLDLPQSSPQTISNAQGTSKPSVRTRAVRSLAVAEPVVNAADAKGTNVNDKVTASNFKLEKTTFDPNQSGNTF
MAANFTVTDKVKSGDYFTAKLPDSLTGNGDVDYSNSNNTMPIADIKSTNGDVVAKATYDILTKTYTFVFTDYVNNKENIN
GQFSLPLFTDRAKAPKSGTYDANINIADEMFNNKITYNYSSPIAGIDKPNGANISSQIIGVDTASGQNTYKQTVFVNPKQ
RVLGNTWVYIKGYQDKIEESSGKVSATDTKLRIFEVNDTSKLSDSYYADPNDSNLKEVTDQFKNRIYYEHPNVASIKFGD
ITKTYVVLVEGHYDNTGKNLKTQVIQENVDPVTNRDYSIFGWNNENVVRYGGGSADGDSAVNPKDPTPGPPVDPEPSPDP
EPEPTPDPEPSPDPEPEPSPDPDPDSDSDSDSGSDSDSGSDSDSESDSDSDSDSDSDSDSDSESDSDSESDSDSDSDSDS
DSDSDSESDSDSDSDSDSDSDSESDSDSESDSESDSDSDSDSDSDSDSDSDSDSDSDSDSDSDSDSDSDSESDSDSDS
DSDSDSDSDSDSDSDSDSDSDSDSDSDSDSDSDSDSDSDSDSDSDSDSDSDSDSDSDSDSDSDSDSDSDSDSDSDSDS
DSDSRVTPPNNEQKAPSNPKGEVNHSNKVSKQHKTDALPETGDKSENTNATLFGAMMALLGSLLLFRKRKQDHKEKA

SEQ ID NO:33 polypeptide sequence
MKKQIISLGALAVASSLFTWDNKADAIVTKDYSKESRVNEKSKKGATVSDYYYWKIIDSLEAQFTGAIDLLEDYKYGDPI
YKEAKDRLMTRVLGEDQYLLKKKIDEYELYKKWYKSSNKNTNMLTFHKYNLYNLTMNEYNDIFNSLKDAVYQFNKEVKEI
EHKNVDLKQFDKDGEDKATKEVYDLVSEIDTLVVTYYADKDYGEHAKELRAKLDLILGDTDNPHKITNERIKKEMIDDLN
SIIDDFFMETKQNRPNSITKYDPTKHNFKEKSENKPNFDKLVEETKKAVKEADESWKNKTVKKYEETVTKSPVVKEEKKV
EEPQLPKVGNQQEVKTTAGKAEETTQPVAQPLVKIPQETIYGETVKGPEYPTMENKTLQGEIVQGPDFLTMEQNRPSLSD
NYTQPTTPNPILEGLEGSSSKLEIKPQGTESTLKGIQGESSDIEVKPQATETTEASQYGPRPQFNKTPKYVKYRDAGTGI
REYNDGTFGYEARPRFNKPSETNAYNVTTNQDGTVSYGARPTQNKPSETNAYNVTTHANGQVSYGARPTQKKPSKTNAYN
VTTHANGQVSYGARPTQKKPSKTNAYNVTTHANGQVSYGARPTYKKPSETNAYNVTTHANGQVSYGARPTQKKPSETNAY
NVTTHADGTATYGPRVTK

SEQ ID NO:67 polypeptide sequence
MKSNLRYGIRKHKLGAASVFLGTMIVVGMGQEKEAAASEQNNTTVEESGSSATESKASETQTTTNNVNT
IDETQSYSATSTEQPSKSTQVTTEEAPTTVQAPKVETEMKSQEDLPSEKVADKETTGTQVDIAQPSNVS
EIKPRMKRSADVTAVSEKEVAEEAKATGTDVTNKVEVTESSLEGHNKDSNIVNPHNAQRVTLKYKWKFG
EGIKAGDYFDFTLSDNVETHGISTLRKVPEIKS
STEDKVMANGQVINERTIRYTFTDYINNKKDLTAELNLNLFIDPTTVTKQGSQKVEVTLGQNKVSKEFD
IKYLDGVKDRMGVTVNGRIDTLNKEEGKFSHFAYVKPNNQSLTSVTVTGQVTSGYKQSANNPTVKVYKH
IGSDELAESVYAKLDDTSKFEDVTEKVNLSYTSNGGYTLNLGDLDNSKDYVIKYEGEYDQNAKDLNFRT
HLSGYHKYYPYYPYYPYYPVQLTWNNGVAFYSN
NAKGDGKDKPNDPIIEKSEPIDLDIKSEPPVEKHELTGTIEESNDSKPIDFEYHTAVEGAEGHAEGIIE
TEEDSIHVDFEESTHENSKHHADVVEYEEDTNPGGGQVTTESNLVEFDEESTKGIVTGAVSDHTTVEDT
KEYTTESNLIELVDELPEEHGQAQGPIEEITENNHHISHSGLGTENGHGNYGVIDEIEENSHVDIKSEL
GYEGGQNSGNQSFEEDTEEDKPKYEQGGNIVDI
DFDSVPQIHGQNNGNQSFEEDTEEDKPKYEQGGNIIDIDFDSVPQIHGFNKHNEIIEEDTNKDKPNYQF
GGHNSVDFEEDTLPKVSGQNEGQQTIEEDTTPPTPPTPEVPSEPETPTPPTPEVPSEPGEPTPPKPEVP
SEPETPVPPTPEVPSEPGKPVPPAKEEPKKPSKPVEQGKVVTPVIEINEKVKAVAPTKQKQSKKSELPE
TGGEESTNKGMLFGGLFSILGLVLLRRNKKNNKA

FIGURE 1 cont.
SEQ ID NO:68 polypeptide sequence
MKFKSLITTTLALGVIASTGANFNTNEASAAAKPLDKSSSTLHHGHSNIQIPYTITVNGTSQNILSSLT
FNKNQNISYKDIENKVKSVLYFNRGISDIDLRLSKQAEYTVHFKNGTKRVIDLKSGIYTADLINTSDIK
AISVNVDTKKQPKDKAKANVQVPYTITVNGTSQNILSNLTFNKNQNISYKDLEGKVKSVLESNRGITDV
DLRLSKQAKYTVNFKNGTKKVIDLKSGIYTANLINSSDIKSININVDTKKHIENKAKRNYQVPYSINLN
GTSTNILSNLSFSNKPWTNYKNLTSQIKSVLKHDRGISEQDLKYAKKAYYTVYFKNGGKRILQLNSKNY
TANLVHAKDVKRIEITVKTGTKAKADRYVPYTIAVNGTSTPILSKLKISNKQLISYKYLNDKVKSVLKS
ERGISDLDLKFAKQAKYTVYFKNGKKQVVNLKSDIFTPNLFSAKDIKKIDIDVKQYTKSKKKINKSNNV
KFPVTINKFENIVSNEFVFYNASKITINDLSIKLKSAMANDQGITKHDIGLAERAVYKVYFKNGSSKYV
DLKTEYKDERVFKATDIKKVDIELKF

SEQ ID NO:69 polypeptide sequence
MNKHHPKLRSFYSIRKSTLGVASVIVSTLFLITSQHQAQAAENTNTSDKISENQNNNATT
TQPPKDTNQTQPATQPANTAKNYPAADESLKDAIKDPALENKEHDIGPREQVNFQLLDKN
NETQYYHFFSIKDPADVYYTKKKAEVELDINTASTWKKFEVYENNQKLPVRLVSYSPVPE
DHAYIRFPVSDGTQELKIVSSTQIDDGEETNYDYTKLVFAKPIYNDPSLVKSDTNDAVVT
NDQSSSVASNQTNTNTSNQNISTINNANNQPQATTNMSQPAQPKSSTNADQASSQPAHET
NSNGNTNDKTNESSNQSDVNQQYPPADESLQDAIKNPAIIDKEHTADNWRPIDFQMKNDK
GERQFYHYASTVEPATVIFTKTGPIIELGLKTASTWKKFEVYEGDKKLPVELVSYDSDKD
YAYIRFPVSNGTREVKIVSSIEYGENIHEDYDYTLMVFAQPITNNPDDYVDEETYNLQKL
LAPYHKAKTLERQVYELEKLQEKLPEKYKAEYKKKLDQTRVELADQVKSAVTEFENVTPT
NDQLTDLQEAHFVVFESEENSESVMDGFVEHPFYTATLNGQKYVVMKTKDDSYWKDLIVE
GKRVTTVSKDPKNNSRTLIFPYIPDKAVYNAIVKVVVANIGYEGQYHVRIINQDINTKDD
DTSQNNTSEPLNVQTGQEGKVADTDVAENSSTATNPKDASDKADVIEPESDVVKDADNNI
DKDVQHDVDHLSDMSDNNHFDKYDLKEMDTQIAKDTDRNVDKDADNSVGMSSNVDTDKDS
NKNKDKVIQLNHIADKNNHTGKAAKLDVVKQNYNNTDKVTDKKTTEHLPSDIHKTVDKTV
KTKEKAGTPSKENKLSQSKMLPKTGETTSSQSWWGLYALLGMLALFIPKFRKESK

SEQ ID NO:70 polypeptide sequence
MAETTQDQTTNKNVLDSNKVKATTEQAKAEVKNPTQNISGTQVYQDPAIVQPKTANNKTG
NAQVSQKVDTAQVNGDTRANQSATTNNTQPVAKSTSTTAPKTNTNVTNAGYSLVDDEDDN
SENQINPELIKSAAKPAALETQYKTAAPKAATTSAPKAKTEATPKVTTFSASAQPRSVAA
TPKTSLPKYKPQVNSSINDYICKNNLKAPKIEEDYTSYFPKYAYRNGVGRPEGIVVHDTA
NDRSTINGEISYMKNNYQNAFVHAFVDGDRIIETAPTDYLSWGVGAVGNPRFINVEIVHT
HDYASFARSMNNYADYAATQLQYYGLKPDSAEYDGNGTVWTHYAVSKYLGGTDHADPHGY
LRSHNYSYDQLYDLINEKYLIKMGKVAPWGTQSTTTPTTPSKPTTPSKPSTGKLTVAANN
GVAQIKPTNSGLYTTVYDKTGKATNEVQKTFAVSKTATLGNQKFYLVQDYNSGNKFGWVK
EGDVVYNTAKSPVNVNQSYSIKPGTKLYTVPWGTSKQVAGSVSGSGNQTFKASKQQQIDK
SIYLYGSVNGKSGWVSKAYLVDTAKPTPTPTPKPSTPTTNNKLTVSSLNGVAQINAKNNG
LFTTVYDKTGKPTKEVQKTFAVTKEASLGGNKFYLVKDYNSPTLIGWVKQGDVIYNNAKS
PVNVMQTYTVKPGTKLYSVPWGTYKQEAGAVSGTGNQTFKATKQQQIDKSIYLFGTVNGK
SGWVSKAYLAVPAAPKKAVAQPKTAVK

SEQ ID NO: 71 polypeptide sequence
MAYTVTKPQTTQTVSKIAQVKPNNTGIRASVYEKTAKNGAKYADRTFYVTKERAHGNETY
VLLNNTSHNIPLGWFNVKDLNVQNLGKEVKTTQKYTVNKSNNGLSMVPWGTKNQVILTGN
NIAQGTFNATKQVSVGKDVYLYGTINNRTGWVNAKDLTAPTAVKPTTSAAKDYNYTYVIK
NGNGYYYVTPNSDTAKYSLKAFNEQPFAVVKEQVINGQTWYYGKLSNGKLAWIKSTDLAK
ELIKYNQTGMTLNQVAQIQAGLQYKPQVQRVPGKWTDAKFNDVKHAMDTKRLAQDPALKY
QFLRLDQPQNISIDKINQFLKGKGVLENQGAAFNKAAQMYGINEVYLISHALLETGNGTS
QLAKGADVVNNKVVTNSNTKYHNVFGIAAYDNDPLREGIKYAKQAGWDTVSKAIVGGAKF
IGNSYVKAGQNTLYKMRWNPAHPGTHQYATDVDWANINAKIIKGYYDKIGEVGKYFDIPQ
YK

FIGURE 1 cont.
SEQ ID NO:72 polypeptide sequence
DRVLASHPDVATIRQNVTAANAAKSALDQARNGLTVDKAPLENAKNQLQHSIDTQTSTTG
MTQDSINAYNAKLTAARNKIQQINQVLAGSPTVEQINTNTSTANQAKSDLDHARQALTPD
KAPLQTAKTQLEQSINQPTDTTGMTTASLNAYNQKLQAARQKLTEINQVLNGNPTVQNIN
DKVTEANQAKDQLNTARQGLTLDRQPALTTLHGASNLNQAQQNNFTQQINAAQNHAALET
IKSNITALNTAMTKLKDSVADNNTIKSDQNYTDATPANKQAYDNAVNAAKGVIGETTNPT
MDVVNTVNQKAASVKSTKDALDGQQNLQRAKTEATNAITHASDLNQAQKNALTQQVNSAQN
VQAVNDIKQTTQSLNTAMTGLKRGVANHNQVVQSDNYVNADTNKKNDYNNAYNHANDIIN
GNAQHPVITPSDVNNALSNVTSKEHALNGEAKLNAAKQEANTALGHLNNLNNAQRQNLQS
QINGAHQIDAVNTIKQNATNLNSAMGNLRQAVADKDQVKRTEDYADADTAKQNAYNSAVS
SAETIINQTTNPTMSVDDVNRATSAVTSNKNALNGYEKLAQSKTDAARAIDALPHLNNAQ
KADVKSKINAASNIAGVNTVKQQGTDLNTAMGNLQGAINDEQTTLNSQNYQDATPSKKTA
YTNAVQAAKDILNKSNGQNKTKDQVTEAMNQVNSAKNNLDGTRLLD

SEQ ID NO: 73 polypeptide sequence
ASTQHTVQSGESLWSIAQKYNTSVESIKQNNQLDNNLVFPGQVISVGGSDAQNTSNTSPQ
AGSASSHTVQAGESLNIIASRYGVSVDQLMAANNLRGYLIMPNQTLQIPNGGSGGTTPTA
TTGSNGNASSFNHQNLYTAGQCTWYVFDRRAQAGSPISTYWSDAKYWAGNAANDGYQVNN
TPSVGSIMQSTPGPYGHVAYVERVNGDGSILISEMNYTYGPYNMNYRTIPASEVSSYAFI
H

SEQ ID NO: 74 polypeptide sequence
MNNKKTATNRKGMIPNRLNKFSIRKYSVGTASILVGTTLIFGLSGHEAKAAEHTNGELNQ
SKNETTAPSENKTTKKVDSRQLKDNTQTATADQPKVTMSDSATVKETSSNMQSPQNATAN
QSTTKTSNVTTNDKSSTTYSNETDKSNLTQAKDVSTTPKTTTIKPRTLNRMAVNTVAAPQ
QGTNVNDKVHFSNIDIAIDKGHVNQTTGKTEFWATSSDVLKLKANYTIDDSVKEGDTFTF
KYGQYFRPGSVRLPSQTQNLYNAQGNIIAKGIYDSTTNTTYTFTNYVDQYTNVRGSFEQ
VAFAKRKNATTDKTAYKMEVTLGNDTYSEEIIVDYGNKKAQPLISSTNYINNEDLSRNMT
AYVNQPKNTYTKQTFVTNLTGYKFNPNAKNFKIYEVTDQNQFVDSFTPDTSKLKDVTDQF
DVIYSNDNKTATVDLMKGQTSSNKQYIIQQVAYPDNSSTDNGKIDYTLDTDKTKYSWSNS
YSNVNGSSTANGDQKKYNLGDYVWEDTNKDGKQDANEKGIKGVYVILKDSNGKELDRTTT
DENGKYQFTGLSNGTYSVEFSTPAGYTPTTANVGTDDAVDSDGLTTTGVIKDADNMTLDS
GFYKTPKYSLGDYVWYDSNKDGKQDSTEKGIKGVKVTLQNEKGEVIGTTETDENGKYRFD
NLDSGKYKVIFEKPAGLTQTGTNTTEDDKDADGGEVDVTITDHDDFTLDNGYYEEETSDS
DSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDSDSDSDSDSDSDSDSDSDSDSDSDS
DSDSDSDSDSDSDNDSDSDSDSDSDSDSDSDSDSDSDSDSDSDSDSDSDSDSDSDSDSDS
DSDSDSDSDSDSDSDSDSDNDSDSDSDSDSDAGKHTPAKPMSTVKDQHKTAKALPE
TGSENNNSNNGTLFGGLFAALGSLLLFGRRKKQNK

SEQ ID NO: 75 polypeptide sequence
MNLLKKNKYSIRKYKVGIFSTLIGTVLLLSNPNGAQALTTDNNVQSDTNQATPVNSQDKD
VANNRGLANSAQNTPNQSATTNQATNQALVNHNNGSIVNQATPTSVQSSTPSAQNNNHTD
GNTTATETVSNANNNDVVSNNTALNVPTKTNENGSGGHLTLKEIQEDVRHSSNKPELVAI
AEPASNRPKKRSRRAAPADPNATPADPAAAAVGNGGAPVAITAPYTPTTDPNANNAGQNA
PNEVLSFDDNGIRPSTNRSVPTVNVVNNLPGFTLINGGKVGVFSHAMVRTSMFDSGDNKN
YQAQGNVIALGRIHGTDTNDHGDFNGIEKALTVNPNSELIFEFNTMTTKNGQGATNVIIK
NADTNDTIAEKTVEGGPTLRLFKVPDNVRNLKIQFVPKNDAITDARGIYQLKDGYKYYSF
VDSIGLHSGSHVFVERRTMDPTATNNKEFTVTTSLKNNGNSGASLDTNDFVYQVQLPEGV
EYVNNSLTKDFPSNNSGVDVNDMNVTYDAANRVITIKSTGGGTANSPARLMPDKILDLRY
KLRVNNVPTPRTVTFNETLTYKTYTQDFINSAAESHTVSTNPYTIDIIMNKDALQAEVDR
RIQQADYTFASLDIFNGLKRRAQTILDENRNNVPLNKRVSQAYIDSLTNQMQHTLIRSVD
AENAVNKKVDQMEDLVNQNDELTDEEKQAAIQVIEEHKNEIIGNIGDQTTDDGVTRIKDQ
GIQTLSGDTATPVVKPNAKKAIRDKATKQREIINATPDATEDEIQDALNQLATDETDAID
NVTNATTNADVETAKNNGINTIGAVVPQVTHKKAARDAINQATATKRQQINSNREATQEE
KNAALNELTQATNHALEQINQATTNANVDNAKGDGLNAINPIAPVTVVKQAARDAVSHDA
QQHIAEINANPDATQEERQAAIDKVNAAVTAANTNILNANTNADVEQVKTNAIQGIQAIT

FIGURE 1 cont.

PATKVKTDAKNAIDKSAETQHNTIFNNNDATLEEQQAAQQLLDQAVATAKQNINAADTNQ
EVAQAKDQGTQNIVVIQPATQVKTDTRNVVNDKAREAITNINATTGATREEKQEAINRVN
TLKNRALTDIGVTSTTAMVNSIRDDAVNQIGAVQPHVTKKQTATGVLNDLATAKKQEINQ
NTNATTEEKQVALNQVDQELATAINNINQADTNAEVDQAQQLGTKAINAIQPNIVKKPAA
LAQINQHYNAKLAEINATPDATNDEKNAAINTLNQDRQQAIESIKQANTNAEVDQAATVA
ENNIDAVQVDVVKKQAARDKITAEVAKRIEAVKQTPNATDEEKQAAVNQINQLKDQAINQ
INQNQTNDQVDTTTNQAVNAIDNVEAEVVIKTKAIADIEKAVKEKQQQIDNSLDSTDNEK
EVASQALAKEKEKALAAIDQAQTNSQVNQAATNGVSAIKIIQPETKVKPAAREKINQKAN
ELRAKINQDKEATAEERQVALDKINEFVNQAMTDITNNRTNQQVDDTTSQALDSIALVTP
DHIVRAAARDAVKQQYEAKKREIEQAEHATDEEKQVALNQLANNEKRALQNIDQAIANND
VKRVETNGIATLKGVQPHIVIKPEAQQAIKASAENQVESIKDTPHATVDELDEANQLISD
TLKQAQQEIENTNQDAAVTDVRNQTIKAIEQIKPKVRRKRAALDSIEENNKNQLDAIRNT
LDTTQDERDVAIDTLNKIVNTIKNDIAQNKTNAEVDRTETDGNDNIKVILPKVQVKPAAR
QSVGVKAEAQNALIDQSDLSTEEERLAAKHLVEQALNQAIDQINHADKTAQVNQDSINAQ
NIISKIKPATTVKATALQQIQNIATNKINLIKANNEATDEEQNIAIAQVEKELIKAKQQI
ASAVTNADVAYLLHDEKNEIREIEPVINRKASAREQLTTLFNDKKQAIEANIQATVEERN
SILAQLQNIYDTAIGQIDQDRSNAQVDKTASLNLQTIHDLDVHPIKKPDAEKTINDDLAR
VTALVQNYRKVSNRNKADALKAITALKLQMDEELKTARTNADVDAVLKRFNVALSDIEAV
ITEKENSLLRIDNIAQQTYAKFKAIATPEQLAKVKVLIDQYVADGNRMIDEDATLNDIKQ
HTQFIVDEILAIKLPAEATKVSPKEIQPAPKVCTPIKKEETHESRKVEKELPNTGSEGMD
LPLKEFALITGAALLARRRTKNEKES

SEQ ID NO: 76 polypeptide sequence
EENSVQDVKDSNTDDELSDSNDQSSDEEKNDVINNNQSINTDDNNQIIKKEETNNYDGIE
KRSEDRTESTTNVDENEATFLQKTPQDNTHLTEEEVKESSSVESSNSSIDTAQQPSHTTI
NREESVQTSDNVEDSHVSDFANSKIKESNTESGKEENTIEQPNKVKEDSTTSQPSGYTNI
DEKISNQDELLNLPINEYENKARPLSTTSAQPSIKRVTVNQLAAEQGSNVNHLIKVTDQS
ITEGYDDSEGVIKAHDAENLIYDVTFEVDDKVKSGDTMTVDIDKNTVPSDLTDSFTIPKI
KDNSGEIIATGTYDNKNKQITYTFTDYVDKYENIKAHLKLTSYIDKSKVPNNNTKLDVEY
KTALSSVNKTITVEYQRPNENRTANLQSMFTNIDTKNHTVEQTIYINPLRYSAKETNVNI
SGNGDEGSTIIDDSTIIKVYKVGDNQNLPDSNRIYDYSEYEDVTNDDYAQLGNNNDVNIN
FGNIDSPYIIKVISKYDPNKDDYTTIQQTVTMQTTINEYTGEFRTASYDNTIAFSTSSGQ
GQGDLPPEKTYKIGDYVWEDVDKDGIQNTNDNEKPLSNVLVTLTYPDGTSKSVRTDEDGK
YQFDGLKNGLTYKITFETPEGYTPTLKHSGTNPALDSEGNSVWVTINGQDDMTIDSGFYQ
TPKYSLGNYVWYDTNKDGIQGDDEKGISGVKVTLKDENGNIISTTTTDENGKYQFDNLNS
GNYIVHFDKPSGMTQTTTDSGDDDEQDADGEEVHVTITDHDDFSIDNGYYDDE

SEQ ID NO: 87 polypeptide sequence
MINRDNKKAITKKGMISNRLNKFSIRKYTVGTASILVGTLIFGLGNQEAKAAENTSTEN
AKQDDATTSDNKEVVSETEKNSTTENDSTNPIKKETNTDSQPEAKEESTTSSTQQQQNNV
TATTETKPQNTKENVKPSTDKTATEDTSVILEKKAPNYTNNDVTTKPSTSETQTKPTT
PQESTNIEKSQPQPTPSKVNQVIDATNPKEPVNVSKEELKNNPEKLKELVRNDKNTDRS
TKPVATAPTSVAFKRLNAKMRFAVAQPAAVASANVNDLTVTKQTIKVGDGKDNVAAAHD
GKDIEYDIEFTIIDNKVKKGDIMTINYDKNVIPSDLTDKNDPIDIIDPSGEVIAKGTFDKA
TKQITYTFTDYVDKYEDIKARLTLYSYIDKQAVPNETSINLTFATAGKETSQNVSVDYQD
PMVHGDSNIQSIFTKLDENKQTIEQQIYVNPLKKTATNTKVDIAGSQVDEYGNIKLGNGS
TTIDQNTEIKVYKVNPNQQLPQSNRTYDFSQYEDVTSQFDNKKSFENNVATLDFGDINSA
YEIKVVSKYIPTSDGELDIAQGTSMRTDKYGYYNYAGYSNFIVTSNDTGGGDGTVKPEE
KLYKIGDYVWEDVDKDGVQGTDSKEKPMANVLVTLTYPDGTTKSVRTDANGHYEFGGLKD
GETYTVKFETPAGYLPTKVNGTTDGEKDSNGSSITVKINGKDDMSLDTGFYKEPKYNLCD
YVWEDTNKDGIQDANEPGIKDVKVTLKDSTGKVIGTTTTDASGKYKFTDLDNGNYTVEFE
TPAGYTPTVKNTTAEDKDSNGLTTTGVKDADNMTLDSGFYKTPKYSLGDYVWYDSNKDG
KQDSTEKGIKDVKVTLLNEKGEVIGTTKTDENGKYRFDNLDSGKYKVIFEKPAGLTQTVT
NTTEDDKDADGGEVDVTITDHDDFILDNGYFEEDTSDSDSDSDSDSDSDSDSDSDSDSDS
DSDSDSDSDSDSESDSDSDSDSDSDSDSDSDSDSDSDSDSDSDSDSDSDSDSDSDSDSDS
DSDSDSDSDSDSESDSDSDSDSDSDSDSDSDSDSDSDSDSDSDSDSDSDSDSDSDSDSDS
DAGKHTPVKPMSTTKDHHNKAKALPETGSEKNGSNNATLFGGLFAALGSLLLFGRRKKQN
K

FIGURE 1 cont.
SEQ ID NO: 89 polypeptide sequence

```
MLNRENKTAITRKGMVSNRLNKFSIRKYTVGTASILVGTTLIFGLGNQEAKAAESTNKEL
NEATTSASDNQSSDKVDMQQLNQEDNTKNDNQKEMVSSQGNETTSNGNKLIEKESVQSTT
GNKVEVSTAKSDEQASPKSTNEDLNTKQTISNQEALQPDLQENKSVVNVQPTNEENKKVD
AKTESTTLNVKSDAIKSNDETLVDNNSNSNNENNADIILPKSTAPKRLNTRMRIAAVQPS
STEAKNVNDLITSNTTLTVVDADKNNKIVPAQDYLSLKSQITVDDKVKSGDYFTIKYSDT
VQVYGLNPEDIKNIGDIKDPNNGETIATAKHDTANNLITYTFTDYVDRFNSVQMGINYSI
YMDADTIPVSKNDVEFNVTIGNTTTKTTANIQYPDYVVNEKNSIGSAFTETVSHVGNKEN
PGYYKQTIYVNPSENSLTNAKLKVQAYHSSYPNNIGQINKDVTDIKIYQVPKGYTLNKGY
DVNTKELTDVTNQYLQKITYGDNNSAVIDFGNADSAYVVMVNTKFQYTNSESPTLVQMAT
LSSTGNKSVSTGNALGFTNNQSGGAGQEVYKIGNYVWEDTNKNGVQELGEKGVGNVTVTV
FDNNTNTKVGEAVTKEDGSYLIPNLPNGDYRVEFSNLPKGYEVTPSKQGNNEELDSNGLS
SVITVNGKDNLSADLGIYKPKYNLGDYVWEDTNKNGIQDQDEKGISGVTVTLKDENGNVL
KTVTTDADGKYKFTDLDNGNYKVEFTTPEGYTPTTVTSGSDIEKDSNGLTTTGVINGADN
MTLDSGFYKTPKYNLGNYVWEDTNKDGKQDSTEKGISGVTVTLKNENGEVLQTTKTDKDG
KYQFTGLENGTYKVEFETPSGYTPTQVGSGTDEGIDSNGTSTTGVIKDKDNDTIDSGFYK
PTYNLGDYVWEDTNKNGVQDKDEKGISGVTVTLKDENDKVLKTVTTDENGKYQFTDLNNG
TYKVEFETPSGYTPTSVTSGNDTEKDSNGLTTTGVIKDADNMTLDSGFYKTPKYSLGDYV
WYDSNKDGKQDSTEKGIKDVKVTLLNEKGEVIGTTKTDENGKYCFDNLDSGKYKVIFEKP
AGLTQTVTNTTEDDKDADGGEVDVTITDHDDFTLDNGYFEEDTSDSDSDSDSDSDSDSDS
DSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDSDSDSDSDSDSDSDSDSDSDSDSDS
DSDSDSDSDSDSDSDSDSDSDSDSDSDAGKHTPVKPMSTTKDHHNKAKALPETGSENN
GSNNATLFGGLFAALGSLLLFGRRKKQNK
```

SEQ ID NO: 91 polypeptide sequence

```
MAKYRGKPFQLYVKLSCSTMMATSIILTNILPYDAQAASEKDTEITKEILSKQDLLDKVDKAIRQEEQLKQLSASSKEHY
KAQLNEAKTASQIDEIIKRANELDSKDNKSSHTEMNGQSDIDSKLDQLLKDLNEVSSNVDRGQQSGEDDLNAMKNDMSQT
ATTKHGEKDDKNDEAMVNKALEDLDLHLNQQIHKSKDASKDTSEDPAVSTTDNNHEVAKTPNNDGSGHVVLNKFLSNEENQ
SHSNRLTDKLQGSDKINHAMIEKLAKSNASTQHYTYHKLNTLQSLDQRIANTQLPKNQKSDLMSEVNKTKERIKSQRNII
LEELARTDDKKYATQSILESIFNKDEAVKILKDIRVDGKTDQQIADQITRHIDQLSLTTSDDLLTSLIDQSQDKSLLISQ
ILQTKLGKAEADKLAKDWTNKGLSNRQIVDQLKKHFASTGDTSSDDILKAILNNAKDKKQAIETILATRIERQKAKLLAD
LIPKIETDQNKIFNLVKSALNGKADDTLNLQKRLNQTKKDIDYILSPIVNRPSLLDRLNKNGKTTDLNKLANLMNQGSDL
LDSIPDIPTPKPEKTLTLGKGNGLLSGLLNADGNVSLPKAGETIKEIIWLPISVIVGAMGVLMIWLSRRNKLKNKA
```

SEQ ID NO: 93 polypeptide sequence

```
MKKLATVGSLIVTSTLVFSSMPFQNAHADTTSMNVSNKQSQNVQNHRPYGGVVPQGM
TQAQYTELEKALPQLSAGSNMQDYNMKLYDATQNIADKYNVIITTNVGVFKPHAVRD
MNGHALPLTKDGNFYQTNVDANGVNHGGSEMVQNKTGHMSQQGHMNQNTHMNQQPHM
QQGHMQSSNHQMMSPKANMHSSNHQMNQSNKKVLPAAGESMTSSILTASIAALLLVS
GLFLAFRRRSTNK
```

FIGURE 2

SEQ ID NO:34 polynucleotide sequence
ATGTTACAAGTAACTGATGTGAGTTTACGTTTTGGAGATCGTAAACTATTTGAAGATGTAAATATTAAATTTACAGAAGG
TAATTGTTATGGATTAATTGGTGCGAATGGTGCAGGTAAATCAACATTCTTAAAAATATTATCTGGTGAATTAGATTCTC
AAACAGGACATGTTTCATTAGGTAAAAATGAACGTCTAGCTGTTTTAAAACAGGACCACTATGCTTATGAAGATGAACGC
GTGCTTGATGTTGTAATTAAAGGTCACGAACGTCTTTATGAGGTTATGAAAGAAAAAGATGAAATCTATATGAAGCCAGA
TTTCAGTGATGAAGATGGTATCCGTGCTGCTGAACTTGAAGGTGAATTTGCAGAAATGAATGGTTGGAATGCTGAAGCTG
ATGCTGCTAACCTTTTATCTGGTTTAGGTATCGATCCAACTTTACACGATAAAAAAATGGCTGAATTAGAAAACAACCAA
AAAATTAAAGTATTATTAGCGCAAAGTTTATTCGGTGAACCAGACGTACTATTACTGGATGAGCCTACTAACGGTCTCGA
TATTCCAGCAATCAGTTGGTTAGAAGATTTCTTAATTAACTTTGATAATACTGTTATCGTAGTATCGCATGACCGTCATT
TCTTAAATAATGTATGTACTCATATCGCTGATTTAGACTTCGGTAAAATTAAAGTTTATGTTGGTAACTATGATTTTTGG
TATCAATCTAGTCAGTTAGCTCAAAAGATGGCTCAAGAACAAAACAAGAAAAAGAAGAAAAATGAAAGAGTTACAGGA
CTTTATTGCACGTTTCTCAGCTAACGCTTCTAAATCTAAACAAGCAACAAGTCGTAAAAAACAACTTGAGAAAATTGAAT
TAGATGATATTCAACCATCATCAAGAAGATATCCTTTCGTTAAATTCACGCCTGAGCGTGAGATTGGTAACGACTTATTA
ATCGTTCAAAATCTTTCTAAAACAATTGACGGCGAAAAGTATTAGATAATGTATCATTCACAATGAATCCAAATGATAA
AGCGATTTTAATTGGAGATAGTGAAATTGCAAAAACAACATTACTTAAAATATTAGCTGGCGAAATGGAACCAGACGAAG
GTTCATTTAAATGGGGTGTTACTACATCATTAAGTTACTTCCCTAAAGATAACTCAGAGTTCTTTGAGGGTGTAAATATG
AATCTCGTTGATTGGTTAAGACAATATGCTCCTGAAGATGAACAAACAGAAACATTTTTACGTGGTTTCTTAGGTCGTAT
GTTATTTAGTGGTGAAGAAGTTAAGAAAAAAAGCTAGTGTGCTTTCAGGTGGAGAAAAAGTACGTTGTATGCTAAGTAAAA
TGATGTTATCAAGTGCGAATGTACTTTTACTTGACGAACCTACTAACCACTTAGACTTAGAAAGTATTACTGCTGTCAAT
GATGGTCTTAAATCATTTAAAGGTTCTATCATCTTTACTTCTTATGACTTCGAATTTATCAACACGATTGCAAACCGTGT
TATCGATTTAAATAAACAAGGCGGCGTTTCAAAAGAAATTCCATATGAAGAATACTTGCAAGAAATCGGCGTTTTAAAAT
AA

SEQ ID NO:35 polynucleotide sequence
ATGTTACAAGTAACTGATGTAAGTTTACGTTTTGGTGATCGTAAACTATTTGAAGATGTAAATATAAAATTTACAGAGGG
TAATTGTTATGGATTAATTGGTGCAAATGGTGCTGGGAAATCTACATTCTTGAAGATTTTATCAGGCGAAATTGATTCAC
AGACTGGTCATGTATCTCTAGGTAAAGATGAGCGTTTGGCTGTGTTAAAACAAGATCATTTGCTTATGAAGATGAACGT
GTTTTAGATGTTGTGATTAAAGGACATGAACGTTTGTATCAAGTGATGAAAGAGAAAGATGAAATTTATATGAAACCTGA
TTTCAGCGATGAGGACGGTATTCGCGCTGCAGAACTTGAAGGAGAATTTGCAGAAATGAACGGTTGGAATGCTGAAGCTG
ATGCTGCTAACTTATTATCAGGATTAGGCATAGAACCTGACTTACATGATAAAAATATGTCTGAACTTGAAAATAATCAA
AAAGTTAAGGTATTGTTAGCTCAAAGTTTATTTGGTGATCCTGACGTTCTTTTACTAGATGAGCCTACCAATGGTTTAGA
TATACCAGCAATAAGTTGGTTAGAAGACTTTTTAATTAATTTTGAAAATACTGTCATTGTCGTTTCGCATGACCGTCACT
TCTTAAATAATGTTTGTACTCATATTGCTGATTTAGACTTTGGCAAAATTAAACTTTATGTTGGTAACTATGATTTTTGG
TATCAATCAAGTCAATTAGCACAAAAAATGGCACAAGAACAAAATAAGAAAAAAGAAGAAAAATGAAAGAGTTACAGGA
TTTCATCGCACGCTTCTCAGCAAATGCTTCTAAATCTAAACAGGCAACAAGTCGTAAGAAACAATTAGAAAAAATTGAAT
TAGATGATATCCAGCCATCATCTCGTAGATACCCTTACGTGAAATTTACTCCTGAACGTGAAATTGGAAATGATTTACTT
ACAGTAGAAAATCTTTCTAAAACAATTGACGGCGAAAAGTACTAGACAATGTTTCATTCACTATGAATCCTAATGATAA
AGCTATTTTAGTTGGTGATAGCGAAATTGCTAAAACAACATTGTTAAAAATTTTAGCTGGAGAAATGGAACCAGATGAAG
GTACATTTAAATGGGGTGTAACGACATCTTTAAGTTACTTCCCTAAAGATAACTCTGAGTTCTTTGATGGTGTCGATATG
AATTTAGTTGAATGGTTACGTCAATACGCTCCAGAAGATGAACAAACTGAAACATTTTACGTGGTTTCTTAGGTCGCAT
GTTATTTAGTGGTGAGGAAGTTAAGAAAAAAGCAAGCGTGCTTTCAGGTGGAGAAAAAGTACGTTGCATGTTAAGTAAAA
TGATGTTATCAAGTGCTAACGTACTTTTACTTGATGAGCCAACAAACCATTTAGATTTGGAAAGTATCACTGCTGTAAAT
GACGGATTAAAATCATTTAAAGGTTCTATCATCTTCACTTCTTATGATTTTGAATTTATTAATACAATCGCAAATCGAGT
GATTGACTTGAATCAAGCTGGTGCCCTTTCTAAAGAAGTACCTTATGAGGAATACTTACAAGAAATTGGTGTATTACAAA
ATAATTAA

SEQ ID NO:36 polynucleotide sequence
ATGCCAATTATTACAGATGTTTACGCTCGCGAAGTCTTAGACTCTCGTGGTAACCCAACTGTTGAAGTAGAAGTATTAAC
TGAAAGTGGCGCATTTGGTCGTGCATTAGTACCATCAGGTGCTTCAACTGGTGAACACGAAGCTGTTGAATTACGTGATG
GAGACAAATCACGTTATTTAGGTAAAGGTGTTACTAAAGCAGTTGAAAACGTTAATGAAATCATCGCACCAGAAATTATT
GAAGGTGAATTTTCAGTATTAGATCAAGTATCTATTGATAAAATGATGATCGCATTAGACGGTACTCCAAACAAAGGTAA
ATTAGGTGCAAATGCTATTTAGGTGTATCTATCGCAGTAGCACGTGCAGCAGCTGACTTATTAGGTCAACCACTTTACA
AATATTTAGGTGGATTTAATGGTAAGCAGTTACCAGTACCAATGATGAACATCGTTAATGGTGGTTCTCACTCAGATGCT
CCAATTGCATTCCAAGAATTCATGATTTTACCTGTAGGTGCTACAACGTTCAAAGAATCATTACGTTGGGGTACTGAAAT
TTTCCACAACTTAAAATCAATTTTAAGCAAACGTGGTTTAGAAACTGCAGTAGGTGACGAAGGTGGTTTCGCTCCTAAAT
TTGAAGGTACTGAAGATGCTGTTGAAACAATTATCCAAGCAATCGAAGCAGCTGGTTACAAACCAGGTGAAGAAGTATTC
TTAGGATTTGACTGTGCATCATCAGAATTCTATGAAAATGGTGTATATGACTACAGTAAGTTCGAAGGCGAACACGGTGC
AAAACGTACAGCTGCAGAACAAGTTGACTACTTAGAACAATTAGTAGACAAATATCCTATCATTACAATTGAAGACGGTA
TGGACGAAAACGACTGGGATGGTTGGAAACAACTTACAGAACGTATCGGTGACCGTGTACAATTAGTAGGTGACGATTTA

FIGURE 2 cont.
TTCGTAACAAACACTGAAATTTTAGCAAAAGGTATTGAAAACGGAATTGGTAACTCAATCTTAATTAAAGTTAACCAAAT
CGGTACATTAACTGAAACATTTGATGCAATCGAAATGGCTCAAAAAGCTGGTTACACAGCAGTAGTTTCTCACCGTTCAG
GTGAAACAGAAGATACAACAATTGCTGATATTGCTGTTGCTACAAACGCTGGTCAAATTAAAACTGGTTCATTATCACGT
ACTGACCGTATTGCTAAATACAATCAATTATTACGTATCGAAGATGAATTATTTGAAACTGCTAAATATGACGGTATCAA
ATCATTCTATAACTTAGATAAATAA

SEQ ID NO:37 polynucleotide sequence
ATGCCAATTATTACAGATGTTTACGCTCGCGAAGTCTTAGACTCACGTGGTAACCCAACAGTTGAAGTTGAAGTATTAAC
TGAAAGCGGTGCTTTCGGACGTGCATTAGTACCTTCTGGTGCTTCTACTGGTGAACATGAAGCAGTTGAATTACGTGATG
GAGATAAATCACGTTATTTAGGTAAAGGTGTGACTAAAGCGGTAGAAAATGTTAACGAAATGATCGCACCAGAAATCGTT
GAAGGTGAATTTTCAGTTTTAGATCAAGTATCTATTGATAAAATGATGATTCAATTAGACGGTACACACAACAAAGGTAA
ATTAGGTGCAAATGCCATTTTAGGTGTTTCTATTGCCGTAGCTCGTGCAGCTGCTGACTTATTAGGTCAACCATTATATA
AATATTTAGGTGGATTTAATGGTAAACAATTGCCAGTACCTATGATGAATATTGTTAATGGTGGTTCTCACTCAGATGCA
CCAATTGCTTTCCAAGAGTTCATGATTTTACCTGTAGGTGCTGAGTCATTCAAAGAATCATTACGTTGGGGTGCAGAAAT
CTTCCATAACCTTAAATCAATCTTAAGTGAACGTGGTTTAGAAACTGCAGTAGGTGATGAAGGTGGTTTCGCTCCTAGAT
TTGAAGGCACTGAAGACGCTGTAGAAACTATTATTAAAGCTATCGAAAAAGCAGGATACAAACCAGGTGAAGATGTATTC
TTAGGATTTGACTGTGCTTCTTCTGAATTCTATGAAATGGTGTTTATGATTACACTAAATTCGAAGGTGAACACGGTGC
TAAACGTAGTGCAGCAGAGCAAGTTGACTACTTAGAAGAATTAATTGGTAAATATCCAATCATCACTATTGAAGATGGTA
TGGATGAAAACGATTGGGAAGGTTGGAAACAATTAACTGATCGTATCGGTGATAAAGTTCAATTAGTTGGTGATGATTTA
TTCGTAACTAACACTGAAATTTTATCTAAAGGTATCGAACAAGGTATTGGTAACTCAATCTTAATCAAAGTAAACCAAAT
CGGTACATTAACTGAAACATTCGATGCTATTGAAATGGCTCAAAAAGCTGGATATACTGCGGTTGTATCTCACCGTTCTG
GTGAAACTGAAGATACTACAATTGCTGATATCGCAGTTGCTACAAATGCAGGCCAAATTAAAACAGGTTCATTATCTAGA
ACTGACCGTATTGCTAAATACAATCAATTATTACGTATTGAAGATGAATTATACGAAACAGCTAAATTTGAAGGAATTAA
ATCTTTCTACAATTTAGATAAATAA

SEQ ID NO:38 polynucleotide sequence
ATGAAAAAAATCGTTACAGCTACAATCGCTACAGCAGGACTTGCCACTATCGCATTTGCAGGACATGATGCACAAGCCGC
AGAACAAAATAACAATGGATATAATTCTAATGACGCTCAATCATACAGCTATACGTATACAATTGATGCACAAGGTAATT
ATCATTACACTTGGACAGGAAATTGGAATCCAAGTCAATTAACGCAAAACAACACATACTACTACAACAACTACAATACT
TATAGTTATAACAATGCATCTTACAATAACTACTATAATCATTCATATCAATACAATAACTATACAAACAATAGCCAAAC
AGCAACAAATAACTATTATACTGGTGGTTCAGGTGCAAGTTATAGCACAACAAGTAATAATGTTCATGTGACTACAACTG
CAGCGCCATCTTCAAATGGTCGTTCAATTTCTAATGGTTATGCATCAGGAAGTAACTTATATACTTCAGGACAATGTACT
TATTATGTATTTGATCGTGTTGGTGGGAAAATTGGTTCAACATGGGGTAACGCAAGTAATTGGGCTAACGCAGCTGCATC
ATCTGGCTATACAGTGAACAATACACCAAAAGTTGGTGCTATCATGCAAACAACACAAGGCTATTACGGTCATGTTGCTT
ACGTTGAAGGCGTTAACAGCAACGGTTCTGTTCGTGTTTCAGAAATGAACTATGGACATGGTGCTGGTGTGGTTACGTCT
CGTACAATTTCAGCAAACCAAGCAGGTTCATATAATTTCATTCATTAA

SEQ ID NO:39 polynucleotide sequence
ATGAAGAAAATCGCTACAGCTACTATCGCAACTGCAGGATTCGCTACAATCGCAATTGCATCAGGAAATCAAGCTCATGC
TTCTGAGCAAGATAACTACGGTTATAATCCAAACGACCCAACATCATATAGCTATACTTACACTATTGATGCACAAGGTA
ACTACCATTACACATGGAAAGGTAACTGGCATCCAAGTCAATTAAACCAAGATAATGGCTACTACAGCTATTACTACTAC
AATGGCTACAATAACTACAACAATTACAACAATGGTTATAGCTACAATAATTACAGCCGTTACAACAACTACTCAAATAA
TAATCAATCATATAACTACAATAACTATAATAGTTACAACACAAACAGCTACCGTACTGGTGGTTTAGGTGCAAGCTACA
GCACTTCAAGCAACAATGTTCAAGTAACTACAACTATGGCTCCATCATCAAATGGCCGTTCAATCTCAAGTGGTTATACT
TCAGGACGTAACTTATACACTTCTGGTCAATGTACATACTACGTATTTGATCGTGTAGGTGGTAAAATCGGTTCAACTTG
GGGCAATGCAAGTAACTGGGCTAACGCAGCTGCAAGAGCTGGTTACACAGTGAACAATACACCAAAAGCTGGTGCAATTA
TGCAAACAACTCAAGGTGCATACGGTCACGTTGCATACGTTGAAAGTGTTAACAGCAATGGTTCAGTAAGAGTTTCAGAA
ATGAACTATGGTTATGGCCCAGGTGTTGTAACTTCACGTACAATCTCAGCTAGCCAAGCTGCTGGTTATAACTTCATTCA
CTAA

SEQ ID NO:40 polynucleotide sequence
ATGAAAAAAATCGCTACAGCTACAATTGCAACTGCAGGAATCGCTACTTTCGCATTTGCACACCATGACGCACAAGCAGC
AGAACAAAATAATGATGGGTACAATCCAAACGACCCTTATTCATATAGCTACACTTACACAATCGATGCTGAAGGTAACT
ACCACTACACTTGGAAAGGTAACTGGAGTCCAGATCGTGTAAATACTTCATATAACTATAATAATTATAATAACTACAAC
TACTATGGTTACAATAACTATAGCAACTACAATAACTACAGTAATTACAACAATTACAACAACTATCAATCAAACAACAC
GCAATCACAAAGAACAACTCAACCGACTGGTGGTTTAGGCGCAAGCTATTCAACATCAAGTAGTAATGTTCACGTTACAA
CAACTTCTGCGCCATCATCAAACGGTGTATCTTTATCAAACGCTCGCTCAGCATCTGGTAACTTATACACTTCAGGTCAA
TGTACATATTATGTATTTGACAGAGTAGGTGGCAAAATCGGTTCAACGTGGGGTAACGCAAACAACTGGGCAAACGCTGC

FIGURE 2 cont.
AGCACGTTCTGGTTACACAGTAAACAATTCGCCTGCTAAAGGTGCAATCTTACAAACGTCACAAGGTGCATACGGACACG
TAGCATACGTTGAAGGTGTAAACAGCAATGGTTCAATCAGAGTTTCAGAAATGAACTACGGTCACGGTGCAGGTGTTGTC
ACTTCACGTACAATCTCTGCGAGCCAAGCTGCTTCATATAACTATATTCACTAA

SEQ ID NO:41 polynucleotide sequence
ATGAAAAAATTAGTACCTTTATTATTAGCCTTATTACTTCTAGTTGCTGCATGTGGTACTGGTGGTAAACAAAGCAGTGA
TAAGTCAAATGGCAAATTAAAAGTAGTAACGACGAATTCATTTTATATGATATGGCTAAAAATGTTGGTGGAGACAACG
TCGATATTCATAGTATTGTACCTGTTGGTCAAGATCCTCATGAATATGAAGTTAAACCTAAAGATATTAAAAAGTTAACT
GACGCTGACGTTATTTTATACAACGGATTAAATTTAGAGACTGGTAACGGTTGGTTTGAAAAAGCCTTAGAACAGGCTGG
TAAATCATTAAAAGATAAAAAAGTTATCGCAGTATCAAAAGATGTTAAACCTATCTATTTAAACGGTGAAGAAGGCAACA
AAGATAAACAAGATCCACACGCATGGTTAAGTTTAGATAATGGTATTAAATACGTAAAAACAATTCAACAAACATTTATC
GATAACGACAAAAAACATAAAGCAGATTATGAAAAGCAAGGTAACAAATACATTGCTCAATTGGAAAAATTAAATAATGA
CAGTAAAGACAAATTTAATGACATTCCAAAAGAACAACGTGCCATGATTACAAGTGAAGGTGCCTTCAAGTACTTCTCAA
AACAATACGGTATTACACCAGGTTATATTTGGGAAATTAACACTGAAAAACAAGGTACACCTGAACAAATGAGACAAGCT
ATTGAGTTTGTTAAAAAGCACAAATTAAAACACTTATTAGTAGAAACAAGTGTTGATAAGAAAGCAATGGAAAGTTTATC
TGAAGAAACGAAGAAAGATATCTTTGGTGAAGTGTACACAGATTCAATCGGTAAAGAAGGCACTAAAGGTGACTCTTACT
ACAAAATGATGAAATCAAATATTGAAACTGTACACGGAAGCATGAAATAA

SEQ ID NO:42 polynucleotide sequence
GTGAAAAAAATTCTCGCTTTAGCAATAGCATTTTTTAATTATCCTTGCCGCATGTGGGAATCACAGTAACCATGAACATCA
CTCACATGAAGGAAAATTAAAAGTTGTAACTACAAACTCTATTCTCTATGACATGGTTAAACGTGTCGGTGGAAATAAGG
TCGATGTTCATAGCATCGTTCCAGTAGGACAAGACCCACATGAATATGAGGTTAAACCTAAAGATATTAAAGCATTAACA
GATGCTGACGTTGTATTTTATAACGGTTTAAACCTAGAAACTGGAAATGGTTGGTTTGAAAAAGCACTTGACCAAGCAGG
AAAATCAACAAAAGATAAAAATGTGATAGCAGCATCAAATAATGTTAAACCAATATACTTAAATGGTGAGGAAGGTAACA
AAAACAAACAAGATCCACATGCATGGTTAAGTTTAGAGAATGGAATTAAATACGTAAAAACAATACAAAAATCACTAGAA
CATCATGATAAAAAAGATAAGTCTACATATGAAAAACAAGGGAATGCATATATATCAAAATTAGAAGAACTTAATAAAGA
TAGTAAAAATAAATTTGATGACATACCCAAAAATCAACGTGCCATGATGACAAGTGAAGGTGCATTTAAATATTTTGCTC
AACAATTCGATGTTAAACCAGGTTATATTTGGGAGATAAACACAGAAAAACAAGGTACACCTGGTCAAATGAAACAAGCC
ATTAAATTTGTTAAAGATAATCATTTAAAACATTTATTAGTCGAAACAAGCGTAGATAAAAAAGCTATGCAAAGTTTATC
AGAAGAAACTAAGAAAGATATTTATGGTGAAGTATTTACCGACTCTATAGGTAAGGAAGGTACTAAAGGTGACTCATACT
ATAAAATGATGAAATCTAATATTGATACAATACATGGTAGTATGAAATAA

SEQ ID NO:43 polynucleotide sequence
ATGAAAAAGACAATTATGGCATCATCATTAGCAGTGGCATTAGGTGTAACAGGTTACGCAGCAGGTACAGGACATCAAGC
ACACGCTGCTGAAGTAAACGTTGATCAAGCACACTTAGTTGACTTAGCGCATAATCACCAAGATCAATTAAATGCAGCTC
CAATCAAAGATGGTGCATATGACATCCACTTTGTAAAAGATGGTTTCCAATATAACTTTACTTCAAATGGTACTACATGG
TCATGGAGCTATGAAGCAGCTAATGGTCAAACTGCTGGTTTCTCAAACGTTGCAGGTGCAGACTACACTACTTCATACAA
CCAAGGTTCAGATGTACAATCAGTAAGCTACAATGCACAATCAAGTAACTCAAACGTTGAAGCTGTTTCAGCTCCAACTT
ACCATAACTACAGCACTTCAACTACTTCAAGTTCAGTGAGATTAAGCAATGGTAATACTGCAGGTGCTACTGGTTCATCA
GCAGCTCAAATCATGGCTCAACGTACTGGTGTTTCAGCTTCTACATGGGCTGCAATCATCGCTCGTGAATCAAATGGTCA
AGTAAATGCTTACAACCCATCAGGTGCTTCAGGTTTATTCCAAACTATGCCAGGTTGGGGTCCGACAAACACTGTTGACC
AACAAATCAACGCAGCTGTTAAAGCATACAAAGCACAAGGTTTAGGTGCTTGGGGATTCTAA

SEQ ID NO:44 polynucleotide sequence
ATGAAAAAAACAGTTATCGCTTCTACATTAGCAGTATCTTTAGGAATTGCAGGTTACGGTTTATCAGGACATGAAGCACA
CGCTTCAGAAACTACAAACGTTGATAAAGCACACTTAGTAGATTTAGCACAACATAATCCTGAAGAATTAAATGCTAAAC
CAGTTCAAGCTGGTGCTTACGATATTCATTTCGTAGACAATGGATACCAATACAACTTCACTTCAAATGGTTCTGAATGG
TCATGGAGCTACGCTGTAGCTGGTTCAGATGCTGATTACACAGAATCATCATCAAACCAAGAAGTAAGTGCAAATACACA
ATCTAGTAACACAAATGTACAAGCTGTTTCAGCTCCAACTTCTTCAGAAAGTCGTAGCTACAGCACATCAACTACTTCAT
ACTCAGCACCAAGCCATAACTACAGCTCTCACAGTAGTTCAGTAAGATTATCAAATGGTAATACTGCTGGTTCTGTAGGT
TCATATGCTGCTGCTCAAATGGCTGCACGTACTGGTGTATCTGCTTCAACATGGGAACACATCATTGCTAGAGAATCAAA
TGGTCAATTACATGCACGTAATGCTTCAGGTGCTGCTGGATTATTCCAAACTATGCCAGGTTGGGGTTCAACTGGTTCAG
TAAATGATCAAATCAATGCCGCTTATAAAGCATATAAAGCACAAGGTTTATCTGCTTGGGGTATGTAA

SEQ ID NO:45 polynucleotide sequence
GTGAATTATCGTGATAAAATTCAAAAGTTTAGTATTCGTAAATATACAGTTGGTACATTTTCAACTGTCATTGCGACATT
GGTATTTTTAGGATTCAATACATCACAAGCACATGCTGCTGAAACAAATCAACCAGCAAGCGTGGTTAAACAGAAACAAC

FIGURE 2 cont.

```
AAAGTAATAATGAACAGACTGAGAATCGAGAATCTCAAGTACAAAATTCTCAAAATTCACAAAATAGTCAATCATTATCC
GCTACTCATGAAAATGAGCAACCAAATAATAGTCAAGCTAATTTAGTAAATCAAAAAGTAGCGCAATCATCTACTACTAA
TGATGAACAACCAGCATCTCAAAATGTAAATACAAAGAAAGATTCGGCAACGGCTGCGACAACACAACCAGATAAAGAAG
AAAGTAAGCATAAACAAAACGAAAGTCAATCTGCTAATAAAAATGGAAACGACAATAGAGCGGCTCATGTAGAAAATCAT
GAAGCAAATGTAGTAACAGCTTCAGATTCATCTGATAATGGTAACGTACAACATGACCGAAATGAATTACAAGCATTTTT
TGATGCAAATTATCATGATTATCGCTTTATTGACCGTGAAAATGCAGATTCTGGCACATTTAACTATGTAAAAGGCATTT
TTGACAAGATTAATACTTTATTAGGCAGTAATGATCCAATTAACAATAAAGACTTGCAACTTGCATACAAAGAATTGGAA
CAAGCTGTTGCTTTAATTCGTACAATGCCTCAACGTCAACAAACTAGCCGTCGATCAAACAGAATTCAAACGCGTTCTGT
TGAGTCTAGAGCTGCAGAGCCTAGATCAGTATCAGACTATCAAAATGCAAATTCATCATATTATGTTGAAAATGCTAATG
ATGGTTCAGGATATCCTGTAGGTACATATATCAATGCTTCTAGTAAAGGGGCGCCATATAATTTACCAACTACACCATGG
AATACATTGAAGGCCTCTGACTCAAAGGAAATTGCTCTTATGACAGCGAAACAAACTGGAGATGGCTACCAATGGGTTAT
TAAGTTTAATAAAGGACATGCTCCACATCAAAATATGATTTTCTGGTTTGCATTACCAGCAGACCAAGTGCCAGTAGGAA
GAACTGACTTTGTAACAGTTAATTCAGATGGAACAAATGTACAATGGAGTCATGGAGCAGGAGCAGGTGCAAATAAACCA
CTTCAACAAATGTGGGAATATGGAGTAAATGATCCTGATCGTTCACATGACTTTAAAATAAGAAATAGAAGTGGCCAAGT
AATATATAGCTGGCCAACTGTCCATGTTTATTCTTTAGAAGATTTATCTAGAGCGAGTGATTATTTTAGTGAAGCTGGAG
CGACACCTGCTACTAAAGCATTTGGTAGACAAAATTTTGAATATATTAATGGTCAAAAACCTGCTGAATCACCGGGTGTT
CCTAAAGTTTATACTTTCATCGGTCAAGGTGATGCAAGTTATACAATTTCATTTAAAACACAAGGTCCAACTGTTAATAA
ATTGTATTATGCAGCAGGTGGGCGTGCTTTAGAGTACAATCAATTATTTATGTACAGTCAACTATACGTCGAATCAACGC
AAGACCATCAACAACGTCTTAATGGTTTAAGACAAGTGGTTAATCGTACATATCGCATAGGTACAACTAAACGTGTAGAA
GTGAGTCAAGGAAATGTACAAACGAAAAAGGTATTAGAAAGTACAAACCTAAATATAGATGATTTTGTTGATGATCCTTT
AAGTTATGTTAAGACGCCCGAGTAATAAAGTGTTAGGTTTTTACCCAACTAATGCAAATACTAACGCTTTTAGACCGGGGG
GCGTTCAAGAATTAAATGAATATCAATTAAGTCAATTATTTACTGATCAAAAATTACAAGAAGCAGCAAGAACTAGAAAC
CCAATAAGATTAATGATTGGTTTCGACTATCCTGATGGTTATGGTAATAGTGAAACTTTAGTTCCTGTTAACTTAACGGT
ATTACCTGAAATCCAACATAATATTAAATTCTTTAAAAATGACGATACTCAAAATATTGCTGAAAAACCATTTTCAAAAC
AAGCTGGGCATCCAGTTTTCTATGTATATGCAGGTAACCAAGGGAATGCTTCCGTGAATTTAGGTGGTAGCGTAACATCT
ATTCAACCATTACGTATTAATTTAACAAGTAATGAGAATTTTACAGATAAAGATTGGCAAATTACAGGTATTCCGCGTAC
ATTACACATTGAAAACTCGACAAATAGAACTAATAATGCTAGAGAACGTAACATTGAACTTGTTGGTAATTTATTACCAG
GGGATTACTTTGGTACGATACGTTTTGGACGTAAAGAACAATTATTTGAAATTCGTGTTAAACCACATACACCAACAATT
ACAACGACAGCTGAGCAATTAAGAGGTACAGCATTACAAAAAGTGCCTGTTAATATTTCGGGAATACCGTTGGATCCATC
GGCATTGGTTTATTTAGTTGCACCAACAAATCAAACTACGAATGGTGGTAGTGAGGCAGATCAAATACCATCTGGTTATA
CGATACTTGCGACTGGTACACCTGATGGGGTGCATAATACAATTACTATACGACCGCAAGATTATGTTGTATTCATACCA
CCTGTAGGTAAACAAATTAGAGCAGTAGTTTATTATAATAAAGTAGTTGCATCTAATATGAGTAATGCTGTTACTATTTT
GCCAGATGACATTCCACCAACAATCAATAATCCTGTTGGAATAAATGCCAAATACTATCGAGGCGACGAAGTCAACTTTA
CAATGGGAGTCTCTGATAGACATTCTGGTATAAAAAATACAACTATTACTACTTTGCCAAGTGGTTGGACATCAAATTTA
ACTAAATCCGACAACAAAAACGGCTCATTAGCTATTACAGGTAGAGTCTCTATGAATCAGGCATTTAACAGTGATATTAC
ATTTAAAGTATCAGCGACAGACAATGTCAATAATACGACAAATGATAGTCAATCTAAACATGTGTCAATTCATGTAGGTA
AAATTAGTGAAGATGCTCATCCGATTGTATTAGGAAATACTGAGAAAGTTGTAGTAGTCAATCCGACTGCTGTATCTAAT
GATGAAAAGCAAAGCATAATTACTGCCTTTATGAATAAAAACCAAAATATAAGAGGATATTTAGCATCAACTGATCCAGT
AACTGTCGATAATAATGGTAACGTCACATTACATTACCGTGATGGCTCATCAACAACGCTTGATGCTACAAATGTGATGA
CATACGAACCAGTTGTGAAATCTGAATATCAAACTGCCAATGCTGCTAAAACAGCAACGGTAACGATTGCTAAAGGACAA
TCATTTAATATTGGTGATATTAAACAATATTTTACTTTAAGTAATGGACAAGCTATTCCAAATGGCACATTTACAAATAT
TACATCTGATAGAACTATTCCAACTGCACAAGAAGTTAGTCAAATGAATGCAGGTACGCAGTTATATCATATAGTTGCTT
CAAATGCATATCATAAAGACACTGAAGATTTCTATATTAGTTTAAAAATCGTTGATGTGAAACAACCTGAAGGCGATCAA
CGTGTCTATCGTACGTCAACATATGATTTAACCACTGATGAAATCTCAAAAGTAAAACAAGCTTTTATTAATGCAAATAG
AGATGTAATTACGCTTGCCGAAGGTGATATTTCAGTTACAACACACCTAATGGTGCTAATGTAAGTACTATTACAGTAA
ATATTAATAAAGGTCGATTAACGAAATCATTCGCGTCTAACCTAGCTAATATGAATTCTTGCGTTGGGTTAATTTCCCA
CAAGATTATACAGTGACATGGACGAATGCAAAAATTGCAAACAGACCAACAGATGGTGGTTTATCATGGTCCGATGACCA
TAAATCTTTAATTTATCGTTATGATGCTACATTAGGCACACAAATTACAACTAATGATATTTTAACGATGCTAAAAGCGA
CTACTACAGTGCCTGGATTGCGTAATAATATTACTGGTAATGAAAAAGCACAAGCAGAAGCAGGTGGAAGACCAAACTAT
AGAACAACTGGTTATTCACAATCAAATGCGACAACTGATGGTCAACGTCAATTTACGTTGAATGGTCAAGTGATTCAAAT
ATTAGACATCATCAACCCTTCAAACGGTTATGGTGGGCAACCTGTTACAAATTCAAATACTCGTGCAAACCATAGTAACT
CAACTGTTGTTAACGTAAACGAACCGGCAGCTAATGGTGCTGGCGCATTTACAATTGACCACGTTGTAAAAGTAATTCT
ACACATAATGCAAGTGATGCAGTTTATAAAGCGCAGTTATACTTAACGCCATATGGTCCAAAACAATATGTTGAACATTT
AAATCAAAATACAGGAAATACTACTGACGCTATTAACATTTATTTTGTACCAAGTGACTTAGTGAATCCAACAATTTCAG
TAGGTAATTACACTAATCATCAAGTGTTCTCAGGTGAAACATTTACAAATACGATTACAGCGAATGATAACTTTGGTGTG
CAATCGGTAACTGTACCAAATACATCACAAATTACAGGTACTGTTGATAATAACCATCAACATGTTTCTGCAACGGCACC
AAATGTGACATCAGCAACTAGTAAGACAATCAATTTATTAGCAACTGATACAAGTGGTAATACAGCTACAACTTCATTCA
ATGTAACAGTGAAACCTTTGCGTGATAAATATCGAGTTGGTACTTCATCAACGGCTGCTAATCCTGTTAGAATTGCCAAT
ATTTCGAATAATGCGACAGTATCACAAGCTGATCAAACGACAATTATTAATTCGTTAACGTTTACAAGTAATGCACCCAAA
TAGAAACTATGCAACAGCAAGCGCAAATGAAATCACTAGTAAAACAGTTAGTAATGTCAGTCGTACTGGAAATAATGCCA
```

FIGURE 2 cont.
```
ATGTCACAGTAACTGTTACTCATCAAGATGGAACAACATCAACAGTGACTGTACCTGTAAAGCATGTCATTCCAGAAATC
GTTGCACATTCGCATTACACTGTACAAGGCCAAGACTTCCCAGCAGGTAATGGTTCTAGTGCAGCAGATTACTTTAAGTT
ATCTAATGGTAGTGCCATTCCAGATGCAACGATTACATGGGTAAGTGGACAAGCGCCAAATAAAGATAATACACGTATTG
GTGAAGATATAACAGTAACTGCACATATCTTAATTGATGGCGAAACAACGCCGATTACGAAAACAGCAACATATAAAGTA
GTAAGAACTGTACCGAAACATGTCTTTGAAACAGCCAGAGGTGTTTTATACCCAGGTGTTTCAGATATGTATGATGCGAA
ACAATATGTTAAGCCAGTAAATAATTCTTGGTCGACAAATGCGCAACATATGAATTTTCAATTTGTTGGAACATATGGTC
CTAACAAAGATGTTGTAGGTATATCAACGCGTCTTATTAGAGTGACTTATGATAATAGACAAACTGAAGATTTAACTATT
TTATCTAAAGTTAAACCTGACCCACCAAGAATTGACGCAAACTCTGTGACATATAAAGCAGGTCTTACAAACCAAGAAAT
TAAAGTTAATAACGTATTAAATAACTCGTCAGTAAAATTATTTAAAGCAGATAATACACCATTAAATGTCACAAATATTA
CTCATGGTAGTGGTTTTAGTTCGGTTGTGACAGTAAGTGACGCGTTACCAAATGGCGGAATTAAAGCAAAATCTTCAATT
TCAATGAACAATGTGACGTATACGACGCAAGACGAACATGGTCAAGTTGTTACAGTAACAAGAAATGAATCTGTTGATTC
AAATGATAGTGCTTCTGTTACAGTAACACCACAATTACAAGCAACTACTGAAGGCGCTGTATTTATTAAAGGTGGCGACG
GTTTTGATTTCGGTCATGTAGAACGATTTATTCAAAATCCGCCACATGGGGCAACGGTCGCATGGCATGATAGTCCAGAT
ACATGGAAGAATACAGTCGGCAACACACATAAAACTGCGGTTGTAACATTACCTAGTGGTCAAGGTACGCGTAATGTTGA
AGTTCCAGTCAAAGTTTATCCAGTTGCTAATGCTAAGGCGCCATCACGTGATGTGAAAGGTCAAAATTTGACACATGGTA
CAAACGCTATTGATTACATTACATTTGATCCAAATACTAATACGAATGGTATTACAGCAGCATGGGCAAATAGACAACAA
CCAAATAACCAGCAAGCAGGCGTTCAACATTTAAATGTCGATGTCACATATCCAGGTATTTCAGCTGCTAAACGAGTTCC
TGTAACTGTGAACGTATATCAATTTGAATTCCCTCAAACTACTTATACAACAACAGTTGGTGGCACTTTAGCAAGTGGTA
CGCAAGCATCAGGATATGCACATATGCAAAACGCTTCAGGTTTACCAACAGATGGATTTACGTATAAATGGAATCGTGAT
ACTACGGGTACAAACGATGCAAACTGGGCAGCAATGAATAAACCAAATACTGCACAAGTCGTTAATGCAAAATATGATGT
CATCTATAATGGACATACATTTGCAACATCTTTACCAGCGAAATTTGTAGTAAAAGATGTTCAACCAGCGAAACCAACTG
TCACTGAAACAGCGGCAGGGAGCGATTACAATTGCACCTGGTGCGAACCAAACAGTCAATACTCATGCTGGTAATGTTACG
ACATATGCTGACAAATTAGTTATTAAACGTAATGGAAATGTTGTAACGACATTTACACGTCGTAATAATACGAGCCCATG
GGTGAAAGAAGCATCAGCAGATAATGTAACAGGTATTGTTGGAACTAATAATGGTATTACTGTGGCAGCAGGTACTTTCA
ATCCTGCTGATACAATTCAAGTTGTTGCAACACAAGGTAGTGGCGAAACAATCAGTGACGAGCAACGTAGTGATGATTTC
ACAGTTGTCGCACCACAACCGAACCAAGCGACTACGAAAATTTGGCAAAATGGTCATATTGATATCACGCCTAATAATCC
ATCAGGACATTTAATTAATCCAACACAAGCAATGGATATTGCTTACACTGAAAAAGTGGGTAATGGTGCAGAACATAGTA
AGACAATTAATGTTGTTCGTGGTCAAAATAATCAATGGACAATTGCGAATAAGCCTGACTATGTAACGTTAGATGCACAA
ACTGGTAAAGTGACGTTCAATGCCAATACTATAAAACCAAATTCATCAATCACAATTACTCCGAAAGCAGGTACAGGTCA
CTCAGTAAGTAGTAATCCAAGTACATTAACTGCACCGGCAGCTCATACTGTCAACACAACTGAAATTGTGAAAGATTATG
GTTCAAATGTAACAGCAGCTGAAATTAACAATGCAGTTCAAGTTGCTAATAAACGTACTGCAACGATTAAAAATGGCACA
GCAATGCCTACTAATTTAGCTGGTGGTAGCACAACGACGATTCCTGTGACAGTAACTTACAATGATGGTAGTACTGAAGA
AGTACAAGAGTCCATTTTCACAAAAGCGGATAAACGTGAGTTAATCACAGCTAAAAATCATTTAGATGATCCAGTAAGCA
CTGAAGGTAAAAAGCCAGGTACAATTACGCAGTACAATAATGCAATGCATAATGCGCAACAACAAATCAATACCGCGAAA
ACAGAAGCACAACAAGTGATTAATAATGACGCTGCAACACCACAACAAGTTTCTGACGCACTAACTAAAGTTCGTGCAGC
ACAAACTAAGATTGATCAAGCTAAAGCATTACTTCAAAATAAAGAAGATAATAGCCAATTAGTAACGTCTAAAAATAACT
TACAAAGTTCTGTGAACCAAGTACCATCAACTGCTGGTATGACGCAACAAAGTATTGATAACTATAATGCGAAGAAGCGT
GAAGCAGAAACTGAAATAACTGCAGCTCAACGTGTTATTGACAATGGCGATGCAACTGCACAACAAATTTCAGATGAAAA
ACATCGTGTCGATAACGCATTAACAGCATTAAACCAAGCGAAACATGATTTAACTGCAGATACACATGCCTTAGAGCAAG
CAGTGCAACAATTGAATCGCACAGGTACAACGACTGGTAAGAAGCCGGCAAGTATTACTGCTTACAATAATTCGATTCGT
GCACTTCAAAGTGACTTAACAAGTGCTAAAAATAGCGCTAATGCTATCATTCAGAAGCCAATAAGAACAGTGCAAGAGGT
ACAATCTGCGTTAACAAATGTAAATCGTGTCAATGAGCGATTAACGCAAGCAATTAATCAATTAGTACCTTTAGCTGATA
ATAGTGCTTTAAGAACTGCTAAGACGAAACTTGATGAAGAAATCAATAAATCAGTAACTACTGATGGTATGACACAATCA
TCAATCCAAGCATATGAAATGCTAAACGTGCAGGTCAAACAGAAACAACAAATGCACAAAATGTTATTAACAATGGTGA
CGCGACAGACCAACAAATTGCCGCAGAAAAAACAAAAGTAGAAGAAAAATATAATAGCTTAAAACAAGCAATTGCTGGAT
TAACACCAGACTTGGCACCATTACAAACTGCAAAAACTCAGTTGCAAAATGATATTGATCAGCCAACGAGTACGACTGGT
ATGACAAGCGCATCTGTTGCTGCATTTAATGACAAACTTTCAGCAGCTAGAACTAAAATTCAAGAAATTGATCGCGTACT
AGCATCTCATCCAGATGTAGCAACGATTCGTCAACAACGTGACAGCGACGAATGCTGCTAAAACAGCACTTGATCAAGCGC
GCAATGGCTTAACAGTCGATAAAGCACCTTTAGAAAATGCGAAAAATCAACTACAACATAGTATTGATACGCAAACAAGT
ACAACTGGTATGACACAAGACTCTATAAATGCATACAATGCGAAGTTAACAGCTGCACGTAATAAGGTTCAACAAATCAA
TCAAGTATTAGCAGGTTCACCTACTGTAGATCAAATTAATACAAATACGTCTGCAGCAAATCAAGCGAAATCTGATTTAG
ATCATGCACGTCAAGCGTTAACACCAGATAAAGCGCCGCTTCAAAATGCGAAAACGCAATTAGAACAAAGCATTAATCAA
CCAACAGATACAACAGGTATGACAACCGCTTCGTTAAATGCATACAACCAAAAATTACAAGCAGCACGTCAAAAGTTAAC
TGAAATTAATCAAGTGTTGAATGGCAACCCAACTGTCCAAAATATCAATGATAAAGTGGCAGAGGCAAACCAAGCTAAGG
ATCAATTAAATACAGCACGTCAAGGTTTAACATTAGATAGACAGCCAGCGTTAACAACATTACATGGTGCATCTAACTTA
AACCAAGCACAACAAATAATTTCACGCAACAAATTAATGCTGCTCAAAATCATGCTGCGCTTGAAACAATTAAGTCTAA
CATTACGGCTTTAAATACTGCGATGACGAAATTAAAAGACAGTGTTGCGGATAATAATACAATTAAATCAGGTCAAATT
ACACTGACGCAACACCAGCTAATAAACAAGCCTATGATAATGCAGTTAATGCGGCTAAAGGTGTCATTGGAGAAACGACT
AATCCAACGATGGATGTTAACACAGTGAACCAAAAAGCAGCATCTGTTAAATCGACGAAAGATGCTTTAGATGGTCAACA
AAACTTACAACGTGCGAAAACAGAAGCAACAAATGCGATTACGCATGCAAGTGATTTAAACCAAGCACAAAAGAATGCAT
```

FIGURE 2 cont.
```
TAACACAACAAGTGAATAGTGCACAAAACGTGCAAGCAGTAAATGATATTAAACAAACGACTCAAAGCTTAAATACTGCT
ATGACAGGTTTAAAACGTGGCGTTGCTAATCATAACCAAGTCGTACAAAGTGATAATTATGTCAACGCAGATACTAATAA
GAAAAATGATTACAACAATGCATACAACCATGCGAATGACATTATTAATGGTAATGCACAACATCCAGTTATAACACCAA
GTGATGTTAACAATGCTTTATCAAATGTCACAAGTAAAGAACATGCATTGAATGGTGAAGCTAAGTTAAATGCTGCGAAA
CAAGAAGCGAATACTGCATTAGGTCATTTAAACAATTTAAATAATGTACAACGTCAAAACTTACAATCGCAAATTAATGG
TGCGCATCAAATTGATGCAGTTAATACAATTAAGCAAAATGCAACAAACTTGAATAGTGCAATGGGTAACTTAAGACAAG
CTGTTGCAGATAAAGATCAAGTGAAACGTACAGAAGATTATGCGGATGCAGATACAGCTAAACAAAATGCATATAACAGT
GCAGTTTCAAGTGCTGAAACAATTATTAATCAAACAGCTAATCCGACAATGTCTGTTGATGATGTTAATCGTGCAACTTC
AGCTGTTACTACTAATAAAAATGCATTAAATGGTGATGAAAAATTAGTACAATCTAAAACAGATGCTGCAAGAGCAATTG
ATGCATTACCACATTTAAATAATGCACAAAAAGCAGATGTTAAATCTAAAATTAATGCTGCATCAAATATTGCTGGTGTA
AATACCGTTAAACAACAAGGTACAGATTTAAATACAGCGATGGGTAACTTGCAGGGTGCAATCAATGATGAACAAACGAC
GCTTAATAGTCAAAATTATCAAGATGCGACACCTAGTAAGAAAACAGCATACACAAATGCGGTGCAAGCTGCGAAAGATA
TTTTAAATAAATCAAATGGTCAAAATAAAACGAAAGATCAAGTTACTGAAGCGATGAATCAAGTGAATTCGGCTAAAAAT
AACTTAGATGGTACGCGTTTATTAGATCAAGCGAAGCAAACAGCGAAACAGCAGTTAAATAATATGACGCATTTAACAAC
TGCACAAAAAACGAATTTAACAAATCAAATTAATAGTGGTACTACTGTTGCTGGTGTTCATACGGTTCAATCAAATGCCA
ACACATTAGATCAAGCGATGAATACGTTAAGACAAAGTATTGCTAACAATGATGCGACTAAAGCAAGTGAAGATTACGTA
GATGCTAATAATGATAAGCAAACAGCATATAACAACGCGGTAGCTGCTGCTGAAACGATTATTAATGCGAATAGTAATCC
AGAAATGAATCCAAGTACGATTACACAAAAAGCAGAGCAAGTGAATAGTTCTAAAACGGCACTTAACGGTGATGAAAACT
TAGCTACGGCAAAACAAAATGCGAAAACGTACTTAAACACATTAACGAGTATTACAGATGCTCAAAAGAACAATTTGATT
AGTCAAATTAGTAGTGCGACAAGAGTGAGTGGTGTTGATACTGTAAAACAAAATGCACAACATTTAGATCAAGCTATGGC
TAACTTACAAAATGGTATTAACAACGAATCTCAAGTGAAATCATCTGAGAAATATCGTGATGCTGATACAAATAAACAAC
AAGAGTATGATAATGCTATTACTGCAGCGAAAGCGATTTTAAATAAATCGACAGGTCCAAACACTGCGCAAAATGCAGTT
GAAGCAGCATTGCAACGTGTTAATACTGCGAAAGATGCATTGAATGGTGATGCAAAATTAATTGCAGCTCAAAACGCAGC
GAAACAACATTTAGGTACTTTAACGCATATCACTACAGCACAACGCAATGATTTAACAAATCAAATTTCA
```

SEQ ID NO:46 polynucleotide sequence
```
ATGGGTAACTTACAAACGGCTATCAACGATAAGTCAGGAACATTAGCGAGCCAAAACTTCTTGGATGCTGATGAGCAAAA
ACGTAATGCTTACAATCAAGCTATATCAGCTGCCGAAACCATTTTAAATAAACAAACTGGACCGAATACAGCGAAAACAG
CGGTTGAACAAGCACTTAATAATGTTAATAGTGCGAAACATGCATTAAATGGTACGCAAAACTTAAATAATGCGAAACAA
GCAGCGATTACAGCAATTAATGGCGCATCTGATTTAAATCAAAAACAAAAAGATGCATTAAAAGCACAAGCTAATGGTGC
TCAACGCGTATCTAATGCAAATGATGTACAACGTAATGCGACTGAACTGAACACGGCAATGGGTCAATTACAACATGCCA
TCGCAGATAAGACGAATACGTTAGCAAGCAGTAAATATGTCAACGCCGATAGCACTAAACAAATGCTTACACAACTAAA
GTTACCAATGCTGAACATATTATTAGCGGTACGCCAACGGTTGTTACAACACCTTCAGAAGTAACAGCTGCAGCTAATCA
AGTAAACAGCGCGAAACAAGAATTAAATGGTGACGAAAGATTACGTGTTGCAAAACAAAACGCCAATACTGCTATTGATG
CATTAACGCAATTAAATACTCCTCAAAAAGCTAAATTAAAAGAACAAGTGGGACAAGCCAATAGATTAGAAGACGTACAA
TCTGTTCAAACAAATGGACAATCATTGAACAATGCAATGAAAGGCTAAGAGATAGTATTGCTAACGAAACAACAGTCAA
AGCAAGTCAAAACTATACAGACGCAAGTCCGAATAACCAATCAACATATAATAGCGCTGTGTCAAATGCGAAAGGTATCA
TTAATCAAACTAACAATCCAACTATGGATACTAGTGCGATTACCCAAGCTACAACACAAGTGAATAATGCTAAAAATGGT
TTAAACGGTGCTGAAAACTTAAGAAATGCACAAAAACACTGCTAAGCAAAACTTAAATACGTTATCACACTTAACAAATAA
CCAAAAATCTGCAATCTCATCACAAATTGATCGTGCAGGTCATGTGAGTGAGGTAACAGCTGCTAAAAATGCAGCAACTG
AGTTAAACGCGCAAATGGGCAACTTGGAACAAGCTATCCATGATCAAAACACAGTTAAACAAGGTGTTAACTTCACTGAT
GCAGATAAAGCTAAACGTGATGCTTATACAAATGCGGTAAGCAGAGCAGAAACAATTCTGAATAAAACGCAAGGTGCAAA
TACGTCTAAACAAGATGTTGAAGCGGCTATTCAAAATGTTACAAGTGCTAAAAATGCATTGAATGGTGATCAAAACGTTA
CAAATGCGAAGAATGCAGCTAAAAATGCATTAAATAACTTAACGTCAATTAATAATGCACAAAAACGTGACTTAACAACT
AAAATTGATCAAGCAACAACAGTAGCTGGTGTTGAAGCGGTATCTAATACAGGTACACAATTGAATACAGCGATGGCTAA
CTTGCAAAATGGTATTAATGATAAAGCGAATACTTTAGCGAGCGAAAACTATCATGATGCTGATTCAGATAAGAAAACTG
CTTATACTCAAGCCGTTACGAACGCAGAAAATATTTTAAATAAAAATAGTGGATCAAATTTAGATAAAGCTGCCGTTGAA
AACGCGTTGTCACAAGTGACAAATGCGAAAGGTGCCCTAAATGGTAACCATAATTTAGAGCAAGCTAAATCAAATGCAAA
CACTACTATAAACGGCCTTCAACATTTAACAACAGCACAAAAAGATAAATTGAAACAACAAGTGCAACAAGCACAAAATG
TTGCAGGTGTAGATACTGTTAAATCAAGTGCCAACACATTAAATGGTGCTATGGGTACGTTAAGAAATAGCATACAAGAT
AACACAGCTACGAAAAATGGCCAAAACTATCTTGATGCTACAGAACGTAACAAAACAAACTATAACAATGCTGTTGATAG
TGCTAATGGTGTCATTAATGCAACAAGCAATCCAAATATGGATGCTAATGCAATTAACCAAATCGCTACACAAGTGACAT
CAACGAAAAATGCATTAGATGGTACACATAATTTAACGCAAGCGAAACAAACAGCAACAAATGCCATCGATGGTGCTACT
AACTTAAATAAAGCGCAAAAAGATGCGTTAAAAGCACAAGTTACAAGTGCGCAACGTGTTGCAAATGTAACAAGTATCCA
ACAAACTGCAAATGAACTTAATACAGCTATGGGTCAATTACAACATGGTATTGATGATGAAAATGCAACAAAACAAACTC
AAAAATATCGTGACGCTGAACAAAGTAAGAAAACTGCTTATGATCAAGCTGTAGCTGCTGCGAAAGCAATTTTAAATAAA
CAAACAGGTTCCAATTCAGATAAAGCAGCAGTTGACCGTGCATTACAACAAGTAACAAGTACGAAAGATGCATTGAATGG
GGATGCTAAACTGGCAGAAGCGAAAGCGGCAGCTAGACAAAACTTAGGTACTTTAAACCATATTACGAATGCACAACGTA
CTGCGTTAGAAGGTCAAATCAATCAAGCGACGACTGTTGATGGCGTTAATACTGTAAAACAAATGCCAATACATTAGAC
```

FIGURE 2 cont.
```
GGCGCTATGAATAGCTTACAAGGTGCAATCAATGATAAAGATGCGACATTAAGAAATCAAAATTATCTTGATGCAGATGA
ATCAAAACGAAATGCATATACGCAAGCTGTCACAGCGGCTGAAGGCATTTTAAATAAACAAACAGGTGGTAACACATCTA
AAGCAGACGTTGATAATGCATTAAATGCAGTTACAAGAGCGAAAGCGGCTTTAAATGGTGCTGAAAACTTAAGAAATGCG
AAAACTTCAGCAACAAATACGATTAATGGTTTACCTAACTTAACACAATTACAAAAAGACAACTTGAAGCATCAAGTTGA
ACAAGCGCAAAATGTAGTTGGTGTAAATGGTGTTAAAGATAAAGGTAATACATTAAATACTGCCATGGGTGCATTACGTA
CAAGTATCCAAAATGATAATACGACGAAAACAAGTCAAAATTATCTTGATGCATCTGATAGCAACAAAAATAATTACAAT
ACTGCTGTAAATAATGCAAATGGTGTTATTAATGCAACGAACAATCCAAATATGGATGCTAATGCGATTAATGACATGGC
AAATCAAGTCAATACAACAAAAGCAGCGTTAAATGGTGCACAAAACTTAGCTCAAGCTAAAACAAATGCGACGAACACAA
TTAACAACGCGCAAGACTTAAACCAAAAACAAAAAGATGCATTAAAAACACAAGTTAACAATGCACAACGTGTATCTGAT
GCAAATAACGTTCAACATACAGCTACTGAATTGAACGGTGCGATGACAGCACTTAAAGCAGCTATTGCGGATAAAGAAAG
AACAAAAGCAAGCGGTAATTATGTCAATGCTGATCAAGAAAACGTCAAGCGTATGATTCAAAAGTGACTAACGCTGAAA
ATATCATTAATGGTACACCAAATGCGACATTAACAGTCAATGACGTAAATAGTGCGGCATCACAAGTCAATGCGGCTAAA
ACAGCATTAAATGGTGATAACAACTTACGTGTAGCGAAAGAGCATGCTAACAATACAATTGACGGCTTAGCACAATTGAA
TAATGTACAAAAAGCAAAATTAAAAGAACAAGTTCAAAGTGCAACTACATTAGATGGTGTTCAAACTGTTAAAAATAGTT
CTCAAACGTTGAATACAGCGATGAAAGGCTTAAGAGATAGTATTGCGAATGAAGCAACGATTAAAGCAGGTCAAAACTAC
ACTGACGCAAGTCCAAATAATCGTAACGAGTACGACAGCGCAGTTACTGCAGCAAAAGCAATCATTAATCAAACATCGAA
CCCAACGATGGAACCAAATACTATTACGCAAGCAACATCACAAGTGACAACTAAAGAACATGCATTAAATGGTGCGCAAA
ACTTAGCTCAAGCTAAGACAACAGCGAAAAACAACTTGAATAACTTAACATCAATTAACAATGCACAAAAAGATGCGTTA
ACGCGTAACATTGATGGTGCAACTACAGTAGCTGGTGTAAATCAAGAAACTGCAAAAGCAACAGAATTAAATAACGCAAT
GCACAGTTTACAAAATGGTATCAATGATGAGACACAAACAAAACAAACTCAGAAATACCTAGATGCTGAGCCAAGTAAGA
AATCAGCTTATGATCAAGCAGTAAATGCAGCAAAAGCAATTTTAACAAAAGCTAGTGGTCAAATGTAGACAAAGCAGCA
GTTGAACAAGCATTACAAAATGTGAACAGTACGAAGACGGCGTTGAACGGTGATGCGAAATTAAATGAAGCTAAAGCTGC
TGCGAAACAAACGTTAGGTACATTAACACACATTAATAATGCACAACGTAATGCGTTAGATAATGAAATTACACAAGCAA
CAAATGTTGAAGGTGTTAATACAGTTAAAGCCAAAGCGCAACAATTAGATGGTGCTATGGGTCAATTAGAAACATCAATT
CGTGATAAAGACACGACGTTACAAAGTCAAAATTATCAAGATGCTGATGATGCTAAACGAACGGCTTATTCTCAAGCAGT
AAATGCAGCAGCAACTATTTTAAATAAAACAGCTGGAGGAAATACACCTAAAGCAGATGTCGAAAGAGCAATGCAAGCTG
TTACACAAGCCAATACTGCATTAAACGGTATTCAAAACTTAGAACGTGCGAAACAGGCTGCGAACACAGCGATTACAAAT
GCTTCGGACTTAAATACAAAACAAAAGAAGCATTGAAAGCACAAGTAACAAGTGCAGGACGCGTATCTGCAGCAAATGG
TGTTGAACATACTGCGACTGAATTAAATACTGCGATGACAGCTTTAAAACGTGCCATTGCTGATAAAGCTGACACAAAAG
CTAGTGGTAATTATGTCAATGCTGATGCGAATAAACGCCAAGCATATGATGAAAAAGTGACAGCTGCAGAACATATCGTT
AGTGGTACACCAACACCAACGTTAACACCATCAGATGTTACAAATGCAGCAACGCAAGTAACGAATGCGAAGACGCAGTT
AAACGGTAATCATAATTTAGAAGTAGCGAAACAAAATGCTAACACAGCAATTGATGGTTTAACTTCTTTAAATGGTCCGC
AAAAAGCAAAACTTAAAGAACAAGTGGGTCAAGCGACGACGTTGCCAAATGTTCAAACTGTTCGTGATAATGCACAAACA
TTAAACACTGCAATGAAAGGTCTACGAGATAGCATTGCGAATGAAGCAACGATTAAAGCAGGTCAAAACTACACAGATGC
AAGTCAAAACAAACAAAATGACTACAACAATGCAGTCACTGCAGCAAAAGCAATCATTGGTCAAACAACTAGTCCATCAA
TGATTGCGCAAGAAATTAATCAAGCGAAAGACCAAGTGACAGCTAAACAACAAGCGTTAAACGGTCAAGAAAACTTAAGA
ACTGCGCAAACAAATGCGAAGCAACATTTGAATGGCTTAAGTGACTTAACTAATGCACAAAAAGATGCAGCGAAACGCCA
AATCGAAGGTGCAACGCATGTTAATGAAGTAACACAAGCGCAAAATAATGCGGACGCATTAAATACAGCTATGACGAACT
TGAAAAATGGTATTCAAGATCAAAATACGATTAAGCAAGGTGTTAACTTCACTGATGCAGATGAAGCGAAACGTAATGCA
TATACAAATGCAGTGACGCAAGCTGAACAAATTTAAATAAAGCACAAGGTCCAAATACTGCAAAAGACGGTGTCGAAAC
TGCGTTACAAAATGTACAACGTGCTAAAAACGAATTGAACGGTAATCAAAATGTTGCGAACGCTAAGACAACTGCGAAAA
ATGCATTGAATAACCTTACATCAATTAATAATGCACAAAAAGCAGCATTGAAATCACAAATTGAAGGTGCGACAACAGTT
GCAGGTGTAAATCAAGTGTCTACAATGGCATCTGAATTAAATACTGCAATGAGCAACTTACAACGTGGTATTAATGACGA
AGCAGCTACAAAAGCAGCTCAGAAATATACTGAAGCAGATAGAGATAAACAAACTGCATACAATGATGCTGTAACAGCAG
CTAAAACGTTATTAGATAAAACAGCTGGTTCAAATGACAATAAAGTAGCCGTTGAACAAGCATTACAACGTGTGAATACT
GCTAAAACAGCATTAAATGGTGACGCGCGATTAAATGAAGCGAAGAACACAGCTAAACAACAATTAGCGACAATGTCACA
TTTAACTAATGCTCAAAAAGCAAACTTAACAGAACAAATTGAACGTGGTACAACTGTTGCTGGTGTTCAAGGCATCCAAG
CAAATGCTGGTACTTTAAATCAAGCAATGAATCAATTAAGACAAGTATTGCTTCTAAAGATGCGACTAAATCAAGCAGA
GATTATCAAGACGCGAATGCAGATTTACAAAATGCATACAATGATGCGGTAACTAATGCTGAAGGTATTATTAGTGCAAC
GAATAACCCTGAAATGAATCCTGATACAATTAACCAAAAAGCGAGCCAAGTGAACAGTGCGAAGTCTGCATTGAACGGTG
ATGAAAAATTAGCAGCAGTAAAACAAACTGCGAAATCAGATATCGGTCGTTTGACAGACTTGAACAATGCACAACGAACT
GCGGCAAATGCTGAAGTGGATCAAGCACCCAAATCTTGCAGCTGTCACAGCGGCTAAAAATAAAGCAACATCGTTAAACAC
AGCGATGGGTAATTTGAAACATGCACTTGCTGAAAAGGATAATACGAAACGTAGTGTCAATTACACAGATGCGGATCAAC
CAAAACAACAAGCGTATGATACTGCAGTTACACAAGCAGAAGCAATTACTAATGCAAATGGCAGTAACGCGAATGAAACA
CAAGTTCAAGCAGCGCTTAACCAATTGAATCAAGCTAAAAACGACTTGAATGGTGATAATAAAGTTGCTCAAGCGAAAGA
AACAGCAAAACGTGCATTAGCTTCATATAGTAACTTGAATAACGCGCAATCAACTGCAGCAACTAGTCAAATTGACAATG
CAACGACAGTAGCAGACGTAACTGCTGCACAAAATACTGCTAATGAATTAAATACAGCAATGGGTCAACTTCAAAATGGT
ATTAATGACCAAAACACTGTTAAACAACAAGTGAACTTTACAGATGCTGACCAAGGTAAGAAAGATGCTTACACAAATGC
TGTTACGAATGCTCAAGGTATTTTAGATAAAGCAAACGGTCAAAATATGACAAAAGCACAAGTTGAAGCTGCATTAAATC
AAGTAACGACTGCTAAGAATGCTTTAAACGGTGATGCAAATGTAAGACAAGCAAAATCAGATGCGAAAGCAAACTTAGGT
```

FIGURE 2 cont.
ACATTAACACACTTAAATAATGCACAAAAACAAGATTTAACATCACAAATCGAAGGTGCAACAACAGTCAACGGTGTAAA
TAGTGTTAAAACGAAAGCACAAGACTTAGATGGTGCAATGCAACGATTAGAGTCAGCAATCGCAAATAAAGATCAAACTA
AAGCGAGCGAAAACTACATTGACGCAGATCCAACTAAGAAAACAGCATTTGATAATGCCATCACACAAGCTGAATCTTAC
TTAAATAAAGATCATGGTACGAATAAAGATAAGCAAGCTGTTGAACAAGCAATTCAAAGTGTAACGTCTACTGAAAATGC
TTTGAACGGTGACGCGAACTTACAATGCGCTAAAACTGAAGCTACACAAGCTATCGATAACTTGACACAATTGAATACAC
CGCAAAAAACAGCATTGAAACAACAAGTGAATGCTGCACAACGCGTATCAGGTGTAACTGATCTGAAAATAGTGCTACA
TCACTTAATAATGCGATGGATCAATTAAAACAAGCAATTGGTGATCATGACACAATTGTAGCTGGTGGTAATTACACTAA
CGCAAGTCCTGATAAACAAGGTGCTTACACTGATGCATATAATGCTGCGAAGAATATCGTAAATGGTTCACCTAATGTGA
TTACAAATGCAGCAGATGTTACTGCGGCAACACAACGTGTCAATAATGCTGAAACAAGTTTAAATGGTGATACAAACTTA
GCAACTGCGAAGCAACAAGCTAAAGATGCATTACGTCAAATGACACATTTATCTGATGCACAAAAACAAAGTATTACTGG
TCAAATTGATAGCGCGACACAAGTAACTGGTGTACAAAGTGTGAAAGACAATGCAACAAATCTTGACAATGCAATGAATC
AACTTCGAAATAGTATTGCGAATAAAGATGAAGTAAAAGCGAGTCAACCATATGTTGATGCAGATACAGATAAACAAAAT
GCATACAATACAGCAGTTACAAGTGCTGAAAATATCATTAATGCAACGAGTCAGCCAACACTTGATCCATCTGCCAGTAAC
ACAAGCAGCTAATCAAGTGAACACTAACAAAACTGCGCTTAATGGTGCGCAAAACTTAGCAAATAAAAAGCAAGAAACAA
CTGCTAACATCAACCGATTAAGTCATTTAAACAATGCTCAAAAGCAAGATTTAAATACACAAGTGACAAATGCACCAAAT
ATTAGCACAGTAAATCAAGTGAAAACTAAAGCTGAACAATTAGATCAAGCAATGGAACGTTTAATCAACGGAATCCAAGA
CAAAGATCAAGTGAAACAAAGTGTTAACTTTACAGATGCAGATCCAGAAAAACAAACAGCATACAACAATGCGGTAACTG
CTGCTGAAAATATTATTAATCAAGCAAATGGTACAAATGCGAACCAATCACAAGTTGAAGCAGCACTTTCAACTGTAACA
ACTACTAAACAAGCGTTGAATGGTGATAGAAAAGTAACAGATGCTAAAAACAATGCAAACCAAACATTATCTACGTTAGA
TAACTTAAACAATGCACAAAAAGGTGCTGTTACTGGAAACATCAATCAAGCGCACACTGTAGCTGAAGTAACGCAAGCCA
TTCAAACCGCTCAGGAACTGAATACAGCGATGGGTAACTTGAAAAATAGCTTGAATGATAAAGACACTACACTTGGCAGT
CAAAACTTTGCAGATGCAGATCCAGAGAAGAAAAATGCATACAATGAAGCGGTTCGTAATGCTGAAAATATTTTAAATAA
ATCTACAGGTACGAACGTGCCTAAAGATCAAGTTGAAGCAGCTATGAATCAAGTGAATACTACAAAAGCAGCGCTTAATG
GTACTCAAAACCTTGAAAAAGCGAAACAACACGCAAATACAGCAATTGACGGTTTAAGCCATTTAACAAATGCACAAAAA
GAGGCATTAAAACAATTGGTACAACAATCGACTACTGTTGCAGAAGCACAAGGTAATGAACAAAAAGCAAACAATGTTGA
TGCAGCAATGGACAAATTACGTCAAAGTATTGCAGATAATGCGACAACAAAACAAAACCAAAATTATACTGATGCAAGTC
CGAATAAAAAGGATGCGTACAATAATGCTGTCACAACTGCACAAGGTATTATTGATCAAACTACAAACCCTTCATTAGAT
CCGACTGTTATCAATCAAGCTGCTGGACAAGTAAGCACGTCTAAAAATGCTTTAAATGGTAATGAAAACTTAGAGGCAGC
GAAGCAACAAGCAACGCAATCTTTAGGTTCATTAGACAACTTAAATAATGCGCAAAAACAAGCTGTTACTAATCAAATTA
ATGGCGCGCATACTGTTGATGAAGCAAATCAAATTAAGCAAAATGCGCAAAACTTAAATACTGCGATGGGTAACTTGAAA
CAAGCGATAGCTGATAAAGATGCTACGAAAGCAACAGTTAACTTCACTGATGCAGATCAAGCAAAACAACAAGCATATAA
CACTGCAGTTACAAATGCTGAAAATATCATTTCAAAAGCTAATGGTGGTAATGCAACACAAACTGAAGTTGAACAAGCAA
TCCAACAAGTAAATGCAGCAAAACAAGCATTAAATGGTAATGCCAACGTTCAACATGCAAAAGACGAAGCAACAGCATTA
ATTAATAACTCTAATGATCTTAACCAAGCACAGAAAGATGCATTAAAACAACAAGTACAAAATGCAACTACTGTAGCTGG
TGTAAACAATGTTAAACAAACGGCGCAAGAGTTAAACAATGCGATGACACAATTAAAACAAGGCATTGCAGATAAAGAAC
AAACAAAAGCTGATGGTAACTTTGTCAATGCAGATTCTGACAAGCAAAATGCATATAATCAAGCAGTAGCGAAAGCTGAA
GCATTAATTAGTGGTACGCCTGATGTTGTCGTTACACCTAGCGAAATTACTGCAGCGTTAAATAAAGTTACGCAAGCTAA
AAATGATTTAAATGGTAATACAAACTTAGCAACGGCGAAACAAAATGTTCAACATGCTATTGATCAATTGCCAAACTTAA
ACCAAGCGCAACGTGATGAATACAGCAAACAAATCACGCAAGCAACACTTGTACCAAACGTCAATGCTATTCAACAAGCG
GCAACAACGCTTAATGACGCGATGACACAATTGAAACAAGGTATTGCGAATAAAGCACAAATTAAAGGTAGCGAGAACTA
TCACGATGCTGATACTGACAAGCAAACAGCATATGATAATGCAGTAACAAAAGCAGAAGAATTGTTAAAACAAACAACAA
ATCCAACAATGGATCCAAATACAATTCAACAAGCATTAACTAAAGTGAATGACACAAATCAAGCACTTAACGGTAATCAA
AAATTAGCTGATGCCAAACAAGATGCTAAGACAACACTTGGTACACTAGATCATTTAAATGATGCTCAAAAACAAGCGCT
AACAACTCAAGTTGAACAAGCACCAGATATTGCAACAGTTAATAATGTTAAGCAAAATGCTCAAAATCTGAATAATGCTA
TGACTAACTTAAACAATGCATTACAAGATAAAACTGAGACATTAAATAGCATTAACTTTACTGATGCAGATCAAGCTAAG
AAAGATGATTATACTAATGCGGTTTCACATGCAGAAGGTATTTATCTAAAGCAAATGGCAGCAATGCAAGTCAAACTGA
AGTGGAACAAGCGATGCAACGTGTGAACGAAGCGAAACAAGCATTGAATGGTAATGACAATGTACAACGTGCAAAAGATG
CAGCGAAACAAGTAATTACAAATGCAAATGATTTAAATCAAGCGCAAAAAGATGCATTAAAACAACAAGTCGATGCTGCG
CAAACTGTTGCAAATGTAAACACGATTAAGCAAACAGCACAAGATTTAAATCAAGCAATGACACAATTGAAACAAGGTAT
TGCAGATAAAGACCAAACTAAAGCAAATGGTAACTTTGTCAATGCTGATACTGATAAGCAAAATGCATATAACAATGCGG
TAGCGCATGCTGAACAAATCATTAGTGGTACACCAAATGCAAACGTGGATCCACAACAAGTGGCTCAAGCGTTACAACGA
GTGAATCAAGCTAAGGGTGATTTAAACGGTAACCACAACTTACAAGTTGCTAAAGACAATGCAAATACAGCCATTGATCA
GTTACCAAACTTAAATCAACCACAAAAAACAGCATTAAAAGACCAAGTGTCGCATGCAGAACTTGTTACAGGTGTTAATG
CTATTAAGCAAATGCTGATGCGTTAAATAATGCAATGGGTACGTTGAACAACAAATTCAAGCGAATAGTCAAGTACCA
CAATCAGTTGACTTTACACAAGCGGATCAAGACAAACAACAAGCTTATAACAATGCAGCTAACCAAGCGCAACAAATCGC
AAATGGCACACCAACACCTGTATTGGCGCCTGATACAGTAACAAAAGCAGTTACAACTATGAATCAAGCGAAAGATGCAT
TAAACGGTGATGAAAAATTAGCGCAAGCGAAACAAGATGCTTTAGCAAATCTTGATACGTTACGTGACTTAAATCAACCA
CAACGTGATGCATTACGAAACCAAATCAATCAAGCACAAGCTTTAGCTACAGTTGAACAAACTAAACAAATGCACAAAA
TGTGAATACAGCAATGGGTAACTTGAAACAAGGTATTGCAAATAAAGATACTGTGAAGCAAGTGAGAACTACCACGATG
CTGATGTCGATAAGCAAACAGCATATACAAATGCAGTGTCTCAAGCGGAAGGTATTATCAATCAAACGACAAATCCAACG

FIGURE 2 cont.
```
CTTAACCCAGATGACATTACTCGTGCATTAACTCAAGTGACTGATGCTAAAAATAGCTTAAACGGTGAAGCTAAATTAGC
CACTGAAAAGCAAAATGCTAAAGATGCCGTAAGTGGAATGACGCATTTAAACGATGCTCAAAAACAAGCATTAAAAGGTC
AAATCGATCAATCGCCTGAAATTGCTACAGTGAACCAAGTTAAACAAACAGCAACGAGCCTAGATCAAGCAATGGATCAA
TTATCACAAGCTATTAATGATAAAGATCAAATATTAGCGGACGGTAATTACTTAAATGCAGATCCTGACAAACAAAATGC
GTATAAACAGGCAGTAGCAAAAGCTGAAGCATTATTGAATAAACAAAGTGGTACTAATGAAGTACAAGCACAAGTTGAAA
GCATCACTAATGAAGTGAACGCAGCGAAACAAGCATTAAATGGTAATGACAATTTGGCAAATGCAAAACAACAAGCAAAA
CAACAATTGGCGAACTTAACACACTTAAATGATGCACAAAAACAATCATTTGAAAGTCAAATTACACAAGCGCCACTTGT
TACAGATGTCACTACGATTAATCAAAAAGCACAAACGTTAGATCATGCGATGGAATTATTAAGAAATAGTGTTGCGGATA
ATCAAACGACATTAGCGTCTGAAGATTATCATGATGCAACTGCGCAAAGACAAAATGACTATAACAAAGCTGTAACAGCT
GCTAATAATATCATTAATCAAACTACATCGCCTACGATGAATCCAGATGATGTTAATGGTGCAACGACACAAGTGAATAA
TACGAAAGTTGCATTAGATGGTGATGAAAACCTTGCAGCAGCTAAACAACAAGCAAACAACAGACTTGATCAATTAGATC
ATTTGAATAATGCGCAAAAGCAACAGTTACAATCACAAATTACGCAATCATCTGATATTGCTGCAGTTAATGGTCACAAA
CAAACAGCAGAATCTTTAAATACTGCGATGGGTAACTTAATTAATGCGATTGCAGATCATCAAGCCGTTGAACAACGTGG
TAACTTCATCAATGCTGATACTGATAAACAAACTGCTTATAATACAGCGGTAAATGAAGCAGCAGCAATGATTAACAAAC
AAACTGGTCAAAATGCGAACCAAACAGAAGTAGAACAAGCTATTACTAAAGTTCAAACAACACTTCAAGCGTTAAATGGA
GATCATAATTTACAAGTTGCTAAAACAAATGCGACGCAAGCAATTGATGTTTTAACAAGCTTAAATGATCCTCAAAAAAC
AGCATTAAAAGACCAAGTTACAGCTGCAACTTTAGTAACTGCAGTTCATCAAATTGAACAAAATGCGAATACGCTTAACC
AAGCAATGCATGGTTTAAGACAGAGCATTCAAGATAACGCAGCAACTAAAGCAAATAGCAAATATATCAACGAAGATCAA
CCAGAGCAACAAAACTATGATCAAGCTGTTCAAGCCGCAAATAATATTATCAATGAACAAACTGCAACATTAGATAATAA
TGCGATTAATCAAGTAGCGGCAACTGTGAATACAACGAAAGCAGCATTACATGGTGATGTGAAATTACAAAATGATAAAG
ATCATGCTAAACAAACAGGTTAGCCAATTAGCACATCTAAACAATGCACAAAAACATATGGAAGATACGTTAATTGATAGT
GAAACAACTAGAACAGCAGTTAAGCAAGATTTGACTGAAGTACAAGCATTAGATCAACTTATGGATGCATTACAACAAAG
TATTGCTGACAAAGATGCAACACGTGCGAGCAGTGCATATGTCAATGCAGAACCGAATAAAAAACAAGCCTATGATGAAG
CAGTTCAAAATGCTGAGTCTATCATTGCAGGATTAAATAATCCAACTATCAATAAAGGTAATGTATCAAGTGCGACTCAA
GCAGTAATATCATCTAAAAATGCATTAGATGGTGTTGAACGATTAGCTCAAGATAAGCAAACTGCTGGAAATTCTCTAAA
TCATTTAGATCAATTAACACCAGCTCAACAACAAGCGCTAGAAAATCAAATTAATAATGCAACAACTTGTGATAAAGTGG
CTGAAATCATTGCACAAGCGCAAGCATTAAATGAAGCGATGAAAGCATTAAAAGAAAGTATTAAGGATCAACCACAAACT
GAAGCAAGTAGTAAATTTATTAACGAGGATCAAGCGCAAAAAGATGCATATACGCAAGCAGTACAACACGCGAAAGATTT
GATTAACAAAACAACTGATCCTACATTAGCTAAATCAATCATTGATCAAGCGACACAGGCAGTGACTGATGCTAAAAACA
ATTTACATGGTGATCAAAAACTAGCTCAAGATAAGCAACGTGCAACAGAAACGTTAAATAACTTGTCTAACTTGAATACA
CCACAACGTCAAGCACTTGAAAATCAAATCAATAATGCAGCAACTCGTGGTGAAGTAGCACAAAAATTAACTGAAGCACA
AGCACTTAACCAAGCAATGGAAGCTTTACGTAATAGCATTCAAGATCAACAACAAACAGAATCTGGTAGCAAGTTTATTA
ATGAAGATAAACCGCAAAAAGATGCTTACCAAGCAGCAGTTCAAAATGCAAAAGATTTAATTAACCAAACAGGTAATCCA
ACGCTTGATAAAGCACAAGTTGAACAATTGACACATGCTTTTAAACAAGCTAAAGATAACCTACACGGTGATCAAAAACT
TGCAGACGATAAACAACATGCGGTTACTGATTTAAATCAATTAAATGGTTTGAATAATCCGCAACGTCAAGCACTTGAAA
GCCAAATAAACAACGCAGCAACTCGTGGCGAAGTAGCGCAAAAATTAGCTGAAGCAAAAGCGCTTGATCAAGCAATGCAA
GCATTACGAAATAGTATTCAAGATCAACAACAAACGGAAGCGGGTAGCAAGTTTATCAATGAAGATAAACCGCAAAAAGA
TGCTTACCAAGCAGCAGTTCAAAATGCAAAAGATTTAATTAACCAAACAGGTAATCCAACACTCGACAAATCACAAGTAG
AACAATTAACACAAGCAGTAACAACTGCAAAAGATAATCTACATGGTGATCAAAAACTTGCTCGTGATCAACAACAAGCA
GTAACAACTGTAAATGCATTGCCAAACTTAAATCATGCACAACAACAAACATTAACTGATGCTATAAATGCAGCGCCTAC
AAGAACAGAGGTTGCACAACATGTTCAAACTGCTACTGAACTTGATCACGCGATGGAAACATTGAAAAATAAAGTTGATC
AAGTGAATACAGATAAGGCTCAACCAAATTACACTGAAGCGTCAACTGATAAAAAGAAGCAGTAGATCAAGCGTTACAA
GCTGCACAAAGCATTACAGATCCAACTAATGGTTCAAATGCGAATAAAGACGCTGTAGAACAAGCATTAACTAAGCTTCA
AGAAAAGTGAATGAGTTAAATGGTAATGAGAGAGTCGCTGAAGCTAAAACACAAGCGAAACAAACTATTGACCAATTAA
CACATTTAAATGCTGATCAAATTGCAACTGCTAAACAAAATATTGATCAAGCGACGAAACTTCAACCAATCGCTGAATTA
GTAGATCAAGCAACGCAATTGAACCAATCAATGGATCAATTACAACAAGCAGTTAATGAACATGCTAACGTTGAGCAAAC
TATAGATTACACACAAGCAGATTCAGATAAGCAAAAGGCTTATAAACAAGCGATTGCTGATGCTGAAAATGTATTGAAAC
AAAATGCGAATAAGCAACAAGTGGATCAAGCACTTCAAAATATTTTAAATGCAAAACAAGCATTAAATGGTGATGAACGT
GTAGCACTTGCTAAAACAAATGGTAAACATGACATCGACCAATTGAATGCATTAAACAATGCTCAACAAGATGGATTTAA
AGGTCGCATCGATCAATCAAACGATTTAAATCAAATCCAACAAATTGTAGATGAGGCTAAGGCACTTAATCGTGCAATGG
ATCAATTGTCACAAGAAATCACTGGCAATGAAGGACGCACGAAAGGTAGCACGAACTATGTCAATGCAGATACACAAGTC
AAACAAGTATATGATGAAGCGGTTGATAAAGCGAAACAAGCACTTGATAAATCGTCTGGGCAAAACTTAACTGCAGAACA
AGTTATCAAATTAAATGATGCAGTCACTCGACGTAAGAAAGCATTAAATGGTGAAGAAAGACTTAATAATCGTAAAGCTG
AAGCATTACAAAGATTGGATCAATTAACACATCTAAACAATGCTCAAAGACAATTAGCAATCCAACAAATTAATAATGCT
GAAACGCTAAATAAAGCATCTCGAGCAATTAATAGAGCAACTAAATTAGATAATGCAATGGGTGCAGTACAACAATATAT
TGACGAACAGCACCTTGGTGTTATCAGCAGCACAAATTACATCAATGCAGATGACAATTTGAAAGCAAATTATGATAATG
CAATTGCGAATGCAGCACATGAGTTAGATAAAGTGCAAGGTAATGCAATTGCAAAAGCTGAAGCAGAGCAATTGAAACAA
AATATTATCGATGCTCAAAATGCATTAAATGGAGACCAAAACCTTGCAAATGCCAAAGATAAAGCAAATGCGTTTGTTAA
TTCGTTAAATGGATTAAATCAACAGCAACAAGATCTTGCACATAAAGCAATTAACAATGCCGATACTGTATCAGATGTAA
CAGATATTGTTAATAATCAAATTGACTTAAATGATGCAATGGAAACATTGAAACATTTAGTTGACAATGAAATTCCAAAT
```

FIGURE 2 cont.
```
GCAGAGCAAACTGTCAATTACCAAAACGCTGACGATAATGCTAAAACAAACTTCGATGATGCCAAACGTCTAGCAAATAC
ATTGCTAAATAGTGATAACACAAATGTGAATGATATCAATGGCGCAATCCAAGCAGTCAATGATGCAATCCATAATCTTA
ATGGTGATCAACGACTACAAGATGCTAAAGACAAGGCAATTCAATCAATTAATCAAGCTTTAGCTAATAAGCTAAAAGAA
ATCGAAGCTTCAAATGCGACGGATCAAGACAAGCTTATTGCGAAAAATAAAGCAGAAGAATTGGCAAACAGCATCATCAA
CAACATTAATAAAGCAACAAGTAATCAGGCTGTATCTCAAGTTCAAACAGCAGGCAACCACGCGATTGAACAAGTGCATG
CTAATGAAATACCAAAAGCAAAAATTGATGCCAATAAAGACGTTGATAAGCAAGTTCAAGCATTAATTGACGAAATTGAT
CGAAATCCAAATCTAACAGATAAGGAAAAACAAGCACTTAAAGATCGTATTAATCAAATACTTCAACAAGGTCATAACGA
CATTAACAATGCGCTGACTAAAGAAGAAATTGAACAAGCTAAAGCACAACTTGCGCAAGCATTACAAGACATCAAAGATT
TAGTGAAAGCTAAAGAAGATGCGAAACAAGATGTTGATAAACAAGTTCAAGCATTAATTGACGAAATCGATCAAAATCCA
AATCTAACAGATAAGGAAAAACAAGCACTTAAAGATCGTATTAATCAAATACTTCAACAAGGTCATAACGGCATTAACAA
TGCGATGACTAAAGAAGAAATTGAACAAGCCAAAGCACAACTTGCACAAGCATTAAAAGAAATTAAAGATTTAGTGAAAG
CTAAAGAAAATGCGAAACAAGATGTTGATAAACAAGTTCAAGCATTAATTGACGAAATCGATCAAAATCCAAATCTAACA
GATAAGGAAAAACAAGCGCTTAAAGATCGAATCAATCAAATACTGCAACAAGGTCATAACGACATTAACAATGCGATGAC
TAAAGAAGAAATTGAACAAGCCAAAGCACAACTTGCACAAGCATTACAAGACATCAAAGATTTAGTGAAAGCTAAAGAAG
ATGCGAAAAATGCAATAAAAGCCTTAGCTAATGCGAAGCGTGATCAAATCAATTCAAATCCAGATTTAACACCTGAGCAA
AAAGCAAAAGCGCTCAAAGAAATTGACGAAGCTGAAAAACGAGCACTACAAAACGTTGAGAATGCTCAAACTATAGATCA
ATTAAATCGAGGATTAAACTTAGGTTTAGATGACATTAGAAATACACATGTATGGGAGGTTGATGAACAACCTGCTGTAA
ATGAAATTTTTGAAGCAACACCTGAGCAAATCCTAGTTAATGGTGAACTCATTGTACATCGTGATGACATCATTACAGAA
CAAGATATTCTTGCACACATAAACTTAATTGATCAGCTTTCAGCAGAAGTTATTGATACACCATCAACTGCAACGATTTC
TGATAGCTTAACAGCAAAAGTTGAAGTTACATTGCTTGATGGATCAAAAGTGATTGTTAATGTTCCTGTAAAAGTTGTAG
AAAAAGAATTGTCAGTAGTCAAACAACAGGCAATTGAATCAATCGAAAATGCGGCACAACAAAAGATTGATGAAATCAAT
AATAGTGTGACATTAACACTGGAACAAAAAGAAGCTGCAATTGCAGAAGTTAATAAGCTTAAACAACAAGCAATTGATCA
TGTTAACAATGCACCTGATGTTCATTCAGTTGAAGAAATTCAACAACAAGAACAAGCGTATATTGAACAATTTAATCCAG
AACAATTTACGATTGAACAAGCAAATCAAATGCAATTAAATCGATTGAAGATGCAATTCAACATATGATTGATGAAATC
AAAGCTCGTACTGATCTAACAGATAAAGAGAAGCAAGAAGCTATTGCTAAGTTAAATCAATTAAAAGAACAAGCAATTCA
AGCGATTCAACGTGCGCAAAGCATCAGTGAAATAACTGAGCAATTGGAACAATTTAAAGCTCAAATGAAAGCAGCTAATC
CAACAGCAAAAGAACTAGCTAAACGCAAGCAAGAAGCTATTAGTAGAATTAAAGACTTTTCAAATGAAAAATAAATAGT
ATTCGAAATAGTGAAATTGGCACAGCTGATGAAAACAAGCAGCAATGAATCAAATTAACGAAATTGTGCTTGAAACAAT
TAGAGATATTAATAATGCGCATACATTACAGCAAGTTGAGGCTGCATTGAACAATGGTATTGCTCGAATTTCAGCAGTAC
AAATTGTAATATCTGATCGTGCTAAACAATCGTCAAGTACTGGAAATGAATCTAATAGCCATTTAACAATTGGTTATGGA
ACTGCAAATCATCCATTTAACAGTTCGACTATTGGACATAAAAAGAAACTTGATGAAGATGATGACATTGATCCACTTCA
TATGCGTCACTTTAGTAATAATTTCGGTAATGTTATTAAAAACGCTATTGGTGTGGTGGGTATCTCTGGCTTACTAGCTA
GTTTCTGGTTCTTCATTGCCAAACGTCGTCGTAAAGAAGATGAAGAGGAAGAATTAGAAATAAGAGATAATAATAAAGAT
TCAATAAAAGAGACTTTAGACGATACAAAACATTTACCACTTTTATTTGCGAAACGTCGCAGAAAAGAAGATGAAGAAGA
TGTTACTGTTGAAGAAAAAGATTCGCTAAATAATGGCGAGTCACTCGATAAAGTTAAACATACGCCGTTCTTCTTACCAA
AACGTCGTCGTAAAGAAGATGAAGAAGATGTGAAGTTACAAATGAAAACACAGATGAAAAAGTGTTGAAAGATAACGAA
CATTCACCACTCTTATTCGCAAAACGACGCAAAGATAAAGAGGAAGATGTTGAAACAACAACTAGTATTGAATCTAAAGA
TGAGGACGTTCCTTTATTATTGGCTAAAAAGAAAAATCAAAAAGATAACCAATCCAAAGACAAAAAGTCAGCATCAAAAA
ATACTTCTAAAAAGGTAGCAGCTAAAAAGAAGAAAAAGAAATCTAAGAAAAATAAAAAA
```

SEQ ID NO:47 polynucleotide sequence
```
TTGAATAATCGTGATAAATTACAAAAATTTAGTATTCGAAAATACGCAATTGGAACATTTTCTACTGTGATTGCAACACT
TGTGTTCATGGGTATCAATACAAACCATGCAAGTGCCGACGAGTTGAATCAAATCAAAAGTTAATTAAACAATTAAATC
AAACAGATGATGATGATTCGAATACGCATAGTCAAGAAATCGAAAATAACAAACAAAATTCTAGTGGGCAGACTGAATCA
TTACGTTCATCAACTAGTCAAAATCAAGCAAATGCACGACTGTCGGATCAATTCAAAGACACTAATGAAACATCGCAACA
ATTACCTACAAATGTTTCGGATGATAGTATCAATCAATCGCATAGTGAAGCAAATATGAATAACGAACCATTGAAAGTTG
ATAATAGTACTATGCAAGCACATAGTAAAATAGTAAGCGATAGCGATGGGAATGCTTCTGAAAATAAACATCATAAACTA
ACAGAAAATGTACTTGCAGAAAGCCGAGCAAGTAAAAATGACAAAGAGAAAGAGAATCTACAAGAGAAAGATAAATCGCA
GCAAGTACATCCACCATTAGATAAAAATGCATTACAAGCTTTTTTTGACGCATCATATCACAATTACAGAATGATTGATA
GAGATCGTGCGGATGCAACAGAATATCAAAAAGTCAAATCTACTTTTGACTACGTCAATGACTTACTAGGTAATAATCAA
AATATTCCTTCAGAACAGCTTGTTTCGGCATATCAACAATTAGAGAAAGCATTAGAACTTGCACGTACGTTACCACAACA
ATCTACTACAGAAAAACGTGGTAGAAGAAGTACGAGAAGTGTTGTTGAGAATCGTTCATCAAGAAGCGATTACTTAGATG
CTAGAACTGAATATTATGTTTCAAAGACGATGATGATTCTGGTTTCCCTCCTGGTACTTTCTTCCATGCTTCAAATAGA
AGATGGCCTTATAATTTACCAAGATCTAGGAACATCTTACGTGCTTCTGATGTACAAGGTAATGCTTATATCACTACAAA
ACGACTTAAAGATGGATATCAATGGGATATTTATTTAATAGTAATCATAAAGGGCATGAATATATGTACTATTGGTTTG
GACTTCCAAGTGATCAAACACCAACTGGTCCAGTAACTTTCACTATTATCAACCGTGATGGTTCAAGTACATCTACTGGT
GGCGTTGGATTTGGATCAGGTGCACCACTACCTCAATTTTGGAGATCAGCAGGTGCTATTAATTCTAGCGTAGCGAATGA
TTTTAAACATGGCTCCGCTACAAATTATGCATTTTATGATGGTGTTAATAATTTTTCTGACTTTGCTAGAGGGGGAGAAT
TATACTTCGACAGAGAAGGCGCTACACAAACTAATAAATATTATGGCGATGAAAACTTCGCATTGCTAAATAGTGAGAAA
```

FIGURE 2 cont.
CCAGATCAAATAAGAGGATTAGATACAATATATAGTTTTAAAGGTAGTGGTGATGTAAGTTATCGTATTTCATTTAAAAC
TCAAGGAGCTCCAACTGCAAGATTGTATTATGCTGCTGGCGCGCGTTCTGGTGAATATAAACAAGCAACGAACTATAACC
AACTCTATGTCGAACCTTATAAGAATTATCGAAATCGAGTACAGTCAAATGTCCAAGTTAAAAATCGTACACTTCATTTA
AAAAGAACAATCAGACAATTCGATCCTACATTACAGAGAACTACTGATGTTCCTATTTTGGATAGTGACGGTTCCGGAAG
TATTGATTCGGTATACGACCCATTAAGTTATGTAAAGAATGTGACTGGTACAGTCCTAGGTATTTATCCATCTTATCTTC
CTTATAATCAGGAAAGATGGCAGGGAGCTAATGCAATGAATGCCTATCAAATTGAAGAACTTTTTTCACAAGAAAATCTT
CAAAATGCAGCACGTTCAGGCCGTCCAATTCAATTTCTTGTAGGTTTTGATGTTGAAGATAGCCATCATAACCCTGAAAC
TCTTTTACCAGTAAATTTATATGTAAAACCTGAGTTAAAACATACAATTGAGTTATATCACGATAATGAAAAACAAGATA
GAAAGGAATTTTCAGTATCGAAA

SEQ ID NO:48 polynucleotide sequence
ATGAGTGGAACGCTTCATAACACTGTAGGATCAGGAATATTACCTTATCAACAAGAGATACGTATCAAACTTACTAGTAA
TGAACCAATTAAAGATAGTGAATGGTCTATTACAGGATATCCTAACACGCTTACATTACAAAACGCTGTGGGTAGAACAA
ATAATGCTACTGAAAAAAACTTAGCTCTTGTTGGTCATATTGATCCAGGAAATTATTTCATCACTGTTAAGTTTGGTGAT
AAAGTAGAACAATTTGAAATTAGATCAAAACCAACTCCACCAAGAATCATTACAACTGCTAATGAATTACGTGGAAATCC
TAACCATAAGCCTGAAATAAGAGTAACAGATATACCAAATGATACTACTGCTAAAATCAAACTTGTGATGGGCGGAACCG
ATGGCGATCATGATCCAGAAATAAATCCATATACTGTCCCTGAAAACTACACAGTAGTTGCAGAAGCATACCATGATAAT
GATCCAAGTAAAAATGGGGTCTTAACATTCCGTTCATCAGACTACCTTAAAGATCTACCATTAAGCGGTGAATTAAAGGC
AATTGTTTATTACAATCAATATGTACAATCAAACTTTAGTAAAAGCGTTCCGTTTAGTAGCGATACAACACCACCTACAA
TTAATGAACCGGCAGGACTAGTTCATAAGTATTACAGGGGAGATCATGTAGAAATTACTCTTCCAGTCACTGATAATACT
GGCGGTTCAGGTTTAAGAGATGTAAACGTCAATTTACCTCAAGGTTGGACAAAAACCTTTACAATCAATCCTAATAATAA
TACTGAGGGTACGCTTAAGTTAATTGGTAATATACCTAGTAATGAAGCATATAATACGACATATCATTTCAATATTACTG
CAACCGATAATTCTGGAAATACAACAAATCCAGCTAAAACCTTTATTTTAAATGTTGGTAAGTTGCTGATGATTTAAAT
CCAGTCGGATTATCTAGAGATCAACTACAATTAGTGACAGACCCTTCTTCATTATCTAATTCCGAACGAGAAGAGGTAAA
AAGAAAAATAAGTGAAGCAAATGCTAATATAAGATCATATTTATTACAAAATAACCCAATACTCGCTGGAGTAAACGGCG
ATGTTACATTTTATTATAGAGATGGTTCTGTAGATGTTATTGATGCTGAAAATGTAATCACATATGAGCCCGAAAGAAAA
TCCATTTTCAGTGAAAATGGTAATACAAATAAAAAAGAAGCAGTAATCACTATTGCTAGAGGACAAAACTATACCATTGG
TCCAAACTTAAGAAAATATTTCTCATTAAGTAATGGTTCGGATTTACCTAATAGAGATTTCACCTCTATATCAGCTATTG
GATCTTTACCTTCATCGAGTGAAATTAGTCGACTCAATATTGGAAATTATAACTATAGAGTTAATGCTAAAAATGCTTAT
CATAAGACTCAACAAGAACTTAATTTAAAACTTAAAATAGTAGAGGTTAATGCACCTACTGGTAATAATCGTGTATATAG
AGTTAGTACTTATAATTTAACTAATGATGAAATCAATAAAATCAAACAAGCATTTAAAGCAGCTAATTCTGGACTTAATT
TAAACGATAACGATATCACTGTTTCGAATAACTTTGACCATAGAAATGTTAGTAGTGTGACAGTAACTATACGTAAGGGC
GATTTGATAAAAGAGTTTTCATCAAATCTCAATAATATGAATTTCTTACGTTGGGTTAATATAAGGGATGATTATACCAT
TTCGTGGACTTCTAGTAAGATTCAAGGTAGAAATACAGATGGTGGATTAGAATGGTCACCAGATCATAAATCACTTATTT
ATAAATATGATGCAACATTAGGTAGACAAATAAATACTAATGACGTGTTAACTTACTTCAAGCAACAGCTAAAAACTCA
AATTTACGTTCAAATATCAATAGTAATGAAAAACAGTTAGCAGAACGAGGGTCTAATGGGTATTCTAAATCTATAATTAG
AGATGATGGCGAGAAATCTTATTTACTTAACTCAAATCCTATTCAAGTATTAGACTTAGTAGAACCAGATAATGGTTACG
GTGGACGTCAAGTCAGTCATTCTAACGTTATATATAATGAAAAAAATTCTTCTATCGTAAATGGTCAAGTTCCAGAAGCT
AATGGGGCATCCGCTTTTAATATTGATAAAGTTGTTAAAGCTAATGCGGCAAATAATGGTATTATGGGTGTTATCTATAA
GGCACAATTATACTTAGCACCATACAGTCCAAAAGGTTACATTGAAAAATTAGGCCAAAATTTAAGCAATACCAATAACG
TGATTAATGTTTATTTTGTGCCTTCTGATAAAGTAAATCCTAGTATAACTGTAGGTAATTACGACCATCATACGGTATAT
TCTGGTGAAACATTTAAAAATACTATCAATGTAAATGATAATTATGGATTAAATACAGTAGCTTCTACAAGTGATAGTGC
AATTACTATGACCAGAAACAACAACGAGTTAGTAGGTCAGGCTCCTAATGTTACTAATAGCATAAATAAAATTGTAAAAG
TTAAAGCCACAGATAAAAGTGGAAATGAAAGTATTGTTTCTTTCACAGTAAATATAAAACCATTAAACGAGAAATATAGA
ATAACAACTTCATCAAGTAATCAAACACCAGTGAGAATTAGTAATATTCAAAACAATGCTAACCTTTCAATTGAAGATCA
AAATAGAGTAAAATCTTCACTCAGCATGACTAAAATTTTAGGTACAAGAAATTATGTCAATGAGTCAAATAATGACGTTC
GTAGTCAAGTTGTAAGTAAAGTAAATAGAAGTGGGAACAATGCTACAGTTAATGTTACAACTACATTTTCTGATGGTACA
ACTAATACAATAACCGTTCCAGTTAAACATGTGTTATTAGAAGTTGTACCTACTACTAGAACAACAGTAAGAGGACAACA
ATTTCCAACCGGCAAAGGAACTTCCCCAAATGATTTCTTTAGTTTAAGAACGGGAGGTCCAGTTGATGCGAGAATAGTTT
GGGTTAATAATCAGGGACCCGATATAAATAGTAATCAAATTGGTAGAGATTTAACATTACACGCTGAAATATTCTTTGAT
GGTGAAACAACACCAATTAGAAAAGATACTACTTACAAACTTAGTCAATCTATTCCAAAGCAAATATATGAAACAACTAT
CAATGGTCGATTTAATTCATCAGGTGATGCATATCCAGGAAATTTTGTTCAAGCAGTAAATCAATATTGGCCAGAACATA
TGGACTTCAGATGGGCCCAAGGATCAGGCACACCAAGTTCTCGTAATGCAGGTTCATTTACTAAAACAGTTACGGTAGTT
TATCAAAACGGCCAAACTGAAAACGTTAATGTACTATTCAAAGTCAAACCAATAAACCTGTTATTGATAGTAATAGTGT
GATTTCAAAAGGACAATTAAATGGTCAACAAATTTTAGTTCGAAATGTTCCACAAAATGCACAAGTCACTCTATATCAAT
CAAATGGAACTGTTATTCCTAATACAAATACAACATAGATTCTAATGGTATAGCTACTGTAACAATTCAAGGCACTCTA
CCAACCGGAAATATTACTGCTAAAACCTCAATGACAAATAATGTAACGTACACTAAACAAAATAGTAGTGGAATTGCTTC
AAATACAACTGAAGATATAAGTGTTTTTTCAGAAAACAGTGATCAAGTAAATGTTACCGCTGGCATGCAAGCTAAAAATG
ATGGTATTAAAATAATTAAAGGTACAAACTATAATTTTAATGACTTCAATAGTTTCATAAGTAATATACCAGCCCATTCT

FIGURE 2 cont.
```
ACTCTTACATGGAACGAGGAGCCTAATAGTTGGAAAAACAACATCGGTACTACAACAAAAACTGTTACAGTTACTCTACC
TAATCATCAAGGTACGAGAACTGTAGATATTCCAATAACAATCTATCCAACAGTTACAGCTAAGAATCCAGTAAGAGATC
AAAAAGGACGAAACTTAACCAATGGTACTGACGTTTATAATTATATTATTTTTGAAAATAATAACCGTCTTGGAGGAACA
GCTTCTTGGAAAGACAATCGTCAACCTGATAAAAACATAGCCGGTGTACAAAATTTAATTGCACTTGTTAATTATCCTGG
CATATCTACACCATTAGAAGTTCCTGTTAAAGTGTGGGTATATAATTTTGATTTCACTCAACCTATCTACAAAATTCAAG
TAGGAGATACATTCCCTAAAGGAACATGGGCAGGCTATTACAAACATCTTGAAAATGGAGAGGGATTACCAATAGATGGT
TGGAAATTTTATTGGAACCAGCAAAGTACAGGAACTACTAGTGATCAATGGCAATCATTAGCATATACTAGAACTCCTTT
TGTTAAAACTGGTACTTATGATGTCGTTAATCCTAGCAACTGGGGTGTTTGGCAAACATCACAATCAGCTAAATTTATAG
TTACAAATGCTAAACCTAATCAACCAACCATAACTCAGTCTAAAACTGGTGATGTAACAGTAACACCTGGTGCTGTGCGT
AATATACTAATAAGTGGGACAAATGATTATATCCAAGCATCTGCAGATAAGATTGTTATTAATAAAAATGGAAATAAATT
AACTACATTTGTTAAAAATAATGATGGTCGTTGGACTGTTGAAACTGGGTCACCTGACATAAATGGTATCGGACCAACAA
ATAACGGAACTGCTATATCTTTAAGTCGATTAGCAGTTAGACCTGGGGATTCAATAGAAGCAATAGCGACTGAAGGTTCC
GGAGAAACTATAAGTACTTCAGCAACTAGTGAAATTTATATTGTCAAAGCTCCACAACCTGAACAAGTAGCAACTCATAC
TTATGATAATGGAACATTCGATATATTACCTGACAATTCACGTAATTCTTTAAATCCAACTGAACGTGTCGAAATTAATT
ACACTGAAAAATTAAATGGCAATGAAACACAAAAATCATTCACTATTACTAAAAATAACAACGGCAAATGGACGATAAAT
AATAAACCAAATTATGTCGAGTTCAATCAGGATAATGGTAAAGTTGTATTTTCGGCCAATACAATTAAACCTAATTCTCA
AATTACAATAACTCCTAAAGCAGGTCAGGGTAACACTGAAAACACAAATCCTACTGTAATTCAAGCACCTGCGCAACATA
CTTTAACAATCAATGAAATTGTTAAAGAACAGGGTCAAAATGTGACTAATGATGATATTAATAATGCGGTTCAAGTGCCA
AATAAAAATAGAGTTGCGATTAAACAAGGAAACGCTCTTCCAACAAATTTAGCTGGTGGTAGTACATCACATATTCCAGT
AGTTATTTATTACAGTGATGGAAGTTCTGAAGAAGCTACTGAGACTGTTAGAACTAAAGTTAATAAAACCGAATTAATCA
ATGCTCGTCGTCGACTAGATGAAGAAATTAGTAAAGAGAACAAAACACCATCAAGTATCAGAAACTTTGATCAAGCTATG
AATCGTGCTCAATCACAAATTAATACAGCTAAAAGTGATGCTGACCAAGTTATAGGCACAGAATTTGCAACACCTCAACA
AGTAAATTCAGCTTTATCTAAAGTTCAAGCGGCACAAAATAAAATAAATGAAGCTAAAGCATTATTACAAAACAAGGCTG
ATAATAGTCAACTTGTGAGAGCAAAAGAACAATTACAACAATCGATTCAACCAGCCGCTTCAACTGATGGTATGACTCAA
GATAGCACAAGGAACTACAACAATAAACGCCAAGCAGCTGAACAAGCAATACAACATGCAAATAGCGTTATAAATAATGG
AGATGCAACATCCCAACAAATTAATGATGCTAAAAACACAGTTGAACAGGCACAGAGAGATTATGTTGAAGCTAAAAGCA
ACTTACGTGCTGATAAGTCACAGTTACAAAGCGCTTATGATACGTTAAATAGAGATGTTTTAACAAATGATAAAAAGCCA
GCATCTGTAAGACGCTATAATGAAGCCATTTCAAATATTAGAAAAGAATTAGATACAGCTAAAGCGGATGCAAGTAGTAC
TTTGCGAAACACCAATCCTTCCGTTGAACAAGTTAGAGACGCTTTAAATAAAATAAATACTGTTCAACCTAAAGTGAATC
AAGCAATTGCTTTACTTCAACCAAAAGAAAATAATTCAGAACTTGTACAAGCTAAAAAACGTTTACAAGACGCTGTAAAT
GACATACCTCAAACACAAGGTATGACACAACAAACAATTAATAATTATAATGACAAACAACGTGAAGCTGAAAGAGCACT
TACATCTGCACAAAGAGTGATTGATAATGGGGATGCTACAACTCAAGAAATTACTTCTGAAAAATCTAAAGTAGAGCAAG
CAATGCAAGCTTTAACTAATGCTAAAAGTAATCTGAGAGCTGATAAGAATGAGTTACAGACTGCATATAACAAATTAATT
GAGAACGTATCTACCAATGGTAAAAAACCGGCGAGTATACGTCAATACGAAACAGCCAAAGCCAGAATACAAAATCAAAT
TAATGATGCTAAAAATGAAGCGGAGCGAATTTTAGGTAATGATAATCCACAAGTATCACAAGTAACTCAAGCATTGAACA
AAATCAAAGCTATTCAACCAAAATTAACAGAAGCTATCAACATGCTTCAAAACAAAGAAAATAATACAGAATTAGTCAAT
GCTAAAAACAGACTTGAAAATGCAGTAAATGATACAGATCCAACACACGGTATGACTCAAGAAACAATTAATAATTACAA
CGCTAAAAAGCGAGAAGCTCAAAATGAAATACAAAAAGCGAACATGATTATTAATAATGGAGATGCTACTGCTCAAGATA
TTTCTTCTGAAAAATCTAAAGTAGAGCAAGTATTACAAGCATTACAAAATGCTAAGAATGACTTAAGAGCTGATAAAAGA
GAATTACAGACTGCATACAATAAACTTATACAAAATGTTAATACCAATGGTAAAAAACCATCTAGTATTCAAAACTATAA
GTCTGCAAGACGAAATATCGAAAACCAATATAATACCGCTAAAAATGAAGCACATAATGTTCTTGAAAATACAAACCCTA
CTGTAAATGCAGTAGAAGATGCTTTACGTAAGATAAATGCAATTCAACCAGAGGTTACAAAAGCTATTAATATACTTCAA
GATAAAGAAGATAATAGCGAACTTGTTAGAGCAAAAGAAAAATTAGATCAAGCGATTAATAGTCAACCATCACTAAATGG
TATGACTCAAGAATCTATTAATAATTACACAACAAAACGTAGAGAAGCACAAAATATAGCAAGTTCTGCTGACACTATTA
TTAATAATGGGGATGCATCTATTGAACAAATAACAGAAAATAAAATTCGAGTTGAAGAGGCAACTAATGCACTTAACGAA
GCAAAACAACATTTAACGGCAGATACAACTTCTTTAAAAACTGAAGTACGGAAATTAAGTAGGAGAGGCGACACAAACAA
CAAAAAGCCTAGCAGTGTTAGTGCTTATAACAATACTATTCATTCGCTACAATCTGAAATTACACAGACTGAAAATAGAG
CAAATACTATCATCAATAAGCCTATTCGTTCTGTTGAAGAAGTAAATAATGCATTGCATGAAGTAAACCAATTGAACCAA
CGCTTAACAGATACAATTAACTTATTACAACCCTTAGCGAATAAAGAAAGCTTAAAAGAAGCTCGTAATCTGACTTGAAA
TAAATTAATGAAACCGTTCAAACAGACGGTATGACTCAACAATCTGTTGAGAATTATAAGCAAGCTAAAATAAAAGCTC
AAAATGAATCTAGTATTGCACAAACTCTTATTAATAATGGTGATGCATCTGATCAAGAAGTTTCTACAGAAATAGAAAAA
TTAAATCAAAAGCTGTCTGAATTAACAAATTCAATCAATCACTTAACAGTTAATAAAGAACCTTTAGAAACTGCCAAAAA
TCAGTTACAAGCAAATATTGACCAAAAACCTAGCACTGATGGTATGACGCAACAATCTGTACAAAGCTATGAACGTAAAC
TACAAGAAGCCAAAGATAAAATAAACTCAATTAATAATGTCTTAGCTAACAATCCAGATGTTAATGCTATCAGAACAAAC
AAAGTTGAGACGGAACAAATCAATAATGAATTAACACAGGCGAAACAAGGTCTTACTGTTGATAAACAACCATTGATTAA
TGCAAAAACTGCTTTGCAACAAAGTCTAGATAATCAACCAAGTACTACTGGTATGACTGAAGCAACAATTCAAATTATA
ACGCTAAACGTCAAAAAGCAGAGCAAGTTATACAAAATGCAAATAAAATTATTGAAAACGCTCAACCTAGTGTACAACAA
GTGTCTGATGAGAAATCTAAGGTAGAGCAAGCACTCAGTGAATTGAACAACGCCAAATCAGCGCTTAGAGCTGATAAACA
AGAATTACAGCAAGCATATAATCAGTTGATTCAACCAACGGATTTAAATAATAAGAAACCAGCTTCTATCACTGCGTACA
ATCAAAGATATCAACAATTTAGTAACGAATTGAACAGCACTAAAACAAATACAGATCGCATTTTAAAAGAGCAAAATCCA
```

FIGURE 2 cont.
```
AGTGTAGCTGATGTCAACAATGCACTAAATAAAGTAAGAGAAGTACAACAAAAATTAAACGAAGCCAGAGCACTTTTACA
AAATAAAGAAGATAATAGTGCACTAGTTCGAGCCAAAGAACAACTTCAACAGGCAGTTGACCAAGTCCCTTCAACAGAAG
GTATGACGCAACAAACTAAAGATGATTACAATTCAAAACAACAAGCTGCTCAACAAGAAATATCAAAAGCACAACAAGTT
ATCGATAATGGCGATGCGACTACACAACAAATTTCTAACGCCAAAACAAATGTTGAACGCGCTTTAGAAGCATTAAATAA
TGCAAAAACTGGTTTAAGAGCAGATAAAGAGGAACTTCAAAATGCATATAATCAATTAACTCAAAATATTGATACGAGCG
GTAAAACGCCTGCAAGTATCAGGAAATACAATGAAGCTAAGTCACGTATTCAAACTCAAATTGATTCAGCTAAAAATGAA
GCAAACAGTATTTTAACAAATGACAATCCTCAAGTATCACAAGTGACTGCTGCGTTAAACAAAATAAAAGCTGTTCAACC
TGAATTAGATAAAGCGATAGCAATGCTTAAAAATAAAGAGAATAATAATGCATTGGTTCAAGCGAAACAACAACTTCAAC
AAATTGTTAATGAAGTAGATCCAACACAAGGCATGACAACAGATACTGCTAATAACTATAAATCAAAAAAACGTGAAGCT
GAAGATGAAATACAAAAAGCTCAACAAATCATTAACAATGGCGATGCCACTGAGCAACAAATTACTAACGAAACAAATAG
AGTAAATCAAGCGATTAATGCAATAAACAAAGCCAAAAACGATTTACGTGCTGATAAGTCTCAATTGGAAAATGCTTATA
ACCAATTAATACAAAATGTTGATACAAATGGTAAAAAACCTGCTAGTATTCAACAATACCAAGCTGCTCGACAAGCTATT
GAGACGCAATACAATAACGCTAAATCAGAAGCACATCAAATTCTTGAAAATAGTAACCCTTCAGTTAATGAAGTAGCACA
AGCATTACAAAAAGTTGAAGCTGTACAACTTAAAGTTAATGACGCGATTCATATACTTCAAAATAAAGAGAATAATAGTG
CACTTGTCACAGCTAAAAATCAACTTCAGCAATCAGTTAATGATCAACCATTAACAACAGGTATGACTCAAGATTCTATT
AATAACTATGAAGCTAAGAGAAATGAGGCTCAAAGTGCTATCAGAAATGCAGAAGCTGTCATCAACAATGGCGATGCAAC
TGCAAAACAAATTTCAGACGAGAAATCTAAAGTTGAACAAGCACTAGCACATTTGAATGATGCTAAACAGCAATTAACTG
CAGATACTACTGAATTACAAACAGCAGTTCAACAATTAAACAGAAGAGGCGATACAAATAATAAAAAGCCAAGAAGTATC
AATGCATATAATAAAGCAATTCAATCATTAGAAACACAAATTACTTCTGCTAAAGATAATGCCAACGCTGTGATACAAAA
ACCTATACGTACTGTTCAAGAGGTAAATAATGCATTACAACAAGTAAATCAGTTGAATCAACAATTAACTGAAGCAATTA
ATCAACTTCAACCGCTATCAAATAATGATGCATTAAAAGCTGCAAGATTAAATTTAGAAAATAAAATTAATCAAACTGTA
CAAACTGATGGTATGACACAACAATCTATAGAGGCTTATCAAAACGCTAAACGCGTAGCCCAAAATGAATCTAACACTGC
TTTAGCATTAATTAATAACGGCGATGCCGATGAACAACAAATTACAACTGAAACAGACCGAGTCAATCAGCAAACTACAA
ACTTAACTCAAGCAATTAACGGGTTAACAGTTAATAAAGAACCATTAGAAACCGCTAAAACAGCGTTACAAAATAACATC
GACCAGGTACCTAGTACAGATGGTATGACTCAGCAATCTGTTGCAAATTATAATCAAAACTACAAATAGCTAAAAACGA
AATTAACACAATTAATAACGTTTTAGCGAACAATCCAGATGTTAATGCAATCAAAACGAATAAAGCAGAAGCGGAACGAA
TCAGTAACGATTTAACACAAGCTAAGAATAACTTACAAGTTGATACTCAACCTTTAGAAAAAATAAAAAGACAACTTCAA
GATGAAATTGATCAAGGTACTAACACAGATGGAATGACTCAAGATTCAGTGGATAATTACAATGATAGCTTAAGTGCAGC
AATTATAGAAAAAGGCAAAGTAAATAAATTACTTAAACGTAATCCGACAGTAGAACAAGTTAAAGAGAGCGTTGCTAATG
CACAACAAGTCATACAAGATTTACAAAATGCTCGAACTTCACTTGTTCCAGACAAAACTCAACTTCAAGAAGCTAAAAAT
AGATTAGAAAACAGTATTAACCAACAAACAGATACTGACGGCATGACTCAAGATTCGCTTAACAATTATAATGATAAATT
AGCAAAAGCTAGACAAAACCTTGAAAAAATATCTAAAGTTTTAGGTGGTCAACCTACTGTAGCTGAAATTAGACAAAATA
CAGATGAAGCAAATGCACATAAACAAGCATTAGACACTGCACGTTCTCAACTTACATTAAATAGAGAGCCATATATCAAT
CATATTAATAATGAAAGTCATTTAAATAACGCGCAAAAAGATAATTTTAAAGCTCAAGTTAACTCAGCACCTAATCATAA
TACTTTAGAAACGATTAAAAATAAGGCTGATACTTTAAATCAATCTATGACAGCATTAAGTGAAAGTATTGCAGATTACG
AAAATCAAAAACAACAAGAAATTATTTAGATGCATCTAACAATAAACGTCAAGACTATGACAATGCAGTCAATGCGGCT
AAAGGTATTTTAAACCAAACTCAAAGTCCGACAATGAGTGCTGATGTGATTGATCAAAAAGCTGAAGATGTTAAACGTAC
GAAAACTGCGTTAGATGGAAATCAAAGATTAGAAGTTGCTAAACAACAAGCACTTAATCATTTAAATACCTTAAATGATT
TAAACGATGCTCAGCGACAAACTTTAACTGATACTATAAATCACTCTCCAAACATCAATTCAGTGAATCAAGCTAAAGAA
AAAGCTAATACTGTTAACACAGCCAATGACTCAACTGAAACAAACTATTGCTAACTATGACGATGAATTGCATGACGGCAA
TTACATTAATGCAGATAAAGACAAAAAGATGCTTATAATAACGCTGTTAACAATGCTAAACAACTGATTAATCAATCTG
ATGCTAATCAAGCACAACTTGATCCAGCTGAAATTAATAAAGTTACACAAAGAGTCAATACGACTAAAAATGATCTAAAT
GGTAATGACAAATTGGCTGAAGCTAAAAGAGATGCTAATACAACCATTGATGGTTTAACTTATCTAAATGAAGCTCAACG
TAACAAAGCTAAAGAAATGTAGGCAAAGCTTCTACAAAAACAAATATTACGAGTCAGTTACAAGATTACAATCAATTGA
ATATTGCTATGCAAGCATTACGTAACAGTGTGAACGACGTTAACAATGTTAAAGCAAATAGCAATTATATAAATGAAGAT
AATGGTCCAAAAGAAGCTTACAATCAAGCCGTTACTCATGCTCAAACATTGATAAATGCACAATCTAACCCTGAAATGAG
CCGTGACGTAGTAAATCAAAAAACACAAGCAGTAAATACTGCCCATCAGAATTTACATGGACAACAAAAGTTAGAACAAG
CACAAAGTAGTGCTAATACAGAAATCGGTAACTTACCAAACTTAACTAATACTCAAAAAGCTAAAGAAAAGGAACTGGTA
AATAGTAAACAAACTCGTACGGAAGTACAAGAACAACTTAACCAAGCTAAGTCACTAGATAGTTCTATGGGCACGTTAAA
ATCATTAGTTGCTAAACAACCTACAGTACAAAAAACAAGTGTTTATATTAACGAAGATCAACCTGAGCAATCTGCCTACA
ATGATTCCATTACAATGGGACAAACTATAATTAATAAAACAGCTGATCCAGTACTTGATAAAACTTTAGTTGATAACGCA
ATCAGTAACATTTCAACTAAAGAGAATGCACTGCATGGTGAACAAAAATTAACAACTGCTAAAACGGAAGCAATTAATGC
ACTTAATACATTAGCTGATTTAAACACACCTCAGAAAGAGGCTATTAAAACAGCTATTAACACTGCTCATACAAGAACTG
ATGTAACTGCAGAGCAAAGTAAGGCTAATCAAATAAATAGTGCAATGCACACGTTGAGACAAAACATTTCTGACAACGAA
TCAGTAACAAACGAAAGTAATTATATTAACGCTGAACCCGAAAAACAACATGCCTTTACTGAGGCTCTAAATAATGCTAA
AGAAATAGTTAATGAACAACAAGCCACTCTTGATGCCAATTCAATTAACCAAAAAGCACAAGCGATTCTTACTACTAAAA
ATGCTTTAGATGGTGAAGAACAATTACGTCGTGCTAAAGAAAATGCCGATCAAGAAATCAATACGTTAAATCAATTGACT
GATGCGCAAAGAAATAGTGAAAAAGGTTTAGTCAACAGTTCTCAAACTAGAACAGAAGTTGCTTCTCAATTAGCAAAAGC
TAAAGAACTAAATAAGGTGATGGAACAACTGAATCACCTTATCAATGGTAAAAACCAAATGATAAATAGCAGTAAATTTA
TCAATGAAGATGCGAACCAACAACAAGCATATTCAAATGCGATTGCAAGTGCAGAAGCGCTTAAAAACAAATCACAAAAC
```

FIGURE 2 cont.
CCTGAATTAGATAAAGTAACAATTGAACAAGCAATTAATAATATTAATTCTGCAATTAACAATCTAAACGGTGAAGCTAA
ACTGACTAAAGCTAAAGAAGATGCTGTTGCTTCAATAAACAACCTAAGCGGATTAACAAACGAGCAAAAAACAAAAGAAA
ATCAAGCCGTTAATGGCGCTCAAACTAGAGACCAAGTTGCTAATAAATTACGTGATGCTGAAGCATTAGATCAATCAATG
CAAACATTACGTGACTTAGTTAACAATCAAAATGCAATACATTCAACAAGTAATTATTTTAACGAGGATTCAACTCAAAA
GAATACTTATGATAATGCAATTGATAATGGCTCGACATATATAACTGGTCAACACAATCCAGAATTAAATAAATCTACTA
TTGATCAAACGATTAGCCGAATTAACACAGCTAAAAATGATTTACATGGTGTAGAAAAGTTACAAAGAGATAAGGGAACT
GCTAATCAAGAAATTGGACAATTAGGTTATTTAAATGACCCTCAAAAATCTGGTGAGGAATCCTTAGTCAACGGTTCAAA
TACACGTTCTGAAGTAGAAGAGCATCTTAATGAAGCTAAATCATTAAATAATGCAATGAAACAATTAAGAGATAAAGTAG
CTGAAAAGACTAATGTCAAACAAAGTAGCGATTACATTAATGATTCAACTGAACATCAACGTGGGTATGATCAAGCACTT
CAAGAAGCAGAAAATATTATTAATGAAATCGGTAATCCAACATTAAATAAATCGGAAATTGAACAAAAGTTACAACAATT
GACTGACGCTCAAAATGCGTTACAAGGTTCACATCTATTAGAAGAAGCTAAAAATAATGCGATTACTGGAATCAATAAAC
TTACAGCATTAAATGATGCACAACGTCAAAAAGCAATTGAAAATGTTCAAGCACAGCAGACAATCCCAGCAGTTAATCAA
CAATTAACTTTGGATAGAGAAATAAATACTGCAATGCAAGCTTTACGAGATAAAGTAGGCCAACAAAATAACGTTCACCA
ACAAAGTAATTATTTCAATGAAGATGAACAACCAAAACATAACTATGATAATTCTGTACAAGCCGGTCAAACTATTATTG
ATAAACTTCAAGATCCAATCATGAACAAAATGAAATTGAGCAGGCTATTAATCAAATCAATACGACTCAAACAGCGTTA
AGTGGAGAAAATAAATTACACACTGACCAAGAAAGCACAAATAGACAAATAGAAGGTTTATCTAGTTTGAACACAGCTCA
AATCAACGCCGAAAAAGATTTAGTCAATCAAGCTAAAACAAGAACAGATGTTGCTCAAAAGTTAGCTGCAGCTAAAGAAA
TAAATTCTGCTATGAGTAATTTAAGAGATGGCATTCAAAATAAAGAGGACATCAAACGTAGCAGTGCATATATCAACGCA
GATCCGACTAAAGTTACAGCTTACGATCAAGCACTACAGAACGCAGAAAATATCATCAATGCCACACCAAACGTAGAGCT
TAATAAAGCTACAATTGAACAAGCGCTATCACGCGTTCAACAAGCACAACAAGATCTTGATGGTGTTCAACAATTAGCTA
ATGCTAAACAACAAGCTACACAAACTGTCAATGGGTTAAATAGCTTAAATGACGGTCAAAAGCGTGAATTAAATCTATTA
ATTAATTCAGCTAATACCCGTACAAAAGTACAAGAAGAATTAAACAAAGCAACTGAATTGAACCATGCGATGGAAGCTTT
AAGAAACAGTGTTCAAAACGTTGATCAAGTAAAACAAAGTAGCAATTATGTCAATGAAGATCAACCTGAACAGCACAATT
ATGATAATGCTGTCAATGAAGCTCAAGCTACAATCAACAACAATGCTCAACCTGTTCTAGACAAATTAGCTATAGAACGT
TTAACTCAAACTGTTAACACTACAAAAGATGCATTACATGGTGCTCAAAAACTGACACAAGACCAACAAGCTGCTGAAAC
TGGAATACGTGGTTTAACGAGTCTCAATGAACCTCAGAAAAATGCTGAAGTAGCTAAAGTAACTGCAGCAACAACACGTG
ATGAAGTGAGAAATATTCGTCAAGAAGCAACAACATTAGATACTGCAATGCTTGGTTTACGTAAAAGCATTAAAGATAAA
AACGATACTAAAAATAGTAGTAAATATATTAATGAGGATCATGACCAACAACAAGCTTATGACAATGCTGTAAATAATGC
TCAACAAGTTATCGATGAAACTCAAGCAACGTTAAGCTCAGATACAATCAATCAATTGGCAAATGCCGTAACTCAAGCTA
AATCTAATCTTCATGGAGATACTAAACTACAACACGATAAAGATAGTGCTAAACAAACGATTGCTCAATTACAGAATTTG
AATTCAGCTCAAAAACATATGGAAGATTCTTTAATTGATAATGAATCTACACGTACGCAAGTCCAACACGATTTAACAGA
AGCTCAAGCTTTAGATGGTTTAATGGGTGCCTTAAAAGAAAGTATTAAAGATTATACTAATATTGTTTCAAACGGTAATT
ACATCAATGCGGAACCATCTAAGAAACAAGCATATGATGCAGCTGTACAAAATGCTCAAAATATAATAAATGGAACGAAT
CAACCAACAATTAATAAAGGTAATGTCACTACAGCAACACAAACCGTGAAAAATACTAAAGATGCCTTAGACGGTGATCA
TAGATTAGAGGAAGCTAAAAATAATGCCAATCAAACAATCAGAAATCTATCTAATTTGAACAATGCCCAAAAAGATGCAG
AGAAAAATCTAGTTAATAGCGCATCAACATTAGAACAAGTTCAACAAAAACTTACAAACCGCTCAACAATTAGATAATGCT
ATGGGTGAGTTGACAAGTATTGCTAAAAAAGATCAAGTGAAAGCAGATAGTAAATATCTAAATGAAGATCCTCAAAT
TAAGCAAAACTATGATGATGCAGTTCAACGTGTTGAAACATATTATTAACGAAACTCAAAACCCTGAATTACTTAAAGCAA
ACATTGACCAAGCAACTCAATCCGTTCAAAATGCAGAACAAGCTTTACATGGTGCTGAAAAATTAAATCAAGACAAACAA
ACGTCTTCGACAGAACTAGATGGATTAACAGATTTAACAGATGCACAACGTGAAAAACTCAGAGAACAAATTAACACTTC
TAATAGTAGAGATGATATTAAGCAAAAAATTGAGCAAGCAAAGCACTAAATGACGCAATGAAAAAACTTAAAGAACAAG
TTGCGCAAAAAGATGGTGTTCATGCTAACAGTGATTATACAAATGAAGATTCTGCACAAAAAGATGCGTATAATAATGCA
CTTAAACAAGCGGAAGACATTATTAATAACAGCTCAAATCCTAACTTAAATGCACAAGACATTACTAATGCTTTAAATAA
TATTAAACAAGCACAAGATAACCTTCATGGAGCTCAAAAATTACAGCAAGACAAAAATACAACTAATCAAGCCATTGGTA
ACTTAAATCATCTTAATCAACCTCAAAAAGATGCGCTTATACAAGCTATTAATGGAGCTACATCTAGGGACCAAGTTGCA
GAAAAACTTAAAGAGGCCGAAGCGCTTGATGAAGCTATGAAACAACTTGAAGATCAAGTGAATCAAGATGATCAAATTTC
AAATAGCAGCCCATTCATAAATGAAGACTCAGACAAACAAAAAACTTATAATGATAAAATCCAAGCTGCAAAAGAAATAA
TTAATCAAACATCTAATCCAACCTTAGATAAACAAAAAATTGCTGATACACTTCAAAATATTAAAGATGCAGTGAATAAT
TTACATGGTGATCAAAAATTAGCTCAATCTAAACAAGATGCTAATAATCAATTAAATCATTTAGATGACTTAACCGAAGA
ACAAAAAAACCATTTTAAACCGTTAATTAATGCTGATACTGAGATGAGGTAAATAAACAACTAGAGATTGCTAAAC
AATTAAATGGTGATATGAGTACACTTCATAAAGTCATAAATGATAAAGATCAAATTCAACATTTAAGCAATTACATTAAT
GCTGATAATGATAAAAACAAAATTATGATAATGCTATTAAAGAAGCTGAGGATTTAATTCATAATCATCCAGATACATT
AGATCATAAAGCATTACAAGATTTATTAAACAAGATAGACCAAGCGCATAACGAATTAATGGAGAATCCAGATTTAAAC
AGGCTTTAGACAATGCTTTAAACGACATAGATAGCTTAAACAGTCTCAATGTTCCACAACGCCAAACTGTTAAGGATAAC
ATCAACCATGTGACAACTCTAGAAAGTTTAGCTCAAGAATTGCAGAAAGCAAAAGAGCTTAATGATGCTATGAAAGCAAT
GAGAGATAGCATTATGAATCAAGAGCAAATTCGTAAAAATAGCAATTATACTAATGAAGACTTAGCTCAACAAAATGCCT
ATAATCATGCAGTAGATAAAATAAATAACATTATTGGTGAAGACAATGCGACGATGGATCCTCAAATAATCAAACAAGCA
ACTCAAGATATAAATACAGCTATAAATGGATTAAATGGAGATCAAAAACTTCAAGATGCAAAGACAGATGCTAAACAACA
AATTACTAACTTTACTGGTTTAACTGAACCACAAAAACAAGCATTGGAAAACATCATTAACCAACAAACAAGCAGAGCAA
ATGTTGCTAAACAGTTAAGTCATGCTAAATTCTTAAATGGAAAAATGGAAGAATTAAAAGTTGCAGTAGCCAAAGCGTCA

FIGURE 2 cont.
```
TTAGTAAGACAAAATAGTAACTATATTAATGAAGATGTCTCTGAAAAAGAAGCATATGAACAAGCTATCGCAAAAGGTCA
GGAAATAATTAATTCAGAAAATAATCCAACAATAAGTAGTACTGATATCAATCGTACCATTCAAGAAATTAATGATGCTG
AACAAAATCTTCATGGTGATAATAAATTAAGACAAGCACAGGAAATTGCAAAGAATGAAATACAAAATCTAGACGGATTA
AATTCAGCTCAAATAACAAAATTAATCCAAGATATAGGCAGAACAACAACTAAACCTGCAGTAACTCAGAAACTAGAAGA
AGCAAAAGCAATAAACCAAGCTATGCAACAACTTAAACAAAGTATAGCCGATAAGGATGCTACTCTAAATTCTAGTAACT
ATCTCAATGAAGATTCTGAGAAAAAGTTAGCGTACGATAATGCTGTAAGCCAAGCTGAACAACTCATAAATCAACTTAAC
GACCCAACTATGGATATAAGTAATATTCAAGCTATTACTCAAAAGGTCATTCAAGCAAAAGATTCATTGCACGGTGCGAA
TAAACTTGCACAAAATCAAGCAGATTCAAATTTAATAATAAATCAATCAACAAATTTAAATGATAAACAAAAGCAAGCAT
TAAATGACTTAATTAATCATGCTCAAACTAAACAGCAAGTGGCAGAAATAATTGCACAAGCTAATAAGTTAAATAACGAA
ATGGGCACACTAAAAACACTCGTAGAAGAACAGTCAAACGTTCATCAACAAAGTAAATATATTAATGAAGATCCGCAAGT
TCAAAATATTTATAATGACTCCATTCAAAAGGTCGAGAAATATTAAACGGCACTACAGATGATGTTTTAAACAACAATA
AAATAGCAGATGCCATTCAAAACATTCATTTAACTAAAAACGATTTACATGGTGATCAAAAATTACAAAAAGCACAACAA
GATGCAACCAATGAATTAAACTATTTAACAAATCTAAACAATTCTCAAAGACAAAGCGAGCATGATGAGATTAACTCTGC
TCCTTCAAGAACTGAAGTTTCTAATGATTTAAATCATGCTAAAGCACTTAATGAAGCTATGCGTCAACTTGAGAATGAAG
TTGCTCTTGAAAACAGTGTTAAAAAATTAAGCGACTTTATCAATGAAGATGAAGCGGCACAAAATGAATATAGTAATGCA
CTTCAAAAAGCTAAAGACATTATCAACGGCGTTCCAAGTAGCACTTTAGATAAAGCTACAATTGAAGATGCTTTATTAGA
ATTGCAAAATGCTAGAGAAAGTTTACATGGTGAGCAAAAACTTCAAGAGGCTAAAAATCAAGCTGTTGCTGAAATTGATA
ATTTACAAGCATTAAATCCTGGACAGGTTCTTGCTGAAAAAACATTAGTTAACCAAGCATCAACCAAACCAGAAGTTCAA
GAAGCCTTACAAAAAGCAAAAGAACTTAATGAAGCTATGAAAGCACTGAAAACTGAAATAAATAAAAAAGAACAAATCAA
GGCTGATAGTAGATATGTAAATGCTGACAGTGGTCTTCAAGCAAATTACAATTCTGCGTTAAATTATGGTTCTCAAATTA
TTGCAACTACCCAACCACCAGAGCTTAATAAAGATGTAATAAATAGAGCAACTCAAACGATTAAAACTGCTGAAAATAAT
TTAAATGGGCAATCTAAATTAGCAGAGGCTAAGTCAGACGGAAATCAAAGCATCGAACATTTGCAAGGATTAACACAATC
ACAAAAAGATAAACAACATGATTTAATTAATCAAGCTCAAACTAAACAACAGGTAGATGATATCGTAAATAACTCTAAAC
AATTAGATAACTCTATGAATCAACTACAACAAATTGTTAACAATGACAATACAGTAAAACAAAATAGTGATTTCATTAAT
GAAGATTCCAGCCAACAGGATGCTTATAATCATGCAATTCAAGCAGCAAAAGATTTGATAACTGCTCATCCAACTATCAT
GGATAAAAATCAAATAGATCAAGCTATTGAAAATATCAAACAAGCACTTAATGATTTACACGGTAGTAATAAACTATCAG
AAGATAAAAAAGAAGCTTCAGAACAACTACAAAACCTTAATAGCTTGACGAACGGGCAAAAAGATACGATTTTAAATCAT
ATTTTCAGTGCACCAACAAGAAGCCAAGTAGGAGAAAAAATTGCAAGTGCTAAACAATTAAATAATACAATGAAAGCACT
TAGAGATTCTATTGCTGATAATAATGAAATTTTACAAAGTAGTAAGTACTTCAATGAAGATTCTGAACAACAAATGCTT
ATAATCAAGCCGTAAATAAAGCTAAAAATATAATTAATGATCAACCAACACCAGTAATGGCAAATGATGAGATTCAAAGT
GTCCTAAATGAAGTTAAACAAACTAAAGATAATTTACATGGTGATCAAAAACTTGCTAACGACAAGACAGATGCTCAAGC
AACATTAAATGCGTTAAATTACTTAAATCAAGCGCAAAGAGGTAATCTTGAAACTAAAGTTCAAAACTCTAATTCTAGAC
CAGAAGTACAAAAAGTAGTTCAATTAGCAAATCAACTTAATGATGCGATGAAAAAATTAGATGATGCTTTAACTGGTAAT
GACGCAATAAAACAAACGAGTAATTATATTAATGAAGATACTTCTCAACAAGTTAACTTTGATGAGTATACAGATAGAGG
TAAAAACATAGTTGCTGAACAAACAAATCCAAATATGTCTCCAACTAATATTAACACTATTGCTGATAAAATTACTGAAG
CTAAAAACGATTTACATGGCGTACAAAAACTAAAACAAGCTCAACAACAGTCCATCAATACTATTAATCAAATGACTGGT
CTAAACCAAGCTCAAAAAGAACAATTAAATCAAGAAATTCAACAAACTCAAACCCGTTCTGAAGTACATCAAGTAATTAA
TAAAGCACAAGCTTTAAATGATTCAATGAATACTTTACGTCAAAGTATTACTGATGAACATGAAGTTAAACAAACAAGTA
ACTACATCAATGAAACTGTTGGTAATCAAACTGCATATAACAATGCCGTTGATCGTGTAAAACAAATAATCAATCAAACA
TCTAATCCAACTATGAATCCTTTAGAGGTGGAACGTGCAACATCAAATGTAAAAATTCTAAAGATGCACTTCATGGTGA
ACGTGAATTGAATGACAATAAAAATTCAAAAACTTTTGCAGTCAATCACTTAGATAACCTCAATCAAGCTCAAAAAGAAG
CATTAACTCATGAAATTGAACAAGCAACTATAGTTTCACAAGTAAATAATATCTATAACAAAGCGAAAGCTTTAAATAAT
GATATGAAAAAACTTAAAGATATCGTTGCTCAACAAGATAATGTGAGACAATCAAACAATTATATAAACGAGGATAGTAC
ACCTCAAAATATGTACAACGATACAATTAATCATGCACAATCAATCATTGATCAAGTAGCAAACCCTACGATGTCTCATG
ACGAAATAGAGAATGCAATCAATAACATAAAGCATGCCATCAATGCACTCGATGGAGAACATAAATTACAACAAGCAAA
GAAAATGCAAACTTATTGATTAATAGTTTAAACGATTTAAATGTGCACCACAAAAGAGATGCCATAAATAGATTGGTTAATGA
AGCTCAAACAAGAGAAAAAGTAGCTGAACAACTTCAAAGTGCTGAAGCTTTAAATGACGCTATGAAGCATTTAAGAAACA
GCATTCAAAATCAATCATCCGTAAGACAAGAGAGCAAATATATTAATGCAAGTGATGCTAAAAAAGAGCAATATAATCAC
GCAGTTAGAGAAGTCGAAAATATTATCAATGAACAACATCCAACATTGGATAAAGAATAATTAAGCAACTAACGGATGG
TGTAAATCAAGCGAATAATGACTTAAATGGCGTTGAATTATTAGATGCTGATAAGCAAAACGCACATCAATCGATACCTA
CATTGATGCACTTAAATCAAGCACAACAAAACGCATTAAATGAAAAAATTAATAACGCAGTTACCAGAACTGAAGTTGCG
GCTATTATTGGCCAAGCAAAACTACTCGATCATGCTATGGAGAATTTAGAAGAAAGTATCAAAGATAAAGAGCAAGTCAA
ACAGTCAAGTAACTATATTAATGAAGATTCTGATGTTCAAGAAACATACGATAACGCCGTTGATCATGTGACAGAAATAC
TTAATCAAACAGTAAATCCAACTTTATCTATTGAAGATATAGAGCATGCTATCAACGAAGTTAATCAAGCGAAAAACAA
CTCAGAGGTAAACAAAAACTTTATCAAACTATCGATTTAGCTGATAAAGAATTAAGTAAATTGGATGATTTAACATCACA
ACAAAGCAGTTCAATATCTAATCAAATATATACTGCTAAAACGAGAACAGAAGTTGCCCAAGCAATTGAAAAAGCAAAT
CATTAAATCATGCAATGAAAGCACTTAACAAAGTATATAAAAATGCAGATAAAGTGTTAGATAGTAGTCGATTCATTAAC
GAAGATCAACCTGAAAAAAAGGCGTATCAACAAGCTATAAATCATGTTGATTCAATCATTCATAGACAAACAAATCCTGA
AATGGATCCAACAGTAATCAATAGCATAACTCATGAACTCGAAACAGCTCAAAATAACTTACATGGTGATCAGAAACTTG
CTCATGCACAACAAGATGCCGCTAATGTAATTAATGGTCTAATTCATCTTAATGTTGCTCAACGTGAGGTAATGATAAAT
```

FIGURE 2 cont.
```
ACGAATACAAATGCTACAACACGCGAAAAAGTTGCAAAGAACTTAGATAATGCTCAAGCTCTTGATAAAGCTATGGAAAC
ACTACAACAAGTAGTTGCTCATAAAAATAATATATTGAACGATAGTAAATATTTAAATGAAGATTCAAAATATCAACAAC
AATACGATCGAGTTATTGCTGATGCCGAACAACTACTTAATCAGACAACAAATCCAACATTAGAACCTTATAAAGTCGAT
ATTGTTAAGGATAATGTCCTAGCTAACGAAAAAATACTATTTGGCGCAGAAAAACTATCATATGACAAATCAAATGCAAA
TGATGAAATTAAACATATGAATTATCTTAATAATGCACAAAAGCAATCTATAAAAGATATGATTTCTCACGCAGCATTAA
GAACTGAAGTTAAACAACTTCTGCAACAAGCTAAAATCCTTGATGAAGCCATGAAATCACTTGAAGATAAAACTCAAGTA
GTGATTACAGATACTACTTTGCCTAATTACACTGAAGCTTCAGAGGATAAAAAGGAAAAAGTAGACCAAACTGTATCACA
TGCTCAAGCGATTATTGATAAAATAAATGGCTCAAATGTAAGTTTAGATCAAGTACGACAAGCACTAGAACAATTAACTC
AAGCATCAGAAAACCTCGATGGTGATCAGCGAGTTGAAGAAGCTAAAGTTCATGCTAATCAAACAATTGATCAATTAACA
CATCTTAATTCATTACAACAACAAACTGCGAAAGAAAGTGTTAAAAACGCAACAAAACTAGAAGAAATCGCTACTGTTAG
TAACAATGCTCAGGCATTAAACAAAGTAATGGGTAAATTAGAACAATTCATTAATCATGCTGATTCTGTTGAAAATAGTG
ATAATTATAGACAAGCCGACGACGACAAAATCATCGCTTATGATGAAGCACTTGAACATGGACAAGATATACAAAAAACT
AACGCAACCCAAATGAAACAAAACAAGCGTTACAACAATTAATATATGCAGAAACATCGTTAAATGGTTTCGAAAGATT
AAATCATGCTAGACCACGAGCTTTAGAATATATCAAATCACTAGAAAAAATAAACAATGCTCAAAAGTCTGCTTTAGAGG
ATAAAGTAACGCAATCGCATGATTTATTAGAATTAGAACATATTGTCAACGAGGGCACAAACCTCAATGACATTATGGGT
GAATTAGCTAACGCAATCGTTAATAACTATGCTCCAACCAAAGCAAGTATAAATTATATTAACGCCGATAACCTACGCAA
AGATAACTTTACTCAAGCTATCAACAATGCACGTGATGCACTCAACAAAACTCAAGGTCAGAACTTAGATTTCAATGCAA
TTGATACATTTAAAGATGATATATTCAAAACTAAAGATGCACTTAACGGTATTGAACGTTTAACAGCTGCAAAATCAAAA
GCAGAAAAACTAATTGATAGTTTAAAATTTATTAATAAAGCTCAATTCACACATGCAAATGATGAAATTATGAATACTAA
TTCTATTGCACAATTGTCTAGAATCGTGAATCAAGCATTTGATTTAAATGATGCAATGAAATCTTTAAGAGATGAACTTA
ATAATCAAGCTTTTCCTGTCCAAGCAAGCTCAAATTATATAAATTCAGATGAAGATTTAAAACAACAATTTGACCATGCT
TTAAGTAATGCTCGAAAAGTTCTTGCAAAAGAAAATGGTAAAATTGATGAAAAACAAATTCAGGGACTCAAACAAGT
GATTGAGGATACTAAAGATGCTTTAAATGGTATCCAACGTTTATCAAAAGCTAAAGCTAAAGCAATTCAATACGTACAAT
CTTTATCTTATATCAATGATGCACAGCGTCATATTGCTGAAAATAATATTCACAACTCTGATGATTTATCATCTTTAGCA
AATACATTATCTAAAGCTAGTGATTTAGATAATGCAATGAAAGACTTACGAGATACTATAGAAAGTAATTCAACTTCTGT
TCCAAATAGTGTGAATTATATTAATGCTGATAAGAATTTACAAATTGAATTTGATGAGGCGCTACAACAAGCAAGTGCAA
CAAGTTCTAAAACTTCAGAAAATCCAGCAACGATTGAAGAAGTATTAGGTCTTAGTCAAGCCATTTACGATACAAAAAAT
GCATTAAATGGTGAACAACGACTTGCAACTGAGAAGAGCAAAGATCTAAAATTAATAAAAGGATTAAAAGATTTAAATAA
AGCACAACTTGAAGATGTCACAAACAAGGTAAATTCAGCAAATACTTTAACAGAGTTATCTCAGCTCACTCAATCAACGT
TAGAATTAAACGATAAAATGAAATTATTGAGAGATAAGCTTAAAACTTTAGTAAATCCTGTTAAAGCAAGTTTAAATTAT
AGAAACGCTGATTATAATTTAAAACGTCAATTTAACAAAGCTTTAAAAGAAGCTAAAGGCGTATTAAATAAAAATAGCGG
TACAAATGTCAATATCAATGACATTCAACATCTTTTAACACAAATAGATAATGCTAAAGACCAATTAAATGGTGAACGAC
GTCTAAAAGAACATCAACAAAAATCTGAAGTATTTATTATTAAAGAATTAGATATACTTAATAATGCTCAAAAAGCTGCA
ATAATTAATCAGATTAGAGCGTCTAAAGACATTAAAATAATTAATCAAATCGTTGATAATGCAATAGAATTAAATGATGC
TATGCAAGGTTTAAAAGAACATGTAGCTCAATTAACAGCAACTACAAAAGACAACATTGAATATTTAAATGCTGATGAAG
ACCATAAATTACAATATGATTACGCTATCAACTTAGCGAATAATGTTCTTGACAAAGAAAACGGTACAAATAAAGACGCT
AATATCATAATTGGAATGATTCAAAACATGGATGATGCTAGAGCACTTCTAAATGGAATTGAAAGACTTAAAGATGCTCA
AACAAAAGCACATAATGACATTAAAGATACGCTCAAACGTCAACTTGATGAAATTGAACACGCTAATGCAACATCAAATT
CTAAAGCTCAAGCTAAACAAATGGTAAATGAGGAAGCTAGAAAAGCGCTTTCTAATATTAATGACGCAACATCAAATGAT
TTAGTTAATCAAGCAAAAGATGAAGGGCAATCTGCAATTGAACACATACATGCAGATGAATTACCTAAAGCAAAACTAGA
TGCTAATCAAATGATTGACCAAAAAGTTGAAGATATAAATCACTTAATTAGTCAAAATCCAAACTTATCAAATGAAGAAA
AAAATAAACTAATATCTCAAATTAATAAGTTAGTAAATGGAATTAAGAATGAAATTCAACAAGCTATAAACAAACAACAA
ATAGAAAATGCTACAACAAAACTAGATGAAGTCATTGAAACTACTAAAAAATTAATTATCGCCAAAGCAGAAGCTAAACA
AATGATAAAAGAGTTATCACAAAAGAAACGAGATGCAATAAATAACAACACTGATTTAACACCTTCTCAAAAGGCACATG
CTTTAGCAGATATTGATAAAACAGAAAAAGATGCACTTCAACATATCGAAAATTCTAATTCAATTGATGATATCAATAAC
AATAAAGAGCATGCATTTAATACTTTAGCTCATATCATTATTTGGGATACTGATCAGCAACCATTAGTTTTTGAACTACC
TGAATTGAGCCTTCAAAATGCTCTAGTAACAAGTGAGGTGGTTGTTCACAGAGATGAAACTATTTCATTAGAATCTATAA
TTGGAGCTATGACTTTAACTGATGAACTTAAAGTCAATATTGTTTCATTACCGAACACTGATAAAGTAGCTGATCACCTA
ACCGCTAAAGTTAAGGTTATTTTAGCTGATGGCTCATATGTCACTGTAAATGTTCCAGTCAAAGTTGTAGAAAAAGAATT
ACAAATAGCTAAAAAGGATGCTATAAAAACAATTGATGTTCTGGTAAAACAAAAATCAAAGATATAGATTCTAATAACG
AATTAACGTCTACTCAACGTGAAGATGCAAAAGCTGAAATTGAAAGATTGAAAAAGCAAGCCATCGATAAAGTGAATCAT
TCAAAATCGATTAAAGATATTGAAACAGTAAAACGAACTGATTTTGAAGAAATAGATCAGTTTGATCCTAAACGCTTTAC
GCTAAATAAAGCTAAAAAGGATATCATTACTGATGTTAATACTCAAATCCAAAATGGTTTCAAAGAAATTGAAACAATAA
AAGGTTTAACTTCTAATGAAAAAACTCAGTTTGATAAACAATTAACTGCACTACAAAAAGAATTTTTAGAAAAAGTCGAG
CATGCTCATAATTTAGTAGAATTAAATCAATTACAACAAGAGTTTAATAATAGATATAAACATATTTTAAACCAAGCACA
TTTACTAGGTGAAAAACATATAGCGAACAATAAATTAGGATATGTTGTAGTAAACAAAACTCAGCAAATACTAAAATAATC
AATCTGCTTCTTACTTTATAAAACAATGGGCACTTGATAGAATTAAACAAATTCAACTAGAAACGATGAATTCAATTCGT
GGTGCGCATACCGTACAAGATGTACACAAAGCATTATTACAAGGTATAGAGCAAATCTTGAAAGTAAATGTAAGTATTAT
AAATCAATCTTTCAACGATTCCTTGCATAACTTTAATTATCTTCATTCAAAATTTGATGCTAGATTAAGAGAAAAGGATG
TTGCAAACCATATCGTACAAACTGAAACATTCAAAGAAGTTCTAAAAGGAACGGGTGTTGAACCAGGTAAAATCAACAAA
```

FIGURE 2 cont.
GAAACACAGCAACCAAAACTTCATAAGAATGATAATGATAGCCTATTCAAACATTTAGTTGATAATTTCGGCAAAACTGT
AGGTGTTATTACATTAACTGGTTTACTTTCTAGTTTCTGGTTAGTTTTGGCTAAAAGACGTAAAAAAGAAGAAGAAGAAA
AACAATCGATAAAAAATCATCACAAAGATATTCGTCTTTCAGATACTGATAAAATAGATCCAATTGTAATAACTAAGCGT
AAAATAGATAAAGAAGAACAAATTCAAAACGATGACAAACATTCAATTCCAGTTGCTAAACATAAGAAATCTAAAGAAAA
GCAATTGAGTGAAGAGGATATTCATTCAATCCCCGTCGTTAAGCGTAAACAAAACAGTGATAACAAAGATACAAAACAGA
AGAAAGTTACTTCTAAAAAGAAGAAAACGCCTCAGTCAACTAAAAAAGTTGTAAAAACCAAAAAGCGTTCTAAAAAG

SEQ ID NO:49 polynucleotide sequence
ATGAGAGATAAGAAAGGACCGGTAAATAAAAGAGTAGATTTTCTATCAAATAAATTGAATAAATATTCAATAAGAAAATT
TACAGTTGGAACAGCATCTATTTTAATTGGCTCACTAATGTATTTGGGAACTCAACAAGAAGCAGAAGCAGCTGAAAACA
ATATTGAGAATCCAACTACATTAAAAGATAATGTCCAATCAAAAGAAGTGAAGATTGAAGAAGTAACAAACAAAGACACT
GCACCACAAGGTGTAGAAGCTAAATCTGAAGTAACTTCAAACAAAGACACAATCGAACATGAAGCATCAGTAAAAGCTGA
AGATATATCAAAAAGGAGGATACACCAAAAGAAGTAGCTAATGTTGCTGAAGTTCAGCCGAAATCGTCAGTCACTCATA
ACGCAGAGGCACCTAAGGTTAGAAAAGCTCGTTCTGTTGATGAAGGCTCTTTTGATATTACAAGAGATTCTAAAAATGTA
GTTGAATCTACCCCAATTACAATTCAAGGTAAAGAACATTTTGAAGGTTACGGAAGTGTTGATATACAAAAAAACCCAAC
AGATTTAGGGGTATCAGAGGTAACCAGGTTAATGTTGGTAATGAAAGTAATGGTTTGATAGGAGCTTTACAATTAAAAA
ATAAAATAGATTTTAGTAAGGATTTCAATTTTAAAGTTAGAGTGGCAAATAACCATCAATCAAATACCACAGGTGCTGAT
GGTTGGGGGTTCTTATTTAGTAAAGGAAATGCAGAAGAATATTTAACTAATGGTGGAATCCTTGGGGATAAAGGTCTGGT
AAATTCAGGCGGATTTAAAATTGATACTGGATACATTTATACAAGTTCCATGGACAAAACTGAAAAGCAAGCTGGACAAG
GTTATAGAGGATACGGAGCTTTTGTGAAAAATGACAGTTCTGGTAATTCACAAATGGTTGGAGAAAATATTGATAAATCA
AAAACTAATTTTTTAAACTATGCGGACAATTCAACTAATACATCAGATGGAAAGTTTCATGGGCAACGTTTAAATGATGT
CATCTTAACTTATGTTGCTTCAACTGGTAAAATGAGAGCAGAATATGCTGGTAAAACTTGGGAGACTTCAATAACAGATT
TAGGTTTATCTAAAAATCAGGCATATAATTTCTTAATTACATCTAGTCAAAGATGGGGCCTTAATCAAGGGATAAATGCA
AATGGCTGGATGAGAACTGACTTGAAAGGTTCAGAGTTTACTTTTACACCAGAAGCGCCAAAAACAATAACAGAATTAGA
AAAAAAAGTTGAAGAGATTCCATTCAAGAAAGAACGTAAATTTAATCCGGATTTAGCACCAGGGACAGAAAAAGTAACAA
GAGAAGGACAAAAAGGTGAGAAGACAATAACAACACCAACACTAAAAAATCCATTAACTGGAGAAATTATTAGTAAAGGT
GAATCGAAAGAAGAGATCACAAAAGATCCGATTAATGAATTAACAGAATACGGACCAGAAACGATAGCACCAGGTCATCG
AGACGAATTTGATCCGAAGTTACCAACAGGAGAGAAAGAAGAAGTTCCAGGTAAACCAGGAATTAAGAATCCAGAAACAG
GAGACGTAGTTAGACCACCGGTCGATAGTGTAACAAAATATGGACCTGTAAAAGGAGACTCGATTGTAGAAAAAGAAGAA
ATTCCATTCGAGAAAGAACGTAAATTTAATCCTGATTTAGCACCAGGAACAGAAAAAGTAACAAGAGAAGGACAAAAAGG
TGAGAAGACAATAACGACACCAACACTAAAAAATCCATTAACTGGAGAAATTATTAGTAAAGGTGAATCGAAAGAAGAGA
TCACAAAAGATCCGATTAATGAATTAACAGAATACGGACCTGAAACAATAGCGCCAGGTCATCGAGACGAATTTGATCCG
AAGTTACCAACAGGAGAGAAAGAAGAAGTTCCAGGTAAACCAGGAATTAAGAATCCAGAAACAGGAGACGTAGTTAGACC
GCCGGTCGATAGCGTAACAAAATATGGACCTGTAAAAGGAGACTCGATTGTAGAAAAAGAAGAAATTCCATTCAAGAAAG
AACGTAAATTTAATCCTGATTTAGCACCAGGGACAGAAAAAGTAACAAGAGAAGGACAAAAAGGTGAGAAGACAATAACG
ACGCCAACACTAAAAAATCCATTAACTGGAGAAATTATTAGTAAAGGTGAATCGAAAGAAGAAATCACAAAAGATCCGAT
TAATGAATTAACAGAATACGGACCAGAAACGATAACACCAGGTCATCGAGACGAATTTGATCCGAAGTTACCAACAGGAG
AGAAAGAGGAAGTTCCAGGTAAACCAGGAATTAAGAATCCAGAAACAGGAGATGTAGTTAGACCACCGGTCGATAGCGTA
ACAAAATATGGACCTGTAAAAGGAGACTCGATTGTAGAAAAAGAAGAAATTCCATTCGAGAAAGAACGTAAATTTAATCC
TGATTTAGCACCAGGGACAGAAAAAGTAACAAGAGAAGGACAAAAAGGTGAGAAGACAATAACGACGCCAACACTAAAAA
ATCCATTAACTGGAGAAATTATTAGTAAAGGTGAATCGAAAGAAGAAATCACAAAAGATCCAGTTAATGAATTAACAGAA
TTCGGTGGCGAGAAAATACCGCAAGGTCATAAAGATATCTTTGATCCAAACTTACCAACAGATCAAACGGAAAAAGTACC
AGGTAAACCAGGAATCAAGAATCCAGACACAGGAAAAGTGATCGAAGAGCCAGTGGATGATGTGATTAAACACGGACCAA
AAACGGGTACACCAGAAACAAAAACAGTAGAGATACCGTTTGAAACAAAACGTGAGTTTAATCCAAAATTACAACCTGGT
GAAGAGCGAGTGAAACAAGAAGGACAACCAGGAAGTAAGACAATCACAACACCAATCACAGTGAACCCATTAACAGGTGA
AAAAGTTGGCGAGGGTCAACCAACAGAAGAGATCACAAAACAACCAGTAGATAAGATTGTAGAGTTCGGTGGAGAGAAAC
CAAAAGATCCAAAAGGACCTGAAAACCCAGAGAAGCCGAGCAGACCAACTCATCCAAGTGGCCCAGTAAATCCTAACAAT
CCAGGATTATCGAAAGACAGAGCAAAACCAAATGGCCCAGTTCATTCAATGGATAAAAATGATAAAGTTAAAAAATCTAA
AATTGCTAAAGAATCAGTAGCTAATCAAGAGAAAAACGAGCAGAATTACCAAAAACAGGTTTAGAAAGCACGCAAAAAG
GTTTGATCTTTAGTAGTATAATTGGAATTGCTGGATTAATGTTATTGGCTCGTAGAAGAAAGAATTAA

SEQ ID NO:50 polynucleotide sequence
ATGGGCAAACGTAGACAAGGTCCTATTAATAAAAAAGTGGATTTTTTACCTAACAAATTAAACAAGTATTCTATAAGAAA
ATTCACTGTTGGTACGGCCTCAATATTACTTGGTTCGACACTTATTTTGGAAGTAGTAGCCATGAAGCGAAAGCTGCAG
AAGAAAAACAAGTTGATCCAATTACACAAGCTAATCAAATGATAGTAGTGAAAGATCACTTGAAAACACAAATCAACCT
ACTGTAAACAATGAAGCACCACAGATGTCTTCTACATTGCAAGCAGAAGAAGGAAGCAATGCAGAAGCACCGAATGTTCC
AACTATCAAAGCTAATTCAGATAATGATACACAAACACAATTTTCAGAAGCCCCTACAAGAAATGACCTAGCTAGAAAAG
AAGATATCCCTGCTGTTTCTAAAAACGAGGAATTACAATCATCACAACCAAACACTGACAGTAAAATAGAACCTACAACT
TCAGAACCTGTGAATTTAAATTATAGTTCTCCGTTTATGTCCTTATTAAGCATGCCTGCTGATAGTTCATCCAATAACAC

FIGURE 2 cont.
```
TAAAAATACAATAGATATACCGCCAACTACGGTTAAAGGTAGAGATAATTACGATTTTTACGGTAGAGTAGATATCCAAA
GTAATCCTACAGATTTAAATGCGACAAATTTAACGAGATATAATTATGGACAGCCACCTGGTACAACAACAGCTGGTGCA
GTTCAATTTAAAAATCAAGTTAGTTTTGATAAAGATTTCGACTTTAACATTAGAGTAGCAAACAATCGTCAAAGTAATAC
AACTGGTGCAGATGGTTGGGGCTTTATGTTCAGCAAGAAAGATGGGGATGATTTCCTAAAAAACGGTGGTATCTTACGTG
AAAAAGGTACACCTAGTGCAGCTGGTTTCAGAATTGATACAGGATATTATAATAACGATCCATTAGATAAAATACAGAAA
CAAGCTGGTCAAGGCTATAGAGGGTATGGGACATTTGTTAAAAATGACTCCCAAGGTAATACTTCTAAAGTAGGATCAGG
TACTCCATCAACAGATTTTCTTAACTACGCAGATAATACTACTAATGATTTAGATGGTAAATTCCATGGTCAAAAATTAA
ATAATGTTAATTTGAAATATAATGCTTCAAATCAAACTTTTACAGCTACTTATGCTGGTAAAACTTGGACGGCTACGTTA
TCTGAATTAGGATTGAGTCCAACTGATAGTTACAATTTTTTAGTTACATCAAGTCAATATGGAAATGGTAATAGTGGTAC
ATACGCAGATGGCGTTATGAGAGCTGATTTAGATGGTGCAACATTGACATATACTCCTAAAGCAGTCGATGGAGACCCAA
TTACATCAACTAAGGAAATACCATTTAATAAAAAACGCGAATTTGATCCAAACTTAGCGCCAGGTACAGAAAAAGTCGTT
CAAAAAGGTGAACCAGGAATTGAAACAACAACAACACCAACTTATGTCAATCCTAATACTGGAGAAAAAGTAGGTGAAGG
CACACCTACAACAAAGATCACTAAACAACCAGTGGATGAAATCGTTCATTATGGTGGCGAAGAAATCAAGCCAGGACATA
AAGATGAATTTGATCCAAATGCACCGAAAGGTAGTCAAACAACGCAACCAGGTAAGCCAGGAGTTAAAAATCCTGATACA
GGCGAAGTAGTCACACCACCAGTGGATGATGTGACAAAATATGGTCCAGTTGATGGAGATCCGATTACGTCAACGGAAGA
AATTCCATTCGACAAGAAACGTGAATTCAATCCTGATTTAAAACCAGGTGAAGAGCGTGTTAAACAAAAGGTGAACCAG
GAACAAAAACAATTACAACACCAACAACTAAGAACCCATTAACAGGGGAAAAAGTTGGCGAAGGTGAACCAACAGAAAAA
ATAACAAAACAACCAGTAGATGAAATCACAGAATATGGTGGCGAAGAAATCAAGCCAGGCCATAAGGATGAATTTGATCC
GAACGCACCGAAAGGTAGCCAAGAGGACGTTCCAGGTAAACCAGGAGTTAAAAATCCTGATACAGGCGAAGTAGTCACAC
CACCAGTGGATGATGTGACAAAATATGGTCCAGTTGATGGAGATCCGATTACGTCAACGGAAGAAATTCCGTTTGATAAA
AAACGCGAATTTGATCCAAACTTAGCGCCAGGTACAGAGAAAGTCGTTCAAAAAGGTGAACCAGGAACAAAAACAATTAC
AACACCAACAACTAAGAACCCATTAACAGGAGAAAAAGTTGGCGAAGGTGAACCAACAGAAAAAATAACAAAACAACCAG
TGGATGAAATCGTTCATTATGGTGGCGAAGAAATCAAGCCAGGCCATAAGGATGAATTTGATCCGAACGCACCGAAAGGT
AGCCAAGAGGACGTTCCAGGTAAGCCAGGAGTTAAAAATCCTGATACAGGCGAAGTAGTCACACCACCAGTGGATGATGT
GACAAAATATGGTCCAGTTGATGGAGATCCGATTACGTCAACGGAAGAAATTCCATTCGACAAGAAACGTGAATTCAATC
CTGATTTAAAACCAGGTGAAGAGCGTGTTAAACAAAAGGTGAACCAGGAACAAAAACAATTACAACACCAACAACTAAG
AACCCATTAACAGGGGAAAAAGTTGGCGAAGGTGAACCAACAGAAAAAGTAACAAAACAACCAGTGGATGAAATCGTTCA
TTATGGTGGCGAAGAAATCAAGCCAGGCCATAAGGATGAATTTGATCCAAATGCACCGAAAGGTAGCCAAGAAGACGTTC
CAGGTAAACCAGGAGTTAAAAACCCTGATACAGGCGAAGTAGTTACTCCACCAGTGGATGATGTGACAAAATATGGTCCA
GTTGATGGAGATCCGATTACGTCAACGGAAGAAATTCCGTTTGATAAAAAACGCGAATTTGATCCAAACTTAGCGCCAGG
TACAGAGAAAGTCGTTCAAAAAGGTGAACCAGGAACAAAAACAATTACAACACCAACAACTAAGAACCCATTAACAGGAG
AAAAAGTTGGCGAAGGTGAACCAACAGAAAAAATAACAAAACAACCAGTGGATGAGATCGTTCATTATGGTGGCGAAGAA
ATCAAGCCAGGCCATAAGGATGAATTTGATCCGAACGCACCGAAAGGTAGTCAAACAACGCAACCAGGTAAGCCAGGAGT
TAAAAATCCTGATACAGGCGAAGTAGTCACACCACCAGTGGATGATGTGACAAAATATGGTCCAGTTGATGGAGATCCGA
TTACGTCAACGGAAGAAATTCCGTTTGATAAAAAACGCGAATTTGATCCAAACTTAGCGCCAGGTACAGAGAAAGTCGTT
CAAAAAGGTGAACCAGGAACAAAAACAATTACAACGCCAACAACTAAGAACCCATTAACAGGAGAAAAAGTTGGCGAAGG
TGAACCAACAGAAAAAATAACAAAACAACCAGTGGATGAGATTGTTCATTATGGTGGTGAACAAATACCACAAGGTCATA
AAGATGAATTTGATCCAAATGCACCTGTAGATAGTAAAACTGAAGTTCCAGGTAAACCAGGAGTTAAAAATCCTGATACA
GGTGAAGTTGTTACCCCACCAGTGGATGATGTGACAAAATATGGTCCGAAAGTTGGTAATCCAATCACATCAACGGAAGA
GATTCCATTTGATAAGAAACGTGTATTTAATCCTGATTTAAAACCAGGTGAAGAGCGCGTTAAACAAAAGGTGAACCAG
GAACAAAAACAATTACAACACCAATATTAGTTAATCCTATTACAGGAGAAAAAGTTGGCGAAGGTAAATCAACAGAAAAA
GTCACTAAACAACCTGTTGACGAAATTGTTGAGTATGGTCCAACAAAAGCAGAACCAGGTAAACCAGCGGAACCAGGTAA
ACCAGCGGAACCAGGTAAACCAGCGGAACCAGGTAAACCAGCGGAACCAGGTACGCCAGCAGAACCAGGTAAACCAGCGG
AACCAGGTAAACCAGCGGAACCAGGTAAACCAGCGGAACCAGGTAAACCAGCGGAACCAGGTAAACCAGCGGAACCAGGT
ACGCCAGCAGAACCAGGTAAACCAGCGGAACCAGGTAAACCAGCGGAACCAGGTAAACCAGCGGAACCAGGTACGCCAGC
AGAACCAGGTAAACCAGCGGAACCAGGTACGCCAGCAGAACCAGGTAAACCAGCGGAACCAGGTACGCCAACACAATCAG
GTGCACCAGAACAACCAAATAGATCAATGCATTCAACAGATAATAAAAATCAATTACCTGATACAGGTGAAATCGTCAA
GCTAATGAGGGAACTTTAGTCGGATCTCTATTAGCAATTGTCGGATCATTGTTCATATTTGGTCGTCGTAAAAAAGGTAA
TGAAAAATAA
```

SEQ ID NO:51 polynucleotide sequence
```
ATGAAGAAACTATATACATCTTATGGCACTTATGGGATTTTTACATCAAATAAAAATCAATAACCCGACCCATCAACTATT
CCAATTTTCAGCATCAGATACTTCAGTTATTTTTGAAGAAACTGATGGTGAGACTGTTTTAAAATCACCTTCAATATATG
AAGTTATTAAAGAAATTGGTGAATTCAGTGAACATCATTTCTATTGTGCAATCTTCATTCCTTCAACAGAAGATCATGCA
TATCAACTTGAAAAGAAACTGATTAGTGTAGACGATAATTTCAGAAACTTTGGTGGCTTTAAAAGCTATCGTTTGTTAAG
ACCTGCTAAAGGTACAACATATAAAATTTATTTCGGATTTGCTGATCGACATGCATACGAAGACTTTAAGCAATCTGATG
CCTTTAATGACCATTTTTCAAAAGACGCATTAAGTCATTACTTTGGTTCAAGCGGACAACATTCAAGTTATTTTGAAAGA
TATCTATACCCAATAAAAGAATAG
```

FIGURE 2 cont.
SEQ ID NO:52 polynucleotide sequence
ATGTATTTATATACATCTTATGGGACTTACCAATTTTTAAATCAAATTAAACTTAATCATCAAGAACGTAGTTTATTTCA
ATTTTCCACTAATGATTCCTCAATAATCTTAGAAGAGTCTGAGGGAAAATCAATCTTAAAACATCCTAGTGCATATCAAG
TGATTGATAGCACAGGTGAATTTAACGAACATCATTTTTATAGTGCTATTTTTGTCCCTACATCTGAAGATCATCGTCAA
CAGCTAGAGAAAAAATTATTACTCGTAGACGTACCTTTAAGAAATTTTGGTGGTTTTAAAAGCTATCGTTTATTAAAACC
CACTGAGGGGTCTACCTACAAAATTTACTTTGGTTTTGCAAATCGAACAGCATATGAAGATTTCAAAGCTTCTGATATAT
TTAATGAAAACTTTTCAAAAGATGCATTGAGCCAATACTTTGGTGCTAGTGGTCAACATTCTAGCTACTTTGAAAGATAT
TTATATCCAATAGAAGATCATTAA

SEQ ID NO:53 polynucleotide sequence
ATGATTAACAGGGATAATAAAAAGGCAATAACAAAAAAGGGTATGATTTCAAATCGCTTAAACAAATTTTCGATTAGAAA
GTATACTGTAGGAACTGCATCGATTTTAGTAGGTACGACATTGATTTTTGGTCTAGGGAACCAAGAAGCTAAAGCTGCTG
AAAACACTAGTACAGAAAATGCGAAACAAGATGATGCAACGACTAGTGATAATAAAGAAGTAGTGTCGGAAACTGAAAAT
AATTCGACAACAGAAAATGATTCAACAAATCCAATTAAGAAAGAAACAAATACTGATTCACAACCAGAAGCTAAAGAAGA
ATCAACTACATCAAGTACTCAACAACAGCAAAATAACGTTACAGCTACAACTGAAACTAAGCCTCAAAACATTGAAAAAG
AAAATGTTAAACCTTCAACTGATAAAACTGCGACAGAAGATACATCTGTTATTTAGAAGAGAAGAAAGCACCAAATTAT
ACAAATAACGATGTAACTACAAAACCATCTACAAGTGAAATTCAAACAAAACCAACTACACCTCAAGAATCTACAAATAT
TGAAAATTCACAACCGCAACCAACGCCTTCAAAAGTAGACAATCAAGTTACAGATGCAACTAATCCAAAAGAACCAGTAA
ATGTGTCAAAAGAAGAACTTAAAAATAATCCTGAGAAATTAAAAGAATTAGTTAGAAATGATAACAATACAGATCGTTCA
ACTAAACCAGTTGCTACAGCTCCAACAAGTGTTGCACCAAAACGATTAAATGCGAAAATGCGTTTTGCAGTTGCACAACC
AGCAGCAGTTGCTTCAAATAATGTAAATGACTTAATTACAGTTACGAAACAGACGATCAAAGTTGGCGATGGTAAAGATA
ATGTGGCAGCAGCGCATGACGGTAAAGATATTGAATATGATACAGAGTTTACAATTGACAATAAAGTCAAAAAGGCGAT
ACAATGACGATTAATTATGATAAGAATGTAATTCCTTCGGATTTAACAGATAAAAATGATCCTATCGATATTACTGATCC
ATCAGGAGAGGTCATTGCCAAAGGAACATTTGATAAAGCGACTAAGCAAATCACATATACATTTACAGATTATGTAGATA
AATATGAAGATATAAAAGCACGTTTAACTTTATACTCATATATTGATAAGCAAGCAGTACCTAATGAAACTAGTTTGAAT
TTAACGTTTGCAACAGCAGGTAAAGAAACTAGCCAAAACGTTTCTGTTGATTATCAAGACCCAATGGTTCATGGTGATTC
AAACATTCAATCTATCTTTACAAAGTTAGATGAAAACAAACAAACTATTGAACAACAAATTTATGTTAATCCTTTGAAAA
AAACAGCAACTAACACTAAAGTTGATATAGCTGGTAGTCAAGTAGATGATTATGGAAATATTAAACTAGGAAATGGTAGT
ACCATTATTGACCAAAATACAGAAATAAAAGTTTATAAAGTTAACCCTAATCAACAATTGCCTCAAAGTAATAGAATCTA
TGATTTTAGTCAATACGAAGATGTAACAAGTCAATTTGATAATAAAAAATCATTTAGTAATAATGTAGCAACATTGGATT
TTGGTGATATTAATTCAGCCTATATTATCAAAGTTGTTAGTAAATATACACCTACATCAGATGGCGAACTAGATATTGCT
CAAGGTACTAGTATGAGAACAACTGATAAATATGGTTATTATAATTATGCAGGATATTCAAACTTCATCGTAACTTCTAA
TGACACTGGCGGTGGCGACGGTACTGTTAAACCTGAAGAAAGTTATACAAAATTGGTGACTATGTATGGGAAGACGTTG
ATAAAGACGGTGTCCAAGGTACAGATTCGAAAGAAAAGCCAATGGCAAACGTTTTAGTTACATTAACTTACCCGGACGGT
ACTACAAAATCAGTAAGAACAGATGCTAACGGTCATTATGAATTCGGTGGTTTGAAAGACGGAGAAACTTATACAGTTAA
ATTCGAAACGCCAGCTGGATATCTTCCAACAAAAGTAAATGGAACAACTGATGGTGAAAAAGACTCAAATGGTAGTTCTA
TAACTGTTAAAATTAAATGGTAAAGATGATATGTCTTTAGACACTGGTTTTTATAAAGAACCTAAATATAATCTTGGTGAC
TATGTATGGGAAGATACAAATAAAGATGGTATCCAAGATGCTAATGAACCTGGTATCAAAGATGTTAAGGTTACATTAAA
AGATAGTACTGGAAAAGTTATTGGTACAACTACTACTGATGCCTCGGGTAAATATAAATTTACAGATTTAGATAATGGTA
ACTATACAGTAGAATTTGAAACACCAGCAGGTTACACGCCAACGGTTAAAAATACTACAGCTGAAGATAAAGATTCTAAT
GGTTTAACAACAACAGGTGTCATTAAAGATGCAGATAATATGACATTAGACAGTGGTTTCTATAAAACACCAAATACAG
TTAGGTGATTATGTTTGGTACGACAGTAATAAAGACGGTAAACAAGATTCAACTGAAAAAGGTATCAAAGATGTTAAAG
TTACTTTATTAAATGAAAAAGGCGAAGTAATTGGAACAACTAAAACAGATGAAAATGGTAAATATCGTTTCGATAATTTA
GATAGCGGTAAATACAAAGTTATTTTGAAAAGCCTGCTGGCTTAACACAAACAGTTACAAATACAACTGAAGATGATAA
AGATGCCGATGGTGGCGAAGTTGACGTAACAATTACGGATCATGATGATTTCATACTTGATAACGGATACTTCGAAGAAG
ATACATCAGACAGTGATTCAGACTCAGACAGTGATTCAGACTCAGACAGCGACTCAGATTCAGACAGTGATTCAGACTCA
GATAGCGATTCAGATTCAGACAGCGACTCAGACTCAGATAGCGACTCAGACTCAGACAGCGACTCAGACTCAGATAGCGA
CTCAGATTCGGACAGCGATTCAGACTCAGATAGCGACTCAGATTCAGACAGCGATTCAGACTCAGATAGCGACTCAGATT
CAGACAGTGACTCAGACTCAGATAGCGACTCAGACTCAGACAGTGACTCAGACTCAGACAGCGATTCAGATTCAGATAGC
GACTCAGATTCGGACAGTGATTCAGACTCAGATAGCGACTCAGATTCAGACAGCGACTCAGACTCAGATAGCGACTCAGA
CTCAGACAGTGATTCAGACTCAGATAGCGATTCGGACTCGGATGCAGGAAAACATACACCTGTTAAACCAATGAGTACTA
CTAAAGACCATCACAATAAAGCAAAGCATTACCAGAAACAGGTAGTGAAAATAACGGCTCAAATAACGCAACGTTATTT
GGTGGATTATTTGCAGCATTAGGTTCATTATTGTTATTCGGTCGTCGCAAAAAACAAACAAATAA

SEQ ID NO:54 polynucleotide sequence
ATGATTAATAAAAAAATAATTTACTAACTAAAAAGAAACCTATAGCAAATAAATCCAATAAATATGCAATTAGAAAATT
CACAGTAGGTACAGCGTCTATTGTAATAGGTGCAACATTATTGTTTGGTTTAGGTCATAATGAGGCCAAAGCCAGGAGA
ATTCAGTACAAGACGTTAAAGATTCGAATACGGATGATGAATTATCAGACAGCAATGATCAGTCTAGTGATGAAGAAAG
AATGATGTGATCAATAATAATCAGTCAATAAACACCGACGATAATAACCAAATAATTAAAAAAGAAGAAACGAATAACTA

FIGURE 2 cont.
CGATGGCATAGAAAAACGCTCAGAAGATAGAACAGAGTCAACAACAAATGTAGATGAAAACGAAGCAACATTTTTACAAA
AGACCCCTCAAGATAATACTCATCTTACAGAAGAAGAGGTAAAAGAATCCTCATCAGTCGAATCCTCAAATTCATCAATT
GATACTGCCCAACAACCATCTCACACAACAATAAATAGAGAAGAATCTGTTCAAACAAGTGATAATGTAGAAGATTCACA
CGTATCAGATTTTGCTAACTCTAAAATAAAAGAGAGTAACACTGAATCTGGTAAAGAAGAGAATACTATAGAGCAACCTA
ATAAAGTAAAAGAAGATTCAACAACAAGTCAGCCGTCTGGCTATACAAATATAGATGAAAAAATTTCAAATCAAGATGAG
TTATTAAATTTACCAATAAATGAATATGAAAATAAGGCTAGACCATTATCTACAACATCTGCCCAACCATCGATTAAACG
TGTAACCGTAAATCAATTAGCGGCGGAACAAGGTTCGAATGTTAATCATTTAATTAAAGTTACTGATCAAAGTATTACTG
AAGGATATGATGATAGTGAAGGTGTTATTAAAGCACATGATGCTGAAAACTTAATCTATGATGTAACTTTTGAAGTAGAT
GATAAGGTGAAATCTGGTGATACGATGACAGTGGATATAGATAAGAATACAGTTCCATCAGATTTAACCGATAGCTTTAC
AATACCAAAAATAAAAGATAATTCTGGAGAAATCATCGCTACAGGTACTTATGATAACAAAAATAAACAAATCACCTATA
CTTTTACAGATTATGTAGATAAGTATGAAAATATTAAAGCACACCTTAAATTAACGTCATACATTGATAAATCAAAGGTT
CCAAATAATAATACCAAGTTAGATGTAGAATATAAAACGGCCCTTTCATCAGTAAATAAAACAATTACGGTTGAATATCA
AAGACCTAACGAAAATCGGACTGCTAACCTTCAAAGTATGTTTACAAACATAGATACGAAAAATCATACAGTTGAGCAAA
CGATTTATATTAACCCTCTTCGTTATTCAGCCAAGGAAACAAATGTAAATATTTCAGGGAATGGTGATGAAGGTTCAACA
ATTATAGACGATAGCACAATAATTAAAGTTTATAAGGTTGGAGATAATCAAAATTTACCAGATAGTAACAGAATTTATGA
TTACAGTGAATATGAAGATGTCACAAATGATGATTATGCCCAATTAGGAAATAATAATGATGTGAATATTAATTTTGGTA
ATATAGATTCACCATATATTATTAAAGTTATTAGTAAATATGACCCTAATAAGGATGATTACACGACTATACAGCAAACT
GTGACAATGCAGACGACTATAAATGAGTATACTGGTGAGTTTAGAACAGCATCCTATGATAATACAATTGCTTTCTCTAC
AAGTTCAGGTCAAGGACAAGGTGACTTGCCTCCTGAAAAAACTTATAAAATCGGAGATTACGTATGGGAAGATGTAGATA
AAGATGGTATTCAAAATACAAATGATAATGAAAAACCGCTTAGTAATGTATTGGTAACTTTGACGTATCCTGATGGAACT
TCAAAATCAGTCAGAACAGATGAAGATGGGAAATATCAATTTGATGGATTGAAAAACGGATTGACTTATAAAATTACATT
CGAAACACCTGAAGGATATACGCCGACGCTTAAACATTCAGGAACAAATCCTGCACTAGACTCAGAAGGTAATTCTGTAT
GGGTAACTATTAATGGACAAGACGATATGACGATTGATAGTGGATTTTATCAAACACCTAAATACAGCTTAGGGAACTAT
GTATGGTATGACACTAATAAAGATGGTATTCAAGGTGATGATGAAAAAGGAATCTCTGGAGTTAAAGTGACGTTAAAAGA
TGAAAACGGAAATATCATTAGTACAACTACAACCGATGAAAATGGAAAGTATCAATTTGATAATTTAAATAGTGGTAATT
ATATTGTTCATTTTGATAAACCTTCAGGTATGACTCAAACAACAACAGATTCTGGTGATGATGACGAACAGGATGCTGAT
GGGGAAGAAGTTCATGTAACAATTACTGATCATGATGACTTTAGTATAGATAACGGATACTATGATGACGAATCGGATTC
CGATAGTGACTCAGACAGCGACTCAGATTCCGATAGTGATTCAGACTCCGATAGCGACTCGGATTCAGACAGCGACTCAG
ATTCAGACAGCGACTCGGATTCTGATAGCGACTCGGATTCAGACAGCGACTCAGACTCAGACAGTGATTCAGATTCAGAC
AGCGACTCAGATTCCGATAGTGATTCAGACTCAGACAGCGACTCAGATTCTGATAGTGATTCAGACTCAGACAGTGATTC
AGATTCAGACAGCGACTCAGATTCCGATAGTGATTCAGACTCAGACAGCGACTCAGATTCCGATAGTGATTCAGACTCAG
ACAGCGACTCAGATTCTGATAGTGATTCAGACTCAGACAGTGATTCAGATTCCGATAGTGATTCAGACTCCGATAGCGAC
TCAGACTCGGATAGTGACTCAGATTCTGATAGTGATTCAGACTCAGACAGTGATTCGGATTCCGATAGTGATTCAGACTC
AGACAGCGACTCAGATTCTGATAGTGATTCAGACTCAGACAACGACTCAGATTTAGGCAATAGCTCAGATAAGAGTACAA
AAGATAAATTACCTGATACAGGAGCTAATGAAGATTATGGCTCTAAAGGCACGTTACTTGGAACTCTGTTTGCAGGTTTA
GGAGCGTTATTATTAGGGAAACGTCGCAAAAATAGAAAAAATAAAAATTAA

SEQ ID NO:55 polynucleotide sequence
ATGTCTAATAATTTTAAAGATGACTTTGAAAAAAATCGTCAATCGATAGACACAAATTCACATCAAGACCATACGGAAGA
TGTTGAAAAAGACCAATCAGAATTAGAACATCAGGATACAATAGAGAATACGGAGCAACAGTTTCCGCCAAGAAATGCCC
AAAGAAGAAAAAGACGCCGTGATTTAGCAACGAATCATAATAAACAAGTTCACAATGAATCACAAACATCTGAAGACAAT
GTTCAAAATGAGGCTGGCACAATAGATGATCGTCAAGTCGAATCATCACACAGTACTGAAAGTCAAGAACCTAGCCATCA
AGACAGTACACCTCAACATGAAGAGGAATATTATAATAAGAATGCTTTTGCAATGGATAAATCACATCCAGAACCAATCG
AAGACAATGATAAACACGAGACTATTAAAGATGCAGAAAATAACACTGAGCATTCAACAGTTTCTGATAAGAGTATAGCT
GAACAATCTCAGCAACCTAAACCATATTTTGCAACAGGTGCTAACCAAGCAAATACATCAAAAGATAAACATGATGATGT
AACTGTTAAGCAAGACAAAGATGAATCTAAAGATCATCATAGTGGTAAAAAGGCGCAGCAATTGGTGCTGGAACAGCGG
GTGTTGCAGGTGCAGCTGGTGCAATGGGTGTTTCTAAAGCTAAGAAACATTCAAATGACGCTCAAAACAAAGTAATTCT
GACAAGTCGAATAACTCGACTGAGGATAAAGCGTCTCAAGATAAGTCTAAAGATCATCATAATGGCAAAAAGGTGCAGC
GATCGGTGCTGGAACAGCAGGTTTGGCTGGAGGCGCAGCAAGTAAAGTGCTTCTGCCGCTTCAAAACCACATGCCTCTA
ATAATGCAAGCCAAAACCATGATGAACATGACAATCATGACAGAGATAAAGAACGTAAAAAGGTGGCATGGCCAAAGTA
TTGTTACCATTAATTGCAGCTGTACTAATTATCGGTGCATTAGCGATATTGGAGGCATGGCATTAAACAATCATAATAA
TGGTACAAAAGAAATAAAATCGCGAATACAAATAAAAATAATGCTGATGAAAGTAAAGACAAAGACACATCTAAAGACG
CTTCTAAAGATAAATCAAATCTACAGACAGTTGATAAATCAAAAGAGGATCAAGACAAAGCGACTAAAGATGAATCTGAT
AATGATCAAAACAACGCTAATCAAGCGAACAATCAAGCACAAAATAATCAAAATCAACAACAAGCTAATCAAAATCAACA
ACAGCAACAACAACAACGTCAAGGTGGTGCCAAAGACATACAGTGAATGGTCAAGAAAACTTATACCGTATCGCAATTCAAT
ACTACGGTTCAGGTTCACCGGAAAATGTTGAAAAAATTAGACGTGCCAATGGTTTAAGTGGTAACAATATTAGAAACGGT
CAACAAATCGTTATTCCATAA

FIGURE 2 cont.
SEQ ID NO:56 polynucleotide sequence
GTGATTGAATTAATTAAAATGGAAGGGATGATAGTTGTGTCTAATAATAATTTTAAAGATGATTTCGAAAAGAATCGTCA
ATCTATTAATCCAGACGAACAGCAAACAGAATTAAAAGAAGATGATAAAACAAATGAAAATAAAAAAGAAGCTGACTCTC
AAAACAGTTTATCTAATAACTCAAATCAACAATTTCCTCCGAGAAATGCCCAACGACGAAAAAGACGTAGAGAGACAGCA
ACTAATCAAAGCAAACAACAAGACGACAAACATCAAAAAAATAGTGACGCTAAAACTACAGAAGGTTCATTAGATGACCG
TTATGACGAAGCACAGTTACAGCAACAACATGATAAATCGCAACAACAAAATAAAACTGAAAAACAATCACAAGATAATA
GAATGAAAGATGGAAAAGATGCAGCTATTGTAAATGGAACATCTGAGTCACCAGAACATAAATCAAATCAACACAAAAT
AGACCCGGCCCTAAAGCTCAACAACAAAAGCGTAAATCAGAAAGTACGCAATCAAAACCGTCAACAAACAAAGATAAAAA
AGCAGCTACAGGTGCTGGAATAGCTGGTGCAGCTGGTGTTGCTGGTGCAGCAGAAACATCCAAACGTCATCATAATAAAA
AAGATAAACAAGATTCTAAACACTCAAACCATGAGAATGACGAAAAATCTGTTAAAAATGATGACCAAAAGCAATCTAAA
AAAGGCAAAAAAGCAGCAGTCGGTGCTGGCGCAGCTGCAGGAGTTGGTGCGGCTGGTGTTGCGCATCATAATAATCAAAA
TAAACATCATAATGAGGAAAAAAATTCTAATCAAACAATCAGTACAATGACCAATCAGAAGGTAAGAAAAAAGGTGGTT
TCATGAAAATCTTGTTACCACTTATAGCAGCCATTCTTATTCTAGGTGCAATAGCAATATTCGGTGGTATGGCTCTAAAT
AATCACAACGATAGTAAAAGTGATGACCAAAAAATAGCGAATCAAAGTAAGAAAGACTCAGATAAAAAAGATGGTGCGCA
ATCCGAAGATAACAAAGACAAAAAATCTGATAGTAACAAAGACAAAAAATCTGATTCTGATAAGAACGCAGATGATGACT
CTGATAATAGTTCCTCAAATCCTAACGCTACTTCAACTAATAATAACGATAATGTAGCCAATAATAACTCAAATTATACA
AACCAAAATCAACAAGATAATGCAAACCAAAATAGCAATAATCAACAGGCAACTCAAGGTCAACAATCACATACAGTATA
CGGTCAAGAAAACTTATATCGTATCGCCATACAATATTATGGAGAAGGAACTCAAGCTAACGTAGATAAAATTAAACGTG
CGAATGGATTAAGCAGTAATAATATTCATAATGGTCAAACATTAGTTATTCCTCAATAA

SEQ ID NO:57 polynucleotide sequence
ATGAAAAATAAATTGATAGCAAAATCTTTATTAACAATAGCGGCAATTGGTATTACTACAACTACAATTGCGTCAACAGC
AGATGCGAGCGAAGGATACGGTCCAAGAGAAAAGAAACCAGTGAGTATTAATCACAATATCGTAGAGTACAATGATGGTA
CTTTTAAATATCAATCTAGACCAAAATTTAACTCAACACCTAAATATATTAAATTCAAACATGACTATAATATTTTAGAA
TTTAACGATGGTACATTCGAATATGGTGCACGTCCACAATTTAATAAACCAGCAGCGAAAACTGATGCAACTATTAAAAA
AGAACAAAAATTGATTCAAGCTCAAAATCTTGTGAGAGAATTTGAAAAAACACATACTGTCAGTGCACACAGAAAAGCAC
AAAAGGCAGTCAACTTAGTTTCGTTTGAATACAAAGTGAAGAAAATGGTCTTACAAGAGCGAATTGATAATGTATTAAAA
CAAGGATTAGTGAGATAA

SEQ ID NO:58 polynucleotide sequence
ATGAAAACACGTATAGTCAGCTCAGTAACAACAACACTATTGCTAGGTTCCATATTAATGAATCCTGTCGCTAATGCCGC
AGATTCTGATATTAATATTAAACCGGTACTACAGATATTGGAAGCAATACTACAGTAAAAACAGGTGATTTAGTCACTT
ATGATAAAGAAAATGGCATGCACAAAAAAGTATTTTATAGTTTTATCGATGATAAAAATCACAATAAAAAACTGCTAGTT
ATTAGAACGAAAGGTACCATTGCTGGTCAATATAGAGTTTATAGCGAAGAAGGTGCTAACAAAAGTGGTTTAGCCTGGCC
TTCAGCCTTTAAGGTACAGTTGCAACTACCTGATAATGAAGTAGCTCAAATATCTGATTACTATCCAAGAAATTCGATTG
ATACAAAAGAGTATATGAGTACTTTAACTTATGGATTCAACGGTAATGTTACTGGTGATGATACAGGAAAAATTGGCGGC
CTTATTGGTGCAAATGTTTCGATTGGTCATACACTGAAATATGTTCAACCTGATTTCAAAACAATTTTAGAGAGCCCAAC
TGATAAAAAAGTAGGCTGGAAAGTGATATTTAACAATATGGTGAATCAAAATTGGGGACCATATGATAGAGATTCTTGGA
ACCCGGTATATGGCAATCAACTTTTCATGAAAACTAGAAATGGTTCTATGAAAGCAGCAGAGAACTTCCTTGATCCTAAC
AAAGCAAGTTCTCTATTATCTTCAGGGTTTTCACCAGACTTCGCTACAGTTATTACTATGGATAGAAAAGCATCCAAACA
ACAAACAAATATAGATGTAATATACGAACGAGTTCGTGATGACTACCAATTGCATTGGACTTCAACAAATTGGAAAGGTA
CCAATACTAAAGATAAATGGACAGATCGTTCTTCAGAAAGATATAAAATCGATTGGGAAAAGAAGAAATGACAAATTAA

SEQ ID NO:59 polynucleotide sequence
ATACACATGAAAATAAATATATCTCGAAGTTGCTAGTTGGGGCAGCAACAATTACTTTAGCTACAATGATTTCAAATGG
GGAAGCAAAAGCGAGTGAAAACACGCAACAAACTTCAACTAAGCACCAAACAACTCAAAACAACTACGTAACAGATCAAC
AAAAAGCTTTTTATCAAGTATTACATCTAAAAGGTATCACAGAAGAACAACGTAACCAATACATCAAAACATTACGCGAA
CACCCAGAACGTGCACAAGAAGTATTCTCTGAATCACTTAAAGACAGCAAGAACCCAGACCGACGTGTTGCACAACAAAA
CGCTTTTTACAATGTTCTTAAAAATGATAACTTAACTGAACAAGAAAAAAATAATTACATTGCACAAATTAAAGAAAACC
CTGATAGAAGCCAACAAGTTTGGGTAGAATCAGTACAATCTTCTAAAGCTAAGAACGTCAAAATATTGAAAATGCGGAT
AAAGCAATTAAAGATTTCCAAGATAACAAAGCACCACACAGATAAATCAGCAGCATATGAAGCTAACTCAAAATTACCTAA
AGATTTACGCGATAAAAATAACCGCTTTGTAGAAAAAGTTTCAATTGAAAAAGCAATCGTTCGTCATGATGAGCGTGTGA
AATCAGCAAATGATGCAATCTCAAAATTAAATGAAAAAGATTCAATTGAAAACAGACGTTTAGCACAACGTGAAGTTAAC
AAAGCACCTATGGATGTAAAAGAGCATTTACAGAAACAATTAGACGCATTAGTAGCTCAAAAAGATGCTGAAAAGAAAGT
GGCGCCAAAAGTTGAGGCTCCTCAAATTCAATCACCACAAATTGAAAAACCTAAAGCAGAATCACCAAAAGTTGAAGTCC
CTCAATCTAAATTATTAGGTTACTACCAATCATTAAAAGATTCATTTAACTATGGTTACAAGTATTTAACAGATACTTAT
AAAAGCTATAAAGAAAAATATGATACAGCAAAGTACTACTATAATACGTACTATAAATACAAAGGTGCGATTGATCAAAC
AGTATTAACAGTACTAGGTAGTGGTTCTAAATCTTACATCCAACCATTGAAAGTTGATGATAAAAACGGCTACTTAGCTA

FIGURE 2 cont.
AATCATATGCACAAGTAAGAAACTATGTAACTGAGTCAATCAATACTGGTAAAGTATTATATACTTTCTACCAAAACCCA
ACATTAGTAAAAACAGCTATTAAAGCTCAAGAAACTGCATCATCAATCAAAAATACATTAAGTAATTTATTATCATTCTG
GAAATAA

SEQ ID NO:60 polynucleotide sequence
ATGACAAAACATTATTTAAACAGTAAGTATCAATCAGAACAACGTTCATCAGCTATGAAAAAGATTACAATGGGTACAGC
ATCTATCATTTTAGGTTCCCTTGTATACATAGGCGCAGACAGCCAACAAGTCAATGCGGCAACAGAAGCTACGAACGCAA
CTAATAATCAAAGCACACAAGTTTCTCAAGCAACATCACAACCAATTAATTTCCAAGTGCAAAAAGATGGCTCTTCAGAG
AAGTCACACATGGATGACTATATGCAACACCCTGGTAAAGTAATTAAACAAAATAATAAATATTATTTCCAAACCGTGTT
AAACAATGCATCATTCTGGAAAGAATACAAATTTTACAATGCAAACAATCAAGAATTAGCAACAACTGTTGTTAACGATA
ATAAAAAAGCGGATACTAGAACAATCAATGTTGCAGTTGAACCTGGATATAAGAGCTTAACTACTAAAGTACATATTGTC
GTGCCACAAATTAATTACAATCATAGATATACTACGCATTTGGAATTTGAAAAAGCAATTCCTACATTAGCTGACGCAGC
AAAACCAAACAATGTTAAACCGGTTCAACCAAAACCAGCTCAACCTAAAACACCTACTGAGCAAACTAAACCAGTTCAAC
CTAAAGTTGAAAAAGTTAAACCTACTGTAACTACAACAAGCAAAGTTGAAGACAATCACTCTACTAAAGTTGTAAGTACT
GACACAACAAAAGATCAAACTAAAACACAAACTGCTCATACAGTTAAAACAGCACAAACTGCTCAAGAACAAAATAAAGT
TCAAACACCTGTTAAAGATGTTGCAACAGCGAAATCTGAAAGCAACAATCAAGCTGTAAGTGATAATAAATCACAACAAA
CTAACAAAGTTACAAAACATAACGAAACGCCTAAACAAGCATCTAAAGCTAAAGAATTACCAAAAACTGGTTTAACTTCA
GTTGATAACTTTATTAGCACAGTTGCCTTCGCAACACTTGCCCTTTTAGGTTCATTATCTTTATTACTTTTCAAAAGAAA
AGAATCTAAATAA

SEQ ID NO:61 polynucleotide sequence
ATGAACAAACAGCAAAAAGAATTTAAATCATTTTATTCAATTAGAAAGTCATCACTAGGCGTTGCATCTGTAGCGATTAG
TACACTTTTATTATTAATGTCAAATGGCGAAGCACAAGCAGCAGCTGAAGAAACAGGTGGTACAAATACAGAAGCACAAC
CAAAAACTGAAGCAGTTGCAAGTCCAACAACAACATCTGAAAAAGCTCCAGAAACTAAACCAGTAGCTAATGCTGTCTCA
GTATCTAATAAAGAAGTTGAGGCCCCTACTTCTGAAACAAAAGAAGCTAAAGAAGTTAAAGAAGTTAAAGCCCCTAAGGA
AACAAAAGCAGTTAAACCAGCAGCAAAAGCCACTAACAATACATATCCTATTTTGAATCAGGAACTTAGAGAAGCGATTA
AAAACCCTGCAATAAAAGATAAAGATCATAGCGCACCAAACTCTCGTCCAATTGATTTTGAAATGAAAAAAGAAAATGGT
GAGCAACAATTTTATCATTATGCCAGCTCTGTTAAACCTGCTAGAGTTATTTTCACTGATTCAAAACCAGAAATTGAATT
AGGATTACAATCAGGTCAATTTTGGAGAAAATTTGAAGTTTATGAAGGTGACAAAAAGTTGCCAATTAAATTAGTATCAT
ACGATACTGTTAAAGATTACGCTTACATTCGCTTCTCTGTTTCAAATGGAACAAAAGCCGTTAAAATTGTAAGTTCAACT
CACTTCAATAACAAAGAAGAAAAATACGATTACACATTAATGGAATTCGCACAACCAATTTATAACAGTGCAGATAAATT
CAAAACTGAAGAAGATTATAAAGCTGAAAAATTATTAGCGCCATATAAAAAAGCGAAAACACTAGAAAGACAAGTTTATG
AATTAAATAAAATTCAAGATAAACTTCCTGAAAAATTAAAGGCTGAGTACAAGAAGAAATTAGAGGATACAAAGAAAGCT
TTAGATGAGCAAGTGAAATCAGCTATTACTGAATTCCAAAATGTACAACCAACAAATGAAAAAATGACTGATTTACAAGA
TACAAAATATGTTGTTTATGAAAGTGTTGAGAATAACGAATCTATGATGGATACTTTTGTTAAACACCCTATTAAAACAG
GTATGCTTAACGGCAAAAAATATATGGTCATGGAAACTACTAATGACGATTACTGGAAAGATTTCATGGTTGAAGGTCAA
CGTGTTAGAACTATAAGCAAAGATGCTAAAAATAATACTAGAACAATTATTTTCCCATATGTTGAAGGTAAAACTCTATA
TGATGCTATCGTTAAAGTTCACGTAAAAACGATTGATTATGATGGACAATACCATGTCAGAATCGTTGATAAGAAGCAT
TTACAAAAGCCAATACCGATAAATCTAACAAAAAGAACAACAAGATAACTCAGCTAAGAAGGAAGCTACTCCAGCTACG
CCTAGCAAACCAACACCATCACCTGTTGAAAAAGAATCACAAAAACAAGACAGCCAAAAAGATGACAATAAACAATTACC
AAGTGTTGAAAAAGAAATGACGCATCTAGTGAGTCAGGTAAAGACAAAACGCCTGCTACAAAACCAACTAAAGGTGAAG
TAGAATCAAGTAGTACAACTCCAACTAAGGTAGTATCTACGACTCAAAATGTTGCAAAACCAACAACTGCTTCATCAAAA
ACAACAAAAGATGTTGTTCAAACTTCAGCAGGTTCTAGCGAAGCAAAAGATAGTGCTCCATTACAAAAAGCAAACATTAA
AAACACAAATGATGGACACACTCAAAGCCAAAACAATAAAAATACACAAGAAATAAAGCAAATCATTACCACAAACTG
GTGAAGAATCAAATAAAGATATGACATTACCATTAATGGCATTACTAGCTTTAAGTAGCATCGTTGCATTCGTATTACCT
AGAAAACGTAAAAACTAA

SEQ ID NO:62 polynucleotide sequence
ATGAATAATAAAAAGACAGCAACAAATAGAAAAGGCATGATACCAAATCGATTAAACAAATTTTCGATAAGAAAGTATTC
TGTAGGTACTGCTTCAATTTTAGTAGGGACAACATTGATTTTTGGGTTAAGTGGTCATGAAGCTAAAGCGGCAGAACATA
CGAATGGAGAATTAAATCAATCAAAAAATGAAACGACAGCCCCAAGTGAGAATAAAACAACTGAAAAAGTTGATAGTCGT
CAACTAAAAGACAATACGCAAACTGCAACTGCAGATCAGCCTAAAGTGACAATGAGTGATAGTGCAACAGTTAAAGAAAC
TAGTAGTAACATGCAATCACCACAAAACGCTACAGCTAGTCAATCTACTACACAAACTAGCAATGTAACAACAAATGATA
AATCATCAACTACATATAGTAATGAAACTGATAAAAGTAATTTAACACAAGCAAAAACGTTTCAACTACACCTAAAACA
ACGACTATTAAACAAAGAGCTTTAAATCGCATGGCAGTGAATACTGTTGCAGCTCCACAACAAGGAACAAATGTTAATGA
TAAAGTACATTTTACGAACATTGATATTGCGATTGATAAAGGACATGTTAATAAAACAACAGGAAATACTGAATTTTGGG
CAACTTCAAGTGATGTTTTAAAATTAAAAGCGAATTACACAATCGATGATTCTGTTAAGAGGGCGATACATTTACTTTT
AAATATGGTCAATATTTCCGTCCAGGTTCTGTAAGATTACCTTCACAAACTCAAAATTTATATAATGCCCAAGGTAATAT

FIGURE 2 cont.
```
TATTGCAAAAGGTATTTACGATAGTAAAACAAATACAACAACGTATACTTTTACGAATTATGTAGATCAATACACAAATG
TTAGCGGTAGCTTTGAACAAGTCGCATTTGCGAAACGTGAAAATGCAACAACTGATAAAACTGCTTATAAAATGGAAGTA
ACTTTAGGTAATGATACATATAGTAAAGATGTCATTGTCGATTATGGTAATCAAAAAGGTCAACAACTTATTTCGAGTAC
AAATTATATTAATAATGAAGATTTGTCACGTAATATGACTGTTTATGTAAATCAACCTAAAAAGACCTATACAAAAGAAA
CATTTGTAACAAATTTAACTGGTTATAAATTTAATCCAGATGCTAAAAACTTCAAAATTTACGAAGTGACAGATCAAAAT
CAATTTGTGGATAGTTTCACCCCAGATACTTCAAAACTTAAAGATGTTACTGGTCAATTCGATGTTATTTATAGTAATGA
TAATAAGACGGCGACAGTAGATTTATTGAATGGTCAATCTAGTAGTGATAAACAGTACATCATTCAACAAGTTGCTTATC
CAGATAATAGTTCAACAGATAATGGGAAATTGATTATACTTTAGAAACACAAAATGGAAAAGTAGTTGGTCAAACAGT
TATTCAAATGTGAATGGCTCATCAACTGCAAATGGCGACCAAAAGAAATATAATCTAGGTGACTATGTATGGGAAGATAC
AAATAAAGATGGTAAACAAGATGCCAATGAAAAGGGATTAAAGGTGTTTATGTCATTCTTAAAGATAGTAACGGTAAAG
AATTAGATCGTACGACAACAGATGAAAATGGTAAATATCAGTTCACTGGTTTAAGCAATGGAACTTATAGTGTAGAGTTT
TCAACACCAGCCGGTTATACACCGACAACTGCAAATGCAGGTACAGATGATGCTGTAGATTCTGATGGACTAACTACAAC
AGGTGTCATTAAAGACGCTGACAACATGACATTAGATAGTGGATTCTACAAAACACCAAAATATAGTTTAGGTGATTATG
TTTGGTACGACAGTAATAAAGATGGTAAACAAGATTCGACTGAAAAAGGAATTAAAGGTGTTAAAGTTACTTTGCAAAAC
GAAAAAGGCGAAGTAATTGGTACAACTGAAACAGATGAAAATGGTAAATACCGCTTTGATAATTTAGATAGTGGTAAATA
CAAAGTTATCTTTGAAAAGCCTGCTGGTTTAACTCAAACAGGTACAAATACAACTGAAGATGATAAAGATGCCGATGGTG
GCGAAGTTGATGTAACAATTACGGATCATGATGATTTCACACTTGATAATGGCTACTACGAAGAAGAAACATCAGATAGT
GACTCAGATTCGGACAGCGATTCAGACTCAGATAGCGACTCAGATTCAGATAGTGACTCAGACTCAGATAGCGACTCAGA
CTCAGATAGCGACTCAGACAGCGACTCAGACTCAGATAGTGATTCAGATTCGGACAGCGACTCAGATTCAGACAGCGAAT
CAGATTCGGATAGCGACTCAGACTCAGATAGCGACTCAGACAGCGACTCAGATTCAGACAGTGACTCAGACTCAGACAGC
GACTCAGATTCAGACAGCGATTCAGATTCGGATAGCGACTCAGATTCAGATAGCGATTCGGACTCAGACAACGACTCAGA
TTCTGACAGCGATTCAGACTCAGATAGCGACTCAGATTCAGACAGCGACTCAGATTCAGACAGCGATTCAGATTCAGATA
GCGATTCAGATTCAGACAGCGACTCAGATTCAGATAGCGACTCAGACTCAGACAGCGATTCAGACTCAGATAGCGACTCA
GACAGCGATTCAGATTCGGATAGCGATTCAGATTCAGATGCAGGTAAACATACTCCGACTAAACCAATGAGTACGGTTAA
AGATCAGCATAAAACAGCTAAAGCATTACCAGAAACAGGTAGTGAAAATAATAATTCAAATAATGGCACATTATTCGGTG
GATTATTCGCGGCATTAGGATCATTATTGTTATTCGGTCGTCGTAAAAAACAAAATAAATAA
```

SEQ ID NO:63 polynucleotide sequence
```
ATGAATATGAAGAAAAAGAAAAACACGCAATTCGGAAAAATCGATTGGCGTGGCTTCAGTGCTTGTAGGTACGTTAAT
CGGTTTTGGACTACTCAGCAGTAAAGAAGCAGATGCAAGTGAAAATAGTGTTACGCAATCTGATAGCGCAAGTAACGAAA
GCAAAAGTAATGATTCAAGTAGCGTTAGTGCTGCACCTAAAACAGACGACACAAACGTGAGTGATACTAAAACATCGTCA
AACACTAATAATGGCGAAACGAGTGTGGCGCAAAATCCAGCACAACAGGAAACGACACAATCATCATCAACAAATGCAAC
TACGGAAGAAACGCCGGTAACTGGTGAAGCTACTACTACGACAACGAATCAAGCTAATACACCGGCAACAACTCAATCAA
GCAATACAAATGCGGAGGAATTAGTGAATCAAACAAGTAATGAAACGACTTCTAATGATACTAATACAGTATCATCTGTA
AATTCACCTCAAAATTCTACAAATGCGGAAAATGTTTCAACAACGCAAGATACTTCAACTGAAGCAACACCTTCAAACAA
TGAATCAGCTCCACAGAATACAGATGCAAGTAATAAAGATGTAGTTAGTCAAGCGGTTAATCCAAGTACGCCTAGAATGA
GAGCATTTAGTTTAGCGGCAGTAGCTGCAGATGCACCGGCAGCTGGCACAGATATTACGAATCAGTTGACAGATGTGAAA
GTTACTATTGACTCTGGTACGACTGTGTATCCGCACCAAGCAGGTTATGTCAAACTGAATTATGGTTTTTCAGTGCCTAA
TTCTGCTGTTAAAGGTGACACATTCAAAATAACTGTACCTAAAGAATTAAACTTAAATGGTGTAACTTCAACTGCTAAAG
TGCCACCAATTATGGCTGGAGATCAAGTATTGGCAAATGGTGAATCGATAGTGATGGTAATGTTATTTATACATTTACA
GACTATGTTGATAATAAAGAAAATGTAACAGCTAATATTACTATGCCAGCTTATATTGACCCTGAAAATGTTACAAAGAC
AGGTAATGTGACATTGACAACTGGCATAGGAACCAATACTGCTAGTAAGACAGTATTAATCGACTATGAGAAATATGGAC
AATTCCATAATTTATCAATTAAAGGTACGATTGATCAAATCGATAAAACAAATAATACGTATCGCCAAACAATTTATGTC
AATCCAAGCGGAGATAACGTTGTGTTACCTGCCTTAACAGGTAATTTAATTCCTAATACAAAGAGTAATGCGTTAATAGA
TGCAAAAAACACTGATATTAAAGTTTATAGAGTCGATAATGCTAATGATTTATCTGAAAGTTATTATGTGAATCCTAGCG
ATTTTGAAGATGTAACTAATCAAGTTAGAATTTCATTTCCAAATGCTAATCAATACAAAGTAGAATTTCCTACGGACGAT
GACCAAATTACAACACCGTATATTGTAGTTGTTAATGGCCATATTGATCCTGCTAGTACAGGTGATTTAGCACTACGTTC
GACATTTTATGGTTATGATTCTAATTTTATATGGAGATCTATGTCATGGGACAACGAAGTAGCATTTAATAACGGATCAG
GTTCTGGTGACGGTATCGATAAACCAGTTGTTCCTGAACAACCTGGTGAGCCTGGTGAAATTGAACCAATTCCAGAGGAT
TCAGATTCTGACCCAGGTTCAGATTCTGGCAGCGATTCTAATTCAGATAGCGGTTTCAGATTCTGGCAGTGATTCTACATC
AGATAGTGGTTCAGATTCAGCGAGTGATTCAGATTCAGCAAGTGATTCAGACTCAGCGAGTGATTCAGATTCAGCAAGTG
ATTCAGATTCAGCAAGTGATTCAGATTCAGCAAGTGATTCAGACTCAGCAAGTGATTCAGATTCAGCAAGTGATTCAGAT
TCAGCAAGCGATTCAGATTCAGCGAGCGATTCAGATTCAGCGAGCGATTCAGATTCAGCGAGTGATTCCGACTCAGCGAG
CGATTCAGACTCAGATAGTGACTCAGATTCCGATAGCGATTCCGACTCAGATAGCGACTCAGATTCAGACAGCGATTCTG
ACTCAGACAGCGATTCTGACTCAGACAGTGACTCAGATTCCGATAGCGATTCTGACTCAGACAGTGACTCAGATTCCGAT
AGCGATTCAGATTCAGACAGTGATTCAGACTCAGATAGCGATTCAGATTCCGACAGTGACTCAGACTCAGACAGCGATTC
AGATTCCGATAGCGATTCAGATTCCGACAGTGACTCAGATTCCGATAGTGACTCGGATTCAGCGAGTGATTCAGATTCAG
ATAGCGATTCAGAATCAGATAGTGACTCAGACTCAGACAGTGATTCAGATTCAGATAGTGACTCAGACTCAGACAGCGAT
TCAGAATCAGATAGTGACTCCGATTCAGACAGCGATTCAGAATCAGATAGTGACTCCGATTCAGATAGCGATTCGGATTC
```

FIGURE 2 cont.
```
AGCGAGTGATTCAGACTCAGGTAGTGACTCCGATTCATCAAGTGATTCAGATTCCGATTCAACGAGTGACACAGGATCAG
ACAACGACTCAGACAGTGATTCAAATAGCGATTCCGAGTCAGGTTCTAACAATAATGTAGTTCCGCCTAATTCACCTAAA
AATGGTACTAATGCTTCTAATAAAAATGAGGCTAAAGATAGTAAAGAACCATTACCAGATACAGGTTCTGAAGATGAAGC
GAATACGTCACTAATTTGGGGATTATTAGCATCATTAGGTTCATTACTACTTTTCAGAAGAAAAAAAGAAAATAAAGATA
AGAAATAA
```

SEQ ID NO:64 polynucleotide sequence
```
GTGAAAAACAATCTTAGGTACGGCATTAGAAAACATAAATTGGGAGCAGCATCAGTATTCTTAGGAACAATGATCGTTGT
TGGGATGGGACAAGATAAAGAAGCTGCAGCATCAGAACAAAAGACAACTACAGTAGAAGAAAATGGGAATTCAGCTACTG
ATAATAAAACAAGTGAAACACAAACAACTGCTACTAACGTTAATCATATAGAAGAAACTCAATCATATAACGCAACAGTA
ACAGAACAACCGTCAAACGCAACACAAGTAACAACTGAAGAAGCACCAAAAGCAGTACAAGCACCACAAACTGCACAACC
AGCAAATGTAGAAACAGTTAAAGAAGAAGAGAAACCTCAAGTTAAGGAAACGACACAACCTCAAGACAATAGCGGAAATC
AAAGACAAGTAGATTTAACACCTAAAAAGGTTACACAAAATCAAGGGACAGAAACACAAGTTGAAGTGGCACAGCCAAGA
ACGGCATCAGAAAGTAAGCCACGTGTGACAAGATCAGCAGATGTAGCGGAAGCTAAGGAAGCTAGTGACGTTTCAGAAGT
TAAAGGCACAGATGTTACAAGTAAAGTTACAGTAGAAAGTGGTTCTATTGAGGCACCTCAAGGAAATAAAGTAGAGCCAC
ATGCTGGTCAACGTGTCGTATTGAAATACAAATTGAAATTCGCAGATGGATTAAAAAGAGGAGATTATTTTGATTTTACA
TTATCAAATAATGTAAATACTTATGGGGTTTCAACAGCTAGAAAGGTACCAGAGATTAAAAATGGCTCAGTTGTAATGGC
TACAGGTGAGATCTTAGGGAATGGTAACATAAGATATACATTTACTAACGAAATTGAACACAAGGTAGAGGTAACAGCTA
ATTTAGAAATCAACTTATTTATTGACCCTAAAACTGTACAAAGCAATGGAGAACAAAAGATTACTTCTAAATTAAATGGT
GAAGAAACAGAAAAAACAATACCAGTTGTTTATAATCCAGGTGTTAGCAATAGTTATACAAATGTAAATGGATCAATTGA
AACATTTAATAAAGAATCTAATAAATTTACACATATAGCTTATATTAAGCCAATGAATGGAAACCAGTCAAACACTGTAT
CAGTAACAGGGACGTTGACTGAAGGTAGTAATTTAGCTGGTGGACAACCTACTGTTAAAGTATATGAATATCTAGGGAAA
AAAGATGAATTGCCACAAAGTGTTTATGCAAATACATCAGATACTAACAAATTCAAAGATGTAACAAAGGAAATGAATGG
AAAATTGAGTGTGCAAGACAATGGTAGTTACTCATTGAATTTAGATAAGTTGGATAAAACGTATGTCATTCATTATACAG
GTGAATATTTGCAAGGGTCAGATCAGGTTAATTTTAGAACTGAATTATATGGGTATCCAGAACGAGCATATAAATCTTAC
TATGTTTATGGGGGATATCGTTTAACTTGGGATAATGGTTTAGTTTTATATAGCAATAAAGCTGACGGCAATGGTAAAAA
TGGACAAATTATTCAAGATAATGATTTTGAATATAAAGAAGATACTGCAAAAGGAACTATGAGCGGGCAGTACGATGCCA
AGCAAATTATTGAAACAGAAGAAAATCAAGACAATACACCGCTTGACATTGATTACCACACAGCTATAGATGGTGAGGGT
GGTTATGTTGATGGGTATATTGAAACAATAGAAGAAACGGATTCATCAGCTATTGATATCGATTACCATACTGCTGTGGA
TAGTGAAGTGGGTCACGTTGGAGGATACACTGAGTCCTCTGAGGAATCAAATCCAATTGACTTTGAAGAATCGACACATG
AAAATTCAAAACATCACGCTGATGTTGTTGAATATGAAGAGGATACAAATCCAGGTGGTGGCCAAGTAACAACTGAGTCT
AACTTAGTTGAATTTGACGAAGAGTCTACAAAAGGTATTGTAACTGGCGCAGTGAGCGACCATACAACAATTGAAGATAC
GAAAGAATATACGACTGAAAGTAATCTGATTGAACTAGTAGATGAACTACCTGAAGAACATGGTCAAGCACAAGGACCAA
TCGAGGAAATTACTGAAAACAATCATCATATTTCTCATTCTGGTTTAGGAACTGAAAATGGTCACGGTAATTATGGCGTG
ATTGAAGAAATCGAAGAAAATAGCCACGTTGATATTAAGAGTGAATTAGGTTACGAAGGTGGCCAAAATAGCGGTAACCA
GTCATTCGAGGAAGACACAGAAGAAGACAAACCTAAATATGAACAAGGTGGCAATATCGTAGATATCGATTTCGACAGTG
TACCTCAAATTCATGGTCAAAATAAAGGTGACCAGTCATTCGAAGAAGATACAGAGAAAGACAAGCCTAAATATGAACAT
GGCGGTAATATCATTGATATCGACTTCGACAGTGTGCCACAAATTCATGGATTCAATAAGCATAATGAAATTATTGAAGA
AGATACAAACAAAGATAAACCTAATTATCAATTCGGTGGACACAATAGTGTTGACTTTGAAGAAGATACACTTCCAAAAG
TAAGCGGCCAAAATGAAGGTCAACAAACGATTGAAGAAGATACAACGCCGCCAACGCCACCGACACCAGAAGTACCGAGT
GAGCCGGAAACACCAATGCCACCGACACCAGAAGTACCGAGTGAGCCGGAAACACCAACGCCACCAACACCAGAGGTACC
AAGTGAGCCGGAAACACCAACACCACCGACTCCGGAAGTACCAAGTGAGCCGGAAACACCAACACCACCGACACCAGAAG
TGCCGAGTGAGCCAGAAACACCAACACCGCCAACACCAGAGGTACCAGCTGAACCTGGTAAACCAGTACCACCCGCAAAA
GAAGAACCTAAAAAGCCTTCTAAACCAGTGGAACAAGGTAAAGTAGTAACACCTGTTATTGAAATCAATGAAAAGGTTAA
AGCAGTGGCACCAACTAAAAAAGCACAATCTAAGAAATCTGAACTACCTGAAACAGGTGGAGAAGAATCAACAAACAAAG
GTATGTTGTTCGGCGGATTATTCAGCATTCTAGGTTTAGCATTATTACGCAGAAATAAAAAGAATAACAAAGCATAA
```

SEQ ID NO:65 polynucleotide sequence
```
TTGAAAAAAAGAATTGATTATTTGTCGAATAAGCAGAATAAGTATTCGATTAGACGTTTTACAGTAGGTACCACATCAGT
AATAGTAGGGGCAACTATACTATTTGGGATAGGCAATCATCAAGCACAAGCTTCAGAACAATCGAACGATACAACGCAAT
CTTCGAAAAATAATGCAAGTGCAGATTCCGAAAAAAACAATATGATAGAAACACCTCAATTAAATACAACGGCTAATGAT
ACATCTGATATTAGTGCAAACACAAACAGTGCGAATGTAGATAGCACAACAAAACCAATGTCTACACAAACGAGCAATAC
CACTACAACAGAGCCAGCTTCAACAAATGAAACACCTCAACCGACGGCAATTAAAAATCAAGCAACTGCTGCAAAAATGC
AAGATCAAACTGTTCCTCAAGAAGCAAATTCTCAAGTAGATAATAAAACAACGAATGATGCTAATAGCATAGCAACAAAC
AGTGAGCTTAAAAATTCTCAAACATTAGATTTACCACAATCATCACCACAAACGATTTCCAATGCGCAAGGAACTAGTAA
ACCAAGTGTTAGAACGAGAGCTGTACGTAGTTTAGCTGTTGCTGAACCGGTAGTAAATGCTGCTGATGCTAAAGGTACAA
ATGTAAATGATAAAGTTACGGCAAGTAATTTCAAGTTAGAAAAGACTACATTTGACCCTAATCAAAGTGGTAACACATTT
ATGGCGGCAAATTTTACAGTGACAGATAAAGTGAAATCAGGGGATTATTTTACAGCGAAGTTACCAGATAGTTTAACTGG
TAATGGAGACGTGGATTATTCTAATTCAAATAATACGATGCCAATTGCAGACATTAAAAGTACGAATGGCGATGTTGTAG
```

FIGURE 2 cont.
CTAAAGCAACATATGATATCTTGACTAAGACGTATACATTTGTCTTTACAGATTATGTAAATAATAAAGAAAATATTAAC
GGACAATTTTCATTACCTTTATTTACAGACCGAGCAAAGGCACCTAAATCAGGAACATATGATGCGAATATTAATATTGC
GGATGAAATGTTTAATAATAAAATTACTTATAACTATAGTTCGCCAATTGCAGGAATTGATAAACCAAATGGCGCGAACA
TTTCTTCTCAAATTATTGGTGTAGATACAGCTTCAGGTCAAAACACATACAAGCAAACAGTATTTGTTAACCCTAAGCAA
CGAGTTTTAGGTAATACGTGGGTGTATATTAAAGGCTACCAAGATAAAATCGAAGAAAGTAGCGGTAAAGTAAGTGCTAC
AGATACAAAACTGAGAATTTTTGAAGTGAATGATACATCTAAATTATCAGATAGCTACTATGCAGATCCAAATGACTCTA
ACCTTAAAGAAGTAACAGACCAATTTAAAAATAGAATCTATTATGAGCATCCAAATGTAGCTAGTATTAAATTTGGTGAT
ATTACTAAAACATATGTAGTATTAGTAGAAGGGCATTACGACAATACAGGTAAGAACTTAAAAACTCAGGTTATTCAAGA
AAATGTTGATCCTGTAACAAATAGAGACTACAGTATTTTCGGTTGGAATAATGAGAATGTTGTACGTTATGGTGGTGGAA
GTGCTGATGGTGATTCAGCAGTAAATCCGAAAGACCCAACTCCAGGGCCGCCGGTTGACCCAGAACCAAGTCCAGACCCA
GAACCAGAACCAACGCCAGATCCAGAACCAAGTCCAGACCCAGAACCGGAACCAAGCCCAGACCCGGATCCGGATTCGGA
TTCAGACAGTGACTCAGGCTCAGACAGCGACTCAGGTTCAGATAGCGACTCAGAATCAGATAGCGATTCGGATTCAGACA
GTGATTCAGATTCAGACAGCGACTCAGAATCAGATAGCGATTCAGAATCAGATAGCGACTCAGATTCAGATAGCGATTCA
GATTCAGATAGCGATTCAGAATCAGATAGCGATTCGGATTCAGACAGTGATTCAGATTCAGACAGCGACTCAGAATCAGA
TAGCGACTCAGAATCAGATAGTGAGTCAGATTCAGACAGTGACTCGGACTCAGACAGTGATTCAGACTCAGATAGCGATT
CAGACTCAGATAGCGATTCAGACTCAGACAGCGATTCAGATTCAGACAGCGACTCAGAATCAGACAGCGACTCAGACTCA
GATAGCGACTCAGACTCAGACAGCGACTCAGATTCAGATAGCGATTCAGACTCAGACAGCGACTCAGACTCAGACAGCGA
CTCAGACTCAGATAGCGATTCAGACTCAGACAGCGACTCAGATTCAGATAGCGATTCGGACTCAGACAGCGATTCAGATT
CAGACAGCGACTCAGACTCGGATAGCGATTCAGATTCAGACAGCGACTCAGACTCGGATAGCGACTCGGATTCAGATAGT
GACTCCGATTCAAGAGTTACACCACCAAATAATGAACAGAAAGCACCATCAAATCCTAAAGGTGAAGTAAACCATTCTAA
TAAGGTATCAAAACAACACAAAACTGATGCTTTACCAGAAACAGGAGATAAGAGCGAAAACACAAATGCAACTTTATTTG
GTGCAATGATGGCATTATTAGGATCATTACTATTGTTTAGAAAACGCAAGCAAGATCATAAAGAAAAAGCGTAA

SEQ ID NO:66 polynucleotide sequence
ATGAAAAAGCAAATAATTTCGCTAGGCGCATTAGCAGTTGCATCTAGCTTATTTACATGGGATAACAAAGCAGATGCGAT
AGTAACAAAGGATTATAGTAAAGAATCAAGAGTGAATGAGAAAGTAAAAAGGGAGCTACTGTTTCAGATTATTACTATT
GGAAAATAATTGATAGTTTAGAGGCACAATTTACTGGAGCAATAGACTTATTGGAAGATTATAAATATGGAGATCCTATC
TATAAAGAAGCGAAAGATAGATTGATGACAAGAGTTATTAGGAGAAGACCAGTATTTATTAAAGAAAAAGGATTGATGAATA
TGAGCTTTATAAAAAGTGGTATAAAAGTTCAAATAAGAACACTAATATGCTTACTTTCCATAAATATAATCTTTACAATT
TAACAATGAATGAATATAACGATATTTTTAACTCTTTGAAAGATGCAGTTTATCAATTTAATAAAGAAGTTAAAGAAATA
GAGCATAAAAATGTTGACTTGAAGCAGTTTGATAAAGATGGAGAAGACAAGGCAACTAAAGAAGTTTATGACCTTGTTTC
TGAAATTGATACATTAGTTGTAACTTATTATGCTGATAAGGATTATGGGGAGCATGCGAAAGAGTTACGAGCAAAACTGG
ACTTAATCCTTGGAGATACAGACAATCCACATAAAATTACAAATGAGCGTATAAAAAAAGAAATGATCGATGACTTAAAT
TCAATTATAGATGATTTCTTTATGGAGACTAAACAAAATAGACCGAATTCTATAACAAAATATGATCCAACAAAACACAA
TTTTAAAGAGAAGAGTGAAAATAAACCTAATTTTGATAAATTAGTTGAAGAAACAAAAAAAGCAGTTAAAGAAGCAGACG
AATCTTGGAAAAATAAAACTGTCAAAAAATACGAGGAAACTGTAACAAAATCTCCTGTTGTAAAAGAAGAGAAGAAAGTT
GAAGAACCTCAATTACCTAAAGTTGGAAACCAGCAAGAGGTTAAAACTACGGCTGGTAAAGCTGAAGAAAACAACACAACC
AGTGGCACAGCCATTAGTAAAAATTCCACAAGAAACAATCTATGGTGAAACTGTAAAAGGTCCAGAATATCCAACGATGG
AAAATAAAACGTTACAAGGTGAAATCGTTCAAGGTCCCGATTTTCTAACAATGGAACAAAACAGACCATCTTTAAGCGAT
AATTATACTCAACCGACGACACCGAACCCTATTTTAGAAGGTCTTGAAGGTAGCTCATCTAAACTTGAAATAAAACCACA
AGGTACTGAATCAACGTTGAAAGGTATTCAAGGAGAATCAAGTGATATTGAAGTTAAACCTCAAGCAACTGAAACAACAG
AAGCTTCTCAATATGGTCCGAGACCGCAATTTAACAAAACACCTAAGTATGTGAAATATAGAGATGCTGGTACAGGTATC
CGTGAATACAACGATGGAACATTTGGATATGAAGCGAGACCAAGATTCAACAAGCCAAGTGAAACAAATGCATACAACGT
AACGACAAATCAAGATGGCACAGTATCATACGGAGCTCGCCCAACACAAAACAAGCCAAGTGAAACAAACGCATATAACG
TAACAACACATGCAAATGGTCAAGTATCATACGGTGCTCGCCCAACACAAAAAAGCCAAGCAAACAAATGCATACAAC
GTAACAACACATGCAAATGGTCAAGTATCATATGGCGCTCGCCCGACACAAAAAAAGCCAAGCAAACAAATGCATATAA
CGTAACAACACATGCAAATGGTCAAGTATCATACGGAGCTCGCCCGACATACAAGAAGCCAAGCGAAACAAATGCATACA
ACGTAACAACACATGCAAATGGTCAAGTATCATATGGCGCTCGCCCGACACAAAAAAGCCAAGCGAAACAAACGCATAT
AACGTAACAACACATGCAGATGGTACTGCGACATATGGGCCTAGAGTAACAAAATAA

SEQ ID NO:77 polynucleotide sequence
GTGAAAAGCAATCTTAGATACGGCATAAGAAAACACAAATTGGGAGCGGCCTCAGTATTCTTAGGAACAATGATCGTTGT
TGGAATGGGACAAGAAAAAGAAGCTGCAGCATCGGAACAAAACAATACTACAGTAGAGGAAAGTGGGAGTTCAGCTACTG
AAAGTAAAGCAAGCGAAACACAAACAACTACAAATAACGTTAATACAATAGATGAAACACAATCATACAGCGCGACATCA
ACTGAGCAACCATCAAAATCAACTCAAGTAACAACAGAAGAAGCACCAACAACTGTGCAAGCACCAAAAGTAGAAACCGA
AATGAAATCACAAGAAGATTTACCATCAGAAAAAGTTGCTGATAAGGAAACTACAGGAACTCAAGTTGACATAGCTCAAC
CAAGTAACGTCTCAGAAATTAAACCAAGAATGAAAAGATCAGCTGACGTTACAGCAGTTTCAGAGAAAGAAGTAGCGGAA
GAAGCTAAAGCGACAGGTACAGATGTAACAAATAAAGTGGAAGTTACTGAAAGCTCTTTAGAAGGACATAATAAAGATTC
GAATATTGTTAATCCGCATAATGCTCAAAGAGTAACTTTAAAATACAAATGGAAATTTGGAGAAGGAATTAAGGCAGGAG

FIGURE 2 cont.
ATTATTTTGATTTCACATTAAGTGATAATGTTGAAACACATGGTATATCAACACTGCGTAAAGTTCCGGAGATAAAAAGT
TCAACAGAAGATAAAGTTATGGCAAATGGTCAAGTTATAAATGAACGTACAATTCGCTATACATTTACTGATTATATAAA
TAACAAAAAAGATTTAACTGCTGAATTAAACTTAAACCTATTCATTGACCCAACAACAGTGACAAAGCAAGGGAGTCAAA
AAGTTGAAGTAACACTAGGTCAAAATAAAGTCTCAAAAGAATTTGATATCAAATATTTAGACGGCGTTAAAGATAGAATG
GGTGTTACTGTTAATGGTCGTATTGATACTTTGAATAAAGAAGAGGGTAAATTTAGCCATTTTGCATATGTGAAGCCTAA
CAACCAGTCGTTAACTTCTGTCACAGTAACTGGTCAAGTAACATCTGGATATAAACAAAGTGCTAATAATCCAACAGTCA
AAGTATATAAACACATTGGTTCAGATGAATTAGCTGAAAGTGTTTATGCAAAGCTTGATGATACCAGTAAATTTGAAGAT
GTGACTGAAAAAGTAAATCTATCTTACACAAGTAATGGTGGGTACACATTGAACCTTGGCGATTTAGATAATTCGAAAGA
CTATGTAATTAAATATGAAGGTGAATATGATCAAAATGCTAAGGATCTAAATTTCCGAACACATCTTTCAGGATATCATA
AATACTACCCATACTATCCTTATTACCCGTATTATCCAGTTCAATTAACTTGGAACAACGGTGTTGCATTTTACTCTAAT
AATGCTAAAGGCGATGGTAAAGATAAACCAAATGATCCTATCATTGAGAAGAGTGAACCAATTGATTTAGACATTAAATC
AGAGCCACCAGTGGAGAAGCATGAATTGACTGGTACAATCGAAGAAAGTAACGATTCTAAGCCAATTGATTTTGAATATC
ATACAGCTGTTGAAGGTGCAGAAGGTCATGCAGAAGGTATTATTGAAACTGAAGAAGATTCTATTCATGTGGATTTTGAA
GAATCTACACATGAAAATTCAAAACATCACGCTGATGTTGTTGAATATGAAGAGGATACAAACCCAGGTGGTGGCCAAGT
AACAACTGAGTCTAACTTAGTTGAATTTGACGAAGAGTCTACAAAAGGTATTGTAACTGGCGCAGTGAGCGACCATACAA
CAGTTGAAGATACGAAAGAATATACAACTGAAAGTAATCTGATTGAATTAGTGGATGAATTACCTGAAGAACATGGTCAA
GCACAAGGGCCAATCGAGGAAATTACTGAAAACAATCATCATATTTCTCATTCTGGTTTAGGAACTGAAAATGGTCACGG
TAATTATGGCGTGATTGATGAAATCGAAGAAAATAGCCACGTTGATATTAAGAGTGAATTAGGTTATGAAGGTGGCCAAA
ATAGCGGTAATCAGTCATTCGAGGAAGACACAGAAGAAGATAAACCTAAATATGAACAAGGTGGTAATATCGTAGATATC
GATTTCGACAGTGTACCTCAAATTCATGGTCAAAATAATGGTAACCAGTCATTCGAGGAAGACACAGAAGAAGACAAGCC
TAAGTATGAACAAGGTGGTAACATCATTGATATCGACTTCGACAGTGTGCCACAAATTCATGGATTCAATAAGCATAATG
AAATTATTGAAGAAGATACAAACAAAGATAAACCTAATTATCAATTTGGTGGACACAACAGTGTTGATTTGAAGAAGAT
ACACTTCCAAAAGTAAGTGGTCAAAATGAAGGTCAACAAACGATTGAAGAAGATACAACGCCGCCAACACCGCCAACACC
AGAGGTACCAAGTGAGCCGGAAACACCAACACCACCAACACCAGAAGTACCGAGTGAGCCAGGCGAACCAACGCCACCAA
AACCGGAAGTACCAAGTGAGCCGGAAACACCAGTACCACCAACACCAGAGGTACCATCTGAACCTGGTAAACCAGTACCA
CCTGCTAAAGAAGAACCTAAAAAACCTTCTAAACCAGTGGAACAAGGTAAGGTAGTAACACCTGTTATTGAAATCAATGA
AAAGGTTAAAGCAGTGGCACCAACTAAACAAAAACAATCTAAGAAATCTGAACTACCTGAAACAGGTGGAGAAGAATCAA
CAAACAAAGGTATGTTGTTCGGCGGATTATTCAGCATTCTAGGTTTAGTATTATTACGCAGAAATAAAAAGAATAACAAA
GCATAA

SEQ ID NO:78 polynucleotide sequence
ATGAAATTTAAGTCATTGATTACAACAACATTAGCATTAGGCGTTATAGCATCAACAGGAGCAAACTTTAATACTAACGA
AGCATCTGCCGCAGCTAAGCCATTAGATAAATCATCAAGTACATTACACCATGGACATTCTAACATCCAGATTCCATATA
CAATTACTGTGAACGGTACAAGCCAAAACATTTTATCAAGCTTAACATTTAATAAGAATCAAAATATTAGTTATAAAGAT
ATAGAGAATAAAGTTAAATCAGTTTTATACTTTAATAGAGGTATTAGTGATATCGATTTAAGACTTTCAAAGCAAGCGGA
ATATACGGTTCATTTTAAAAATGGAACAAAAAGAGTTATCGATTTGAAATCAGGTATCTACACAGCTGACTTAATCAATA
CAAGTGACATTAAAGCTATCAGTGTTAACGTAGATACTAAAAAGCAACCTAAAGATAAAGCTAAAGCAAATGTTCAAGTG
CCATATACAATCACAGTGAACGGCACAAGCCAAAACATTTTATCAAACCTAACATTTAATAAAAATCAAAATATTAGTTA
CAAAGATTTAGAGGGTAAAGTTAAATCAGTTTTTAGAATCAAATAGAGGTATTACTGATGTTGATTTAAGACTTTCGAAGC
AAGCGAAATATACAGTTAATTTTAAAAATGGAACGAAGAAAGTTATCGATTTGAAATCAGGTATTTACACAGCGAATTTA
ATCAATTCAAGTGATATTAAAAGTATCAATATTAACGTAGATACAAAAAAACATATCGAAAATAAAGCTAAAAGAAACTA
TCAAGTTCCATATTCAATTAATCTAAATGGTACATCTACAAACATTTTATCGAATCTTTCATTTTCAAATAAACCTTGGA
CAAATTACAAAAATTTAACTAGTCAAATAAATCAGTACTGAAGCATGATAGAGGTATTAGTGAACAAGATTTAAAAATAT
GCTAAGAAAGCTTATTATACTGTTTATTTTAAAAATGGTGGTAAAAGAATCTTACAGTTAAATTCAAAAAATTACACAGC
AAACTTAGTTCATGCGAAAGATGTTAAGAGAATTGAAATTACTGTTAAAACAGGAACTAAAGCGAAAGCAGACAGATATG
TACCATACACAATTGCAGTAAATGGCACATCAACACCAATTTTATCAAAACTAAAAATTTCGAATAAACAATTAATTAGT
TACAAATATTTAAACGACAAAGTGAAATCTGTATTAAAAAGTGAAAGAGGTATCAGTGATCTTGACTTAAAATTTGCGAA
ACAAGCAAAATATACAGTATATTTCAAAAATGGAAAGAAACAAGTAGTGAATTTAAAATCAGACATCTTTACACCTAATT
TATTTAGTGCCAAAGATATTAAAAAGATTGATATTGATGTAAAACAATACACTAAATCAAAAAAAAAATAAATAAATCT
AATAATGTGAAATTCCCAGTAACAATAAATAAATTTGAAAACATAGTTTCAAATGAATTTGTGTTCTATAATGCAAGCAA
AATTACAATTAATGATTTAAGTATAAAACTTAAATCAGCAATGGCAAATGATCAAGGGATAACTAAACATGACATAGGAC
TTGCTGAACGCGCAGTGTATAAAGTGTATTTTAAAAATGGTTCGTCAAAATATGTAGACTTAAAAACTGAGTATAAAGAT
GAAAGAGTATTTAAAGCAACTGACATTAAAAAGGTAGATATTGAACTTAAATTCTAA

SEQ ID NO:79 polynucleotide sequence
ATGAACAAACATCACCCAAAATTAAGGTCTTTCTATTCTATTAGAAAATCAACTCTAGGC
GTTGCATCGGTCATTGTCAGTACACTATTTTTAATTACTTCTCAACATCAAGCACAAGCA
GCAGAAAATACAAATACTTCAGATAAAATCTCGGAAAATCAAAATAATAATGCAACTACA
ACTCAGCCACCTAAGGATACAAATCAAACACAACCTGCTACGCAACCAGCAAACACTGCG

FIGURE 2 cont.
```
AAAAACTATCCTGCAGCGGATGAATCACTTAAAGATGCAATTAAAGATCCTGCATTAGAA
AATAAAGAACATGATATAGGTCCAAGAGAACAAGTCAATTTCCAGTTATTAGATAAAAAC
AATGAAACGCAGTACTATCACTTTTTCAGCATCAAAGATCCAGCAGATGTGTATTACACT
AAAAAGAAAGCAGAAGTTGAATTAGACATCAATACTGCTTCAACATGGAAGAAGTTTGAA
GTCTATGAAAACAATCAAAAATTGCCAGTGAGACTTGTATCATATAGTCCTGTACCAGAA
GACCATGCCTATATTCGATTCCCAGTTTCAGATGGCACACAAGAATTGAAAATTGTTTCT
TCGACTCAAATTGATGATGGAGAAGAAACAAATTATGATTATACTAAATTAGTATTTGCT
AAACCTATTTATAACGATCCTTCACTTGTAAAATCAGATACAAATGATGCAGTAGTAACG
AATGATCAATCAAGTTCAGTCGCAAGTAATCAAACAAACACGAATACATCTAATCAAAAT
ATATCAACGATCAACAATGCTAATAATCAACCGCAGGCAACGACCAATATGAGTCAACCT
GCACAACCAAAATCGTCAACGAATGCAGATCAAGCGTCAAGCCAACCAGCTCATGAAACA
AATTCTAATGGTAATACTAACGATAAAACGAATGAGTCAAGTAATCAGTCGGATGTTAAT
CAACAGTATCCACCAGCAGATGAATCACTACAAGATGCAATTAAAAACCCGGCTATCATC
GATAAAGAACATACAGCTGATAATTGGCGACCAATTGATTTTCAAATGAAAATGATAAA
GGTGAAAGACAGTTCTATCATTATGCTAGTACTGTTGAACCAGCAACTGTCATTTTTACA
AAAACAGGACCAATAATTGAATTAGGTTTAAAGACAGCTTCAACATGGAAGAAATTTGAA
GTTTATGAAGGTGACAAAAGTTACCAGTCGAATTAGTATCATATGATTCTGATAAAGAT
TATGCCTATATTCGTTTCCCAGTATCTAATGGTACGAGAGAAGTTAAAATTGTGTCATCT
ATTGAATATGGTGAGAACATCCATGAAGACTATGATTATACGCTAATGGTCTTTGCACAG
CCTATTACTAATAACCCAGACGACTATGTGGATGAAGAAACATACAATTTACAAAAATTA
TTAGCTCCGTATCACAAAGCTAAAACGTTAGAAAGACAAGTTTATGAATTAGAAAAATTA
CAAGAGAAATTGCCAGAAAAATATAAGGCGGAATATAAAAAGAAATTAGATCAAACTAGA
GTAGAGTTAGCTGATCAAGTTAAATCAGCAGTGACGGAATTTGAAAATGTTACACCTACA
AATGATCAATTAACAGATTTACAAGAAGCGCATTTTGTTGTTTTTGAAAGTGAAGAAAAT
AGTGAGTCAGTTATGGACGGCTTTGTTGAACATCCATTCTATACAGCAACTTTAAATGGT
CAAAAATATGTAGTGATGAAAACAAAGGATGACAGTTACTGGAAAGATTTAATTGTAGAA
GGTAAACGTGTCACTACTGTTTCTAAAGATCCTAAAAATAATTCTAGAACGCTGATTTTC
CCATATATACCTGACAAAGCAGTTTACAATGCGATTGTTAAAGTCGTTGTGGCAAACATT
GGTTATGAAGGTCAATATCATGTCAGAATTATAAATCAGGATATCAATACAAAAGATGAT
GATACATCACAAAATAACACGAGTGAACCGCTAAATGTACAAACAGGACAAGAAGGTAAG
GTTGCTGATACAGATGTAGCTGAAAATAGCAGCACTGCAACAAATCCTAAAGATGCGTCT
GATAAAGCAGATGTGATAGAACCAGAGTCTGACGTGGTTAAAGATGCTGATAATAATATT
GATAAAGATGTGCAACATGATGTTGATCATTTATCCGATATGTCGGATAATAATCACTTC
GATAAATATGATTTAAAAGAAATGGATACTCAAATTGCCAAAGATACTGATAGAAATGTG
GATAAAGATGCCGATAATAGCGTTGGTATGTCATCTAATGTCGATACTGATAAAGACTCT
AATAAAAATAAAGACAAAGTCATACAGCTGAATCATATTGCCGATAAAAATAATCATACT
GGAAAAGCAGCAAAGCTTGACGTAGTGAAACAAAATTATAATAATACAGACAAAGTTACT
GACAAAAAACAACTGAACATCTGCCGAGTGATATTCATAAAACTGTAGATAAAACAGTG
AAAACAAAAGAAAAAGCCGGCACACCATCGAAAGAAAACAAACTTAGTCAATCTAAAATG
CTACCAAAAACTGGAGAAACAACTTCAAGCCAATCATGGTGGGGCTTATATGCGTTATTA
GGTATGTTAGCTTTATTCATTCCTAAATTCAGAAAAGAATCTAAATAA
```

SEQ ID NO:80 polynucleotide sequence
```
GCTGAGACGACACAAGATCAAACTACTAATAAAAACGTTTTAGATAGTAATAAAGTTAAA
GCAACTACTGAACAAGCAAAAGCTGAGGTAAAAAATCCAACGCAAAACATTTCTGGCACT
CAAGTATATCAAGACCCTGCTATTGTCCAACCAAAAACAGCAAATAACAAAACAGGCAAT
GCTCAAGTAAGTCAAAAAGTTGATACTGCACAAGTAAATGGTGACACTCGTGCTAATCAA
TCAGCGACTACAAATAATACGCAGCCTGTTGCAAAGTCAACAAGCACTACAGCACCTAAA
ACTAACACTAATGTTACAAATGCTGGTTATAGTTTAGTTGATGATGAAGATGATAATTCA
GAAAATCAAATTAATCCAGAATTAATTAAATCAGCTGCTAAACCTGCAGCTCTTGAAACG
CAATATAAAACCGCAGCACCTAAAGCTGCAACTACATCAGCACCTAAAGCTAAAACTGAA
GCGACACCTAAAGTAACTACTTTTAGCGCTTCAGCACAACCAAGATCAGTTGCTGCAACA
CCAAAAACGAGTTTGCCAAAATATAAACCACAAGTAAACTCTTCAATTAACGATTACATT
TGTAAAAATAACTTAAAAGCACCTAAATTGAAGAAGATTATACATCTTACTTCCCTAAA
TACGCATACCGTAACGGCGTAGGTCGTCCTGAAGGTATCGTAGTTCATGATACAGCTAAT
GATCGTTCGACGATAAATGGTGAAATTAGTTATATGAAAATAACTATCAAACGCATTC
GTACATGCATTTGTTGATGGGGATCGTATAATCGAAACAGCACCAACGGATTACTTATCT
TGGGGTGTCGGTGCAGTCGGTAACCCTAGATTCATCAATGTTGAAATCGTACACACACAC
```

FIGURE 2 cont.

GACTATGCTTCATTTGCACGTTCAATGAATAACTATGCTGACTATGCAGCTACACAATTA
CAATATTATGGTTTAAAACCAGACAGTGCTGAGTATGATGGAAATGGTACAGTATGGACT
CACTACGCTGTAAGTAAATATTTAGGTGGTACTGACCATGCCGATCCACATGGATATTTA
AGAAGTCATAATTATAGTTATGATCAATTATATGACTTAATTAATGAAAAATATTTAATA
AAAATGGGTAAAGTGGCGCCATGGGGTACGCAATCTACAACTACCCCTACTACACCATCA
AAACCAACAACACCGTCGAAACCATCAACTGGTAAATTAACAGTTGCTGCAAACAATGGT
GTCGCACAAATCAAACCAACAAATAGTGGTTTATATACTACTGTATACGACAAAACTGGT
AAAGCAACTAATGAAGTTCAAAAAACATTTGCTGTATCTAAAACAGCTACATTAGGTAAT
CAAAAATTCTATCTTGTTCAAGATTACAATTCTGGTAATAAATTTGGTTGGGTTAAAGAA
GGCGATGTGGTTTACAACACAGCTAAATCACCTGTAAATGTAAATCAATCATATTCAATC
AAACCTGGTACGAAACTTTATACAGTACCTTGGGGTACATCTAAACAAGTTGCTGGTAGT
GTGTCTGGCTCTGGAAACCAAACATTTAAGGCTTCAAAGCAACAACAAATTGATAAATCA
ATTTATTTATATGGCTCTGTGAATGGTAAATCTGGTTGGGTAAGTAAAGCATATTTAGTT
GATACTGCTAAACCTACGCCTACACCAACACCTAAGCCATCAACACCTACAACAAATAAT
AAATTAACAGTTTCATCATTAAACGGTGTTGCTCAAATTAATGCTAAAAACAATGGCTTA
TTCACTACAGTTTATGACAAAACTGGTAAGCCAACGAAAGAAGTTCAAAAAACATTTGCT
GTAACAAAAGAAGCAAGTTTAGGTGGAAACAAATTCTACTTAGTTAAAGATTACAATAGT
CCAACTTTAATTGGTTGGGTTAAACAAGGTGACGTTATTTATAACAATGCAAAATCACCT
GTAAATGTAATGCAAACATATACAGTAAAACCAGGCACTAAATTATATTCAGTACCTTGG
GGCACTTATAAACAAGAAGCTGGTGCAGTTTCTGGTACAGGTAACCAAACTTTTAAAGCG
ACTAAGCAACAACAAATTGATAAATCTATCTATTTATTTGGAACTGTAAATGGTAAATCT
GGTTGGGTAAGTAAAGCATATTTAGCTGTACCTGCTGCACCTAAAAAAGCAGTAGCACAA
CCAAAAACAGCTGTAAAA

SEQ ID NO: 81 polynucleotide sequence

GCTTATACTGTTACTAAACCACAAACGACTCAAACAGTTAGCAAGATTGCTCAAGTTAAA
CCAAACAACACTGGTATTCGTGCTTCTGTTTATGAAAAAACAGCGAAAAACGGTGCGAAA
TATGCAGACCGTACGTTCTATGTAACAAAAGAGCGTGCTCATGGTAATGAAACGTATGTA
TTATTAAACAATACAAGCCATAACATCCCATTAGGTTGGTTCAATGTAAAAGACTTAAAT
GTTCAAAACTTAGGCAAAGAAGTTAAAACGACTCAAAAATATACTGTTAATAAATCAAAT
AACGGCTTATCAATGGTTCCTTGGGGTACTAAAAACCAAGTCATTTTAACAGGCAATAAC
ATTGCTCAAGGTACATTTAATGCAACGAAACAAGTATCTGTAGGCAAAGATGTTTATTTA
TACGGTACTATTAATAACCGCACTGGTTGGGTAAATGCAAAAGATTTAACTGCACCAACT
GCTGTGAAACCAACTACATCAGCTGCCAAAGATTATAACTACACTTATGTAATTAAAAAT
GGTAATGGTTATTACTATGTAACACCAAATTCTGATACAGCTAAATACTCATTAAAAGCA
TTTAATGAACAACCATTCGCAGTTGTTAAAGAACAAGTCATTAATGGACAAACTTGGTAC
TATGGTAAATTATCTAACGGTAAATTAGCATGGATTAAATCAACTGATTTAGCTAAAGAA
TTAATTAAGTATAATCAAACAGGTATGACATTAAACCAAGTTGCTCAAATACAAGCTGGT
TTACAATATAAACCACAAGTACAACGTGTACCAGGTAAGTGGACAGATGCTAAATTTAAT
GATGTTAAGCATGCAATGGATACGAAGCGTTTAGCTCAAGATCCAGCATTAAAATATCAA
TTCTTACGCTTAGACCAACCACAAAATATTTCTATTGATAAAATTAATCAATTCTTAAAA
GGTAAAGGTGTATTAGAAAACCAAGGTGCTGCATTTAACAAAGCTGCTCAAATGTATGGC
ATTAATGAAGTTTATCTTATCTCACATGCCCTATTAGAAACAGGTAACGGTACTTCTCAA
TTAGCGAAAGGTGCAGATGTAGTGAACAACAAAGTTGTAACTAACTCAAACACGAAATAC
CATAACGTATTTGGTATTGCTGCATATGATAACGATCCTTTACGTGAAGGTATTAAATAT
GCTAAACAAGCTGGTTGGGACACAGTATCAAAAGCAATCGTTGGTGGTGCTAAATTCATC
GGCAACTCATATGTAAAAGCTGGTCAAAATACACTTTACAAAATGAGATGGAATCCTGCA
CATCCAGGAACACACCAATATGCTACAGATGTAGATTGGGCTAACATCAATGCTAAAATC
ATCAAAGGCTACTATGATAAAATTGGCGAAGTCGGCAAATACTTCGACATCCCACAATAT
AAA

SEQ ID NO: 82 polynucleotide sequence

GATCGTGTATTAGCCTCACATCCAGATGTTGCGACAATACGTCAAAACGTGACAGCAGCG
AATGCCGCTAAATCAGCACTTGATCAAGCACGTAATGGCTTAACAGTCGATAAAGCGCCT
TTAGAAAATGCGAAAAATCAACTACAACATAGTATTGACACGCAAACAAGTACAACTGGT
ATGACACAAGACTCTATAAATGCATACAATGCGAAGTTAACAGCTGCACGTAATAAGATT

FIGURE 2 cont.

CAACAAATCAATCAAGTATTAGCAGGTTCACCGACTGTAGAACAAATTAATACAAATACG
TCTACAGCAAATCAAGCTAAATCTGATTTAGATCATGCACGTCAAGCTTTAACACCAGAT
AAAGCGCCGCTTCAAACTGCGAAAACGCAATTAGAACAAAGCATTAATCAACCAACGGAT
ACAACAGGTATGACGACCGCTTCGTTAAATGCGTACAACCAAAAATTACAAGCAGCGCGT
CAAAAGTTAACTGAAATTAATCAAGTGTTGAATGGCAACCCAACTGTCCAAAATATCAAT
GATAAAGTGACAGAGGCAAACCAAGCTAAGGATCAATTAAATACAGCACGTCAAGGTTTA
ACATTAGATAGACAGCCAGCGTTAACAACATTACATGGTGCATCTAACTTAAACCAAGCA
CAACAAAATAATTTCACGCAACAAATTAATGCTGCTCAAAATCATGCTGCGCTTGAAACA
ATTAAGTCTAACATTACGGCTTTAAATACTGCGATGACGAAATTAAAAGACAGTGTTGCG
GATAATAATACAATTAAATCAGATCAAAATTACACTGACGCAACACCAGCTAATAAACAA
GCGTATGATAATGCAGTTAATGCGGCTAAAGGTGTCATTGGAGAAACGACTAATCCAACG
ATGGATGTTAACACAGTGAACCAAAAAGCAGCATCTGTTAAATCGACGAAAGATGCTTTA
GATGGTCAACAAAACTTACAACGTGCGAAAACAGAAGCAACAAATGCGATTACGCATGCA
AGTGATTTAAACCAAGCACAAAAGAATGCATTAACACAACAAGTGAATAGTGCACAAAAC
GTGCAAGCAGTAAATGATATTAAACAAACGACTCAAAGCTTAAATACTGCTATGACAGGT
TTAAAACGTGGCGTTGCTAATCATAACCAAGTCGTACAAAGTGATAATTATGTCAACGCA
GATACTAATAAGAAAAATGATTACAACAATGCATACAACCATGCGAATGACATTATTAAT
GGTAATGCACAACATCCAGTTATAACACCAAGTGATGTTAACAATGCTTTATCAAATGTC
ACAAGTAAAGAACATGCATTGAATGGTGAAGCTAAGTTAAATGCTGCGAAACAAGAAGCG
AATACTGCATTAGGTCATTTAAACAATTTAAATAATGCACAACGTCAAAACTTACAATCG
CAAATTAATGGTGCGCATCAAATTGATGCAGTTAATACAATTAAGCAAAATGCAACAAAC
TTGAATAGTGCAATGGGTAACTTAAGACAAGCTGTTGCAGATAAAGATCAAGTGAAACGT
ACAGAAGATTATGCGGATGCAGATACAGCTAAACAAAATGCATATAACAGTGCAGTTTCA
AGTGCCGAAACAATCATTAATCAAACAACAAATCCAACGATGTCTGTTGATGATGTTAAT
CGTGCAACTTCAGCTGTTACTTCTAATAAAAATGCATTAAATGGTTATGAAAAATTAGCA
CAATCTAAAACAGATGCTGCAAGAGCAATTGATGCATTACCACATTTAAATAATGCACAA
AAAGCAGATGTTAAATCTAAAATTAATGCTGCATCAAATATTGCTGGCGTAAATACTGTT
AAACAACAAGGTACAGATTTAAATACAGCGATGGGTAACTTGCAAGGTGCAATCAATGAT
GAACAAACGACGCTTAATAGTCAAAACTATCAAGATGCGACACCTAGTAAGAAAACAGCA
TACACAAATGCGGTACAAGCTGCGAAAGATATTTTAAATAAATCAAATGGTCAAAATAAA
ACGAAAGATCAAGTTACTGAAGCGATGAATCAAGTGAATTCTGCTAAAAATAACTTAGAT
GGTACGCGTTTATTAGAT

SEQ ID NO: 83 polynucleotide sequence
GCTTCTACACAACATACAGTACAATCTGGTGAATCATTATGGAGTATTGCTCAAAAATAC
AACACTTCAGTAGAGAGTATTAAACAAAATAACCAATTAGATAACAACTTGGTATTCCCT
GGTCAAGTTATCTCAGTAGGTGGAAGTGATGCACAAAATACGTCAAACACTTCTCCACAA
GCTGGTTCAGCATCATCTCATACTGTACAAGCTGGTGAATCATTAAATATCATTGCTAGC
AGATATGGTGTTTCAGTTGATCAATTAATGGCAGCCAATAACTTACGTGGTTATTTAATT
ATGCCTAACCAAACATTACAAATTCCTAATGGTGGATCAGGTGGTACAACACCAACAGCT
ACAACAGGTAGCAATGGCAATGCATCATCTTTTAATCACCAAAATTTATACACTGCTGGT
CAATGTACATGGTACGTATTTGACCGTCGTGCTCAAGCTGGTAGTCCAATTAGCACATAT
TGGTCAGACGCTAAGTATTGGGCTGGTAACGCAGCTAATGATGGTTACCAAGTAAACAAC
ACACCATCAGTTGGTTCAATTATGCAAAGCACACCTGGTCCATATGGTCATGTTGCTTAT
GTTGAACGTGTCAATGGTGATGGTAGTATCTTGATTTCTGAAATGAATTACACATATGGT
CCATACAATATGAACTACCGTACAATTCCAGCTTCAGAAGTTTCTAGCTATGCATTCATC
CATTAA

SEQ ID NO:84 polynucleotide sequence
ATGAATAATAAAAAGACAGCAACAAATAGAAAAGGCATGATACCAAATCGATTAAACAAA
TTTTCGATAAGAAAGTATTCTGTAGGTACTGCTTCAATTTTAGTAGGGACAACATTGATT
TTTGGGTTAAGTGGTCATGAAGCTAAAGCGGCAGAACATACGAATGGAGAATTAAATCAA
TCAAAAAATGAAACGACAGCCCCAAGTGAGAATAAAACAACTAAAAAAGTTGATAGTCGT
CAACTAAAAGACAATACGCAAACTGCAACTGCAGATCAGCCTAAAGTGACAATGAGTGAT
AGTGCAACAGTTAAAGAAACTAGTAGTAACATGCAATCACCACAAAACGCTACAGCTAAT
CAATCTACTACAAAAACTAGCAATGTAACAACAAATGATAAATCATCAACTACATATAGT
AATGAAACTGATAAAAGTAATTTAACACAAGCAAAAGATGTTTCAACTACACCTAAAACA

FIGURE 2 cont.
```
ACGACTATTAAACCAAGAACTTTAAATCGCATGGCAGTGAATACTGTTGCAGCTCCACAA
CAAGGAACAAATGTTAATGATAAAGTACATTTTTCAAATATTGACATTGCGATTGATAAA
GGACATGTTAATCAGACTACTGGTAAAACTGAATTTTGGGCAACTTCAAGTGATGTTTTA
AAATTAAAAGCAAATTACACAATCGATGATTCTGTTAAAGAGGGCGATACATTTACTTTT
AAATATGGTCAATATTTCCGTCCAGGATCAGTAAGATTACCTTCACAAACTCAAAATTTA
TATAATGCCCAAGGTAATATTATTGCAAAAGGTATTTATGATAGTACAACAAACACAACA
ACATATACTTTTACGAACTATGTAGATCAATATACAAATGTTAGAGGTAGCTTTGAACAA
GTTGCATTTGCGAAACGTAAAAATGCAACAACTGATAAAACAGCTTATAAAATGGAAGTA
ACTTTAGGTAATGATACATATAGCGAAGAAATCATTGTCGATTATGGTAATAAAAAAGCA
CAACCGCTTATTTCAAGTACAAACTATATTAACAATGAAGATTTATCGCGTAATATGACT
GCATATGTAAATCAACCTAAAAATACATATACTAAACAAACGTTTGTTACTAATTTAACT
GGATATAAATTTAATCCAAATGCAAAAAACTTCAAAATTTACGAAGTGACAGATCAAAAT
CAATTTGTGGATAGTTTCACCCCTGATACTTCAAAACTTAAAGATGTTACTGATCAATTC
GATGTTATTTATAGTAATGATAATAAAACAGCTACAGTCGATTTAATGAAAGGCCAAACA
AGCAGCAATAAACAATACATCATTCAACAAGTTGCTTATCCAGATAATAGTTCAACAGAT
AATGGAAAAATTGATTATACTTTAGACACTGACAAAACTAAATATAGTTGGTCAAATAGT
TATTCAAATGTGAATGGCTCATCAACTGCTAATGGCGACCAAAAGAAATATAATCTAGGT
GACTATGTATGGGAAGATACAAATAAAGATGGTAAACAAGATGCCAATGAAAAAGGGATT
AAAGGTGTTTATGTCATTCTTAAAGATAGTAACGGTAAAGAATTAGATCGTACGACAACA
GATGAAAATGGTAAATATCAGTTCACTGGTTTAAGCAATGGAACTTATAGTGTAGAGTTT
TCAACACCAGCCGGTTATACACCGACAACTGCAAATGTAGGTACAGATGATGCTGTAGAT
TCTGATGGACTAACTACAACAGGTGTCATTAAAGACGCTGACAACATGACATTAGATAGT
GGATTCTACAAAACACCAAAATATAGTTTAGGTGATTATGTTTGGTACGACAGTAATAAA
GATGGTAAACAAGATTCGACTGAAAAAGGAATTAAAGGTGTTAAAGTTACTTTGCAAAAC
GAAAAAGGCGAAGTAATTGGTACAACTGAAACAGATGAAAATGGTAAATACCGCTTTGAT
AATTTAGATAGTGGTAAATACAAAGTTATCTTTGAAAAACCTGCTGGCTTAACTCAAACA
GGTACAAATACAACTGAAGATGATAAAGATGCCGATGGTGGCGAAGTTGATGTAACAATT
ACGGATCATGATGATTTCACACTTGATAATGGCTACTACGAAGAAGAAACATCAGATAGC
GACTCAGATTCTGACAGCGATTCAGACTCAGATAGCGACTCAGATTCAGATAGCGACTCA
GATTCAGACAGCGATTCAGACAGCGACTCAGACTCAGATAGCGATTCAGATTCAGACAGC
GACTCAGACTCAGACAGCGATTCAGACTCGGATAGCGACTCAGACTCAGATAGCGACTCA
GATTCGGATAGCGACTCAGACTCAGATAGCGATTCAGATTCAGATAGCGATTCGGACTCA
GACAGTGATTCAGATTCAGACTCAGATAGCGACTCAGATTCTGACAGCGATTCAGACTCA
GACAGCGACTCAGACTCAGACAGTGATTCAGATTCAGACAGCGACTCAGATTCAGATAGC
GACTCAGACTCAGATAGCGACTCAGATTCAGATAGCGACTCAGACAACGACTCA
GATTCAGATAGCGATTCAGATTCAGATAGCGACTCAGATTCGGACAGCGATTCAGACTCA
GATAGCGATTCAGACTCAGACAGCGATTCAGATTCAGATAGCGACTCAGACTCAGATAGC
GACTCAGACTCGGATAGCGATTCAGATTCAGACAGCGACTCAGATTCAGATAGCGATTCG
GACTCAGACAACGACTCAGATTCAGATAGCGATTCAGATTCAGATGCAGGTAAACATACT
CCGGCTAAACCAATGAGTACGGTTAAAGATCAGCATAAAACAGCTAAAGCATTACCAGAA
ACAGGTAGTGAAAATAATAATTCAAATAATGGCACATTATTCGGTGGATTATTCGCGGCA
TTAGGATCATTATTGTTATTCGGTCGTCGTAAAAAACAAAATAAATAA
```

SEQ ID NO: 85 polynucleotide sequence
```
ATGAATTTGTTAAAGAAAAATAAATATAGTATTAGGAAGTATAAAGTAGGCATATTCTCT
ACTTTAATCGGAACAGTTTTATTACTTTCAAACCCAAATGGTGCACAAGCCTTAACTACG
GATAATAATGTACAAAGCGATACTAATCAAGCAACACCTGTAAATTCACAAGATAAAGAT
GTTGCTAATAATAGAGGTTTAGCAAATAGTGCGCAGAATACACCTAATCAATCTGCAACA
ACCAATCAAGCAACGAATCAAGCATTGGTTAATCATAATAATGGTAGTATAGTAAATCAA
GCTACGCCAACATCAGTGCAATCAGTACGCCTTCAGCACAAAACAATAATCATACAGAT
GGCAATACAACAGCAACTGAGACAGTGTCAAACGCTAATAATAATGATGTAGTGTCGAAT
AATACCGCATTAAATGTACCAACTAAAACAAATGAAATGGTTCAGGAGGACATCTAACT
TTAAAGGAAATTCAAGAAGATGTTCGTCATTCTTCAAATAAACCAGAGCTAGTTGCAATT
GCTGAACCAGCATCTAATAGACCGAAAAAGAGAAGTAGACGTGCGGCACCGGCAGATCCT
AATGCAACTCCAGCAGATCCAGCGGCTGCAGCGGTAGGAAACGGTGGTGCACCAGTTGCA
ATTACAGCGCCATATACGCCAACAACTGATCCTAATGCCAATAATGCAGGACAAAATGCA
CCTAACGAAGTGCTGTCATTTGATGACAATGGTATTAGACCAAGTACCAACCGTTCTGTG
CCAACAGTAAACGTTGTTAATAACTTGCCGGGCTTCACACTAATCAATGGTGGCAAAGTA
GGGGTGTTTAGTCATGCAATGGTAAGAACGAGCATGTTTGATTCAGGAGATAATAAGAAC
```

FIGURE 2 cont.
```
TATCAAGCACAAGGAAATGTAATTGCATTAGGTCGTATACATGGAACTGATACGAATGAC
CATGGCGATTTTAATGGTATCGAGAAAGCATTAACAGTAAATCCGAATTCTGAATTAATC
TTTGAATTTAATACAATGACTACTAAAAACGGTCAAGGCGCAACAAATGTTATTATCAAA
AATGCTGATACTAATGATACGATTGCTGAAAAGACTGTTGAAGGCGGTCCAACTTTGCGT
TTATTTAAAGTACCTGATAATGTGAGAAATCTCAAAATTCAATTTGTACCTAAAAATGAC
GCAATAACAGATGCGCGTGGCATTTATCAACTAAAAGATGGTTACAAATACTATAGCTTT
GTTGACTCTATCGGACTTCATTCTGGGTCACATGTTTTTGTTGAAAGACGAACAATGGAT
CCAACAGCAACAAATAATAAAGAGTTTACTGTAACAACATCATTAAAGAATAATGGTAAT
TCTGGTGCTTCTCTAGATACAAATGACTTTGTATATCAAGTTCAATTACCTGAAGGTGTT
GAATATGTGAACAATTCATTGACTAAAGATTTTCCAAGTAACAATTCAGGCGTTGATGTT
AATGATATGAATGTTACATATGATGCAGCAAATCGTGTGATAACAATTAAAAGTACTGGA
GGAGGTACAGCAAACTCTCCGGCACGACTTATGCCTGATAAAATACTCGATTTAAGATAT
AAATTACGTGTAAATAATGTGCCGACACCAAGAACAGTAACATTTAACGAGACATTAACG
TATAAAACATATACACAAGATTTCATTAATTCAGCTGCAGAAAGTCATACTGTAAGTACA
AATCCATATACTATCGATATCATCATGAATAAAGATGCATTACAAGCCGAAGTTGACAGA
CGTATTCAACAAGCTGATTATACATTTGCGTCATTAGATATCTTTAATGGTCTGAAACGA
CGCGCACAAACGATTTTAGATGAAAATCGTAACAATGTACCATTAAATAAAAGAGTTTCT
CAAGCATATATTGATTCATTAACTAATCAAATGCAACATACGTTAATTCGAAGTGTTGAT
GCTGAAAATGCAGTTAATAAAAAAGTTGACCAAATGGAAGATTTAGTTAATCAAAATGAT
GAATTGACAGATGAAGAAAAACAAGCAGCAATACAAGTTATCGAGGAACATAAAAATGAA
ATAATTGGTAATATTGGTGACCAAACGACTGATGATGGCGTTACTAGAATCAAAGATCAA
GGTATACAGACCTTAAGTGGGGATACTGCAACACCGGTTGTTAAACCAAATGCTAAAAAA
GCAATACGTGATAAAGCAACGAAACAAAGGGAAATTATCAATGCAACACCAGATGCTACT
GAAGACGAGATTCAAGATGCACTAAATCAATTAGCTACGGATGAAACAGATGCTATTGAT
AATGTTACGAATGCTACTACAAATGCTGACGTTGAAACAGCTAAAAATAATGGCATCAAT
ACTATTGGAGCAGTTGTTCCTCAAGTAACTCATAAAAAAGCTGCAAGAGATGCAATTAAC
CAAGCAACAGCAACGAAAAGACAACAAATAAATAGTAATAGAGAAGCAACTCAGGAAGAG
AAAAATGCAGCATTGAACGAATTAACTCAAGCAACCAACCATGCTTTAGAACAAATCAAT
CAAGCAACAACAAATGCTAATGTTGATAACGCCAAAGGAGATGGTCTAAATGCCATTAAT
CCAATTGCTCCTGTAACTGTTGTTAAGCAAGCTGCAAGGGATGCCGTATCACATGATGCA
CAACAACATATCGCAGAGATCAATGCTAATCCTGATGCGACTCAAGAAGAAAGACAAGCA
GCAATTGACAAAGTGAATGCTGCTGTAACTGCAGCAAACACAAACATTTTAAACGCTAAT
ACCAATGCTGATGTTGAACAAGTAAAGACAAATGCGATTCAAGGAATACAAGCAATTACA
CCAGCTACAAAAGTAAAAACAGATGCAAAAAATGCCATCGATAAAAGTGCGGAAACGCAA
CATAATACGATATTTAATAATAATGATGCGACGCTCGAAGAACAACAAGCAGCACAACAA
TTACTTGATCAAGCTGTAGCCACAGCGAAGCAAAATATTAATGCAGCAGATACGAATCAA
GAAGTTGCACAAGCAAAAGATCAGGGCACACAAAATATAGTAGTGATTCAACCGGCAACA
CAAGTTAAAACGGATACTCGCAATGTTGTAAATGATAAAGCGCGAGAGGCGATAACAAAT
ATCAATGCTACAACTGGCGCGACTCGAGAAGAGAAACAAGAAGCGATAAATCGTGTCAAT
ACACTTAAAAATAGAGCATTAACTGATATTGGTGTGACGTCTACTACTGCGATGGTCAAT
AGTATTAGAGACGATGCAGTCAATCAAATCGGCGCAGTTCAACCGCATGTAACGAAGAAA
CAAACTGCTACAGGTGTATTAAATGATTTAGCAACTGCTAAAAAGCAAGAAATTAATCAA
AACACAAATGCAACAACTGAAGAAAGCAAGTGGCTTTAAATCAAGTGGATCAAGAGTTA
GCAACGGCAATTAATAATATAAATCAAGCTGATACAAATGCGGAAGTAGATCAAGCGCAA
CAATTAGGTACAAAAGCAATTAATGCGATTCAGCCAAATATTGTTAAAAAACCTGCAGCA
TTAGCACAAATCAATCAGCATTATAATGCTAAATTAGCTGAAATCAATGCTACACCAGAT
GCAACGAATGATGAGAAAAATGCTGCGATCAATACTTTAAATCAAGACAGACAACAAGCT
ATTGAAAGTATTAAACAAGCTAACACAAATGCAGAAGTAGACCAAGCTGCGACAGTAGCA
GAGAATAATATCGATGCTGTTCAAGTTGATGTAGTAAAAAAACAAGCAGCGCGAGATAAA
ATCACTGCTGAAGTGGCGAAGCGTATTGAAGCGGTTAAACAAACACCTAATGCAACTGAC
GAAGAAAAGCAGGCTGCTGTTAATCAAATCAATCAACTTAAAGATCAAGCAATTAATCAA
ATTAATCAAAACCAAACAAATGATCAGGTAGACACAACTACAAATCAAGCGGTAAATGCT
ATAGATAATGTTGAAGCTGAAGTAGTAATTAAAACAAAGGCAATTGCAGATATTGAAAAA
GCTGTTAAAGAAAAGCAACAGCAAATTGATAATAGTCTTGATTCAACAGATAATGAGAAA
GAAGTTGCTTCACAAGCATTAGCTAAAGAAAAAGAAAAAGCACTTGCAGCTATTGACCAA
GCTCAAACGAATAGTCAGGTGAATCAAGCAGCAACAAATGGTGTATCAGCGATTAAAATT
ATTCAACCTGAAACAAAAGTTAAACCAGCTGCACGTGAAAAAATCAATCAAAAAGCGAAT
GAATTACGTGCTAAGATTAATCAGGATAAAGAAGCAACAGCAGAAGAAAGACAAGTAGCA
CTAGATAAAATCAATGAATTTGTAAATCAAGCCATGACAGATATTACGAATAATAGAACA
AATCAACAAGTTGATGATACAACAAGTCAAGCGCTTGATAGCATTGCTTTAGTGACGCCT
```

FIGURE 2 cont.
GACCATATTGTTAGAGCAGCTGCTAGAGATGCAGTTAAGCAACAATATGAAGCTAAAAAG
CGCGAAATTGAGCAAGCGGAACATGCGACTGATGAAGAAAAACAAGTTGCTTTAAATCAA
TTAGCGAATAATGAAAAACGTGCATTACAAAACATCGATCAAGCAATAGCGAATAATGAT
GTGAAACGTGTTGAAACAAATGGCATTGCTACACTAAAAGGTGTACAACCTCATATTGTA
ATTAAGCCTGAAGCACAACAAGCAATAAAAGCAAGTGCAGAAAATCAAGTAGAATCAATA
AAAGATACACCACATGCAACAGTTGATGAATTAGATGAAGCGAATCAATTAATTAGCGAC
ACACTCAAACAAGCGCAACAAGAAATAGAAAATACAAATCAAGATGCTGCTGTTACTGAT
GTTAGAAATCAAACAATCAAGGCAATAGAGCAAATAAAACCTAAAGTAAGACGTAAACGA
GCTGCGCTTGATAGCATTGAAGAAAATAATAAAAATCAACTCGATGCAATCCGAAATACG
TTGGATACTACTCAAGATGAAAGAGATGTTGCTATTGATACTTTAAATAAAATTGTAAAT
ACAATTAAAAATGACATTGCACAAAACAAAACGAATGCAGAAGTGGATCGAACTGAGACT
GATGGCAACGACAACATCAAAGTGATTTTACCTAAAGTTCAAGTTAAACCAGCAGCGCGT
CAATCTGTTGGTGTAAAAGCCGAAGCTCAAATGCACTAATCGATCAAAGCGATTTATCA
ACTGAAGAAGAAAGACTAGCTGCTAAACATTTAGTAGAACAAGCACTTAATCAGGCTATT
GATCAGATCAATCATGCAGATAAGACTGCCCAAGTTAATCAAGATAGTATAAATGCTCAA
AATATTATTTCAAAAATTAAACCAGCGACAACAGTTAAAGCAACAGCATTACAACAAATT
CAAAATATCGCTACAAATAAAATTAATTTAATTAAAGCAAATAACGAAGCGACAGATGAA
GAACAAAATATTGCAATAGCACAAGTTGAAAAAGAGTTAATTAAAGCTAAACAACAAATT
GCTAGTGCAGTGACTAATGCAGATGTGGCATATTTATTGCATGATGAGAAAAACGAAATT
CGTGAAATCGAACCTGTTATTAACAGAAAGGCGTCTGCTCGAGAACAATTGACAACATTA
TTCAACGATAAAAAACAAGCAATTGAAGCGAATATTCAAGCAACGGTAGAAGAAAGAAAT
AGTATATTAGCACAGTTACAAAATATTTATGACACTGCTATTGGACAAATTGATCAAGAT
CGTAGCAATGCACAAGTTGATAAAACAGCATCATTAAATCTACAAACAATACATGATTTA
GATGTACATCCTATTAAAAAGCCAGATGCTGAAAAAACGATTAATGATGATCTTGCACGC
GTCACTGCTTTAGTGCAAAATTATCGAAAGTAAGTAATCGTAATAAGGCTGATGCATTA
AAAGCTATAACTGCTTTAAAATTACAAATGGATGAAGAATTAAAAACAGCACGCACTAAT
GCTGATGTTGATGCAGTTTTAAAACGATTTAATGTTGCATTAAGCGATATAGAAGCAGTA
ATTACTGAAAAAGAAAATAGCTTACTGCGAATTGATAACATTGCTCAACAAACATATGCG
AAATTCAAAGCGATCGCAACACCAGAACAATTAGCTAAAGTAAAAGTATTAATTGATCAA
TATGTTGCAGATGGCAATAGAATGATTGATGAAGATGCGACATTAAATGACATCAAACAA
CACACGCAATTCATTGTTGATGAAATTTTAGCAATTAAATTACCAGCTGAAGCGACGAAA
GTATCACCAAAAGAAATTCAGCCAGCTCCAAAAGTTTGTACGCCTATTAAAAAAGAAGAG
ACACATGAATCGCGCAAAGTTGAAAAAGAACTTCCAAATACAGGTTCTGAAGGAATGGAT
TTACCATTGAAAGAATTTGCACTGATTACAGGTGCGGCTTTGTTAGCTAGAAGACGTACT
AAAAAACGAAAAAGAATCATAA

SEQ ID NO: 86 polynucleotide sequence
GAGGAGAATTCAGTACAAGACGTTAAAGATTCGAATACGGATGATGAATTATCAGACAGC
AATGATCAGTCTAGTGATGAAGAAAAGAATGATGTGATCAATAATAATCAGTCAATAAAC
ACCGACGATAATAACCAAATAATTAAAAAAGAAGAAACGAATAACTACGATGGCATAGAA
AAACGCTCAGAAGATAGAACAGAGTCAACAACAAATGTAGATGAAAACGAAGCAACATTT
TTACAAAAGACCCCTCAAGATAATACTCATCTTACGAAGAAGAGGTAAAAGAATCCTCA
TCAGTCGAATCCTCAAATTCATCAATTGATACTGCCCAACAACCATCTCACACAACAATA
AATAGAGAAGAATCTGTTCAAACAAGTGATAATGTAGAAGATTCACACGTATCAGATTTT
GCTAACTCTAAAATAAAAGAGAGTAACACTGAATCTGGTAAAGAAGAGAATACTATAGAG
CAACCTAATAAAGTAAAAGAAGATTCAACAACAAGTCAGCCGTCTGGCTATACAAATATA
GATGAAAAATTTCAAATCAAGATGAGTTATTAAATTTACCAATAAATGAATATGAAAAT
AAGGCTAGACCATTATCTACAACATCTGCCCAACCATCGATTAAACGTGTAACCGTAAAT
CAATTAGCGGCGGAACAAGGTTCGAATGTTAATCATTTAATTAAAGTTACTGATCAAAGT
ATTACTGAAGGATATGATGATAGTGAAGGTGTTATTAAAGCACATGATGCTGAAAACTTA
ATCTATGATGTAACTTTTGAAGTAGATGATAAGGTGAAATCTGGTGATACGATGACAGTG
GATATAGATAAGAATACAGTTCCATCAGATTTAACCGATAGCTTTACAATACCAAAAATA
AAAGATAATTCTGGAGAAATCATCGCTACAGGTACTTATGATAACAAAAATAAACAAATC
ACCTATACTTTTACAGATTATGTAGATAAGTATGAAAATATTAAAGCACACCTTAAATTA
ACGTCATACATTGATAAATCAAAGGTTCCAAATAATAATACCAAGTTAGATGTAGAATAT
AAAACGGCCCTTTCATCAGTAAATAAAACAATTACGGTTGAATATCAAAGACCTAACGAA
AATCGGACTGCTAACCTTCAAAGTATGTTTACAAACATAGATACGAAAAATCATACAGTT
GAGCAAACGATTTATATTAACCCTCTTCGTTATTCAGCCAAGGAAACAAATGTAAATATT
TCAGGGAATGGTGATGAAGGTTCAACAATTATAGACGATAGCACAATAATTAAAGTTTAT

FIGURE 2 cont.
AAGGTTGGAGATAATCAAAATTTACCAGATAGTAACAGAATTTATGATTACAGTGAATAT
GAAGATGTCACAAATGATGATTATGCCCAATTAGGAAATAATAATGATGTGAATATTAAT
TTTGGTAATATAGATTCACCATATATTATTAAAGTTATTAGTAAATATGACCCTAATAAG
GATGATTACACGACTATACAGCAAACTGTGACAATGCAGACGACTATAAATGAGTATACT
GGTGAGTTTAGAACAGCATCCTATGATAATACAATTGCTTTCTCTACAAGTTCAGGTCAA
GGACAAGGTGACTTGCCTCCTGAAAAAACTTATAAAATCGGAGATTACGTATGGGAAGAT
GTAGATAAAGATGGTATTCAAAATACAAATGATAATGAAAAACCGCTTAGTAATGTATTG
GTAACTTTGACGTATCCTGATGGAACTTCAAAATCAGTCAGAACAGATGAAGATGGGAAA
TATCAATTTGATGGATTGAAAAACGGATTGACTTATAAAATTACATTCGAAACACCTGAA
GGATATACGCCGACGCTTAAACATTCAGGAACAAATCCTGCACTAGACTCAGAAGGTAAT
TCTGTATGGGTAACTATTAATGGACAAGACGATATGACGATTGATAGTGGATTTTATCAA
ACACCTAAATACAGCTTAGGGAACTATGTATGGTATGACACTAATAAAGATGGTATTCAA
GGTGATGATGAAAAAGGAATCTCTGGAGTTAAAGTGACGTTAAAAGATGAAAACGGAAAT
ATCATTAGTACAACTACAACCGATGAAATGGAAAGTATCAATTTGATAATTTAAATAGT
GGTAATTATATTGTTCATTTTGATAAACCTTCAGGTATGACTCAAACAACAACAGATTCT
GGTGATGATGACGAACAGGATGCTGATGGGGAAGAAGTTCATGTAACAATTACTGATCAT
GATGACTTTAGTATAGATAACGGATACTATGATGACGAA

SEQ ID NO: 88 polynucleotide sequence

ATGATTAACAGGGATAATAAAAAGGCAATAACAAAAAAGGGTATGATTTCAAATCGCTTAAACAAATTTTCGATTAGAAA
GTATACTGTAGGAACTGCATCGATTTTTAGTAGGTACGACATTGATTTTTGGTCTAGGGAACCAAGAAGCTAAAGCTGCTG
AAAACACTAGTACAGAAAATGCGAAACAAGATGATGCAACGACTAGTGATAATAAAGAAGTAGTGTCGGAAACTGAAAAT
AATTCGACAACAGAAAATGATTCAACAAATCCAATTAAGAAAGAAACAAATACTGATTCACAACCAGAAGCTAAAGAAGA
ATCAACTACATCAAGTACTCAACAACAGCAAAATAACGTTACAGCTACAACTGAAACTAAGCCTCAAAACATTGAAAAG
AAAATCTTAAACCTTCAACTGATAAAACTGCCACACAACATACATCTGTTATTTTACAACAGAACAAAGCCACCAAATTAT
ACAAATAACCATGTAACTACAAAACCATCTACAAGTGAAATTCAAACAAAACCAACTACACCTCAAGAATCTACAAATAT
TGAAAATTCACAACCGCAACCAACGCCTTCAAAAGTAGACAATCAAGTTACAGATGCAACTAATCCAAAAGAACCAGTAA
ATGTGTCAAAAGAAGAACTTAAAAATAATCCTGAGAAATTAAAAGAATTAGTTAGAAATGATAACAATACAGATCGTTCA
ACTAAACCAGTTGCTACAGCTCCAACAAGTGTTGCACCAAAACGATTAAATGCGAAAATGCGTTTTGCAGTTGCACAACC
AGCAGCAGTTGCTTCAAATAATGTAAATGACTTAATTACAGTTACGAAACAGACGATCAAAGTTGGCGATGGTAAAGATA
ATGTGGCAGCAGCGCATGACGGTAAAGATATTGAATATGATACAGAGTTTACAATTGACAATAAAGTCAAAAAAGGCGAT
ACAATCACGATTAATTATGATAAGAATCTAATTCCTTCCGATTTAACGATAAAATGATCCTATCGATATTACTGATCC
ATCAGGAGAGGTCATTGCCAAAGGAACATTTGATAAAGCGACTAAGCAAATCACATATACATTTACAGATTATGTAGATA
AATATGAAGATATAAAAGCACGTTTAACTTTATACTCATATATTGATAAGCAAGCAGTACCTAATGAAACTAGTTTGAAT
TTAACGTTTGCAACAGCAGGTAAAGAAACTAGCCAAAACGTTTCTGTTGATTATCAAGACCCAATGGTTCATGGTGATTC
AAACATTCAATCTATCTTTACAAAGTTAGATGAAAACAAACAAACTATTGAACAACAAATTTATGTTAATCCTTTGAAAA
AAACAGCAACTAACACTAAAGTTGATATAGCTGGTAGTCAAGTAGATGATTATGGAAATATTAAACTAGGAAATGGTAGT
ACCATTATTGACCAAAATACAGAAATAAAAGCTTTATAAAGTTAACCCTAATCAACAATTGCCTCAAAGTAATAGAATCTA
TGATTTAGTCAATACCAAGATGTAACAAGTCAATTTGATAATAAAAAATCATTTACTAATAATGTAGCAACATGGATT
TTGGTGATACTAATTCAGCCTATATTATCAAAGTTGTTAGTAAATATACACCTACATCAGATGGCGAACTAGATATTGCT
CAAGGTACTAGTATGAGAACAACTGATAAATATGGTTACTATAATTATGCAGGATATTCAAACTTCATCGTAACCTCTAA
TGACACTGGCGGTTGGCGACGGTACTGTTAAACCTGAAGAAAAGTTATACAAAATTGGTGACTATGTATGGGAAGACGTTG
ATAAAGACGGTGTCCAAGGTACAGATTCGAAAGAAAAGCCAATGGCAAACGTTTTAGTTACATTAACTTACCCGGACGGT
ACTACAAAATCAGTAAGAACAGATGCTAACGGTCATTATGAATTCGGTGCTTTGAAAGACGGAGAAACTTATACAGTTAA
ATTCGAAACGCCAGCTGGATATCTTCCAACAAAAGTAAATGGAACAACTCGATGGTGAAAAAGACTCAAATGGTAGTTCTA
TAACTGTTAAAATTAATGGTAAAGATGATATGTCTTTAGACACTGGTTTTTATAAAGAACCTAAATATAATCTTGGTGAC
TATGTATGGGAAGATACAAATAAAGATGGTATCCAAGATGCTAATGAACCTGGTATCAAAGATGTTAAGGTTACATTAAA
AGATAGTACTGGAAAAGTTATTGGTACAACTACTACTGATGCCTCGGGTAAATATAAATTTACAGATTTAGATAATGGTA
ACTATACAGTAGAATTTGAAACACCAGCAGGTTACACGCCAACGGTTAAAAATACTACAGCTGAAGATAAAGATTCTAAT
GGTTTAACAACAACAGGTGTCATTAAAGATGCAGATAACATGACATTAGACAGTGGTTTCTATAAAACACCAAAATACAG
TTTAGGTGATTATGTTGGTGACAGCAATAAAGACGGTAAACAAGATTCAACTGAAAAAGGTATCAAAGATGTTAAAG
TTACTTTATTAAATGAAAAAGGCGAAGTAATTGGAACAACTAAAACAGATGAAAATGGTAAATATCGTTTCGATAATTTA
GATAGCCGGTAAATACAAAGTTATTTTTCAAAAGCCTGCTGGCTTAACACAAACAGTTACAAATACAACTGAACATGATAA
AGATGCCGATGGTGGCGAAGTGACGTAACAATTACGGATCATGATGATTTCATACTTGATAACGGATACTTCGAAGAAG
ATACATCAGACAGTGATTCAGACTCAGAAGATCGAGACTCAGATTCAGACTCAGACAGCGACTCAGACTCAGATAGCGA
CTCAGATTCGGACAGCGATTCAGACTCAGATAGCGACTCAGATTCAGACAGCGATTCAGACTCAGATAGCGACTCAGATT
CAGACAGTGACTCAGACTCAGATAGCGACTCAGACTCAGACAGTGACTCAGACTCAGACAGCGATTCAGATTCAGATAGC
GACTCAGATCGGACAGTGATTCAGACTCAGATAGCGACTCAGATTCAGACAGCGACTCAGACTCAGATAGCGACTCAGA
CTCAGACAGTGATTCACACTCAGATAGCCATTCGGACTCCGATCCAGGAAAACATACACCTGTTAAACCAATCTACTA
CTAAAGACCATCACAATAAAGCAAAAGCATTACCAGAAACAGGTAGTGAAAATAACGGCTCAAATAACGCAACGTTATTT
GGTGGATTACTTGCAGCATTAGGTTCATTATTGTTATTCGGTCGTCGCAAAAAACAAAACAAATAA

SEQ ID NO: 90 polynucleotide sequence

ATGCTAAACAGAGAAAATAAAACGGCAATAACAAGGAAAGGCATGGTATCCAATCGATTAAATAAATTTTCGATTAGAAA

FIGURE 2 cont.

```
GTACACAGTGGGAACAGCATCAATTTTAGTAGGTACAACATTAATTTTTGGTCTGGGGAACCAAGAAGCAAAGGCTGCAG
AAAGTACTAATAAAGAATTGAACGAAGCGACAACTTCAGCAAGTGATAATCAATCGAGTGATAAAGTTGATATGCAGCAA
CTAAATCAAGAAGACAATACTAAAAATGATAATCAAAAAGAAAATGGTATCATCTCAAGGTAATGAAACGACTTCAAATGG
GAATAAATTAATAGAAAAAGAAAGTGTACAATCTACCACTGGAAATAAAGTTGAAGTTTCAACTGCCAAATCAGATGAGC
AAGCTTCACCAAAATCTACGAATGAAGATTTAAACACTAAACAAACTATAAGTAATCAAGAAGCGTTACAACCTGATTTG
CAAGAGAATAAATCAGTGGTAAATGTTCAACCAACTAATGAGGAAAACAAAAAGGTAGATGCCAAAACTGAATCAACTAC
ATTAAATGTTAAAAGTGATGCTATCAAGAGTAATGATGAAACTCTTGTTGATAACAATAGTAATTCAAATAATGAAAATA
ATGCAGATATCATTTTGCCAAAAAGTACAGCACCTAAACGTTTGAATACAAGAATGCGTATAGCAGCAGTACAGCCATCA
TCAACAGAGGCTAAAAATGTTAATGATTTAATCACATCAAATACAACATTAACTGTCGTTGATGCAGATAAAAACAATAA
AATCGTACCAGCCCAAGATTATTTATCATTAAAATCACAAATTACAGTTGATGACAAAGTTAAATCAGGTGATTATTTCA
CAATTAAATACTCAGATACAGTACAACTATATGGATTGAATCCGCAAGATATTAAAAATATTGGTCATATTAAACATCCA
AATAATGGTGAAACAATTGCGACTGCAAAACATGACTGCAAATAATTTAATTACATATACATTTACAGATTATGTTGA
TCGATTTAACTCTGTACAAATGGGAATTAATTATTCAATTTATATGGATGCTGATACAATTCCTGTTAGTAAAAACGATG
TTCAGTTTAATGTTACGATAGGCTAATACTACAACAAAAACAACTGCTAACATTCAATATCCAGATTATGTTGTAAATCAG
AAAAATTCAATTGGATCAGCGTTCACTGAAACAGTTTCACATGTTGGAAATAAAGAAAATCCAGGGTACTATAAACAAAC
GATTTATGTAAATCCATCGGAAAATTCTTTAACAAATGCCAAACTAAAAGTTCAAGCTTACCACTCAAGTTATCCTAATA
ATATCGGGCAAATAAATAAAGATGTAACAGATATAAAAATATATCAAGTTCCTAAAGGTTATACATTAAATAAAGGATAC
GATGTGAATACTAAAGAGCTTACAGATGTAACAAATCAATACTTGCAGAAAATTACATATGGCGACAACAATAGCGCTGT
TATTGATTTGGAAATGCAGATTCTGCTTATGTGTGAATGGTTAATACAAAATTCCAATATACAAATAGCGAAAGCCCAA
CACTTGTTCAAATGGCTACTTTATCTTCAACAGGTAATAAATCCGTTTCTACTGGCAATGCTTTAGGATTTACTAATAAC
CAAAGTGGCGGAGCTGGTCAAGAAGTATATAAAATTGGTAACTACGTATGGGAAGATACTAATAAAAACGGTGTTCAAGA
ATTAGGAGAAAAACGCGTTGGCAATGTAACTGTAACTGTATTTGATAATAATACAAATACAAAAGTAGGAGAAGCAGTTA
CTAAAGAAGATGGGTCATACTTGATTCCAAACTTACCTAATGGAGATTACCGTGTAGAATTTTCAAACTTACCAAAAGGT
TATGAAGTAACCCCTTCAAAACAAGGTAATAACGAAGAATTAGATTCAAACGGCTTATCTTCAGTTATTCACAGTTAATGG
CAAAGATAACTTATCTGCAGACTTAGCTCATTTACAAACCTAAATACAACTTACGTCACTATGTCTGGCAAGATACAAATA
AAAATGGTATCCAAGACCAAGATGAAAAAGGTATATCTGGCGTAACGGTAACATTAAAAGATGAAAACGGTAACGTGTTA
AAAACAGTTACAACAGACGCTGATGGCAAATATAAATTTACTGATTTAGATAATGGTAATTATAAAGTTGAATTTACTAC
ACCAGAAGGCTATACACCGACTACAGTAACATCTGGTAGCGACATTGAAAAAGACTCTAATGGTTTAACAACAACAGGTG
TTATTAATGGTGCTGATAACATGACATTAGATAGTGGATTCTACAAAACACCAAAATATAATTTAGGTAATTATGTATGG
GAAGATACAAATAAAGATGGTAAGCAGGATTCAACTGAAAAAGGTATTTCAGGCGTAACAGTTACATTGAAAAATGAAAA
CGGTGAAGTTTTACAAACAACTAAAACAGATAAAGATGGTAAATATCAATTTACTGGATTAGAAAATGGAACTTATAAAG
TTGAATTCGAAACACCATCAGGTTACACACCAACACAAGTAGGTTCAGGAACTGATGAAGGTATAGATTCAAATGGTACA
TCAACAACAGGTTGCATTAAAGATAAAGATAACGACTACTATTGACTCTGGTTTCTACAAACCGACTTACAACTTAGGTGA
CTATGTATGGGAAGATACAAATAAAAACGGTGTTCAAGATAAAGATGAAAAGGGCATTTCAGGTGTAACAGTTACGTTAA
AAGATGAAAACGACAAAGTTTAAAAACAGTTACAACAGATGAAAATGGTAAATATCAATTCACTGATTTAAACAATGGA
ACTTATAAAGTTGAATTCGAGACACCATCAGGTTATACACCAACTTCAGTAACTTCTGGAAATGATACTGAAAAAGATTC
TAATGGTTTAACAACAACAGGTGTCATTAAAGATGCAGATAACATGACATTAGACAACTGGTTCTTCTATAAAACACCAAAAT
ATAGTTTAGGTGATTATGTTTGGTACGACAGTAATAAAGACGGCAAACAAGATTCAACTGAAAAAGGTATCAAAGATGTT
AAAGTTACTTTATTAAATCAAAAAGCCGAACTAATTGCAACAACTAAAACACATCAAAATGGTAAATACTGCTTTCATAA
TTTAGATAGCGGTAAATACAAAGTTATTTTTGAAAAGCCTGCTGGCTTAACACAAACAGTTACAAATACAACTGAAGATG
ATAAAGATGCAGATGTGGCGAAGTTGACGTAACAATTACGGATCATGATGATTTCACACTTGATAACGGATACTTCGAA
GAAGATACAATCAGACAGCGATTCGACTCAGATAGTGACTCAGACAGCGACTCAGACTCAGACAGCGACTCAGACTCAGA
CAGTGACTCAGATTCAGACAGCGACTCAGATTCAGATAGCGACTCAGATTCGGACAGCGATTCAGACTCAGATAGCGACT
CAGATTCAGATAGCGATTCAGACTCAGACAGCGACTCAGATTCAGATAGCGATTCGGACTCAGACAGCGATTCAGACTCA
GATAGCGACTCAGACAGCGACTCAGATTCAGATAGCGATTCGGACTCAGATAGCGACTCAGATAGCGACTCAGACAGCGA
TTCAGACTCAGATAGCGACTCAGATTCAGACAGCGATTCAGACTCAGATAGCGATTCAGACTCAGACAGCGATTCAGATT
CAGACAGCGACTCAGACTCAGATAGCGACTCAGATTCGGACAGCGACTCAGACTCTGATAGCGACTCAGACTCAGACAGT
GATTCAGACAGCGATTCAGACTCGGATGCAGGAAAACATACACCTGTTAAACCAATGAGTACTACTAAAGACCATCACAA
TAAAGCAAAAGCATTACCAGAAACAGGTAGTGAAAATAACGGCTCAAATAACGCAACGTTATTTGGTGGATTATTTGCAG
CATTAGCTTCATTATTGTTATTCGGTCGTCGCAAAAAACAAAACAAATAA
```

SEQ ID NO: 92 polynucleotide sequence

```
ATGGCTAAATATCGAGGGAAACCGTTTCAATTATATGTAAAGTTATCGTGTTCGACAATGATGGCGACAAGTATCATTTT
AACGAATATCTTGCCGTACGATGCCCAAGCTGCATCTGAAAAGGATACTGAAATTACAAAAGAGATATTATCTAAGCAAG
ATTTATTGACAAAGTTGACAAGGCAATTCGTCAAATTGAGCAATTAAAACAGTTATCGGCTTCATCTAAAGAACATTAT
AAAGCACAACTAAATGAAGCGAAAACAGCATCGCAAATACATAAAACATAAAACATAAAGCGTAATGAGTTGGATAGCAAACA
CAATAAAAAGTTCTCACACTGAAATGAACGGTCAAAGTGATATAGACAGTAAATTAGATCAATTGCTTAAAGATTTAAATG
AGGTTTCTTCAAATGTTGATAGGGGTCAACAAAGTGGCGAGGACGATCTTAATGCAATGAAAAATGATATGTCACAAACG
GCTACAACAAAACATGGAGAAAAAGATGATAAAAATGATGAAGCAATGGTAAATAAGGCGTTAGAAGACCTAGACCATTT
CAATCACCAAATACAAAATCCAAACATCCATCCAAACATACATCCAAACATCCCTACAACACATAATAATC
ATGAAGTAGCTAAACGCCAAATAATGATGGTTCTGGACATGTTGTGTTAAATAAATTCCTTCAAATGAAGAGAATCAA
AGCCATAGTAATCGACTCACTGATAAATTACAAGGAAGCGATAAAATTAATCATGCTATGATTGAAAATTAGCTAAAAG
TAATCCCTCAACCGCAACATTACACATATCATAAACTGAATACCTTACAATCTTTACATCAACGTATTCCAAATACCCAAC
TTCCTAAAAATCAAAAATCAGACTTAATGAGCGAAGTAAATAAGACAAGAGCGTATAAAAAGTCAACGAAATATTATT
TTGGAAGAACTTGCACGTACTGATGATAAAAAGTATGCTACACAAAGCATTTTAGAAAGTATATTTAAAAAGACGAGGC
AGTTAAAATTCTAAAACATATACCGTGTTGATGGTAAAACAGATCAACAAATTCCACATCAAATTACTCGTCATATTGATC
AATTATCTTGACAACGAGTGATGATTTATTAACGTTCATTGATTGATCAATCACAAGATAAGTCGCTATTGATTTCTCAA
ATTTTACAAACGAAATTAGGAAAAGCTGAAGAGCAAATTGGCTAAAAGATTGGCTGAATAAAGGATTATCAAATCGCCA
AATCGTTTGACCAATTGAAGAAACATTTTGCATCAACTGGCACGTCTTCAGATGATATATTAAAAGCAATTTCAATA
ATGCCAAAGATAAAAAACAAGCAATTGAAACGATTCTAGCGAACACGTATAGAAAAGACAAAAGGCAAAATACTGGCAGAT
TTAATTACTAAAATAGAAACAGATCAAAATAAAATTTTTAATTTAGTTAAATCGGCATTGAATGGTAAAGCGGATCATTT
ATTGAATTACAAAAGAGACTCAATCAAACGAAAAAGATATAGATTATATTTTATCACCAATAGTAAATCGTCCAAGTT
TACTAGATCGATTGAATAAAATGGGAAAACGACAGATTTAAATAAGTTAGCAAATTTAATGAATCAAGGATCAGATTA
```

FIGURE 2 cont.
```
TTAGACAGTATTCCAGATATACCCACACCAAAGCCAGAAAAGACGTTAACACTTGGTAAAGGTAATGGATTGTTAAGTGG
ATTATTAAATGCTGATGGTAATGTATCTTTGCCTAAAGCGGGGAAACGATAAAAGAACATTGGTTGCCGATATCTGTAA
TTGTTGGTGCAATGGGTGTACTAATGATTTGGTTATCACGACGCAATAAGTTGAAAAATAAAGCATAA
```

SEQ ID NO: 94 polynucleotide sequence
```
ATGAAAAAATTAGCAACAGTAGGTTCTTTAATTGTAACAAGCACTTTAGTATTCTCAAGTATGCCTTTT
CAAAATGCGCATGCCGACACAACTTCAATGAATGTGTCGAATAAACAAAGCCAAAATGTACAAAATCAT
CGTCCTTATGGCGGAGTAGTACCACAAGGAATGACGCAAGCACAATATACTGAATTAGAGAAAGCTTTA
CCCCAATTAAGCGCTGGCAGTAATATGCAAGACTATAATATGAAATTGTATGATGCGACGCAAAATATT
GCTGATAAATACAATGTGATAATTACAACTAATGTAGGGGTATTTAAACCACATGCTGTTAGAGATATG
AATGGCCATGCGTTACCTTTAACAAAAGATGGCAATTTTTATCAAACGAATGTAGATGCAAATGGTGTT
AATCATGGTGGTAGTGAAATGGTGCAAAATAAAACAGGTCATATGAGTCAACAAGGCCATATGAATCAG
AACACACACATGAACCAACAGCCACACATGCAACAAGGTCATATGCAATCATCAAACCATCAAATGATG
AGTCCAAAAGCAAATATGCATTCATCAAATCATCAAATGAACCAAAGTAACAAAAAAGTTTTACCAGCT
GCTGGTGAAAGTATGACATCAAGTATTCTTACTGCAAGTATTGCCGCACTACTATTAGTATCTGGGTTA
TTCTTAGCATTTAGACGACGTTCAACAAATAAATAA
```

Figure 3
Purification of alpha toxin
A
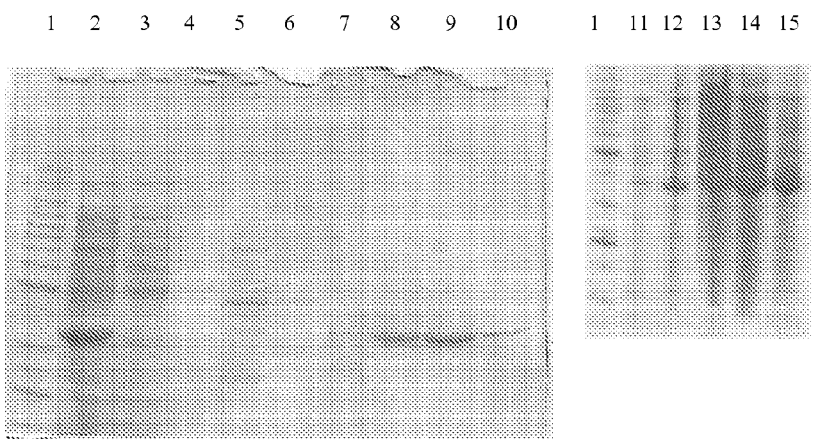
B
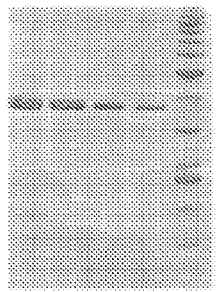

Figure 4
Purification of SdrC
A
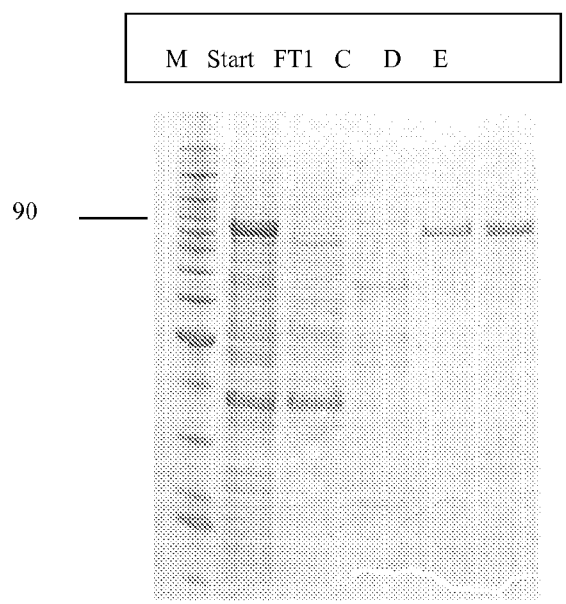
B
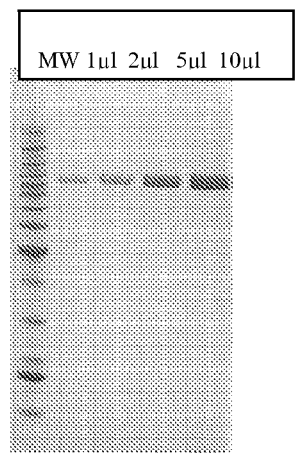

Figure 5
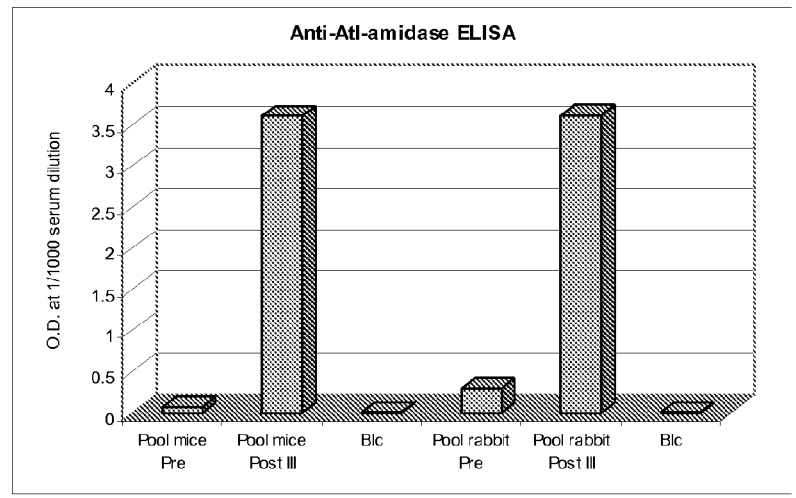
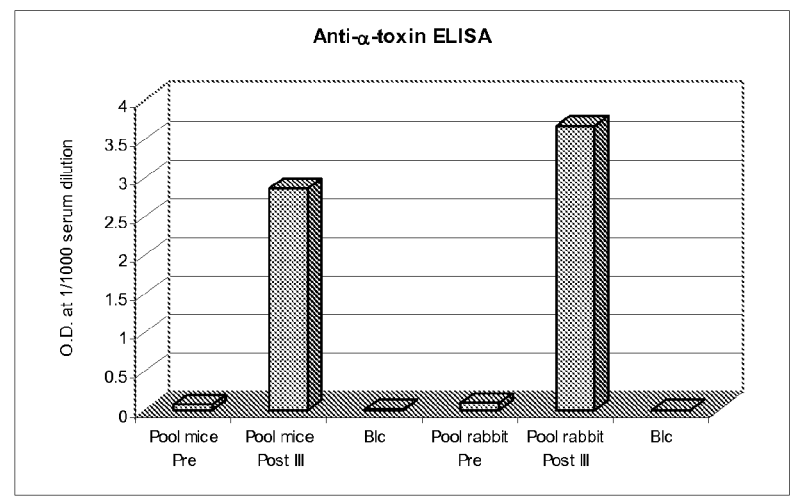
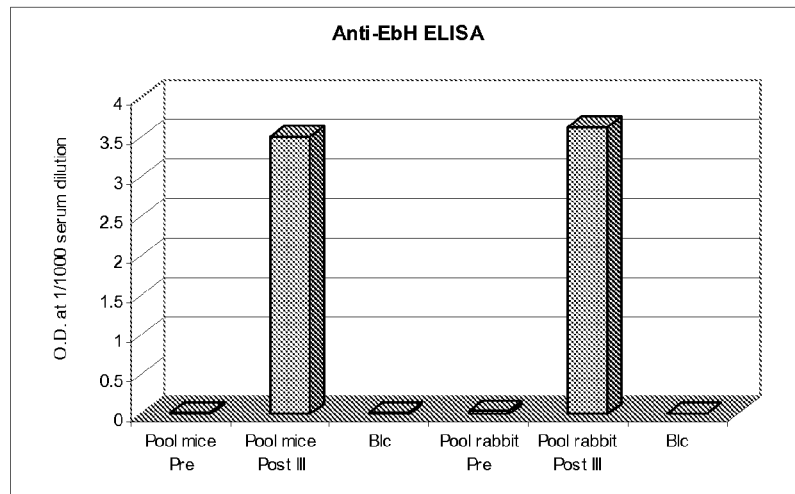

Figure 5 cont.
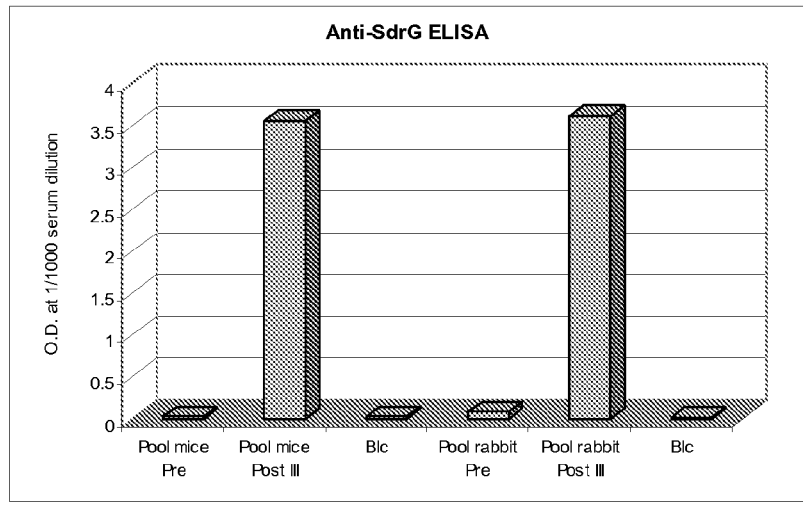
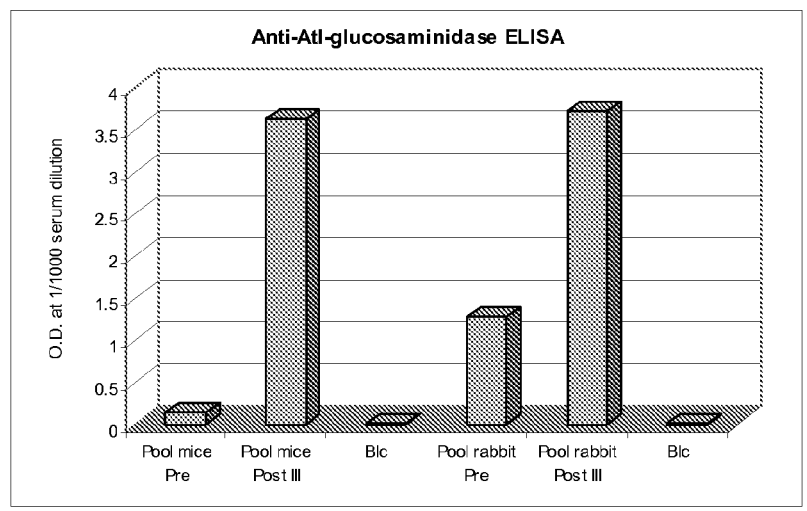
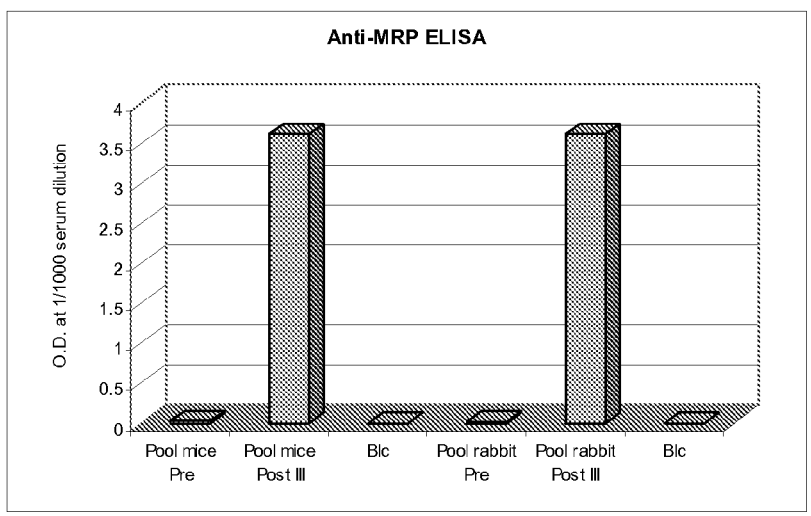

Figure 5 cont.
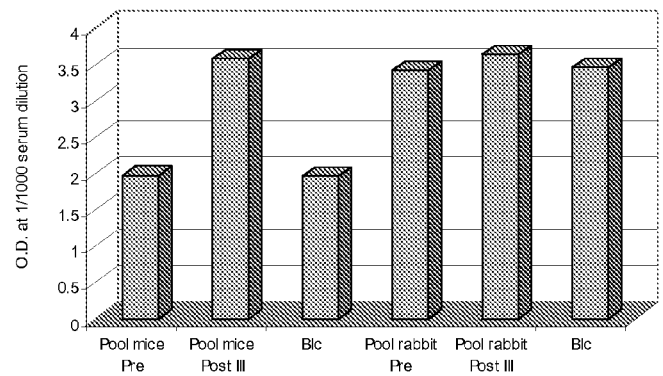
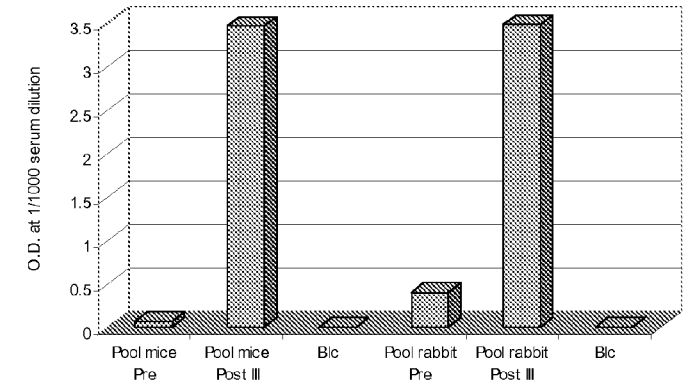
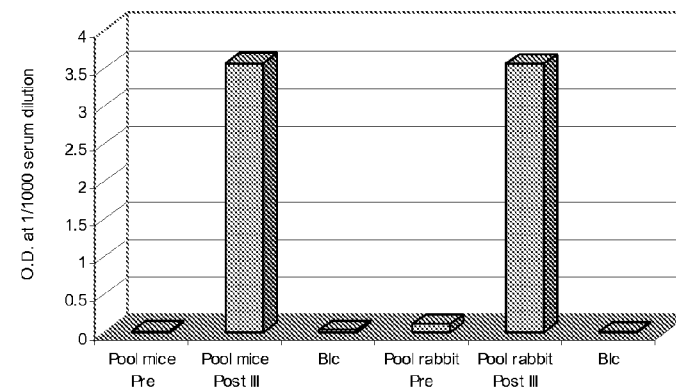

Figure 5 cont.
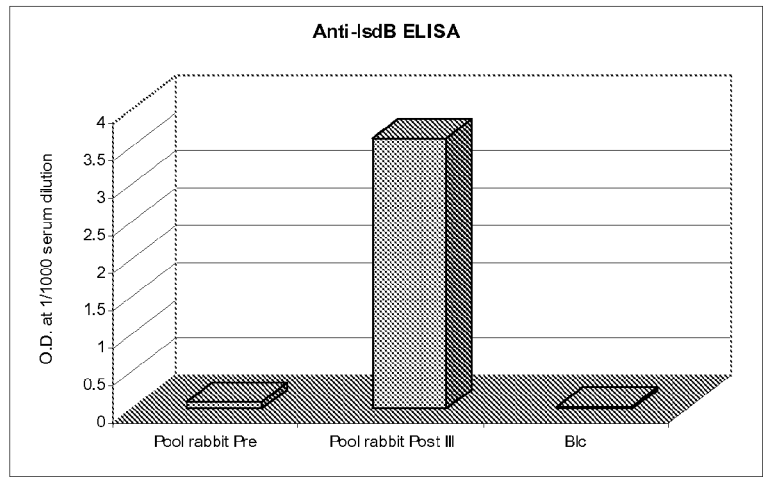
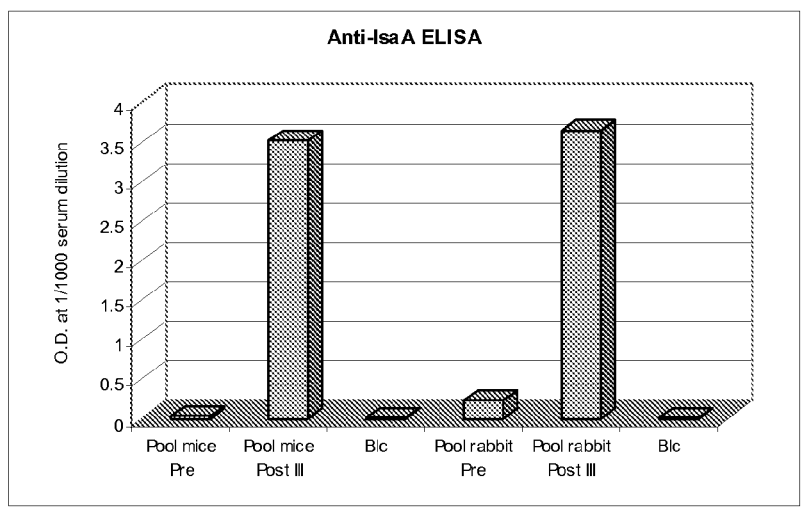
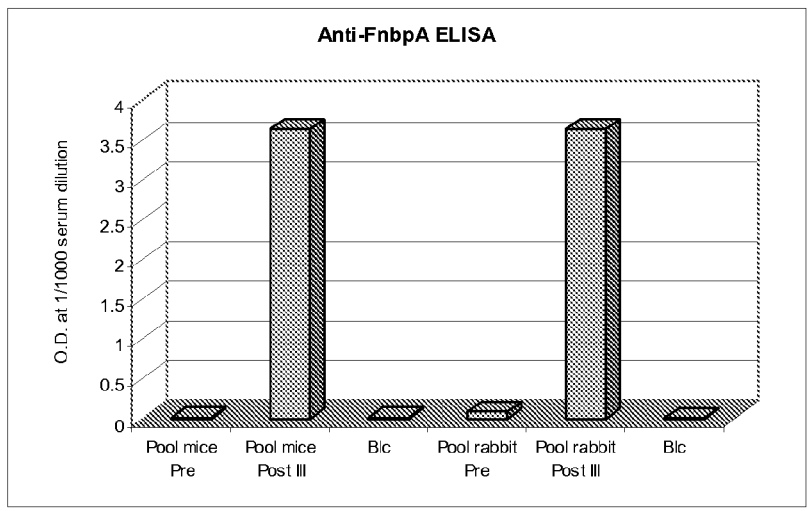

Figure 5 cont.
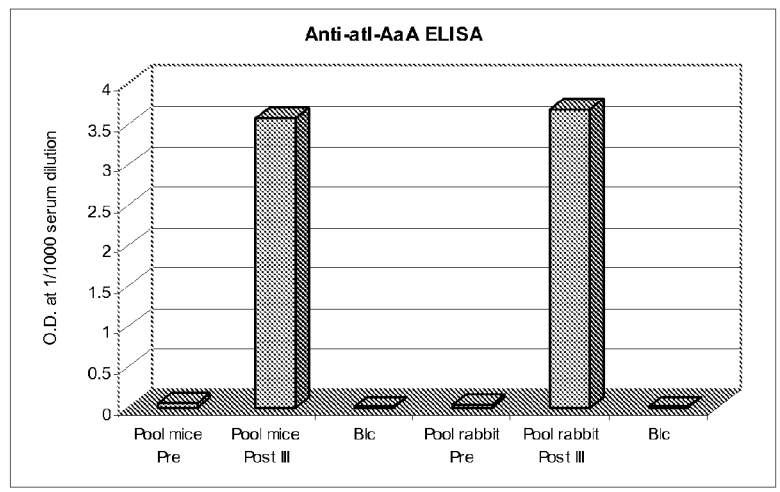
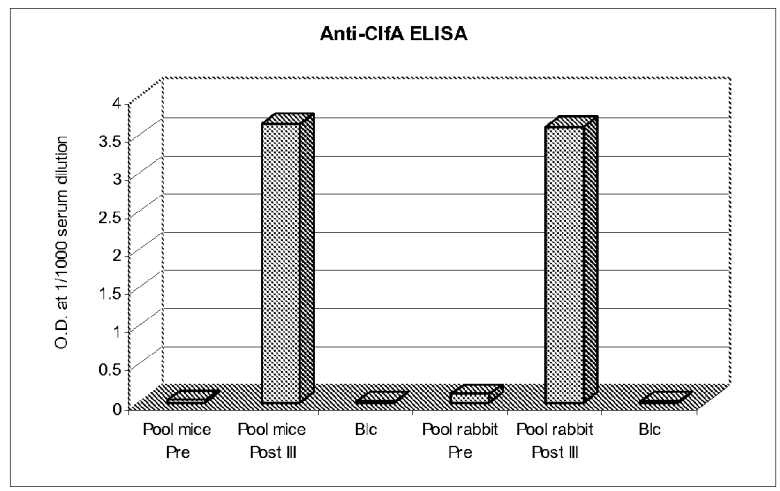
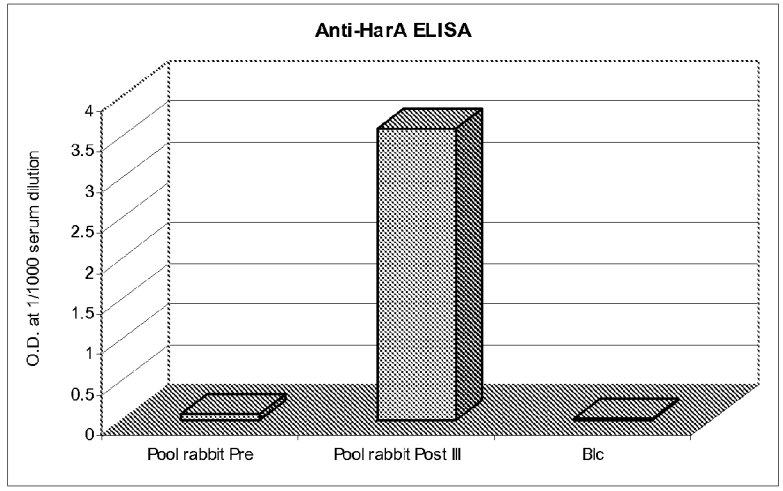

Figure 7 cont.
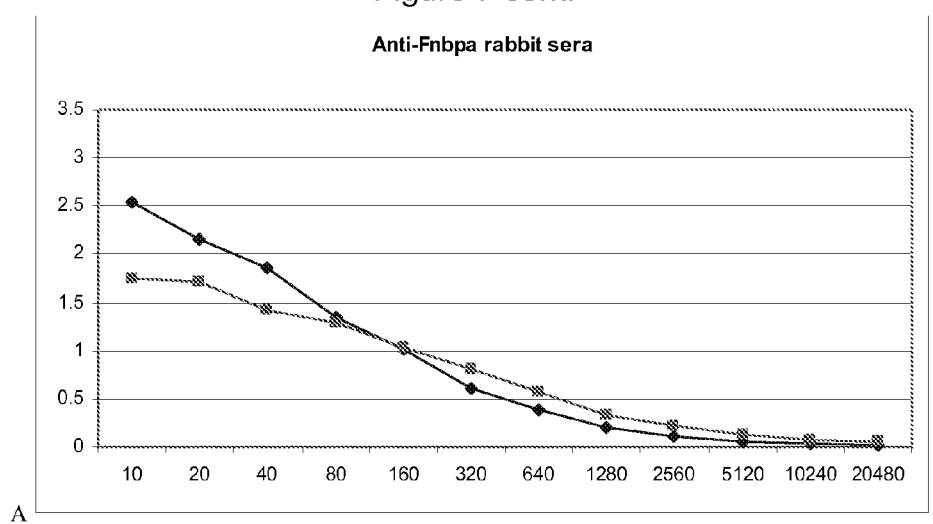
A
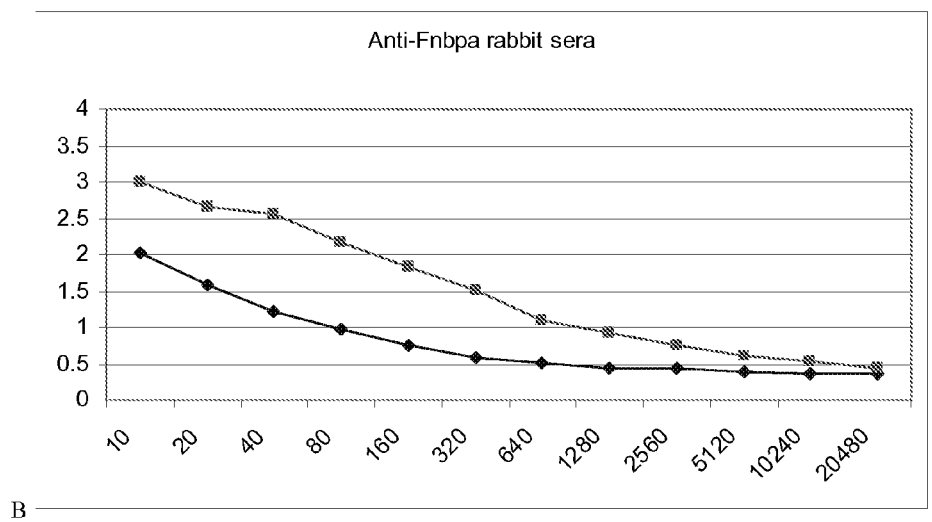
B
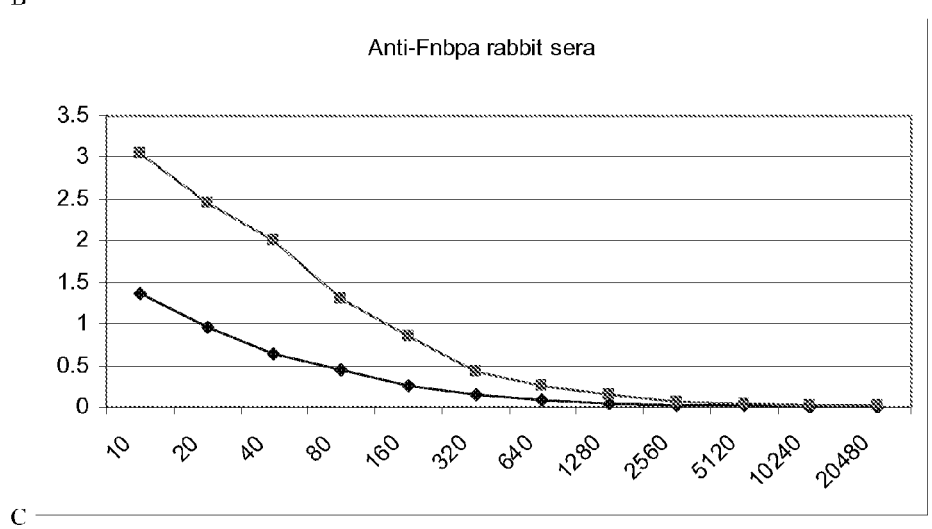
C

IMMUNOGENIC COMPOSITION

This application is filed pursuant to 35 U.S.C. §371 as a United States National Phase Application of International Patent Application Serial No. PCT/EP2007/053059 filed Mar. 29, 2007, which claims priority from Great Britain Applications No. 0606416.6 and 0606417.4 filed in the United Kingdom on Mar. 30, 2006, and from U.S. Applications No. 60/787,249 and 60/787,587 filed in the United States on Mar. 30, 2006, the contents of which are incorporated herein by reference.

TECHNICAL FIELD

The present invention relates to the field of Staphylococcal immunogenic compositions and vaccines, their manufacture and the use of such compositions in medicine. More particularly, it relates to vaccine compositions comprising a PNAG polysaccharide or oligosaccharide conjugate made by particular conjugation methods, optionally combined with type 5 and/or 8 polysaccharides or oligosaccharides from *S. aureus*. Methods for the treatment or prevention of staphylococcal infections using such vaccines are also provided.

BACKGROUND

The number of both community acquired and hospital acquired infections have increased over recent years with the increased use of intravascular devices. Hospital acquired (nosocomial) infections are a major cause of morbidity and mortality, more particularly in the US, where they affect more than 2 million patients annually. Following various studies, about 6 percent of the US patients will acquire an infection during their stay in hospital. The economic burden in the USA was estimated to be more than $4.5 billion in 1992 (Emori and Gaynes, 1993, Clin. Microbiol. Rev. 6; 428). The most frequent infections are urinary tract infections (UTI-33% of the infections), followed by pneumonia (15.5%), surgical site infections (14.8%) and primary bloodstream infections (13%) Emori and Gaynes, 1993, Clin. Microbiol. Rev. 6; 428).

*Staphylococcus aureus*, Coagulase-negative Staphylococci (mostly *Staphylococcus epidermidis*), enterococcus spp, *Esherichia coli* and *Pseudomonas aeruginosa* are the major nosocomial pathogens. Although those pathogens almost cause the same number of infections, the severity of the disorders they can produce combined with the frequency of antibiotic resistant isolates balance this ranking towards *S. aureus* and *S. epidermidis* as being the most significant nosocomial pathogens.

*Staphylococcus aureus* is the most common cause of nosocomial infections with a significant morbidity and mortality (Romero-Vivas et al 1995, Infect. Dis. 21; 1417). It is the cause of some cases of osteomyelitis, endocarditis, septic arthritis, pneumonia, abscesses and toxic shock syndrome.

*S. epidermidis* is a normal skin commensal which is also an important opportunistic pathogen responsible for infections of implanted medical devices and infections at sites of surgery. Medical devices infected by *S. epidermidis* include cardiac pacemakers, cerebrospinal fluid shunts, continuous ambulatory peritoneal dialysis catheters, orthopaedic devices and prosthetic heart valves.

*S. aureus* and *S. epidermidis* infections are treated with antibiotics, with penicillin being the drug of choice whereas vancomycin is used for methicillin resistant isolates. The percentage of staphylococcal strains exhibiting wide-spectrum resistance to antibiotics has become increasingly prevalent since the 1980's (Panlilo et al 1992, Infect. Control. Hosp. Epidemiol. 13; 582), posing a threat for effective antimicrobial therapy. In addition, the recent emergence of vancomycin resistant *S. aureus* strain has aroused fear that methicillin resistant *S. aureus* strains will emerge and spread for which no effective therapy is available.

An alternative approach of using antibodies against staphylococcal antigens in passive immunotherapy has been investigated. Therapy involving administration of polyclonal antisera are under development (WO 00/15238, WO 00/12132) as well as treatment with a monoclonal antibody against lipoteichoic acid (WO 98/57994).

An alternative approach would be use of active vaccination to generate an immune response against staphylococci. Several candidates for inclusion as vaccine components have been identified. These include Fibronectin binding protein (U.S. Pat. No. 5,840,846), MHC II analogue (U.S. Pat. No. 5,648,240), fibrinogen binding protein (U.S. Pat. No. 6,008, 341), GehD (US 2002/0169288), collagen binding protein (U.S. Pat. No. 6,288,214), SdrF, SdrG and SdrH (WO 00/12689), mutant SEA and SEB exotoxins (WO 00/02523) and 52 kDa vitronectin binding protein (WO 01/60852).

The *S. aureus* genome has been sequenced and many of the coding sequences have been identified (EP786519, WO02/094868). The same is true for *S. epidermidis* (WO 01/34809). As a refinement of this approach, others have identified proteins that are recognised by hyperimmune sera from patients who have suffered staphylococcal infection (WO01/98499, WO 02/059148).

The first generation of vaccines targeted against *S. aureus* or against the exoproteins it produces have met with limited success (Lee 1996 Trends Microbiol. 4; 162). There remains a need to develop effective vaccines against staphylococcal infections.

DESCRIPTION OF FIGURES

FIG. 1—Polypeptide sequences of preferred proteins. Table 1 provides information on which protein is represented by each SEQ ID.

FIG. 2—Nucleotide sequences encoding preferred proteins. Table 1 provides information on which protein is encoded by each SEQ ID.

FIGS. 3A and 3B—Purification of alpha toxin under native conditions. Panel A shows a COOMMASSIE® stained SDS-PAGE of samples prepared during the purification of alpha toxin. Lane 1—molecular weight markers, lane 2—soluble fraction containing over-expressed alpha toxin, lane 3—flow through from the Ni-NTA column, lane 4—fractions eluted with 10% buffer B, lane 5—fractions eluted with 20% buffer B, lane 6—fractions eluted with 30% buffer B, lane 7—fractions eluted with 50% buffer B, lane 8—fractions eluted with 75% buffer B, lane 9 and 10 fractions eluted with 100% buffer B, lane 11 bacteria at T=0 before induction, lane 12—bacteria at T=4 hours after induction, lane 13 —cell lysate, lane 14—soluble fraction, lane 15—insoluble fraction.

Panel B shows a COOMMASSIE® stained SDS-PAGE of 10, 5, 2 and 10 of the purified alpha toxin.

FIGS. 4A and 4B—Purification of SdrC underdenaturing conditions. Panel A shows a COOMMASSIE® stained SDS-PAGE of samples prepared during the purification of alpha toxin. Lane M—molecular weight markers, lane Start—supernatant formed from the insoluble fraction containing over-expressed SdrC, lane FT1—flow through from the Ni-NTA column, lane C—fractions eluted with wash buffer C, lane D—fractions eluted with buffer D, lane E—fractions eluted with buffer E.

Panel B shows a COOMMASSIE® stained SDS-PAGE of 1, 2, 5 and 100 of the purified SdrC.

FIG. 5 (multiple panels)—ELISA results for antisera against staphylococcal proteins (Atl-amidase, alpha toxin, EbH, SdrG, Atl-glucosaminidase, MRP, Sbi, IsdA, SdrC, IsdB, IsaA, FnbpA, Atl-AaA, ClfA, and HarA) in plates coated with purified proteins. Pool mice pre—result using pooled sera extracted from mice pre-innoculation. Pool mice Post III—result using pooled mouse sera extracted post-immunisation. Pool rabbit pre—result using pooled sera extracted from rabbits pre-innoculation. Pool rabbit Post III—result using pooled rabbit sera extracted post-immunisation. Blc—negative control.

Figure 6:
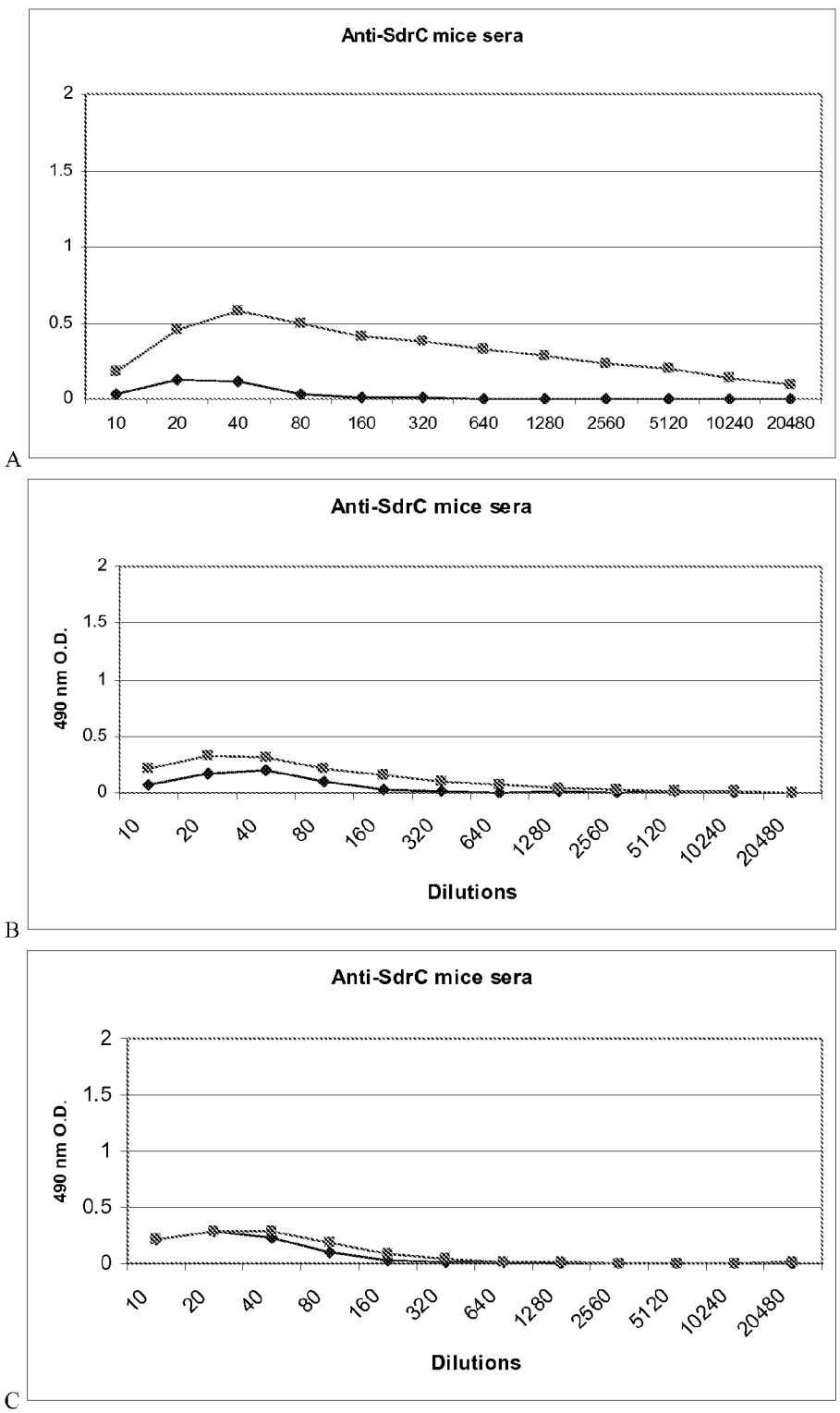
Figure 6:
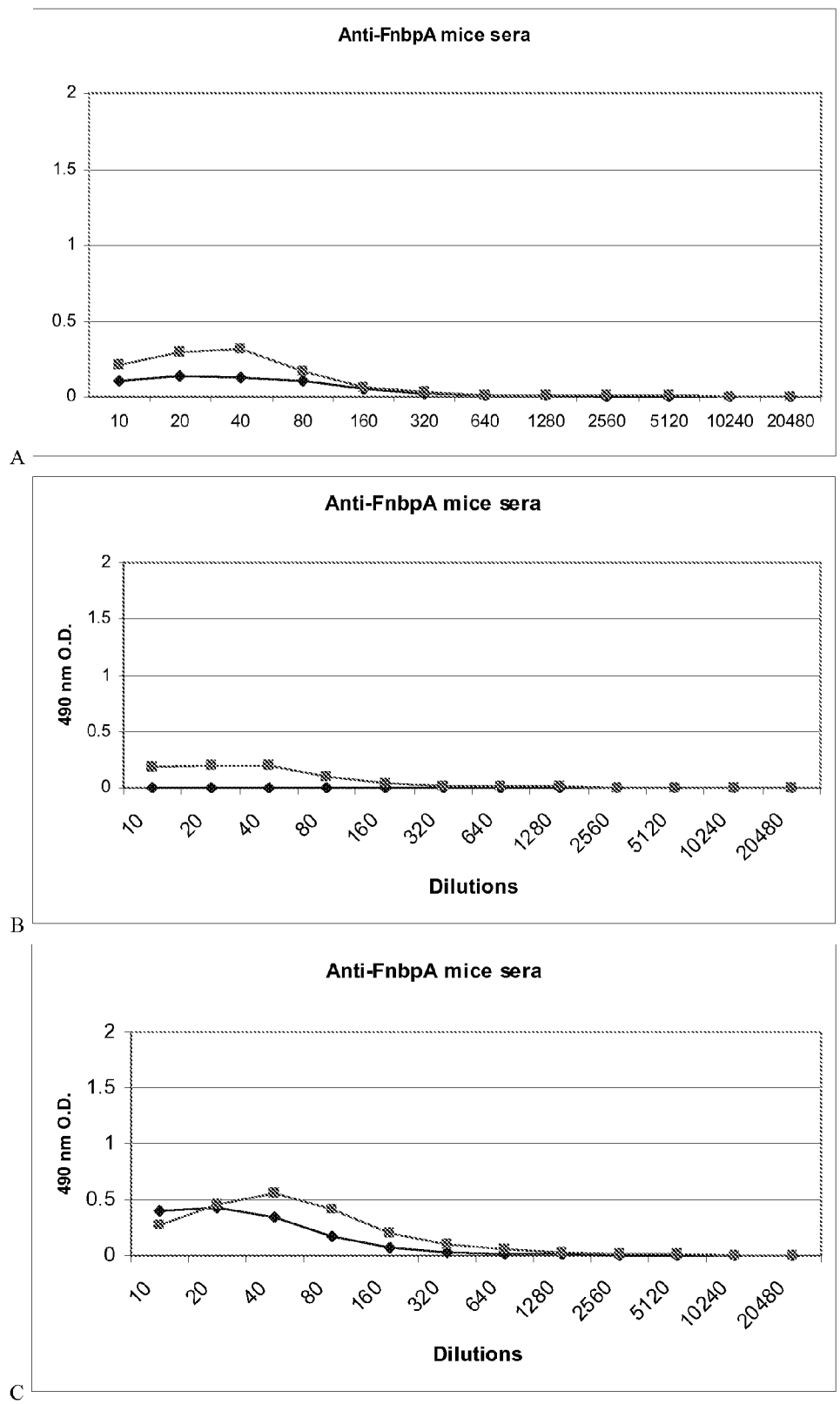
Figure 6:
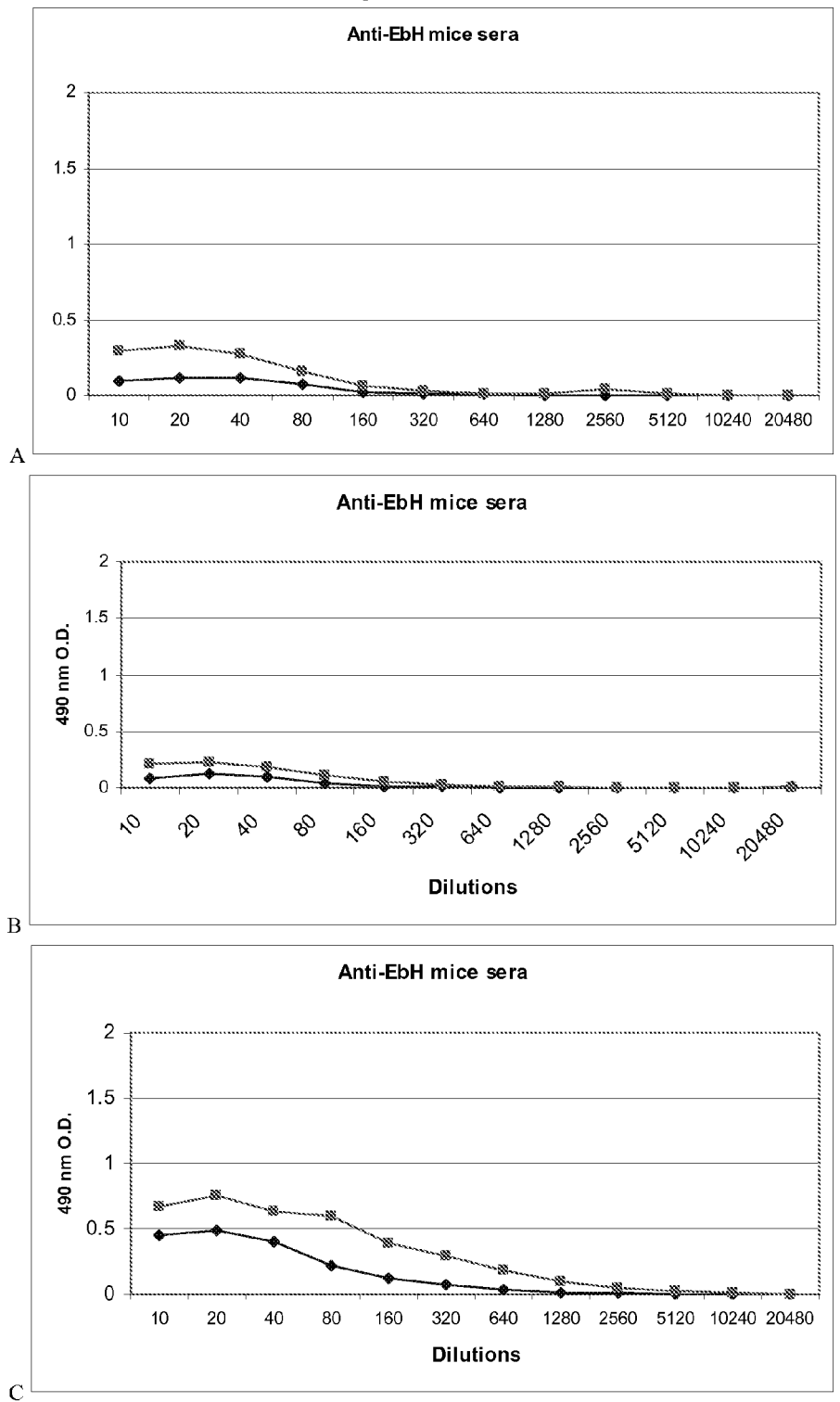
Figure 6:
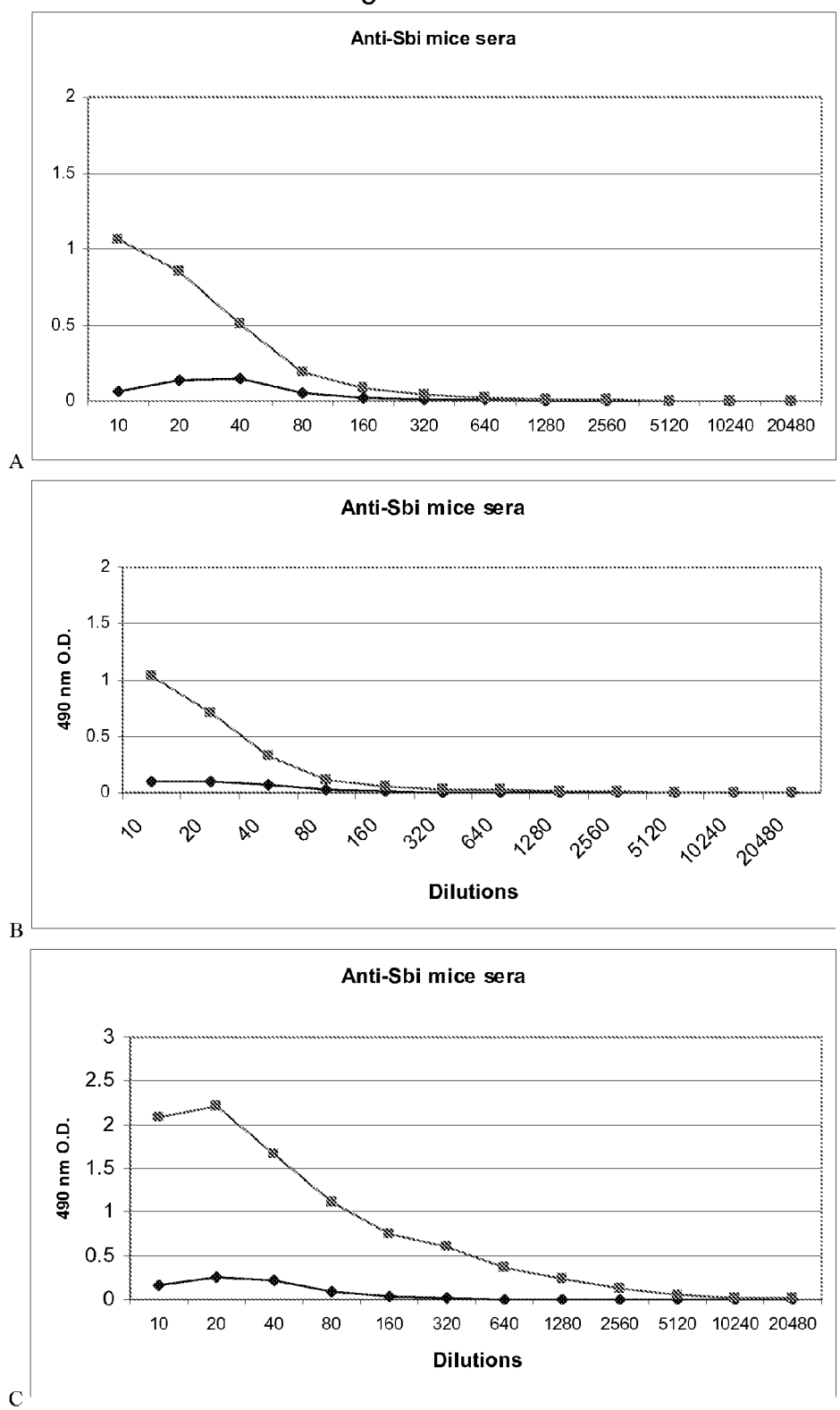
Figure 6:
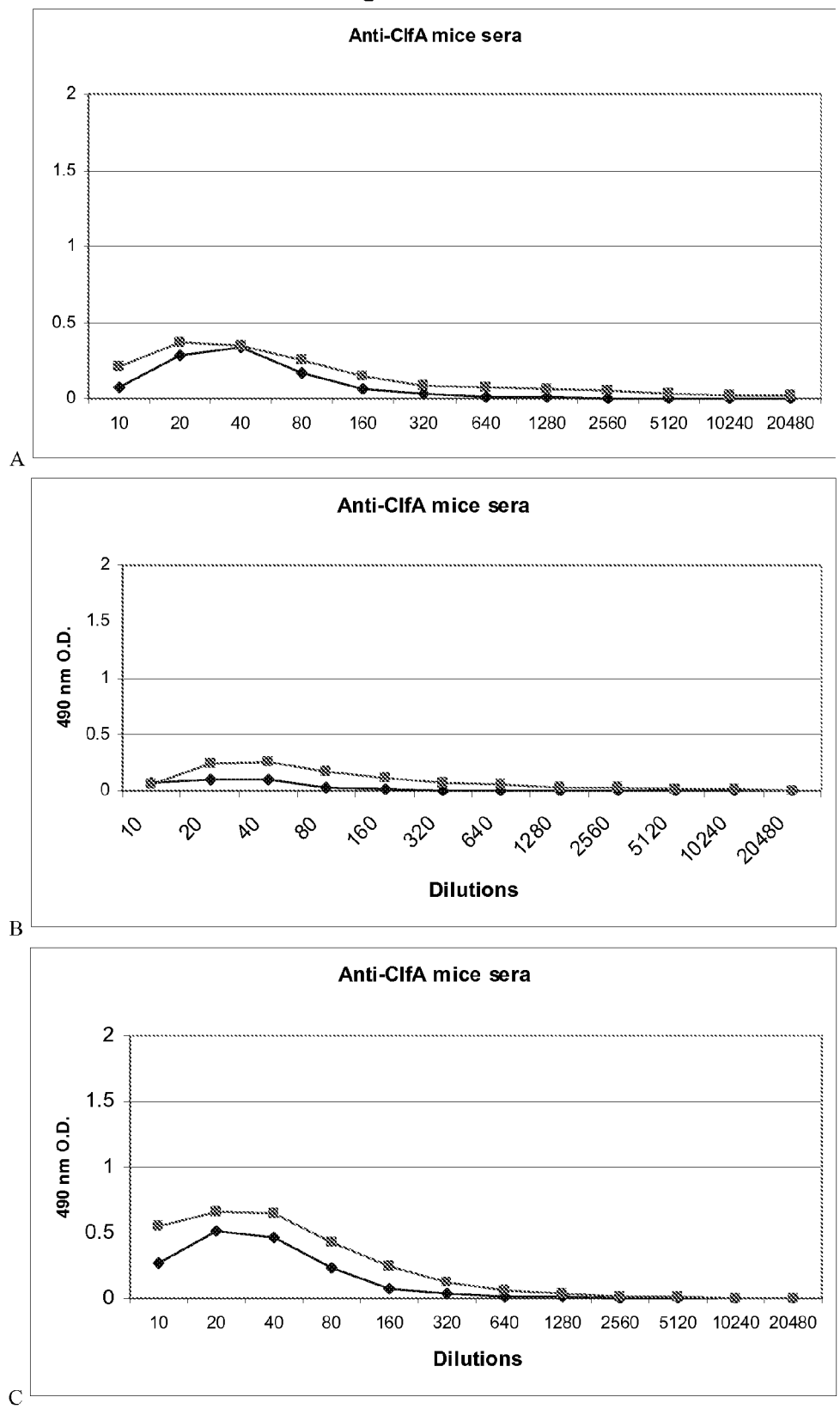

FIG. 6 (multiple panels)—ELISA results for mouse antisera raised against staphylococcal proteins (SdrC, FnbpA, EbH, Sbi, and ClfA) in plates coated with killed staphylococci. Panel A uses plates coated with *S. aureus* serotype 5 killed whole cells. Panel B uses plates coated with *S. aureus* serotype 8 killed whole cells. Panel C uses plates coated with *S. epidermidis* killed whole cells. The line marked with square signs shows the ELISA result using antisera from mice immunised three times with the indicated staphylococcal protein. The line marked with diamond signs shows the ELISA result for pre-immune mouse sera.

Figure 7:
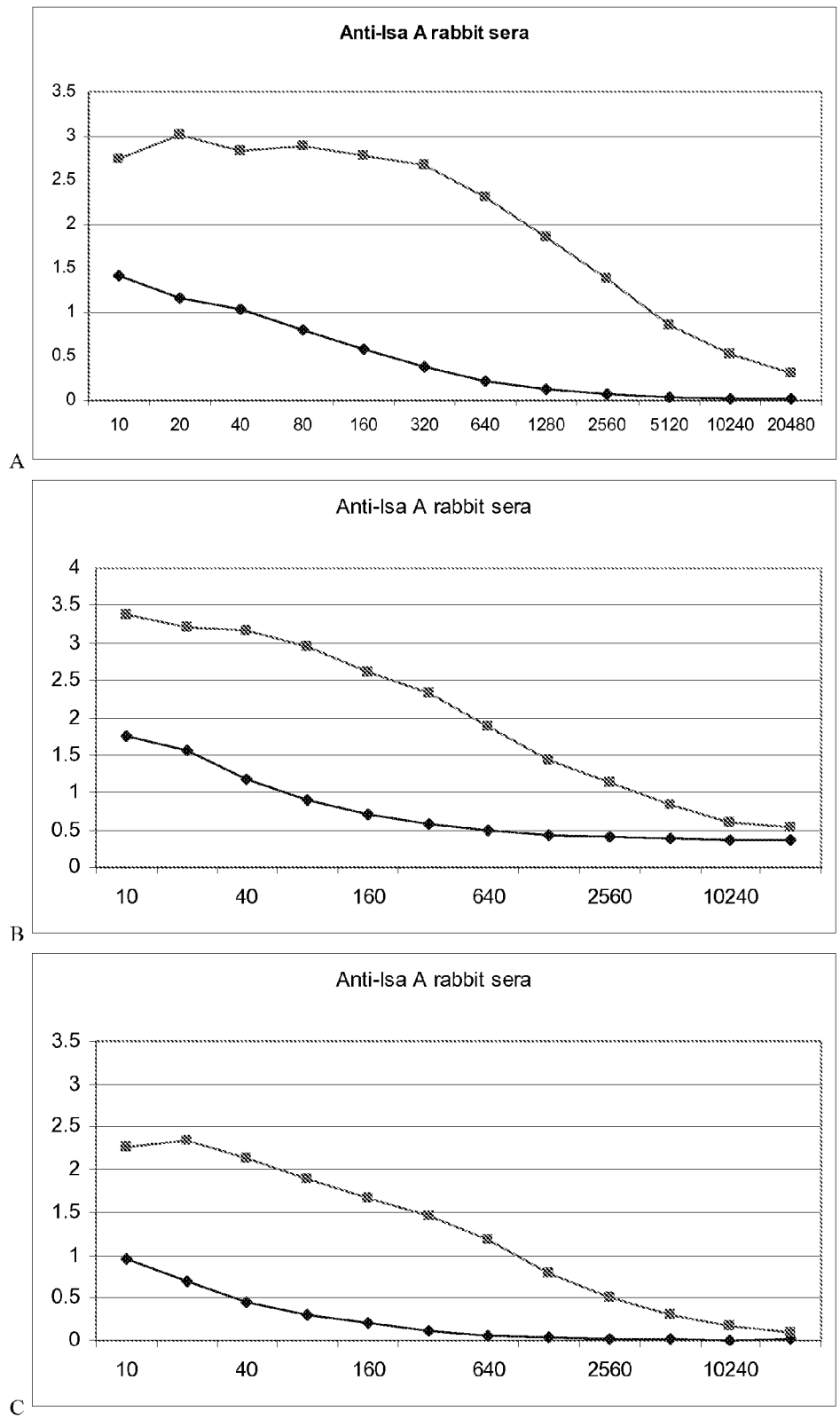
Figure 7:
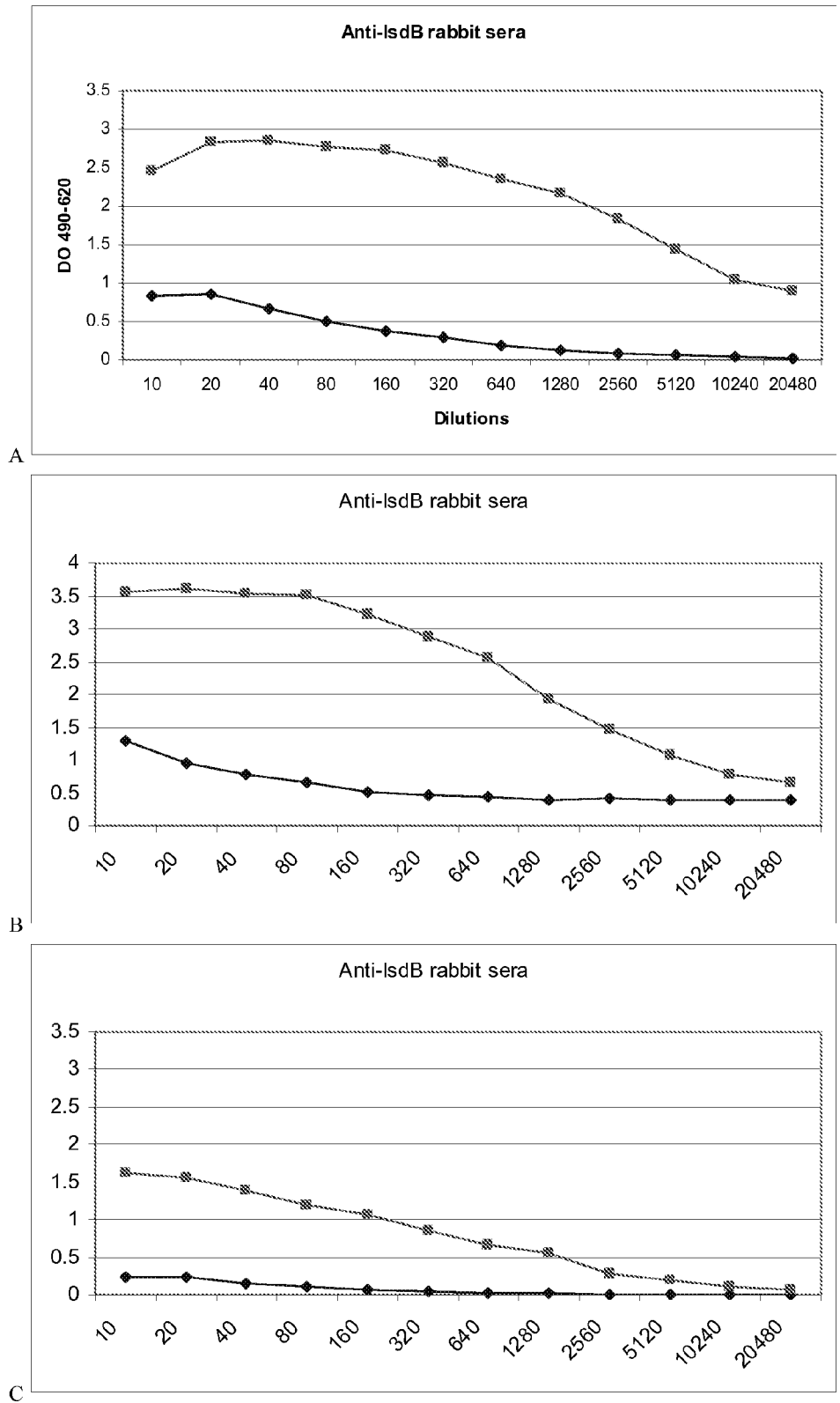
Figure 7:
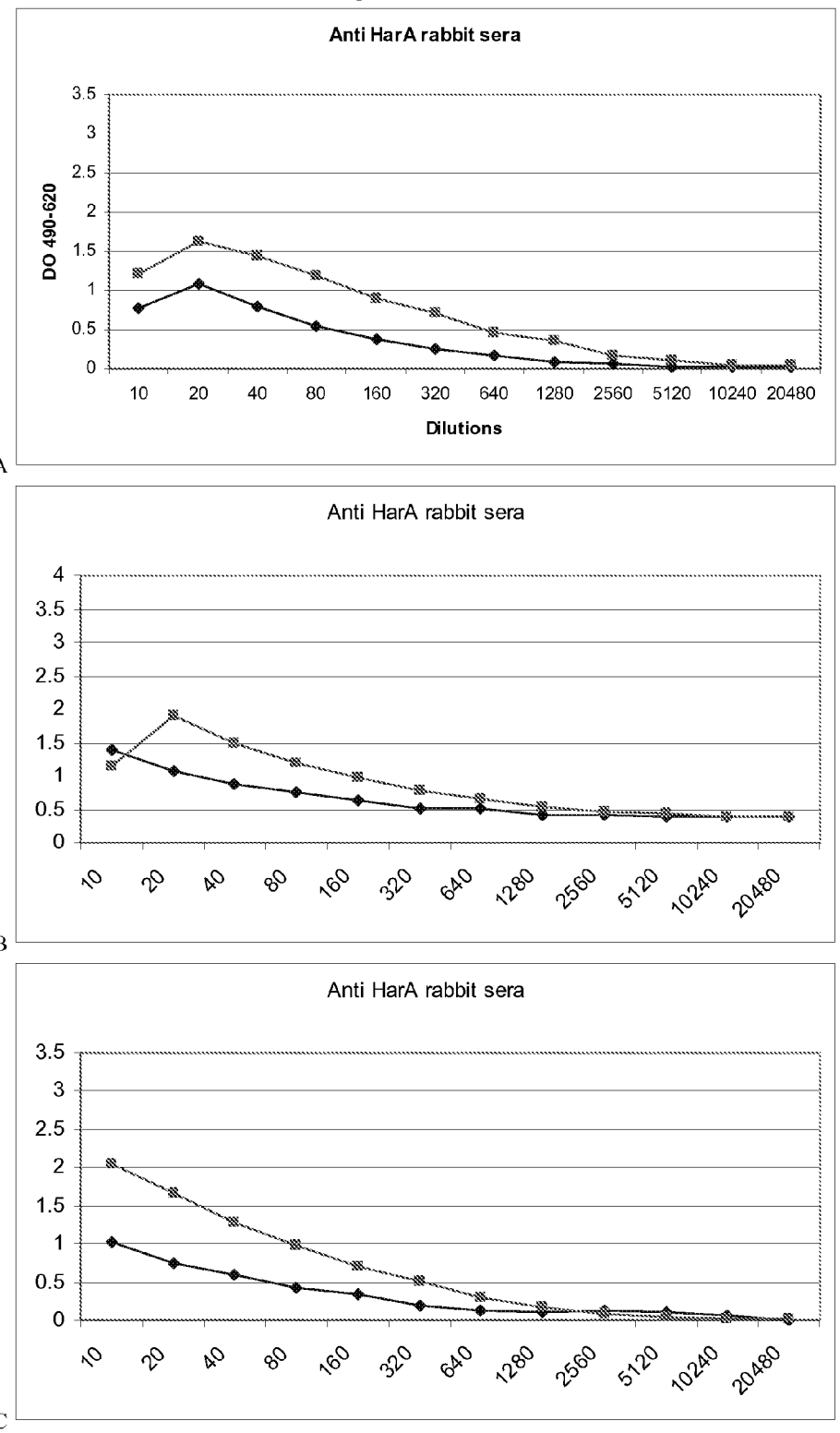
Figure 7:
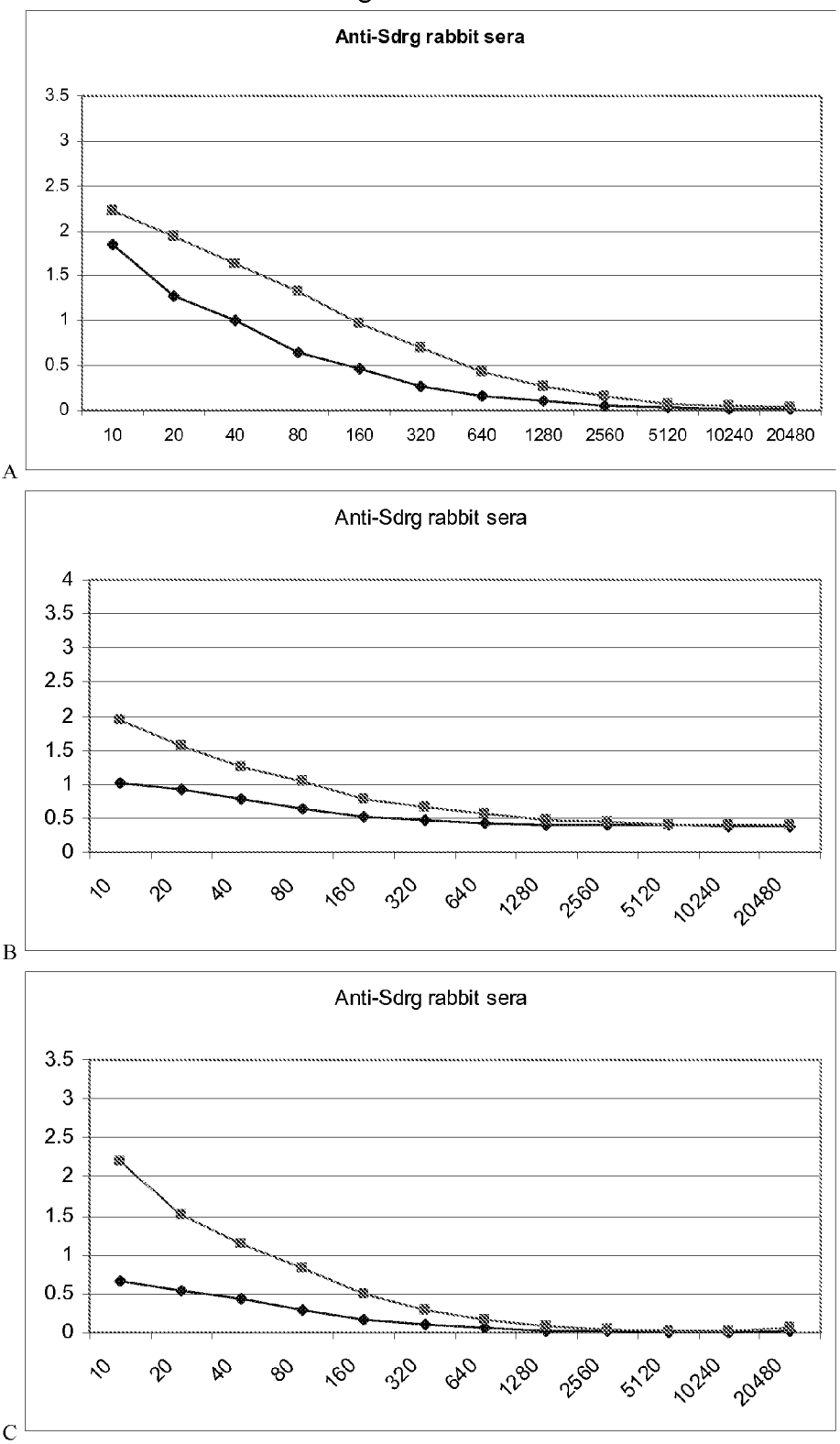
Figure 7:
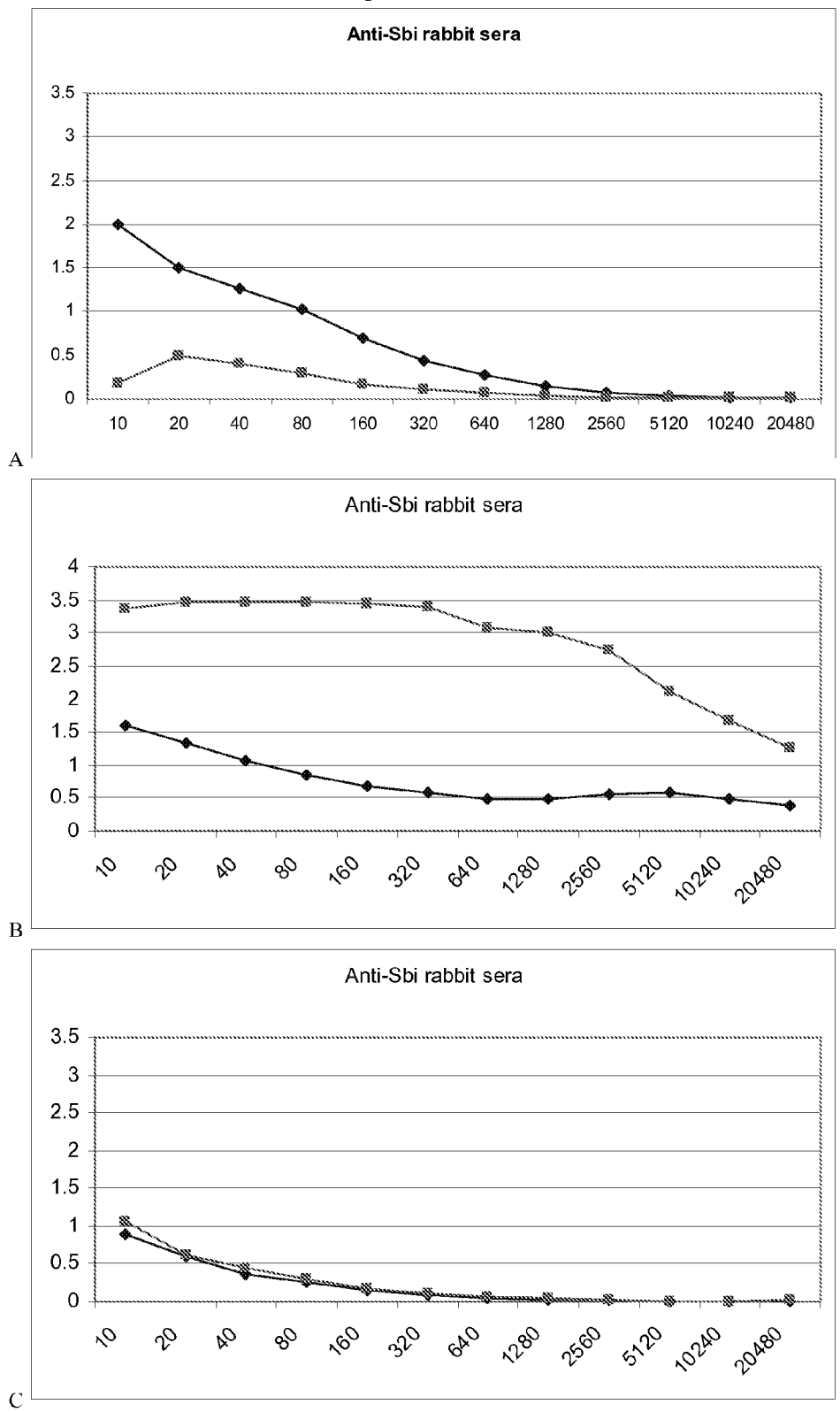
Figure 7:
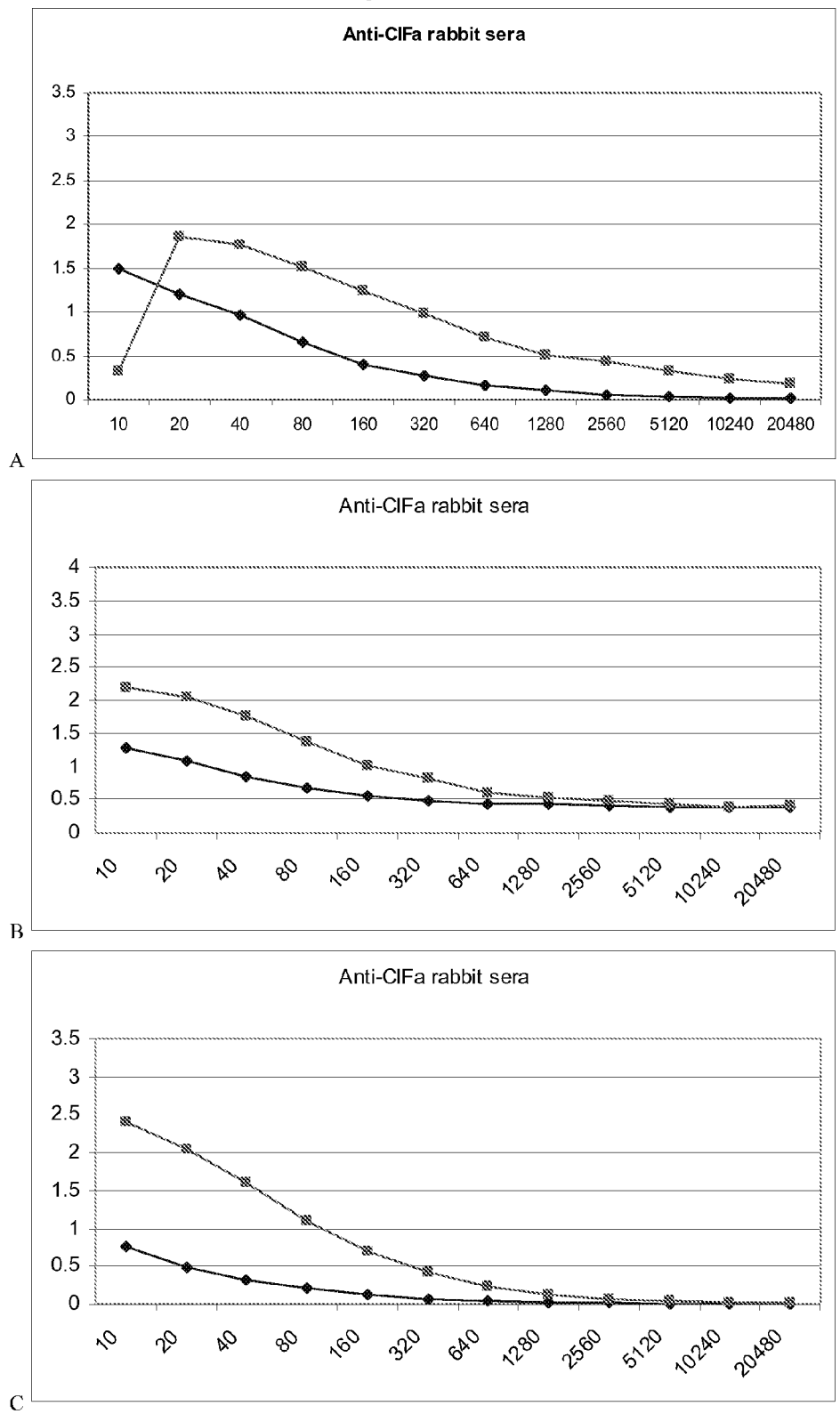
Figure 7:
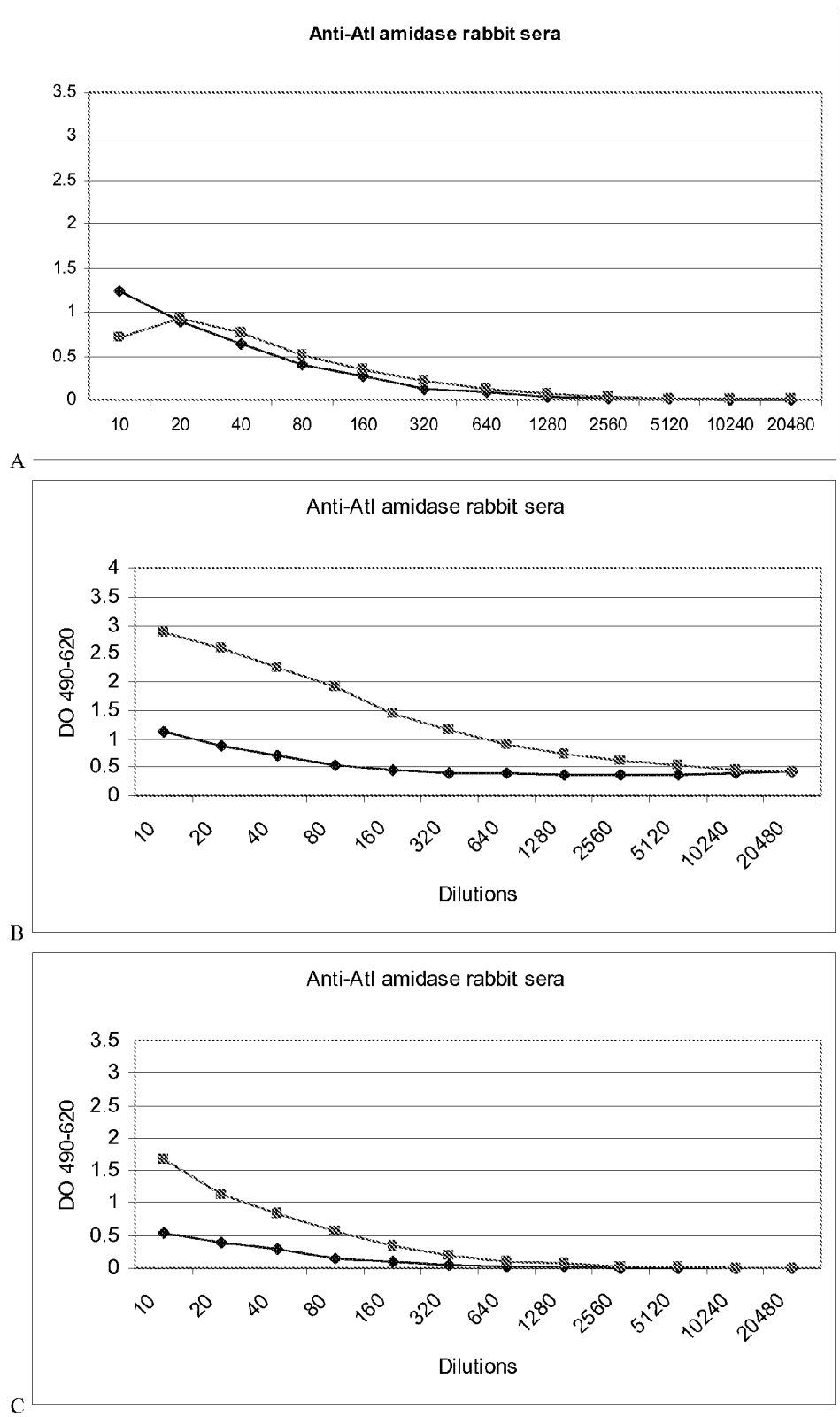

FIG. 7 (multiple panels)—ELISA results for rabbit antisera raised against staphylococcal proteins (IsaA, IsdB, HarA, SdrG, Sbi, ClfA, FnbpA, and Atl-amidase) in plates coated with killed staphylococci. Panel A uses plates coated with *S. aureus* serotype 5 killed whole cells. Panel B uses plates coated with *S. aureus* serotype 8 killed whole cells. Panel C uses plates coated with *S. epidermidis* killed whole cells. The line marked with square signs shows the ELISA result using antisera from rabbits immunised three times with the indicated staphylococcal protein (except for HarA where only one immunisation was given). The line marked with diamond signs shows the ELISA result for pre-immune rabbit sera.

DETAILED DESCRIPTION

The present invention discloses an immunogenic composition comprising staphylococcal PNAG which is less than 40%, 35%, 30%, 25%, 20%, 15%, 10% or 5% N-acetylated wherein the PNAG is conjugated to a carrier protein by a linker bonded to an amine group on PNAG to form a PNAG conjugate. Such immunogenic compositions optionally comprise Type 5 and/or 8 capsular polysaccharide or oligosaccharide from *S. aureus*.

This combination of antigens is capable of eliciting an immune response against a range of staphylococcal infections. PNAG is highly conserved among Gram positive bacteria and provides protection against a broad range of bacteria whereas Type 5 and 8 polysaccharides are potent immunogens that elicit an immune response against most strains of *S. aureus* which is the most common cause of nosocomial infection.

Polysaccharides
Poly N-acetylated glucosamine (PNAG)

PNAG is a polysaccharide intercellular adhesin and is composed of a polymer of β-(1→6)-linked glucosamine, optionally substituted with N-acetyl groups. This polysaccharide is present in both *S. aureus* and *S. epidermidis* and can be isolated from either source (Joyce et al 2003, Carbohydrate Research 338; 903; Maira-Litran et al 2002, Infect. Imun. 70; 4433). For example, PNAG may be isolated from *S. aureus* strain MN8m (WO 04/43407).

The polysaccharide previously known as poly-N-succinyl-β-(1→6)-glucosamine (PNSG) was recently shown not to have the expected structure since the identification of N-succinylation was incorrect (Maira-Litran et al 2002, Infect. Imun. 70; 4433). Therefore the polysaccharide formally known as PNSG and now found to be PNAG is also encompassed by the term PNAG.

PNAG may be of different sizes varying from over 400 kDa to between 75 and 400 kDa to between 10 and 75 kDa to oligosaccharides composed of up to 30 repeat units (of β-(1→6)-linked glucosamine substituted with N-acetyl and O-succinyl constituents). Any size of PNAG polysaccharide or oligosaccharide may be use in an immunogenic composition of the invention, for example a size of over 40 kDa. Sizing may be achieved by any method known in the art, for instance by microfluidisation, ultrasonic irradiation or by chemical cleavage (WO 03/53462, EP497524, EP497525).

Examples of size ranges of PNAG are 40-400 kDa, 50-350 kDa, 40-300 kDa, 60-300 kDa, 50-250 kDa and 60-200 kDa.

The term PNAG comprises both dPNAG and PNAG. The PNAG is less than 40, 35, 30, 25, 20, 15, 10, 5, 2 or 1% N-acetylated so that it is predominantly in the deacetylated form. De-acetylated epitopes of PNAG can elicit antibodies that are capable of mediating opsonic killing of Gram positive bacteria, for example *S. aureus* and/or *S. epidermidis*. In an embodiment, the PNAG is not O-succinylated or is O-succinylated on less than 25, 20, 15, 10, 5, 2, 1 or 0.1% of residues.

In an embodiment, the PNAG has a size between 40 kDa and 300 kDa (or between 75 KDa and 150 KDa) and is deacetylated so that less than 40%, 35%, 30%, 25%, 20%, 15% or 10% of amino groups are acetylated.

In an embodiment, the PNAG is not O-succinylated or is O-succinilated on less than 25, 20, 15, 10, 5, 2, 1 or 0.1% of residues.

The term deacetylated PNAG (dPNAG) refers to a PNAG polysaccharide or oligosaccharide in which less than 60%, 50%, 40%, 30%, 20%, 10% or 5% of the amino groups are acetylated.

As used herein, the term PNAG encompasses both acetylated and deacetylated forms of the saccharide.

In an embodiment, PNAG is deacetylated to form dPNAG by chemically treating the native polysaccharide. For example, the native PNAG is treated with a basic solution such that the pH rises to above 10. For instance the PNAG is treated with 0.1-5M, 0.2-4M, 0.3-3M, 0.5-2M, 0.75-1.5M or 1M NaOH, KOH or NH₄OH. Treatment is for at least 10 or 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

In an embodiment, the polysaccharide(s) included in the immunogenic composition of the invention are conjugated to a carrier protein as described below.

Type 5 and Type 8 polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al Carbohydrate Res. 201; 285 (1990) and Fournier et al Infect. Immun. 45; 87 (1984). Both have FucNAcp in their repeat unit as well as ManNAcA which can be used to introduce a sulfhydryl group.

Recently (Jones Carbohydrate Research 340, 1097-1106 (2005)) NMR spectroscopy revised the structures or the capsular polysaccharides to:

Type 5
→4)-β-D-ManNAcA-(1→4)-α-L-FucNAc(3OAc)-(1→43)-β-D-FucNAc-(1→

Type 8

→3)-β-D-ManNAcA(4OAc)-(1→3)-α-L-FucNAc(1→3)-α-D-FucNAc(1→

Polysaccharides may be extracted from the appropriate strain of S. aureus using methods well known to the skilled man, for instance as described in U.S. Pat. No. 6,294,177. For example, ATCC 12902 is a Type 5 S. aureus strain and ATCC 12605 is a Type 8 S. aureus strain. Type 5 and type 8 polysaccharides may be extracted from S. aureus as described in Infection and Immunity (1990) 58(7); 2367.

Polysaccharides are of native size or alternatively may be sized, for instance by microfluidisation, ultrasonic irradiation or by chemical treatment. The invention also covers oligosaccharides derived from the type 5 and 8 polysaccharides from S. aureus.

The type 5 and 8 capsular polysaccharide or oligosaccharides included in the immunogenic composition of the invention are O-acetylated. In an embodiment, the degree of O-acetylation of type 5 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 8 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%.

In an embodiment, the degree of O-acetylation of type 5 and type 8 capsular polysaccharides or oligosaccharides is 10-100%, 20-100%, 30-100%, 40-100%, 50-100%. 60-100%, 70-100%, 80-100%, 90-100%, 50-90%, 60-90%, 70-90% or 80-90%.

The type 5 and 8 polysaccharides included in the immunogenic composition of the invention are optionally conjugated to a carrier protein as described below or are alternatively unconjugated.

The immunogenic compositions of the invention optionally contains either type 5 or type 8 polysaccharide or both of these.

S. aureus 336 Antigen

In an embodiment, the immunogenic composition of the invention comprises the S. aureus 336 antigen described in U.S. Pat. No. 6,294,177.

The 336 antigen comprises O-linked hexosamine, contains no O-acetyl groups and specifically binds to antibodies to S. aureus Type 336 deposited under ATCC 55804.

In an embodiment, the 336 antigen is a polysaccharide which is of native size or alternatively may be sized, for instance by microfluidisation, ultrasonic irradiation or by chemical treatment. The invention also covers oligosaccharides derived from the 336 antigen.

The 336 antigen, where included in the immunogenic composition of the invention is optionally conjugated to a carrier protein as described below or are alternatively unconjugated.

Type I, II and III polysaccharides from S. epidermidis

Strains ATCC-31432, SE-360 and SE-10 of S. epidermidis are characteristic of three different capsular types, I, II and III respectively (Ichiman and Yoshida 1981, J. Appl. Bacteriol. 51; 229). Capsular polysaccharides extracted from each serotype of S. epidermidis constitute Type I, II and III polysaccharides. Polysaccharides may be extracted by several methods including the method described in U.S. Pat. No. 4,197,290 or as described in Ichiman et al 1991, J. Appl. Bacteriol. 71; 176.

In one embodiment of the invention, the immunogenic composition comprises type I and/or II and/or III polysaccharides or oligosaccharides from S. epidermidis.

Polysaccharides are of native size or alternatively may be sized, for instance by microfluidisation, ultrasonic irradiation or chemical cleavage. The invention also covers oligosaccharides extracted from S. epidermidis strains.

These polysaccharides are unconjugated or are optionally conjugated as described below.

Conjugation of Polysaccharides

Amongst the problems associated with the use of polysaccharides in vaccination, is the fact that polysaccharides per se are poor immunogens. Strategies, which have been designed to overcome this lack of immunogenicity, include the linking of the polysaccharide to large protein carriers, which provide bystander T-cell help. It is preferred that the polysaccharides utilised in the invention are linked to a protein carrier which provide bystander T-cell help. Examples of these carriers which are currently used for coupling to polysaccharide or oligosaccharide immunogens include the Diphtheria and Tetanus toxoids (DT, DT CRM197 and TT), Keyhole Limpet Haemocyanin (KLH), Pseudomonas aeruginosa exoprotein A (rEPA) and the purified protein derivative of Tuberculin (PPD), protein D from Haemophilus influenzae, pneumolysin or fragments of any of the above. Fragments suitable for use include fragments encompassing T-helper epitopes. In particular protein D fragment will preferably contain the N-terminal ⅓ of the protein. Protein D is an IgD-binding protein from Haemophilus influenzae (EP 0 594 610 B1).

The immunogenic compositions of the invention comprise staphylococcal PNAG which is at least 60%, 70%, 75%, 80%, 85%, 90% or 95% de-N-acetylated (or N-acetylated on no more that 40%, 30%, 25%, 20%, 15%, 10% or 5% of residues) wherein the PNAG is conjugated to a carrier protein by a linker bonded to an amine group on PNAG to form a PNAG conjugate.

The term linker refers to the molecule which covalently links the PNAG and the carrier protein in the completed conjugate. The linker may originate from the covalent bonding of two molecules which were used in the conjugation reaction. Alternatively, the linker may derive from a single molecule used in the conjugation reaction or from three molecules used in the conjugation reaction. In an embodiment, the linker may be a single peptide bond with the NH derived from the amine of PNAG and the CO derived from a carboxylic acid group on the carrier protein.

The amine group on PNAG is the primary amine on the glucosamine ring and becomes a secondary amine after bonding to the linker.

In an embodiment, the linker is bonded to an amine group on the carrier protein. For example, the amine group on the carrier protein is a lysine residue or the amino terminus of the carrier protein.

Alternatively, the linker is bonded to a carboxylic acid group on the carrier protein. For example a glutamic acid or aspartic acid residue or the carboxyl terminus of the carrier protein.

In an embodiment, the linker contains a peptide bond at the position at which the linker is covalently bonded to either or both of PNAG and the carrier protein. In an embodiment the linker contains two peptide bonds, the first at the position at which the linker is covalently bonded to PNAG and the second at the position at which the linker is covalently bonded to the carrier protein.

In an embodiment, the linker is between 1-40, 5-30, 5-20, 10-20, 12-18, 14-16, or 1-5 Angstroms in length.

In an embodiment the linker contains a maleimide group. Optionally the maleimide group is linked (i.e. covalently bonded) to a sulphur atom.

In an embodiment the PNAG conjugate is of formula (I):

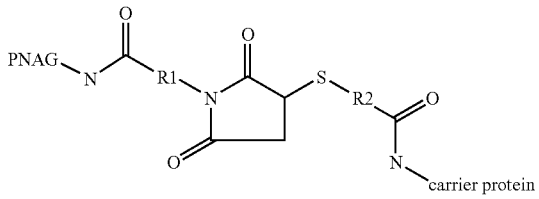
(I)

wherein R1 and R2 are independently selected from an aromatic or aliphatic chain, optionally substituted, or a bond. For example R1 is C1-C6 alkyl, C2-C5 alkyl, C3-C4 alkyl, C2 alkyl, C3 alkyl, C4 alkyl or C5 alkyl. For example R2 is C1-C6 alkyl, C2-C5 alkyl, C3-C4 alkyl, C2 alkyl, C3 alkyl, C4 alkyl or C5 alkyl.

In an embodiment, the PNAG conjugate has the structure of formula II:

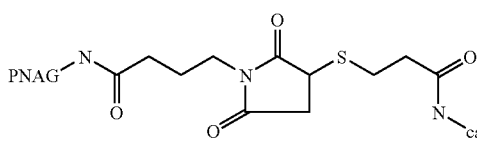
(II)

In an embodiment, the PNAG conjugate has the structure of formula III:

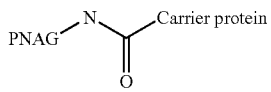
(III)

In an embodiment, the PNAG conjugate has the structure of formula IV:

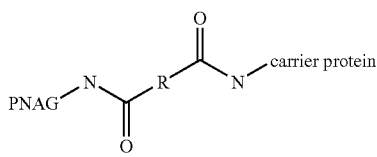
(IV)

wherein R is an aromatic or aliphatic chain, optionally substituted, or a bond. For example R is C1-C12 alkyl, C3-C10 alkyl, C4-C8 alkyl or C6 alkyl.

In an embodiment, the PNAG conjugate has the structure of formula V:

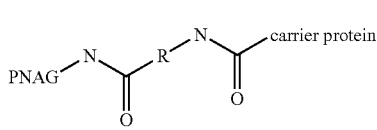
(V)

wherein R is an aromatic or aliphatic chain, optionally substituted, or a bond. For example R is C1-C12 alkyl, C3-C10 alkyl, C4-C8 alkyl or C6 alkyl.

In an embodiment the PNAG conjugate is of formula (VI):

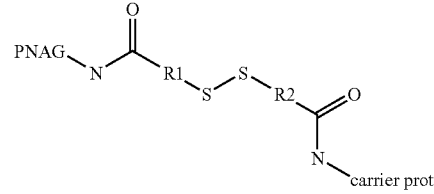
(VI)

wherein R1 and R2 are independently selected from an aromatic or aliphatic chain, optionally substituted, or a bond. For example R1 is C1-C6 alkyl, C2-C5 alkyl, C3-C4 alkyl, C2 alkyl, C3 alkyl, C4 alkyl or C5 alkyl. For example R2 is C1-C6 alkyl, C2-C5 alkyl, C3-C4 alkyl, C2 alkyl, C3 alkyl, C4 alkyl or C5 alkyl. For example R1 and R2 are C2 and C2; C2 and C3; C2 and C4; C2 and C5; C3 and C2; C3 and C3; C3 and C4; C3 and C5; C4 and C2; C4 and C3; C4 and C5; C5 and C2; C5 and C4; C5 and C3; C5 and C4 or C5 and C5 respectively.

In an embodiment the PNAG conjugate is of formula (VII):

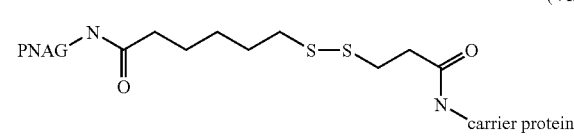
(VII)

In an embodiment the carrier protein is selected from the group consisting of tetanus toxoid, diphtheria toxoid, CRM197, *Haemophilus influenzae* protein D, *Pseudomonas aeruginosa* exoprotein A, pneumococcal pneumolysin and alpha toxoid.

In an embodiment, the carrier protein comprises a staphylococcal protein or fragment thereof selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, Lipase GehD, SasA, SasB, SasC, SasD, SasF, SasK, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, Immunodominant ABC transporter, IsdA, IsdB, HarA, Mg2+ transporter, SitC and Ni ABC transporter, alpha toxin (Hla), alpha toxin H35R mutant and RNA III activating protein (RAP).

An alternative carrier protein to use in the immunogenic composition of the invention is a single staphylococcal protein or fragment thereof or a fusion protein comprising at least or exactly 1, 2, 3 or 4 or more of the staphylococcal proteins listed in the section below or fragments thereof.

A new carrier protein that would be particularly advantageous to use in the context of a staphylococcal vaccine is staphylococcal alpha toxoid. The native form may be conjugated to a polysaccharide since the process of conjugation reduces toxicity. Preferably a genetically detoxified alpha toxin such as the His35Leu or His 35 Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity. Other staphylococcal proteins or fragments thereof, particularly those listed above may be used as a carrier protein for the polysaccharides listed above. The carrier protein may be a fusion protein comprising at least or exactly 1, 2, 3, 4 or 5 of the staphylococcal proteins listed above.

The PNAG or polysaccharides may be linked to the carrier protein(s) by known methods (for example, by Marburg U.S. Pat. No. 4,830,852, by Likhite, U.S. Pat. No. 4,372,945 by Armor et al., U.S. Pat. No. 4,474,757, Jennings et al., U.S. Pat. No. 4,356,170 or Kossaczka and Szu Glycoconjugates Journal 17, 425-433. 2000). Alternatively, CDAP conjugation chemistry is carried out (see WO95/08348).

In CDAP, the cyanylating reagent 1-cyano-dimethylaminopyridinium tetrafluoroborate (CDAP) is preferably used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

The polysaccharide may be solubilized in water or a saline solution. CDAP may be dissolved in acetonitrile and added immediately to the polysaccharide solution. The CDAP reacts with the hydroxyl groups of the polysaccharide to form a cyanate ester. After the activation step, the carrier protein is added. Amino groups of lysine react with the activated polysaccharide to form an isourea covalent link. After the coupling reaction, a large excess of glycine is then added to quench residual activated functional groups. The product is then passed through a gel permeation column to remove unreacted carrier protein and residual reagents.

In an embodiment, the PNAG is conjugated by a method involving the conjugation of an amine group on the PNAG to a carboxyl group on the carrier protein, for example using carbodiimide chemistry, for example using EDAC (Kossaczka and Szu Glycoconjugates Journal 17; 425-433, 2000). In an embodiment, the PNAG is conjugated to the carrier protein via a spacer, for instance a bifunctional spacer. The spacer is optionally heterobifunctional or homobifunctional, having for example a reactive amino group and a reactive carboxylic acid group, 2 reactive amino groups or two reactive carboxylic acid groups. The spacer has for example between 4 and 20, 4 and 12, 5 and 10 carbon atoms. A possible spacer is ADH. Other spacers include B-propionamido (WO 00/10599), nitrophenyl-ethylamine (Geyer et al (1979) Med. Microbiol. Immunol. 165; 171-288), haloalkyl halides (U.S. Pat. No. 4,057,685) glycosidic linkages (U.S. Pat. No. 4,673,574, U.S. Pat. No. 4,808,700) and 6-aminocaproic acid (U.S. Pat. No. 4,459,286).

Conjugation of *S. aureus* Capsular Polysaccharides or Oligosaccharides Using CDAP In a further embodiment of the invention, there is provided a process for producing a conjugate comprising a bacterial saccharide (for example *S. aureus* type 5 or 8 polysaccharide or oligosaccharide) and a carrier protein comprising the steps of:

a) activating the bacterial saccharide (for example *S. aureus* type 5 or 8 polysaccharide or oligosaccharide) with a cyanylating reagent to form an activated bacterial (for example *S. aureus* type 5 or 8) polysaccharide of oligosaccharide; and
b) covalently linking the activated bacterial (for example *S. aureus* type 5 or 8) polysaccharide or oligosaccharide to a carrier protein to form a bacterial (for example *S. aureus* type 5 or 8) polysaccharide or oligosaccharide conjugate.

The cyanylating reagent conjugation process of the invention may be used for conjugating a carbohydrate containing moiety to a protein. For example, the bacterial capsular saccharide, optionally selected from Neisserial capsular saccharides from serogroups A, B, C, W or Y, pneumococcal saccharides from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F, staphylococcal capsular saccharides from type 5 or 8 strains, *S. epidermidis*, GBS, GAS or *Haemophilus influenzae* PRP.

The *S. aureus* or *S. epidermidis* saccharides may have any of the attributes described above.

For example, the *S. aureus* type 5 or 8 saccharide is of native size or is sized, for example by microfluidisation, ultrasonic irradiation or chemical treatment. Type 5 or 8 saccharide optionally has a molecular weight of between 100 kDa-1000 kDa, 100-300 kDa, 300-1000 kDa, 30-300 kDa, 10-100 kDa or 5-50 kDa as measured by MALLS. Type 5 or 8 saccharide is optionally sized to give a viscosity of 1-3, 2.0-3.0, 2.5-2.9 or 2.6-2.8 cp.

The Type 5 or 8 polysaccharide or oligosaccharide optionally has a degree of O-acetylation of 10-100, 20-100, 30-100, 40-100, 50-100 60-100, 70-100 or 80-100%.

The carrier protein used in the process of the invention may be as described above. In an embodiment, the carrier protein is selected from the group consisting of diphtheria toxoid, Crm197, tetanus toxoid, keyhole limpet haemocyanin, *Pseudomonas* aeruginose exoprotein A, *Haemophilus influenzae* protein D, pneumococcal pneumolysin and a staphylococcal protein or fragment thereof. The staphylococcal protein or fragment thereof is optionally selected from the group consisting of laminin receptor, SitC/MntC/saliva binding protein, EbhA, EbhB, Elastin binding protein (EbpS), EFB (FIB), SBI, Protein A, autolysin, ClfA, SdrC, SdrG, SdrH, Lipase GehD, SasA, SasB, SasC, SasD, SasF, SasK, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, Immunodominant ABC transporter, IsdA, IsdB, HarA, MRPII, Mg2+ transporter, proteinA, Aaa, Ant, SdrD, SdrE, SitC and Ni ABC transporter, alpha toxin (Hla), alpha toxin H35R mutant and RNA III activating protein (RAP).

In an embodiment, the cyanylating reagent is 1-cyano-dimethylaminopyridinium tetraborate (CDAP).

In an embodiment, the type 5 or 8 polysaccharide or oligosaccharide is directly linked to the carrier protein for example via a isourea covalent link.

In an embodiment the type 5 or 8 polysaccharide of oligosaccharide is linked to the carrier protein via a spacer. In order to conjugate a *S. aureus* polysaccharide to a carrier protein via a spacer, the following method was used. The covalent binding of the polysaccharide and the spacer (for example ADH) is carried out by a coupling chemistry by which the polysaccharide is activated under controlled conditions by a cyanylating agent, 1-cyano-4-dimethylaminopyridinium tetrafluoroborate (CDAP). The spacer reacts with the cyanylated PS through its hydrazino groups, to form a stable isourea link between the spacer and the polysaccharide.

In an embodiment, the spacer is bifunctional and/or contains a C4-12 alkyl group and/or contains two amino group and/or contains two carboxylic acid groups. In an embodiment the spacer is ADH.

In an embodiment, the ratio of cyanylating reagent to polysaccharide or oligosaccharide in step a) is between 0.25/1 and 1/1 (w/w) or between 0.3/1 and 0.7/1 (w/w), 0.5-0.75, or around 0.5/l or around 0.75/1.

In an embodiment step a) is carried out at pH 5.0-7.0, pH 5.5-6.5 or around pH 6.0.

In an embodiment step a) is carried out for between 30 seconds and 10 minutes, 1 minute and 5 minutes or 2-5 minutes.

In an embodiment step a) is terminated by raising the pH to between 8.0-10.0 or to around pH 9.0.

In an embodiment the ratio of carrier protein to type 5 or 8 polysaccharide or oligosaccharide in step b) is between 1/1 and 10/1, between 1.1/1 and 5/1 or between 1.2/1 and 2.5/1 (w/w).

In an embodiment step b) is carried out at pH 8.0-10.0 or at around pH 9.0.

In an embodiment step b) is carried out for between 10 minutes and 12 hours, 25 minutes and 4 hours, 30 minutes and 2 hours or for around 1 hour.

In an embodiment, the process comprises a further step of combining the type 5 or 8 polysaccharide or oligosaccharide conjugate with at least one additional staphylococcal antigen. For example, any of the staphylococcal antigens (including saccharides and proteins) described above.

In an embodiment, the process of the invention comprises a further step of combining the type 5 or 8 polysaccharide or oligosaccharide conjugate with a pharmaceutically acceptable excipient or diluent to form a vaccine. In an embodiment, the conjugate is combined with an adjuvant. Any of the excipients or adjuvants described below may be combined with the conjugate.

A further aspect of the invention is a conjugate comprising a *S. aureus* type 5 or 8 polysaccharide or oligosaccharide and a carrier protein bonded by a linker comprising an isourea covalent link.

In an embodiment the *S. aureus* type 5 or 8 polysaccharide has any of the attributes described above. For example, it is optionally of native size or is sized as described above.

A further aspect of the invention is a conjugate obtainable by the process of the invention.

A further aspect of the invention is a vaccine comprising the conjugate of the invention and a pharmaceutically acceptable excipient or diluent, optionally comprising an adjuvant. The excipient and adjuvants are optionally as described below.

A further aspect of the invention is a method of making a vaccine comprising the steps of mixing the conjugate of in the invention and adding a pharmaceutically acceptable excipient.

A further aspect of the invention is a method of preventing or treating staphylococcal infection comprising the step of administering the vaccine of the invention to a patient in need thereof. In an embodiment, this method is as described below.

A further aspect of the invention is a use of the conjugate of the invention in the manufacture of a vaccine for treatment or prevention of staphylococcal infection.

Proteins

The immunogenic composition of the invention optionally further comprises a staphylococcal protein, for example a protein from *S. aureus* or *S. epidermidis*. Some embodiments of the invention contain proteins from both *S. aureus* and *S. epidermidis*. Immunogenic compositions of the invention comprise an isolated protein which comprises an amino acid sequence which has at least 85% identity, optionally at least 90% identity, at least 95% identity, at least 97-99% or exact identity, to that of any sequence of FIG. 1.

Where a protein is specifically mentioned herein, it is optionally a reference to a native or recombinant, full-length protein or optionally a mature protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, at least 20 amino acids, at least 30 amino acids, at least 40 amino acids, at least 50 amino acids or at least 100 amino acids, taken contiguously from the amino acid sequence of the protein. In addition, such immunogenic fragments are typically immunologically reactive with antibodies generated against the Staphylococcal proteins or with antibodies generated by infection of a mammalian host with Staphylococci or contain T cell epitopes. In an embodiment, immunogenic fragments also includes fragments that when administered at an effective dose, (either alone or as a hapten bound to a carrier), elicit a protective immune response against Staphylococcal infection, optionally it is protective against *S. aureus* and/or *S. epidermidis* infection. Such an immunogenic fragment may include, for example, the protein lacking an N-terminal leader sequence, and/or a transmembrane domain and/or a C-terminal anchor domain. In an embodiment, the immunogenic fragment according to the invention comprises substantially all of the extracellular domain of a protein which has at least 85%, 90%, 95%, 97% or 99% identity, to that a sequence selected from FIG. 1 over the entire length of the fragment sequence.

In an embodiment, immunogenic compositions of the invention may contain fusion proteins of Staphylococcal proteins, or fragments of staphylococcal proteins. Such fusion proteins may be made recombinantly and may comprise one portion of at least 2, 3, 4, 5 or 6 staphylococcal proteins, for example the combinations of staphylococcal proteins listed below. Alternatively, a fusion protein may comprise multiple portions of at least 2, 3, 4 or 5 staphylococcal proteins. These may combine different Staphylococcal proteins or fragments thereof in the same protein. Alternatively, the invention also includes individual fusion proteins of Staphylococcal proteins or fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197. The fusion protein may be present in the immunogenic composition of the invention as a free protein or it may be a carrier protein linked to a saccharide.

Proteins

In an embodiment, the immunogenic composition of the invention further comprises one or more of the proteins mentioned below or immunogenic fragments thereof. Many of the proteins fall into the categories of extracellular component binding proteins, transporter proteins or toxins and regulators of virulence. The immunogenic composition of the invention optionally further comprises a staphylococcal extracellular component binding protein or a staphylococcal transporter protein or a staphylococcal toxin or regulator of virulence. The immunogenic composition of the invention optionally comprises at least or exactly 1, 2, 3, 4, 5 or 6 staphylococcal proteins.

TABLE 1

The following table sets out the SEQ ID numbers of preferred protein sequences and DNA sequences that are found in FIG. 1 and FIG. 2 respectively. SA indicates a sequence from *S. aureus* and SE indicates a sequence from *S. epidermidis*.

| Name | Protein sequence | DNA sequence |
|---|---|---|
| Immunodominant ABC transporter | | |
| SA | SEQ ID 1 | SEQ ID 34 |
| SE | SEQ ID 2 | SEQ ID 35 |

TABLE 1-continued

The following table sets out the SEQ ID numbers of preferred protein sequences and DNA sequences that are found in FIG. 1 and FIG. 2 respectively. SA indicates a sequence from *S. aureus* and SE indicates a sequence from *S. epidermidis*.

| Name | Protein sequence | DNA sequence |
|---|---|---|
| Laminin receptor | | |
| SA | SEQ ID 3 | SEQ ID 36 |
| SE | SEQ ID 4 | SEQ ID 37 |
| Secretory Antigen A SsaA | | |
| SA 1 | SEQ ID 5 | SEQ ID 38 |
| SA 2 | SEQ ID 6 | SEQ ID 39 |
| SE | SEQ ID 7 | SEQ ID 40 |
| SitC | | |
| SA | SEQ ID 8 | SEQ ID 41 |
| SE | SEQ ID 9 | SEQ ID 42 |
| IsaA/PisA (IssA) | | |
| SA | SEQ ID 10 | SEQ ID 43 |
| SE | SEQ ID 11 | SEQ ID 44 |
| EbhA/B | | |
| SA EbhA | SEQ ID 12 | SEQ ID 45 |
| SA EbhB | SEQ ID 13 | SEQ ID 46 |
| SE EbhA | SEQ ID 14 | SEQ ID 47 |
| SE EbhB | SEQ ID 15 | SEQ ID 48 |
| Accumulation-assoc pro Aap | | |
| SA | SEQ ID 16 | SEQ ID 49 |
| SE | SEQ ID 17 | SEQ ID 50 |
| RNA III activating protein RAP | | |
| SA | SEQ ID 18 | SEQ ID 51 |
| SE | SEQ ID 19 | SEQ ID 52 |
| FIG/SdrG | | |
| SA | SEQ ID 20 | SEQ ID 53 |
| SE | SEQ ID 21 | SEQ ID 54 |
| Elastin binding protein EbpS | | |
| SA | SEQ ID 22 | SEQ ID 55 |
| SE | SEQ ID 23 | SEQ ID 56 |
| Extracellular protein EFB SA | SEQ ID 24 | SEQ ID 57 |
| alpha toxin SA | SEQ ID 25 | SEQ ID 58 |
| SBI SA | SEQ ID 26 | SEQ ID 59 |
| IsdA SA | SEQ ID 27 | SEQ ID 60 |
| IsdB SA | SEQ ID 28 | SEQ ID 61 |
| SdrC SA | SEQ ID 29 | SEQ ID 62 |
| ClfA SA | SEQ ID 30 | SEQ ID 63 |
| FnbA SA | SEQ ID 31 | SEQ ID 64 |
| ClfB SA | SEQ ID 32 | SEQ ID 65 |
| Coagulase SA | SEQ ID 33 | SEQ ID 66 |
| FnbB SA | SEQ ID 67 | SEQ ID 77 |
| MAP SA | SEQ ID 68 | SEQ ID 78 |
| HarA SA | SEQ ID 69 | SEQ ID 79 |
| Autolysin glucosaminidase SA | SEQ ID 70 | SEQ ID 80 |
| Autolysin amidase SA | SEQ ID 71 | SEQ ID 81 |
| Ebh fragment SA | SEQ ID 72 | SEQ ID 82 |
| Autolysin Ant SA | SEQ ID 73 | SEQ ID 83 |
| SdrC SA | SEQ ID 74 | SEQ ID 84 |
| MRPII SA | SEQ ID 75 | SEQ ID 85 |
| SdrG SA | SEQ ID 76 | SEQ ID 86 |
| SdrE SA | SEQ ID 87 | SEQ ID 88 |
| SdrD SA | SEQ ID 89 | SEQ ID 90 |
| SasF SA | SEQ ID 91 | SEQ ID 92 |

Extracellular Component Binding Proteins

Extracellular component binding proteins are proteins that bind to host extracellular components. The term includes, but is not limited to adhesins.

Examples of extracellular component binding proteins include laminin receptor (Naidu et al J. Med. Microbiol. 1992, 36; 177), SitC/MntC/saliva binding protein (U.S. Pat. No. 5,801,234, Wiltshire and Foster Infec. Immun. 2001, 69; 5198), EbhA (Williams et al Infect. Immun. 2002, 70; 6805), EbhB, Elastin binding protein (EbpS) (Park et al 1999, J. Biol. Chem. 274; 2845), EFB (FIB) (Wastfelt and Flock 1995, J. Clin. Microbiol. 33; 2347), SBI (Zhang et al FEMS Immun. Med. Microbiol. 2000, 28; 211), autolysin (Rupp et al 2001, J. Infect. Dis. 183; 1038), ClfA (U.S. Pat. No. 6,008,341, McDevitt et al Mol. Microbiol. 1994, 11; 237), SdrC, SdrG (McCrea et al Microbiology 2000, 146; 1535), SdrH (McCrea et al Microbiology 2000, 146; 1535), Lipase GehD (US2002/0169288), SasA, FnbA (Flock et al Mol Microbiol. 1994, 12; 599, U.S. Pat. No. 6,054,572), FnbB (WO 97/14799, Booth et al 2001 Infec. Immun. 69; 345), collagen binding protein Cna (Visai et al 2000, J. Biol. Chem. 275; 39837), ClfB (WO 99/27109), SdrD (WO 99/27109), SdrE (WO 99/27109), FbpA (Phonimdaeng et al 1988 J. Gen Microbiol. 134; 75), Npase (Flock 2001 J. Bacteriol. 183; 3999), IsaA/PisA (Lonerz et al FEMS Immuno. Med. Microbiol. 2000, 29; 145), SsaA (Lang et al FEMS Immunol. Med. Microbiol. 2000, 29; 213), EPB (Hussain and Hermann symposium on Staph Denmark 14-17th 2000), SSP-1 (Veenstra et al 1996, J. Bacteriol. 178; 537), SSP-2 (Veenstra et al 1996, J. Bacteriol. 178; 537), 17 kDa heparin binding protein HBP (Fallgren et al 2001, J. Med. Microbiol. 50; 547), Vitronectin binding protein (Li et al 2001, Curr. Microbiol. 42; 361), fibrinogen binding protein, coagulase, Fig (WO 97/48727) and MAP (U.S. Pat. No. 5,648,240)

SitC/MntC/Saliva Binding Protein

This is an ABC transporter protein which is a homologue of adhesin PsaA in *S. pneumoniae*. It is a highly immunogenic 32 kDa lipoprotein which is distributed through the bacterial cell wall (Cockayne et al Infect. Immun. 1998 66; 3767). It is expressed in *S. aureus* and *S. epidermidis* as a 32 kDa lipoprotein and a 40 kDa homologue is present in *S. hominis*. In *S. epidermidis*, it is a component of an iron-regulated operon. It shows considerable homology to both adhesins including FimA of *Streptococcus parasanguis*, and with lipoproteins of a family of ABC transporters with proven or putative metal iron transport functions. Therefore SitC is included as an extracellular biding protein and as a metal ion transporter.

The saliva binding protein disclosed in U.S. Pat. No. 5,801,234 is also a form of SitC and can be included in an immunogenic composition of the invention.

ClfA and ClfB

Both these proteins have fibrinogen binding activity and trigger *S. aureus* to form clumps in the presence of plasma. They contain a LPXTG (SEQ ID NO:95) motif common to wall associated proteins.

ClfA is described in U.S. Pat. No. 6,008,341 and ClfB is described in WO 99/27109.

Coagulase (FbpA)

This is a fibrinogen binding protein which triggers *S. aureus* to form clumps in the presence of plasma. It is described in references related to Coagulase:Phonimdaeng et al (J. Gen. Microbio. 1988, 134:75-83), Phonimdaeng et al. (Mol Microbiol 1990; 4:393-404), Cheung et al. (Infect Immun 1995; 63:1914-1920) and Shopsin et al. (J. CLin. Microbiol. 2000; 38:3453-3456).

Preferred fragments for inclusion in the immunogenic composition of the invention include the mature protein in which the signal peptide has been removed (amino acids 27 to the C-terminus).

Coagulase has three distinct domains. Amino acids 59-297 which is a coiled coil region, amino acids 326-505 which is a proline and glycine rich region and the C-terminal domain from amino acid 506 to 645 which has a beta sheet conformation. Each of these domains is a fragment which may be incorporated into the immunogenic composition of the invention.

SdrG

This protein is described in WO 00/12689. SdrG is found in coagulase negative staphylococci and is a cell wall associated protein containing a LPXTG (SEQ ID NO: 95) sequence.

SdrG contains a signal peptide (amino acids 1-51), a region containing fibrinogen binding sites and collagen binding sites (amino acids 51-825), two CnaB domains (amino acids 627-698 and 738-809), a SD repeat region (amino acids 825-1000) and an anchor domain (amino acids 1009-1056).

Preferred fragments of SdrG include polypeptides in which the signal peptide and/or the SD repeats and the anchor domain have been removed. These include polypeptides comprising or consisting of amino acids 50-825, amino acids 50-633, amino acids 50-597 (SEQ ID NO 2 of WO 03/76470), amino acids 273-597 (SEQ ID NO 4 of WO 03/76470), amino acids 273-577 (SEQ ID NO 6 of WO 03/76470) amino acids 1-549, amino acids 219-549, amino acids 225-549, amino acids 219-528, amino acids 225-528 of SEQ ID NO: 70 or 20 or 21.

Preferably, an SdrG polypeptide having a sequence at least 80%, 85%, 90%, 92%, 95%, 97%, 98%, 99% or 100% homologous to the sequence of SEQ ID NO: 70, 20 or 21 is incorporated into the immunogenic composition of the invention.

The compositions of the invention optionally comprise a fragment of the SdrG polypeptides described above.

In an embodiment fragments have the signal peptide and/or the SD repeat domain and/or the anchoring domain deleted. For example sequences corresponding to amino acids 1-713, 1-549, 225-549, 225-529, 24-717, 1-707, 1-690, 1-680, 1-670, 1-660, 1-650, 1-640, 1-630, 1-620, 1-610, 1-600, 34-707, 44-697, 36-689 of SEQ ID 70 or sequences having 85%, 90%, 92%, 95%, 97%, 98%, 99% or 100% identity to SEQ ID 70 or 20 or 21.

In an embodiment, fragments with the signal peptide deleted have a methionine residue at the N-terminus of the fragment to ensure correct translation.

In an embodiment, the fragment has the following sequence:—

MEENSVQDVKDSNTDDELSDSNDQSSDEEKNDVINNNQSINTDDNNQIIK

KEETNNYDGIEKRSEDRTESTTNVDENEATFLQKTPQDNTHLTEEEVKES

SSVESSNSSIDTAQQPSHTTINREESVQTSDNVEDSHVSDFANSKIKESN

TESGKEENTIEQPNKVKEDSTTSQPSGYTNIDEKISNQDE

LLNLPINEYENKARPLSTTSAQPSIKRVTVNQLAAEQGSNVNHLIKVTDQ

SITEGYDDSEGVIKAHDAENLIYDVTFEVDDKVKSGDTMTVDIDKNTVPS

DLTDSFTIPKIKDNSGEIIATGTYDNKNKQITYTFTDYVDKYENIKAHLK

LTSYIDKSKVPNNNTKLDVEYKTALSSVNKTITVEYQRPNENRTANLQSM

FTNIDTKNHTVEQTIYINPLRYSAKETNVNISGNGDEGST

IIDDSTIIKVYKVGDNQNLPDSNRIYDYSEYEDVTNDDYAQLGNNNDVNI

NFGNIDSPYIIKVISKYDPNKDDYTTIQQTVTMQTTINEYTGEFRTASYD

NTIAFSTSSGQGQGDLPPEKTYKIGDYVWEDVDKDGIQNTNDNEKPLSNV

LVTLTYPDGTSKSVRTDEDGKYQFDGLKNGLTYKITFETPEGYTPTLKHS

GTNPALDSEGNSVWVTINGQDDMTIDSGFYQTPKYSLGNY

VWYDTNKDGIQGDDEKGISGVKVTLKDENGNIISTTTTDENGKYQFDNLN

SGNYIVHFDKPSGMTQTTTDSGDDDEQDADGEEVHVTITDHDDFSIDNGY

YDDE (SEQ ID NO: 96)

EbhA and EbhB

EbhA and EbhB are proteins that are expressed in both *S. aureus* and *S. epidermidis* (Clarke and Foster Infect. Immun. 2002, 70; 6680, Williams et al Infect. Immun. 2002, 20; 6805) and which bind to fibronectin. Since fibronectin is an important component of extracellular matrix, EbhA and EbhB have an important function in adhering staphylococci to host extracellular matrix.

The Ebh proteins are large, having a molecular weight of 1.1 megadaltons. It is advantageous to use a fragment of the Ebh protein rather than the complete sequence due to ease of production and formulation. The central region of the protein contains imperfect repeats which contain fibronectin binding sites. Fragments containing one or more of the repeat domains described below are preferred fragments for incorporation into the immunogenic composition of the invention.

Ebh proteins contain imperfect repeats units of 127 amino acids in length which are characterised by containing the consensus sequence:—

L.G.{10}A.{131}Q.{26}L...M..L.{33}A or

.{19}L.G.{10}A.{13}Q.{26}L...M..L.{33}A.{12} or

.....I/V..A...I/V..AK.ALN/
DG..NL..AK..A.{6}L..LN.AQK..L..QI/V..A..V..
V.{6}A..LN/D.AM..L...I/V.D/E...TK.S.NY/F.N/DAD..K..
AY/F..AV..A..I/V.N/D.......

Where '.' means any amino acid and '.{10}' means any 10 amino acids and I/V indicates alternative choices of amino acid.

By reference to the sequence disclosed in Kuroda et al (2001) Lancet 357; 1225-1240, and Table 2, the repeat sequences within Ebh proteins are readily deduced.

In an embodiment, fragments to be included in the immunogenic composition of the invention include proteins containing of one, two, three, four, five, six, seven, eight, nine, ten or more than 10 of the 127 amino acid repeat units. Such fragments may consist of 1, 2, 3, 4, 5, 6, 7, 8, 9, 10 or more repeats of the 127 amino acid repeat region or may consist of 1, 2, 3, 4, 5, 6, 7, 8, 9, 10 or more repeats with additional amino acid residues present at either or both ends of the fragment. Optionally the fragment is the H2 polypeptide of about 44 kDa spanning three repeats (amino acids 3202-3595) as described in Clarke et al Infection and Immunity 70, 6680-6687, 2002. Such fragments will preferably be able to bind fibronectin and/or to elicit antibodies that are reactive against the whole Ebh protein.

The Ebh proteins are capable of binding to fibronectin. Preferred fragments of these polypeptides sequences retain the ability to bind to fibronectin. Binding to fibronectin can be assessed by ELISA as described by Clarke et al (Infection and Immunity 70; 6680-6687 2002).

In an embodiment, the fragment is one which comprises a B-cell or T-helper epitope, for example those fragments/peptides described in Tables 3 and 4.

TABLE 2

Repeat sequences in the full-length sequence of Ebh.
The full-length sequence of Ebh is disclosed in Kuroda
et al (2001) Lancet 357; 1225-1240.
The following table shows the amino acid residues at
which the 127 amino acid repeats begin and end within
the full length sequence.

|    | Begin | End  |
|----|-------|------|
| 1  | 3204  | 3330 |
| 2  | 3331  | 3457 |
| 3  | 3457  | 3583 |
| 4  | 3583  | 3709 |
| 5  | 3709  | 3835 |
| 6  | 3835  | 3961 |
| 7  | 3961  | 4087 |
| 8  | 4200  | 4326 |
| 9  | 4326  | 4452 |
| 10 | 4452  | 4578 |
| 11 | 4578  | 4704 |
| 12 | 4704  | 4830 |
| 13 | 4830  | 4956 |
| 14 | 4956  | 5082 |
| 15 | 5082  | 5208 |
| 16 | 5208  | 5334 |
| 17 | 5334  | 5460 |
| 18 | 5460  | 5586 |
| 19 | 5585  | 5711 |
| 20 | 5711  | 5837 |
| 21 | 5837  | 5963 |
| 22 | 5963  | 6089 |
| 23 | 6089  | 6215 |
| 24 | 6215  | 6341 |
| 25 | 6341  | 6467 |
| 26 | 6467  | 6593 |
| 27 | 6593  | 6719 |
| 28 | 6719  | 6845 |
| 29 | 6845  | 6971 |
| 30 | 6971  | 7097 |
| 31 | 7097  | 7223 |
| 32 | 7223  | 7349 |
| 33 | 7349  | 7475 |
| 34 | 7475  | 7601 |
| 35 | 7601  | 7727 |
| 36 | 7727  | 7853 |
| 37 | 7852  | 7978 |
| 38 | 7978  | 8104 |
| 39 | 8104  | 8230 |
| 40 | 8230  | 8356 |
| 41 | 8356  | 8482 |
| 42 | 8482  | 8608 |
| 43 | 8604  | 8730 |
| 44 | 8858  | 8984 |

TABLE 3

B-cell epitope prediction for a 127 amino acid
repeat:
The full-length sequence is disclosed in Kuroda
et al (2001) Lancet 357; 1225-1240. One of
these repeats, encoded by amino acids
3204-3331 of the full-length sequence was
chosen to carry out an epitope prediction:-
MDVNTVNQKAASVKSTKDALDGQQNLQRAKTEATNAITHASDLNQAQ
KNALTQQVNSAQNVHAVNDIKQTTQSLNTAMTGLKRGVANHNQVVQS
DNYVNADTNKKNDYNNAYNHANDIINGNAQHPVI
(SEQ ID NO: 97)

| Begin (Amino Acid position relative to SEQ ID NO: 97) | End (Amino Acid position relative to SEQ ID NO: 97) | Start | Stop |
|---|---|---|---|
| 5 | 10 | 3208 | 3213 |
| 14 | 19 | 3217 | 3222 |
| 21 | 33 | 3224 | 3236 |
| 42 | 51 | 3245 | 3254 |
| 66 | 74 | 3269 | 3277 |
| 100 | 112 | 3303 | 3315 |
| 117 | 123 | 3320 | 3326 |

The "Begin" and "End" columns present the position of the predicted B-cell epitopes in the 127 amino acid repeat
The "Start" and "Stop" columns present the position of the predicted B-cell epitopes in the Ebh full length sequence

TABLE 4

T-helper cell epitope prediction in Ebh:
The full-length sequence is disclosed in
TrEMBL database, sequence reference Q8NWQ6.
One of these repeats, encoded by amino acids
3204-3331 of the full-length sequence was
chosen to carry out an epitope prediction:-
MDVNTVNQKAASVKSTKDALDGQQNLQRAKTEATNAITHASDLNQAQKNA
LTQQVNSAQNVHAVNDIKQTTQSLNTAMTGLKRGVANHNQVVQSDNYVNA
DTNKKNDYNNAYNHANDIINGNAQHPVI
(SEQ ID NO: 98)

| Corresponding Amino Acids Numbers of SEQ ID NO: 99 (the repeat encoded by amino acids 3204-3331 of sequence reference Q8NWQ6) | Position sequence |
|---|---|
| 1-9 | 3204 |
| 3-11 | 3206 |
| 6-14 | 3209 |
| 26-34 | 3229 |
| 37-45 | 3240 |
| 43-50 | 3246 |
| 51-59 | 3254 |
| 55-63 | 3258 |
| 61-69 | 3264 |
| 64-72 | 3267 |
| 67-75 | 3270 |
| 74-82 | 3277 |
| 78-86 | 3281 |
| 81-89 | 3284 |
| 85-93 | 3288 |
| 91-99 | 3294 |
| 92-100 | 3295 |
| 97-105 | 3301 |
| 98-106 | 3302 |
| 108-116 | 3311 |
| 112-120 | 3315 |
| 118-126 | 3321 |
| 119-127 | 3322 |

The "Position repeat" column presents the position of the predicted T-cell epitopes in the repeat
The "Position sequence" column presents the position of the predicted T-cell epitopes in the Ebh full length sequence Fragments of the proteins of the invention may be employed for producing the corresponding full-length polypeptide by peptide synthesis; therefore, these fragments may be employed as intermediates for producing the full-length proteins of the invention.

In an embodiment, variants are used in which several, 5-10, 1-5, 1-3, 1-2 or 1 amino acids are substituted, deleted, or added in any combination.

Elastin Binding Protein (EbpS)

EbpS is a protein containing 486 amino acids with a molecular weight of 83 kDa. It is associated with the cytoplasmic membrane of *S. aureus* and has three hydrophobic regions which hold the protein in the membrane (Downer et al 2002, J. Biol. Chem. 277; 243; Park et al 1996, J. Biol. Chem. 271; 15803).

Two regions between amino acids 1-205 and 343-486 are surface exposed on the outer face of the cytoplasmic membrane. The ligand binding domain of EbpS is located between residues 14-34 at the N-terminus (Park et al 1999, J. Biol. Chem. 274; 2845).

In an embodiment, the fragment to be incorporated into the immunogenic composition of the invention is the surface exposed fragment containing the elastin binding region (amino acids 1-205). Optionally the fragments do not contain the entire exposed loop but should contain the elastin binding region (amino acids 14-34). An alternative fragment which could be used consists of amino acids forming the second surface exposed loop (amino acids 343-486). Alternative fragments containing up to 1, 2, 5, 10, 20, 50 amino acids less at one or both ends are also possible.

Laminin Receptors

The laminin receptor of *S. aureus* plays an important role in pathogenicity. A characteristic feature of infection is bloodstream invasion which allows widespread metastatic abscess formation. Bloodstream invasion requires the ability to extravasate across the vascular basement membrane. This is achieved through binding to laminin through the laminin receptor (Lopes et al Science 1985, 229; 275).

Laminin receptors are surface exposed and are present in many strains of staphylococci including *S. aureus* and *S. epidermidis*.

SBI

Sbi is a second IgG binding protein in addition to protein A and it is expressed in most strains of *S. aureus* (Zhang et al 1998, Microbiology 144; 985).

The N-terminus of the sequence of Sbi has a typical signal sequence with a cleavage site after amino acid 29. Therefore a fragment of Sbi which could be used in an immunogenic composition of the invention starts at amino acid residue 30, 31, 32 or 33 and continues to the C-terminus of Sbi, for example of SEQ ID NO: 26.

The IgG binding domain of Sbi has been identified as a region towards the N-terminus of the protein from amino acids 41-92. This domain is homologous to the IgG binding domains of protein A.

The minimal IgG binding domain of Sbi contains the following sequence (SEQ ID NO: 99):—

```
QTTQNNYVTDQQKAFYQVLHLKGITEEQRNQYIKTLREHPERA
         ** ***  *        ***  *  *   *

QEVFSESLK
   *  *
*- denotes amino acids which are similar between
IgG binding domains
```

In an embodiment, a fragment of Sbi to be included in the immunogenic composition of the invention contains an IgG binding domain. This fragment contains the consensus sequence for an IgG binding domain as designated by * as shown in the above sequence. Optionally the fragment contains or consists of the complete sequence shown above. Optionally, the fragment contains or consists of amino acids 30-92, 33-92, 30-94, 33-94, 30-146, 33-146, 30-150, 33-150, 30-160, 33-160, 33-170, 33-180, 33-190, 33-200, 33-205 or 33-210 of Sbi, for example of SEQ ID NO:26.

A fragment may contain 1, 2, 3, 4, 5, 6, 7, 8, 9, 10 amino acid substitutions from the sequences indicated.

A fragments may contain multiple repeats (2, 3, 4, 5, 6, 7, 8, 9 or 10) of the IgG binding domain.

EFB-FIB

Fib is a 19 kDa fibrinogen binding protein which is secreted into the extracellular medium by *S. aureus*. It is produced by all *S. aureus* isolates tested (Wastfelt and Flock 1995, J. Clin. Microbiol. 33; 2347).

*S. aureus* clumps in the presence of fibrinogen and binds to fibrinogen coated surfaces. This ability facilitates staphylococcal colonisation of catheters and endothelial cells.

Fib contains a signal sequence at the N-terminus of the protein with a putative cleavage site at about amino acid 30. In an embodiment, the immunogenic composition of the invention comprises or consists of the sequence of the mature protein (from about amino acid 30 to the C-terminus of the protein).

Fbe-EfB/FIG

Fbe is a fibrinogen binding protein that is found in many isolates of *S. epidermidis* and has a deduced molecular weight of 119 kDa (Nilsson et al 1998. Infect. Immun. 66; 2666). Its sequence is related to that of clumping factor from *S. aureus* (ClfA). Antibodies against Fbe can block the binding of *S. epidermidis* to fibrinogen coated plates and to catheters (Pei and Flock 2001, J. Infect. Dis. 184; 52).

Fbe has a putative signal sequence with a cleavage site between amino acids 51 and 52. Therefore a preferred fragment of Fbe contains the mature form of Fbe extending from amino acid 52 to the C-terminus (amino acid 1,092).

The domain of Fbe from amino acid 52 to amino acid 825 is responsible for fibrinogen binding. In an embodiment, the fragment of Fbe consists of or contains amino acids 52-825.

The region between amino acid 373 and 516 of Fbe shows the most conservation between Fbe and ClfA. In an embodiment, the fragment contains amino acids 373-516 of Fbe.

Amino acids 825-1041 of Fbe contains a highly repetitive region composed of tandemly repeated aspartic acid and serine residues.

IsaA/PisA

IsaA is a 29 kDa protein, also known as PisA has been shown to be a immunodominant staphylococcal protein during sepsis in hospital patients (Lorenz et al 2000, FEMS Immunol. Med. Microb. 29; 145).

The first 29 amino acids of the IsaA sequence are thought to be a signal sequence. In an embodiment, the fragment of IsaA to be included in an immunogenic composition of the invention contains amino acid residues 30 onwards, to the end of the coded sequence.

Fibronectin Binding Protein

Fibronectin binding protein A contains several domains that are involved in binding to fibronectin (WO 94/18327). These are called D1, D2, D3 and D4. In an embodiment fragments of fibronectin binding protein A or B comprise or consist of D1, D2, D3, D4, D1-D2, D2-D3, D3-D4, D1-D3, D2-D4 or D1-D4.

Fibronectin binding protein contains a 36 amino acid signal sequence. For example:

```
VKNNLRYGIRKHKLGAASVFLGTMIVVGMGQDKEAA
(SEQ ID NO: 100)
```

Optionally, the mature protein omitting this signal sequence is included in the immunogenic composition of the invention.

Transporter Proteins

The cell wall of Gram positive bacteria acts as a barrier preventing free diffusion of metabolites into the bacterium. A family of proteins orchestrates the passage of essential nutrients into the bacterium and are therefore essential for the viability of the bacterium. The term transporter protein covers proteins involved in the initial step of binding to metabolites such as iron as well as those involved in actually transporting the metabolite into the bacterium.

Molecular iron is an essential co-factor for bacterial growth. Siderophores are secreted that bind free iron and then are captured by bacterial surface receptors that deliver iron for transport across the cytoplasmic membrane. Iron acquisition is critical for the establishment of human infections so that the generation of an immune response against this class of proteins leads to a loss of staphylococcal viability.

Examples of transporter proteins include Immunodominant ABC transporter (Burnie et al 2000 Infect. Imun. 68; 3200), IsdA (Mazmanian et al 2002 PNAS 99; 2293), IsdB (Mazmanian et al 2002 PNAS 99; 2293), IsdC (WO 06/59247), Mg2+ transporter, SitC (Wiltshire and Foster 2001 Infect. Immun. 69; 5198) and Ni ABC transporter.

Immunodominant ABC Transporter

Immunodominant ABC transporter is a well conserved protein which may be capable of generating an immune response that is cross-protective against different staphylococcal strains (Mei et al 1997, Mol. Microbiol. 26; 399). Antibodies against this protein have been found in patients with septicaemia (Burnie et al 2000, Infect. Immun. 68; 3200).

Optional fragments of immunodominant ABC transporter will include the peptides DRHFLN (SEQ ID NO: 101), GNYD (SEQ ID NO: 102), RRYPF (SEQ ID NO: 103), KTTLLK (SEQ ID NO: 104), GVTTSLS (SEQ ID NO: 105), VDWLR (SEQ ID NO: 106), RGFL (SEQ ID NO: 107), KIKVYVGNYDFWYQS (SEQ ID NO: 108), TVIWSHDRHFLYNNV (SEQ ID NO: 109) and/or TETFLRGFLGRMLFS (SEQ ID NO: 110) since these sequences contain epitopes that are recognised by the human immune system.

IsdA-IsdB

The isd genes (iron-regulated surface determinant) of S. aureus encode proteins responsible for haemoglobin binding and passage of haem iron to the cytoplasm, where it acts as an essential nutrient. IsdA and IsdB are located in the cell wall of staphylococci. IsdA appear to be exposed on the surface of bacterium since it is susceptible to proteinase K digestion. IsdB was partially digested suggesting that it is partially exposed on the surface of the bacterium (Mazmanian et al 2003 Science 299; 906).

IsdA and IsdB are both 29 kDa proteins which bind heme. Their expression is regulated by the availability of iron via the Fur repressor. Their expression will be high during infection in a host where the concentration of iron will be low.

They are also known as FrpA and FrpB (Morrissey et al 2002, Infect. Immun. 70; 2399). FrpA and FrpB are major surface proteins with a high charge. They have been shown to provide a major contribution to adhesion to plastic.

In an embodiment, the immunogenic composition of the invention comprises a fragment of IsdA and/or IsdB which is described in WO 01/98499 or WO 03/11899.

Toxins and Regulators of Virulence

Members of this family of proteins include toxin such as alpha toxin, hemolysin, enterotoxin B and TSST-1 as well as proteins that regulate the production of toxins such as RAP.

Alpha Toxin (Hla)

Alpha toxin is an important virulence determinant produced by most strains of S. aureus. It is a pore forming toxin with haemolytic activity. Antibodies against alpha toxin have been shown to neutralise the detrimental and lethal effects of alpha toxin in animal models (Adlam et al 1977 Infect. Immun. 17; 250). Human platelets, endothelial cells and mononuclear cells are susceptible to the effects of alpha toxin.

The high toxicity of alpha toxin requires that it should be detoxified before being used as an immunogen. This can be achieved by chemical treatment, for instance by treating with formaldehyde, glutaraldehyde of other cross-linking reagents or by chemically conjugating it to bacterial polysaccharides as described below.

A further way of removing toxicity is to introduce point mutations that remove toxicity while retaining the antigenicity of the toxin. The introduction of a point mutation at amino acid 35 of alpha toxin where a histidine residue is replaced with a leucine residue results in the removal of toxicity whilst retaining immunogenicity (Menzies and Kernodle 1996; Infect. Immun. 64; 1839). Histidine 35 appears to be critical for the proper oligomerization required for pore formation and mutation of this residue leads to loss of toxicity.

When incorporated into immunogenic compositions of the invention, alpha toxin is optionally detoxified by mutation of His 35, for example by replacing His 35 with Leu or Arg. In an alternative embodiment, alpha toxin is detoxified by conjugation to other components of the immunogenic composition, for example capsular polysaccharides or PNAG, most preferably to S. aureus type 5 polysaccharide and/or S. aureus Type 8 polysaccharide and/or PNAG.

RNA III Activating Protein (RAP)

RAP is not itself a toxin, but is a regulator of the expression of virulence factors. RAP is produced and secreted by staphylococci. It activates the agr regulatory system of other staphylococci and activates the expression and subsequent release of virulence factors such as hemolysin, enterotoxin B and TSST-1.

Other Immunodominant Proteins

Accumulation-Associated Protein (Aap)

Aap is a 140 kDa protein which is essential for the accumulation of S. epidermidis strains on surfaces (Hussain et al Infect. Immun. 1997, 65; 519). Strains expressing this protein produced significantly larger amounts of biofilm and Aap appear to be involved in biofilm formation. Antibodies against Aap are able to inhibit biofilm formation and inhibit the accumulation of S. epidermidis.

Staphylococcal Secretory Antigen SsaA

SsaA is a strongly immunogenic protein of 30 kDa found in both S. aureus and S. epidermidis (Lang et al 2000 FEMS Immunol. Med. Microbiol. 29; 213). Its expression during endocarditis suggested a virulence role specific to the pathogenesis of the infectious disease.

SsaA contains an N-terminal leader sequence and a signal peptidase cleavage site. The leader peptide is followed by a hydrophilic region of approximately 100 amino acids from residue 30 to residue 130.

An optional fragment of SsaA to be incorporated into the immunogenic composition of the invention is made up of the mature protein (amino acids 27 to the C-terminus or amino acids 30 to the C-terminus).

A further optional fragments contains the hydrophilic area of SsaA from amino acid 30 to amino acid 130.

Combinations

Staphylococcal infections progress through several different stages. For example, the staphylococcal life cycle involves commensal colonisation, initiation of infection by accessing adjoining tissues or the bloodstream, anaerobic multiplication in the blood, interplay between S. aureus virulence determinants and the host defense mechanisms and induction of complications including endocarditis, metastatic abscess formation and sepsis syndrome. Different molecules on the surface of the bacterium will be involved in different steps of the infection cycle. By targeting the immune response against a combination of particular antigens involved in different processes of Staphylococcal infection, multiple aspects of staphylococcal function are affected and this can result in good vaccine efficacy.

In particular, combinations of certain antigens from different classes, some of which are involved in adhesion to host cells, some of which are involved in iron acquisition or other transporter functions, some of which are toxins or regulators of virulence and immunodominant antigens can elicit an immune response which protects against multiple stages of infection.

Some combinations of antigens are particularly effective at inducing an immune response. This can be measured either in animal model assays as described in the examples and/or using an opsonophagocytic assay as described in the examples. Without wishing to be bound by theory, such effective combinations of antigens are thought to be enabled by a number of characteristics of the immune response to the antigen combination. The antigens themselves are usually exposed on the surface of Staphylococcal cells, they tend to be conserved but also tend not to be present in sufficient quantity on the surface cell for an optimal bactericidal response to take place using antibodies elicited against the single antigen. Combining the antigens of the invention can result in a formulation eliciting an advantageous combination of antibodies which interact with the Staphylococcal cell beyond a critical threshold. At this critical level, sufficient antibodies of sufficient quality bind to the surface of the bacterium to allow either efficient killing by complement or neutralisation of the bacterium. This can be measured in either an animal challenge model or an opsonisation assay as described in the examples.

Preferred immunogenic compositions of the invention comprise a plurality of proteins selected from at least two different categories of protein, having different functions within Staphylococci. Examples of such categories of proteins are extracellular binding proteins, transporter proteins such as Fe acquisition proteins, toxins or regulators of virulence and other immunodominant proteins.

In a preferred embodiment, immunogenic composition of the invention further comprises a number of proteins equal to or greater than 2, 3, 4, 5 or 6 selected from 2, 3 or 4 different groups selected from;
  Group a) extracellular component binding proteins;
  Group b) transporter proteins;
  Group c) toxins or regulators of virulence
  Group d) structural proteins.

In a preferred embodiment, immunogenic composition of the invention further comprises a number of proteins equal to or greater than 2, 3, 4, 5 or 6 selected from 2, 3 or 4 of the following groups:
  group a)—at least one staphylococcal extracellular component binding protein or fragment thereof selected from the group consisting of laminin receptor, SitC/MntC/saliva binding protein, EbhA, EbhB, Elastin binding protein (EbpS), EFB (FIB), SBI, ClfA, SdrC, SdrD, SdrE, SdrG, SdrH, SasF, lipase GehD, SasA, SasB, SasC, SasD, SasK, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP;
  group b)—at least one staphylococcal transporter protein or fragment thereof selected from the group consisting of Immunodominant ABC transporter, IsdA, IsdB, IsdC, Mg2+ transporter, HarA, SitC and Ni ABC transporter;
  group c)—at least one staphylococcal regulator of virulence, toxin or fragment thereof selected from the group consisting of alpha toxin (Hla), alpha toxin H35R mutant, RNA III activating protein (RAP);
  group d)—at least one staphylococcal structural protein or immunogenic fragment thereof selected from the group consisting of MRPII and autolysin.

In a preferred embodiment, the immunogenic composition of the invention comprises a number of proteins equal to or greater than 2, 3, 4, 5 or 6 selected from 2 or 3 of the following groups:
  group a)—at least one staphylococcal extracellular component binding protein or immunogenic fragment thereof selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, SasF, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP;
  group b)—at least one staphylococcal transporter protein or immunogenic fragment thereof selected from the group consisting of Immunodominant ABC transporter, IsdA, IsdB, IsdC, HarA, Mg2+ transporter, SitC and Ni ABC transporter;
  group c)—at least one staphylococcal regulator of virulence, toxin or immunogenic fragment thereof selected from the group consisting of alpha toxin (Hla), alpha toxin H35R mutant, RNA III activating protein (RAP).

In a preferred embodiment, the immunogenic composition of the invention contains at least one protein selected from group a) and an additional protein selected from group b) and/or group c).

In a further embodiment, the immunogenic composition of the invention contains at least one antigen selected from group b) and an additional protein selected from group c) and/or group a).

In a further embodiment, the immunogenic composition of the invention contains at least one antigen selected from group c) and an additional protein selected from group a) and/or group b).

An optional combination of proteins in the immunogenic composition of the invention comprises laminin receptor and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SitC and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises EbhA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises EbhB and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises EbpS and 1, 2, 3, 4 or 5 further antigens selected from the group consisting of immunodominant ABC transporter, IsdA, IsdB, IsdA, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises EFB(FIB) and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SBI and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises autolysin and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises ClfA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SdrC and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SdrD and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SdrE and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SdrG and 1, 2, 3, 4 or 5 further antigens selected from the group consisting of immunodominant ABC transporter, IsdA, IsdB, IsdC. HarA, Mg2+ transporter, SitC, Ni ABC transporter, alpha toxin, alpha toxin H35L or H35R mutant and RAP.

A further combination of proteins in the immunogenic composition of the invention comprises SdrH and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SasF and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises Lipase GehD and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SasA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises FnbA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises FnbB and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises Cna and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises ClfB and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises FbpA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises Npase and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises IsaA/PisA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SsaA and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises EPB and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SSP-1 and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises SSP-2 and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises HPB and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises vitronectin binding protein and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises fibrinogen binding protein and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises coagulase and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises Fig and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of proteins in the immunogenic composition of the invention comprises MAP and 1, 2, 3, 4 or 5 further antigens selected from the group consisting of immunodominant ABC transporter, IsdA, IsdB, IsdC, HarA, Mg2+ transporter, SitC, Ni ABC transporter, alpha toxin, alpha toxin H35L or H35R mutant, RAP, Aap and SsaA.

A further combination of protein in the immunogenic composition of the invention comprises immunodominant ABC transporter and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, Lipase GehD, SasA, FnbA, FnbB, Cna, ClfA, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L or H35R mutant, RAP, Aap and SsaA.

A further combination of protein in the immunogenic composition of the invention comprises IsdA and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrC, SdrE, SdrG, SdrH, SasF, Lipase GehD, SasA, FnbA, FnbB, Cna, ClfA, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L or H35R mutant, RAP, Aap and SsaA.

A further combination of protein in the immunogenic composition of the invention comprises IsdB and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, SasF, Lipase GehD, SasA, FnbA, FnbB, Cna, ClfA, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L or H35R mutant, RAP, Aap and SsaA.

A further combination of protein in the immunogenic composition of the invention comprises SitC and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, SasF, Lipase GehD, SasA, FnbA, FnbB, Cna, ClfA, ClfB, FbpA, Npase, IsaA/PisA, SsaA, EPB, SSP-1, SSP-2, HBP, Vitronectin binding protein, fibrinogen binding protein, coagulase, Fig, MAP, alpha toxin, alpha toxin H35L or H35R mutant, RAP, Aap and SsaA.

A further combination of protein in the immunogenic composition of the invention comprises alpha toxin and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, SasF, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, IsdC, HarA, Mg2+ transporter, SitC, Ni ABC transporter, Aap and SsaA.

A further combination of protein in the immunogenic composition of the invention comprises alpha toxin H35L OR H35R variant and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, SasF, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, IsdC, HarA, Mg2+ transporter, SitC, Ni ABC transporter, Aap and SsaA.

A further combination of protein in the immunogenic composition of the invention comprises RAP and 1, 2, 3, 4 or 5 further antigens selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, SasF, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig, MAP, immunodominant ABC transporter, IsdA, IsdB, IsdC, HarA, Mg2+ transporter, SitC, Ni ABC transporter, Aap and SsaA.

A further combinations of protein in the immunogenic composition of the invention comprises IsdA and IsdB; IsdA and ClfA; IsdA and ClfB; IsdA and SdrC; IsdA and SdrD; IsdA and SdrE; IsdA and SdrG; IsdA and SasF; IsdB and ClfA; IsdB and ClfB; IsdB and SdrC; IsdB and SdrD; IsdB and SdrE; IsdB and SdrG; IsdB and SasF; ClfA and ClfB; ClfA and SdrC; ClfA and SdrD; ClfA and SdrE; ClfA and SasF; ClfB and SdrC; ClfB and SdrD; ClfB and SdrE; ClfB and SasF; SdrC and SdrD; SdrC and SdrE; SdrC and SasF; SdrD and SdrE; SdrD and SasF; SdrE and SasF.

In the above and below combinations, the specified proteins may optionally be present in the immunogenic composition of the invention as a fragment or fusion protein as described above.

Combinations of Three Proteins

In an embodiment, the immunogenic composition of the invention further comprises three protein components in a combination of alpha-toxin, an extracellular component binding protein (for example an adhesin) and a transporter protein (for example an iron-binding protein).

In such a combination, the alpha toxin may be chemically detoxified or genetically detoxified by introduction of point mutation(s), for example the His35Leu point mutation. The alpha toxin is present as a free protein or alternatively is conjugated to a polysaccharide or PNAG component of the immunogenic composition.

Examples of combinations include:—

An immunogenic composition comprising alpha toxin, IsdA and an extracellular component binding protein selected from the group consisting of laminin receptor, SitC/MntC/saliva binding protein, EbhA, EbhB, Elastin binding protein (EbpS), EFB (FIB), SBI, autolysin, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP.

An immunogenic composition comprising alpha toxin, IsdB and an extracellular component binding protein selected from the group consisting of laminin receptor, SitC/MntC/saliva binding protein, EbhA, EbhB, Elastin binding protein (EbpS), EFB (FIB), SBI, autolysin, ClfA, SdrC, SdrD, SdrE, SdrG, SdrH, Lipase GehD, SasA, FnbA, FnbB, Cna, ClfB, FbpA, Npase, IsaA/PiSA, SsaA, EPB, SSP-1, SSP-2, HBP, Vitronectin binding protein, fibrinogen binding protein, coagulase, Fig and MAP.

An immunogenic composition comprising alpha toxin, IsdA and an adhesin selected from the group consisting of laminin receptor, EbhA, EbhB, Elastin binding protein (EbpS), EFB (FIB), ClfA, SdrC, SdrD, SdrE, SdrG, SdrH, autolysin, FnbA, FnbB, Cna, ClfB, FbpA, Npase, SSP-1, SSP-2, Vitronectin binding protein, fibrinogen binding protein, coagulase, Fig and MAP.

An immunogenic composition comprising alpha toxin, IsdB and an adhesin selected from the group consisting of laminin receptor, EbhA, EbhB, Elastin binding protein (EbpS), EFB (FIB), autolysin, ClfA, SdrC, SdrD, SdrE, SdrG, SdrH, FnbA, FnbB, Cna, ClfB, FbpA, Npase, SSP-1, SSP-2, Vitronectin binding protein, fibrinogen binding protein, coagulase, Fig and MAP.

An immunogenic composition comprising alpha toxin, IsdA and laminin receptor.

An immunogenic composition comprising alpha toxin, IsdA and EbhA.

An immunogenic composition comprising alpha toxin, IsdA and EbhB.

An immunogenic composition comprising alpha toxin, IsdA and EbpS.

An immunogenic composition comprising alpha toxin, IsdA and EFB (FIB).

An immunogenic composition comprising alpha toxin, IsdA and SdrG.

An immunogenic composition comprising alpha toxin, IsdA and ClfA.

An immunogenic composition comprising alpha toxin, IsdA and ClfB.

An immunogenic composition comprising alpha toxin, IsdA and FnbA.

An immunogenic composition comprising alpha toxin, IsdA and coagulase.

An immunogenic composition comprising alpha toxin, IsdA and Fig.

An immunogenic composition comprising alpha toxin, IsdA and SdrH.

An immunogenic composition comprising alpha toxin, IsdA and SdrC.

An immunogenic composition comprising alpha toxin, IsdA and SdrD.

An immunogenic composition comprising alpha toxin, IsdA and SdrE.

An immunogenic composition comprising alpha toxin, IsdA and MAP.

An immunogenic composition comprising IsaA and Sbi.
An immunogenic composition comprising IsaA and IsdB.
An immunogenic composition comprising IsaA and IsdA.
An immunogenic composition comprising IsaA and SdrC.
An immunogenic composition comprising IsaA and Ebh or fragment thereof as described above.
An immunogenic composition comprising Sbi and SdrC.
An immunogenic composition comprising Sbi and Ebh or fragment thereof as described above.
An immunogenic composition of the invention comprising IsaA, Sbi or SdrC Selection of Antigens Expressed in Different Clonal Lineages Analysis of the occurrence of virulence factors in relation with the population structure of *Staphylococcus aureus* showed variable presence of virulence genes in natural populations of *S. aureus*.

Among clinical isolates of *Staphylococcus aureus*, at least five clonal lineages were shown to be highly prevalent (Booth et al., 2001 Infect Immun. 69(1):345-52). Alpha-hemolysin (hla), fibronectin-binding protein A (fnbA) and clumping factor A (clfA) were shown to be present in most of the isolates, regardless of lineage identity, suggesting an important role of these proteins in the survival of *S. aureus* (Booth et al., 2001 Infect Immun. 69(1):345-52). Moreover, according to Peacock et al. 2002 the distributions of fnbA, clfA, coagulase, spa, map, pvl (Panton-Valentine leukocidin), hlg (gamma-toxin), alpha-toxin and ica appeared to be unrelated to the underlying clonal structure suggesting considerable horizontal transfer of these genes.

In contrary, other virulence genes such as fibronectin binding protein B (fnbB), beta-hemolysin (hlb), collagen binding protein (cna), TSST-1 (tst) and methicillin resistance gene (mecA) are strongly associated with specific lineages (Booth et al., 2001 Infect Immun. 69(1):345-52). Similarly, Peacock et al. 2002 (Infect Immun. 70(9):4987-96) showed that the distributions of the enterotoxins, tst, the exfolatins (eta and etb), beta- and delta-toxins, the sdr genes (sdrD, sdrE and bbp), cna, ebpS and efb within the population are all highly significantly related to MLST-derived clonal complexes.

MLST data provide no evidence that strains responsible for nosocomial disease represent a distinct subpopulation from strains causing community-acquired disease or strains recovered from asymptomatic carriers (Feil et al., 2003 J. Bacteriol. 185(11):3307-16).

In an embodiment, immunogenic compositions of the invention are effective against staphylococci from different clonal lineages.

In an embodiment, the immunogenic composition comprises 1, 2, 3, 4, or at least 1 protein that is expressed in most isolates of staphylococci. Examples of such proteins include alpha-hemolysin (h/a), fibronectin-binding protein A (fnbA) and clumping factor A (clfA), coagulase, spa, map, pvl (Panton-Valentine leukocidin), h/g (gamma-toxin), ica, immunodominant ABC transporter, RAP, autolysin (Rupp et al 2001, J. Infect. Dis. 183; 1038), laminin receptors, SitC, IsaA/PisA, SPOIIIE ( ), SsaA, EbpS, SasF (Roche et al 2003, Microbiology 149; 643), EFB(FIB), SBI, ClfB, IsdA, IsdB, FnbB, Npase, EBP, Bone sialo binding protein II, IsaB/PisB (Lorenz et al FEMS Immuno. Med. Microb. 2000, 29; 145), SasH (Roche et al 2003, Microbiology 149; 643), MRPI, SasD (Roche et al 2003, Microbiology 149; 643), SasH (Roche et al 2003, Microbiology 149; 643), aureolysin precursor (AUR)/Sepp1 and novel autolysin.

In an alternative embodiment, 2 or more proteins which are expressed in different sets of clonal strains are included in the immunogenic composition of the invention. Optionally the combination of antigens will allow an immune response to be generated that is effective against multiple clonal strains, or against all clonal stains. For example combinations include FnbB and betahemolysin, FnbB and Cna, FnbB and TSST-1, FnbB and mecA, FnbB and SdrD, FnbB and SdrF, FnbB and EbpS, FnbB and Efb, beta-haemolysin and Cna, beta-haemolysin and TSST-1, beta-haemolysin and mecA, beta-haemolysin and SdrD, beta-haemolysin and SdrF, beta-haemolysin and EbpS, beta-haemolysin and Efb, Cna and TSST-1, Cna and mecA, Cna and SdrD, Cna and SdrF, Cna and EbpS, Cna and Efb, TSST-1 and mecA, TSST-1 and SdrD, TSST-1 and SdrF, TSST-1 and EbpS, TssT-1 and Efb, MecA and SdrD, MecA and SdrF, MecA and EbpS, MecA and Efb, SdrD and SdrF, SdrD and EbpS, SdeD and Efb, SdrF and EbpS, SdrF and Efb, and, EbpS and Efb.

The combinations described above may be combined with additional components described above.

Protection Against *S. aureus* and *S. epidermidis*

In an embodiment of the invention the immunogenic composition provides an effective immune response against more than one strain of staphylococci, for example against strains from both *S. aureus* and *S. epidermidis*. For example, a protective immune response is generated against type 5 and 8 serotypes of *S. aureus*.

One use of the immunogenic composition of the invention is to prevent nosocomial infections, for instance in elective surgery patients, by inoculating prior to hospital treatment. At this stage, it is difficult to accurately predict which staphylococcal strains the patient will be exposed to. It is therefore advantageous to inoculate with a vaccine that is capable of generating an effective immune response against various strains of staphylococci.

An effective immune response is defined as an immune response that gives significant protection in a mouse challenge model or opsonophagocytosis assay as described in the examples. Significant protection in a mouse challenge model, for instance that of example 5, is defined as an increase in the LD50 in comparison with carrier inoculated mice of at least 10%, 20%, 50%, 100% or 200%. Significant protection in a cotton rat challenge model, for instance that of example 8, is defined as a decrease in the mean observed LogCFU/nose of at least 10%, 20%, 50%, 70% or 90%. The presence of opsonising antibodies is known to correlate with protection, therefore significant protection is indicated by a decrease in the bacterial count of at least 10%, 20%, 50%, 70% or 90% in an opsonophagocytosis assay, for instance that of example 7.

Several of the proteins including immunodominant ABC transporter, RNA III activating protein, Laminin receptors, SitC, IsaA/PisA, SsaA, EbhA/EbhB, EbpS and Aap are well conserved between *S. aureus* and *S. epidermidis* and example 8 shows that IsaA, ClfA, IsdB, SdrG, HarA, FnbpA and Sbi can generate a cross-reactive immune response (for example crossreactive between at least one *S. aureus* and at least one *S. epidermidis* strain). PIA is also well conserved between *S. aureus* and *S. epidermidis*.

Therefore in an embodiment, the immunogenic composition of the invention will comprise PNAG and type 5 and 8 polysaccharides and one, two, three or four of the above proteins.

Vaccines

In an embodiment, the immunogenic composition of the invention is mixed with a pharmaceutically acceptable excipient, and optionally with an adjuvant to form a vaccine. Suitable adjuvants include an aluminum salt such as aluminum hydroxide gel (alum) or aluminium phosphate, but may also be a salt of calcium, magnesium, iron or zinc, or may be an insoluble suspension of acylated tyrosine, or acylated sugars, cationically or anionically derivatized polysaccharides, or polyphosphazenes.

In an embodiment, the adjuvant is a preferential inducer of either a TH1 or a TH2 type of response. High levels of Th1-type cytokines tend to favor the induction of cell mediated immune responses to a given antigen, whilst high levels of Th2-type cytokines tend to favour the induction of humoral immune responses to the antigen.

It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A possible adjuvant formulation involving QS21, 3D-MPL and tocopherol in an oil in water emulsion is described in WO 95/17210. Optionally the vaccine additionally comprises a saponin, for example QS21. The formulation may also comprise an oil in water emulsion and tocopherol (WO 95/17210). The present invention also provides a method for producing a vaccine formulation comprising mixing an immunogenic composition of the present invention together with a pharmaceutically acceptable excipient, such as 3D-MPL. Unmethylated CpG containing oligonucleotides (WO 96/02555) are also preferential inducers of a TH1 response and are suitable for use in the present invention.

In an embodiment, the immunogenic compositions of the invention are those forming a liposome or ISCOM structure.

The ratio of QS21:sterol will typically be in the order of 1:100 to 1:1 weight to weight. Preferably excess sterol is present, the ratio of QS21:sterol being at least 1:2 w/w. Typically for human administration QS21 and sterol will be present in a vaccine in the range of about 1 µg to about 100 µg, preferably about 10 µg to about 50 µg per dose.

The liposomes typically contain a neutral lipid, for example phosphatidylcholine, which is preferably non-crystalline at room temperature, for example eggyolk phosphatidylcholine, dioleoyl phosphatidylcholine or dilauryl phosphatidylcholine. The liposomes may also contain a charged lipid which increases the stability of the lipsome-QS21 structure for liposomes composed of saturated lipids. In these cases the amount of charged lipid is preferably 1-20% w/w, most preferably 5-10%. The ratio of sterol to phospholipid is 1-50% (mol/mol), typically 20-25%.

Optionally the compositions of the invention contain MPL (3-deacylated mono-phosphoryl lipid A, also known as 3D-MPL). 3D-MPL is known from GB 2 220 211 (Ribi) as a mixture of 3 types of De-O-acylated monophosphoryl lipid A with 4, 5 or 6 acylated chains and is manufactured by Ribi Immunochem, Montana. A possible form is disclosed in International Patent Application 92/116556.

Suitable compositions of the invention are those wherein liposomes are initially prepared without MPL, and MPL is then added, preferably as 100 nm particles. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane. Optionally soluble antigens are outside and hydrophobic or lipidated antigens are either contained inside or outside the membrane.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal polysaccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, for example, it may be present in combination with the bacterial protein component of the vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

The amount of conjugate antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 0.1-100 µg of polysaccharide, typically 0.1-50 µg, 1-10 µg or 1-5 µg for polysaccharide conjugates.

The content of protein antigens in the vaccine will typically be in the range 1-100 µg, 5-50 µg or 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Optionally the solution is lyophilized in the presence of a sugar such as sucrose, trehalose or lactose. It is typical that they are lyophilized and extemporaneously reconstituted prior to use. Lyophilizing may result in a more stable composition (vaccine).

Methods

The invention also encompasses method of making the immunogenic compositions and vaccines of the invention.

In an embodiment, the process of the invention, is a method to make a vaccine comprising the steps of mixing antigens to make the immunogenic composition of the invention and adding a pharmaceutically acceptable excipient.

Methods of Treatment

The invention also encompasses method of treatment or staphylococcal infection, particularly hospital acquired nosocomial infections.

This immunogenic composition or vaccine of the invention is particularly advantageous to use in cases of elective surgery. Such patients will know the date of surgery in advance and could be inoculated in advance. Since it is not know whether the patient will be exposed to S. aureus or S. epidermidis infection, it is preferred to inoculate with a vaccine of the invention that protects against both, as described above. Typically adults over 16 awaiting elective surgery are treated with the immunogenic compositions and vaccines of the invention. Alternatively children aged 3-16 awaiting elective surgery are treated with the immunogenic compositions and vaccines of the invention.

It is also possible to inoculate health care workers with the vaccine of the invention.

The vaccine preparations of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

The amount of antigen in each vaccine dose is selected as an amount which induces an immunoprotective response without significant, adverse side effects in typical vaccines. Such amount will vary depending upon which specific immunogen is employed and how it is presented. The protein content of the vaccine will typically be in the range 1-100 µg, 5-50 µg, typically in the range 10-25 µg. An optimal amount for a particular vaccine can be ascertained by standard studies involving observation of appropriate immune responses in subjects. Following an initial vaccination, subjects may receive one or several booster immunisations adequately spaced.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are preferably present in as little as 0.1 to 10 µg, preferably 0.1 to 5 µg per dose; and the polysaccharide (preferably conjugated) antigens may be present in the range of 0.01-1 µg, and preferably between 0.01 to 0.5 µg of polysaccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

An embodiment of the invention is a method of preventing or treating staphylococcal infection or disease comprising the step of administering the immunogenic composition or vaccine of the invention to a patient in need thereof.

A further embodiment of the invention is a use of the immunogenic composition of the invention in the manufacture of a vaccine for treatment or prevention of staphylococcal infection or disease, optionally post-surgery staphylococcal infection.

The term 'staphylococcal infection' encompasses infection caused by *S. aureus* and/or *S. epidermidis* and other staphylococcal strains capable of causing infection in a mammalina, preferably human host.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

In order that this invention may be better understood, the following examples are set forth.

These examples are for purposes of illustration only, and are not to be construed as limiting the scope of the invention in any manner.

EXAMPLES

Example 1

Construction of Plasmid to Express Recombinant proteins

A: Cloning.

Appropriate restriction sites engineered into oligonucleotides specific for the staphylococcal gene permitted directional cloning of the PCR product into the *E. coli* expression plasmid pET24d or pQE-30 such that a protein could be expressed as a fusion protein containing a (His)6 affinity chromatography tag at the N- or C-terminus.

The primers used were:

Alpha toxin -
5'-CGCGGATCCGCAGATTCTGATATTAATATTAAAAC-3'
(SEQ ID NO: 111)
and

5'CCCAAGCTTTTAATTTGTCATTTCTTCTTTTTC-3'
(SEQ ID NO: 112)

EbpS -
5'-CGCGGATCCGCTGGGTCTAATAATTTTAAAGATG-3'
(SEQ ID NO: 113)
and

5'CCCAAGCTTTTATGGAATAACGATTTGTTG-3'
(SEQ ID NO: 114)

ClfA -
5'-CGCGGATCCAGTGAAAATAGTGTTACGCAATC-3'
(SEQ ID NO: 115)
and

5'CCCAAGCTTTTACTCTGGAATTGGTTCAATTTC-3'
(SEQ ID NO: 116)

FnbpA -
5'-CGCGGATCCACACAAACAACTGCAACTAACG-3'
(SEQ ID NO: 117)
and

5CCCAAGCTTTTATGCTTTGTGATTCTTTTTCAAAC3'
(SEQ ID NO: 118)

Sbi -
5'-CGCGGATCCAACACGCAACAAACTTC-3'
(SEQ ID NO: 119)
and

5'GGAACTGCAGTTATTTCCAGAATGATAATAAATTAC-3'
(SEQ ID NO: 120)

SdrC -
5'-CGCGGATCCGCAGAACATACGAATGGAG-3'
(SEQ ID NO: 121)
and

5'CCCAAGCTTTTATGTTTCTTCTTCGTAGTAGC-3'
(SEQ ID NO: 122)

SdrG -
5'-CGCGGATCCGAGGAGAATTCAGTACAAG-3'
(SEQ ID NO: 123)
and

5'CCCAAGCTTTTATTCGTCATCATAGTATCCG-3'
(SEQ ID NO: 124)

Ebh -
5'-AAAAGTACTCACCACCACCACCACC-3'
(SEQ ID NO: 125)
and

5'AAAAGTACTCACTTGATTCATCGCTTCAG-3'
(SEQ ID NO: 126)

Aaa -
5'-GCGCGCCATGGCACAAGCTTCTACACAACATAC-3'
(SEQ ID NO: 127)
and

5'GCGCGCTCGAGATGGATGAATGCATAGCTAGA-3'
(SEQ ID NO: 128)

IsaA -
5'-GCATCCATGGCACCATCACCATCACCACGAAGTAAACGTTGATCAAG C-3' (SEQ ID NO: 129)
and

5'-AGCACTCGAGTTAGAATCCCCAAGCACCTAAACC-3'
(SEQ ID NO: 130)

HarA -
5'-GCACCCATGGCAGAAAATACAAATACTTC-3'
(SEQ ID NO: 131)
and

5'TTTTCTCGAGCATTTTAGATTGACTAAGTTG-3'
(SEQ ID NO: 132)

Autolysin glucosaminidase -
5'-CAAGTCCCATGGCTGAGACGACACAAGATCAAC-3'
(SEQ ID NO: 133)
and

5'-CAGTCTCGAGTTTTACAGCTGTTTTTGGTTG-3'
(SEQ ID NO: 134)

Autolysin amidase -
5'-AGCTCATATGGCTTATACTGTTACTAAACC-3'
(SEQ ID NO: 135)
and

5'GCGCCTCGAGTTTATATTGTGGGATGTCG-3'
(SEQ ID NO: 136)

IsdA -
5'-CAAGTCCCATGGCAACAGAAGCTACGAACGCAAC-3'
(SEQ ID NO: 137)
and

5'ACCAGTCTCGAGTAATTCTTTAGCTTTAGAGCTTG-3'
(SEQ ID NO: 138)

IsdB -
5'-TATTCTCGAGGCTTTGAGTGTGTCCATCATTTG-3'
(SEQ ID NO: 139)
and

5'GAAGCCATGGCAGCAGCTGAAGAAACAGGTGG-3'
(SEQ ID NO: 140)

MRPII -
5'-GATTACACCATGGTTAAACCTCAAGCGAAA-3'
(SEQ ID NO: 141)
and

5'AGGTGTCTCGAGTGCGATTGTAGCTTCATT-3'
(SEQ ID NO: 142)

The PCR products were first introduced into the pGEM-T cloning vector (NOVAGEN®) using Top10 bacterial cells, according to the manufacturer's instructions. This intermediate construct was made to facilitate further cloning into an expression vector. Transformants containing the DNA insert were selected by restriction enzyme analysis. Following digestion, a ~20 μl aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the DNA fragments. Plasmid purified from selected transformants for each cloning was then sequentially digested to completion with appropriate restriction enzymes as recommended by the manufacturer (Life Technologies). The digested DNA fragment was then purified using silica gel-based spin columns prior to ligation with the pET24d or pQE-30 plasmid. Cloning of Ebh (H2 fragment), AaA, IsdA, IsdB, HarA, Atl-amidase, Atl-glucosamine, MRPII, IsaA was carried out using the pET24d plasmid and cloning of ClfA, SdrC, SdrE, FnbpA, SdrG/Fbe, alpha toxin and Sbi were carried out using the pQE-30 plasmid.

B: Production of Expression Vector.

To prepare the expression plasmid pET24d or pQE-30 for ligation, it was similarly digested to completion with appropriate restriction enzymes. An approximately 5-fold molar excess of the digested fragments to the prepared vector was used to program the ligation reaction. A standard ~20 µl ligation reaction (~16° C., ~16 hours), using methods well known in the art, was performed using T4 DNA ligase (~2.0 units/reaction, Life Technologies). An aliquot of the ligation (~5 µl) was used to transform M15(pREP4) or BT21::DE3 electro-competent cells according to methods well known in the art. Following a ~2-3 hour outgrowth period at 37° C. in ~1.0 ml of LB broth, transformed cells were plated on LB agar plates containing ampicillin (100 µg/ml) and/or kanamycin (30 µg/ml). Antibiotics were included in the selection. Plates were incubated overnight at 37° C. for ~16 hours. Individual ApR/KanR colonies were picked with sterile toothpicks and used to "patch" inoculate fresh LB ApR/KanR plates as well as a ~1.0 ml LB Ap/Kan broth culture. Both the patch plates and the broth culture were incubated overnight at 37° C. in either a standard incubator (plates) or a shaking water bath. A whole cell-based PCR analysis was employed to verify that transformants contained the DNA insert. Here, the ~1.0 ml overnight LB Ap/Kan broth culture was transferred to a 1.5 ml polypropylene tube and the cells collected by centrifugation in a Beckmann microcentrifuge (~3 min., room temperature, ~12,000×g). The cell pellet was suspended in ~200 µl of sterile water and a ~10 µl aliquot used to program a ~50 µl final volume PCR reaction containing both forward and reverse amplification primers. The initial 95° C. denaturation step was increased to 3 minutes to ensure thermal disruption of the bacterial cells and liberation of plasmid DNA. An ABI Model 9700 thermal cycler and a 32 cycle, three-step thermal amplification profile, i.e. 95° C., 45 sec; 55-58° C., 45 sec, 72° C., 1 min., were used to amplify the BASB203 fragment from the lysed transformant samples. Following thermal amplification, a ~20 µl aliquot of the reaction was analyzed by agarose gel electrophoresis (0.8% agarose in a Tris-acetate-EDTA (TAE) buffer). DNA fragments were visualised by UV illumination after gel electrophoresis and ethidium bromide staining. A DNA molecular size standard (1 Kb ladder, Life Technologies) was electrophoresed in parallel with the test samples and was used to estimate the size of the PCR products. Transformants that produced the expected size PCR product were identified as strains containing a protein expression construct. Expression plasmid containing strains were then analyzed for the inducible expression of recombinant protein.

C: Expression Analysis of PCR-Positive Transformants.

An aliquot of the overnight seed culture (~1.0 ml) was inoculated into a 125 ml erlenmeyer flask containing ~25 ml of LB Ap/Kan broth and was grown at 37° C. with shaking (~250 rpm) until the culture turbidity reached O.D.600 of ~0.5, i.e. mid-log phase (usually about 1.5-2.0 hours). At this time approximately half of the culture (~12.5 ml) was transferred to a second 125 ml flask and expression of recombinant protein induced by the addition of IPTG (1.0 M stock prepared in sterile water, Sigma) to a final concentration of 1.0 mM. Incubation of both the IPTG-induced and non-induced cultures continued for an additional ~4 hours at 37° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 µl of sterile water, then mixed with an equal volume of 2× Laemelli SDS-PAGE sample buffer containing 2-mercaptoethanol, and placed in boiling water bath for ~3 min to denature protein. Equal volumes (~15 µl) of both the crude IPTG-induced and the non-induced cell lysates were loaded onto duplicate 12% Tris/glycine polyacrylamide gel (1 mm thick Mini-gels, NOVEX®). The induced and non-induced lysate samples were electrophoresed together with prestained molecular weight markers (SEEBLUE®, NOVEX®) under conventional conditions using a standard SDS/Tris/glycine running buffer (BioRad). Following electrophoresis, one gel was stained with COOMMASSIE® brilliant blue R250 (BioRad) and then destained to visualize novel IPTG-inducible protein(s). The second gel was electroblotted onto a PVDF membrane (0.45 micron pore size, NOVEX®) for ~2 hrs at 4° C. using a BioRad Mini-Protean 11 blotting apparatus and Towbin's methanol (20%) transfer buffer. Blocking of the membrane and antibody incubations were performed according to methods well known in the art. A monoclonal anti-RGS (His)3 antibody, followed by a second rabbit anti-mouse antibody conjugated to HRP (QIAGEN®), were used to confirm the expression and identity of the recombinant protein. Visualization of the anti-His antibody reactive pattern was achieved using either an ABT insoluble substrate or using HYPERFILM® with the AMERSHAM® ECL chemiluminescence system.

Example 2

Production of Recombinant Protein

Bacterial Strain

A recombinant expression strain of E. coli M15(pREP4) containing a plasmid (pQE30) or BL21::DE3 containing plasmid pET24d encoding staphylococcal protein was used to produce cell mass for purification of recombinant protein.

Media

The fermentation medium used for the production of recombinant protein consisted of 2×YT broth (DIFCO®) containing 100 µg/ml Ap and/or 30 µg/ml Km. Antifoam was added to medium for the fermentor at 0.25 ml/L (Antifoam 204, Sigma). To induce expression of the recombinant protein, IPTG (Isopropyl R-D-Thiogalactopyranoside) was added to the fermentor (1 mM, final).

Production of Recombinant Proteins
Under Native Conditions

IPTG was added at a final concentration of 1 mM and the culture was grown for 4 additional hours. The culture was then centrifuged at 6,000 rpm for 10 minutes and the pellet was resuspended in phosphate buffer (50 mM K2HPO4, KH2PO4 pH 7) including a protease inhibitor cocktail. This sample was subjected to French pressure lysis using 1500 bar pressure (2 runs). After centrifugation for 30 minutes at 15,000 rpm, the supernatant was reserved for further purification and NaCl was added to 0.5M. The sample was then loaded on a Ni-NTA resin (XK 16 column Pharmacia, Ni-NTA resin QIAGEN®) conditioned in 50 mM K2HPO4, KH2PO4 pH 7. After loading the sample, the column was washed with Buffer A (0.2M NaH2PO4 pH7, 0.3M NaCl, 10% glycerol). To elute bound protein, a step gradient was used where different proportions of buffer B (0.2M NaH2PO4 pH7, 0.3M NaCl, 10% glycerol and 200 mM imidazole) were added to buffer A. The proportion of buffer B was gradually increased from 10% to 100%. After purification, eluted fraction containing the protein were pooled, concentrated and dialysed against 0.002M KH2PO4/K2HPO4 pH7, 0.15M NaCl.

This method was used to purify ClfA, SdrG, IsdA, IsaB, HarA, Atl-glucosamine and alpha toxin.

Under Denaturing Conditions

IPTG was added at a final concentration of 1 mM and the culture was grown for 4 additional hours. The culture was then centrifuged at 6,000 rpm for 10 minutes and the pellet was resuspended in phosphate buffer (50 mM K2HPO4, KH2PO4 pH 7) including a protease inhibitor cocktail. This sample was subjected to French pressure lysis using 1500 bar pressure (2 runs). After centrifugation for 30 minutes at 15,000 rpm, the pellet was washed with phosphate buffer including 1M urea. The sample was centrifuged for 30 mins at 15000 rpm and the pellet was resuspended in 8M urea, 0.1M NaH2PO4, 0.5M NaCl, 0.01M Tris-Hcl pH8 and kept overnight at room temperature. The sample was centrifuged fro 20 minutes at 15000 rpm and the supernatant was collected for further purification. The sample was then loaded on a Ni-NTA resin (XK 16 column Pharmacia, Ni-NTA resin QIAGEN®) conditioned in 8M urea, 0.1M NaH2PO4, 0.5M NaCl, 0.01M Tris-Hcl pH8. After passage of the flowthrough, the column was washed successively with buffer A (8M Urea, 0.1MNaH2PO4, 0.5M NaCl, 0.01M Tris, pH 8.0), buffer C (8M Urea, 0.1MNaH2PO4, 0.5M NaCl, 0.01M Tris, pH 6.3), buffer D (8M Urea, 0.1MNaH2PO4, 0.5M NaCl, 0.01M Tris, pH 5.9) and buffer E (8M Urea, 0.1MNaH2PO4, 0.5M NaCl, 0.01M Tris, pH 4.5). The recombinant protein was eluted from the column during washes with buffer D and E. The denatured, recombinant protein could be solubilized in a solution devoid of urea. For this purpose, denatured protein contained in 8M urea was successively dialyzed against 4M urea, 0.1MNa2PO4, 0.01M Tris-HCl, pH7.1, 2M urea, 0.1 M NaH2PO4, 0.01M Tris-HCl, pH 7.1, 0.5M arginine and 0.002M KH2PO4/K2HPO4 pH7.1, 0.15M NaCl, 0.5M arginine.

This method was used to purify Ebh (H2 fragment), AaA, SdrC, FnbpA, Sbi, Atl-amidase and IsaA.

The purified proteins were analysed by SDS-PAGE. The results for one protein purified under native conditions (alpha toxin) and one protein purified under denaturing conditions (SdrC) are shown in FIGS. 3A and 3B and 4A and 4B.

Example 3

Preparation of S. aureus Capsular Polysaccharide Conjugates using CDAP

Activation and Coupling Chemistry for Native PS8 Using CDAP:
SA08-TT004

Activation and coupling were performed at room temperature under continuous stirring. 10 mg of native polysaccharide were dissolved to obtain a final PS concentration of 2.5 mg/ml in 0.2M NaCl. The solution was then adjusted to pH 6.0+/−0.2 before the activation step.

At time 0, 50 µl of a CDAP solution (100 mg/ml freshly prepared in acetonitrile/WFI, 50/50) were added manually to reach the appropriate CDAP/PS (0.5/1) ratio.

After 1.5 minutes the pH was raised to pH 9.00+/−0.05 by addition of 0.5M NaOH.

NaOH addition takes about 1 minutes and pH is stabilised at pH 9.00+/−0.05 up to carrier addition.

At time 4.5 minutes, 1.5 ml of TT (10 mg/ml in 0.2M NaCl) was added to reach the appropriate Protein/PS ratio (1.5/1); pH was immediately adjusted to coupling pH 9.00+/−0.05. The solution is left for one hour under manual pH regulation.

After the coupling step, 0.5 ml of 2M glycine (ratio gly/PS (w/w): 7.5/1) were added; pH was immediately adjusted to 9.00+/−0.05. The solution was left for 30 minutes under manual pH regulation. Then the conjugate was clarified using a 5 µm Minisart filter and injected on SEPHACRYL® S400HR (XK16/100). The flow-rate was fixed at 30 ml/h, using 150 mM NaCl.

The elution fractions were analysed by resorcinol and by µBCA. Interesting fractions were pooled and filtered on 0.22 µm STERIVEX™.

The resulting conjugate had a final TT/PS ratio (w/w) of 1.05 as assessed by resorcinol and Lowry assays.

Example 4

Preparation of S. aureus Capsular Polysaccharide Conjugates Using CDAP on Sized Polysaccharides Activation and Coupling Chemistry for Sized PS8 Using CDAP PS is weighted on the basis of 10% theoretical moisture content. 2 g of native, humid PS was dissolved overnight in WFI at an initial concentration of 10 mg/ml. Before the sizing, the solution of native PS was clarified on 5 µm cut-off filter.

A EMULSIFLEX C-50 homogenizer apparatus, in which the homogenizing cell was replaced with a Microfluidics F20Y-0.75 µm interaction chamber, was used to reduce the molecular weight and the viscosity of the polysaccharide before the activation step The size reduction was realized at 10000 psi during the 10 first cycles and then at 15000 psi for the following 60 cycles. The progress of the size reduction was followed in-process by measuring viscosity. The sizing was stopped after 70 cycles when the target of 2.74±0.2 cp was reached.

Activation and coupling were performed at room temperature under continuous stirring.

50 mg of sized polysaccharide 8 were diluted to obtain a final PS concentration of 5 mg/ml in 0.2M NaCl.

At time 0, 375 µl of a CDAP solution (100 mg/ml freshly prepared in acetonitrile/WFI, 50/50) were added manually to reach the appropriate CDAP/PS (0.75/1) ratio.

After 1 minute the pH was raised to pH 9.00+/−0.05 by addition of 0.5M NaOH.

At time 2.5 minutes, 10 ml of TT at 10 mg/ml in 0.2M NaCl were added to reach the appropriate Protein/PS ratio (2/1); pH was immediately adjusted to coupling pH 9.00+/−0.05. The solution was left for 55 minutes under manual pH regulation.

After the coupling step, 2.5 ml of 2M glycine (ratio gly/PS (w/w): 7.5/1) were added; pH was immediately adjusted to 9.00+/−0.05 by the regulator. The solution was left for 30 minutes under manual pH regulation.

Then the conjugate was clarified using a 5 µm Minisart filter and injected on SEPHACRYL® S400HR (XK26/100). The flow-rate was fixed at 60 ml/h.

The elution fractions were analysed by resorcinol and by protein dosage. Interesting fractions were pooled and filtered on 0.22 µm MILLIPACK® 20.

The resulting conjugate has a final TT/PS ratio of 1.94.

Example 5

Preparation of S. aureus Capsular Polysaccharide Conjugates Using EDAC

Activation and Coupling Chemistry Using EDAC:
S. Aureus Capsular Polysaccharide Type 8-TT Conjugate:
PS Derivatization Activation and coupling were performed at room temperature under continuous stirring. 30 mg of native polysaccharide were diluted to obtain a final polysaccharide concentration of 5 mg/ml in water. The solution was adjusted to pH 4.5-5.0 with 0.5N HCl and then 66 µg of ADH were added (2.2 mg/mg PS). After complete dissolution, 60 mg of EDAC were added (2 mg/mg PS). After 70 min the pH was raised to pH 7.5 with 1N NaOH to stop the reaction. Free ADH was removed by purification on SEPHACRYL® S100HR (XK 16/40). The flow-rate was fixed at 60 ml/h using 0.2 M NaCl as elution buffer. A size reduction was done by sonication of 15 min allowing a sterile filtration on MILLEX® filter (0.22 μm).

Coupling

Tetanus toxoid was added to 5 to 10 mg of derivatized polysaccharide in 0.2M NaCl and the pH was adjusted to pH 5.0 or pH 6.0 by addition of 0.5N HCl. EDAC was dissolved in 0.1M Tris buffer pH 7.5 and then added over a period of 10 min (1/5 vol each 2 min). According to the conditions used (see Table 6), the reaction was stopped after between 30 and 180 minutes by addition of 1M Tris-HCl pH 7.5. Prior to purification on SEPHACRYL® S400HR, the conjugate was clarified using a 5 μm Minisart filter. Alternatively, the conjugate was clarified by a 5 minute sonication step. The conjugate was then injected on SEPHACRYL® S400HR (XK16/100). The flow-rate was fixed at 30 ml/h using 150 mM NaCl as elution buffer. The elution pool was selected on the basis of resorcinol and μBCA profiles (which measure polysaccharide and protein dosage respectively). The conjugate was filtered on a 0.22 μm sterilizing membrane (MILLIPACK® 20) at 10 ml/min.

TABLE 5

| Conjugate | Coupling time | [PS (AH)] (mg/ml) | [TT (AH)] (mg/ml) | [reagent EDAC] (mg/mg PS) |
|---|---|---|---|---|
| SA08-TT011 | 40 min | 3.58 | 6.45 | 0.5/1 |
| SA08-TT015* | 180 min | 2 | 4.0 | 0.25/1 |
| SA08-TT017 | 30 min | 3.75 | 7.5 | 0.25/1 |
| SA08-TT018 | 50 min | 3.75 | 7.5 | 0.10/1 |

Table 5: *coupling done at pH 6.0

The resulting conjugates have the following characteristics shown in Table 6:

TABLE 6

| Conjugate | In. TT/PS ratio (w/w) | F. TT/PS ratio (w/w) | y. PS rec (%) | Filtr. yield (%) |
|---|---|---|---|---|
| SA08-TT011 | 2/1 | 2.43/1 | 48 | 99 |
| SA08-TT015 | 2/1 | 2.40/1 | 53 | 104 |
| SA08-TT017 | 2/1 | 2.41/1 | 44 | 107 |
| SA08-TT018 | 2/1 | 2.40/1 | 42 | 106 |

*S. aureus* polysaccharide type 8 was also treated by microfluidization before derivatization with ADH PS Derivatization Activation and coupling are performed at room temperature under continuous stirring.

200 mg of sized polysaccharide are diluted to obtain a final PS concentration of 10 mg/ml in water. Then 440 mg of ADH were added (2.2 mg/mg PS). The solution was adjusted to pH 4.7 with 1N HCl before the addition of 400 mg of EDAC (2 mg/mg PS). After 60 min the pH was raised to pH 7.5 with 5M NaOH to stop the reaction. The mixture was concentrated on AMICON® Ultra (cut-off 10.000 MWCO). Prior to purification on SEPHACRYL® S200HR (XK16/100), the conjugate was clarified using a 5 μm Minisart filter. The flow-rate was fixed at 30 ml/h using 0.150 M NaCl as elution buffer.

Coupling 100 mg of TT was added to 50 mg of derivatized polysaccharide in 0.2M NaCl. The pH was adjusted to pH 5.0±0.02 by addition of 0.3N HCl. EDAC was dissolved in 0.1 M Tris buffer pH 7.5 and then added over a period of 10 min (1/10 vol each minute). According to the conditions used (see Table 8), the reaction was stopped after between 30 and 180 minutes by addition of 1M Tris-HCl pH 7.5. Prior to purification on SEPHACRYL®S400HR, the conjugate was clarified using a 5 μm Minisart filter. The conjugate was then injected on SEPHACRYL® S400HR (XK50/100). The flow-rate was fixed at 60 ml/h using 150 mM NaCl as elution buffer. The elution pool was selected on the basis of resorcinol and μBCA profiles (which measure polysaccharide and protein dosage respectively). Then, the conjugate was filtered on a 0.22 μm sterilizing membrane (MILLIPACK® 20) at 10 ml/min.

TABLE 7

| Conjugate | Coupling time | [PS-AH] (mg/ml) | [TT] (mg/ml) | [EDAC] (mg/mg PS) |
|---|---|---|---|---|
| SA08-TT045 | 65 min | 3.83 | 7.66 | 0.1 |
| SA08-TT046 | 45 min | 3.75 | 7.5 | 0.2 |
| SA08-TT047 | 30 min | 5.0 | 15.0 | 0.2 |
| SA08-TT048 | 120 min | 5.0 | 10.0 | 0.05 |
| SA08-TT049* | 50 min | 5.0 | 10.0 | 0.1 |

*EDAC added in "one time"

TABLE 8

| Conjugate | In. TT/PS ratio(w/w) | F. TT/PS ratio (w/w) | y. PS rec (%) | Filtr. yield (%) |
|---|---|---|---|---|
| SA08-TT045 | 2/1 | 2.20/1 | 57 | 101 |
| SA08-TT046 | 2/1 | 2.80/1 | — | — |
| SA08-TT047 | 3/1 | Gel - Not purified | — | — |
| SA08-TT048 | 2/1 | 3.35 | 30 | 101 |
| SA08-TT049 | 2/1 | 3.5 | 24 | 106 |

Example 6

Preparation of *S. aureus* Capsular Polysaccharide Conjugates Using EDAC on de-O-acetylated *S. aureus* polysaccharide 8

De-O-acetylation 0.1N NaOH was added to 16 ml of sized PS (10 mg/ml) to target a final PS concentration of 9 mg/ml and a final NaOH concentration of 0.1N. After a treatment of 1 or 2 h at 37° C., the PS had a level of O-acetylation of 35 and 12% (Hestrin dosage) respectively in comparison to the untreated PS.

0.1N NaOH was added to 19 ml of sized PS (10 mg/ml) to target a final PS concentration of 9.5 mg/ml and a final NaOH concentration of 0.05N. After a treatment of 1 or 2 h at 37° C., PS had a level of O-acetylation of 78 and 58% (Hestrin dosage) respectively in comparison to the untreated PS.

The derivatization step was done as shown previously for an untreated PS.

TABLE 9

| Conjugate | O-acetyl level % | ADH/PS w/w* % |
|---|---|---|
| SA08-TT056 | 35 | 9.3 |
| SA08-TT057 | 12 | 13.1 |
| SA08-TT058 | 78 | 5.3 |
| SA08-TT059 | 58 | 8.2 |

*TNBS assay

Removal of the O-acetyl groups resulted in an increased availability of reactive carboxylic groups. Indeed, the derivatization level of a PS having only 12% of O-acetyl groups was ±2.5-fold superior to the one having 78% of O-acetyl groups.

Coupling was done as shown previously for a untreated PS

TABLE 10

| Conjugate | O-acetyl level % | Coupling time | [PS-AH] (mg/ml) | [TT] (mg/ml) | [EDAC] (mg/mg PS) |
|---|---|---|---|---|---|
| SA08-TT056 | 35 | 45 min | 2.87 | 5.74 | 0.5 |
| SA08-TT057 | 12 | 30 min | 2.62 | 5.24 | 0.5 |
| SA08-TT058 | 78 | 50 min | 3.16 | 6.32 | 0.5 |
| SA08-TT059 | 58 | 40 min | 2.53 | 5 | 0.5 |

TABLE 11

| Conjugate | In. TT/PS ratio (w/w) | F. TT/PS ratio (w/w) | y. PS rec (%) | Filtr. yield (%) |
|---|---|---|---|---|
| SA08-TT056 | 2/1 | 1.70/1 | 51.3 | 100 |
| SA08-TT057 | 2/1 | 1.78/1 | 63.0 | 105.4 |
| SA08-TT058 | 2/1 | 2.08/1 | 46.3 | 99.6 |
| SA08-TT059 | 2/1 | 1.86/1 | 50.8 | 99.2 |

Example 7

Conjugation of dPNAG

Activation and Coupling of dPNAG:
dPNAG-TT Conjugates
The following conjugates were produced using the approaches described herebelow:
dPNAG-TT010: dPNAG-S-GMBS+DTT treated TT-LC-SPDP
dPNAG-TT011: dPNAG-S-GMBS+DTT treated TT-LC-SPDP
dPNAG-TT012: dPNAG-S-GMBS+DTT treated TT-SPDP
dPNAG-TT014: dPNAG-SPDP+DTT treated TT-SPDP
dPNAG-TT017: DTT treated dPNAG-SPDP+TT-LC-SPDP
dPNAG-TT019: dPNAG-S-GMBS+DTT treated TT-SPDP
dPNAG-TT020: dPNAG-S-GMBS+DTT treated TT-SPDP
dPNAG 1 g of PNAG was dissolved in 5N HCl at a concentration of 20 mg/ml and was incubated for 1 hour. It was then neutralized with 5N NaOH. The solution was clarified on a 5 µm membrane and purified on SEPHACRYL® S400HR. Interesting fractions, corresponding to the "medium molecular size" (see Infection and Immunity, 70: 4433-4440 (2002)), were pooled and concentrated prior to de-N-acetylation treatment.

The solution was adjusted at 1M NaOH and left 24 hours at 37° C. After neutralization, the product was subjected to dialysis and concentration.
dPNAG Activation S-GMBS (N-(γ-Maleimidobutyryloxy)sulfosuccinimide, Pierce) was added to dPNAG in 0.2M NaCl (ratio S-GMBS/PS (w/w):1/1) and incubated during 2 h at room temperature at pH 7.0 (pH regulation using 1M NaOH). Excess GMBS and by-products were removed by purification on TOYOPEARL® HW-40F using PBS, 10 mM EDTA, 50 mM NaCl pH 7.2 as elution buffer with a flow-rate fixed at 60 ml/h. The elution pool was selected in function of the optical density (UV=206 nm) and then concentrated on VIVASPIN® tubes 3,000 MWCO or AMICON® Ultra 10,000 MWCO.
Coupling GMBS-activated dPNAG and DTT reduced TT-SPDP were mixed and stirred at room temperature. According to the conditions used the reaction was quenched after 20-120 min by the addition of cysteine (4 mg/ml in Na phosphate buffer pH 8.0) for 30 minutes. The conjugate was clarified on 5 µm filter and injected on SEPHACRYL® S300HR resin (XK16/100) for purification. Elution was realized in 200 mM NaCl with a flow-rate fixed at 30 ml/h. The elution fractions were analysed by hexosamine and by protein dosage. Interesting fractions were pooled and filtered on 0.22 µm STERIVEX™. The final conjugate was tested for polysaccharide (hexosamine dosage) and protein composition (Lowry dosage).

TABLE 12

| Conjugate | N-acetylation level % | [dPNAG] mg/ml | [TT] mg/ml | PS scale (mg) | Coupl. time (min) |
|---|---|---|---|---|---|
| dPNAG-TT 010 | 10* | 15 | 15 | 30 | 120 |
| dPNAG-TT 011 | 10* | 12 | 24 | 20 | 120 |
| dPNAG-TT 012 | 10* | 17.5 | 35 | 22 | 80 |
| dPNAG-TT 019 | 34 | 5 | 10 | 10 | 20 |
| dPNAG-TT 020 | 34 | 2 | 2 | 10 | 20 |

*Not done on the lot used in the conjugation but estimated on a previous lot by NMR using the same de-N-acetylation method.

TABLE 13

| Conjugate | In. TT/PS ratio (w/w) | F. TT/PS ratio (w/w) | yield PS rec (%) | Filtration yield (%) |
|---|---|---|---|---|
| dPNAG-TT010 | 1/1 | 1.86/1 | 43 | 99 |
| dPNAG-TT011 | 2/1 | 2.86/1 | 56 | 99 |
| dPNAG-TT012 | 2/1 | 2.29/1 | 61 | 108 |
| dPNAG-TT019 | 2/1 | 1.45/1 | 81 | 97 |
| dPNAG-TT020 | 1/1 | 0.89/1 | 82 | 109 | dPNAG-SPDP:

A 5-fold molar excess of SPDP(N-Succinimidyl-3-(2-Pyridyldithio) Propionate, MW: 312.4, Pierce) dissolved in DMSO (dimethylsulfoxid, Merck) was added to 100 mg of dPNAG at 5 mg/ml in 100 mM Na phosphate, pH 7.2) and incubated 1 h at room temperature. Before purification on SEPHACRYL® S100HR (XK16/40) the reaction mixture was concentrated to ±6 ml on AMICON® Ultra 10,000 MWCO (centrifugation at 3000 rpm during 28 min). Elution was realized in phosphate buffer pH 7.4 with a flow-rate fixed at 60 ml/h. The interesting fractions (read at 206 nm) were pooled and concentrated to 1.1 ml on AMICON® Ultra 10,000 MWCO (centrifugation at 3000 rpm during 30 min).
TT-SPDP:

A 15-fold molar excess of SPDP (Pierce) dissolved in DMSO (dimethylsulfoxid, Merck) was added to 1 g of TT (50 mg/ml) in 100 mM Na phosphate, pH 7.2 and incubated 80 min at room temperature. Then the product was injected on SEPHACRYL® S100HR (XK16/40) and eluted in 100 mM Na acetate pH 5.6, 100 mM NaCl, 1 mM EDTA with a flow-rate fixed at 60 ml/h. The elution pool was selected in function of the optical density (UV=280 nm) and then concentrated to 19.6 ml on AMICON® Ultra 10,000 MWCO (centrifugation at 3000 rpm during 75 min).

TT-LC-SPDP was produced as TT-SPDP but using LC-SPDP (Succinimidyl 6-[3-(2-pyridyldithio)-propionamido] hexanoate, Pierce) and an incubation time of 60 min.
TT-SH or TT-LC-SH DTT was added to TT-SPDP or TT-LC-SPDP in a DTT/TT ratio (mg/mg) of 0.7/1. After 2 h at room temperature, the release of pyridine-2-thione was followed by its characteristic absorbance at 343 nm. The thiolated protein was purified from excess DTT by gel filtration (PD-10, Amersham). After concentration on AMICON® Ultra 10,000 MWCO, protein content was estimated by Lowry dosage.

dPNAG-SPDP+TT-SH or TT-LC-SH (dPNAG-TT014 and 016)

Coupling was performed at room temperature under continuous stirring and with an initial TT/PS ratio (w/w) of 2/1.

dPNAG and TT-SH were mixed in order to obtain a final PS concentration of 20 mg/ml and a final protein concentration of 40 mg/ml. After 30 min, unreacted sulfhydryl groups were quenched by addition of 2-Iodoacetamide (Merck).

dPNAG and TT-LC-SH was mixed in order to obtain a final PS concentration of 10 mg/ml and a final protein concentration of 20 mg/ml. After 75 min, unreacted sulfhydryl groups were quenched by addition of 2-Iodoacetamide (Merck).

Then the conjugate is clarified using a 5 μm Minisart filter and injected on SEPHACRYL®S300HR (XK16/100). Elution was realized in 200 mM NaCl with a flow-rate fixed at 30 ml/h.

The elution fractions were analysed by hexosamine and by protein dosage. Interesting fractions were pooled and filtered on 0.22 μm STERIVEX™.

The resulting conjugates have a final TT/PS ratio (w/w) of 2.18 (TT-SH) and 2.24 (TT-LC-SH).

Thiolation of dPNAG 11.6 mg of DTT (1,4-Dithiothreitol, Boerhinger Mannheim, MW: 154.24) were added to 16.5 mg of dPNAG-SPDP. After 2 h at room temperature, the release of pyridine-2-thione was followed by its characteristic absorbance at 343 nm. The thiolated PS was purified from excess DTT by gel filtration (TOYOPEARL® HW40F) and then concentrated to 860 μl on AMICON® Ultra 10,000 MWCO.

dPNAG-SH+TT-SPDP (dPNAG-TT017)

Coupling was performed at room temperature under continuous stirring and with an initial TT/PS ratio (w/w) of 1.7/1.

dPNAG-SH and TT-SPDP were mixed in order to obtain a final PS concentration of 7.73 mg/ml and a final protein concentration of 13.3 mg/ml. After 90 min, unreacted sulfhydryl groups were quenched by addition of 2-Iodoacetamide (Merck).

Then the conjugate was clarified using a 5 μm Minisart filter and injected on SEPHACRYL® S300HR (XK16/100). Elution was realized in 200 mM NaCl with a flow-rate fixed at 30 ml/h.

The elution fractions are analysed by hexosamine and by protein dosage. Interesting fractions were pooled and filtered on 0.22 μm STERIVEX®.

The resulting conjugate has a final TT/PS ratio (w/w) of 2.74.

Example 8

Formulation

Adjuvant Compositions

The conjugates were inoculated either unadjuvanted or adjuvanted with adjuvant A, having the following composition:

Composition of Adjuvant A
Qualitative Quantitative (per 0.5 mL Dose)
Liposomes:
  DOPC 1 mg
  cholesterol 0.25 mg
3DMPL 50 μg
QS21 50 μg
$KH_2PO_4$ 1 3.124 mg Buffer
$Na_2HPO_4$ 1 0.290 mg Buffer
NaCl 2.922 mg
(100 mM)
WFI q.s. ad 0.5 ml Solvent
pH 6.1
1. Total $PO_4$ concentration=50 mM Example 9

Animal Experiments

Female CD-1 mice, 8 to 10 weeks old, are obtained from Charles River Laboratories, Kingston, Mass. For lethality studies, five groups of 9 to 11 CD-1 mice are challenged intraperitoneally (i.p.) with serial dilutions of *S. aureus* grown on CSA plates. The inocular sizes range from ~$10^{10}$ to $10^8$ CFU/mouse. Mortality is assessed on a daily basis for 3 days. The 50% lethal doses ($LD_{50}$s) is estimated by using a probit model of the dose-response relationship. The null hypothesis of common $LD_{50}$s was tested by the likelihood ratio test. Sublethal bacteremia is initiated by challenging groups of 8 to 20 mice by the intravenous (i.v.) route with ~$2\times10^6$ CFU/mouse or by the i.p. route with ~$2\times10^7$ CFU/mouse. After inoculation separate groups of animals are bled from the tail at specified times, and the bacteremia levels are estimated by quantitative plate counts performed in duplicate on tryptic soy agar plates with 5% sheep blood (Becton Dickinson Microbiology Systems). Statistical significance is determined with the Welch modification of the unpaired Stutent's t test.

Example 10

Immunogenicity of *S. aureus* PS8-TT and dPNAG-TT Conjugates

Groups of 30 mice were inoculated subcutaneously with *S. aureus* PS8-TT conjugate at a saccharide dose of 3 μg, either unadjuvanted or combined with adjuvant A, on days 0, 14, 28 and 42. On day 0, the mice received a first saccharide dose including between 0.001 and 0.013 μg. The further three immunisations were done with a dose of 0.3 μg in saline. On day 55 serum was collected from the mice and each serum sample was tested by ELISA to assess the immune response against PS8. Groups of 10 mice were used in the control groups and these were inoculated with either saline or saline containing adjuvant A.

The purified PS8 was coated at 2 μg/ml in phosphate buffered saline (PBS) on high binding microtitre plates (Nunc Maxisorp) overnight at 4° C. The plates were blocked with PBS-BSA 1% for 30 min at room temperature with agitation. The mice antisera were prediluted 1/100, then further twofold dilutions were made in microplates which were incubated at 37° C. for 1 hour. After washing, bound murine antibody was detected using Jackson ImmunoLaboratories Inc. peroxidase-conjugated AFFINIPURE™ Goat Anti-Mouse IgG (H+L) (ref: 115-035-003) diluted 1:5000 in PBS-TWEEN® 0.05%. The detection antibodies were incubated for 30 minutes at room temperature with agitation. The color was developed using 4 mg OPD (Sigma)+5 μl H2O2 per 10 ml pH 4.5 0.1M citrate buffer for 15 minutes in the dark at room temperature. The reaction was stopped with 50 μl HCl, and the optical density was read at 490 nm relative to 650 nm.

The results were expressed in mid-point titers and the GMT was calculated for the 30 samples (10 for controls). The results are shown in Table 14 below.

TABLE 14

| Conjugate | Anti-PS8 titre (GMT) nonadsorbed | Anti-PS8 titre (GMT) Adjuvant A |
|---|---|---|
| SA08-TT011 | 4714 | 2109 |
| SA08-TT015 | 2806 | 5631 |
| SA08-TT017 | 3770 | 4396 |
| SA08-TT018 | 5349 | 4748 |
| Control | 50 | 50 |

Groups of 30 mice were inoculated subcutaneously with *S. aureus* dPNAG-TT conjugates (containing dPNAG which was between 10% and 30% N-acetylated) at a saccharide dose of 0.3 µg in 200 mM NaCl, either unadjuvanted or combined with adjuvant A. The mice received three inoculations on days 0, 14 and 28. On day 41 or 42 serum was collected from the mice and each serum sample was tested by ELISA to assess the immune response against PNAG. Groups of 10 mice were used in the control groups and these were inoculated with saline or with adjuvant alone.

Anti-PNAG ELISA:

Purified PNAG (2.5 µg/ml) mixed with methylated HSA (2.5 µg/ml) diluted in phosphate buffered saline (PBS) was coated on high binding microtitre plates (Nunc Maxisorp) overnight at 4° C.

The plates were blocked with PBS-BSA 1%, 30 min at RT with agitation. The mice antisera were prediluted 1/100, then further twofold dilutions were made in microplates and incubated at room temperature with agitation for 1 hour. After washing, bound murine antibody was detected using Jackson ImmunoLaboratories Inc. peroxidase-conjugated AFFINIPURE™ Goat Anti-Mouse IgG (H+L) (ref: 115-035-003) diluted 1:5000 in PBS-BSA 0.2%-TWEEN® 0.05%. The detection antibodies were incubated for 30 min. at room temperature with agitation. The color was developed using 4 mg OPD (Sigma)+5 µl $H_2O_2$ per 10 ml pH 4.5 0.1M citrate buffer for 15 minutes in the dark at room temperature. The reaction was stopped with 50 µl HCl, and the optical density was read at 490 nm relative to 650 nm.

A GMT was calculated on the mid-point titers of the 30 samples (10 for the controls).

TABLE 15

| Conjugate | Anti-PNAG GMT Non-adsorbed | Anti-PNAG GMT Adjuvant A |
|---|---|---|
| dPNAG-TT010 | 1371 | 28465 |
| dPNAG-TT011 | 1133 | 40899 |
| dPNAG-TT019 | 425 | 13429 |
| dPNAG-TT020 | 656 | 10080 |
| dPNAG-TT014 | 342 | 9806 |
| dPNAG-TT017 | 203 | 8094 |
| dPNAG-TT012 | 398 | 40509 |
| dPNAG-TT016 | 719 | 7937 |
| Control | 50 | 50 |

Example 11

Immunogenicity of PS*-TT Conjugates Made by the CDAP Method

Results

TABLE 16

| Conjugate | Anti PS8 GMT post three inoculations in mice | Anti-PS8 GMT post two inoculations in mice |
|---|---|---|
| SAPS8-TT-04 SPECOL | 207068 | 41326 |
| SAPS8-TT-04 Adjuvant A | 47405 | 15577 |
| SAPS8-TT-04 AIPO4 | 7380 | 4510 |
| SPECOL | 50 | |
| Adjuvant A | 50 | |
| AIPO4 | 50 | |

Example 12

Opsonophagocytosis Assay

The in vitro opsonophagocytosic killing of *S. aureus* by human polymorphonuclear leykocytes (PMNs) is performed as described in Xu et al 1992 Infect. Immun. 60; 1358. Human PMNs are prepared from heparinized blood by sedimentation in 3% dextran T-250. The opsonic reaction mixture (1 ml) contains ~$10^6$ PMNs in RPMI 1640 medium supplemented with 10% heat-inactivated fetal calf serum, ~$10^8$ CFU of S-aureus, and 0.1 ml of the test serum or IgG preparation. Hyperimmunized rabbit serum is used as a positive control, and 0.1 ml of nonimmune rabbit serum was used as a complete source for the IgG samples. The reaction mixtures are incubated at 37° C., and bacterial samples are transferred at 0, 60, and 120 min into water and subsequently diluted, spread on tryptic soy agar plates, and incubated at 37° C. for bacterial count after overnight incubation.

Example 13

Immunogenicity of Staphylococcal Proteins in Mice and Rabbits

Animals were immunized with purified staphylococcal proteins in order to generate hyper-immune sera. Mice were immunized three times (days 0, 14 and 28) with 10 µg of each proteins adjuvanted in SPECOL. Rabbits were immunized three times (days 0, 21 and 42) with 20 µg of each proteins adjuvanted in SPECOL. Immune sera were collected and evaluated in anti-protein and anti-killed whole cells ELISA.

Anti-Protein ELISA:

The purified protein was coated at 1 µg/ml in phosphate buffered saline (PBS) on high binding microtitre plates (Nunc Maxisorp) overnight at 4° C. The plates were blocked with PBS-BSA 1%, for 30 min at RT with agitation. The test samples were then diluted 1/1000 and incubated at room temperature for 1 hour with agitation. After washing, bound murine or rabbit antibody was detected using Jackson ImmunoLaboratories Inc. peroxidase-conjugated AFFINIPURE™ Goat Anti-Mouse IgG (H+L) (ref: 115-035-003) or AFFINIPURE™ Goat Anti-Rabbit IgG (H+L) (ref: 11-035-003) diluted 1:5000 in PBS-TWEEN® 0.05%. The detection antibodies were incubated for 30 min at room temperature with agitation. The color was developed using 4 mg OPD (Sigma)+5 µl H2O2 per 10 ml pH 4.5 0.1M citrate buffer for 15 minutes in the dark at room temperature. The reaction was stopped with 50 μl HCl, and the optical density was read at 490 nm relative to 650 nm.

The O.D. for a 1/1000 dilution of Post III was compared to the O.D. obtained with the same dilution of Pre-immune sera.

Results generated with mice and rabbit sera are presented in FIG. 5. A good seroconversion against each antigen was observed. Evaluation of sera directed against SBI was impaired due to the Ig binding activity of this protein.

Anti-Killed Whole Cells ELISA:

Killed whole cells (heat or formaldehyde inactivated) from *S. aureus* type 5 and 8 or *S. epidermidis* strain Hay were coated at 20 μg/ml in phosphate buffered saline (PBS) on high binding microtitre plates (Nunc Maxisorp) overnight at 4° C. with evaporation. The plates were blocked with PBS-BSA 1% 30 min at room temperature with agitation. Protein A was neutralised by addition of 10 μg/ml of Affinity Purified Chicken anti-ProteinA (ICL ref: CPA-65A-2) diluted in PBS-TWEEN® 0.05% followed by incubation for 1 hour at room temperature. The test samples were then diluted two-fold on the microplate in PBS-0.05% from a starting dilution at 1/10 and incubated 1 hour at room temperature with agitation. After washing, bound murine or rabbit antibody was detected using Jackson ImmunoLaboratories Inc. peroxidase-conjugated AFFINIPURE™ Goat Anti-Mouse IgG (H+L) (ref: 115-035-003) or AFFINIPURE™ Goat Anti-Rabbit IgG (H+L) (ref: 11-035-003) diluted 1:5000 in PBS-TWEEN® 0.05%. This detection antibodies were incubated for 30 min. at room temperature with agitation. The color was developed using 4 mg OPD (Sigma)+5 μl H2O2 per 10 ml pH 4.5 0.1M citrate buffer for 15 minutes in the dark, at room temperature. The reaction was stopped with 50 μl HCl, and the optical density was read at 490 nm relative to 650 nm.

It should be noted that expression levels of proteins in staphylococci will vary depending on culture conditions. Therefore a negative result may reflect the choice of incorrect culture conditions rather than a lack of immunogenicity.

The results using mice sera are shown in Table 17 and some of the graphs are shown in FIG. 6. A weak recognition of *S. aureus* strain 5 is observed with sera directed against SdrC, FnbpA, Ebh, Sbi and IsaA. Recognition of *S. aureus* strain 8 is only observed with the serum directed against Sbi. Weak recognition of *S. epidermidis* Hay is observed with sera directed against Atl amidase, MRPII, IsdA, IsaA, Ebh, Aaa and Sbi.

A selection of results generated using rabbit sera are shown in FIG. 7 and summarized in Table 18. Very good recognition of the three strains was observed with IsaA and IsdB. A weak recognition of the three stains was observed with HarA although animals only received one injection rather than the three injections used for the other proteins.

TABLE 17

| Protein name | React on SA5 | React on SA8 | React on SE Hay |
| --- | --- | --- | --- |
| IsaA | (+) | (+) | (+) |
| ClfA | – | (+) | (+) |
| Atl amidase | – | – | ++ |
| SdrG | – | – | – |
| Glucosamidase | – | – | – |
| IsdA | – | – | ++ |
| Alpha toxin | – | – | – |
| SrdC | ++ | (+) | – |
| Ebh | + | – | + |
| AaA | – | – | ++ |
| MRPII | – | – | ++ |

TABLE 17-continued

| Protein name | React on SA5 | React on SA8 | React on SE Hay |
| --- | --- | --- | --- |
| Sbi | ++ | ++ | +++ |
| FnbpA | + | + | (+) |

TABLE 18

| Protein name | React on SA5 | React on SA8 | React on SE Hay |
| --- | --- | --- | --- |
| IsaA | +++ | +++ | +++ |
| ClfA | + | ++ | ++ |
| Atl amidase | – | ++ | + |
| IsdB | +++ | +++ | +++ |
| SdrG | + | + | + |
| Glucosamidase | – | – | – |
| HarA (1 inject.) | + | + | + |
| IsdA | – | – | – |
| Alpha toxin | – | – | + |
| SrdC | – | – | – |
| Ebh | – | + | – |
| AaA | – | – | – |
| MRPII | – | – | ++ |
| Sbi | – | +++ | – |
| FnbpA | – | ++ | ++ |

Example 14

Efficacy of Combinations of Staphylococcal Proteins in a Nasal Colonization Model Fifteen groups of three cotton rats were inoculated with combinations of eight staphylococcal antigens and five cotton rats which acted as controls were treated with no antigen. These sixteen groups are as follows:

Group 1—Atl-glucosamine, Atl-amidase, AAA, alpha toxin, SdrC, SdrG, Ebh, Sbi
Group 2-Atl-glucosamine, Atl-amidase, IsdA, IsdB, ClfA, SdrC, Ebh, FnbpA
Group 3-Atl-glucosamine, Atl-amidase, HarA, IsdA, MRPII, IsdB, AAA, alpha toxin
Group 4-Atl-glucosamine, HarA, IsdA, AAA, ClfA, IsaA, Ebh, Sbi
Group 5—HarA, MRPII, AAA, alpha toxin, ClfA, SdrC, Ebh, FnbpA
Group 6—IsdA, IsdB, AAA, alpha toxin, ClfA, SdrG, Sbi, FnbpA
Group 7—Atl-aminidase, IsdA, MRPII, AAA, IsaA, SdrG, Ebh, FnbpA
GROUP 8—Control
GROUP 9—Atl-glucosamine, IsdA, MRPII, alpha toxin, IsaA, SdrC, Sbi, FnbpA
Group 10-Atl-glucosamine, MRPII, IsdB, AAA, ClfA, IsaA, SdrC, SdrG
Group 11—Atl-amindase, MRPII, IsdB, alpha toxin, ClfA, IsaA, Ebh, Sbi
Group 12—Atl-glucosamine, HarA, IsdB, alpha toxin, IsaA, SdrG, Ebh, FnbpA
Group 13—Atl-amidase, HarA, IsdB, AAA, IsaA, SdrC, Sbi, FnbpA
Group 14—Atl-glucosamine, Atl-amidase, HarA, MRPII, ClfA, SdrG, Sbi, FnbpA
Group 15—Atl-amidase, HarA, IsdA, alpha toxin, ClfA, IsaA, SdfC, SdrG
Group 16—HarA, IsdA, MRPII, IsdB, SdrC, SdrG, Ebh, Sbi Each mix of antigens contained 3 μg of each antigen mixed with an adjuvant made of liposomes containing MPL and QS21. The cotton rats were inoculated three times on days 1, 14 and 28 of the experiment. Two weeks after inoculation, the efficacy of the immunisations were assessed using a nasal colonisation assay as described in Kokai-Kun et al (2003) Antimicrob. Agents. Chemother. 47; 1589-1597.

Classical multiple linear regression analysis was carried out on the data using "Design Expert 6" software. The presence of an antigen was coded as +1 and the absence of an antigen by −1. Using the equation of the model it was possible to determine which antigens were the key antigens which produced a large decrease in the number of colonies per nose.

Results

The results of the nasal colonisation assay are shown in Table 19. The control group had a mean logCFU/nose of 3.51335 and a decrease in nasal colonisation could be seen for all the groups of cotton rats inoculated with staphylococcal proteins. Groups 4, 9 and 13 showed the greatest decrease in nasal colonisation with a decrease of over 2 logs in CFU/nose. Groups 12 and 16 also gave good results, showing a decease of about 2 logs in CFU/nose.

TABLE 19

| Group | Mean observed LogCFU/nose | Predicted LogCFU/nose |
|---|---|---|
| 1 | 1.77527 | 2.03560 |
| 2 | 2.90435 | 2.52684 |
| 3 | 1.96556 | 2.23033 |
| 4 | 1.27748 | 1.21872 |
| 5 | 1.67304 | 1.93128 |
| 6 | 2.79745 | 2.98193 |
| 7 | 2.21481 | 2.30705 |
| 8 | 3.51355 | 3.47317 |
| 9 | 1.22480 | 1.44080 |
| 10 | 2.03085 | 1.93204 |

TABLE 19-continued

| Group | Mean observed LogCFU/nose | Predicted LogCFU/nose |
|---|---|---|
| 11 | 2.02522 | 1.81581 |
| 12 | 1.53402 | 1.70996 |
| 13 | 1.36063 | 1.49100 |
| 14 | 2.31201 | 1.73909 |
| 15 | 2.22979 | 1.98223 |
| 16 | 1.58109 | 1.44004 |

The contribution of specific antigens within the antigen mix was calculated using multiple regression analysis of the nasal colonisation data. The final model contains the seven best antigens. Results for these antigens are shown in Table 20. Within the context of the protein mix, the inclusion of HarA gave the greatest decrease in nasal colonisation, followed by IsaA, Sbi, SdrC, autolysin-glucosamine, MRPII and Ebh.

TABLE 20

Effects in difference of logCFU/nose and ratio of CFU/nose for the seven best antigens in the model and corresponding p-values.

| antigen | prob > F | Effect estimate | Reduction ratio | Cumulative effect | Cumulative ratio |
|---|---|---|---|---|---|
| HarA | 0.033 | −0.596 | 3.9 | −0.596 | 3.9 |
| IsaA | 0.046 | −0.558 | 3.6 | −1.154 | 14.3 |
| Sbi | 0.077 | −0.491 | 3.1 | −1.645 | 44.2 |
| SdrC | 0.22 | −0.337 | 2.2 | −1.982 | 96.0 |
| Atl-glucos | 0.238 | −0.324 | 2.1 | −2.306 | 202.2 |
| MRPII | 0.239 | −0.323 | 2.1 | −2.629 | 425.3 |
| Ebh | 0.297 | −0.286 | 1.9 | −2.914 | 821.0 |

The invention claimed is:

1. An immunogenic composition comprising an isolated staphylococcal poly-N-acetylglucosamine (PNAG) which is less than 40% N-acetylated wherein the PNAG is conjugated to a carrier protein by a maleimide linker bonded to an amine group on the PNAG to form a PNAG conjugate, wherein the PNAG conjugate has the structure:

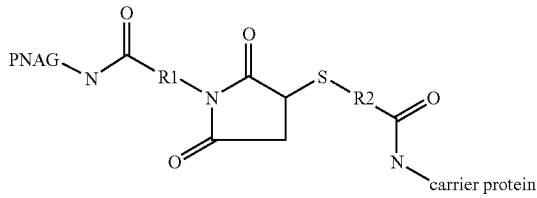

wherein R1 is C1-C6 alkyl and R2 is C1-C6 alkyl;

wherein the linker has a spacer length of 10-20 Angstroms; and further comprising an isolated Type 8 capsular polysaccharide or oligosaccharide of *Staphylococcus aureus*.

2. The immunogenic composition of claim 1 comprising an isolated Type 5 capsular polysaccharide or oligosaccharide of *S. aureus*.

3. The immunogenic composition of claim 1 wherein the linker comprises a peptide bond.

4. An immunogenic composition comprising an isolated staphylococcal poly-N-acetylglucosamine (PNAG) which is less than 40% N-acetylated wherein the PNAG is conjugated to a carrier protein by a maleimide linker bonded to an amine group on the PNAG to form a PNAG conjugate, wherein the PNAG conjugate has the structure:

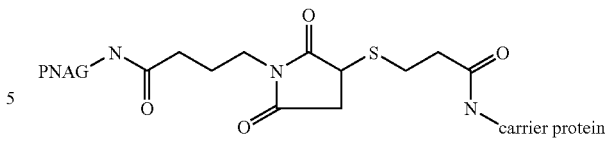

wherein the linker has a spacer length of 10-20 Angstroms; and further comprising an isolated Type 8 capsular polysaccharide or oligosaccharide of *Staphylococcus aureus*.

5. The immunogenic composition of claim 1 wherein the carrier protein is selected from the group consisting of tetanus toxoid, diphtheria toxoid, diphtheria toxoid CRM197, *Haemophilus influenzae* protein D, *Pseudomonas aeruginosa* exoprotein A, pneumococcal pneumolysin and alpha toxoid.

6. The immunogenic composition of claim 1, comprising a pharmaceutically acceptable excipient.

7. The immunogenic composition of claim 4, wherein the carrier protein is selected from the group consisting of tetanus toxoid, diphtheria toxoid, diphtheria toxoid CRM197, *Haemophilus influenzae* protein D, *Pseudomonas aeruginosa* exoprotein A, pneumococcal pneumolysin and alpha toxoid.

8. The immunogenic composition of claim 4, comprising a pharmaceutically acceptable excipient.

9. A method of eliciting an immune response to staphylococcal PNAG in a mammal comprising administering to the mammal an immunogenically effective amount of the immunogenic composition of claim 6.

10. A method of making the immunogenic composition of claim 1 comprising mixing the PNAG conjugate and the isolated Type 8 capsular polysaccharide *S. aureus* or the isolated capsular oligosaccharide of *S. aureus* and adding a pharmaceutically acceptable excipient.

* * * * *

SEQUENCE LISTING

<160> NUMBER OF SEQ ID NOS: 142

<210> SEQ ID NO 1
<211> LENGTH: 533
<212> TYPE: PRT
<213> ORGANISM: Staphylococcus aureus

<400> SEQUENCE: 1

```
Met Leu Gln Val Thr Asp Val Ser Leu Arg Phe Gly Asp Arg Lys Leu
 1               5                  10                  15

Phe Glu Asp Val Asn Ile Lys Phe Thr Glu Gly Asn Cys Tyr Gly Leu
            20                  25                  30

Ile Gly Ala Asn Gly Ala Gly Lys Ser Thr Phe Leu Lys Ile Leu Ser
        35                  40                  45

Gly Glu Leu Asp Ser Gln Thr Gly His Val Ser Leu Gly Lys Asn Glu
    50                  55                  60

Arg Leu Ala Val Leu Lys Gln Asp His Tyr Ala Tyr Glu Asp Glu Arg
65                  70                  75                  80

Val Leu Asp Val Val Ile Lys Gly His Glu Arg Leu Tyr Glu Val Met
                85                  90                  95

Lys Glu Lys Asp Glu Ile Tyr Met Lys Pro Asp Phe Ser Asp Glu Asp
            100                 105                 110

Gly Ile Arg Ala Ala Glu Leu Glu Gly Glu Phe Ala Glu Met Asn Gly
        115                 120                 125
```

```
Trp Asn Ala Glu Ala Asp Ala Ala Asn Leu Leu Ser Gly Leu Gly Ile
    130                 135                 140
Asp Pro Thr Leu His Asp Lys Lys Met Ala Glu Leu Glu Asn Asn Gln
145                 150                 155                 160
Lys Ile Lys Val Leu Leu Ala Gln Ser Leu Phe Gly Glu Pro Asp Val
                165                 170                 175
Leu Leu Leu Asp Glu Pro Thr Asn Gly Leu Asp Ile Pro Ala Ile Ser
            180                 185                 190
Trp Leu Glu Asp Phe Leu Ile Asn Phe Asp Asn Thr Val Ile Val Val
        195                 200                 205
Ser His Asp Arg His Phe Leu Asn Asn Val Cys Thr His Ile Ala Asp
    210                 215                 220
Leu Asp Phe Gly Lys Ile Lys Val Tyr Val Gly Asn Tyr Asp Phe Trp
225                 230                 235                 240
Tyr Gln Ser Ser Gln Leu Ala Gln Lys Met Ala Gln Glu Gln Asn Lys
                245                 250                 255
Lys Lys Glu Glu Lys Met Lys Glu Leu Gln Asp Phe Ile Ala Arg Phe
            260                 265                 270
Ser Ala Asn Ala Ser Lys Ser Lys Gln Ala Thr Ser Arg Lys Lys Gln
        275                 280                 285
Leu Glu Lys Ile Glu Leu Asp Asp Ile Gln Pro Ser Ser Arg Arg Tyr
    290                 295                 300
Pro Phe Val Lys Phe Thr Pro Glu Arg Glu Ile Gly Asn Asp Leu Leu
305                 310                 315                 320
Ile Val Gln Asn Leu Ser Lys Thr Ile Asp Gly Glu Lys Val Leu Asp
                325                 330                 335
Asn Val Ser Phe Thr Met Asn Pro Asn Asp Lys Ala Ile Leu Ile Gly
            340                 345                 350
Asp Ser Glu Ile Ala Lys Thr Thr Leu Leu Lys Ile Leu Ala Gly Glu
        355                 360                 365
Met Glu Pro Asp Glu Gly Ser Phe Lys Trp Gly Val Thr Thr Ser Leu
    370                 375                 380
Ser Tyr Phe Pro Lys Asp Asn Ser Glu Phe Phe Glu Gly Val Asn Met
385                 390                 395                 400
Asn Leu Val Asp Trp Leu Arg Gln Tyr Ala Pro Glu Asp Glu Gln Thr
                405                 410                 415
Glu Thr Phe Leu Arg Gly Phe Leu Gly Arg Met Leu Phe Ser Gly Glu
            420                 425                 430
Glu Val Lys Lys Lys Ala Ser Val Leu Ser Gly Gly Glu Lys Val Arg
        435                 440                 445
Cys Met Leu Ser Lys Met Met Leu Ser Ser Ala Asn Val Leu Leu Leu
    450                 455                 460
Asp Glu Pro Thr Asn His Leu Asp Leu Glu Ser Ile Thr Ala Val Asn
465                 470                 475                 480
Asp Gly Leu Lys Ser Phe Lys Gly Ser Ile Ile Phe Thr Ser Tyr Asp
                485                 490                 495
Phe Glu Phe Ile Asn Thr Ile Ala Asn Arg Val Ile Asp Leu Asn Lys
            500                 505                 510
Gln Gly Gly Val Ser Lys Glu Ile Pro Tyr Glu Glu Tyr Leu Gln Glu
        515                 520                 525
Ile Gly Val Leu Lys
    530
```

```
<210> SEQ ID NO 2
<211> LENGTH: 535
<212> TYPE: PRT
<213> ORGANISM: Staphylococcus epidermidis

<400> SEQUENCE: 2
```

| | | | | | | | | | | | | | | |
|---|---|---|---|---|---|---|---|---|---|---|---|---|---|---|
| Met | Leu | Gln | Val | Thr | Asp | Val | Ser | Leu | Arg | Phe | Gly | Asp | Arg | Lys | Leu |
| 1 | | | | 5 | | | | | 10 | | | | | 15 | |

Phe Glu Asp Val Asn Ile Lys Phe Thr Glu Gly Asn Cys Tyr Gly Leu
            20                  25                  30

Ile Gly Ala Asn Gly Ala Gly Lys Ser Thr Phe Leu Lys Ile Leu Ser
        35                  40                  45

Gly Glu Ile Asp Ser Gln Thr Gly His Val Ser Leu Gly Lys Asp Glu
    50                  55                  60

Arg Leu Ala Val Leu Lys Gln Asp His Phe Ala Tyr Glu Asp Glu Arg
65                  70                  75                  80

Val Leu Asp Val Val Ile Lys Gly His Glu Arg Leu Tyr Gln Val Met
                85                  90                  95

Lys Glu Lys Asp Glu Ile Tyr Met Lys Pro Asp Phe Ser Asp Glu Asp
            100                 105                 110

Gly Ile Arg Ala Ala Glu Leu Glu Gly Glu Phe Ala Glu Met Asn Gly
        115                 120                 125

Trp Asn Ala Glu Ala Asp Ala Ala Asn Leu Leu Ser Gly Leu Gly Ile
130                 135                 140

Glu Pro Asp Leu His Asp Lys Asn Met Ser Glu Leu Glu Asn Asn Gln
145                 150                 155                 160

Lys Val Lys Val Leu Leu Ala Gln Ser Leu Phe Gly Asp Pro Asp Val
                165                 170                 175

Leu Leu Leu Asp Glu Pro Thr Asn Gly Leu Asp Ile Pro Ala Ile Ser
            180                 185                 190

Trp Leu Glu Asp Phe Leu Ile Asn Phe Glu Asn Thr Val Ile Val Val
        195                 200                 205

Ser His Asp Arg His Phe Leu Asn Asn Val Cys Thr His Ile Ala Asp
    210                 215                 220

Leu Asp Phe Gly Lys Ile Lys Leu Tyr Val Gly Asn Tyr Asp Phe Trp
225                 230                 235                 240

Tyr Gln Ser Ser Gln Leu Ala Gln Lys Met Ala Gln Glu Gln Asn Lys
                245                 250                 255

Lys Lys Glu Glu Lys Met Lys Glu Leu Gln Asp Phe Ile Ala Arg Phe
            260                 265                 270

Ser Ala Asn Ala Ser Lys Ser Lys Gln Ala Thr Ser Arg Lys Lys Gln
        275                 280                 285

Leu Glu Lys Ile Glu Leu Asp Asp Ile Gln Pro Ser Ser Arg Arg Tyr
290                 295                 300

Pro Tyr Val Lys Phe Thr Pro Glu Arg Glu Ile Gly Asn Asp Leu Leu
305                 310                 315                 320

Thr Val Glu Asn Leu Ser Lys Thr Ile Asp Gly Glu Lys Val Leu Asp
                325                 330                 335

Asn Val Ser Phe Thr Met Asn Pro Asn Asp Lys Ala Ile Leu Val Gly
            340                 345                 350

Asp Ser Glu Ile Ala Lys Thr Thr Leu Leu Lys Ile Leu Ala Gly Glu
        355                 360                 365

Met Glu Pro Asp Glu Gly Thr Phe Lys Trp Gly Val Thr Thr Ser Leu
370                 375                 380

Ser Tyr Phe Pro Lys Asp Asn Ser Glu Phe Phe Asp Gly Val Asp Met

```
                385                 390                 395                 400
Asn Leu Val Glu Trp Leu Arg Gln Tyr Ala Pro Glu Asp Glu Gln Thr
            405                 410                 415

Glu Thr Phe Leu Arg Gly Phe Leu Gly Arg Met Leu Phe Ser Gly Glu
        420                 425                 430

Glu Val Lys Lys Ala Ser Val Leu Ser Gly Gly Glu Lys Val Arg
            435                 440                 445

Cys Met Leu Ser Lys Met Met Leu Ser Ser Ala Asn Val Leu Leu Leu
        450                 455                 460

Asp Glu Pro Thr Asn His Leu Asp Leu Glu Ser Ile Thr Ala Val Asn
465                 470                 475                 480

Asp Gly Leu Lys Ser Phe Lys Gly Ser Ile Ile Phe Thr Ser Tyr Asp
            485                 490                 495

Phe Glu Phe Ile Asn Thr Ile Ala Asn Arg Val Ile Asp Leu Asn Gln
        500                 505                 510

Ala Gly Ala Leu Ser Lys Glu Val Pro Tyr Glu Glu Tyr Leu Gln Glu
            515                 520                 525

Ile Gly Val Leu Gln Asn Asn
        530                 535

<210> SEQ ID NO 3
<211> LENGTH: 434
<212> TYPE: PRT
<213> ORGANISM: Staphylococcus aureus

<400> SEQUENCE: 3

Met Pro Ile Ile Thr Asp Val Tyr Ala Arg Glu Val Leu Asp Ser Arg
 1               5                  10                  15

Gly Asn Pro Thr Val Glu Val Glu Val Leu Thr Glu Ser Gly Ala Phe
            20                  25                  30

Gly Arg Ala Leu Val Pro Ser Gly Ala Ser Thr Gly Glu His Glu Ala
        35                  40                  45

Val Glu Leu Arg Asp Gly Asp Lys Ser Arg Tyr Leu Gly Lys Gly Val
    50                  55                  60

Thr Lys Ala Val Glu Asn Val Asn Glu Ile Ile Ala Pro Glu Ile Ile
65                  70                  75                  80

Glu Gly Glu Phe Ser Val Leu Asp Gln Val Ser Ile Asp Lys Met Met
                85                  90                  95

Ile Ala Leu Asp Gly Thr Pro Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Thr Thr
                165                 170                 175

Phe Lys Glu Ser Leu Arg Trp Gly Thr Glu Ile Phe His Asn Leu Lys
            180                 185                 190

Ser Ile Leu Ser Lys Arg Gly Leu Glu Thr Ala Val Gly Asp Glu Gly
        195                 200                 205

Gly Phe Ala Pro Lys Phe Glu Gly Thr Glu Asp Ala Val Glu Thr Ile
    210                 215                 220

Ile Gln Ala Ile Glu Ala Ala Gly Tyr Lys Pro Gly Glu Glu Val Phe
```

```
                    225                 230                 235                 240
Leu Gly Phe Asp Cys Ala Ser Ser Glu Phe Tyr Glu Asn Gly Val Tyr
                245                 250                 255

Asp Tyr Ser Lys Phe Glu Gly Glu His Gly Ala Lys Arg Thr Ala Ala
                260                 265                 270

Glu Gln Val Asp Tyr Leu Glu Gln Leu Val Asp Lys Tyr Pro Ile Ile
            275                 280                 285

Thr Ile Glu Asp Gly Met Asp Glu Asn Asp Trp Asp Gly Trp Lys Gln
        290                 295                 300

Leu Thr Glu Arg Ile Gly Asp Arg Val Gln Leu Val Gly Asp Asp Leu
305                 310                 315                 320

Phe Val Thr Asn Thr Glu Ile Leu Ala Lys Gly Ile Glu Asn Gly Ile
                325                 330                 335

Gly Asn Ser Ile Leu Ile Lys Val Asn Gln Ile Gly Thr Leu Thr Glu
                340                 345                 350

Thr Phe Asp Ala Ile Glu Met Ala Gln Lys Ala Gly Tyr Thr Ala Val
            355                 360                 365

Val Ser His Arg Ser Gly Glu Thr Glu Asp Thr Thr Ile Ala Asp Ile
        370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Phe Glu Thr Ala Lys Tyr Asp Gly Ile Lys Ser Phe Tyr Asn Leu
                420                 425                 430

Asp Lys

<210> SEQ ID NO 4
<211> LENGTH: 434
<212> TYPE: PRT
<213> ORGANISM: Staphylococcus epidermidis

<400> SEQUENCE: 4

Met Pro Ile Ile Thr Asp Val Tyr Ala Arg Glu Val Leu Asp Ser Arg
  1               5                  10                  15

Gly Asn Pro Thr Val Glu Val Glu Val Leu Thr Glu Ser Gly Ala Phe
                20                  25                  30

Gly Arg Ala Leu Val Pro Ser Gly Ala Ser Thr Gly Glu His Glu Ala
            35                  40                  45

Val Glu Leu Arg Asp Gly Asp Lys Ser Arg Tyr Leu Gly Lys Gly Val
        50                  55                  60

Thr Lys Ala Val Glu Asn Val Asn Glu Met Ile Ala Pro Glu Ile Val
65                  70                  75                  80

Glu Gly Glu Phe Ser Val Leu Asp Gln Val Ser Ile Asp Lys Met Met
                85                  90                  95

Ile Gln Leu Asp Gly Thr His Asn Lys Gly Lys Leu Gly Ala Asn Ala
                100                 105                 110

Ile Leu Gly Val Ser Ile Ala Val Ala Arg Ala Ala Ala Asp Leu Leu
            115                 120                 125

Gly Gln Pro Leu Tyr Lys Tyr Leu Gly Gly Phe Asn Gly Lys Gln Leu
        130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Glu Ser
                165                 170                 175
```

```
Phe Lys Glu Ser Leu Arg Trp Gly Ala Glu Ile Phe His Asn Leu Lys
            180                 185                 190

Ser Ile Leu Ser Glu Arg Gly Leu Glu Thr Ala Val Gly Asp Glu Gly
        195                 200                 205

Gly Phe Ala Pro Arg Phe Glu Gly Thr Glu Asp Ala Val Glu Thr Ile
    210                 215                 220

Ile Lys Ala Ile Glu Lys Ala Gly Tyr Lys Pro Gly Glu Asp Val Phe
225                 230                 235                 240

Leu Gly Phe Asp Cys Ala Ser Ser Glu Phe Tyr Glu Asn Gly Val Tyr
            245                 250                 255

Asp Tyr Thr Lys Phe Glu Gly Glu His Gly Ala Lys Arg Ser Ala Ala
        260                 265                 270

Glu Gln Val Asp Tyr Leu Glu Glu Leu Ile Gly Lys Tyr Pro Ile Ile
    275                 280                 285

Thr Ile Glu Asp Gly Met Asp Glu Asn Asp Trp Glu Gly Trp Lys Gln
290                 295                 300

Leu Thr Asp Arg Ile Gly Asp Lys Val Gln Leu Val Gly Asp Asp Leu
305                 310                 315                 320

Phe Val Thr Asn Thr Glu Ile Leu Ser Lys Gly Ile Glu Gln Gly Ile
            325                 330                 335

Gly Asn Ser Ile Leu Ile Lys Val Asn Gln Ile Gly Thr Leu Thr Glu
        340                 345                 350

Thr Phe Asp Ala Ile Glu Met Ala Gln Lys Ala Gly Tyr Thr Ala Val
    355                 360                 365

Val Ser His Arg Ser Gly Glu Thr Glu Asp Thr Thr Ile Ala Asp Ile
370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
            405                 410                 415

Leu Tyr Glu Thr Ala Lys Phe Glu Gly Ile Lys Ser Phe Tyr Asn Leu
        420                 425                 430

Asp Lys

<210> SEQ ID NO 5
<211> LENGTH: 255
<212> TYPE: PRT
<213> ORGANISM: Staphylococcus aureus

<400> SEQUENCE: 5

Met Lys Lys Ile Val Thr Ala Thr Ile Ala Thr Ala Gly Leu Ala Thr
1               5                   10                  15

Ile Ala Phe Ala Gly His Asp Ala Gln Ala Ala Glu Gln Asn Asn Asn
            20                  25                  30

Gly Tyr Asn Ser Asn Asp Ala Gln Ser Tyr Ser Tyr Thr Tyr Thr Ile
        35                  40                  45

Asp Ala Gln Gly Asn Tyr His Tyr Thr Trp Thr Gly Asn Trp Asn Pro
    50                  55                  60

Ser Gln Leu Thr Gln Asn Asn Thr Tyr Tyr Asn Asn Tyr Asn Thr
65                  70                  75                  80

Tyr Ser Tyr Asn Asn Ala Ser Tyr Asn Tyr Asn His Ser Tyr
                85                  90                  95

Gln Tyr Asn Asn Tyr Thr Asn Asn Ser Gln Thr Ala Thr Asn Asn Tyr
            100                 105                 110
```

```
Tyr Thr Gly Gly Ser Gly Ala Ser Tyr Ser Thr Thr Ser Asn Asn Val
        115                 120                 125

His Val Thr Thr Thr Ala Ala Pro Ser Ser Asn Gly Arg Ser Ile Ser
    130                 135                 140

Asn Gly Tyr Ala Ser Gly Ser Asn Leu Tyr Thr Ser Gly Gln Cys Thr
145                 150                 155                 160

Tyr Tyr Val Phe Asp Arg Val Gly Gly Lys Ile Gly Ser Thr Trp Gly
                165                 170                 175

Asn Ala Ser Asn Trp Ala Asn Ala Ala Ser Ser Gly Tyr Thr Val
                180                 185                 190

Asn Asn Thr Pro Lys Val Gly Ala Ile Met Gln Thr Thr Gln Gly Tyr
                195                 200                 205

Tyr Gly His Val Ala Tyr Val Glu Gly Val Asn Ser Asn Gly Ser Val
    210                 215                 220

Arg Val Ser Glu Met Asn Tyr Gly His Gly Ala Gly Val Val Thr Ser
225                 230                 235                 240

Arg Thr Ile Ser Ala Asn Gln Ala Gly Ser Tyr Asn Phe Ile His
                245                 250                 255
```

<210> SEQ ID NO 6
<211> LENGTH: 267
<212> TYPE: PRT
<213> ORGANISM: Staphylococcus aureus

<400> SEQUENCE: 6

```
Met Lys Lys Ile Ala Thr Ala Thr Ile Ala Thr Ala Gly Phe Ala Thr
1               5                   10                  15

Ile Ala Ile Ala Ser Gly Asn Gln Ala His Ala Ser Glu Gln Asp Asn
                20                  25                  30

Tyr Gly Tyr Asn Pro Asn Asp Pro Thr Ser Tyr Ser Tyr Thr Tyr Thr
            35                  40                  45

Ile Asp Ala Gln Gly Asn Tyr His Tyr Thr Trp Lys Gly Asn Trp His
50                  55                  60

Pro Ser Gln Leu Asn Gln Asp Asn Gly Tyr Tyr Ser Tyr Tyr Tyr Tyr
65                  70                  75                  80

Asn Gly Tyr Asn Asn Tyr Asn Asn Tyr Asn Asn Gly Tyr Ser Tyr Asn
                85                  90                  95

Asn Tyr Ser Arg Tyr Asn Asn Tyr Ser Asn Asn Gln Ser Tyr Asn
                100                 105                 110

Tyr Asn Asn Tyr Asn Ser Tyr Asn Thr Asn Ser Tyr Arg Thr Gly Gly
                115                 120                 125

Leu Gly Ala Ser Tyr Ser Thr Ser Ser Asn Asn Val Gln Val Thr Thr
        130                 135                 140

Thr Met Ala Pro Ser Ser Asn Gly Arg Ser Ile Ser Ser Gly Tyr Thr
145                 150                 155                 160

Ser Gly Arg Asn Leu Tyr Thr Ser Gly Gln Cys Thr Tyr Tyr Val Phe
                165                 170                 175

Asp Arg Val Gly Gly Lys Ile Gly Ser Thr Trp Gly Asn Ala Ser Asn
                180                 185                 190

Trp Ala Asn Ala Ala Ala Arg Ala Gly Tyr Thr Val Asn Asn Thr Pro
                195                 200                 205

Lys Ala Gly Ala Ile Met Gln Thr Thr Gln Gly Ala Tyr Gly His Val
        210                 215                 220

Ala Tyr Val Glu Ser Val Asn Ser Asn Gly Ser Val Arg Val Ser Glu
225                 230                 235                 240
```

```
Met Asn Tyr Gly Tyr Gly Pro Gly Val Val Thr Ser Arg Thr Ile Ser
            245                 250                 255

Ala Ser Gln Ala Ala Gly Tyr Asn Phe Ile His
            260                 265
```

<210> SEQ ID NO 7
<211> LENGTH: 257
<212> TYPE: PRT
<213> ORGANISM: Staphylococcus epidermidis

<400> SEQUENCE: 7

```
Met Lys Lys Ile Ala Thr Ala Thr Ile Ala Thr Ala Gly Ile Ala Thr
  1               5                  10                  15

Phe Ala Phe Ala His His Asp Ala Gln Ala Ala Glu Gln Asn Asn Asp
                 20                  25                  30

Gly Tyr Asn Pro Asn Asp Pro Tyr Ser Tyr Ser Tyr Thr Tyr Thr Ile
             35                  40                  45

Asp Ala Glu Gly Asn Tyr His Tyr Thr Trp Lys Gly Asn Trp Ser Pro
 50                  55                  60

Asp Arg Val Asn Thr Ser Tyr Asn Tyr Asn Asn Tyr Asn Asn Tyr Asn
 65                  70                  75                  80

Tyr Tyr Gly Tyr Asn Asn Tyr Ser Asn Tyr Asn Tyr Ser Asn Tyr
                 85                  90                  95

Asn Asn Tyr Asn Asn Tyr Gln Ser Asn Thr Gln Ser Gln Arg Thr
                100                 105                 110

Thr Gln Pro Thr Gly Gly Leu Gly Ala Ser Tyr Ser Thr Ser Ser Ser
            115                 120                 125

Asn Val His Val Thr Thr Thr Ser Ala Pro Ser Ser Asn Gly Val Ser
130                 135                 140

Leu Ser Asn Ala Arg Ser Ala Ser Gly Asn Leu Tyr Thr Ser Gly Gln
145                 150                 155                 160

Cys Thr Tyr Tyr Val Phe Asp Arg Val Gly Lys Ile Gly Ser Thr
                165                 170                 175

Trp Gly Asn Ala Asn Asn Trp Ala Asn Ala Ala Arg Ser Gly Tyr
            180                 185                 190

Thr Val Asn Asn Ser Pro Ala Lys Gly Ala Ile Leu Gln Thr Ser Gln
            195                 200                 205

Gly Ala Tyr Gly His Val Ala Tyr Val Glu Gly Val Asn Ser Asn Gly
        210                 215                 220

Ser Ile Arg Val Ser Glu Met Asn Tyr Gly His Gly Ala Gly Val Val
225                 230                 235                 240

Thr Ser Arg Thr Ile Ser Ala Ser Gln Ala Ala Ser Tyr Asn Tyr Ile
                245                 250                 255

His
```

<210> SEQ ID NO 8
<211> LENGTH: 309
<212> TYPE: PRT
<213> ORGANISM: Staphylococcus aureus

<400> SEQUENCE: 8

```
Met Lys Lys Leu Val Pro Leu Leu Leu Ala Leu Leu Leu Val Ala
  1               5                  10                  15

Ala Cys Gly Thr Gly Gly Lys Gln Ser Ser Asp Lys Ser Asn Gly Lys
                 20                  25                  30

Leu Lys Val Val Thr Thr Asn Ser Ile Leu Tyr Asp Met Ala Lys Asn
             35                  40                  45
```

```
Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
                100                 105                 110

Lys Lys Val Ile Ala Val Ser Lys Asp Val Lys Pro Ile Tyr Leu Asn
            115                 120                 125

Gly Glu Gly Asn Lys Asp Lys Gln Asp Pro His Ala Trp Leu Ser
130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
                180                 185                 190

Asn Asp Ile Pro Lys Glu Gln Arg Ala Met Ile Thr Ser Glu Gly Ala
            195                 200                 205

Phe Lys Tyr Phe Ser Lys Gln Tyr Gly Ile Thr Pro Gly Tyr Ile Trp
210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
            275                 280                 285

Lys Gly Asp Ser Tyr Tyr Lys Met Met Lys Ser Asn Ile Glu Thr Val
    290                 295                 300

His Gly Ser Met Lys
305

<210> SEQ ID NO 9
<211> LENGTH: 309
<212> TYPE: PRT
<213> ORGANISM: Staphylococcus epidermidis

<400> SEQUENCE: 9

Met Lys Lys Ile Leu Ala Leu Ala Ile Ala Phe Leu Ile Ile Leu Ala
 1               5                   10                  15

Ala Cys Gly Asn His Ser Asn His Glu His His Ser His Glu Gly Lys
                20                  25                  30

Leu Lys Val Val Thr Thr Asn Ser Ile Leu Tyr Asp Met Val Lys Arg
            35                  40                  45

Val Gly Gly Asn Lys Val Asp Val His Ser Ile Val Pro Val Gly Gln
    50                  55                  60

Asp Pro His Glu Tyr Glu Val Lys Pro Lys Asp Ile Lys Ala Leu Thr
65                  70                  75                  80

Asp Ala Asp Val Val Phe Tyr Asn Gly Leu Asn Leu Glu Thr Gly Asn
                85                  90                  95

Gly Trp Phe Glu Lys Ala Leu Asp Gln Ala Gly Lys Ser Thr Lys Asp
                100                 105                 110
```

```
Lys Asn Val Ile Ala Ala Ser Asn Asn Val Lys Pro Ile Tyr Leu Asn
            115                 120                 125

Gly Glu Glu Gly Asn Lys Asn Lys Gln Asp Pro His Ala Trp Leu Ser
130                 135                 140

Leu Glu Asn Gly Ile Lys Tyr Val Lys Thr Ile Gln Lys Ser Leu Glu
145                 150                 155                 160

His His Asp Lys Lys Asp Lys Ser Thr Tyr Glu Lys Gln Gly Asn Ala
                165                 170                 175

Tyr Ile Ser Lys Leu Glu Glu Leu Asn Lys Asp Ser Lys Asn Lys Phe
                180                 185                 190

Asp Asp Ile Pro Lys Asn Gln Arg Ala Met Met Thr Ser Glu Gly Ala
            195                 200                 205

Phe Lys Tyr Phe Ala Gln Phe Asp Val Lys Pro Gly Tyr Ile Trp
210                 215                 220

Glu Ile Asn Thr Glu Lys Gln Gly Thr Pro Gly Gln Met Lys Gln Ala
225                 230                 235                 240

Ile Lys Phe Val Lys Asp Asn His Leu Lys His Leu Leu Val Glu Thr
                245                 250                 255

Ser Val Asp Lys Lys Ala Met Gln Ser Leu Ser Glu Glu Thr Lys Lys
            260                 265                 270

Asp Ile Tyr Gly Glu Val Phe Thr Asp Ser Ile Gly Lys Glu Gly Thr
            275                 280                 285

Lys Gly Asp Ser Tyr Tyr Lys Met Met Lys Ser Asn Ile Asp Thr Ile
290                 295                 300

His Gly Ser Met Lys
305

<210> SEQ ID NO 10
<211> LENGTH: 233
<212> TYPE: PRT
<213> ORGANISM: Staphylococcus aureus

<400> SEQUENCE: 10

Met Lys Lys Thr Ile Met Ala Ser Ser Leu Ala Val Ala Leu Gly Val
1               5                   10                  15

Thr Gly Tyr Ala Ala Gly Thr Gly His Gln Ala His Ala Ala Glu Val
                20                  25                  30

Asn Val Asp Gln Ala His Leu Val Asp Leu Ala His Asn His Gln Asp
            35                  40                  45

Gln Leu Asn Ala Ala Pro Ile Lys Asp Gly Ala Tyr Asp Ile His Phe
50                  55                  60

Val Lys Asp Gly Phe Gln Tyr Asn Phe Thr Ser Asn Gly Thr Thr Trp
65                  70                  75                  80

Ser Trp Ser Tyr Glu Ala Ala Asn Gly Gln Thr Ala Gly Phe Ser Asn
                85                  90                  95

Val Ala Gly Ala Asp Tyr Thr Thr Ser Tyr Asn Gln Gly Ser Asp Val
            100                 105                 110

Gln Ser Val Ser Tyr Asn Ala Gln Ser Ser Asn Ser Asn Val Glu Ala
            115                 120                 125

Val Ser Ala Pro Thr Tyr His Asn Tyr Ser Thr Ser Thr Thr Ser Ser
130                 135                 140

Ser Val Arg Leu Ser Asn Gly Asn Thr Ala Gly Ala Thr Gly Ser Ser
145                 150                 155                 160

Ala Ala Gln Ile Met Ala Gln Arg Thr Gly Val Ser Ala Ser Thr Trp
                165                 170                 175
```

```
Ala Ala Ile Ile Ala Arg Glu Ser Asn Gly Gln Val Asn Ala Tyr Asn
            180                 185                 190

Pro Ser Gly Ala Ser Gly Leu Phe Gln Thr Met Pro Gly Trp Gly Pro
            195                 200                 205

Thr Asn Thr Val Asp Gln Gln Ile Asn Ala Ala Val Lys Ala Tyr Lys
            210                 215                 220

Ala Gln Gly Leu Gly Ala Trp Gly Phe
225                 230
```

<210> SEQ ID NO 11
<211> LENGTH: 235
<212> TYPE: PRT
<213> ORGANISM: Staphylococcus epidermidis
<400> SEQUENCE: 11

```
Met Lys Lys Thr Val Ile Ala Ser Thr Leu Ala Val Ser Leu Gly Ile
1               5                   10                  15

Ala Gly Tyr Gly Leu Ser Gly His Glu Ala His Ala Ser Glu Thr Thr
            20                  25                  30

Asn Val Asp Lys Ala His Leu Val Asp Leu Ala Gln His Asn Pro Glu
            35                  40                  45

Glu Leu Asn Ala Lys Pro Val Gln Ala Gly Ala Tyr Asp Ile His Phe
50                  55                  60

Val Asp Asn Gly Tyr Gln Tyr Asn Phe Thr Ser Asn Gly Ser Glu Trp
65                  70                  75                  80

Ser Trp Ser Tyr Ala Val Ala Gly Ser Asp Ala Asp Tyr Thr Glu Ser
            85                  90                  95

Ser Ser Asn Gln Glu Val Ser Ala Asn Thr Gln Ser Ser Asn Thr Asn
            100                 105                 110

Val Gln Ala Val Ser Ala Pro Thr Ser Ser Glu Ser Arg Ser Tyr Ser
            115                 120                 125

Thr Ser Thr Thr Ser Tyr Ser Ala Pro Ser His Asn Tyr Ser Ser His
            130                 135                 140

Ser Ser Ser Val Arg Leu Ser Asn Gly Asn Thr Ala Gly Ser Val Gly
145                 150                 155                 160

Ser Tyr Ala Ala Ala Gln Met Ala Ala Arg Thr Gly Val Ser Ala Ser
            165                 170                 175

Thr Trp Glu His Ile Ile Ala Arg Glu Ser Asn Gly Gln Leu His Ala
            180                 185                 190

Arg Asn Ala Ser Gly Ala Ala Gly Leu Phe Gln Thr Met Pro Gly Trp
            195                 200                 205

Gly Ser Thr Gly Ser Val Asn Asp Gln Ile Asn Ala Ala Tyr Lys Ala
            210                 215                 220

Tyr Lys Ala Gln Gly Leu Ser Ala Trp Gly Met
225                 230                 235
```

<210> SEQ ID NO 12
<211> LENGTH: 3890
<212> TYPE: PRT
<213> ORGANISM: Staphylococcus aureus
<400> SEQUENCE: 12

```
Met Asn Tyr Arg Asp Lys Ile Gln Lys Phe Ser Ile Arg Lys Tyr Thr
1               5                   10                  15

Val Gly Thr Phe Ser Thr Val Ile Ala Thr Leu Val Phe Leu Gly Phe
            20                  25                  30
```

```
Asn Thr Ser Gln Ala His Ala Ala Glu Thr Asn Gln Pro Ala Ser Val
         35                  40                  45

Val Lys Gln Lys Gln Ser Asn Asn Glu Gln Thr Glu Asn Arg Glu
 50                  55                  60

Ser Gln Val Gln Asn Ser Gln Asn Ser Gln Asn Ser Gln Ser Leu Ser
 65                  70                  75                  80

Ala Thr His Glu Asn Glu Gln Pro Asn Ser Gln Ala Asn Leu Val
                 85                  90                  95

Asn Gln Lys Val Ala Gln Ser Ser Thr Thr Asn Asp Glu Gln Pro Ala
                100                 105                 110

Ser Gln Asn Val Asn Thr Lys Lys Asp Ser Ala Thr Ala Thr Thr
                115                 120                 125

Gln Pro Asp Lys Glu Glu Ser Lys His Lys Gln Asn Glu Ser Gln Ser
130                 135                 140

Ala Asn Lys Asn Gly Asn Asp Asn Arg Ala Ala His Val Glu Asn His
145                 150                 155                 160

Glu Ala Asn Val Val Thr Ala Ser Asp Ser Asp Asn Gly Asn Val
                165                 170                 175

Gln His Asp Arg Asn Glu Leu Gln Ala Phe Phe Asp Ala Asn Tyr His
                180                 185                 190

Asp Tyr Arg Phe Ile Asp Arg Glu Asn Ala Asp Ser Gly Thr Phe Asn
                195                 200                 205

Tyr Val Lys Gly Ile Phe Asp Lys Ile Asn Thr Leu Leu Gly Ser Asn
210                 215                 220

Asp Pro Ile Asn Asn Lys Asp Leu Gln Leu Ala Tyr Lys Glu Leu Glu
225                 230                 235                 240

Gln Ala Val Ala Leu Ile Arg Thr Met Pro Gln Arg Gln Gln Thr Ser
                245                 250                 255

Arg Arg Ser Asn Arg Ile Gln Thr Arg Ser Val Glu Ser Arg Ala Ala
                260                 265                 270

Glu Pro Arg Ser Val Ser Asp Tyr Gln Asn Ala Asn Ser Ser Tyr Tyr
                275                 280                 285

Val Glu Asn Ala Asn Asp Gly Ser Gly Tyr Pro Val Gly Thr Tyr Ile
290                 295                 300

Asn Ala Ser Ser Lys Gly Ala Pro Tyr Asn Leu Pro Thr Thr Pro Trp
305                 310                 315                 320

Asn Thr Leu Lys Ala Ser Asp Ser Lys Glu Ile Ala Leu Met Thr Ala
                325                 330                 335

Lys Gln Thr Gly Asp Gly Tyr Gln Trp Val Ile Lys Phe Asn Lys Gly
                340                 345                 350

His Ala Pro His Gln Asn Met Ile Phe Trp Phe Ala Leu Pro Ala Asp
                355                 360                 365

Gln Val Pro Val Gly Arg Thr Asp Phe Val Thr Val Asn Ser Asp Gly
370                 375                 380

Thr Asn Val Gln Trp Ser His Gly Ala Gly Ala Asn Lys Pro
385                 390                 395                 400

Leu Gln Gln Met Trp Glu Tyr Gly Val Asn Asp Pro Asp Arg Ser His
                405                 410                 415

Asp Phe Lys Ile Arg Asn Arg Ser Gly Gln Val Ile Tyr Ser Trp Pro
                420                 425                 430

Thr Val His Val Tyr Ser Leu Glu Asp Leu Ser Arg Ala Ser Asp Tyr
                435                 440                 445

Phe Ser Glu Ala Gly Ala Thr Pro Ala Thr Lys Ala Phe Gly Arg Gln
450                 455                 460
```

-continued

```
Asn Phe Glu Tyr Ile Asn Gly Gln Lys Pro Ala Glu Ser Pro Gly Val
465                 470                 475                 480

Pro Lys Val Tyr Thr Phe Ile Gly Gln Gly Asp Ala Ser Tyr Thr Ile
                485                 490                 495

Ser Phe Lys Thr Gln Gly Pro Thr Val Asn Lys Leu Tyr Tyr Ala Ala
            500                 505                 510

Gly Gly Arg Ala Leu Glu Tyr Asn Gln Leu Phe Met Tyr Ser Gln Leu
        515                 520                 525

Tyr Val Glu Ser Thr Gln Asp His Gln Gln Arg Leu Asn Gly Leu Arg
    530                 535                 540

Gln Val Val Asn Arg Thr Tyr Arg Ile Gly Thr Thr Lys Arg Val Glu
545                 550                 555                 560

Val Ser Gln Gly Asn Val Gln Thr Lys Lys Val Leu Glu Ser Thr Asn
                565                 570                 575

Leu Asn Ile Asp Asp Phe Val Asp Asp Pro Leu Ser Tyr Val Lys Thr
                580                 585                 590

Pro Ser Asn Lys Val Leu Gly Phe Tyr Pro Thr Asn Ala Asn Thr Asn
            595                 600                 605

Ala Phe Arg Pro Gly Gly Val Gln Glu Leu Asn Glu Tyr Gln Leu Ser
        610                 615                 620

Gln Leu Phe Thr Asp Gln Lys Leu Gln Glu Ala Ala Arg Thr Arg Asn
625                 630                 635                 640

Pro Ile Arg Leu Met Ile Gly Phe Asp Tyr Pro Asp Gly Tyr Gly Asn
                645                 650                 655

Ser Glu Thr Leu Val Pro Val Asn Leu Thr Val Leu Pro Glu Ile Gln
                660                 665                 670

His Asn Ile Lys Phe Phe Lys Asn Asp Asp Thr Gln Asn Ile Ala Glu
            675                 680                 685

Lys Pro Phe Ser Lys Gln Ala Gly His Pro Val Phe Tyr Val Tyr Ala
        690                 695                 700

Gly Asn Gln Gly Asn Ala Ser Val Asn Leu Gly Gly Ser Val Thr Ser
705                 710                 715                 720

Ile Gln Pro Leu Arg Ile Asn Leu Thr Ser Asn Glu Asn Phe Thr Asp
                725                 730                 735

Lys Asp Trp Gln Ile Thr Gly Ile Pro Arg Thr Leu His Ile Glu Asn
                740                 745                 750

Ser Thr Asn Arg Thr Asn Asn Ala Arg Glu Arg Asn Ile Glu Leu Val
            755                 760                 765

Gly Asn Leu Leu Pro Gly Asp Tyr Phe Gly Thr Ile Arg Phe Gly Arg
        770                 775                 780

Lys Glu Gln Leu Phe Glu Ile Arg Val Lys Pro His Thr Pro Thr Ile
785                 790                 795                 800

Thr Thr Thr Ala Glu Gln Leu Arg Gly Thr Ala Leu Gln Lys Val Pro
                805                 810                 815

Val Asn Ile Ser Gly Ile Pro Leu Asp Pro Ser Ala Leu Val Tyr Leu
                820                 825                 830

Val Ala Pro Thr Asn Gln Thr Thr Asn Gly Gly Ser Glu Ala Asp Gln
            835                 840                 845

Ile Pro Ser Gly Tyr Thr Ile Leu Ala Thr Gly Thr Pro Asp Gly Val
        850                 855                 860

His Asn Thr Ile Thr Ile Arg Pro Gln Asp Tyr Val Val Phe Ile Pro
865                 870                 875                 880

Pro Val Gly Lys Gln Ile Arg Ala Val Val Tyr Tyr Asn Lys Val Val
```

```
                885                 890                 895
Ala Ser Asn Met Ser Asn Ala Val Thr Ile Leu Pro Asp Asp Ile Pro
            900                 905                 910

Pro Thr Ile Asn Asn Pro Val Gly Ile Asn Ala Lys Tyr Tyr Arg Gly
            915                 920                 925

Asp Glu Val Asn Phe Thr Met Gly Val Ser Asp Arg His Ser Gly Ile
            930                 935                 940

Lys Asn Thr Thr Ile Thr Thr Leu Pro Ser Gly Trp Thr Ser Asn Leu
945                 950                 955                 960

Thr Lys Ser Asp Asn Lys Asn Gly Ser Leu Ala Ile Thr Gly Arg Val
            965                 970                 975

Ser Met Asn Gln Ala Phe Asn Ser Asp Ile Thr Phe Lys Val Ser Ala
            980                 985                 990

Thr Asp Asn Val Asn Asn Thr Asn Asp Ser Gln Ser Lys His Val
            995                 1000                1005

Ser Ile His Val Gly Lys Ile Ser Glu Asp Ala His Pro Ile Val Leu
            1010                1015                1020

Gly Asn Thr Glu Lys Val Val Val Asn Pro Thr Ala Val Ser Asn
1025                1030                1035                1040

Asp Glu Lys Gln Ser Ile Ile Thr Ala Phe Met Asn Lys Asn Gln Asn
            1045                1050                1055

Ile Arg Gly Tyr Leu Ala Ser Thr Asp Pro Val Thr Val Asp Asn Asn
            1060                1065                1070

Gly Asn Val Thr Leu His Tyr Arg Asp Gly Ser Ser Thr Thr Leu Asp
            1075                1080                1085

Ala Thr Asn Val Met Thr Tyr Glu Pro Val Val Lys Ser Glu Tyr Gln
            1090                1095                1100

Thr Ala Asn Ala Ala Lys Thr Ala Thr Val Thr Ile Ala Lys Gly Gln
1105                1110                1115                1120

Ser Phe Asn Ile Gly Asp Ile Lys Gln Tyr Phe Thr Leu Ser Asn Gly
            1125                1130                1135

Gln Ala Ile Pro Asn Gly Thr Phe Thr Asn Ile Thr Ser Asp Arg Thr
            1140                1145                1150

Ile Pro Thr Ala Gln Glu Val Ser Gln Met Asn Ala Gly Thr Gln Leu
            1155                1160                1165

Tyr His Ile Val Ala Ser Asn Ala Tyr His Lys Asp Thr Glu Asp Phe
            1170                1175                1180

Tyr Ile Ser Leu Lys Ile Val Asp Val Lys Gln Pro Glu Gly Asp Gln
1185                1190                1195                1200

Arg Val Tyr Arg Thr Ser Thr Tyr Asp Leu Thr Thr Asp Glu Ile Ser
            1205                1210                1215

Lys Val Lys Gln Ala Phe Ile Asn Ala Asn Arg Asp Val Ile Thr Leu
            1220                1225                1230

Ala Glu Gly Asp Ile Ser Val Thr Asn Thr Pro Asn Gly Ala Asn Val
            1235                1240                1245

Ser Thr Ile Thr Val Asn Ile Asn Lys Gly Arg Leu Thr Lys Ser Phe
            1250                1255                1260

Ala Ser Asn Leu Ala Asn Met Asn Phe Leu Arg Trp Val Asn Phe Pro
1265                1270                1275                1280

Gln Asp Tyr Thr Val Thr Trp Thr Asn Ala Lys Ile Ala Asn Arg Pro
            1285                1290                1295

Thr Asp Gly Gly Leu Ser Trp Ser Asp Asp His Lys Ser Leu Ile Tyr
            1300                1305                1310
```

-continued

Arg Tyr Asp Ala Thr Leu Gly Thr Gln Ile Thr Thr Asn Asp Ile Leu
    1315                1320                1325

Thr Met Leu Lys Ala Thr Thr Thr Val Pro Gly Leu Arg Asn Asn Ile
    1330                1335                1340

Thr Gly Asn Glu Lys Ala Gln Ala Glu Ala Gly Gly Arg Pro Asn Tyr
1345                1350                1355                1360

Arg Thr Thr Gly Tyr Ser Gln Ser Asn Ala Thr Thr Asp Gly Gln Arg
        1365                1370                1375

Gln Phe Thr Leu Asn Gly Gln Val Ile Gln Ile Leu Asp Ile Ile Asn
        1380                1385                1390

Pro Ser Asn Gly Tyr Gly Gly Gln Pro Val Thr Asn Ser Asn Thr Arg
        1395                1400                1405

Ala Asn His Ser Asn Ser Thr Val Val Asn Val Asn Glu Pro Ala Ala
        1410                1415                1420

Asn Gly Ala Gly Ala Phe Thr Ile Asp His Val Val Lys Ser Asn Ser
1425                1430                1435                1440

Thr His Asn Ala Ser Asp Ala Val Tyr Lys Ala Gln Leu Tyr Leu Thr
        1445                1450                1455

Pro Tyr Gly Pro Lys Gln Tyr Val Glu His Leu Asn Gln Asn Thr Gly
        1460                1465                1470

Asn Thr Thr Asp Ala Ile Asn Ile Tyr Phe Val Pro Ser Asp Leu Val
        1475                1480                1485

Asn Pro Thr Ile Ser Val Gly Asn Tyr Thr Asn His Gln Val Phe Ser
        1490                1495                1500

Gly Glu Thr Phe Thr Asn Thr Ile Thr Ala Asn Asp Asn Phe Gly Val
1505                1510                1515                1520

Gln Ser Val Thr Val Pro Asn Thr Ser Gln Ile Thr Gly Thr Val Asp
        1525                1530                1535

Asn Asn His Gln His Val Ser Ala Thr Ala Pro Asn Val Thr Ser Ala
        1540                1545                1550

Thr Ser Lys Thr Ile Asn Leu Leu Ala Thr Asp Thr Ser Gly Asn Thr
        1555                1560                1565

Ala Thr Thr Ser Phe Asn Val Thr Val Lys Pro Leu Arg Asp Lys Tyr
        1570                1575                1580

Arg Val Gly Thr Ser Ser Thr Ala Ala Asn Pro Val Arg Ile Ala Asn
1585                1590                1595                1600

Ile Ser Asn Asn Ala Thr Val Ser Gln Ala Asp Gln Thr Thr Ile Ile
        1605                1610                1615

Asn Ser Leu Thr Phe Thr Ser Asn Ala Pro Asn Arg Asn Tyr Ala Thr
        1620                1625                1630

Ala Ser Ala Asn Glu Ile Thr Ser Lys Thr Val Ser Asn Val Ser Arg
        1635                1640                1645

Thr Gly Asn Asn Ala Asn Val Thr Val Thr Val Thr His Gln Asp Gly
        1650                1655                1660

Thr Thr Ser Thr Val Thr Val Pro Val Lys His Val Ile Pro Glu Ile
1665                1670                1675                1680

Val Ala His Ser His Tyr Thr Val Gln Gly Gln Asp Phe Pro Ala Gly
        1685                1690                1695

Asn Gly Ser Ser Ala Ala Asp Tyr Phe Lys Leu Ser Asn Gly Ser Ala
        1700                1705                1710

Ile Pro Asp Ala Thr Ile Thr Trp Val Ser Gly Gln Ala Pro Asn Lys
        1715                1720                1725

Asp Asn Thr Arg Ile Gly Glu Asp Ile Thr Val Thr Ala His Ile Leu
        1730                1735                1740

-continued

```
Ile Asp Gly Glu Thr Thr Pro Ile Thr Lys Thr Ala Thr Tyr Lys Val
1745                1750                1755                1760

Val Arg Thr Val Pro Lys His Val Phe Glu Thr Ala Arg Gly Val Leu
            1765                1770                1775

Tyr Pro Gly Val Ser Asp Met Tyr Asp Ala Lys Gln Tyr Val Lys Pro
        1780                1785                1790

Val Asn Asn Ser Trp Ser Thr Asn Ala Gln His Met Asn Phe Gln Phe
    1795                1800                1805

Val Gly Thr Tyr Gly Pro Asn Lys Asp Val Val Gly Ile Ser Thr Arg
1810                1815                1820

Leu Ile Arg Val Thr Tyr Asp Asn Arg Gln Thr Glu Asp Leu Thr Ile
1825                1830                1835                1840

Leu Ser Lys Val Lys Pro Asp Pro Arg Ile Asp Ala Asn Ser Val
            1845                1850                1855

Thr Tyr Lys Ala Gly Leu Thr Asn Gln Glu Ile Lys Val Asn Asn Val
        1860                1865                1870

Leu Asn Asn Ser Ser Val Lys Leu Phe Lys Ala Asp Asn Thr Pro Leu
    1875                1880                1885

Asn Val Thr Asn Ile Thr His Gly Ser Gly Phe Ser Ser Val Val Thr
    1890                1895                1900

Val Ser Asp Ala Leu Pro Asn Gly Gly Ile Lys Ala Lys Ser Ser Ile
1905                1910                1915                1920

Ser Met Asn Asn Val Thr Tyr Thr Thr Gln Asp Glu His Gly Gln Val
            1925                1930                1935

Val Thr Val Thr Arg Asn Glu Ser Val Asp Ser Asn Asp Ser Ala Ser
        1940                1945                1950

Val Thr Val Thr Pro Gln Leu Gln Ala Thr Thr Glu Gly Ala Val Phe
    1955                1960                1965

Ile Lys Gly Gly Asp Gly Phe Asp Phe Gly His Val Glu Arg Phe Ile
    1970                1975                1980

Gln Asn Pro Pro His Gly Ala Thr Val Ala Trp His Asp Ser Pro Asp
1985                1990                1995                2000

Thr Trp Lys Asn Thr Val Gly Asn Thr His Lys Thr Ala Val Val Thr
            2005                2010                2015

Leu Pro Ser Gly Gln Gly Thr Arg Asn Val Glu Val Pro Val Lys Val
        2020                2025                2030

Tyr Pro Val Ala Asn Ala Lys Ala Pro Ser Arg Asp Val Lys Gly Gln
        2035                2040                2045

Asn Leu Thr His Gly Thr Asn Ala Ile Asp Tyr Ile Thr Phe Asp Pro
    2050                2055                2060

Asn Thr Asn Thr Asn Gly Ile Thr Ala Ala Trp Ala Asn Arg Gln Gln
2065                2070                2075                2080

Pro Asn Asn Gln Gln Ala Gly Val Gln His Leu Asn Val Asp Val Thr
            2085                2090                2095

Tyr Pro Gly Ile Ser Ala Ala Lys Arg Val Pro Val Thr Val Asn Val
        2100                2105                2110

Tyr Gln Phe Glu Phe Pro Gln Thr Thr Tyr Thr Thr Val Gly Gly
    2115                2120                2125

Thr Leu Ala Ser Gly Thr Gln Ala Ser Gly Tyr Ala His Met Gln Asn
    2130                2135                2140

Ala Ser Gly Leu Pro Thr Asp Gly Phe Thr Tyr Lys Trp Asn Arg Asp
2145                2150                2155                2160

Thr Thr Gly Thr Asn Asp Ala Asn Trp Ala Ala Met Asn Lys Pro Asn
```

-continued

```
                    2165                2170                2175
Thr Ala Gln Val Val Asn Ala Lys Tyr Asp Val Ile Tyr Asn Gly His
                2180                2185                2190
Thr Phe Ala Thr Ser Leu Pro Ala Lys Phe Val Val Lys Asp Val Gln
            2195                2200                2205
Pro Ala Lys Pro Thr Val Thr Glu Thr Ala Ala Gly Ala Ile Thr Ile
        2210                2215                2220
Ala Pro Gly Ala Asn Gln Thr Val Asn Thr His Ala Gly Asn Val Thr
2225                2230                2235                2240
Thr Tyr Ala Asp Lys Leu Val Ile Lys Arg Asn Gly Asn Val Val Thr
                2245                2250                2255
Thr Phe Thr Arg Arg Asn Asn Thr Ser Pro Trp Val Lys Glu Ala Ser
            2260                2265                2270
Ala Asp Asn Val Thr Gly Ile Val Gly Thr Asn Asn Gly Ile Thr Val
        2275                2280                2285
Ala Ala Gly Thr Phe Asn Pro Ala Asp Thr Ile Gln Val Val Ala Thr
    2290                2295                2300
Gln Gly Ser Gly Glu Thr Ile Ser Asp Glu Gln Arg Ser Asp Asp Phe
2305                2310                2315                2320
Thr Val Val Ala Pro Gln Pro Asn Gln Ala Thr Thr Lys Ile Trp Gln
                2325                2330                2335
Asn Gly His Ile Asp Ile Thr Pro Asn Pro Ser Gly His Leu Ile
            2340                2345                2350
Asn Pro Thr Gln Ala Met Asp Ile Ala Tyr Thr Glu Lys Val Gly Asn
        2355                2360                2365
Gly Ala Glu His Ser Lys Thr Ile Asn Val Val Arg Gly Gln Asn Asn
    2370                2375                2380
Gln Trp Thr Ile Ala Asn Lys Pro Asp Tyr Val Thr Leu Asp Ala Gln
2385                2390                2395                2400
Thr Gly Lys Val Thr Phe Asn Ala Asn Thr Ile Lys Pro Asn Ser Ser
                2405                2410                2415
Ile Thr Ile Thr Pro Lys Ala Gly Thr Gly His Ser Val Ser Ser Asn
            2420                2425                2430
Pro Ser Thr Leu Thr Ala Pro Ala Ala His Thr Val Asn Thr Thr Glu
        2435                2440                2445
Ile Val Lys Asp Tyr Gly Ser Asn Val Thr Ala Ala Glu Ile Asn Asn
    2450                2455                2460
Ala Val Gln Val Ala Asn Lys Arg Thr Ala Thr Ile Lys Asn Gly Thr
2465                2470                2475                2480
Ala Met Pro Thr Asn Leu Ala Gly Gly Ser Thr Thr Ile Pro Val
                2485                2490                2495
Thr Val Thr Tyr Asn Asp Gly Ser Thr Glu Glu Val Gln Glu Ser Ile
            2500                2505                2510
Phe Thr Lys Ala Asp Lys Arg Glu Leu Ile Thr Ala Lys Asn His Leu
        2515                2520                2525
Asp Asp Pro Val Ser Thr Glu Gly Lys Lys Pro Gly Thr Ile Thr Gln
    2530                2535                2540
Tyr Asn Asn Ala Met His Asn Ala Gln Gln Gln Ile Asn Thr Ala Lys
2545                2550                2555                2560
Thr Glu Ala Gln Gln Val Ile Asn Asn Glu Arg Ala Thr Pro Gln Gln
                2565                2570                2575
Val Ser Asp Ala Leu Thr Lys Val Arg Ala Ala Gln Thr Lys Ile Asp
            2580                2585                2590
```

-continued

Gln Ala Lys Ala Leu Leu Gln Asn Lys Glu Asp Asn Ser Gln Leu Val
    2595                2600                2605

Thr Ser Lys Asn Asn Leu Gln Ser Ser Val Asn Gln Val Pro Ser Thr
    2610                2615                2620

Ala Gly Met Thr Gln Gln Ser Ile Asp Asn Tyr Asn Ala Lys Lys Arg
2625                2630                2635                2640

Glu Ala Glu Thr Glu Ile Thr Ala Ala Gln Arg Val Ile Asp Asn Gly
            2645                2650                2655

Asp Ala Thr Ala Gln Gln Ile Ser Asp Glu Lys His Arg Val Asp Asn
            2660                2665                2670

Ala Leu Thr Ala Leu Asn Gln Ala Lys His Asp Leu Thr Ala Asp Thr
        2675                2680                2685

His Ala Leu Glu Gln Ala Val Gln Gln Leu Asn Arg Thr Gly Thr Thr
    2690                2695                2700

Thr Gly Lys Lys Pro Ala Ser Ile Thr Ala Tyr Asn Asn Ser Ile Arg
2705                2710                2715                2720

Ala Leu Gln Ser Asp Leu Thr Ser Ala Lys Asn Ser Ala Asn Ala Ile
            2725                2730                2735

Ile Gln Lys Pro Ile Arg Thr Val Gln Glu Val Gln Ser Ala Leu Thr
        2740                2745                2750

Asn Val Asn Arg Val Asn Glu Arg Leu Thr Gln Ala Ile Asn Gln Leu
    2755                2760                2765

Val Pro Leu Ala Asp Asn Ser Ala Leu Arg Thr Ala Lys Thr Lys Leu
    2770                2775                2780

Asp Glu Glu Ile Asn Lys Ser Val Thr Thr Asp Gly Met Thr Gln Ser
2785                2790                2795                2800

Ser Ile Gln Ala Tyr Glu Asn Ala Lys Arg Ala Gly Gln Thr Glu Thr
            2805                2810                2815

Thr Asn Ala Gln Asn Val Ile Asn Asn Gly Asp Ala Thr Asp Gln Gln
        2820                2825                2830

Ile Ala Ala Glu Lys Thr Lys Val Glu Glu Lys Tyr Asn Ser Leu Lys
    2835                2840                2845

Gln Ala Ile Ala Gly Leu Thr Pro Asp Leu Ala Pro Leu Gln Thr Ala
    2850                2855                2860

Lys Thr Gln Leu Gln Asn Asp Ile Asp Gln Pro Thr Ser Thr Thr Gly
2865                2870                2875                2880

Met Thr Ser Ala Ser Val Ala Ala Phe Asn Asp Lys Leu Ser Ala Ala
            2885                2890                2895

Arg Thr Lys Ile Gln Glu Ile Asp Arg Val Leu Ala Ser His Pro Asp
        2900                2905                2910

Val Ala Thr Ile Arg Gln Asn Val Thr Ala Ala Asn Ala Ala Lys Thr
    2915                2920                2925

Ala Leu Asp Gln Ala Arg Asn Gly Leu Thr Val Asp Lys Ala Pro Leu
    2930                2935                2940

Glu Asn Ala Lys Asn Gln Leu Gln His Ser Ile Asp Thr Gln Thr Ser
2945                2950                2955                2960

Thr Thr Gly Met Thr Gln Asp Ser Ile Asn Ala Tyr Asn Ala Lys Leu
            2965                2970                2975

Thr Ala Ala Arg Asn Lys Val Gln Gln Ile Asn Gln Val Leu Ala Gly
        2980                2985                2990

Ser Pro Thr Val Asp Gln Ile Asn Thr Asn Thr Ser Ala Ala Asn Gln
    2995                3000                3005

Ala Lys Ser Asp Leu Asp His Ala Arg Gln Ala Leu Thr Pro Asp Lys
    3010                3015                3020

```
Ala Pro Leu Gln Asn Ala Lys Thr Gln Leu Glu Gln Ser Ile Asn Gln
3025                3030                3035                3040

Pro Thr Asp Thr Thr Gly Met Thr Thr Ala Ser Leu Asn Ala Tyr Asn
            3045                3050                3055

Gln Lys Leu Gln Ala Ala Arg Gln Lys Leu Thr Glu Ile Asn Gln Val
        3060                3065                3070

Leu Asn Gly Asn Pro Thr Val Gln Asn Ile Asn Asp Lys Val Ala Glu
        3075                3080                3085

Ala Asn Gln Ala Lys Asp Gln Leu Asn Thr Ala Arg Gln Gly Leu Thr
    3090                3095                3100

Leu Asp Arg Gln Pro Ala Leu Thr Thr Leu His Gly Ala Ser Asn Leu
3105                3110                3115                3120

Asn Gln Ala Gln Gln Asn Asn Phe Thr Gln Gln Ile Asn Ala Ala Gln
                3125                3130                3135

Asn His Ala Ala Leu Glu Thr Ile Lys Ser Asn Ile Thr Ala Leu Asn
        3140                3145                3150

Thr Ala Met Thr Lys Leu Lys Asp Ser Val Ala Asp Asn Asn Thr Ile
            3155                3160                3165

Lys Ser Gly Gln Asn Tyr Thr Asp Ala Thr Pro Ala Asn Lys Gln Ala
        3170                3175                3180

Tyr Asp Asn Ala Val Asn Ala Ala Lys Gly Val Ile Gly Glu Thr Thr
3185                3190                3195                3200

Asn Pro Thr Met Asp Val Asn Thr Val Asn Gln Lys Ala Ala Ser Val
                3205                3210                3215

Lys Ser Thr Lys Asp Ala Leu Asp Gly Gln Gln Asn Leu Gln Arg Ala
        3220                3225                3230

Lys Thr Glu Ala Thr Asn Ala Ile Thr His Ala Ser Asp Leu Asn Gln
        3235                3240                3245

Ala Gln Lys Asn Ala Leu Thr Gln Gln Val Asn Ser Ala Gln Asn Val
    3250                3255                3260

Gln Ala Val Asn Asp Ile Lys Gln Thr Thr Gln Ser Leu Asn Thr Ala
3265                3270                3275                3280

Met Thr Gly Leu Lys Arg Gly Val Ala Asn His Asn Gln Val Val Gln
            3285                3290                3295

Ser Asp Asn Tyr Val Asn Ala Thr Asn Lys Lys Asn Asp Tyr Asn
        3300                3305                3310

Asn Ala Tyr Asn His Ala Asn Asp Ile Ile Asn Gly Asn Ala Gln His
        3315                3320                3325

Pro Val Ile Thr Pro Ser Asp Val Asn Asn Ala Leu Ser Asn Val Thr
    3330                3335                3340

Ser Lys Glu His Ala Leu Asn Gly Glu Ala Lys Leu Asn Ala Ala Lys
3345                3350                3355                3360

Gln Glu Ala Asn Thr Ala Leu Gly His Leu Asn Asn Leu Asn Asn Val
            3365                3370                3375

Gln Arg Gln Asn Leu Gln Ser Gln Ile Asn Gly Ala His Gln Ile Asp
        3380                3385                3390

Ala Val Asn Thr Ile Lys Gln Asn Ala Thr Asn Leu Asn Ser Ala Met
        3395                3400                3405

Gly Asn Leu Arg Gln Ala Val Ala Asp Lys Asp Gln Val Lys Arg Thr
    3410                3415                3420

Glu Asp Tyr Ala Asp Ala Asp Thr Ala Lys Gln Asn Ala Tyr Asn Ser
3425                3430                3435                3440

Ala Val Ser Ser Ala Glu Thr Ile Ile Asn Gln Thr Ala Asn Pro Thr
```

-continued

```
                  3445           3450           3455
Met Ser Val Asp Asp Val Asn Arg Ala Thr Ser Ala Val Thr Thr Asn
                3460           3465           3470
Lys Asn Ala Leu Asn Gly Asp Glu Lys Leu Val Gln Ser Lys Thr Asp
                3475           3480           3485
Ala Ala Arg Ala Ile Asp Ala Leu Pro His Leu Asn Asn Ala Gln Lys
                3490           3495           3500
Ala Asp Val Lys Ser Lys Ile Asn Ala Ala Ser Asn Ile Ala Gly Val
3505           3510           3515           3520
Asn Thr Val Lys Gln Gln Gly Thr Asp Leu Asn Thr Ala Met Gly Asn
                3525           3530           3535
Leu Gln Gly Ala Ile Asn Asp Glu Gln Thr Thr Leu Asn Ser Gln Asn
                3540           3545           3550
Tyr Gln Asp Ala Thr Pro Ser Lys Lys Thr Ala Tyr Thr Asn Ala Val
                3555           3560           3565
Gln Ala Ala Lys Asp Ile Leu Asn Lys Ser Asn Gly Gln Asn Lys Thr
                3570           3575           3580
Lys Asp Gln Val Thr Glu Ala Met Asn Gln Val Asn Ser Ala Lys Asn
3585           3590           3595           3600
Asn Leu Asp Gly Thr Arg Leu Leu Asp Gln Ala Lys Gln Thr Ala Lys
                3605           3610           3615
Gln Gln Leu Asn Asn Met Thr His Leu Thr Thr Ala Gln Lys Thr Asn
                3620           3625           3630
Leu Thr Asn Gln Ile Asn Ser Gly Thr Thr Val Ala Gly Val His Thr
                3635           3640           3645
Val Gln Ser Asn Ala Asn Thr Leu Asp Gln Ala Met Asn Thr Leu Arg
                3650           3655           3660
Gln Ser Ile Ala Asn Asn Asp Ala Thr Lys Ala Ser Glu Asp Tyr Val
3665           3670           3675           3680
Asp Ala Asn Asn Asp Lys Gln Thr Ala Tyr Asn Asn Ala Val Ala Ala
                3685           3690           3695
Ala Glu Thr Ile Ile Asn Ala Asn Ser Asn Pro Glu Met Asn Pro Ser
                3700           3705           3710
Thr Ile Thr Gln Lys Ala Glu Gln Val Asn Ser Ser Lys Thr Ala Leu
                3715           3720           3725
Asn Gly Asp Glu Asn Leu Ala Thr Ala Lys Gln Asn Ala Lys Thr Tyr
                3730           3735           3740
Leu Asn Thr Leu Thr Ser Ile Thr Asp Ala Gln Lys Asn Asn Leu Ile
3745           3750           3755           3760
Ser Gln Ile Ser Ser Ala Thr Arg Val Ser Gly Val Asp Thr Val Lys
                3765           3770           3775
Gln Asn Ala Gln His Leu Asp Gln Ala Met Ala Asn Leu Gln Asn Gly
                3780           3785           3790
Ile Asn Asn Glu Ser Gln Val Lys Ser Ser Glu Lys Tyr Arg Asp Ala
                3795           3800           3805
Asp Thr Asn Lys Gln Gln Glu Tyr Asp Asn Ala Ile Thr Ala Ala Lys
                3810           3815           3820
Ala Ile Leu Asn Lys Ser Thr Gly Pro Asn Thr Ala Gln Asn Ala Val
3825           3830           3835           3840
Glu Ala Ala Leu Gln Arg Val Asn Thr Ala Lys Asp Ala Leu Asn Gly
                3845           3850           3855
Asp Ala Lys Leu Ile Ala Ala Gln Asn Ala Ala Lys Gln His Leu Gly
                3860           3865           3870
```

```
Thr Leu Thr His Ile Thr Thr Ala Gln Arg Asn Asp Leu Thr Asn Gln
        3875                3880                3885

Ile Ser
    3890

<210> SEQ ID NO 13
<211> LENGTH: 6713
<212> TYPE: PRT
<213> ORGANISM: Staphylococcus aureus

<400> SEQUENCE: 13

Met Gly Asn Leu Gln Thr Ala Ile Asn Asp Lys Ser Gly Thr Leu Ala
 1               5                  10                  15

Ser Gln Asn Phe Leu Asp Ala Asp Glu Gln Lys Arg Asn Ala Tyr Asn
             20                  25                  30

Gln Ala Ile Ser Ala Ala Glu Thr Ile Leu Asn Lys Gln Thr Gly Pro
         35                  40                  45

Asn Thr Ala Lys Thr Ala Val Glu Gln Ala Leu Asn Asn Val Asn Ser
     50                  55                  60

Ala Lys His Ala Leu Asn Gly Thr Gln Asn Leu Asn Asn Ala Lys Gln
 65                  70                  75                  80

Ala Ala Ile Thr Ala Ile Asn Gly Ala Ser Asp Leu Asn Gln Lys Gln
                 85                  90                  95

Lys Asp Ala Leu Lys Ala Gln Ala Asn Gly Ala Gln Arg Val Ser Asn
            100                 105                 110

Ala Asn Asp Val Gln Arg Asn Ala Thr Glu Leu Asn Thr Ala Met Gly
        115                 120                 125

Gln Leu Gln His Ala Ile Ala Asp Lys Thr Asn Thr Leu Ala Ser Ser
    130                 135                 140

Lys Tyr Val Asn Ala Asp Ser Thr Lys Gln Asn Ala Tyr Thr Thr Lys
145                 150                 155                 160

Val Thr Asn Ala Glu His Ile Ile Ser Gly Thr Pro Thr Val Val Thr
                165                 170                 175

Thr Pro Ser Glu Val Thr Ala Ala Asn Gln Val Asn Ser Ala Lys
            180                 185                 190

Gln Glu Leu Asn Gly Asp Glu Arg Leu Arg Val Ala Lys Gln Asn Ala
        195                 200                 205

Asn Thr Ala Ile Asp Ala Leu Thr Gln Leu Asn Thr Pro Gln Lys Ala
    210                 215                 220

Lys Leu Lys Glu Gln Val Gly Gln Ala Asn Arg Leu Glu Asp Val Gln
225                 230                 235                 240

Ser Val Gln Thr Asn Gly Gln Ser Leu Asn Asn Ala Met Lys Gly Leu
                245                 250                 255

Arg Asp Ser Ile Ala Asn Glu Thr Thr Val Lys Ala Ser Gln Asn Tyr
            260                 265                 270

Thr Asp Ala Ser Pro Asn Gln Ser Thr Tyr Asn Ser Ala Val Ser
        275                 280                 285

Asn Ala Lys Gly Ile Ile Asn Gln Thr Asn Asn Pro Thr Met Asp Thr
    290                 295                 300

Ser Ala Ile Thr Gln Ala Thr Thr Gln Val Asn Ala Lys Asn Gly
305                 310                 315                 320

Leu Asn Gly Ala Glu Asn Leu Arg Asn Ala Gln Asn Thr Ala Lys Gln
                325                 330                 335

Asn Leu Asn Thr Leu Ser His Leu Thr Asn Asn Gln Lys Ser Ala Ile
            340                 345                 350
```

```
Ser Ser Gln Ile Asp Arg Ala Gly His Val Ser Glu Val Thr Ala Ala
        355                 360                 365

Lys Asn Ala Ala Thr Glu Leu Asn Ala Gln Met Gly Asn Leu Glu Gln
370                 375                 380

Ala Ile His Asp Gln Asn Thr Val Lys Gln Gly Val Asn Phe Thr Asp
385                 390                 395                 400

Ala Asp Lys Ala Lys Arg Asp Ala Tyr Thr Asn Ala Val Ser Arg Ala
                405                 410                 415

Glu Thr Ile Leu Asn Lys Thr Gln Gly Ala Asn Thr Ser Lys Gln Asp
                420                 425                 430

Val Glu Ala Ala Ile Gln Asn Val Thr Ser Ala Lys Asn Ala Leu Asn
                435                 440                 445

Gly Asp Gln Asn Val Thr Asn Ala Lys Asn Ala Ala Lys Asn Ala Leu
450                 455                 460

Asn Asn Leu Thr Ser Ile Asn Asn Ala Gln Lys Arg Asp Leu Thr Thr
465                 470                 475                 480

Lys Ile Asp Gln Ala Thr Thr Val Ala Gly Val Glu Ala Val Ser Asn
                485                 490                 495

Thr Gly Thr Gln Leu Asn Thr Ala Met Ala Asn Leu Gln Asn Gly Ile
                500                 505                 510

Asn Asp Lys Ala Asn Thr Leu Ala Ser Glu Asn Tyr His Asp Ala Asp
                515                 520                 525

Ser Asp Lys Lys Thr Ala Tyr Thr Gln Ala Val Thr Asn Ala Glu Asn
                535                 540

Ile Leu Asn Lys Asn Ser Gly Ser Asn Leu Asp Lys Ala Ala Val Glu
545                 550                 555                 560

Asn Ala Leu Ser Gln Val Thr Asn Ala Lys Gly Ala Leu Asn Gly Asn
                565                 570                 575

His Asn Leu Glu Gln Ala Lys Ser Asn Ala Asn Thr Thr Ile Asn Gly
                580                 585                 590

Leu Gln His Leu Thr Thr Ala Gln Lys Asp Lys Leu Lys Gln Gln Val
                595                 600                 605

Gln Gln Ala Gln Asn Val Ala Gly Val Asp Thr Val Lys Ser Ser Ala
610                 615                 620

Asn Thr Leu Asn Gly Ala Met Gly Thr Leu Arg Asn Ser Ile Gln Asp
625                 630                 635                 640

Asn Thr Ala Thr Lys Asn Gly Gln Asn Tyr Leu Asp Ala Thr Glu Arg
                645                 650                 655

Asn Lys Thr Asn Tyr Asn Asn Ala Val Asp Ser Ala Asn Gly Val Ile
                660                 665                 670

Asn Ala Thr Ser Asn Pro Asn Met Asp Ala Asn Ala Ile Asn Gln Ile
                675                 680                 685

Ala Thr Gln Val Thr Ser Thr Lys Asn Ala Leu Asp Gly Thr His Asn
                690                 695                 700

Leu Thr Gln Ala Lys Gln Thr Ala Thr Asn Ala Ile Asp Gly Ala Thr
705                 710                 715                 720

Asn Leu Asn Lys Ala Gln Lys Asp Ala Leu Lys Ala Gln Val Thr Ser
                725                 730                 735

Ala Gln Arg Val Ala Asn Val Thr Ser Ile Gln Gln Thr Ala Asn Glu
                740                 745                 750

Leu Asn Thr Ala Met Gly Gln Leu Gln His Gly Ile Asp Asp Glu Asn
                755                 760                 765

Ala Thr Lys Gln Thr Gln Lys Tyr Arg Asp Ala Glu Gln Ser Lys Lys
770                 775                 780
```

```
Thr Ala Tyr Asp Gln Ala Val Ala Ala Lys Ala Ile Leu Asn Lys
785                 790                 795                 800

Gln Thr Gly Ser Asn Ser Asp Lys Ala Ala Val Asp Arg Ala Leu Gln
            805                 810                 815

Gln Val Thr Ser Thr Lys Asp Ala Leu Asn Gly Asp Ala Lys Leu Ala
            820                 825                 830

Glu Ala Lys Ala Ala Ala Arg Gln Asn Leu Gly Thr Leu Asn His Ile
            835                 840                 845

Thr Asn Ala Gln Arg Thr Ala Leu Glu Gly Gln Ile Asn Gln Ala Thr
    850                 855                 860

Thr Val Asp Gly Val Asn Thr Val Lys Thr Asn Ala Asn Thr Leu Asp
865                 870                 875                 880

Gly Ala Met Asn Ser Leu Gln Gly Ala Ile Asn Asp Lys Asp Ala Thr
                885                 890                 895

Leu Arg Asn Gln Asn Tyr Leu Asp Ala Asp Glu Ser Lys Arg Asn Ala
                900                 905                 910

Tyr Thr Gln Ala Val Thr Ala Ala Glu Gly Ile Leu Asn Lys Gln Thr
            915                 920                 925

Gly Gly Asn Thr Ser Lys Ala Asp Val Asp Asn Ala Leu Asn Ala Val
930                 935                 940

Thr Arg Ala Lys Ala Ala Leu Asn Gly Ala Glu Asn Leu Arg Asn Ala
945                 950                 955                 960

Lys Thr Ser Ala Thr Asn Thr Ile Asn Gly Leu Pro Asn Leu Thr Gln
                965                 970                 975

Leu Gln Lys Asp Asn Leu Lys His Gln Val Glu Gln Ala Gln Asn Val
                980                 985                 990

Val Gly Val Asn Gly Val Lys Asp Lys Gly Asn Thr Leu Asn Thr Ala
            995                 1000                1005

Met Gly Ala Leu Arg Thr Ser Ile Gln Asn Asp Asn Thr Thr Lys Thr
    1010                1015                1020

Ser Gln Asn Tyr Leu Asp Ala Ser Asp Ser Asn Lys Asn Asn Tyr Asn
1025                1030                1035                1040

Thr Ala Val Asn Asn Ala Asn Gly Val Ile Asn Ala Thr Asn Asn Pro
                1045                1050                1055

Asn Met Asp Ala Asn Ala Ile Asn Asp Met Ala Asn Gln Val Asn Thr
                1060                1065                1070

Thr Lys Ala Ala Leu Asn Gly Ala Gln Asn Leu Ala Gln Ala Lys Thr
    1075                1080                1085

Asn Ala Thr Asn Thr Ile Asn Asn Ala Gln Asp Leu Asn Gln Lys Gln
    1090                1095                1100

Lys Asp Ala Leu Lys Thr Gln Val Asn Asn Ala Gln Arg Val Ser Asp
1105                1110                1115                1120

Ala Asn Asn Val Gln His Thr Ala Thr Glu Leu Asn Gly Ala Met Thr
                1125                1130                1135

Ala Leu Lys Ala Ala Ile Ala Asp Lys Glu Arg Thr Lys Ala Ser Gly
            1140                1145                1150

Asn Tyr Val Asn Ala Asp Gln Glu Lys Arg Gln Ala Tyr Asp Ser Lys
            1155                1160                1165

Val Thr Asn Ala Glu Asn Ile Ile Asn Gly Thr Pro Asn Ala Thr Leu
            1170                1175                1180

Thr Val Asn Asp Val Asn Ser Ala Ala Ser Gln Val Asn Ala Ala Lys
1185                1190                1195                1200

Thr Ala Leu Asn Gly Asp Asn Asn Leu Arg Val Ala Lys Glu His Ala
```

-continued

```
                1205                1210                1215
Asn Asn Thr Ile Asp Gly Leu Ala Gln Leu Asn Asn Val Gln Lys Ala
                1220                1225                1230
Lys Leu Lys Glu Gln Val Gln Ser Ala Thr Thr Leu Asp Gly Val Gln
                1235                1240                1245
Thr Val Lys Asn Ser Ser Gln Thr Leu Asn Thr Ala Met Lys Gly Leu
                1250                1255                1260
Arg Asp Ser Ile Ala Asn Glu Ala Thr Ile Lys Ala Gly Gln Asn Tyr
1265                1270                1275                1280
Thr Asp Ala Ser Pro Asn Asn Arg Asn Glu Tyr Asp Ser Ala Val Thr
                1285                1290                1295
Ala Ala Lys Ala Ile Ile Asn Gln Thr Ser Asn Pro Thr Met Glu Pro
                1300                1305                1310
Asn Thr Ile Thr Gln Ala Thr Ser Gln Val Thr Thr Lys Glu His Ala
                1315                1320                1325
Leu Asn Gly Ala Gln Asn Leu Ala Gln Ala Lys Thr Thr Ala Lys Asn
                1330                1335                1340
Asn Leu Asn Asn Leu Thr Ser Ile Asn Asn Ala Gln Lys Asp Ala Leu
1345                1350                1355                1360
Thr Arg Asn Ile Asp Gly Ala Thr Thr Val Ala Gly Val Asn Gln Glu
                1365                1370                1375
Thr Ala Lys Ala Thr Glu Leu Asn Asn Ala Met His Ser Leu Gln Asn
                1380                1385                1390
Gly Ile Asn Asp Glu Thr Gln Thr Lys Gln Thr Gln Lys Tyr Leu Asp
                1395                1400                1405
Ala Glu Pro Ser Lys Lys Ser Ala Tyr Asp Gln Ala Val Asn Ala Ala
                1410                1415                1420
Lys Ala Ile Leu Thr Lys Ala Ser Gly Gln Asn Val Asp Lys Ala Ala
1425                1430                1435                1440
Val Glu Gln Ala Leu Gln Asn Val Asn Ser Thr Lys Thr Ala Leu Asn
                1445                1450                1455
Gly Asp Ala Lys Leu Asn Glu Ala Lys Ala Ala Ala Lys Gln Thr Leu
                1460                1465                1470
Gly Thr Leu Thr His Ile Asn Asn Ala Gln Arg Asn Ala Leu Asp Asn
                1475                1480                1485
Glu Ile Thr Gln Ala Thr Asn Val Glu Gly Val Asn Thr Val Lys Ala
                1490                1495                1500
Lys Ala Gln Gln Leu Asp Gly Ala Met Gly Gln Leu Glu Thr Ser Ile
1505                1510                1515                1520
Arg Asp Lys Asp Thr Thr Leu Gln Ser Gln Asn Tyr Gln Asp Ala Asp
                1525                1530                1535
Asp Ala Lys Arg Thr Ala Tyr Ser Gln Ala Val Asn Ala Ala Ala Thr
                1540                1545                1550
Ile Leu Asn Lys Thr Ala Gly Gly Asn Thr Pro Lys Ala Asp Val Glu
                1555                1560                1565
Arg Ala Met Gln Ala Val Thr Gln Ala Asn Thr Ala Leu Asn Gly Ile
                1570                1575                1580
Gln Asn Leu Glu Arg Ala Lys Gln Ala Ala Asn Thr Ala Ile Thr Asn
1585                1590                1595                1600
Ala Ser Asp Leu Asn Thr Lys Gln Lys Glu Ala Leu Lys Ala Gln Val
                1605                1610                1615
Thr Ser Ala Gly Arg Val Ser Ala Ala Asn Gly Val Glu His Thr Ala
                1620                1625                1630
```

```
Thr Glu Leu Asn Thr Ala Met Thr Ala Leu Lys Arg Ala Ile Ala Asp
        1635                1640                1645

Lys Ala Asp Thr Lys Ala Ser Gly Asn Tyr Val Asn Ala Asp Ala Asn
    1650                1655                1660

Lys Arg Gln Ala Tyr Asp Glu Lys Val Thr Ala Ala Glu His Ile Val
1665                1670                1675                1680

Ser Gly Thr Pro Thr Pro Thr Leu Thr Pro Ser Asp Val Thr Asn Ala
            1685                1690                1695

Ala Thr Gln Val Thr Asn Ala Lys Thr Gln Leu Asn Gly Asn His Asn
                1700                1705                1710

Leu Glu Val Ala Lys Gln Asn Ala Asn Thr Ala Ile Asp Gly Leu Thr
        1715                1720                1725

Ser Leu Asn Gly Pro Gln Lys Ala Lys Leu Lys Glu Gln Val Gly Gln
    1730                1735                1740

Ala Thr Thr Leu Pro Asn Val Gln Thr Val Arg Asp Asn Ala Gln Thr
1745                1750                1755                1760

Leu Asn Thr Ala Met Lys Gly Leu Arg Asp Ser Ile Ala Asn Glu Ala
            1765                1770                1775

Thr Ile Lys Ala Gly Gln Asn Tyr Thr Asp Ala Ser Gln Asn Lys Gln
        1780                1785                1790

Asn Asp Tyr Asn Asn Ala Val Thr Ala Ala Lys Ala Ile Ile Gly Gln
    1795                1800                1805

Thr Thr Ser Pro Ser Met Ile Ala Gln Glu Ile Asn Gln Ala Lys Asp
1810                1815                1820

Gln Val Thr Ala Lys Gln Gln Ala Leu Asn Gly Gln Glu Asn Leu Arg
1825                1830                1835                1840

Thr Ala Gln Thr Asn Ala Lys Gln His Leu Asn Gly Leu Ser Asp Leu
            1845                1850                1855

Thr Asn Ala Gln Lys Asp Ala Ala Lys Arg Gln Ile Glu Gly Ala Thr
        1860                1865                1870

His Val Asn Glu Val Thr Gln Ala Gln Asn Asn Ala Asp Ala Leu Asn
    1875                1880                1885

Thr Ala Met Thr Asn Leu Lys Asn Gly Ile Gln Asp Gln Asn Thr Ile
1890                1895                1900

Lys Gln Gly Val Asn Phe Thr Asp Ala Asp Glu Ala Lys Arg Asn Ala
1905                1910                1915                1920

Tyr Thr Asn Ala Val Thr Gln Ala Glu Gln Ile Leu Asn Lys Ala Gln
            1925                1930                1935

Gly Pro Asn Thr Ala Lys Asp Gly Val Glu Thr Ala Leu Gln Asn Val
        1940                1945                1950

Gln Arg Ala Lys Asn Glu Leu Asn Gly Asn Gln Asn Val Ala Asn Ala
    1955                1960                1965

Lys Thr Thr Ala Lys Asn Ala Leu Asn Asn Leu Thr Ser Ile Asn Asn
1970                1975                1980

Ala Gln Lys Ala Ala Leu Lys Ser Gln Ile Glu Gly Ala Thr Thr Val
1985                1990                1995                2000

Ala Gly Val Asn Gln Val Ser Thr Met Ala Ser Glu Leu Asn Thr Ala
            2005                2010                2015

Met Ser Asn Leu Gln Arg Gly Ile Asn Asp Glu Ala Ala Thr Lys Ala
        2020                2025                2030

Ala Gln Lys Tyr Thr Glu Ala Asp Arg Asp Lys Gln Thr Ala Tyr Asn
    2035                2040                2045

Asp Ala Val Thr Ala Ala Lys Thr Leu Leu Asp Lys Thr Ala Gly Ser
2050                2055                2060
```

-continued

Asn Asp Asn Lys Val Ala Val Glu Gln Ala Leu Gln Arg Val Asn Thr
2065                2070                2075                2080

Ala Lys Thr Ala Leu Asn Gly Asp Ala Arg Leu Asn Glu Ala Lys Asn
            2085                2090                2095

Thr Ala Lys Gln Gln Leu Ala Thr Met Ser His Leu Thr Asn Ala Gln
        2100                2105                2110

Lys Ala Asn Leu Thr Glu Gln Ile Glu Arg Gly Thr Thr Val Ala Gly
    2115                2120                2125

Val Gln Gly Ile Gln Ala Asn Ala Gly Thr Leu Asn Gln Ala Met Asn
2130                2135                2140

Gln Leu Arg Gln Ser Ile Ala Ser Lys Asp Ala Thr Lys Ser Ser Glu
2145                2150                2155                2160

Asp Tyr Gln Asp Ala Asn Ala Asp Leu Gln Asn Ala Tyr Asn Asp Ala
            2165                2170                2175

Val Thr Asn Ala Glu Gly Ile Ile Ser Ala Thr Asn Asn Pro Glu Met
        2180                2185                2190

Asn Pro Asp Thr Ile Asn Gln Lys Ala Ser Gln Val Asn Ser Ala Lys
    2195                2200                2205

Ser Ala Leu Asn Gly Asp Glu Lys Leu Ala Ala Val Lys Gln Thr Ala
2210                2215                2220

Lys Ser Asp Ile Gly Arg Leu Thr Asp Leu Asn Asn Ala Gln Arg Thr
2225                2230                2235                2240

Ala Ala Asn Ala Glu Val Asp Gln Ala Pro Asn Leu Ala Ala Val Thr
            2245                2250                2255

Ala Ala Lys Asn Lys Ala Thr Ser Leu Asn Thr Ala Met Gly Asn Leu
        2260                2265                2270

Lys His Ala Leu Ala Glu Lys Asp Asn Thr Lys Arg Ser Val Asn Tyr
    2275                2280                2285

Thr Asp Ala Asp Gln Pro Lys Gln Gln Ala Tyr Asp Thr Ala Val Thr
2290                2295                2300

Gln Ala Glu Ala Ile Thr Asn Ala Asn Gly Ser Asn Ala Asn Glu Thr
2305                2310                2315                2320

Gln Val Gln Ala Ala Leu Asn Gln Leu Asn Gln Ala Lys Asn Asp Leu
            2325                2330                2335

Asn Gly Asp Asn Lys Val Ala Gln Ala Lys Glu Thr Ala Lys Arg Ala
        2340                2345                2350

Leu Ala Ser Tyr Ser Asn Leu Asn Asn Ala Gln Ser Thr Ala Ala Thr
    2355                2360                2365

Ser Gln Ile Asp Asn Ala Thr Thr Val Ala Asp Val Thr Ala Ala Gln
2370                2375                2380

Asn Thr Ala Asn Glu Leu Asn Thr Ala Met Gly Gln Leu Gln Asn Gly
2385                2390                2395                2400

Ile Asn Asp Gln Asn Thr Val Lys Gln Gln Val Asn Phe Thr Asp Ala
            2405                2410                2415

Asp Gln Gly Lys Lys Asp Ala Tyr Thr Asn Ala Val Thr Asn Ala Gln
        2420                2425                2430

Gly Ile Leu Asp Lys Ala Asn Gly Gln Asn Met Thr Lys Ala Gln Val
    2435                2440                2445

Glu Ala Ala Leu Asn Gln Val Thr Thr Ala Lys Asn Ala Leu Asn Gly
2450                2455                2460

Asp Ala Asn Val Arg Gln Ala Lys Ser Asp Ala Lys Ala Asn Leu Gly
2465                2470                2475                2480

Thr Leu Thr His Leu Asn Asn Ala Gln Lys Gln Asp Leu Thr Ser Gln

```
                        2485                2490                2495
Ile Glu Gly Ala Thr Thr Val Asn Gly Val Asn Ser Val Lys Thr Lys
                2500                2505                2510

Ala Gln Asp Leu Asp Gly Ala Met Gln Arg Leu Glu Ser Ala Ile Ala
        2515                2520                2525

Asn Lys Asp Gln Thr Lys Ala Ser Glu Asn Tyr Ile Asp Ala Asp Pro
2530                2535                2540

Thr Lys Lys Thr Ala Phe Asp Asn Ala Ile Thr Gln Ala Glu Ser Tyr
2545                2550                2555                2560

Leu Asn Lys Asp His Gly Thr Asn Lys Asp Lys Gln Ala Val Glu Gln
                2565                2570                2575

Ala Ile Gln Ser Val Thr Ser Thr Glu Asn Ala Leu Asn Gly Asp Ala
        2580                2585                2590

Asn Leu Gln Cys Ala Lys Thr Glu Ala Thr Gln Ala Ile Asp Asn Leu
                2595                2600                2605

Thr Gln Leu Asn Thr Pro Gln Lys Thr Ala Leu Lys Gln Gln Val Asn
        2610                2615                2620

Ala Ala Gln Arg Val Ser Gly Val Thr Asp Leu Lys Asn Ser Ala Thr
2625                2630                2635                2640

Ser Leu Asn Asn Ala Met Asp Gln Leu Lys Gln Ala Ile Gly Asp His
                2645                2650                2655

Asp Thr Ile Val Ala Gly Gly Asn Tyr Thr Asn Ala Ser Pro Asp Lys
        2660                2665                2670

Gln Gly Ala Tyr Thr Asp Ala Tyr Asn Ala Ala Lys Asn Ile Val Asn
                2675                2680                2685

Gly Ser Pro Asn Val Ile Thr Asn Ala Ala Asp Val Thr Ala Ala Thr
        2690                2695                2700

Gln Arg Val Asn Asn Ala Glu Thr Ser Leu Asn Gly Asp Thr Asn Leu
2705                2710                2715                2720

Ala Thr Ala Lys Gln Gln Ala Lys Asp Ala Leu Arg Gln Met Thr His
                2725                2730                2735

Leu Ser Asp Ala Gln Lys Gln Ser Ile Thr Gly Gln Ile Asp Ser Ala
        2740                2745                2750

Thr Gln Val Thr Gly Val Gln Ser Val Lys Asp Asn Ala Thr Asn Leu
        2755                2760                2765

Asp Asn Ala Met Asn Gln Leu Arg Asn Ser Ile Ala Asn Lys Asp Glu
2770                2775                2780

Val Lys Ala Ser Gln Pro Tyr Val Asp Ala Asp Thr Asp Lys Gln Asn
2785                2790                2795                2800

Ala Tyr Asn Thr Ala Val Thr Ser Ala Glu Asn Ile Ile Asn Ala Thr
                2805                2810                2815

Ser Gln Pro Thr Leu Asp Pro Ser Ala Val Thr Gln Ala Ala Asn Gln
        2820                2825                2830

Val Asn Thr Asn Lys Thr Ala Leu Asn Gly Ala Gln Asn Leu Ala Asn
                2835                2840                2845

Lys Lys Gln Glu Thr Thr Ala Asn Ile Asn Arg Leu Ser His Leu Asn
2850                2855                2860

Asn Ala Gln Lys Gln Asp Leu Asn Thr Gln Val Thr Asn Ala Pro Asn
2865                2870                2875                2880

Ile Ser Thr Val Asn Gln Val Lys Thr Lys Ala Glu Gln Leu Asp Gln
                2885                2890                2895

Ala Met Glu Arg Leu Ile Asn Gly Ile Gln Asp Lys Asp Gln Val Lys
                2900                2905                2910
```

```
Gln Ser Val Asn Phe Thr Asp Ala Asp Pro Glu Lys Gln Thr Ala Tyr
    2915                2920                2925

Asn Asn Ala Val Thr Ala Ala Glu Asn Ile Ile Asn Gln Ala Asn Gly
    2930                2935                2940

Thr Asn Ala Asn Gln Ser Gln Val Glu Ala Ala Leu Ser Thr Val Thr
2945                2950                2955                2960

Thr Thr Lys Gln Ala Leu Asn Gly Asp Arg Lys Val Thr Asp Ala Lys
        2965                2970                2975

Asn Asn Ala Asn Gln Thr Leu Ser Thr Leu Asp Asn Leu Asn Asn Ala
            2980                2985                2990

Gln Lys Gly Ala Val Thr Gly Asn Ile Asn Gln Ala His Thr Val Ala
        2995                3000                3005

Glu Val Thr Gln Ala Ile Gln Thr Ala Gln Glu Leu Asn Thr Ala Met
    3010                3015                3020

Gly Asn Leu Lys Asn Ser Leu Asn Asp Lys Asp Thr Thr Leu Gly Ser
3025                3030                3035                3040

Gln Asn Phe Ala Asp Ala Asp Pro Glu Lys Lys Asn Ala Tyr Asn Glu
        3045                3050                3055

Ala Val Arg Asn Ala Glu Asn Ile Leu Asn Lys Ser Thr Gly Thr Asn
        3060                3065                3070

Val Pro Lys Asp Gln Val Glu Ala Ala Met Asn Gln Val Asn Thr Thr
    3075                3080                3085

Lys Ala Ala Leu Asn Gly Thr Gln Asn Leu Glu Lys Ala Lys Gln His
    3090                3095                3100

Ala Asn Thr Ala Ile Asp Gly Leu Ser His Leu Thr Asn Ala Gln Lys
3105                3110                3115                3120

Glu Ala Leu Lys Gln Leu Val Gln Gln Ser Thr Thr Val Ala Glu Ala
        3125                3130                3135

Gln Gly Asn Glu Gln Lys Ala Asn Asn Val Asp Ala Ala Met Asp Lys
        3140                3145                3150

Leu Arg Gln Ser Ile Ala Asp Asn Ala Thr Thr Lys Gln Asn Gln Asn
        3155                3160                3165

Tyr Thr Asp Ala Ser Pro Asn Lys Lys Asp Ala Tyr Asn Asn Ala Val
    3170                3175                3180

Thr Thr Ala Gln Gly Ile Ile Asp Gln Thr Thr Asn Pro Ser Leu Asp
3185                3190                3195                3200

Pro Thr Val Ile Asn Gln Ala Ala Gly Gln Val Ser Thr Ser Lys Asn
        3205                3210                3215

Ala Leu Asn Gly Asn Glu Asn Leu Glu Ala Ala Lys Gln Gln Ala Thr
        3220                3225                3230

Gln Ser Leu Gly Ser Leu Asp Asn Leu Asn Asn Ala Gln Lys Gln Ala
    3235                3240                3245

Val Thr Asn Gln Ile Asn Gly Ala His Thr Val Asp Glu Ala Asn Gln
    3250                3255                3260

Ile Lys Gln Asn Ala Gln Asn Leu Asn Thr Ala Met Gly Asn Leu Lys
3265                3270                3275                3280

Gln Ala Ile Ala Asp Lys Asp Ala Thr Lys Ala Thr Val Asn Phe Thr
        3285                3290                3295

Asp Ala Asp Gln Ala Lys Gln Gln Ala Tyr Asn Thr Ala Val Thr Asn
        3300                3305                3310

Ala Glu Asn Ile Ile Ser Lys Ala Asn Gly Gly Asn Ala Thr Gln Thr
        3315                3320                3325

Glu Val Glu Gln Ala Ile Gln Gln Val Asn Ala Ala Lys Gln Ala Leu
    3330                3335                3340
```

```
Asn Gly Asn Ala Asn Val Gln His Ala Lys Asp Glu Ala Thr Ala Leu
            3345                3350                3355                3360

Ile Asn Asn Ser Asn Asp Leu Asn Gln Ala Gln Lys Asp Ala Leu Lys
            3365                3370                3375

Gln Gln Val Gln Asn Ala Thr Thr Val Ala Gly Val Asn Asn Val Lys
            3380                3385                3390

Gln Thr Ala Gln Glu Leu Asn Asn Ala Met Thr Gln Leu Lys Gln Gly
        3395                3400                3405

Ile Ala Asp Lys Glu Gln Thr Lys Ala Asp Gly Asn Phe Val Asn Ala
        3410                3415                3420

Asp Ser Asp Lys Gln Asn Ala Tyr Asn Gln Ala Val Ala Lys Ala Glu
            3425                3430                3435                3440

Ala Leu Ile Ser Gly Thr Pro Asp Val Val Thr Pro Ser Glu Ile
        3445                3450                3455

Thr Ala Ala Leu Asn Lys Val Thr Gln Ala Lys Asn Asp Leu Asn Gly
        3460                3465                3470

Asn Thr Asn Leu Ala Thr Ala Lys Gln Asn Val Gln His Ala Ile Asp
        3475                3480                3485

Gln Leu Pro Asn Leu Asn Gln Ala Gln Arg Asp Glu Tyr Ser Lys Gln
        3490                3495                3500

Ile Thr Gln Ala Thr Leu Val Pro Asn Val Asn Ala Ile Gln Gln Ala
3505                3510                3515                3520

Ala Thr Thr Leu Asn Asp Ala Met Thr Gln Leu Lys Gln Gly Ile Ala
        3525                3530                3535

Asn Lys Ala Gln Ile Lys Gly Ser Glu Asn Tyr His Asp Ala Asp Thr
        3540                3545                3550

Asp Lys Gln Thr Ala Tyr Asp Asn Ala Val Thr Lys Ala Glu Glu Leu
        3555                3560                3565

Leu Lys Gln Thr Thr Asn Pro Thr Met Asp Pro Asn Thr Ile Gln Gln
        3570                3575                3580

Ala Leu Thr Lys Val Asn Asp Thr Asn Gln Ala Leu Asn Gly Asn Gln
3585                3590                3595                3600

Lys Leu Ala Asp Ala Lys Gln Asp Ala Lys Thr Thr Leu Gly Thr Leu
        3605                3610                3615

Asp His Leu Asn Asp Ala Gln Lys Gln Ala Leu Thr Thr Gln Val Glu
        3620                3625                3630

Gln Ala Pro Asp Ile Ala Thr Val Asn Asn Val Lys Gln Asn Ala Gln
        3635                3640                3645

Asn Leu Asn Asn Ala Met Thr Asn Leu Asn Asn Ala Leu Gln Asp Lys
3650                3655                3660

Thr Glu Thr Leu Asn Ser Ile Asn Phe Thr Asp Ala Gln Ala Lys
3665                3670                3675                3680

Lys Asp Asp Tyr Thr Asn Ala Val Ser His Ala Glu Gly Ile Leu Ser
        3685                3690                3695

Lys Ala Asn Gly Ser Asn Ala Ser Gln Thr Glu Val Glu Gln Ala Met
        3700                3705                3710

Gln Arg Val Asn Glu Ala Lys Gln Ala Leu Asn Gly Asn Asp Asn Val
        3715                3720                3725

Gln Arg Ala Lys Asp Ala Ala Lys Gln Val Ile Thr Asn Ala Asn Asp
        3730                3735                3740

Leu Asn Gln Ala Gln Lys Asp Ala Leu Lys Gln Gln Val Asp Ala Ala
3745                3750                3755                3760

Gln Thr Val Ala Asn Val Asn Thr Ile Lys Gln Thr Ala Gln Asp Leu
```

-continued

```
                3765                3770                3775
Asn Gln Ala Met Thr Gln Leu Lys Gln Gly Ile Ala Asp Lys Asp Gln
            3780                3785                3790
Thr Lys Ala Asn Gly Asn Phe Val Asn Ala Asp Thr Asp Lys Gln Asn
            3795                3800                3805
Ala Tyr Asn Asn Ala Val Ala His Ala Glu Gln Ile Ile Ser Gly Thr
            3810                3815                3820
Pro Asn Ala Asn Val Asp Pro Gln Gln Val Ala Gln Ala Leu Gln Gln
3825                3830                3835                3840
Val Asn Gln Ala Lys Gly Asp Leu Asn Gly Asn His Asn Leu Gln Val
            3845                3850                3855
Ala Lys Asp Asn Ala Asn Thr Ala Ile Asp Gln Leu Pro Asn Leu Asn
            3860                3865                3870
Gln Pro Gln Lys Thr Ala Leu Lys Asp Gln Val Ser His Ala Glu Leu
            3875                3880                3885
Val Thr Gly Val Asn Ala Ile Lys Gln Asn Ala Asp Ala Leu Asn Asn
            3890                3895                3900
Ala Met Gly Thr Leu Lys Gln Gln Ile Gln Ala Asn Ser Gln Val Pro
3905                3910                3915                3920
Gln Ser Val Asp Phe Thr Gln Ala Asp Gln Asp Lys Gln Gln Ala Tyr
            3925                3930                3935
Asn Asn Ala Ala Asn Gln Ala Gln Gln Ile Ala Asn Gly Thr Pro Thr
            3940                3945                3950
Pro Val Leu Ala Pro Asp Thr Val Thr Lys Ala Val Thr Thr Met Asn
            3955                3960                3965
Gln Ala Lys Asp Ala Leu Asn Gly Asp Glu Lys Leu Ala Gln Ala Lys
            3970                3975                3980
Gln Asp Ala Leu Ala Asn Leu Asp Thr Leu Arg Asp Leu Asn Gln Pro
3985                3990                3995                4000
Gln Arg Asp Ala Leu Arg Asn Gln Ile Asn Gln Ala Gln Ala Leu Ala
                    4005                4010                4015
Thr Val Glu Gln Thr Lys Gln Asn Ala Gln Asn Val Asn Thr Ala Met
            4020                4025                4030
Gly Asn Leu Lys Gln Gly Ile Ala Asn Lys Asp Thr Val Lys Ala Ser
            4035                4040                4045
Glu Asn Tyr His Asp Ala Asp Val Asp Lys Gln Thr Ala Tyr Thr Asn
            4050                4055                4060
Ala Val Ser Gln Ala Glu Gly Ile Ile Asn Gln Thr Thr Asn Pro Thr
4065                4070                4075                4080
Leu Asn Pro Asp Asp Ile Thr Arg Ala Leu Thr Gln Val Thr Asp Ala
            4085                4090                4095
Lys Asn Ser Leu Asn Gly Glu Ala Lys Leu Ala Thr Glu Lys Gln Asn
            4100                4105                4110
Ala Lys Asp Ala Val Ser Gly Met Thr His Leu Asn Asp Ala Gln Lys
            4115                4120                4125
Gln Ala Leu Lys Gly Gln Ile Asp Gln Ser Pro Glu Ile Ala Thr Val
            4130                4135                4140
Asn Gln Val Lys Gln Thr Ala Thr Ser Leu Asp Gln Ala Met Asp Gln
4145                4150                4155                4160
Leu Ser Gln Ala Ile Asn Asp Lys Asp Gln Ile Leu Ala Asp Gly Asn
                    4165                4170                4175
Tyr Leu Asn Ala Asp Pro Asp Lys Gln Asn Ala Tyr Lys Gln Ala Val
            4180                4185                4190
```

-continued

```
Ala Lys Ala Glu Ala Leu Leu Asn Lys Gln Ser Gly Thr Asn Glu Val
    4195            4200            4205

Gln Ala Gln Val Glu Ser Ile Thr Asn Glu Val Asn Ala Ala Lys Gln
    4210            4215            4220

Ala Leu Asn Gly Asn Asp Asn Leu Ala Asn Ala Lys Gln Gln Ala Lys
4225            4230            4235            4240

Gln Gln Leu Ala Asn Leu Thr His Leu Asn Asp Ala Gln Lys Gln Ser
            4245            4250            4255

Phe Glu Ser Gln Ile Thr Gln Ala Pro Leu Val Thr Asp Val Thr Thr
            4260            4265            4270

Ile Asn Gln Lys Ala Gln Thr Leu Asp His Ala Met Glu Leu Leu Arg
    4275            4280            4285

Asn Ser Val Ala Asp Asn Gln Thr Thr Leu Ala Ser Glu Asp Tyr His
    4290            4295            4300

Asp Ala Thr Ala Gln Arg Gln Asn Asp Tyr Asn Lys Ala Val Thr Ala
4305            4310            4315            4320

Ala Asn Asn Ile Ile Asn Gln Thr Thr Ser Pro Thr Met Asn Pro Asp
            4325            4330            4335

Asp Val Asn Gly Ala Thr Thr Gln Val Asn Asn Thr Lys Val Ala Leu
            4340            4345            4350

Asp Gly Asp Glu Asn Leu Ala Ala Ala Lys Gln Gln Ala Asn Asn Arg
    4355            4360            4365

Leu Asp Gln Leu Asp His Leu Asn Asn Ala Gln Lys Gln Gln Leu Gln
    4370            4375            4380

Ser Gln Ile Thr Gln Ser Ser Asp Ile Ala Ala Val Asn Gly His Lys
4385            4390            4395            4400

Gln Thr Ala Glu Ser Leu Asn Thr Ala Met Gly Asn Leu Ile Asn Ala
            4405            4410            4415

Ile Ala Asp His Gln Ala Val Glu Gln Arg Gly Asn Phe Ile Asn Ala
            4420            4425            4430

Asp Thr Asp Lys Gln Thr Ala Tyr Asn Thr Ala Val Asn Glu Ala Ala
    4435            4440            4445

Ala Met Ile Asn Lys Gln Thr Gly Gln Asn Ala Asn Gln Thr Glu Val
    4450            4455            4460

Glu Gln Ala Ile Thr Lys Val Gln Thr Thr Leu Gln Ala Leu Asn Gly
4465            4470            4475            4480

Asp His Asn Leu Gln Val Ala Lys Thr Asn Ala Thr Gln Ala Ile Asp
            4485            4490            4495

Val Leu Thr Ser Leu Asn Asp Pro Gln Lys Thr Ala Leu Lys Asp Gln
            4500            4505            4510

Val Thr Ala Ala Thr Leu Val Thr Ala Val His Gln Ile Glu Gln Asn
    4515            4520            4525

Ala Asn Thr Leu Asn Gln Ala Met His Gly Leu Arg Gln Ser Ile Gln
    4530            4535            4540

Asp Asn Ala Ala Thr Lys Ala Asn Ser Lys Tyr Ile Asn Glu Asp Gln
4545            4550            4555            4560

Pro Glu Gln Gln Asn Tyr Asp Gln Ala Val Gln Ala Ala Asn Asn Ile
            4565            4570            4575

Ile Asn Glu Gln Thr Ala Thr Leu Asp Asn Asn Ala Ile Asn Gln Val
            4580            4585            4590

Ala Ala Thr Val Asn Thr Thr Lys Ala Ala Leu His Gly Asp Val Lys
    4595            4600            4605

Leu Gln Asn Asp Lys Asp His Ala Lys Gln Thr Val Ser Gln Leu Ala
    4610            4615            4620
```

```
His Leu Asn Asn Ala Gln Lys His Met Glu Asp Thr Leu Ile Asp Ser
4625                4630                4635                4640

Glu Thr Thr Arg Thr Ala Val Lys Gln Asp Leu Thr Glu Val Gln Ala
                4645                4650                4655

Leu Asp Gln Leu Met Asp Ala Leu Gln Ser Ile Ala Asp Lys Asp
            4660                4665                4670

Ala Thr Arg Ala Ser Ser Ala Tyr Val Asn Ala Glu Pro Asn Lys Lys
            4675                4680                4685

Gln Ala Tyr Asp Glu Ala Val Gln Asn Ala Glu Ser Ile Ile Ala Gly
        4690                4695                4700

Leu Asn Asn Pro Thr Ile Asn Lys Gly Asn Val Ser Ala Thr Gln
4705                4710                4715                4720

Ala Val Ile Ser Ser Lys Asn Ala Leu Asp Gly Val Glu Arg Leu Ala
                4725                4730                4735

Gln Asp Lys Gln Thr Ala Gly Asn Ser Leu Asn His Leu Asp Gln Leu
            4740                4745                4750

Thr Pro Ala Gln Gln Gln Ala Leu Glu Asn Gln Ile Asn Asn Ala Thr
            4755                4760                4765

Thr Cys Asp Lys Val Ala Glu Ile Ile Ala Gln Ala Gln Ala Leu Asn
    4770                4775                4780

Glu Ala Met Lys Ala Leu Lys Glu Ser Ile Lys Asp Gln Pro Gln Thr
4785                4790                4795                4800

Glu Ala Ser Ser Lys Phe Ile Asn Glu Asp Gln Ala Gln Lys Asp Ala
            4805                4810                4815

Tyr Thr Gln Ala Val Gln His Ala Lys Asp Leu Ile Asn Lys Thr Thr
            4820                4825                4830

Asp Pro Thr Leu Ala Lys Ser Ile Ile Asp Gln Ala Thr Gln Ala Val
        4835                4840                4845

Thr Asp Ala Lys Asn Asn Leu His Gly Asp Gln Lys Leu Ala Gln Asp
        4850                4855                4860

Lys Gln Arg Ala Thr Glu Thr Leu Asn Asn Leu Ser Asn Leu Asn Thr
4865                4870                4875                4880

Pro Gln Arg Gln Ala Leu Glu Asn Gln Ile Asn Asn Ala Ala Thr Arg
            4885                4890                4895

Gly Glu Val Ala Gln Lys Leu Thr Glu Ala Gln Ala Leu Asn Gln Ala
        4900                4905                4910

Met Glu Ala Leu Arg Asn Ser Ile Gln Asp Gln Gln Gln Thr Glu Ser
            4915                4920                4925

Gly Ser Lys Phe Ile Asn Glu Asp Lys Pro Gln Lys Asp Ala Tyr Gln
        4930                4935                4940

Ala Ala Val Gln Asn Ala Lys Asp Leu Ile Asn Gln Thr Gly Asn Pro
4945                4950                4955                4960

Thr Leu Asp Lys Ala Gln Val Glu Gln Leu Thr His Ala Phe Lys Gln
            4965                4970                4975

Ala Lys Asp Asn Leu His Gly Asp Gln Lys Leu Ala Asp Asp Lys Gln
            4980                4985                4990

His Ala Val Thr Asp Leu Asn Gln Leu Asn Gly Leu Asn Asn Pro Gln
        4995                5000                5005

Arg Gln Ala Leu Glu Ser Gln Ile Asn Asn Ala Ala Thr Arg Gly Glu
        5010                5015                5020

Val Ala Gln Lys Leu Ala Glu Ala Lys Ala Leu Asp Gln Ala Met Gln
5025                5030                5035                5040

Ala Leu Arg Asn Ser Ile Gln Asp Gln Gln Gln Thr Glu Ala Gly Ser
```

```
                    5045                5050                5055
Lys Phe Ile Asn Glu Asp Lys Pro Gln Lys Asp Ala Tyr Gln Ala Ala
                5060                5065                5070

Val Gln Asn Ala Lys Asp Leu Ile Asn Gln Thr Gly Asn Pro Thr Leu
            5075                5080                5085

Asp Lys Ser Gln Val Glu Gln Leu Thr Gln Ala Val Thr Thr Ala Lys
        5090                5095                5100

Asp Asn Leu His Gly Asp Gln Lys Leu Ala Arg Asp Gln Gln Gln Ala
5105                5110                5115                5120

Val Thr Thr Val Asn Ala Leu Pro Asn Leu Asn His Ala Gln Gln Gln
            5125                5130                5135

Thr Leu Thr Asp Ala Ile Asn Ala Ala Pro Thr Arg Thr Glu Val Ala
        5140                5145                5150

Gln His Val Gln Thr Ala Thr Glu Leu Asp His Ala Met Glu Thr Leu
    5155                5160                5165

Lys Asn Lys Val Asp Gln Val Asn Thr Asp Lys Ala Gln Pro Asn Tyr
    5170                5175                5180

Thr Glu Ala Ser Thr Asp Lys Lys Glu Ala Val Asp Gln Ala Leu Gln
5185                5190                5195                5200

Ala Ala Gln Ser Ile Thr Asp Pro Thr Asn Gly Ser Asn Ala Asn Lys
            5205                5210                5215

Asp Ala Val Glu Gln Ala Leu Thr Lys Leu Gln Glu Lys Val Asn Glu
        5220                5225                5230

Leu Asn Gly Asn Glu Arg Val Ala Glu Ala Lys Thr Gln Ala Lys Gln
            5235                5240                5245

Thr Ile Asp Gln Leu Thr His Leu Asn Ala Asp Gln Ile Ala Thr Ala
        5250                5255                5260

Lys Gln Asn Ile Asp Gln Ala Thr Lys Leu Gln Pro Ile Ala Glu Leu
5265                5270                5275                5280

Val Asp Gln Ala Thr Gln Leu Asn Gln Ser Met Asp Gln Leu Gln Gln
            5285                5290                5295

Ala Val Asn Glu His Ala Asn Val Glu Gln Thr Ile Asp Tyr Thr Gln
        5300                5305                5310

Ala Asp Ser Asp Lys Gln Lys Ala Tyr Lys Gln Ala Ile Ala Asp Ala
            5315                5320                5325

Glu Asn Val Leu Lys Gln Asn Ala Asn Lys Gln Gln Val Asp Gln Ala
        5330                5335                5340

Leu Gln Asn Ile Leu Asn Ala Lys Gln Ala Leu Asn Gly Asp Glu Arg
5345                5350                5355                5360

Val Ala Leu Ala Lys Thr Asn Gly Lys His Asp Ile Asp Gln Leu Asn
            5365                5370                5375

Ala Leu Asn Asn Ala Gln Gln Asp Gly Phe Lys Gly Arg Ile Asp Gln
        5380                5385                5390

Ser Asn Asp Leu Asn Gln Ile Gln Gln Ile Val Asp Glu Ala Lys Ala
    5395                5400                5405

Leu Asn Arg Ala Met Asp Gln Leu Ser Gln Glu Ile Thr Gly Asn Glu
    5410                5415                5420

Gly Arg Thr Lys Gly Ser Thr Asn Tyr Val Asn Ala Asp Thr Gln Val
5425                5430                5435                5440

Lys Gln Val Tyr Asp Glu Ala Val Asp Lys Ala Lys Gln Ala Leu Asp
            5445                5450                5455

Lys Ser Ser Gly Gln Asn Leu Thr Ala Glu Gln Val Ile Lys Leu Asn
        5460                5465                5470
```

```
Asp Ala Val Thr Ala Ala Lys Lys Ala Leu Asn Gly Glu Glu Arg Leu
        5475                5480                5485
Asn Asn Arg Lys Ala Glu Ala Leu Gln Arg Leu Asp Gln Leu Thr His
        5490                5495                5500
Leu Asn Asn Ala Gln Arg Gln Leu Ala Ile Gln Gln Ile Asn Asn Ala
5505                5510                5515                5520
Glu Thr Leu Asn Lys Ala Ser Arg Ala Ile Asn Arg Ala Thr Lys Leu
        5525                5530                5535
Asp Asn Ala Met Gly Ala Val Gln Gln Tyr Ile Asp Glu Gln His Leu
        5540                5545                5550
Gly Val Ile Ser Ser Thr Asn Tyr Ile Asn Ala Asp Asp Asn Leu Lys
        5555                5560                5565
Ala Asn Tyr Asp Asn Ala Ile Ala Asn Ala Ala His Glu Leu Asp Lys
        5570                5575                5580
Val Gln Gly Asn Ala Ile Ala Lys Ala Glu Ala Glu Gln Leu Lys Gln
5585                5590                5595                5600
Asn Ile Ile Asp Ala Gln Asn Ala Leu Asn Gly Asp Gln Asn Leu Ala
        5605                5610                5615
Asn Ala Lys Asp Lys Ala Asn Ala Phe Val Asn Ser Leu Asn Gly Leu
        5620                5625                5630
Asn Gln Gln Gln Gln Asp Leu Ala His Lys Ala Ile Asn Asn Ala Asp
        5635                5640                5645
Thr Val Ser Asp Val Thr Asp Ile Val Asn Asn Gln Ile Asp Leu Asn
        5650                5655                5660
Asp Ala Met Glu Thr Leu Lys His Leu Val Asp Asn Glu Ile Pro Asn
5665                5670                5675                5680
Ala Glu Gln Thr Val Asn Tyr Gln Asn Ala Asp Asp Asn Ala Lys Thr
        5685                5690                5695
Asn Phe Asp Asp Ala Lys Arg Leu Ala Asn Thr Leu Leu Asn Ser Asp
        5700                5705                5710
Asn Thr Asn Val Asn Asp Ile Asn Gly Ala Ile Gln Ala Val Asn Asp
        5715                5720                5725
Ala Ile His Asn Leu Asn Gly Asp Gln Arg Leu Gln Asp Ala Lys Asp
        5730                5735                5740
Lys Ala Ile Gln Ser Ile Asn Gln Ala Leu Ala Asn Lys Leu Lys Glu
5745                5750                5755                5760
Ile Glu Ala Ser Asn Ala Thr Asp Gln Asp Lys Leu Ile Ala Lys Asn
        5765                5770                5775
Lys Ala Glu Glu Leu Ala Asn Ser Ile Ile Asn Ile Asn Lys Ala
        5780                5785                5790
Thr Ser Asn Gln Ala Val Ser Gln Val Gln Thr Ala Gly Asn His Ala
        5795                5800                5805
Ile Glu Gln Val His Ala Asn Glu Ile Pro Lys Ala Lys Ile Asp Ala
        5810                5815                5820
Asn Lys Asp Val Asp Lys Gln Val Gln Ala Leu Ile Asp Glu Ile Asp
5825                5830                5835                5840
Arg Asn Pro Asn Leu Thr Asp Lys Glu Lys Gln Ala Leu Lys Asp Arg
        5845                5850                5855
Ile Asn Gln Ile Leu Gln Gln Gly His Asn Asp Ile Asn Asn Ala Leu
        5860                5865                5870
Thr Lys Glu Glu Ile Glu Gln Ala Lys Ala Gln Leu Ala Gln Ala Leu
        5875                5880                5885
Gln Asp Ile Lys Asp Leu Val Lys Ala Lys Glu Asp Ala Lys Gln Asp
        5890                5895                5900
```

```
Val Asp Lys Gln Val Gln Ala Leu Ile Asp Glu Ile Asp Gln Asn Pro
5905                5910                5915                5920

Asn Leu Thr Asp Lys Glu Lys Gln Ala Leu Lys Asp Arg Ile Asn Gln
                5925                5930                5935

Ile Leu Gln Gln Gly His Asn Gly Ile Asn Asn Ala Met Thr Lys Glu
            5940                5945                5950

Glu Ile Glu Gln Ala Lys Ala Gln Leu Ala Gln Ala Leu Lys Glu Ile
        5955                5960                5965

Lys Asp Leu Val Lys Ala Lys Glu Asn Ala Lys Gln Asp Val Asp Lys
    5970                5975                5980

Gln Val Gln Ala Leu Ile Asp Glu Ile Asp Gln Asn Pro Asn Leu Thr
5985                5990                5995                6000

Asp Lys Glu Lys Gln Ala Leu Lys Asp Arg Ile Asn Gln Ile Leu Gln
                6005                6010                6015

Gln Gly His Asn Asp Ile Asn Asn Ala Met Thr Lys Glu Glu Ile Glu
            6020                6025                6030

Gln Ala Lys Ala Gln Leu Ala Gln Ala Leu Gln Asp Ile Lys Asp Leu
        6035                6040                6045

Val Lys Ala Lys Glu Asp Ala Lys Asn Ala Ile Lys Ala Leu Ala Asn
    6050                6055                6060

Ala Lys Arg Asp Gln Ile Asn Ser Asn Pro Asp Leu Thr Pro Glu Gln
6065                6070                6075                6080

Lys Ala Lys Ala Leu Lys Glu Ile Asp Glu Ala Glu Lys Arg Ala Leu
                6085                6090                6095

Gln Asn Val Glu Asn Ala Gln Thr Ile Asp Gln Leu Asn Arg Gly Leu
            6100                6105                6110

Asn Leu Gly Leu Asp Asp Ile Arg Asn Thr His Val Trp Glu Val Asp
        6115                6120                6125

Glu Gln Pro Ala Val Asn Glu Ile Phe Glu Ala Thr Pro Glu Gln Ile
    6130                6135                6140

Leu Val Asn Gly Glu Leu Ile Val His Arg Asp Asp Ile Ile Thr Glu
6145                6150                6155                6160

Gln Asp Ile Leu Ala His Ile Asn Leu Ile Asp Gln Leu Ser Ala Glu
                6165                6170                6175

Val Ile Asp Thr Pro Ser Thr Ala Thr Ile Ser Asp Ser Leu Thr Ala
            6180                6185                6190

Lys Val Glu Val Thr Leu Leu Asp Gly Ser Lys Val Ile Val Asn Val
        6195                6200                6205

Pro Val Lys Val Val Glu Lys Glu Leu Ser Val Val Lys Gln Gln Ala
    6210                6215                6220

Ile Glu Ser Ile Glu Asn Ala Ala Gln Gln Lys Ile Asp Glu Ile Asn
6225                6230                6235                6240

Asn Ser Val Thr Leu Thr Leu Glu Gln Lys Glu Ala Ala Ile Ala Glu
                6245                6250                6255

Val Asn Lys Leu Lys Gln Gln Ala Ile Asp His Val Asn Asn Ala Pro
            6260                6265                6270

Asp Val His Ser Val Glu Glu Ile Gln Gln Gln Glu Gln Ala Tyr Ile
        6275                6280                6285

Glu Gln Phe Asn Pro Glu Gln Phe Thr Ile Glu Gln Ala Lys Ser Asn
    6290                6295                6300

Ala Ile Lys Ser Ile Glu Asp Ala Ile Gln His Met Ile Asp Glu Ile
6305                6310                6315                6320

Lys Ala Arg Thr Asp Leu Thr Asp Lys Glu Lys Gln Glu Ala Ile Ala
```

```
                  6325                6330                6335
Lys Leu Asn Gln Leu Lys Glu Gln Ala Ile Gln Ala Ile Gln Arg Ala
              6340                6345                6350

Gln Ser Ile Ser Glu Ile Thr Glu Gln Leu Glu Gln Phe Lys Ala Gln
              6355                6360                6365

Met Lys Ala Ala Asn Pro Thr Ala Lys Glu Leu Ala Lys Arg Lys Gln
              6370                6375                6380

Glu Ala Ile Ser Arg Ile Lys Asp Phe Ser Asn Glu Lys Ile Asn Ser
6385                6390                6395                6400

Ile Arg Asn Ser Glu Ile Gly Thr Ala Asp Glu Lys Gln Ala Ala Met
              6405                6410                6415

Asn Gln Ile Asn Glu Ile Val Leu Glu Thr Ile Arg Asp Ile Asn Asn
              6420                6425                6430

Ala His Thr Leu Gln Gln Val Glu Ala Ala Leu Asn Asn Gly Ile Ala
              6435                6440                6445

Arg Ile Ser Ala Val Gln Ile Val Ile Ser Asp Arg Ala Lys Gln Ser
              6450                6455                6460

Ser Ser Thr Gly Asn Glu Ser Asn Ser His Leu Thr Ile Gly Tyr Gly
6465                6470                6475                6480

Thr Ala Asn His Pro Phe Asn Ser Ser Thr Ile Gly His Lys Lys
              6485                6490                6495

Leu Asp Glu Asp Asp Ile Asp Pro Leu His Met Arg His Phe Ser
              6500                6505                6510

Asn Asn Phe Gly Asn Val Ile Lys Asn Ala Ile Gly Val Val Gly Ile
              6515                6520                6525

Ser Gly Leu Leu Ala Ser Phe Trp Phe Phe Ile Ala Lys Arg Arg Arg
              6530                6535                6540

Lys Glu Asp Glu Glu Glu Leu Glu Ile Arg Asp Asn Asn Lys Asp
6545                6550                6555                6560

Ser Ile Lys Glu Thr Leu Asp Asp Thr Lys His Leu Pro Leu Leu Phe
              6565                6570                6575

Ala Lys Arg Arg Arg Lys Glu Asp Glu Glu Asp Val Thr Val Glu Glu
              6580                6585                6590

Lys Asp Ser Leu Asn Asn Gly Glu Ser Leu Lys Val Lys His Thr
              6595                6600                6605

Pro Phe Phe Leu Pro Lys Arg Arg Lys Glu Asp Glu Glu Asp Val
              6610                6615                6620

Glu Val Thr Asn Glu Asn Thr Asp Glu Lys Val Leu Lys Asp Asn Glu
6625                6630                6635                6640

His Ser Pro Leu Leu Phe Ala Lys Arg Arg Lys Asp Lys Glu Glu Asp
              6645                6650                6655

Val Glu Thr Thr Thr Ser Ile Glu Ser Lys Asp Glu Asp Val Pro Leu
              6660                6665                6670

Leu Leu Ala Lys Lys Lys Asn Gln Lys Asp Asn Gln Ser Lys Asp Lys
              6675                6680                6685

Lys Ser Ala Ser Lys Asn Thr Ser Lys Val Ala Ala Lys Lys Lys
              6690                6695                6700

Lys Lys Lys Ser Lys Lys Asn Lys Lys
6705                6710

<210> SEQ ID NO 14
<211> LENGTH: 701
<212> TYPE: PRT
<213> ORGANISM: Staphylococcus epidermidis
```

<400> SEQUENCE: 14

```
Met Asn Asn Arg Asp Lys Leu Gln Lys Phe Ser Ile Arg Lys Tyr Ala
1               5                   10                  15
Ile Gly Thr Phe Ser Thr Val Ile Ala Thr Leu Val Phe Met Gly Ile
            20                  25                  30
Asn Thr Asn His Ala Ser Ala Asp Glu Leu Asn Gln Asn Gln Lys Leu
        35                  40                  45
Ile Lys Gln Leu Asn Gln Thr Asp Asp Asp Ser Asn Thr His Ser
50                  55                  60
Gln Glu Ile Glu Asn Asn Lys Gln Asn Ser Ser Gly Gln Thr Glu Ser
65                  70                  75                  80
Leu Arg Ser Ser Thr Ser Gln Asn Gln Ala Asn Ala Arg Leu Ser Asp
                85                  90                  95
Gln Phe Lys Asp Thr Asn Glu Thr Ser Gln Gln Leu Pro Thr Asn Val
            100                 105                 110
Ser Asp Asp Ser Ile Asn Gln Ser His Ser Glu Ala Asn Met Asn Asn
        115                 120                 125
Glu Pro Leu Lys Val Asp Asn Ser Thr Met Gln Ala His Ser Lys Ile
130                 135                 140
Val Ser Asp Ser Asp Gly Asn Ala Ser Glu Asn Lys His His Lys Leu
145                 150                 155                 160
Thr Glu Asn Val Leu Ala Glu Ser Arg Ala Ser Lys Asn Asp Lys Glu
                165                 170                 175
Lys Glu Asn Leu Gln Glu Lys Asp Lys Ser Gln Gln Val His Pro Pro
            180                 185                 190
Leu Asp Lys Asn Ala Leu Gln Ala Phe Phe Asp Ala Ser Tyr His Asn
        195                 200                 205
Tyr Arg Met Ile Asp Arg Asp Arg Ala Asp Ala Thr Glu Tyr Gln Lys
210                 215                 220
Val Lys Ser Thr Phe Asp Tyr Val Asn Asp Leu Leu Gly Asn Asn Gln
225                 230                 235                 240
Asn Ile Pro Ser Glu Gln Leu Val Ser Ala Tyr Gln Gln Leu Glu Lys
                245                 250                 255
Ala Leu Glu Leu Ala Arg Thr Leu Pro Gln Gln Ser Thr Thr Glu Lys
            260                 265                 270
Arg Gly Arg Arg Ser Thr Arg Ser Val Val Glu Asn Arg Ser Ser Arg
        275                 280                 285
Ser Asp Tyr Leu Asp Ala Arg Thr Glu Tyr Tyr Val Ser Lys Asp Asp
290                 295                 300
Asp Asp Ser Gly Phe Pro Pro Gly Thr Phe Phe His Ala Ser Asn Arg
305                 310                 315                 320
Arg Trp Pro Tyr Asn Leu Pro Arg Ser Arg Asn Ile Leu Arg Ala Ser
                325                 330                 335
Asp Val Gln Gly Asn Ala Tyr Ile Thr Thr Lys Arg Leu Lys Asp Gly
            340                 345                 350
Tyr Gln Trp Asp Ile Leu Phe Asn Ser Asn His Lys Gly His Glu Tyr
        355                 360                 365
Met Tyr Tyr Trp Phe Gly Leu Pro Ser Asp Gln Thr Pro Thr Gly Pro
370                 375                 380
Val Thr Phe Thr Ile Ile Asn Arg Asp Gly Ser Ser Thr Ser Thr Gly
385                 390                 395                 400
Gly Val Gly Phe Gly Ser Gly Ala Pro Leu Pro Gln Phe Trp Arg Ser
                405                 410                 415
```

-continued

```
Ala Gly Ala Ile Asn Ser Ser Val Ala Asn Asp Phe Lys His Gly Ser
            420                 425                 430

Ala Thr Asn Tyr Ala Phe Tyr Asp Gly Val Asn Asn Phe Ser Asp Phe
            435                 440                 445

Ala Arg Gly Gly Glu Leu Tyr Phe Asp Arg Glu Gly Ala Thr Gln Thr
450                 455                 460

Asn Lys Tyr Tyr Gly Asp Glu Asn Phe Ala Leu Leu Asn Ser Glu Lys
465                 470                 475                 480

Pro Asp Gln Ile Arg Gly Leu Asp Thr Ile Tyr Ser Phe Lys Gly Ser
                485                 490                 495

Gly Asp Val Ser Tyr Arg Ile Ser Phe Lys Thr Gln Gly Ala Pro Thr
            500                 505                 510

Ala Arg Leu Tyr Tyr Ala Ala Gly Ala Arg Ser Gly Glu Tyr Lys Gln
            515                 520                 525

Ala Thr Asn Tyr Asn Gln Leu Tyr Val Glu Pro Tyr Lys Asn Tyr Arg
530                 535                 540

Asn Arg Val Gln Ser Asn Val Gln Val Lys Asn Arg Thr Leu His Leu
545                 550                 555                 560

Lys Arg Thr Ile Arg Gln Phe Asp Pro Thr Leu Gln Arg Thr Thr Asp
                565                 570                 575

Val Pro Ile Leu Asp Ser Asp Gly Ser Gly Ser Ile Asp Ser Val Tyr
            580                 585                 590

Asp Pro Leu Ser Tyr Val Lys Asn Val Thr Gly Thr Val Leu Gly Ile
            595                 600                 605

Tyr Pro Ser Tyr Leu Pro Tyr Asn Gln Glu Arg Trp Gln Gly Ala Asn
610                 615                 620

Ala Met Asn Ala Tyr Gln Ile Glu Glu Leu Phe Ser Gln Glu Asn Leu
625                 630                 635                 640

Gln Asn Ala Ala Arg Ser Gly Arg Pro Ile Gln Phe Leu Val Gly Phe
                645                 650                 655

Asp Val Glu Asp Ser His His Asn Pro Glu Thr Leu Leu Pro Val Asn
            660                 665                 670

Leu Tyr Val Lys Pro Glu Leu Lys His Thr Ile Glu Leu Tyr His Asp
            675                 680                 685

Asn Glu Lys Gln Asp Arg Lys Glu Phe Ser Val Ser Lys
690                 695                 700

<210> SEQ ID NO 15
<211> LENGTH: 9439
<212> TYPE: PRT
<213> ORGANISM: Staphylococcus epidermidis

<400> SEQUENCE: 15

Met Ser Gly Thr Leu His Asn Thr Val Gly Ser Gly Ile Leu Pro Tyr
1               5                   10                  15

Gln Gln Glu Ile Arg Ile Lys Leu Thr Ser Asn Glu Pro Ile Lys Asp
            20                  25                  30

Ser Glu Trp Ser Ile Thr Gly Tyr Pro Asn Thr Leu Thr Leu Gln Asn
        35                  40                  45

Ala Val Gly Arg Thr Asn Asn Ala Thr Glu Lys Asn Leu Ala Leu Val
    50                  55                  60

Gly His Ile Asp Pro Gly Asn Tyr Phe Ile Thr Val Lys Phe Gly Asp
65                  70                  75                  80

Lys Val Glu Gln Phe Glu Ile Arg Ser Lys Pro Thr Pro Pro Arg Ile
                85                  90                  95
```

```
Ile Thr Thr Ala Asn Glu Leu Arg Gly Asn Pro Asn His Lys Pro Glu
            100                 105                 110

Ile Arg Val Thr Asp Ile Pro Asn Asp Thr Thr Ala Lys Ile Lys Leu
            115                 120                 125

Val Met Gly Gly Thr Asp Gly Asp His Asp Pro Glu Ile Asn Pro Tyr
130                 135                 140

Thr Val Pro Glu Asn Tyr Thr Val Val Ala Glu Ala Tyr His Asp Asn
145                 150                 155                 160

Asp Pro Ser Lys Asn Gly Val Leu Thr Phe Arg Ser Ser Asp Tyr Leu
                165                 170                 175

Lys Asp Leu Pro Leu Ser Gly Glu Leu Lys Ala Ile Val Tyr Tyr Asn
            180                 185                 190

Gln Tyr Val Gln Ser Asn Phe Ser Lys Ser Val Pro Phe Ser Ser Asp
            195                 200                 205

Thr Thr Pro Pro Thr Ile Asn Glu Pro Ala Gly Leu Val His Lys Tyr
            210                 215                 220

Tyr Arg Gly Asp His Val Glu Ile Thr Leu Pro Val Thr Asp Asn Thr
225                 230                 235                 240

Gly Gly Ser Gly Leu Arg Asp Val Asn Val Asn Leu Pro Gln Gly Trp
                245                 250                 255

Thr Lys Thr Phe Thr Ile Asn Pro Asn Asn Asn Thr Glu Gly Thr Leu
            260                 265                 270

Lys Leu Ile Gly Asn Ile Pro Ser Asn Glu Ala Tyr Asn Thr Thr Tyr
            275                 280                 285

His Phe Asn Ile Thr Ala Thr Asp Asn Ser Gly Asn Thr Thr Asn Pro
            290                 295                 300

Ala Lys Thr Phe Ile Leu Asn Val Gly Lys Leu Ala Asp Asp Leu Asn
305                 310                 315                 320

Pro Val Gly Leu Ser Arg Asp Gln Leu Gln Leu Val Thr Asp Pro Ser
                325                 330                 335

Ser Leu Ser Asn Ser Glu Arg Glu Val Lys Arg Lys Ile Ser Glu
            340                 345                 350

Ala Asn Ala Asn Ile Arg Ser Tyr Leu Leu Gln Asn Asn Pro Ile Leu
            355                 360                 365

Ala Gly Val Asn Gly Asp Val Thr Phe Tyr Tyr Arg Asp Gly Ser Val
370                 375                 380

Asp Val Ile Asp Ala Glu Asn Val Ile Thr Tyr Glu Pro Glu Arg Lys
385                 390                 395                 400

Ser Ile Phe Ser Glu Asn Gly Asn Thr Asn Lys Lys Glu Ala Val Ile
            405                 410                 415

Thr Ile Ala Arg Gly Gln Asn Tyr Thr Ile Gly Pro Asn Leu Arg Lys
            420                 425                 430

Tyr Phe Ser Leu Ser Asn Gly Ser Asp Leu Pro Asn Arg Asp Phe Thr
            435                 440                 445

Ser Ile Ser Ala Ile Gly Ser Leu Pro Ser Ser Glu Ile Ser Arg
            450                 455                 460

Leu Asn Val Gly Asn Tyr Asn Tyr Arg Val Asn Ala Lys Asn Ala Tyr
465                 470                 475                 480

His Lys Thr Gln Gln Glu Leu Asn Leu Lys Leu Lys Ile Val Glu Val
                485                 490                 495

Asn Ala Pro Thr Gly Asn Asn Arg Val Tyr Arg Val Ser Thr Tyr Asn
            500                 505                 510

Leu Thr Asn Asp Glu Ile Asn Lys Ile Lys Gln Ala Phe Lys Ala Ala
            515                 520                 525
```

```
Asn Ser Gly Leu Asn Leu Asn Asp Asn Asp Ile Thr Val Ser Asn Asn
    530                 535                 540

Phe Asp His Arg Asn Val Ser Ser Val Thr Val Thr Ile Arg Lys Gly
545                 550                 555                 560

Asp Leu Ile Lys Glu Phe Ser Ser Asn Leu Asn Asn Met Asn Phe Leu
                565                 570                 575

Arg Trp Val Asn Ile Arg Asp Asp Tyr Thr Ile Ser Trp Thr Ser Ser
            580                 585                 590

Lys Ile Gln Gly Arg Asn Thr Asp Gly Gly Leu Glu Trp Ser Pro Asp
        595                 600                 605

His Lys Ser Leu Ile Tyr Lys Tyr Asp Ala Thr Leu Gly Arg Gln Ile
    610                 615                 620

Asn Thr Asn Asp Val Leu Thr Leu Leu Gln Ala Thr Ala Lys Asn Ser
625                 630                 635                 640

Asn Leu Arg Ser Asn Ile Asn Ser Asn Glu Lys Gln Leu Ala Glu Arg
                645                 650                 655

Gly Ser Asn Gly Tyr Ser Lys Ser Ile Ile Arg Asp Asp Gly Glu Lys
            660                 665                 670

Ser Tyr Leu Leu Asn Ser Asn Pro Ile Gln Val Leu Asp Leu Val Glu
        675                 680                 685

Pro Asp Asn Gly Tyr Gly Gly Arg Gln Val Ser His Ser Asn Val Ile
    690                 695                 700

Tyr Asn Glu Lys Asn Ser Ser Ile Val Asn Gly Gln Val Pro Glu Ala
705                 710                 715                 720

Asn Gly Ala Ser Ala Phe Asn Ile Asp Lys Val Val Lys Ala Asn Ala
                725                 730                 735

Ala Asn Asn Gly Ile Met Gly Val Ile Tyr Lys Ala Gln Leu Tyr Leu
            740                 745                 750

Ala Pro Tyr Ser Pro Lys Gly Tyr Ile Glu Lys Leu Gly Gln Asn Leu
        755                 760                 765

Ser Asn Thr Asn Asn Val Ile Asn Val Tyr Phe Val Pro Ser Asp Lys
    770                 775                 780

Val Asn Pro Ser Ile Thr Val Gly Asn Tyr Asp His His Thr Val Tyr
785                 790                 795                 800

Ser Gly Glu Thr Phe Lys Asn Thr Ile Asn Val Asn Asp Asn Tyr Gly
                805                 810                 815

Leu Asn Thr Val Ala Ser Thr Ser Asp Ser Ala Ile Thr Met Thr Arg
            820                 825                 830

Asn Asn Asn Glu Leu Val Gly Gln Ala Pro Asn Val Thr Asn Ser Ile
        835                 840                 845

Asn Lys Ile Val Lys Val Lys Ala Thr Asp Lys Ser Gly Asn Glu Ser
    850                 855                 860

Ile Val Ser Phe Thr Val Asn Ile Lys Pro Leu Asn Glu Lys Tyr Arg
865                 870                 875                 880

Ile Thr Thr Ser Ser Ser Asn Gln Thr Pro Val Arg Ile Ser Asn Ile
                885                 890                 895

Gln Asn Asn Ala Asn Leu Ser Ile Glu Asp Gln Asn Arg Val Lys Ser
            900                 905                 910

Ser Leu Ser Met Thr Lys Ile Leu Gly Thr Arg Asn Tyr Val Asn Glu
        915                 920                 925

Ser Asn Asn Asp Val Arg Ser Gln Val Val Ser Lys Val Asn Arg Ser
    930                 935                 940

Gly Asn Asn Ala Thr Val Asn Val Thr Thr Thr Phe Ser Asp Gly Thr
```

```
              945                 950                 955                 960
        Thr Asn Thr Ile Thr Val Pro Val Lys His Val Leu Leu Glu Val Val
                          965                 970                 975
        Pro Thr Thr Arg Thr Val Arg Gly Gln Gln Phe Pro Thr Gly Lys
                    980                 985                 990
        Gly Thr Ser Pro Asn Asp Phe Phe Ser Leu Arg Thr Gly Pro Val
                    995                1000                1005
        Asp Ala Arg Ile Val Trp Val Asn Asn Gln Gly Pro Asp Ile Asn Ser
              1010                1015                1020
        Asn Gln Ile Gly Arg Asp Leu Thr Leu His Ala Glu Ile Phe Phe Asp
        1025                1030                1035                1040
        Gly Glu Thr Thr Pro Ile Arg Lys Asp Thr Thr Tyr Lys Leu Ser Gln
                          1045                1050                1055
        Ser Ile Pro Lys Gln Ile Tyr Glu Thr Thr Ile Asn Gly Arg Phe Asn
                    1060                1065                1070
        Ser Ser Gly Asp Ala Tyr Pro Gly Asn Phe Val Gln Ala Val Asn Gln
                    1075                1080                1085
        Tyr Trp Pro Glu His Met Asp Phe Arg Trp Ala Gln Gly Ser Gly Thr
                    1090                1095                1100
        Pro Ser Ser Arg Asn Ala Gly Ser Phe Thr Lys Thr Val Thr Val Val
        1105                1110                1115                1120
        Tyr Gln Asn Gly Gln Thr Glu Asn Val Asn Val Leu Phe Lys Val Lys
                          1125                1130                1135
        Pro Asn Lys Pro Val Ile Asp Ser Asn Ser Val Ile Ser Lys Gly Gln
                          1140                1145                1150
        Leu Asn Gly Gln Gln Ile Leu Val Arg Asn Val Pro Gln Asn Ala Gln
                    1155                1160                1165
        Val Thr Leu Tyr Gln Ser Asn Gly Thr Val Ile Pro Asn Thr Asn Thr
              1170                1175                1180
        Thr Ile Asp Ser Asn Gly Ile Ala Thr Val Thr Ile Gln Gly Thr Leu
        1185                1190                1195                1200
        Pro Thr Gly Asn Ile Thr Ala Lys Thr Ser Met Thr Asn Asn Val Thr
                          1205                1210                1215
        Tyr Thr Lys Gln Asn Ser Ser Gly Ile Ala Ser Asn Thr Thr Glu Asp
                    1220                1225                1230
        Ile Ser Val Phe Ser Glu Asn Ser Asp Gln Val Asn Val Thr Ala Gly
                    1235                1240                1245
        Met Gln Ala Lys Asn Asp Gly Ile Lys Ile Ile Lys Gly Thr Asn Tyr
                    1250                1255                1260
        Asn Phe Asn Asp Phe Asn Ser Phe Ile Ser Asn Ile Pro Ala His Ser
        1265                1270                1275                1280
        Thr Leu Thr Trp Asn Glu Glu Pro Asn Ser Trp Lys Asn Asn Ile Gly
                          1285                1290                1295
        Thr Thr Thr Lys Thr Val Thr Val Thr Leu Pro Asn His Gln Gly Thr
                          1300                1305                1310
        Arg Thr Val Asp Ile Pro Ile Thr Ile Tyr Pro Thr Val Thr Ala Lys
                    1315                1320                1325
        Asn Pro Val Arg Asp Gln Lys Gly Arg Asn Leu Thr Asn Gly Thr Asp
              1330                1335                1340
        Val Tyr Asn Tyr Ile Ile Phe Glu Asn Asn Asn Arg Leu Gly Gly Thr
        1345                1350                1355                1360
        Ala Ser Trp Lys Asp Asn Arg Gln Pro Asp Lys Asn Ile Ala Gly Val
                    1365                1370                1375
```

```
Gln Asn Leu Ile Ala Leu Val Asn Tyr Pro Gly Ile Ser Thr Pro Leu
            1380                1385                1390

Glu Val Pro Val Lys Val Trp Val Tyr Asn Phe Asp Phe Thr Gln Pro
        1395                1400                1405

Ile Tyr Lys Ile Gln Val Gly Asp Thr Phe Pro Lys Gly Thr Trp Ala
    1410                1415                1420

Gly Tyr Tyr Lys His Leu Glu Asn Gly Glu Gly Leu Pro Ile Asp Gly
1425                1430                1435                1440

Trp Lys Phe Tyr Trp Asn Gln Gln Ser Thr Gly Thr Thr Ser Asp Gln
            1445                1450                1455

Trp Gln Ser Leu Ala Tyr Thr Arg Thr Pro Phe Val Lys Thr Gly Thr
        1460                1465                1470

Tyr Asp Val Val Asn Pro Ser Asn Trp Gly Val Trp Gln Thr Ser Gln
    1475                1480                1485

Ser Ala Lys Phe Ile Val Thr Asn Ala Lys Pro Asn Gln Pro Thr Ile
    1490                1495                1500

Thr Gln Ser Lys Thr Gly Asp Val Thr Val Thr Pro Gly Ala Val Arg
1505                1510                1515                1520

Asn Ile Leu Ile Ser Gly Thr Asn Asp Tyr Ile Gln Ala Ser Ala Asp
            1525                1530                1535

Lys Ile Val Ile Asn Lys Asn Gly Asn Lys Leu Thr Thr Phe Val Lys
        1540                1545                1550

Asn Asn Asp Gly Arg Trp Thr Val Glu Thr Gly Ser Pro Asp Ile Asn
    1555                1560                1565

Gly Ile Gly Pro Thr Asn Asn Gly Thr Ala Ile Ser Leu Ser Arg Leu
    1570                1575                1580

Ala Val Arg Pro Gly Asp Ser Ile Glu Ala Ile Ala Thr Glu Gly Ser
1585                1590                1595                1600

Gly Glu Thr Ile Ser Thr Ser Ala Thr Ser Glu Ile Tyr Ile Val Lys
            1605                1610                1615

Ala Pro Gln Pro Glu Gln Val Ala Thr His Thr Tyr Asp Asn Gly Thr
        1620                1625                1630

Phe Asp Ile Leu Pro Asp Asn Ser Arg Asn Ser Leu Asn Pro Thr Glu
    1635                1640                1645

Arg Val Glu Ile Asn Tyr Thr Glu Lys Leu Asn Gly Asn Glu Thr Gln
    1650                1655                1660

Lys Ser Phe Thr Ile Thr Lys Asn Asn Asn Gly Lys Trp Thr Ile Asn
1665                1670                1675                1680

Asn Lys Pro Asn Tyr Val Glu Phe Asn Gln Asp Asn Gly Lys Val Val
            1685                1690                1695

Phe Ser Ala Asn Thr Ile Lys Pro Asn Ser Gln Ile Thr Ile Thr Pro
        1700                1705                1710

Lys Ala Gly Gln Gly Asn Thr Glu Asn Thr Asn Pro Thr Val Ile Gln
    1715                1720                1725

Ala Pro Ala Gln His Thr Leu Thr Ile Asn Glu Ile Val Lys Glu Gln
    1730                1735                1740

Gly Gln Asn Val Thr Asn Asp Asp Ile Asn Asn Ala Val Gln Val Pro
1745                1750                1755                1760

Asn Lys Asn Arg Val Ala Ile Lys Gln Gly Asn Ala Leu Pro Thr Asn
            1765                1770                1775

Leu Ala Gly Gly Ser Thr Ser His Ile Pro Val Val Ile Tyr Tyr Ser
        1780                1785                1790

Asp Gly Ser Ser Glu Glu Ala Thr Glu Thr Val Arg Thr Lys Val Asn
    1795                1800                1805
```

```
Lys Thr Glu Leu Ile Asn Ala Arg Arg Arg Leu Asp Glu Glu Ile Ser
    1810                1815                1820

Lys Glu Asn Lys Thr Pro Ser Ser Ile Arg Asn Phe Asp Gln Ala Met
1825                1830                1835                1840

Asn Arg Ala Gln Ser Gln Ile Asn Thr Ala Lys Ser Asp Ala Asp Gln
                1845                1850                1855

Val Ile Gly Thr Glu Phe Ala Thr Pro Gln Gln Val Asn Ser Ala Leu
        1860                1865                1870

Ser Lys Val Gln Ala Ala Gln Asn Lys Ile Asn Glu Ala Lys Ala Leu
    1875                1880                1885

Leu Gln Asn Lys Ala Asp Asn Ser Gln Leu Val Arg Ala Lys Glu Gln
    1890                1895                1900

Leu Gln Gln Ser Ile Gln Pro Ala Ala Ser Thr Asp Gly Met Thr Gln
1905                1910                1915                1920

Asp Ser Thr Arg Asn Tyr Asn Asn Lys Arg Gln Ala Ala Glu Gln Ala
                1925                1930                1935

Ile Gln His Ala Asn Ser Val Ile Asn Asn Gly Asp Ala Thr Ser Gln
        1940                1945                1950

Gln Ile Asn Asp Ala Lys Asn Thr Val Glu Gln Ala Gln Arg Asp Tyr
    1955                1960                1965

Val Glu Ala Lys Ser Asn Leu Arg Ala Asp Lys Ser Gln Leu Gln Ser
    1970                1975                1980

Ala Tyr Asp Thr Leu Asn Arg Asp Val Leu Thr Asn Asp Lys Lys Pro
1985                1990                1995                2000

Ala Ser Val Arg Arg Tyr Asn Glu Ala Ile Ser Asn Ile Arg Lys Glu
                2005                2010                2015

Leu Asp Thr Ala Lys Ala Asp Ala Ser Ser Thr Leu Arg Asn Thr Asn
        2020                2025                2030

Pro Ser Val Glu Gln Val Arg Asp Ala Leu Asn Lys Ile Asn Thr Val
    2035                2040                2045

Gln Pro Lys Val Asn Gln Ala Ile Ala Leu Leu Gln Pro Lys Glu Asn
    2050                2055                2060

Asn Ser Glu Leu Val Gln Ala Lys Lys Arg Leu Gln Asp Ala Val Asn
2065                2070                2075                2080

Asp Ile Pro Gln Thr Gln Gly Met Thr Gln Gln Thr Ile Asn Asn Tyr
                2085                2090                2095

Asn Asp Lys Gln Arg Glu Ala Glu Arg Ala Leu Thr Ser Ala Gln Arg
        2100                2105                2110

Val Ile Asp Asn Gly Asp Ala Thr Thr Gln Glu Ile Thr Ser Glu Lys
    2115                2120                2125

Ser Lys Val Glu Gln Ala Met Gln Ala Leu Thr Asn Ala Lys Ser Asn
    2130                2135                2140

Leu Arg Ala Asp Lys Asn Glu Leu Gln Thr Ala Tyr Asn Lys Leu Ile
2145                2150                2155                2160

Glu Asn Val Ser Thr Asn Gly Lys Lys Pro Ala Ser Ile Arg Gln Tyr
                2165                2170                2175

Glu Thr Ala Lys Ala Arg Ile Gln Asn Gln Ile Asn Asp Ala Lys Asn
        2180                2185                2190

Glu Ala Glu Arg Ile Leu Gly Asn Asp Asn Pro Gln Val Ser Gln Val
    2195                2200                2205

Thr Gln Ala Leu Asn Lys Ile Lys Ala Ile Gln Pro Lys Leu Thr Glu
    2210                2215                2220

Ala Ile Asn Met Leu Gln Asn Lys Glu Asn Asn Thr Glu Leu Val Asn
```

```
                    2225                2230                2235                2240
Ala Lys Asn Arg Leu Glu Asn Ala Val Asn Asp Thr Asp Pro Thr His
                2245                2250                2255
Gly Met Thr Gln Glu Thr Ile Asn Asn Tyr Asn Ala Lys Lys Arg Glu
                2260                2265                2270
Ala Gln Asn Glu Ile Gln Lys Ala Asn Met Ile Ile Asn Asn Gly Asp
                2275                2280                2285
Ala Thr Ala Gln Asp Ile Ser Ser Glu Lys Ser Lys Val Glu Gln Val
                2290                2295                2300
Leu Gln Ala Leu Gln Asn Ala Lys Asn Asp Leu Arg Ala Asp Lys Arg
2305                2310                2315                2320
Glu Leu Gln Thr Ala Tyr Asn Lys Leu Ile Gln Asn Val Asn Thr Asn
                2325                2330                2335
Gly Lys Lys Pro Ser Ser Ile Gln Asn Tyr Lys Ser Ala Arg Arg Asn
                2340                2345                2350
Ile Glu Asn Gln Tyr Asn Thr Ala Lys Asn Glu Ala His Asn Val Leu
                2355                2360                2365
Glu Asn Thr Asn Pro Thr Val Asn Ala Val Glu Asp Ala Leu Arg Lys
                2370                2375                2380
Ile Asn Ala Ile Gln Pro Glu Val Thr Lys Ala Ile Asn Ile Leu Gln
2385                2390                2395                2400
Asp Lys Glu Asp Asn Ser Glu Leu Val Arg Ala Lys Glu Lys Leu Asp
                2405                2410                2415
Gln Ala Ile Asn Ser Gln Pro Ser Leu Asn Gly Met Thr Gln Glu Ser
                2420                2425                2430
Ile Asn Asn Tyr Thr Thr Lys Arg Arg Glu Ala Gln Asn Ile Ala Ser
                2435                2440                2445
Ser Ala Asp Thr Ile Ile Asn Asn Gly Asp Ala Ser Ile Glu Gln Ile
                2450                2455                2460
Thr Glu Asn Lys Ile Arg Val Glu Glu Ala Thr Asn Ala Leu Asn Glu
2465                2470                2475                2480
Ala Lys Gln His Leu Thr Ala Asp Thr Thr Ser Leu Lys Thr Glu Val
                2485                2490                2495
Arg Lys Leu Ser Arg Arg Gly Asp Thr Asn Asn Lys Lys Pro Ser Ser
                2500                2505                2510
Val Ser Ala Tyr Asn Asn Thr Ile His Ser Leu Gln Ser Glu Ile Thr
                2515                2520                2525
Gln Thr Glu Asn Arg Ala Asn Thr Ile Ile Asn Lys Pro Ile Arg Ser
                2530                2535                2540
Val Glu Glu Val Asn Asn Ala Leu His Glu Val Asn Gln Leu Asn Gln
2545                2550                2555                2560
Arg Leu Thr Asp Thr Ile Asn Leu Leu Gln Pro Leu Ala Asn Lys Glu
                2565                2570                2575
Ser Leu Lys Glu Ala Arg Asn Arg Leu Glu Ser Lys Ile Asn Glu Thr
                2580                2585                2590
Val Gln Thr Asp Gly Met Thr Gln Gln Ser Val Glu Asn Tyr Lys Gln
                2595                2600                2605
Ala Lys Ile Lys Ala Gln Asn Glu Ser Ser Ile Ala Gln Thr Leu Ile
                2610                2615                2620
Asn Asn Gly Asp Ala Ser Asp Gln Glu Val Ser Thr Glu Ile Glu Lys
2625                2630                2635                2640
Leu Asn Gln Lys Leu Ser Glu Leu Thr Asn Ser Ile Asn His Leu Thr
                2645                2650                2655
```

```
Val Asn Lys Glu Pro Leu Glu Thr Ala Lys Asn Gln Leu Gln Ala Asn
            2660                2665                2670

Ile Asp Gln Lys Pro Ser Thr Asp Gly Met Thr Gln Ser Val Gln
        2675                2680                2685

Ser Tyr Glu Arg Lys Leu Gln Glu Ala Lys Asp Lys Ile Asn Ser Ile
            2690                2695                2700

Asn Asn Val Leu Ala Asn Asn Pro Asp Val Asn Ala Ile Arg Thr Asn
2705                2710                2715                2720

Lys Val Glu Thr Glu Gln Ile Asn Asn Glu Leu Thr Gln Ala Lys Gln
                2725                2730                2735

Gly Leu Thr Val Asp Lys Gln Pro Leu Ile Asn Ala Lys Thr Ala Leu
            2740                2745                2750

Gln Gln Ser Leu Asp Asn Gln Pro Ser Thr Thr Gly Met Thr Glu Ala
            2755                2760                2765

Thr Ile Gln Asn Tyr Asn Ala Lys Arg Gln Lys Ala Glu Gln Val Ile
        2770                2775                2780

Gln Asn Ala Asn Lys Ile Ile Glu Asn Ala Gln Pro Ser Val Gln Gln
2785                2790                2795                2800

Val Ser Asp Glu Lys Ser Lys Val Glu Gln Ala Leu Ser Glu Leu Asn
            2805                2810                2815

Asn Ala Lys Ser Ala Leu Arg Ala Asp Lys Gln Glu Leu Gln Gln Ala
            2820                2825                2830

Tyr Asn Gln Leu Ile Gln Pro Thr Asp Leu Asn Asn Lys Pro Ala
        2835                2840                2845

Ser Ile Thr Ala Tyr Asn Gln Arg Tyr Gln Gln Phe Ser Asn Glu Leu
            2850                2855                2860

Asn Ser Thr Lys Thr Asn Thr Asp Arg Ile Leu Lys Glu Gln Asn Pro
2865                2870                2875                2880

Ser Val Ala Asp Val Asn Asn Ala Leu Asn Lys Val Arg Glu Val Gln
            2885                2890                2895

Gln Lys Leu Asn Glu Ala Arg Ala Leu Leu Gln Asn Lys Glu Asp Asn
        2900                2905                2910

Ser Ala Leu Val Arg Ala Lys Glu Gln Leu Gln Gln Ala Val Asp Gln
            2915                2920                2925

Val Pro Ser Thr Glu Gly Met Thr Gln Thr Lys Asp Asp Tyr Asn
        2930                2935                2940

Ser Lys Gln Gln Ala Ala Gln Gln Glu Ile Ser Lys Ala Gln Val
2945                2950                2955                2960

Ile Asp Asn Gly Asp Ala Thr Thr Gln Gln Ile Ser Asn Ala Lys Thr
            2965                2970                2975

Asn Val Glu Arg Ala Leu Glu Ala Leu Asn Asn Ala Lys Thr Gly Leu
            2980                2985                2990

Arg Ala Asp Lys Glu Glu Leu Gln Asn Ala Tyr Asn Gln Leu Thr Gln
        2995                3000                3005

Asn Ile Asp Thr Ser Gly Lys Thr Pro Ala Ser Ile Arg Lys Tyr Asn
        3010                3015                3020

Glu Ala Lys Ser Arg Ile Gln Thr Gln Ile Asp Ser Ala Lys Asn Glu
3025                3030                3035                3040

Ala Asn Ser Ile Leu Thr Asn Asp Asn Pro Gln Val Ser Gln Val Thr
            3045                3050                3055

Ala Ala Leu Asn Lys Ile Lys Ala Val Gln Pro Glu Leu Asp Lys Ala
            3060                3065                3070

Ile Ala Met Leu Lys Asn Lys Glu Asn Asn Ala Leu Val Gln Ala
        3075                3080                3085
```

Lys Gln Gln Leu Gln Gln Ile Val Asn Glu Val Asp Pro Thr Gln Gly
       3090                3095                3100

Met Thr Thr Asp Thr Ala Asn Asn Tyr Lys Ser Lys Lys Arg Glu Ala
3105                3110                3115                3120

Glu Asp Glu Ile Gln Lys Ala Gln Gln Ile Ile Asn Asn Gly Asp Ala
                3125                3130                3135

Thr Glu Gln Gln Ile Thr Asn Glu Thr Asn Arg Val Asn Gln Ala Ile
           3140                3145                3150

Asn Ala Ile Asn Lys Ala Lys Asn Asp Leu Arg Ala Asp Lys Ser Gln
           3155                3160                3165

Leu Glu Asn Ala Tyr Asn Gln Leu Ile Gln Asn Val Asp Thr Asn Gly
       3170                3175                3180

Lys Lys Pro Ala Ser Ile Gln Gln Tyr Gln Ala Ala Arg Gln Ala Ile
3185                3190                3195                3200

Glu Thr Gln Tyr Asn Asn Ala Lys Ser Glu Ala His Gln Ile Leu Glu
                3205                3210                3215

Asn Ser Asn Pro Ser Val Asn Glu Val Ala Gln Ala Leu Gln Lys Val
           3220                3225                3230

Glu Ala Val Gln Leu Lys Val Asn Asp Ala Ile His Ile Leu Gln Asn
       3235                3240                3245

Lys Glu Asn Asn Ser Ala Leu Val Thr Ala Lys Asn Gln Leu Gln Gln
       3250                3255                3260

Ser Val Asn Asp Gln Pro Leu Thr Thr Gly Met Thr Gln Asp Ser Ile
3265                3270                3275                3280

Asn Asn Tyr Glu Ala Lys Arg Asn Glu Ala Gln Ser Ala Ile Arg Asn
           3285                3290                3295

Ala Glu Ala Val Ile Asn Asn Gly Asp Ala Thr Ala Lys Gln Ile Ser
       3300                3305                3310

Asp Glu Lys Ser Lys Val Glu Gln Ala Leu Ala His Leu Asn Asp Ala
           3315                3320                3325

Lys Gln Gln Leu Thr Ala Asp Thr Thr Glu Leu Gln Thr Ala Val Gln
       3330                3335                3340

Gln Leu Asn Arg Arg Gly Asp Thr Asn Asn Lys Lys Pro Arg Ser Ile
3345                3350                3355                3360

Asn Ala Tyr Asn Lys Ala Ile Gln Ser Leu Glu Thr Gln Ile Thr Ser
           3365                3370                3375

Ala Lys Asp Asn Ala Asn Ala Val Ile Gln Lys Pro Ile Arg Thr Val
       3380                3385                3390

Gln Glu Val Asn Asn Ala Leu Gln Gln Val Asn Gln Leu Asn Gln Gln
       3395                3400                3405

Leu Thr Glu Ala Ile Asn Gln Leu Gln Pro Leu Ser Asn Asn Asp Ala
       3410                3415                3420

Leu Lys Ala Ala Arg Leu Asn Leu Glu Asn Lys Ile Asn Gln Thr Val
3425                3430                3435                3440

Gln Thr Asp Gly Met Thr Gln Gln Ser Ile Glu Ala Tyr Gln Asn Ala
                3445                3450                3455

Lys Arg Val Ala Gln Asn Glu Ser Asn Thr Ala Leu Ala Leu Ile Asn
           3460                3465                3470

Asn Gly Asp Ala Asp Glu Gln Gln Ile Thr Thr Glu Thr Asp Arg Val
           3475                3480                3485

Asn Gln Gln Thr Thr Asn Leu Thr Gln Ala Ile Asn Gly Leu Thr Val
       3490                3495                3500

Asn Lys Glu Pro Leu Glu Thr Ala Lys Thr Ala Leu Gln Asn Asn Ile

-continued

```
         3505                3510                3515                3520

Asp Gln Val Pro Ser Thr Asp Gly Met Thr Gln Gln Ser Val Ala Asn
            3525                3530                3535

Tyr Asn Gln Lys Leu Gln Ile Ala Lys Asn Glu Ile Asn Thr Ile Asn
            3540                3545                3550

Asn Val Leu Ala Asn Asn Pro Asp Val Asn Ala Ile Lys Thr Asn Lys
            3555                3560                3565

Ala Glu Ala Glu Arg Ile Ser Asn Asp Leu Thr Gln Ala Lys Asn Asn
            3570                3575                3580

Leu Gln Val Asp Thr Gln Pro Leu Glu Lys Ile Lys Arg Gln Leu Gln
3585                3590                3595                3600

Asp Glu Ile Asp Gln Gly Thr Asn Thr Asp Gly Met Thr Gln Asp Ser
            3605                3610                3615

Val Asp Asn Tyr Asn Asp Ser Leu Ser Ala Ala Ile Ile Glu Lys Gly
            3620                3625                3630

Lys Val Asn Lys Leu Leu Lys Arg Asn Pro Thr Val Glu Gln Val Lys
            3635                3640                3645

Glu Ser Val Ala Asn Ala Gln Gln Val Ile Gln Asp Leu Gln Asn Ala
            3650                3655                3660

Arg Thr Ser Leu Val Pro Asp Lys Thr Gln Leu Gln Glu Ala Lys Asn
3665                3670                3675                3680

Arg Leu Glu Asn Ser Ile Asn Gln Gln Thr Asp Thr Asp Gly Met Thr
            3685                3690                3695

Gln Asp Ser Leu Asn Asn Tyr Asn Asp Lys Leu Ala Lys Ala Arg Gln
            3700                3705                3710

Asn Leu Glu Lys Ile Ser Lys Val Leu Gly Gly Gln Pro Thr Val Ala
            3715                3720                3725

Glu Ile Arg Gln Asn Thr Asp Glu Ala Asn Ala His Lys Gln Ala Leu
            3730                3735                3740

Asp Thr Ala Arg Ser Gln Leu Thr Leu Asn Arg Glu Pro Tyr Ile Asn
3745                3750                3755                3760

His Ile Asn Asn Glu Ser His Leu Asn Asn Ala Gln Lys Asp Asn Phe
            3765                3770                3775

Lys Ala Gln Val Asn Ser Ala Pro Asn His Asn Thr Leu Glu Thr Ile
            3780                3785                3790

Lys Asn Lys Ala Asp Thr Leu Asn Gln Ser Met Thr Ala Leu Ser Glu
            3795                3800                3805

Ser Ile Ala Asp Tyr Glu Asn Gln Lys Gln Glu Asn Tyr Leu Asp
            3810                3815                3820

Ala Ser Asn Asn Lys Arg Gln Asp Tyr Asp Asn Ala Val Asn Ala Ala
3825                3830                3835                3840

Lys Gly Ile Leu Asn Gln Thr Gln Ser Pro Thr Met Ser Ala Asp Val
            3845                3850                3855

Ile Asp Gln Lys Ala Glu Asp Val Lys Arg Thr Lys Thr Ala Leu Asp
            3860                3865                3870

Gly Asn Gln Arg Leu Glu Val Ala Lys Gln Gln Ala Leu Asn His Leu
            3875                3880                3885

Asn Thr Leu Asn Asp Leu Asn Asp Ala Gln Arg Gln Thr Leu Thr Asp
            3890                3895                3900

Thr Ile Asn His Ser Pro Asn Ile Asn Ser Val Asn Gln Ala Lys Glu
3905                3910                3915                3920

Lys Ala Asn Thr Val Asn Thr Ala Met Thr Gln Leu Lys Gln Thr Ile
            3925                3930                3935
```

Ala Asn Tyr Asp Asp Glu Leu His Asp Gly Asn Tyr Ile Asn Ala Asp
            3940                3945                3950

Lys Asp Lys Lys Asp Ala Tyr Asn Asn Ala Val Asn Asn Ala Lys Gln
        3955                3960                3965

Leu Ile Asn Gln Ser Asp Ala Asn Gln Ala Gln Leu Asp Pro Ala Glu
        3970                3975                3980

Ile Asn Lys Val Thr Gln Arg Val Asn Thr Thr Lys Asn Asp Leu Asn
3985                3990                3995                4000

Gly Asn Asp Lys Leu Ala Glu Ala Lys Arg Asp Ala Asn Thr Thr Ile
        4005                4010                4015

Asp Gly Leu Thr Tyr Leu Asn Glu Ala Gln Arg Asn Lys Ala Lys Glu
        4020                4025                4030

Asn Val Gly Lys Ala Ser Thr Lys Thr Asn Ile Thr Ser Gln Leu Gln
        4035                4040                4045

Asp Tyr Asn Gln Leu Asn Ile Ala Met Gln Ala Leu Arg Asn Ser Val
        4050                4055                4060

Asn Asp Val Asn Asn Val Lys Ala Asn Ser Asn Tyr Ile Asn Glu Asp
4065                4070                4075                4080

Asn Gly Pro Lys Glu Ala Tyr Asn Gln Ala Val Thr His Ala Gln Thr
        4085                4090                4095

Leu Ile Asn Ala Gln Ser Asn Pro Glu Met Ser Arg Asp Val Val Asn
        4100                4105                4110

Gln Lys Thr Gln Ala Val Asn Thr Ala His Gln Asn Leu His Gly Gln
        4115                4120                4125

Gln Lys Leu Glu Gln Ala Gln Ser Ser Ala Asn Thr Glu Ile Gly Asn
        4130                4135                4140

Leu Pro Asn Leu Thr Asn Thr Gln Lys Ala Lys Glu Lys Glu Leu Val
4145                4150                4155                4160

Asn Ser Lys Gln Thr Arg Thr Glu Val Gln Glu Gln Leu Asn Gln Ala
        4165                4170                4175

Lys Ser Leu Asp Ser Ser Met Gly Thr Leu Lys Ser Leu Val Ala Lys
        4180                4185                4190

Gln Pro Thr Val Gln Lys Thr Ser Val Tyr Ile Asn Glu Asp Gln Pro
        4195                4200                4205

Glu Gln Ser Ala Tyr Asn Asp Ser Ile Thr Met Gly Gln Thr Ile Ile
        4210                4215                4220

Asn Lys Thr Ala Asp Pro Val Leu Asp Lys Thr Leu Val Asp Asn Ala
4225                4230                4235                4240

Ile Ser Asn Ile Ser Thr Lys Glu Asn Ala Leu His Gly Glu Gln Lys
        4245                4250                4255

Leu Thr Thr Ala Lys Thr Glu Ala Ile Asn Ala Leu Asn Thr Leu Ala
        4260                4265                4270

Asp Leu Asn Thr Pro Gln Lys Glu Ala Ile Lys Thr Ala Ile Asn Thr
        4275                4280                4285

Ala His Thr Arg Thr Asp Val Thr Ala Glu Gln Ser Lys Ala Asn Gln
        4290                4295                4300

Ile Asn Ser Ala Met His Thr Leu Arg Gln Asn Ile Ser Asp Asn Glu
4305                4310                4315                4320

Ser Val Thr Asn Glu Ser Asn Tyr Ile Asn Ala Glu Pro Lys Lys Gln
        4325                4330                4335

His Ala Phe Thr Glu Ala Leu Asn Asn Ala Lys Glu Ile Val Asn Glu
        4340                4345                4350

Gln Gln Ala Thr Leu Asp Ala Asn Ser Ile Asn Gln Lys Ala Gln Ala
        4355                4360                4365

```
Ile Leu Thr Thr Lys Asn Ala Leu Asp Gly Glu Glu Gln Leu Arg Arg
    4370                4375                4380

Ala Lys Glu Asn Ala Asp Gln Glu Ile Asn Thr Leu Asn Gln Leu Thr
4385                4390                4395                4400

Asp Ala Gln Arg Asn Ser Glu Lys Gly Leu Val Asn Ser Gln Thr
                4405                4410                4415

Arg Thr Glu Val Ala Ser Gln Leu Ala Lys Ala Lys Glu Leu Asn Lys
            4420                4425                4430

Val Met Glu Gln Leu Asn His Leu Ile Asn Gly Lys Asn Gln Met Ile
                4435                4440                4445

Asn Ser Ser Lys Phe Ile Asn Glu Asp Ala Asn Gln Gln Gln Ala Tyr
        4450                4455                4460

Ser Asn Ala Ile Ala Ser Ala Glu Ala Leu Lys Asn Lys Ser Gln Asn
4465                4470                4475                4480

Pro Glu Leu Asp Lys Val Thr Ile Glu Gln Ala Ile Asn Asn Ile Asn
                4485                4490                4495

Ser Ala Ile Asn Asn Leu Asn Gly Glu Ala Lys Leu Thr Lys Ala Lys
            4500                4505                4510

Glu Asp Ala Val Ala Ser Ile Asn Asn Leu Ser Gly Leu Thr Asn Glu
        4515                4520                4525

Gln Lys Thr Lys Glu Asn Gln Ala Val Asn Gly Ala Gln Thr Arg Asp
    4530                4535                4540

Gln Val Ala Asn Lys Leu Arg Asp Ala Glu Ala Leu Asp Gln Ser Met
4545                4550                4555                4560

Gln Thr Leu Arg Asp Leu Val Asn Asn Gln Asn Ala Ile His Ser Thr
                4565                4570                4575

Ser Asn Tyr Phe Asn Glu Asp Ser Thr Gln Lys Asn Thr Tyr Asp Asn
        4580                4585                4590

Ala Ile Asp Asn Gly Ser Thr Tyr Ile Thr Gly Gln His Asn Pro Glu
            4595                4600                4605

Leu Asn Lys Ser Thr Ile Asp Gln Thr Ile Ser Arg Ile Asn Thr Ala
    4610                4615                4620

Lys Asn Asp Leu His Gly Val Glu Lys Leu Gln Arg Asp Lys Gly Thr
4625                4630                4635                4640

Ala Asn Gln Glu Ile Gly Gln Leu Gly Tyr Leu Asn Asp Pro Gln Lys
                4645                4650                4655

Ser Gly Glu Glu Ser Leu Val Asn Gly Ser Asn Thr Arg Ser Glu Val
            4660                4665                4670

Glu Glu His Leu Asn Glu Ala Lys Ser Leu Asn Asn Ala Met Lys Gln
        4675                4680                4685

Leu Arg Asp Lys Val Ala Glu Lys Thr Asn Val Lys Gln Ser Ser Asp
    4690                4695                4700

Tyr Ile Asn Asp Ser Thr Glu His Gln Arg Gly Tyr Asp Gln Ala Leu
4705                4710                4715                4720

Gln Glu Ala Glu Asn Ile Ile Asn Glu Ile Gly Asn Pro Thr Leu Asn
                4725                4730                4735

Lys Ser Glu Ile Glu Gln Lys Leu Gln Gln Leu Thr Asp Ala Gln Asn
            4740                4745                4750

Ala Leu Gln Gly Ser His Leu Leu Glu Glu Ala Lys Asn Asn Ala Ile
        4755                4760                4765

Thr Gly Ile Asn Lys Leu Thr Ala Leu Asn Asp Ala Gln Arg Gln Lys
    4770                4775                4780

Ala Ile Glu Asn Val Gln Ala Gln Gln Thr Ile Pro Ala Val Asn Gln
```

```
                4785            4790            4795            4800
Gln Leu Thr Leu Asp Arg Glu Ile Asn Thr Ala Met Gln Ala Leu Arg
                    4805            4810            4815

Asp Lys Val Gly Gln Gln Asn Asn Val His Gln Gln Ser Asn Tyr Phe
            4820            4825            4830

Asn Glu Asp Glu Gln Pro Lys His Asn Tyr Asp Asn Ser Val Gln Ala
        4835            4840            4845

Gly Gln Thr Ile Ile Asp Lys Leu Gln Asp Pro Ile Met Asn Lys Asn
        4850            4855            4860

Glu Ile Glu Gln Ala Ile Asn Gln Ile Asn Thr Thr Gln Thr Ala Leu
4865            4870            4875            4880

Ser Gly Glu Asn Lys Leu His Thr Asp Gln Glu Ser Thr Asn Arg Gln
                4885            4890            4895

Ile Glu Gly Leu Ser Ser Leu Asn Thr Ala Gln Ile Asn Ala Glu Lys
            4900            4905            4910

Asp Leu Val Asn Gln Ala Lys Thr Arg Thr Asp Val Ala Gln Lys Leu
        4915            4920            4925

Ala Ala Ala Lys Glu Ile Asn Ser Ala Met Ser Asn Leu Arg Asp Gly
        4930            4935            4940

Ile Gln Asn Lys Glu Asp Ile Lys Arg Ser Ser Ala Tyr Ile Asn Ala
4945            4950            4955            4960

Asp Pro Thr Lys Val Thr Ala Tyr Asp Gln Ala Leu Gln Asn Ala Glu
                4965            4970            4975

Asn Ile Ile Asn Ala Thr Pro Asn Val Glu Leu Asn Lys Ala Thr Ile
            4980            4985            4990

Glu Gln Ala Leu Ser Arg Val Gln Gln Ala Gln Gln Asp Leu Asp Gly
        4995            5000            5005

Val Gln Gln Leu Ala Asn Ala Lys Gln Gln Ala Thr Gln Thr Val Asn
        5010            5015            5020

Gly Leu Asn Ser Leu Asn Asp Gly Gln Lys Arg Glu Leu Asn Leu Leu
5025            5030            5035            5040

Ile Asn Ser Ala Asn Thr Arg Thr Lys Val Gln Glu Glu Leu Asn Lys
                5045            5050            5055

Ala Thr Glu Leu Asn His Ala Met Glu Ala Leu Arg Asn Ser Val Gln
            5060            5065            5070

Asn Val Asp Gln Val Lys Gln Ser Ser Asn Tyr Val Asn Glu Asp Gln
        5075            5080            5085

Pro Glu Gln His Asn Tyr Asp Asn Ala Val Asn Glu Ala Gln Ala Thr
        5090            5095            5100

Ile Asn Asn Asn Ala Gln Pro Val Leu Asp Lys Leu Ala Ile Glu Arg
5105            5110            5115            5120

Leu Thr Gln Thr Val Asn Thr Thr Lys Asp Ala Leu His Gly Ala Gln
                5125            5130            5135

Lys Leu Thr Gln Asp Gln Gln Ala Ala Glu Thr Gly Ile Arg Gly Leu
            5140            5145            5150

Thr Ser Leu Asn Glu Pro Gln Lys Asn Ala Glu Val Ala Lys Val Thr
        5155            5160            5165

Ala Ala Thr Thr Arg Asp Glu Val Arg Asn Ile Arg Gln Glu Ala Thr
        5170            5175            5180

Thr Leu Asp Thr Ala Met Leu Gly Leu Arg Lys Ser Ile Lys Asp Lys
5185            5190            5195            5200

Asn Asp Thr Lys Asn Ser Ser Lys Tyr Ile Asn Glu Asp His Asp Gln
                5205            5210            5215
```

```
Gln Gln Ala Tyr Asp Asn Ala Val Asn Asn Ala Gln Val Ile Asp
            5220                5225                5230

Glu Thr Gln Ala Thr Leu Ser Ser Asp Thr Ile Asn Gln Leu Ala Asn
        5235                5240                5245

Ala Val Thr Gln Ala Lys Ser Asn Leu His Gly Asp Thr Lys Leu Gln
    5250                5255                5260

His Asp Lys Asp Ser Ala Lys Gln Thr Ile Ala Gln Leu Gln Asn Leu
5265                5270                5275                5280

Asn Ser Ala Gln Lys His Met Glu Asp Ser Leu Ile Asp Asn Glu Ser
            5285                5290                5295

Thr Arg Thr Gln Val Gln His Asp Leu Thr Glu Ala Gln Ala Leu Asp
        5300                5305                5310

Gly Leu Met Gly Ala Leu Lys Glu Ser Ile Lys Asp Tyr Thr Asn Ile
    5315                5320                5325

Val Ser Asn Gly Asn Tyr Ile Asn Ala Glu Pro Ser Lys Lys Gln Ala
    5330                5335                5340

Tyr Asp Ala Ala Val Gln Asn Ala Gln Asn Ile Ile Asn Gly Thr Asn
5345                5350                5355                5360

Gln Pro Thr Ile Asn Lys Gly Asn Val Thr Thr Ala Thr Gln Thr Val
        5365                5370                5375

Lys Asn Thr Lys Asp Ala Leu Asp Gly Asp His Arg Leu Glu Glu Ala
    5380                5385                5390

Lys Asn Asn Ala Asn Gln Thr Ile Arg Asn Leu Ser Asn Leu Asn Asn
        5395                5400                5405

Ala Gln Lys Asp Ala Glu Lys Asn Leu Val Asn Ser Ala Ser Thr Leu
    5410                5415                5420

Glu Gln Val Gln Gln Asn Leu Gln Thr Ala Gln Gln Leu Asp Asn Ala
5425                5430                5435                5440

Met Gly Glu Leu Arg Gln Ser Ile Ala Lys Lys Asp Gln Val Lys Ala
        5445                5450                5455

Asp Ser Lys Tyr Leu Asn Glu Asp Pro Gln Ile Lys Gln Asn Tyr Asp
    5460                5465                5470

Asp Ala Val Gln Arg Val Glu Thr Ile Ile Asn Glu Thr Gln Asn Pro
    5475                5480                5485

Glu Leu Leu Lys Ala Asn Ile Asp Gln Ala Thr Gln Ser Val Gln Asn
    5490                5495                5500

Ala Glu Gln Ala Leu His Gly Ala Glu Lys Leu Asn Gln Asp Lys Gln
5505                5510                5515                5520

Thr Ser Ser Thr Glu Leu Asp Gly Leu Thr Asp Leu Thr Asp Ala Gln
        5525                5530                5535

Arg Glu Lys Leu Arg Glu Gln Ile Asn Thr Ser Asn Ser Arg Asp Asp
        5540                5545                5550

Ile Lys Gln Lys Ile Glu Gln Ala Lys Ala Leu Asn Asp Ala Met Lys
    5555                5560                5565

Lys Leu Lys Glu Gln Val Ala Gln Lys Asp Gly Val His Ala Asn Ser
        5570                5575                5580

Asp Tyr Thr Asn Glu Asp Ser Ala Gln Lys Asp Ala Tyr Asn Asn Ala
5585                5590                5595                5600

Leu Lys Gln Ala Glu Asp Ile Ile Asn Asn Ser Ser Asn Pro Asn Leu
        5605                5610                5615

Asn Ala Gln Asp Ile Thr Asn Ala Leu Asn Asn Ile Lys Gln Ala Gln
        5620                5625                5630

Asp Asn Leu His Gly Ala Gln Lys Leu Gln Gln Asp Lys Asn Thr Thr
        5635                5640                5645
```

```
Asn Gln Ala Ile Gly Asn Leu Asn His Leu Asn Gln Pro Gln Lys Asp
            5650                5655                5660
Ala Leu Ile Gln Ala Ile Asn Gly Ala Thr Ser Arg Asp Gln Val Ala
5665                5670                5675                5680
Glu Lys Leu Lys Glu Ala Glu Ala Leu Asp Glu Ala Met Lys Gln Leu
            5685                5690                5695
Glu Asp Gln Val Asn Gln Asp Gln Ile Ser Asn Ser Ser Pro Phe
            5700                5705                5710
Ile Asn Glu Asp Ser Asp Lys Gln Lys Thr Tyr Asn Asp Lys Ile Gln
            5715                5720                5725
Ala Ala Lys Glu Ile Ile Asn Gln Thr Ser Asn Pro Thr Leu Asp Lys
            5730                5735                5740
Gln Lys Ile Ala Asp Thr Leu Gln Asn Ile Lys Asp Ala Val Asn Asn
5745                5750                5755                5760
Leu His Gly Asp Gln Lys Leu Ala Gln Ser Lys Gln Asp Ala Asn Asn
            5765                5770                5775
Gln Leu Asn His Leu Asp Asp Leu Thr Glu Glu Gln Lys Asn His Phe
            5780                5785                5790
Lys Pro Leu Ile Asn Asn Ala Asp Thr Arg Asp Glu Val Asn Lys Gln
            5795                5800                5805
Leu Glu Ile Ala Lys Gln Leu Asn Gly Asp Met Ser Thr Leu His Lys
            5810                5815                5820
Val Ile Asn Asp Lys Asp Gln Ile Gln His Leu Ser Asn Tyr Ile Asn
5825                5830                5835                5840
Ala Asp Asn Asp Lys Lys Gln Asn Tyr Asp Asn Ala Ile Lys Glu Ala
            5845                5850                5855
Glu Asp Leu Ile His Asn His Pro Asp Thr Leu Asp His Lys Ala Leu
            5860                5865                5870
Gln Asp Leu Leu Asn Lys Ile Asp Gln Ala His Asn Glu Leu Asn Gly
            5875                5880                5885
Glu Ser Arg Phe Lys Gln Ala Leu Asp Asn Ala Leu Asn Asp Ile Asp
            5890                5895                5900
Ser Leu Asn Ser Leu Asn Val Pro Gln Arg Gln Thr Val Lys Asp Asn
5905                5910                5915                5920
Ile Asn His Val Thr Thr Leu Glu Ser Leu Ala Gln Glu Leu Gln Lys
            5925                5930                5935
Ala Lys Glu Leu Asn Asp Ala Met Lys Ala Met Arg Asp Ser Ile Met
            5940                5945                5950
Asn Gln Glu Gln Ile Arg Lys Asn Ser Asn Tyr Thr Asn Glu Asp Leu
            5955                5960                5965
Ala Gln Gln Asn Ala Tyr Asn His Ala Val Asp Lys Ile Asn Asn Ile
            5970                5975                5980
Ile Gly Glu Asp Asn Ala Thr Met Asp Pro Gln Ile Ile Lys Gln Ala
5985                5990                5995                6000
Thr Gln Asp Ile Asn Thr Ala Ile Asn Gly Leu Asn Gly Asp Gln Lys
            6005                6010                6015
Leu Gln Asp Ala Lys Thr Asp Ala Lys Gln Gln Ile Thr Asn Phe Thr
            6020                6025                6030
Gly Leu Thr Glu Pro Gln Lys Gln Ala Leu Glu Asn Ile Ile Asn Gln
            6035                6040                6045
Gln Thr Ser Arg Ala Asn Val Ala Lys Gln Leu Ser His Ala Lys Phe
            6050                6055                6060
Leu Asn Gly Lys Met Glu Glu Leu Lys Val Ala Val Ala Lys Ala Ser
```

```
                6065                6070                6075                6080
Leu Val Arg Gln Asn Ser Asn Tyr Ile Asn Glu Asp Val Ser Glu Lys
                6085                6090                6095
Glu Ala Tyr Glu Gln Ala Ile Ala Lys Gly Gln Glu Ile Ile Asn Ser
                6100                6105                6110
Glu Asn Asn Pro Thr Ile Ser Ser Thr Asp Ile Asn Arg Thr Ile Gln
                6115                6120                6125
Glu Ile Asn Asp Ala Glu Gln Asn Leu His Gly Asp Asn Lys Leu Arg
                6130                6135                6140
Gln Ala Gln Glu Ile Ala Lys Asn Glu Ile Gln Asn Leu Asp Gly Leu
6145                6150                6155                6160
Asn Ser Ala Gln Ile Thr Lys Leu Ile Gln Asp Ile Gly Arg Thr Thr
                6165                6170                6175
Thr Lys Pro Ala Val Thr Gln Lys Leu Glu Glu Ala Lys Ala Ile Asn
                6180                6185                6190
Gln Ala Met Gln Gln Leu Lys Gln Ser Ile Ala Asp Lys Asp Ala Thr
                6195                6200                6205
Leu Asn Ser Ser Asn Tyr Leu Asn Glu Asp Ser Glu Lys Lys Leu Ala
                6210                6215                6220
Tyr Asp Asn Ala Val Ser Gln Ala Glu Gln Leu Ile Asn Gln Leu Asn
6225                6230                6235                6240
Asp Pro Thr Met Asp Ile Ser Asn Ile Gln Ala Ile Thr Gln Lys Val
                6245                6250                6255
Ile Gln Ala Lys Asp Ser Leu His Gly Ala Asn Lys Leu Ala Gln Asn
                6260                6265                6270
Gln Ala Asp Ser Asn Leu Ile Ile Asn Gln Ser Thr Asn Leu Asn Asp
                6275                6280                6285
Lys Gln Lys Gln Ala Leu Asn Asp Leu Ile Asn His Ala Gln Thr Lys
                6290                6295                6300
Gln Gln Val Ala Glu Ile Ile Ala Gln Ala Asn Lys Leu Asn Asn Glu
6305                6310                6315                6320
Met Gly Thr Leu Lys Thr Leu Val Glu Glu Gln Ser Asn Val His Gln
                6325                6330                6335
Gln Ser Lys Tyr Ile Asn Glu Asp Pro Gln Val Gln Asn Ile Tyr Asn
                6340                6345                6350
Asp Ser Ile Gln Lys Gly Arg Glu Ile Leu Asn Gly Thr Asp Asp
                6355                6360                6365
Val Leu Asn Asn Asn Lys Ile Ala Asp Ala Ile Gln Asn Ile His Leu
                6370                6375                6380
Thr Lys Asn Asp Leu His Gly Asp Gln Lys Leu Gln Lys Ala Gln Gln
6385                6390                6395                6400
Asp Ala Thr Asn Glu Leu Asn Tyr Leu Thr Asn Leu Asn Asn Ser Gln
                6405                6410                6415
Arg Gln Ser Glu His Asp Glu Ile Asn Ser Ala Pro Ser Arg Thr Glu
                6420                6425                6430
Val Ser Asn Asp Leu Asn His Ala Lys Ala Leu Asn Glu Ala Met Arg
                6435                6440                6445
Gln Leu Glu Asn Glu Val Ala Leu Glu Asn Ser Val Lys Lys Leu Ser
                6450                6455                6460
Asp Phe Ile Asn Glu Asp Glu Ala Ala Gln Asn Glu Tyr Ser Asn Ala
6465                6470                6475                6480
Leu Gln Lys Ala Lys Asp Ile Ile Asn Gly Val Pro Ser Ser Thr Leu
                6485                6490                6495
```

```
Asp Lys Ala Thr Ile Glu Asp Ala Leu Leu Glu Leu Gln Asn Ala Arg
            6500                6505                6510
Glu Ser Leu His Gly Glu Gln Lys Leu Gln Glu Ala Lys Asn Gln Ala
        6515                6520                6525
Val Ala Glu Ile Asp Asn Leu Gln Ala Leu Asn Pro Gly Gln Val Leu
    6530                6535                6540
Ala Glu Lys Thr Leu Val Asn Gln Ala Ser Thr Lys Pro Glu Val Gln
6545                6550                6555                6560
Glu Ala Leu Gln Lys Ala Lys Glu Leu Asn Glu Ala Met Lys Ala Leu
            6565                6570                6575
Lys Thr Glu Ile Asn Lys Lys Glu Gln Ile Lys Ala Asp Ser Arg Tyr
        6580                6585                6590
Val Asn Ala Asp Ser Gly Leu Gln Ala Asn Tyr Asn Ser Ala Leu Asn
    6595                6600                6605
Tyr Gly Ser Gln Ile Ile Ala Thr Thr Gln Pro Glu Leu Asn Lys
6610                6615                6620
Asp Val Ile Asn Arg Ala Thr Gln Thr Ile Lys Thr Ala Glu Asn Asn
6625                6630                6635                6640
Leu Asn Gly Gln Ser Lys Leu Ala Glu Ala Lys Ser Asp Gly Asn Gln
            6645                6650                6655
Ser Ile Glu His Leu Gln Gly Leu Thr Gln Ser Gln Lys Asp Lys Gln
        6660                6665                6670
His Asp Leu Ile Asn Gln Ala Gln Thr Lys Gln Gln Val Asp Asp Ile
    6675                6680                6685
Val Asn Asn Ser Lys Gln Leu Asp Asn Ser Met Asn Gln Leu Gln Gln
    6690                6695                6700
Ile Val Asn Asn Asp Asn Thr Val Lys Gln Asn Ser Asp Phe Ile Asn
6705                6710                6715                6720
Glu Asp Ser Ser Gln Gln Asp Ala Tyr Asn His Ala Ile Gln Ala Ala
            6725                6730                6735
Lys Asp Leu Ile Thr Ala His Pro Thr Ile Met Asp Lys Asn Gln Ile
        6740                6745                6750
Asp Gln Ala Ile Glu Asn Ile Lys Gln Ala Leu Asn Asp Leu His Gly
    6755                6760                6765
Ser Asn Lys Leu Ser Glu Asp Lys Lys Glu Ala Ser Glu Gln Leu Gln
    6770                6775                6780
Asn Leu Asn Ser Leu Thr Asn Gly Gln Lys Asp Thr Ile Leu Asn His
6785                6790                6795                6800
Ile Phe Ser Ala Pro Thr Arg Ser Gln Val Gly Glu Lys Ile Ala Ser
            6805                6810                6815
Ala Lys Gln Leu Asn Asn Thr Met Lys Ala Leu Arg Asp Ser Ile Ala
        6820                6825                6830
Asp Asn Asn Glu Ile Leu Gln Ser Ser Lys Tyr Phe Asn Glu Asp Ser
    6835                6840                6845
Glu Gln Gln Asn Ala Tyr Asn Gln Ala Val Asn Lys Ala Lys Asn Ile
    6850                6855                6860
Ile Asn Asp Gln Pro Thr Pro Val Met Ala Asn Asp Glu Ile Gln Ser
6865                6870                6875                6880
Val Leu Asn Glu Val Lys Gln Thr Lys Asp Asn Leu His Gly Asp Gln
            6885                6890                6895
Lys Leu Ala Asn Asp Lys Thr Asp Ala Gln Ala Thr Leu Asn Ala Leu
        6900                6905                6910
Asn Tyr Leu Asn Gln Ala Gln Arg Gly Asn Leu Glu Thr Lys Val Gln
    6915                6920                6925
```

```
Asn Ser Asn Ser Arg Pro Glu Val Gln Lys Val Gln Leu Ala Asn
        6930                6935                6940

Gln Leu Asn Asp Ala Met Lys Lys Leu Asp Asp Ala Leu Thr Gly Asn
6945                6950                6955                6960

Asp Ala Ile Lys Gln Thr Ser Asn Tyr Ile Asn Glu Asp Thr Ser Gln
            6965                6970                6975

Gln Val Asn Phe Asp Glu Tyr Thr Asp Arg Gly Lys Asn Ile Val Ala
        6980                6985                6990

Glu Gln Thr Asn Pro Asn Met Ser Pro Thr Asn Ile Asn Thr Ile Ala
            6995                7000                7005

Asp Lys Ile Thr Glu Ala Lys Asn Asp Leu His Gly Val Gln Lys Leu
        7010                7015                7020

Lys Gln Ala Gln Gln Ser Ile Asn Thr Ile Asn Gln Met Thr Gly
7025                7030                7035                7040

Leu Asn Gln Ala Gln Lys Glu Gln Leu Asn Gln Glu Ile Gln Gln Thr
            7045                7050                7055

Gln Thr Arg Ser Glu Val His Gln Val Ile Asn Lys Ala Gln Ala Leu
        7060                7065                7070

Asn Asp Ser Met Asn Thr Leu Arg Gln Ser Ile Thr Asp Glu His Glu
        7075                7080                7085

Val Lys Gln Thr Ser Asn Tyr Ile Asn Glu Thr Val Gly Asn Gln Thr
        7090                7095                7100

Ala Tyr Asn Asn Ala Val Asp Arg Val Lys Gln Ile Ile Asn Gln Thr
7105                7110                7115                7120

Ser Asn Pro Thr Met Asn Pro Leu Glu Val Glu Arg Ala Thr Ser Asn
            7125                7130                7135

Val Lys Ile Ser Lys Asp Ala Leu His Gly Arg Glu Leu Asn Asp
            7140                7145                7150

Asn Lys Asn Ser Lys Thr Phe Ala Val Asn His Leu Asp Asn Leu Asn
        7155                7160                7165

Gln Ala Gln Lys Glu Ala Leu Thr His Glu Ile Glu Gln Ala Thr Ile
        7170                7175                7180

Val Ser Gln Val Asn Asn Ile Tyr Asn Lys Ala Lys Ala Leu Asn Asn
7185                7190                7195                7200

Asp Met Lys Lys Leu Lys Asp Ile Val Ala Gln Gln Asp Asn Val Arg
            7205                7210                7215

Gln Ser Asn Asn Tyr Ile Asn Glu Asp Ser Thr Pro Gln Asn Met Tyr
            7220                7225                7230

Asn Asp Thr Ile Asn His Ala Gln Ser Ile Ile Asp Gln Val Ala Asn
        7235                7240                7245

Pro Thr Met Ser His Asp Glu Ile Glu Asn Ala Ile Asn Asn Ile Lys
        7250                7255                7260

His Ala Ile Asn Ala Leu Asp Gly Glu His Lys Leu Gln Gln Ala Lys
7265                7270                7275                7280

Glu Asn Ala Asn Leu Leu Ile Asn Ser Leu Asn Asp Leu Asn Ala Pro
            7285                7290                7295

Gln Arg Asp Ala Ile Asn Arg Leu Val Asn Glu Ala Gln Thr Arg Glu
            7300                7305                7310

Lys Val Ala Glu Gln Leu Gln Ser Ala Gln Ala Leu Asn Asp Ala Met
        7315                7320                7325

Lys His Leu Arg Asn Ser Ile Gln Asn Gln Ser Ser Val Arg Gln Glu
        7330                7335                7340

Ser Lys Tyr Ile Asn Ala Ser Asp Ala Lys Lys Glu Gln Tyr Asn His
```

```
                7345                7350                7355                7360
Ala Val Arg Glu Val Glu Asn Ile Ile Asn Glu Gln His Pro Thr Leu
                    7365                7370                7375
Asp Lys Glu Ile Ile Lys Gln Leu Thr Asp Gly Val Asn Gln Ala Asn
                    7380                7385                7390
Asn Asp Leu Asn Gly Val Glu Leu Leu Asp Ala Asp Lys Gln Asn Ala
                    7395                7400                7405
His Gln Ser Ile Pro Thr Leu Met His Leu Asn Gln Ala Gln Gln Asn
                    7410                7415                7420
Ala Leu Asn Glu Lys Ile Asn Asn Ala Val Thr Arg Thr Glu Val Ala
7425                7430                7435                7440
Ala Ile Ile Gly Gln Ala Lys Leu Leu Asp His Ala Met Glu Asn Leu
                    7445                7450                7455
Glu Glu Ser Ile Lys Asp Lys Glu Gln Val Lys Gln Ser Ser Asn Tyr
                    7460                7465                7470
Ile Asn Glu Asp Ser Asp Val Gln Glu Thr Tyr Asp Asn Ala Val Asp
                    7475                7480                7485
His Val Thr Glu Ile Leu Asn Gln Thr Val Asn Pro Thr Leu Ser Ile
                    7490                7495                7500
Glu Asp Ile Glu His Ala Ile Asn Glu Val Asn Gln Ala Lys Lys Gln
7505                7510                7515                7520
Leu Arg Gly Lys Gln Lys Leu Tyr Gln Thr Ile Asp Leu Ala Asp Lys
                    7525                7530                7535
Glu Leu Ser Lys Leu Asp Asp Leu Thr Ser Gln Gln Ser Ser Ser Ile
                    7540                7545                7550
Ser Asn Gln Ile Tyr Thr Ala Lys Thr Arg Thr Glu Val Ala Gln Ala
                    7555                7560                7565
Ile Glu Lys Ala Lys Ser Leu Asn His Ala Met Lys Ala Leu Asn Lys
                    7570                7575                7580
Val Tyr Lys Asn Ala Asp Lys Val Leu Asp Ser Ser Arg Phe Ile Asn
7585                7590                7595                7600
Glu Asp Gln Pro Glu Lys Lys Ala Tyr Gln Gln Ala Ile Asn His Val
                    7605                7610                7615
Asp Ser Ile Ile His Arg Gln Thr Asn Pro Glu Met Asp Pro Thr Val
                    7620                7625                7630
Ile Asn Ser Ile Thr His Glu Leu Glu Thr Ala Gln Asn Asn Leu His
                    7635                7640                7645
Gly Asp Gln Lys Leu Ala His Ala Gln Gln Asp Ala Ala Asn Val Ile
                    7650                7655                7660
Asn Gly Leu Ile His Leu Asn Val Ala Gln Arg Glu Val Met Ile Asn
7665                7670                7675                7680
Thr Asn Thr Asn Ala Thr Thr Arg Glu Lys Val Ala Lys Asn Leu Asp
                    7685                7690                7695
Asn Ala Gln Ala Leu Asp Lys Ala Met Glu Thr Leu Gln Val Val
                    7700                7705                7710
Ala His Lys Asn Asn Ile Leu Asn Asp Ser Lys Tyr Leu Asn Glu Asp
                    7715                7720                7725
Ser Lys Tyr Gln Gln Gln Tyr Asp Arg Val Ile Ala Asp Ala Glu Gln
                    7730                7735                7740
Leu Leu Asn Gln Thr Thr Asn Pro Thr Leu Glu Pro Tyr Lys Val Asp
7745                7750                7755                7760
Ile Val Lys Asp Asn Val Leu Ala Asn Glu Lys Ile Leu Phe Gly Ala
                    7765                7770                7775
```

-continued

Glu Lys Leu Ser Tyr Asp Lys Ser Asn Ala Asn Asp Glu Ile Lys His
            7780                7785                7790

Met Asn Tyr Leu Asn Asn Ala Gln Lys Gln Ser Ile Lys Asp Met Ile
        7795                7800                7805

Ser His Ala Ala Leu Arg Thr Glu Val Lys Gln Leu Leu Gln Gln Ala
        7810                7815                7820

Lys Ile Leu Asp Glu Ala Met Lys Ser Leu Glu Asp Lys Thr Gln Val
7825                7830                7835                7840

Val Ile Thr Asp Thr Thr Leu Pro Asn Tyr Thr Glu Ala Ser Glu Asp
            7845                7850                7855

Lys Lys Glu Lys Val Asp Gln Thr Val Ser His Ala Gln Ala Ile Ile
        7860                7865                7870

Asp Lys Ile Asn Gly Ser Asn Val Ser Leu Asp Gln Val Arg Gln Ala
        7875                7880                7885

Leu Glu Gln Leu Thr Gln Ala Ser Glu Asn Leu Asp Gly Asp Gln Arg
        7890                7895                7900

Val Glu Glu Ala Lys Val His Ala Asn Gln Thr Ile Asp Gln Leu Thr
7905                7910                7915                7920

His Leu Asn Ser Leu Gln Gln Gln Thr Ala Lys Glu Ser Val Lys Asn
            7925                7930                7935

Ala Thr Lys Leu Glu Glu Ile Ala Thr Val Ser Asn Asn Ala Gln Ala
            7940                7945                7950

Leu Asn Lys Val Met Gly Lys Leu Glu Gln Phe Ile Asn His Ala Asp
            7955                7960                7965

Ser Val Glu Asn Ser Asp Asn Tyr Arg Gln Ala Asp Asp Lys Ile
            7970                7975                7980

Ile Ala Tyr Asp Glu Ala Leu Glu His Gly Gln Asp Ile Gln Lys Thr
7985                7990                7995                8000

Asn Ala Thr Gln Asn Glu Thr Lys Gln Ala Leu Gln Gln Leu Ile Tyr
            8005                8010                8015

Ala Glu Thr Ser Leu Asn Gly Phe Glu Arg Leu Asn His Ala Arg Pro
            8020                8025                8030

Arg Ala Leu Glu Tyr Ile Lys Ser Leu Glu Lys Ile Asn Asn Ala Gln
            8035                8040                8045

Lys Ser Ala Leu Glu Asp Lys Val Thr Gln Ser His Asp Leu Leu Glu
        8050                8055                8060

Leu Glu His Ile Val Asn Glu Gly Thr Asn Leu Asn Asp Ile Met Gly
8065                8070                8075                8080

Glu Leu Ala Asn Ala Ile Val Asn Asn Tyr Ala Pro Thr Lys Ala Ser
            8085                8090                8095

Ile Asn Tyr Ile Asn Ala Asp Asn Leu Arg Lys Asp Asn Phe Thr Gln
            8100                8105                8110

Ala Ile Asn Asn Ala Arg Asp Ala Leu Asn Lys Thr Gln Gly Gln Asn
            8115                8120                8125

Leu Asp Phe Asn Ala Ile Asp Thr Phe Lys Asp Ile Phe Lys Thr
        8130                8135                8140

Lys Asp Ala Leu Asn Gly Ile Glu Arg Leu Thr Ala Ala Lys Ser Lys
8145                8150                8155                8160

Ala Glu Lys Leu Ile Asp Ser Leu Lys Phe Ile Asn Lys Ala Gln Phe
            8165                8170                8175

Thr His Ala Asn Asp Glu Ile Met Asn Thr Asn Ser Ile Ala Gln Leu
            8180                8185                8190

Ser Arg Ile Val Asn Gln Ala Phe Asp Leu Asn Asp Ala Met Lys Ser
        8195                8200                8205

```
Leu Arg Asp Glu Leu Asn Asn Gln Ala Phe Pro Val Gln Ala Ser Ser
    8210                8215                8220

Asn Tyr Ile Asn Ser Asp Glu Asp Leu Lys Gln Gln Phe Asp His Ala
8225                8230                8235                8240

Leu Ser Asn Ala Arg Lys Val Leu Ala Lys Glu Asn Gly Lys Asn Leu
            8245                8250                8255

Asp Glu Lys Gln Ile Gln Gly Leu Lys Gln Val Ile Glu Asp Thr Lys
            8260                8265                8270

Asp Ala Leu Asn Gly Ile Gln Arg Leu Ser Lys Ala Lys Ala Lys Ala
            8275                8280                8285

Ile Gln Tyr Val Gln Ser Leu Ser Tyr Ile Asn Asp Ala Gln Arg His
            8290                8295                8300

Ile Ala Glu Asn Asn Ile His Asn Ser Asp Asp Leu Ser Ser Leu Ala
8305                8310                8315                8320

Asn Thr Leu Ser Lys Ala Ser Asp Leu Asp Asn Ala Met Lys Asp Leu
            8325                8330                8335

Arg Asp Thr Ile Glu Ser Asn Ser Thr Ser Val Pro Asn Ser Val Asn
            8340                8345                8350

Tyr Ile Asn Ala Asp Lys Asn Leu Gln Ile Glu Phe Asp Glu Ala Leu
            8355                8360                8365

Gln Gln Ala Ser Ala Thr Ser Ser Lys Thr Ser Glu Asn Pro Ala Thr
            8370                8375                8380

Ile Glu Glu Val Leu Gly Leu Ser Gln Ala Ile Tyr Asp Thr Lys Asn
8385                8390                8395                8400

Ala Leu Asn Gly Glu Gln Arg Leu Ala Thr Glu Lys Ser Lys Asp Leu
            8405                8410                8415

Lys Leu Ile Lys Gly Leu Lys Asp Leu Asn Lys Ala Gln Leu Glu Asp
            8420                8425                8430

Val Thr Asn Lys Val Asn Ser Ala Asn Thr Leu Thr Glu Leu Ser Gln
            8435                8440                8445

Leu Thr Gln Ser Thr Leu Glu Leu Asn Asp Lys Met Lys Leu Leu Arg
            8450                8455                8460

Asp Lys Leu Lys Thr Leu Val Asn Pro Val Lys Ala Ser Leu Asn Tyr
8465                8470                8475                8480

Arg Asn Ala Asp Tyr Asn Leu Lys Arg Gln Phe Asn Lys Ala Leu Lys
            8485                8490                8495

Glu Ala Lys Gly Val Leu Asn Lys Asn Ser Gly Thr Asn Val Asn Ile
            8500                8505                8510

Asn Asp Ile Gln His Leu Leu Thr Gln Ile Asp Asn Ala Lys Asp Gln
            8515                8520                8525

Leu Asn Gly Glu Arg Arg Leu Lys Glu His Gln Gln Lys Ser Glu Val
            8530                8535                8540

Phe Ile Ile Lys Glu Leu Asp Ile Leu Asn Asn Ala Gln Lys Ala Ala
8545                8550                8555                8560

Ile Ile Asn Gln Ile Arg Ala Ser Lys Asp Ile Lys Ile Ile Asn Gln
            8565                8570                8575

Ile Val Asp Asn Ala Ile Glu Leu Asn Asp Ala Met Gln Gly Leu Lys
            8580                8585                8590

Glu His Val Ala Gln Leu Thr Ala Thr Thr Lys Asp Asn Ile Glu Tyr
            8595                8600                8605

Leu Asn Ala Asp Glu Asp His Lys Leu Gln Tyr Asp Tyr Ala Ile Asn
            8610                8615                8620

Leu Ala Asn Asn Val Leu Asp Lys Glu Asn Gly Thr Asn Lys Asp Ala
```

```
               8625                8630                8635                8640
Asn Ile Ile Ile Gly Met Ile Gln Asn Met Asp Asp Ala Arg Ala Leu
               8645                8650                8655
Leu Asn Gly Ile Glu Arg Leu Lys Asp Ala Gln Thr Lys Ala His Asn
               8660                8665                8670
Asp Ile Lys Asp Thr Leu Lys Arg Gln Leu Asp Glu Ile Glu His Ala
               8675                8680                8685
Asn Ala Thr Ser Asn Ser Lys Ala Gln Ala Lys Gln Met Val Asn Glu
               8690                8695                8700
Glu Ala Arg Lys Ala Leu Ser Asn Ile Asn Asp Ala Thr Ser Asn Asp
8705                8710                8715                8720
Leu Val Asn Gln Ala Lys Asp Glu Gly Gln Ser Ala Ile Glu His Ile
               8725                8730                8735
His Ala Asp Glu Leu Pro Lys Ala Lys Leu Asp Ala Asn Gln Met Ile
               8740                8745                8750
Asp Gln Lys Val Glu Asp Ile Asn His Leu Ile Ser Gln Asn Pro Asn
               8755                8760                8765
Leu Ser Asn Glu Glu Lys Asn Lys Leu Ile Ser Gln Ile Asn Lys Leu
               8770                8775                8780
Val Asn Gly Ile Lys Asn Glu Ile Gln Gln Ala Ile Asn Lys Gln Gln
8785                8790                8795                8800
Ile Glu Asn Ala Thr Thr Lys Leu Asp Glu Val Ile Glu Thr Thr Lys
               8805                8810                8815
Lys Leu Ile Ile Ala Lys Ala Glu Ala Lys Gln Met Ile Lys Glu Leu
               8820                8825                8830
Ser Gln Lys Lys Arg Asp Ala Ile Asn Asn Asn Thr Asp Leu Thr Pro
               8835                8840                8845
Ser Gln Lys Ala His Ala Leu Ala Asp Ile Asp Lys Thr Glu Lys Asp
               8850                8855                8860
Ala Leu Gln His Ile Glu Asn Ser Asn Ser Ile Asp Asp Ile Asn Asn
8865                8870                8875                8880
Asn Lys Glu His Ala Phe Asn Thr Leu Ala His Ile Ile Ile Trp Asp
               8885                8890                8895
Thr Asp Gln Gln Pro Leu Val Phe Glu Leu Pro Glu Leu Ser Leu Gln
               8900                8905                8910
Asn Ala Leu Val Thr Ser Glu Val Val His Arg Asp Glu Thr Ile
               8915                8920                8925
Ser Leu Glu Ser Ile Ile Gly Ala Met Thr Leu Thr Asp Glu Leu Lys
               8930                8935                8940
Val Asn Ile Val Ser Leu Pro Asn Thr Asp Lys Val Ala Asp His Leu
8945                8950                8955                8960
Thr Ala Lys Val Lys Val Ile Leu Ala Asp Gly Ser Tyr Val Thr Val
               8965                8970                8975
Asn Val Pro Val Lys Val Glu Lys Glu Leu Gln Ile Ala Lys Lys
               8980                8985                8990
Asp Ala Ile Lys Thr Ile Asp Val Leu Val Lys Gln Lys Ile Lys Asp
               8995                9000                9005
Ile Asp Ser Asn Asn Glu Leu Thr Ser Thr Gln Arg Glu Asp Ala Lys
               9010                9015                9020
Ala Glu Ile Glu Arg Leu Lys Lys Gln Ala Ile Asp Lys Val Asn His
9025                9030                9035                9040
Ser Lys Ser Ile Lys Asp Ile Glu Thr Val Lys Arg Thr Asp Phe Glu
               9045                9050                9055
```

```
Glu Ile Asp Gln Phe Asp Pro Lys Arg Phe Thr Leu Asn Lys Ala Lys
            9060                9065                9070

Lys Asp Ile Ile Thr Asp Val Asn Thr Gln Ile Gln Asn Gly Phe Lys
    9075                9080                9085

Glu Ile Glu Thr Ile Lys Gly Leu Thr Ser Asn Glu Lys Thr Gln Phe
    9090                9095                9100

Asp Lys Gln Leu Thr Ala Leu Gln Lys Glu Phe Leu Glu Lys Val Glu
9105                9110                9115                9120

His Ala His Asn Leu Val Glu Leu Asn Gln Leu Gln Gln Glu Phe Asn
            9125                9130                9135

Asn Arg Tyr Lys His Ile Leu Asn Gln Ala His Leu Leu Gly Glu Lys
            9140                9145                9150

His Ile Ala Glu His Lys Leu Gly Tyr Val Val Asn Lys Thr Gln
            9155                9160                9165

Gln Ile Leu Asn Asn Gln Ser Ala Ser Tyr Phe Ile Lys Gln Trp Ala
            9170                9175                9180

Leu Asp Arg Ile Lys Gln Ile Gln Leu Glu Thr Met Asn Ser Ile Arg
9185                9190                9195                9200

Gly Ala His Thr Val Gln Asp Val His Lys Ala Leu Leu Gln Gly Ile
            9205                9210                9215

Glu Gln Ile Leu Lys Val Asn Val Ser Ile Ile Asn Gln Ser Phe Asn
            9220                9225                9230

Asp Ser Leu His Asn Phe Asn Tyr Leu His Ser Lys Phe Asp Ala Arg
            9235                9240                9245

Leu Arg Glu Lys Asp Val Ala Asn His Ile Val Gln Thr Glu Thr Phe
            9250                9255                9260

Lys Glu Val Leu Lys Gly Thr Gly Val Glu Pro Gly Lys Ile Asn Lys
9265                9270                9275                9280

Glu Thr Gln Gln Pro Lys Leu His Lys Asn Asp Asn Asp Ser Leu Phe
            9285                9290                9295

Lys His Leu Val Asp Asn Phe Gly Leu Thr Val Gly Val Ile Thr Leu
            9300                9305                9310

Thr Gly Leu Leu Ser Ser Phe Trp Leu Val Leu Ala Lys Arg Arg Lys
            9315                9320                9325

Lys Glu Glu Glu Glu Lys Gln Ser Ile Lys Asn His His Lys Asp Ile
            9330                9335                9340

Arg Leu Ser Asp Thr Asp Lys Ile Asp Pro Ile Val Ile Thr Lys Arg
9345                9350                9355                9360

Lys Ile Asp Lys Glu Glu Gln Ile Gln Asn Asp Lys His Ser Ile
            9365                9370                9375

Pro Val Ala Lys His Lys Lys Ser Lys Glu Lys Gln Leu Ser Glu Glu
            9380                9385                9390

Asp Ile His Ser Ile Pro Val Val Lys Arg Lys Gln Asn Ser Asp Asn
            9395                9400                9405

Lys Asp Thr Lys Gln Lys Lys Val Thr Ser Lys Lys Lys Thr Pro
9410                9415                9420

Gln Ser Thr Lys Lys Val Val Lys Thr Lys Arg Ser Lys Lys
9425                9430                9435

<210> SEQ ID NO 16
<211> LENGTH: 1115
<212> TYPE: PRT
<213> ORGANISM: Staphylococcus aureus

<400> SEQUENCE: 16
```

-continued

```
Met Arg Asp Lys Lys Gly Pro Val Asn Lys Arg Val Asp Phe Leu Ser
  1               5                  10                  15

Asn Lys Leu Asn Lys Tyr Ser Ile Arg Lys Phe Thr Val Gly Thr Ala
             20                  25                  30

Ser Ile Leu Ile Gly Ser Leu Met Tyr Leu Gly Thr Gln Gln Glu Ala
         35                  40                  45

Glu Ala Ala Glu Asn Asn Ile Glu Asn Pro Thr Thr Leu Lys Asp Asn
     50                  55                  60

Val Gln Ser Lys Glu Val Lys Ile Glu Glu Val Thr Asn Lys Asp Thr
 65                  70                  75                  80

Ala Pro Gln Gly Val Glu Ala Lys Ser Glu Val Thr Ser Asn Lys Asp
                 85                  90                  95

Thr Ile Glu His Glu Ala Ser Val Lys Ala Glu Asp Ile Ser Lys Lys
             100                 105                 110

Glu Asp Thr Pro Lys Glu Val Ala Asn Val Ala Glu Val Gln Pro Lys
         115                 120                 125

Ser Ser Val Thr His Asn Ala Glu Ala Pro Lys Val Arg Lys Ala Arg
    130                 135                 140

Ser Val Asp Glu Gly Ser Phe Asp Ile Thr Arg Asp Ser Lys Asn Val
145                 150                 155                 160

Val Glu Ser Thr Pro Ile Thr Ile Gln Gly Lys Glu His Phe Glu Gly
                165                 170                 175

Tyr Gly Ser Val Asp Ile Gln Lys Asn Pro Thr Asp Leu Gly Val Ser
            180                 185                 190

Glu Val Thr Arg Phe Asn Val Gly Asn Glu Ser Asn Gly Leu Ile Gly
        195                 200                 205

Ala Leu Gln Leu Lys Asn Lys Ile Asp Phe Ser Lys Asp Phe Asn Phe
    210                 215                 220

Lys Val Arg Val Ala Asn Asn His Gln Ser Asn Thr Thr Gly Ala Asp
225                 230                 235                 240

Gly Trp Gly Phe Leu Phe Ser Lys Gly Asn Ala Glu Glu Tyr Leu Thr
                245                 250                 255

Asn Gly Gly Ile Leu Gly Asp Lys Gly Leu Val Asn Ser Gly Gly Phe
            260                 265                 270

Lys Ile Asp Thr Gly Tyr Ile Tyr Thr Ser Ser Met Asp Lys Thr Glu
        275                 280                 285

Lys Gln Ala Gly Gln Gly Tyr Arg Gly Tyr Gly Ala Phe Val Lys Asn
    290                 295                 300

Asp Ser Ser Gly Asn Ser Gln Met Val Gly Glu Asn Ile Asp Lys Ser
305                 310                 315                 320

Lys Thr Asn Phe Leu Asn Tyr Ala Asp Asn Ser Thr Asn Thr Ser Asp
                325                 330                 335

Gly Lys Phe His Gly Gln Arg Leu Asn Asp Val Ile Leu Thr Tyr Val
            340                 345                 350

Ala Ser Thr Gly Lys Met Arg Ala Glu Tyr Ala Gly Lys Thr Trp Glu
        355                 360                 365

Thr Ser Ile Thr Asp Leu Gly Leu Ser Lys Asn Gln Ala Tyr Asn Phe
    370                 375                 380

Leu Ile Thr Ser Ser Gln Arg Trp Gly Leu Asn Gln Gly Ile Asn Ala
385                 390                 395                 400

Asn Gly Trp Met Arg Thr Asp Leu Lys Gly Ser Glu Phe Thr Phe Thr
                405                 410                 415

Pro Glu Ala Pro Lys Thr Ile Thr Glu Leu Glu Lys Lys Val Glu Glu
            420                 425                 430
```

-continued

```
Ile Pro Phe Lys Lys Glu Arg Lys Phe Asn Pro Asp Leu Ala Pro Gly
        435                 440                 445

Thr Glu Lys Val Thr Arg Glu Gly Gln Lys Gly Glu Lys Thr Ile Thr
    450                 455                 460

Thr Pro Thr Leu Lys Asn Pro Leu Thr Gly Glu Ile Ile Ser Lys Gly
465                 470                 475                 480

Glu Ser Lys Glu Glu Ile Thr Lys Asp Pro Ile Asn Glu Leu Thr Glu
                485                 490                 495

Tyr Gly Pro Glu Thr Ile Ala Pro Gly His Arg Asp Glu Phe Asp Pro
            500                 505                 510

Lys Leu Pro Thr Gly Glu Lys Glu Val Pro Gly Lys Pro Gly Ile
        515                 520                 525

Lys Asn Pro Glu Thr Gly Asp Val Val Arg Pro Val Asp Ser Val
        530                 535                 540

Thr Lys Tyr Gly Pro Val Lys Gly Asp Ser Ile Val Glu Lys Glu Glu
545                 550                 555                 560

Ile Pro Phe Glu Lys Glu Arg Lys Phe Asn Pro Asp Leu Ala Pro Gly
                565                 570                 575

Thr Glu Lys Val Thr Arg Glu Gly Gln Lys Gly Glu Lys Thr Ile Thr
            580                 585                 590

Thr Pro Thr Leu Lys Asn Pro Leu Thr Gly Glu Ile Ile Ser Lys Gly
        595                 600                 605

Glu Ser Lys Glu Glu Ile Thr Lys Asp Pro Ile Asn Glu Leu Thr Glu
    610                 615                 620

Tyr Gly Pro Glu Thr Ile Ala Pro Gly His Arg Asp Glu Phe Asp Pro
625                 630                 635                 640

Lys Leu Pro Thr Gly Glu Lys Glu Val Pro Gly Lys Pro Gly Ile
                645                 650                 655

Lys Asn Pro Glu Thr Gly Asp Val Val Arg Pro Val Asp Ser Val
            660                 665                 670

Thr Lys Tyr Gly Pro Val Lys Gly Asp Ser Ile Val Glu Lys Glu Glu
        675                 680                 685

Ile Pro Phe Lys Lys Glu Arg Lys Phe Asn Pro Asp Leu Ala Pro Gly
    690                 695                 700

Thr Glu Lys Val Thr Arg Glu Gly Gln Lys Gly Glu Lys Thr Ile Thr
705                 710                 715                 720

Thr Pro Thr Leu Lys Asn Pro Leu Thr Gly Glu Ile Ile Ser Lys Gly
                725                 730                 735

Glu Ser Lys Glu Glu Ile Thr Lys Asp Pro Ile Asn Glu Leu Thr Glu
            740                 745                 750

Tyr Gly Pro Glu Thr Ile Thr Pro Gly His Arg Asp Glu Phe Asp Pro
        755                 760                 765

Lys Leu Pro Thr Gly Glu Lys Glu Val Pro Gly Lys Pro Gly Ile
        770                 775                 780

Lys Asn Pro Glu Thr Gly Asp Val Val Arg Pro Val Asp Ser Val
785                 790                 795                 800

Thr Lys Tyr Gly Pro Val Lys Gly Asp Ser Ile Val Glu Lys Glu Glu
                805                 810                 815

Ile Pro Phe Glu Lys Glu Arg Lys Phe Asn Pro Asp Leu Ala Pro Gly
            820                 825                 830

Thr Glu Lys Val Thr Arg Glu Gly Gln Lys Gly Glu Lys Thr Ile Thr
        835                 840                 845

Thr Pro Thr Leu Lys Asn Pro Leu Thr Gly Glu Ile Ile Ser Lys Gly
```

```
                 850                 855                 860

Glu Ser Lys Glu Glu Ile Thr Lys Asp Pro Val Asn Glu Leu Thr Glu
865                 870                 875                 880

Phe Gly Gly Glu Lys Ile Pro Gln Gly His Lys Asp Ile Phe Asp Pro
                885                 890                 895

Asn Leu Pro Thr Asp Gln Thr Glu Lys Val Pro Gly Lys Pro Gly Ile
            900                 905                 910

Lys Asn Pro Asp Thr Gly Lys Val Ile Glu Pro Val Asp Val
        915                 920                 925

Ile Lys His Gly Pro Lys Thr Gly Thr Pro Glu Thr Lys Thr Val Glu
    930                 935                 940

Ile Pro Phe Glu Thr Lys Arg Glu Phe Asn Pro Lys Leu Gln Pro Gly
945                 950                 955                 960

Glu Glu Arg Val Lys Gln Glu Gly Gln Pro Gly Ser Lys Thr Ile Thr
                965                 970                 975

Thr Pro Ile Thr Val Asn Pro Leu Thr Gly Glu Lys Val Gly Glu Gly
            980                 985                 990

Gln Pro Thr Glu Glu Ile Thr Lys Gln Pro Val Asp Lys Ile Val Glu
        995                 1000                1005

Phe Gly Gly Glu Lys Pro Lys Asp Pro Lys Gly Pro Glu Asn Pro Glu
   1010                1015                 1020

Lys Pro Ser Arg Pro Thr His Pro Ser Gly Pro Val Asn Pro Asn Asn
1025                1030                1035                1040

Pro Gly Leu Ser Lys Asp Arg Ala Lys Pro Asn Gly Pro Val His Ser
                1045                1050                1055

Met Asp Lys Asn Asp Lys Val Lys Lys Ser Lys Ile Ala Lys Glu Ser
            1060                1065                1070

Val Ala Asn Gln Glu Lys Lys Arg Ala Glu Leu Pro Lys Thr Gly Leu
        1075                1080                1085

Glu Ser Thr Gln Lys Gly Leu Ile Phe Ser Ser Ile Ile Gly Ile Ala
        1090                1095                1100

Gly Leu Met Leu Leu Ala Arg Arg Arg Lys Asn
1105                1110                 1115

<210> SEQ ID NO 17
<211> LENGTH: 1469
<212> TYPE: PRT
<213> ORGANISM: Staphylococcus epidermidis

<400> SEQUENCE: 17

Met Gly Lys Arg Arg Gln Gly Pro Ile Asn Lys Lys Val Asp Phe Leu
  1               5                  10                  15

Pro Asn Lys Leu Asn Lys Tyr Ser Ile Arg Lys Phe Thr Val Gly Thr
             20                  25                  30

Ala Ser Ile Leu Leu Gly Ser Thr Leu Ile Phe Gly Ser Ser His
         35                  40                  45

Glu Ala Lys Ala Ala Glu Glu Lys Gln Val Asp Pro Ile Thr Gln Ala
     50                  55                  60

Asn Gln Asn Asp Ser Ser Glu Arg Ser Leu Glu Asn Thr Asn Gln Pro
 65                  70                  75                  80

Thr Val Asn Asn Glu Ala Pro Gln Met Ser Ser Thr Leu Gln Ala Glu
                 85                  90                  95

Glu Gly Ser Asn Ala Glu Ala Pro Asn Val Pro Thr Ile Lys Ala Asn
            100                 105                 110

Ser Asp Asn Asp Thr Gln Thr Gln Phe Ser Glu Ala Pro Thr Arg Asn
```

```
            115                 120                 125
Asp Leu Ala Arg Lys Glu Asp Ile Pro Ala Val Ser Lys Asn Glu Glu
            130                 135                 140

Leu Gln Ser Ser Gln Pro Asn Thr Asp Ser Lys Ile Glu Pro Thr Thr
145                 150                 155                 160

Ser Glu Pro Val Asn Leu Asn Tyr Ser Ser Pro Phe Met Ser Leu Leu
                165                 170                 175

Ser Met Pro Ala Asp Ser Ser Asn Asn Thr Lys Asn Thr Ile Asp
            180                 185                 190

Ile Pro Pro Thr Thr Val Lys Gly Arg Asp Asn Tyr Asp Phe Tyr Gly
            195                 200                 205

Arg Val Asp Ile Gln Ser Asn Pro Thr Asp Leu Asn Ala Thr Asn Leu
210                 215                 220

Thr Arg Tyr Asn Tyr Gly Gln Pro Pro Gly Thr Thr Ala Gly Ala
225                 230                 235                 240

Val Gln Phe Lys Asn Gln Val Ser Phe Asp Lys Asp Phe Asp Phe Asn
                245                 250                 255

Ile Arg Val Ala Asn Asn Arg Gln Ser Asn Thr Thr Gly Ala Asp Gly
            260                 265                 270

Trp Gly Phe Met Phe Ser Lys Lys Asp Gly Asp Phe Leu Lys Asn
            275                 280                 285

Gly Gly Ile Leu Arg Glu Lys Gly Thr Pro Ser Ala Ala Gly Phe Arg
290                 295                 300

Ile Asp Thr Gly Tyr Tyr Asn Asn Asp Pro Leu Asp Lys Ile Gln Lys
305                 310                 315                 320

Gln Ala Gly Gln Gly Tyr Arg Gly Tyr Gly Thr Phe Val Lys Asn Asp
                325                 330                 335

Ser Gln Gly Asn Thr Ser Lys Val Gly Ser Gly Thr Pro Ser Thr Asp
            340                 345                 350

Phe Leu Asn Tyr Ala Asp Asn Thr Thr Asn Asp Leu Asp Gly Lys Phe
            355                 360                 365

His Gly Gln Lys Leu Asn Asn Val Asn Leu Lys Tyr Asn Ala Ser Asn
            370                 375                 380

Gln Thr Phe Thr Ala Thr Tyr Ala Gly Lys Thr Trp Thr Ala Thr Leu
385                 390                 395                 400

Ser Glu Leu Gly Leu Ser Pro Thr Asp Ser Tyr Asn Phe Leu Val Thr
                405                 410                 415

Ser Ser Tyr Gly Asn Gly Asn Ser Gly Thr Tyr Ala Asp Gly Val
            420                 425                 430

Met Arg Ala Asp Leu Asp Gly Ala Thr Leu Thr Tyr Thr Pro Lys Ala
            435                 440                 445

Val Asp Gly Asp Pro Ile Thr Ser Thr Lys Glu Ile Pro Phe Asn Lys
450                 455                 460

Lys Arg Glu Phe Asp Pro Asn Leu Ala Pro Gly Thr Glu Lys Val Val
465                 470                 475                 480

Gln Lys Gly Glu Pro Gly Ile Glu Thr Thr Thr Pro Thr Tyr Val
                485                 490                 495

Asn Pro Asn Thr Gly Glu Lys Val Gly Glu Gly Thr Pro Thr Thr Lys
            500                 505                 510

Ile Thr Lys Gln Pro Val Asp Glu Ile Val His Tyr Gly Gly Glu
            515                 520                 525

Ile Lys Pro Gly His Lys Asp Glu Phe Asp Pro Asn Ala Pro Lys Gly
            530                 535                 540
```

-continued

```
Ser Gln Thr Thr Gln Pro Gly Lys Pro Gly Val Lys Asn Pro Asp Thr
545                 550                 555                 560

Gly Glu Val Val Thr Pro Pro Val Asp Asp Val Thr Lys Tyr Gly Pro
                565                 570                 575

Val Asp Gly Asp Pro Ile Thr Ser Thr Glu Glu Ile Pro Phe Asp Lys
            580                 585                 590

Lys Arg Glu Phe Asn Pro Asp Leu Lys Pro Gly Glu Glu Arg Val Lys
        595                 600                 605

Gln Lys Gly Glu Pro Gly Thr Lys Thr Ile Thr Thr Pro Thr Thr Lys
    610                 615                 620

Asn Pro Leu Thr Gly Glu Lys Val Gly Glu Glu Pro Thr Glu Lys
625                 630                 635                 640

Ile Thr Lys Gln Pro Val Asp Glu Ile Thr Glu Tyr Gly Gly Glu Glu
                645                 650                 655

Ile Lys Pro Gly His Lys Asp Glu Phe Asp Pro Asn Ala Pro Lys Gly
            660                 665                 670

Ser Gln Glu Asp Val Pro Gly Lys Pro Gly Val Lys Asn Pro Asp Thr
        675                 680                 685

Gly Glu Val Val Thr Pro Pro Val Asp Asp Val Thr Lys Tyr Gly Pro
    690                 695                 700

Val Asp Gly Asp Pro Ile Thr Ser Thr Glu Glu Ile Pro Phe Asp Lys
705                 710                 715                 720

Lys Arg Glu Phe Asp Pro Asn Leu Ala Pro Gly Thr Glu Lys Val Val
                725                 730                 735

Gln Lys Gly Glu Pro Gly Thr Lys Thr Ile Thr Thr Pro Thr Thr Lys
            740                 745                 750

Asn Pro Leu Thr Gly Glu Lys Val Gly Glu Glu Pro Thr Glu Lys
        755                 760                 765

Ile Thr Lys Gln Pro Val Asp Glu Ile Val His Tyr Gly Gly Glu Glu
    770                 775                 780

Ile Lys Pro Gly His Lys Asp Glu Phe Asp Pro Asn Ala Pro Lys Gly
785                 790                 795                 800

Ser Gln Glu Asp Val Pro Gly Lys Pro Gly Val Lys Asn Pro Asp Thr
                805                 810                 815

Gly Glu Val Val Thr Pro Pro Val Asp Asp Val Thr Lys Tyr Gly Pro
            820                 825                 830

Val Asp Gly Asp Pro Ile Thr Ser Thr Glu Glu Ile Pro Phe Asp Lys
        835                 840                 845

Lys Arg Glu Phe Asn Pro Asp Leu Lys Pro Gly Glu Glu Arg Val Lys
    850                 855                 860

Gln Lys Gly Glu Pro Gly Thr Lys Thr Ile Thr Thr Pro Thr Thr Lys
865                 870                 875                 880

Asn Pro Leu Thr Gly Glu Lys Val Gly Glu Gly Glu Pro Thr Glu Lys
                885                 890                 895

Val Thr Lys Gln Pro Val Asp Glu Ile Val His Tyr Gly Gly Glu Glu
            900                 905                 910

Ile Lys Pro Gly His Lys Asp Glu Phe Asp Pro Asn Ala Pro Lys Gly
        915                 920                 925

Ser Gln Glu Asp Val Pro Gly Lys Pro Gly Val Lys Asn Pro Asp Thr
    930                 935                 940

Gly Glu Val Val Thr Pro Pro Val Asp Asp Val Thr Lys Tyr Gly Pro
945                 950                 955                 960

Val Asp Gly Asp Pro Ile Thr Ser Thr Glu Glu Ile Pro Phe Asp Lys
                965                 970                 975
```

```
Lys Arg Glu Phe Asp Pro Asn Leu Ala Pro Gly Thr Glu Lys Val Val
            980                 985                 990
Gln Lys Gly Glu Pro Gly Thr Lys Thr Ile Thr Thr Pro Thr Thr Lys
            995                 1000                1005
Asn Pro Leu Thr Gly Glu Lys Val Gly Glu Gly Pro Thr Glu Lys
            1010                1015                1020
Ile Thr Lys Gln Pro Val Asp Glu Ile Val His Tyr Gly Gly Glu Glu
1025                1030                1035                1040
Ile Lys Pro Gly His Lys Asp Glu Phe Asp Pro Asn Ala Pro Lys Gly
            1045                1050                1055
Ser Gln Thr Thr Gln Pro Gly Lys Pro Gly Val Lys Asn Pro Asp Thr
            1060                1065                1070
Gly Glu Val Val Thr Pro Pro Val Asp Asp Val Thr Lys Tyr Gly Pro
            1075                1080                1085
Val Asp Gly Asp Pro Ile Thr Ser Thr Glu Glu Ile Pro Phe Asp Lys
            1090                1095                1100
Lys Arg Glu Phe Asp Pro Asn Leu Ala Pro Gly Thr Glu Lys Val Val
1105                1110                1115                1120
Gln Lys Gly Glu Pro Gly Thr Lys Thr Ile Thr Thr Pro Thr Thr Lys
            1125                1130                1135
Asn Pro Leu Thr Gly Glu Lys Val Gly Glu Gly Glu Pro Thr Glu Lys
            1140                1145                1150
Ile Thr Lys Gln Pro Val Asp Glu Ile Val His Tyr Gly Gly Glu Gln
            1155                1160                1165
Ile Pro Gln Gly His Lys Asp Glu Phe Asp Pro Asn Ala Pro Val Asp
            1170                1175                1180
Ser Lys Thr Glu Val Pro Gly Lys Pro Gly Val Lys Asn Pro Asp Thr
1185                1190                1195                1200
Gly Glu Val Val Thr Pro Pro Val Asp Asp Val Thr Lys Tyr Gly Pro
            1205                1210                1215
Lys Val Gly Asn Pro Ile Thr Ser Thr Glu Glu Ile Pro Phe Asp Lys
            1220                1225                1230
Lys Arg Val Phe Asn Pro Asp Leu Lys Pro Gly Glu Glu Arg Val Lys
            1235                1240                1245
Gln Lys Gly Glu Pro Gly Thr Lys Thr Ile Thr Thr Pro Ile Leu Val
            1250                1255                1260
Asn Pro Ile Thr Gly Glu Lys Val Gly Glu Gly Lys Ser Thr Glu Lys
1265                1270                1275                1280
Val Thr Lys Gln Pro Val Asp Glu Ile Val Glu Tyr Gly Pro Thr Lys
            1285                1290                1295
Ala Glu Pro Gly Lys Pro Ala Glu Pro Gly Lys Pro Ala Glu Pro Gly
            1300                1305                1310
Lys Pro Ala Glu Pro Gly Lys Pro Ala Glu Pro Gly Thr Pro Ala Glu
            1315                1320                1325
Pro Gly Lys Pro Ala Glu Pro Gly Lys Pro Ala Glu Pro Gly Lys Pro
            1330                1335                1340
Ala Glu Pro Gly Lys Pro Ala Glu Pro Gly Lys Pro Ala Glu Pro Gly
1345                1350                1355                1360
Thr Pro Ala Glu Pro Gly Lys Pro Ala Glu Pro Gly Lys Pro Ala Glu
            1365                1370                1375
Pro Gly Lys Pro Ala Glu Pro Gly Thr Pro Ala Glu Pro Gly Lys Pro
            1380                1385                1390
Ala Glu Pro Gly Thr Pro Ala Glu Pro Gly Lys Pro Ala Glu Pro Gly
```

```
                    1395                1400                1405
Thr Pro Thr Gln Ser Gly Ala Pro Glu Gln Pro Asn Arg Ser Met His
    1410                1415                1420

Ser Thr Asp Asn Lys Asn Gln Leu Pro Asp Thr Gly Glu Asn Arg Gln
1425                1430                1435                1440

Ala Asn Glu Gly Thr Leu Val Gly Ser Leu Leu Ala Ile Val Gly Ser
                1445                1450                1455

Leu Phe Ile Phe Gly Arg Arg Lys Lys Gly Asn Glu Lys
        1460                1465

<210> SEQ ID NO 18
<211> LENGTH: 167
<212> TYPE: PRT
<213> ORGANISM: Staphylococcus aureus

<400> SEQUENCE: 18

Met Lys Lys Leu Tyr Thr Ser Tyr Gly Thr Tyr Gly Phe Leu His Gln
1               5                   10                  15

Ile Lys Ile Asn Asn Pro Thr His Gln Leu Phe Gln Phe Ser Ala Ser
            20                  25                  30

Asp Thr Ser Val Ile Phe Glu Glu Thr Asp Gly Glu Thr Val Leu Lys
        35                  40                  45

Ser Pro Ser Ile Tyr Glu Val Ile Lys Glu Ile Gly Glu Phe Ser Glu
    50                  55                  60

His His Phe Tyr Cys Ala Ile Phe Ile Pro Ser Thr Glu Asp His Ala
65                  70                  75                  80

Tyr Gln Leu Glu Lys Lys Leu Ile Ser Val Asp Asp Asn Phe Arg Asn
                85                  90                  95

Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165

<210> SEQ ID NO 19
<211> LENGTH: 167
<212> TYPE: PRT
<213> ORGANISM: Staphylococcus epidermidis

<400> SEQUENCE: 19

Met Tyr Leu Tyr Thr Ser Tyr Gly Thr Tyr Gln Phe Leu Asn Gln Ile
1               5                   10                  15

Lys Leu Asn His Gln Glu Arg Ser Leu Phe Gln Phe Ser Thr Asn Asp
            20                  25                  30

Ser Ser Ile Ile Leu Glu Glu Ser Glu Gly Lys Ser Ile Leu Lys His
        35                  40                  45

Pro Ser Ala Tyr Gln Val Ile Asp Ser Thr Gly Glu Phe Asn Glu His
    50                  55                  60

His Phe Tyr Ser Ala Ile Phe Val Pro Thr Ser Glu Asp His Arg Gln
65                  70                  75                  80

Gln Leu Glu Lys Lys Leu Leu Leu Val Asp Val Pro Leu Arg Asn Phe
                85                  90                  95
```

```
Gly Gly Phe Lys Ser Tyr Arg Leu Leu Lys Pro Thr Glu Gly Ser Thr
            100                 105                 110

Tyr Lys Ile Tyr Phe Gly Phe Ala Asn Arg Thr Ala Tyr Glu Asp Phe
            115                 120                 125

Lys Ala Ser Asp Ile Phe Asn Glu Asn Phe Ser Lys Asp Ala Leu Ser
            130                 135                 140

Gln Tyr Phe Gly Ala Ser Gly Gln His Ser Ser Tyr Phe Glu Arg Tyr
145                 150                 155                 160

Leu Tyr Pro Ile Glu Asp His
            165

<210> SEQ ID NO 20
<211> LENGTH: 1141
<212> TYPE: PRT
<213> ORGANISM: Staphylococcus aureus

<400> SEQUENCE: 20

Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
            35                  40                  45

Glu Ala Lys Ala Ala Glu Asn Thr Ser Thr Glu Asn Ala Lys Gln Asp
            50                  55                  60

Asp Ala Thr Thr Ser Asp Asn Lys Glu Val Val Ser Glu Thr Glu Asn
65                  70                  75                  80

Asn Ser Thr Thr Glu Asn Asp Ser Thr Asn Pro Ile Lys Lys Glu Thr
            85                  90                  95

Asn Thr Asp Ser Gln Pro Glu Ala Lys Glu Glu Ser Thr Thr Ser Ser
            100                 105                 110

Thr Gln Gln Gln Gln Asn Asn Val Thr Ala Thr Thr Glu Thr Lys Pro
            115                 120                 125

Gln Asn Ile Glu Lys Glu Asn Val Lys Pro Ser Thr Asp Lys Thr Ala
            130                 135                 140

Thr Glu Asp Thr Ser Val Ile Leu Glu Glu Lys Lys Ala Pro Asn Tyr
145                 150                 155                 160

Thr Asn Asn Asp Val Thr Thr Lys Pro Ser Thr Ser Glu Ile Gln Thr
            165                 170                 175

Lys Pro Thr Thr Pro Gln Glu Ser Thr Asn Ile Glu Asn Ser Gln Pro
            180                 185                 190

Gln Pro Thr Pro Ser Lys Val Asp Asn Gln Val Thr Asp Ala Thr Asn
            195                 200                 205

Pro Lys Glu Pro Val Asn Val Ser Lys Glu Glu Leu Lys Asn Asn Pro
            210                 215                 220

Glu Lys Leu Lys Glu Leu Val Arg Asn Asp Asn Asn Thr Asp Arg Ser
225                 230                 235                 240

Thr Lys Pro Val Ala Thr Ala Pro Thr Ser Val Ala Pro Lys Arg Leu
            245                 250                 255

Asn Ala Lys Met Arg Phe Ala Val Ala Gln Pro Ala Ala Val Ala Ser
            260                 265                 270

Asn Asn Val Asn Asp Leu Ile Thr Val Thr Lys Gln Thr Ile Lys Val
            275                 280                 285

Gly Asp Gly Lys Asp Asn Val Ala Ala His Asp Gly Lys Asp Ile
            290                 295                 300
```

```
Glu Tyr Asp Thr Glu Phe Thr Ile Asp Asn Lys Val Lys Lys Gly Asp
305                 310                 315                 320

Thr Met Thr Ile Asn Tyr Asp Lys Asn Val Ile Pro Ser Asp Leu Thr
            325                 330                 335

Asp Lys Asn Asp Pro Ile Asp Ile Thr Asp Pro Ser Gly Glu Val Ile
        340                 345                 350

Ala Lys Gly Thr Phe Asp Lys Ala Thr Lys Gln Ile Thr Tyr Thr Phe
            355                 360                 365

Thr Asp Tyr Val Asp Lys Tyr Glu Asp Ile Lys Ala Arg Leu Thr Leu
        370                 375                 380

Tyr Ser Tyr Ile Asp Lys Gln Ala Val Pro Asn Glu Thr Ser Leu Asn
385                 390                 395                 400

Leu Thr Phe Ala Thr Ala Gly Lys Glu Thr Ser Gln Asn Val Ser Val
            405                 410                 415

Asp Tyr Gln Asp Pro Met Val His Gly Asp Ser Asn Ile Gln Ser Ile
        420                 425                 430

Phe Thr Lys Leu Asp Glu Asn Lys Gln Thr Ile Glu Gln Gln Ile Tyr
            435                 440                 445

Val Asn Pro Leu Lys Lys Thr Ala Thr Asn Thr Lys Val Asp Ile Ala
450                 455                 460

Gly Ser Gln Val Asp Asp Tyr Gly Asn Ile Lys Leu Gly Asn Gly Ser
465                 470                 475                 480

Thr Ile Ile Asp Gln Asn Thr Glu Ile Lys Val Tyr Lys Val Asn Pro
            485                 490                 495

Asn Gln Gln Leu Pro Gln Ser Asn Arg Ile Tyr Asp Phe Ser Gln Tyr
        500                 505                 510

Glu Asp Val Thr Ser Gln Phe Asp Asn Lys Ser Phe Ser Asn Asn
            515                 520                 525

Val Ala Thr Leu Asp Phe Gly Asp Ile Asn Ser Ala Tyr Ile Ile Lys
530                 535                 540

Val Val Ser Lys Tyr Thr Pro Thr Ser Asp Gly Glu Leu Asp Ile Ala
545                 550                 555                 560

Gln Gly Thr Ser Met Arg Thr Thr Asp Lys Tyr Gly Tyr Tyr Asn Tyr
            565                 570                 575

Ala Gly Tyr Ser Asn Phe Ile Val Thr Ser Asn Asp Thr Gly Gly Gly
        580                 585                 590

Asp Gly Thr Val Lys Pro Glu Glu Lys Leu Tyr Lys Ile Gly Asp Tyr
        595                 600                 605

Val Trp Glu Asp Val Asp Lys Asp Gly Val Gln Gly Thr Asp Ser Lys
610                 615                 620

Glu Lys Pro Met Ala Asn Val Leu Val Thr Leu Thr Tyr Pro Asp Gly
625                 630                 635                 640

Thr Thr Lys Ser Val Arg Thr Asp Ala Asn Gly His Tyr Glu Phe Gly
            645                 650                 655

Gly Leu Lys Asp Gly Glu Thr Tyr Thr Val Lys Phe Glu Thr Pro Ala
        660                 665                 670

Gly Tyr Leu Pro Thr Lys Val Asn Gly Thr Thr Asp Gly Glu Lys Asp
            675                 680                 685

Ser Asn Gly Ser Ser Ile Thr Val Lys Ile Asn Gly Lys Asp Asp Met
        690                 695                 700

Ser Leu Asp Thr Gly Phe Tyr Lys Glu Pro Lys Tyr Asn Leu Gly Asp
705                 710                 715                 720

Tyr Val Trp Glu Asp Thr Asn Lys Asp Gly Ile Gln Asp Ala Asn Glu
```

```
                    725                 730                 735
Pro Gly Ile Lys Asp Val Lys Val Thr Leu Lys Asp Ser Thr Gly Lys
                740                 745                 750
Val Ile Gly Thr Thr Thr Thr Asp Ala Ser Gly Lys Tyr Lys Phe Thr
            755                 760                 765
Asp Leu Asp Asn Gly Asn Tyr Thr Val Glu Phe Glu Thr Pro Ala Gly
        770                 775                 780
Tyr Thr Pro Thr Val Lys Asn Thr Thr Ala Glu Asp Lys Asp Ser Asn
785                 790                 795                 800
Gly Leu Thr Thr Thr Gly Val Ile Lys Asp Ala Asp Asn Met Thr Leu
                805                 810                 815
Asp Ser Gly Phe Tyr Lys Thr Pro Lys Tyr Ser Leu Gly Asp Tyr Val
                820                 825                 830
Trp Tyr Asp Ser Asn Lys Asp Gly Lys Gln Asp Ser Thr Glu Lys Gly
                835                 840                 845
Ile Lys Asp Val Lys Val Thr Leu Leu Asn Glu Lys Gly Glu Val Ile
            850                 855                 860
Gly Thr Thr Lys Thr Asp Glu Asn Gly Lys Tyr Arg Phe Asp Asn Leu
865                 870                 875                 880
Asp Ser Gly Lys Tyr Lys Val Ile Phe Glu Lys Pro Ala Gly Leu Thr
                885                 890                 895
Gln Thr Val Thr Asn Thr Thr Glu Asp Asp Lys Asp Ala Asp Gly Gly
                900                 905                 910
Glu Val Asp Val Thr Ile Thr Asp His Asp Asp Phe Ile Leu Asp Asn
                915                 920                 925
Gly Tyr Phe Glu Glu Asp Thr Ser Asp Ser Asp Ser Asp Ser Asp Ser
        930                 935                 940
Asp Ser Asp Ser Asp Ser Asp Ser Asp Ser Asp Ser Asp Ser Asp Ser
945                 950                 955                 960
Asp Ser Asp Ser Asp Ser Asp Ser Asp Ser Asp Ser Asp Ser Asp Ser
                965                 970                 975
Asp Ser Asp Ser Asp Ser Asp Ser Asp Ser Asp Ser Asp Ser Asp Ser
                980                 985                 990
Asp Ser Asp Ser Asp Ser Asp Ser Asp Ser Asp Ser Asp Ser Asp Ser
        995                 1000                1005
Asp Ser Asp Ser Asp Ser Asp Ser Asp Ser Asp Ser Asp Ser Asp Ser
    1010                1015                1020
Asp Ser Asp Ser Asp Ser Asp Ser Asp Ser Asp Ser Asp Ser Asp Ser
1025                1030                1035                1040
Asp Ser Asp Ser Asp Ser Asp Ser Asp Ser Asp Ser Asp Ser Asp Ser
                1045                1050                1055
Asp Ser Asp Ser Asp Ser Asp Ser Asp Ser Asp Ser Asp Ser Asp Ser
                1060                1065                1070
Asp Ser Asp Ser Asp Ser Asp Ser Asp Ala Gly Lys His Thr Pro Val
            1075                1080                1085
Lys Pro Met Ser Thr Thr Lys Asp His His Asn Lys Ala Lys Ala Leu
        1090                1095                1100
Pro Glu Thr Gly Ser Glu Asn Asn Gly Ser Asn Asn Ala Thr Leu Phe
1105                1110                1115                1120
Gly Gly Leu Phe Ala Ala Leu Gly Ser Leu Leu Leu Phe Gly Arg Arg
                1125                1130                1135
Lys Lys Gln Asn Lys
            1140
```

<210> SEQ ID NO 21
<211> LENGTH: 1056
<212> TYPE: PRT
<213> ORGANISM: Staphylococcus epidermidis

<400> SEQUENCE: 21

Met Ile Asn Lys Lys Asn Asn Leu Leu Thr Lys Lys Pro Ile Ala
1               5                   10                  15

Asn Lys Ser Asn Lys Tyr Ala Ile Arg Lys Phe Thr Val Gly Thr Ala
            20                  25                  30

Ser Ile Val Ile Gly Ala Thr Leu Leu Phe Gly Leu Gly His Asn Glu
        35                  40                  45

Ala Lys Ala Glu Glu Asn Ser Val Gln Asp Val Lys Asp Ser Asn Thr
50                  55                  60

Asp Asp Glu Leu Ser Asp Ser Asn Asp Gln Ser Ser Asp Glu Glu Lys
65                  70                  75                  80

Asn Asp Val Ile Asn Asn Gln Ser Ile Asn Thr Asp Asn Asn
                85                  90                  95

Gln Ile Ile Lys Lys Glu Glu Thr Asn Asn Tyr Asp Gly Ile Glu Lys
            100                 105                 110

Arg Ser Glu Asp Arg Thr Glu Ser Thr Thr Asn Val Asp Glu Asn Glu
        115                 120                 125

Ala Thr Phe Leu Gln Lys Thr Pro Gln Asp Asn Thr His Leu Thr Glu
    130                 135                 140

Glu Glu Val Lys Glu Ser Ser Val Glu Ser Ser Asn Ser Ser Ile
145                 150                 155                 160

Asp Thr Ala Gln Gln Pro Ser His Thr Thr Ile Asn Arg Glu Glu Ser
                165                 170                 175

Val Gln Thr Ser Asp Asn Val Glu Asp Ser His Val Ser Asp Phe Ala
            180                 185                 190

Asn Ser Lys Ile Lys Glu Ser Asn Thr Glu Ser Gly Lys Glu Glu Asn
        195                 200                 205

Thr Ile Glu Gln Pro Asn Lys Val Lys Glu Asp Ser Thr Thr Ser Gln
    210                 215                 220

Pro Ser Gly Tyr Thr Asn Ile Asp Glu Lys Ile Ser Asn Gln Asp Glu
225                 230                 235                 240

Leu Leu Asn Leu Pro Ile Asn Glu Tyr Glu Asn Lys Ala Arg Pro Leu
                245                 250                 255

Ser Thr Thr Ser Ala Gln Pro Ser Ile Lys Arg Val Thr Val Asn Gln
            260                 265                 270

Leu Ala Ala Glu Gln Gly Ser Asn Val Asn His Leu Ile Lys Val Thr
        275                 280                 285

Asp Gln Ser Ile Thr Glu Gly Tyr Asp Asp Ser Glu Gly Val Ile Lys
    290                 295                 300

Ala His Asp Ala Glu Asn Leu Ile Tyr Asp Val Thr Phe Glu Val Asp
305                 310                 315                 320

Asp Lys Val Lys Ser Gly Asp Thr Met Thr Val Asp Ile Asp Lys Asn
                325                 330                 335

Thr Val Pro Ser Asp Leu Thr Asp Ser Phe Thr Ile Pro Lys Ile Lys
            340                 345                 350

Asp Asn Ser Gly Glu Ile Ile Ala Thr Gly Thr Tyr Asp Asn Lys Asn
        355                 360                 365

Lys Gln Ile Thr Tyr Thr Phe Thr Asp Tyr Val Asp Lys Tyr Glu Asn
    370                 375                 380

```
Ile Lys Ala His Leu Lys Leu Thr Ser Tyr Ile Asp Lys Ser Lys Val
385                 390                 395                 400

Pro Asn Asn Asn Thr Lys Leu Asp Val Glu Tyr Lys Thr Ala Leu Ser
            405                 410                 415

Ser Val Asn Lys Thr Ile Thr Val Glu Tyr Gln Arg Pro Asn Glu Asn
        420                 425                 430

Arg Thr Ala Asn Leu Gln Ser Met Phe Thr Asn Ile Asp Thr Lys Asn
    435                 440                 445

His Thr Val Glu Gln Thr Ile Tyr Ile Asn Pro Leu Arg Tyr Ser Ala
450                 455                 460

Lys Glu Thr Asn Val Asn Ile Ser Gly Asn Gly Asp Glu Gly Ser Thr
465                 470                 475                 480

Ile Ile Asp Asp Ser Thr Ile Ile Lys Val Tyr Lys Val Gly Asp Asn
            485                 490                 495

Gln Asn Leu Pro Asp Ser Asn Arg Ile Tyr Asp Tyr Ser Glu Tyr Glu
            500                 505                 510

Asp Val Thr Asn Asp Asp Tyr Ala Gln Leu Gly Asn Asn Asn Asp Val
        515                 520                 525

Asn Ile Asn Phe Gly Asn Ile Asp Ser Pro Tyr Ile Ile Lys Val Ile
530                 535                 540

Ser Lys Tyr Asp Pro Asn Lys Asp Asp Tyr Thr Thr Ile Gln Gln Thr
545                 550                 555                 560

Val Thr Met Gln Thr Thr Ile Asn Glu Tyr Thr Gly Glu Phe Arg Thr
            565                 570                 575

Ala Ser Tyr Asp Asn Thr Ile Ala Phe Ser Thr Ser Ser Gly Gln Gly
        580                 585                 590

Gln Gly Asp Leu Pro Pro Glu Lys Thr Tyr Lys Ile Gly Asp Tyr Val
        595                 600                 605

Trp Glu Asp Val Asp Lys Asp Gly Ile Gln Asn Thr Asn Asp Asn Glu
    610                 615                 620

Lys Pro Leu Ser Asn Val Leu Val Thr Leu Thr Tyr Pro Asp Gly Thr
625                 630                 635                 640

Ser Lys Ser Val Arg Thr Asp Glu Asp Gly Lys Tyr Gln Phe Asp Gly
            645                 650                 655

Leu Lys Asn Gly Leu Thr Tyr Lys Ile Thr Phe Glu Thr Pro Glu Gly
            660                 665                 670

Tyr Thr Pro Thr Leu Lys His Ser Gly Thr Asn Pro Ala Leu Asp Ser
        675                 680                 685

Glu Gly Asn Ser Val Trp Val Thr Ile Asn Gly Gln Asp Met Thr
    690                 695                 700

Ile Asp Ser Gly Phe Tyr Gln Thr Pro Lys Tyr Ser Leu Gly Asn Tyr
705                 710                 715                 720

Val Trp Tyr Asp Thr Asn Lys Asp Gly Ile Gln Gly Asp Asp Glu Lys
            725                 730                 735

Gly Ile Ser Gly Val Lys Val Thr Leu Lys Asp Glu Asn Gly Asn Ile
        740                 745                 750

Ile Ser Thr Thr Thr Thr Asp Glu Asn Gly Lys Tyr Gln Phe Asp Asn
    755                 760                 765

Leu Asn Ser Gly Asn Tyr Ile Val His Phe Asp Lys Pro Ser Gly Met
770                 775                 780

Thr Gln Thr Thr Thr Asp Ser Gly Asp Asp Glu Gln Asp Ala Asp
785                 790                 795                 800

Gly Glu Glu Val His Val Thr Ile Thr Asp His Asp Asp Phe Ser Ile
            805                 810                 815
```

```
Asp Asn Gly Tyr Tyr Asp Asp Glu Ser Asp Ser Asp Ser Asp
            820                 825                 830

Ser Asp Ser Asp Ser Asp Ser Asp Ser Asp Ser Asp Ser Asp
        835                 840                 845

Ser Asp Ser Asp Ser Asp Ser Asp Ser Asp Ser Asp Ser Asp
    850                 855                 860

Ser Asp Ser Asp Ser Asp Ser Asp Ser Asp Ser Asp Ser Asp
865                 870                 875                 880

Ser Asp Ser Asp Ser Asp Ser Asp Ser Asp Ser Asp Ser Asp
            885                 890                 895

Ser Asp Ser Asp Ser Asp Ser Asp Ser Asp Ser Asp Ser Asp
        900                 905                 910

Ser Asp Ser Asp Ser Asp Ser Asp Ser Asp Ser Asp Ser Asp
    915                 920                 925

Ser Asp Ser Asp Ser Asp Ser Asp Ser Asp Ser Asp Ser Asp
930                 935                 940

Ser Asp Ser Asp Ser Asp Ser Asp Ser Asp Ser Asp Ser Asp
945                 950                 955                 960

Ser Asp Ser Asp Ser Asp Ser Asp Ser Asp Ser Asp Ser Asp
            965                 970                 975

Ser Asp Ser Asp Ser Asp Ser Asp Ser Asp Ser Asp Ser Asp
        980                 985                 990

Ser Asp Ser Asp Ser Asp Asn Asp Ser Asp Leu Gly Asn Ser
    995                 1000                1005

Ser Asp Lys Ser Thr Lys Asp Lys Leu Pro Asp Thr Gly Ala Asn Glu
    1010                1015                1020

Asp Tyr Gly Ser Lys Gly Thr Leu Leu Gly Thr Leu Phe Ala Gly Leu
1025                1030                1035                1040

Gly Ala Leu Leu Leu Gly Lys Arg Arg Lys Asn Arg Lys Asn Lys Asn
            1045                1050                1055

<210> SEQ ID NO 22
<211> LENGTH: 486
<212> TYPE: PRT
<213> ORGANISM: Staphylococcus aureus

<400> SEQUENCE: 22

Met Ser Asn Asn Phe Lys Asp Asp Phe Glu Lys Asn Arg Gln Ser Ile
1               5                   10                  15

Asp Thr Asn Ser His Gln Asp His Thr Glu Asp Val Glu Lys Asp Gln
            20                  25                  30

Ser Glu Leu Glu His Gln Asp Thr Ile Glu Asn Thr Glu Gln Gln Phe
        35                  40                  45

Pro Pro Arg Asn Ala Gln Arg Arg Lys Arg Arg Arg Asp Leu Ala Thr
    50                  55                  60

Asn His Asn Lys Gln Val His Asn Glu Ser Gln Thr Ser Glu Asp Asn
65                  70                  75                  80

Val Gln Asn Glu Ala Gly Thr Ile Asp Asp Arg Gln Val Glu Ser Ser
            85                  90                  95

His Ser Thr Glu Ser Gln Glu Pro Ser His Gln Asp Ser Thr Pro Gln
        100                 105                 110

His Glu Glu Glu Tyr Tyr Asn Lys Asn Ala Phe Ala Met Asp Lys Ser
    115                 120                 125

His Pro Glu Pro Ile Glu Asp Asn Asp Lys His Glu Thr Ile Lys Asp
    130                 135                 140
```

```
Ala Glu Asn Asn Thr Glu His Ser Thr Val Ser Asp Lys Ser Ile Ala
145                 150                 155                 160

Glu Gln Ser Gln Gln Pro Lys Pro Tyr Phe Ala Thr Gly Ala Asn Gln
                165                 170                 175

Ala Asn Thr Ser Lys Asp Lys His Asp Asp Val Thr Val Lys Gln Asp
            180                 185                 190

Lys Asp Glu Ser Lys Asp His His Ser Gly Lys Lys Gly Ala Ala Ile
        195                 200                 205

Gly Ala Gly Thr Ala Gly Val Ala Gly Ala Ala Gly Ala Met Gly Val
    210                 215                 220

Ser Lys Ala Lys Lys His Ser Asn Asp Ala Gln Asn Lys Ser Asn Ser
225                 230                 235                 240

Asp Lys Ser Asn Asn Ser Thr Glu Asp Lys Ala Ser Gln Asp Lys Ser
                245                 250                 255

Lys Asp His His Asn Gly Lys Lys Gly Ala Ala Ile Gly Ala Gly Thr
            260                 265                 270

Ala Gly Leu Ala Gly Gly Ala Ala Ser Lys Ser Ala Ser Ala Ala Ser
        275                 280                 285

Lys Pro His Ala Ser Asn Asn Ala Ser Gln Asn His Asp Glu His Asp
    290                 295                 300

Asn His Asp Arg Asp Lys Glu Arg Lys Lys Gly Gly Met Ala Lys Val
305                 310                 315                 320

Leu Leu Pro Leu Ile Ala Ala Val Leu Ile Ile Gly Ala Leu Ala Ile
                325                 330                 335

Phe Gly Gly Met Ala Leu Asn Asn His Asn Asn Gly Thr Lys Glu Asn
            340                 345                 350

Lys Ile Ala Asn Thr Asn Lys Asn Asn Ala Asp Glu Ser Lys Asp Lys
        355                 360                 365

Asp Thr Ser Lys Asp Ala Ser Lys Asp Lys Ser Lys Ser Thr Asp Ser
    370                 375                 380

Asp Lys Ser Lys Glu Asp Gln Asp Lys Ala Thr Lys Asp Glu Ser Asp
385                 390                 395                 400

Asn Asp Gln Asn Asn Ala Asn Gln Ala Asn Asn Ala Gln Asn Asn
                405                 410                 415

Gln Asn Gln Gln Gln Ala Asn Gln Asn Gln Gln Gln Gln Gln Arg
            420                 425                 430

Gln Gly Gly Gly Gln Arg His Thr Val Asn Gly Gln Glu Asn Leu Tyr
    435                 440                 445

Arg Ile Ala Ile Gln Tyr Tyr Gly Ser Gly Ser Pro Glu Asn Val Glu
    450                 455                 460

Lys Ile Arg Arg Ala Asn Gly Leu Ser Gly Asn Asn Ile Arg Asn Gly
465                 470                 475                 480

Gln Gln Ile Val Ile Pro
                485

<210> SEQ ID NO 23
<211> LENGTH: 472
<212> TYPE: PRT
<213> ORGANISM: Staphylococcus epidermidis

<400> SEQUENCE: 23

Met Ile Glu Leu Ile Lys Met Glu Gly Met Ile Val Val Ser Asn Asn
1               5                   10                  15

Asn Phe Lys Asp Asp Phe Glu Lys Asn Arg Gln Ser Ile Asn Pro Asp
            20                  25                  30
```

```
Glu Gln Gln Thr Glu Leu Lys Glu Asp Asp Lys Thr Asn Glu Asn Lys
            35                  40                  45

Lys Glu Ala Asp Ser Gln Asn Ser Leu Ser Asn Asn Ser Asn Gln Gln
 50                  55                  60

Phe Pro Pro Arg Asn Ala Gln Arg Arg Lys Arg Arg Glu Thr Ala
 65                  70                  75                  80

Thr Asn Gln Ser Lys Gln Gln Asp Asp Lys His Gln Lys Asn Ser Asp
                85                  90                  95

Ala Lys Thr Thr Glu Gly Ser Leu Asp Asp Arg Tyr Asp Glu Ala Gln
            100                 105                 110

Leu Gln Gln Gln His Asp Lys Ser Gln Gln Gln Asn Lys Thr Glu Lys
            115                 120                 125

Gln Ser Gln Asp Asn Arg Met Lys Asp Gly Lys Asp Ala Ala Ile Val
    130                 135                 140

Asn Gly Thr Ser Glu Ser Pro Glu His Lys Ser Lys Ser Thr Gln Asn
145                 150                 155                 160

Arg Pro Gly Pro Lys Ala Gln Gln Lys Arg Lys Ser Glu Ser Thr
                165                 170                 175

Gln Ser Lys Pro Ser Thr Asn Lys Asp Lys Lys Ala Ala Thr Gly Ala
            180                 185                 190

Gly Ile Ala Gly Ala Ala Gly Val Ala Gly Ala Ala Glu Thr Ser Lys
        195                 200                 205

Arg His His Asn Lys Lys Asp Lys Gln Asp Ser Lys His Ser Asn His
    210                 215                 220

Glu Asn Asp Glu Lys Ser Val Lys Asn Asp Asp Gln Lys Gln Ser Lys
225                 230                 235                 240

Lys Gly Lys Lys Ala Ala Val Gly Ala Gly Ala Ala Gly Val Gly
                245                 250                 255

Ala Ala Gly Val Ala His His Asn Asn Gln Asn Lys His His Asn Glu
            260                 265                 270

Glu Lys Asn Ser Asn Gln Asn Gln Tyr Asn Asp Gln Ser Glu Gly
    275                 280                 285

Lys Lys Lys Gly Gly Phe Met Lys Ile Leu Leu Pro Leu Ile Ala Ala
    290                 295                 300

Ile Leu Ile Leu Gly Ala Ile Ala Ile Phe Gly Gly Met Ala Leu Asn
305                 310                 315                 320

Asn His Asn Asp Ser Lys Ser Asp Asp Gln Lys Ile Ala Asn Gln Ser
            325                 330                 335

Lys Lys Asp Ser Asp Lys Lys Asp Gly Ala Gln Ser Glu Asp Asn Lys
            340                 345                 350

Asp Lys Lys Ser Asp Ser Asn Lys Asp Lys Lys Ser Asp Ser Asp Lys
            355                 360                 365

Asn Ala Asp Asp Asp Ser Asp Asn Ser Ser Ser Asn Pro Asn Ala Thr
    370                 375                 380

Ser Thr Asn Asn Asn Asp Asn Val Ala Asn Asn Ser Asn Tyr Thr
385                 390                 395                 400

Asn Gln Asn Gln Gln Asp Asn Ala Asn Gln Asn Ser Asn Gln Gln
            405                 410                 415

Ala Thr Gln Gly Gln Gln Ser His Thr Val Tyr Gly Gln Glu Asn Leu
        420                 425                 430

Tyr Arg Ile Ala Ile Gln Tyr Tyr Gly Glu Gly Thr Gln Ala Asn Val
            435                 440                 445

Asp Lys Ile Lys Arg Ala Asn Gly Leu Ser Ser Asn Asn Ile His Asn
```

```
                450             455             460
Gly Gln Thr Leu Val Ile Pro Gln
465                 470

<210> SEQ ID NO 24
<211> LENGTH: 165
<212> TYPE: PRT
<213> ORGANISM: Staphylococcus aureus

<400> SEQUENCE: 24

Met Lys Asn Lys Leu Ile Ala Lys Ser Leu Leu Thr Ile Ala Ala Ile
1               5                   10                  15

Gly Ile Thr Thr Thr Thr Ile Ala Ser Thr Ala Asp Ala Ser Glu Gly
                20                  25                  30

Tyr Gly Pro Arg Glu Lys Lys Pro Val Ser Ile Asn His Asn Ile Val
            35                  40                  45

Glu Tyr Asn Asp Gly Thr Phe Lys Tyr Gln Ser Arg Pro Lys Phe Asn
    50                  55                  60

Ser Thr Pro Lys Tyr Ile Lys Phe Lys His Asp Tyr Asn Ile Leu Glu
65                  70                  75                  80

Phe Asn Asp Gly Thr Phe Glu Tyr Gly Ala Arg Pro Gln Phe Asn Lys
                85                  90                  95

Pro Ala Ala Lys Thr Asp Ala Thr Ile Lys Lys Glu Gln Lys Leu Ile
            100                 105                 110

Gln Ala Gln Asn Leu Val Arg Glu Phe Glu Lys Thr His Thr Val Ser
        115                 120                 125

Ala His Arg Lys Ala Gln Lys Ala Val Asn Leu Val Ser Phe Glu Tyr
    130                 135                 140

Lys Val Lys Lys Met Val Leu Gln Glu Arg Ile Asp Asn Val Leu Lys
145                 150                 155                 160

Gln Gly Leu Val Arg
                165

<210> SEQ ID NO 25
<211> LENGTH: 319
<212> TYPE: PRT
<213> ORGANISM: Staphylococcus aureus

<400> SEQUENCE: 25

Met Lys Thr Arg Ile Val Ser Ser Val Thr Thr Thr Leu Leu Leu Gly
1               5                   10                  15

Ser Ile Leu Met Asn Pro Val Ala Asn Ala Ala Asp Ser Asp Ile Asn
                20                  25                  30

Ile Lys Thr Gly Thr Thr Asp Ile Gly Ser Asn Thr Thr Val Lys Thr
            35                  40                  45

Gly Asp Leu Val Thr Tyr Asp Lys Glu Asn Gly Met His Lys Lys Val
    50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
        115                 120                 125

Pro Arg Asn Ser Ile Asp Thr Lys Glu Tyr Met Ser Thr Leu Thr Tyr
    130                 135                 140
```

```
Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
            165                 170                 175

Pro Asp Phe Lys Thr Ile Leu Glu Ser Pro Thr Asp Lys Lys Val Gly
        180                 185                 190

Trp Lys Val Ile Phe Asn Asn Met Val Asn Gln Asn Trp Gly Pro Tyr
    195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Glu Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Thr Asp Arg Ser
    290                 295                 300

Ser Glu Arg Tyr Lys Ile Asp Trp Glu Lys Glu Met Thr Asn
305                 310                 315

<210> SEQ ID NO 26
<211> LENGTH: 428
<212> TYPE: PRT
<213> ORGANISM: Staphylococcus aureus

<400> SEQUENCE: 26

Met His Met Lys Asn Lys Tyr Ile Ser Lys Leu Leu Val Gly Ala Ala
1               5                   10                  15

Thr Ile Thr Leu Ala Thr Met Ile Ser Asn Gly Glu Ala Lys Ala Ser
            20                  25                  30

Glu Asn Thr Gln Gln Thr Ser Thr Lys His Gln Thr Thr Gln Asn Asn
        35                  40                  45

Tyr Val Thr Asp Gln Gln Lys Ala Phe Tyr Gln Val Leu His Leu Lys
    50                  55                  60

Gly Ile Thr Glu Glu Gln Arg Asn Gln Tyr Ile Lys Thr Leu Arg Glu
65                  70                  75                  80

His Pro Glu Arg Ala Gln Glu Val Phe Ser Gly Ser Leu Lys Asp Ser
                85                  90                  95

Lys Asn Pro Asp Arg Arg Val Ala Gln Gln Asn Ala Phe Tyr Asn Val
            100                 105                 110

Leu Lys Asn Asp Asn Leu Thr Glu Gln Glu Lys Asn Asn Tyr Ile Ala
        115                 120                 125

Gln Ile Lys Glu Asn Pro Asp Arg Ser Gln Gln Val Trp Val Glu Ser
    130                 135                 140

Val Gln Ser Ser Lys Ala Lys Glu Arg Gln Asn Ile Glu Asn Ala Asp
145                 150                 155                 160

Lys Ala Ile Lys Asp Phe Gln Asp Asn Lys Ala Pro His Asp Lys Ser
                165                 170                 175

Ala Ala Tyr Glu Ala Asn Ser Lys Leu Pro Lys Asp Leu Arg Asp Lys
            180                 185                 190

Asn Asn Arg Phe Val Glu Lys Val Ser Ile Glu Lys Ala Ile Val Arg
        195                 200                 205
```

His Asp Glu Arg Val Lys Ser Ala Asn Asp Ala Ile Ser Lys Leu Asn
    210                 215                 220

Glu Lys Asp Ser Ile Glu Asn Arg Arg Leu Ala Gln Arg Glu Val Asn
225                 230                 235                 240

Lys Ala Pro Met Asp Val Lys Glu His Leu Gln Lys Gln Leu Asp Ala
                245                 250                 255

Leu Val Ala Gln Lys Asp Ala Glu Lys Val Ala Pro Lys Val Glu
            260                 265                 270

Ala Pro Gln Ile Gln Ser Pro Gln Ile Glu Lys Pro Lys Ala Glu Ser
            275                 280                 285

Pro Lys Val Glu Val Pro Gln Ser Lys Leu Leu Gly Tyr Tyr Gln Ser
290                 295                 300

Leu Lys Asp Ser Phe Asn Tyr Gly Tyr Lys Tyr Leu Thr Asp Thr Tyr
305                 310                 315                 320

Lys Ser Tyr Lys Glu Lys Tyr Asp Thr Ala Lys Tyr Tyr Asn Thr
                325                 330                 335

Tyr Tyr Lys Tyr Lys Gly Ala Ile Asp Gln Thr Val Leu Thr Val Leu
            340                 345                 350

Gly Ser Gly Ser Lys Ser Tyr Ile Gln Pro Leu Lys Val Asp Asp Lys
            355                 360                 365

Asn Gly Tyr Leu Ala Lys Ser Tyr Ala Gln Val Arg Asn Tyr Val Thr
370                 375                 380

Glu Ser Ile Asn Thr Gly Lys Val Leu Tyr Thr Phe Tyr Gln Asn Pro
385                 390                 395                 400

Thr Leu Val Lys Thr Ala Ile Lys Ala Gln Glu Thr Ala Ser Ser Ile
                405                 410                 415

Lys Asn Thr Leu Ser Asn Leu Leu Ser Phe Trp Lys
            420                 425

<210> SEQ ID NO 27
<211> LENGTH: 350
<212> TYPE: PRT
<213> ORGANISM: Staphylococcus aureus

<400> SEQUENCE: 27

Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
            20                  25                  30

Ser Leu Val Tyr Ile Gly Ala Asp Ser Gln Gln Val Asn Ala Ala Thr
        35                  40                  45

Glu Ala Thr Asn Ala Thr Asn Asn Gln Ser Thr Gln Val Ser Gln Ala
50                  55                  60

Thr Ser Gln Pro Ile Asn Phe Gln Val Gln Lys Asp Gly Ser Ser Glu
65                  70                  75                  80

Lys Ser His Met Asp Asp Tyr Met Gln His Pro Gly Lys Val Ile Lys
                85                  90                  95

Gln Asn Asn Lys Tyr Tyr Phe Gln Thr Val Leu Asn Asn Ala Ser Phe
            100                 105                 110

Trp Lys Glu Tyr Lys Phe Tyr Asn Ala Asn Asn Gln Glu Leu Ala Thr
        115                 120                 125

Thr Val Val Asn Asp Asn Lys Lys Ala Asp Thr Arg Thr Ile Asn Val
130                 135                 140

Ala Val Glu Pro Gly Tyr Lys Ser Leu Thr Thr Lys Val His Ile Val
145                 150                 155                 160

```
Val Pro Gln Ile Asn Tyr Asn His Arg Tyr Thr Thr His Leu Glu Phe
                165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
        195                 200                 205

Thr Lys Pro Val Gln Pro Lys Val Glu Lys Val Lys Pro Thr Val Thr
    210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
                245                 250                 255

Thr Ala Gln Thr Ala Gln Glu Gln Asn Lys Val Gln Thr Pro Val Lys
            260                 265                 270

Asp Val Ala Thr Ala Lys Ser Glu Ser Asn Asn Gln Ala Val Ser Asp
        275                 280                 285

Asn Lys Ser Gln Gln Thr Asn Lys Val Thr Lys His Asn Glu Thr Pro
    290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Ala Thr Leu Ala Leu Leu
                325                 330                 335

Gly Ser Leu Ser Leu Leu Leu Phe Lys Arg Lys Glu Ser Lys
            340                 345                 350

<210> SEQ ID NO 28
<211> LENGTH: 645
<212> TYPE: PRT
<213> ORGANISM: Staphylococcus aureus

<400> SEQUENCE: 28

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Ala Glu Glu Thr Gly Gly Thr
        35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Ala Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
    130                 135                 140

Ala Pro Asn Ser Arg Pro Ile Asp Phe Glu Met Lys Lys Glu Asn Gly
145                 150                 155                 160

Glu Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190
```

```
Gln Phe Trp Arg Lys Phe Glu Val Tyr Glu Gly Asp Lys Lys Leu Pro
                195                 200                 205

Ile Lys Leu Val Ser Tyr Asp Thr Val Lys Asp Tyr Ala Tyr Ile Arg
        210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
    290                 295                 300

Lys Leu Lys Ala Glu Tyr Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
```

-continued

```
                610                 615                 620
Leu Met Ala Leu Leu Ala Leu Ser Ser Ile Val Ala Phe Val Leu Pro
625                 630                 635                 640

Arg Lys Arg Lys Asn
                645

<210> SEQ ID NO 29
<211> LENGTH: 953
<212> TYPE: PRT
<213> ORGANISM: Staphylococcus aureus

<400> SEQUENCE: 29

Met Asn Asn Lys Lys Thr Ala Thr Asn Arg Lys Gly Met Ile Pro Asn
  1               5                  10                  15

Arg Leu Asn Lys Phe Ser Ile Arg Lys Tyr Ser Val Gly Thr Ala Ser
                 20                  25                  30

Ile Leu Val Gly Thr Thr Leu Ile Phe Gly Leu Ser Gly His Glu Ala
             35                  40                  45

Lys Ala Ala Glu His Thr Asn Gly Glu Leu Asn Gln Ser Lys Asn Glu
         50                  55                  60

Thr Thr Ala Pro Ser Glu Asn Lys Thr Thr Glu Lys Val Asp Ser Arg
 65                  70                  75                  80

Gln Leu Lys Asp Asn Thr Gln Thr Ala Thr Ala Asp Gln Pro Lys Val
                 85                  90                  95

Thr Met Ser Asp Ser Ala Thr Val Lys Glu Thr Ser Ser Asn Met Gln
                100                 105                 110

Ser Pro Gln Asn Ala Thr Ala Ser Gln Ser Thr Thr Gln Thr Ser Asn
            115                 120                 125

Val Thr Thr Asn Asp Lys Ser Thr Thr Tyr Ser Asn Glu Thr Asp
        130                 135                 140

Lys Ser Asn Leu Thr Gln Ala Lys Asn Val Ser Thr Thr Pro Lys Thr
145                 150                 155                 160

Thr Thr Ile Lys Gln Arg Ala Leu Asn Arg Met Ala Val Asn Thr Val
                165                 170                 175

Ala Ala Pro Gln Gln Gly Thr Asn Val Asn Asp Lys Val His Phe Thr
            180                 185                 190

Asn Ile Asp Ile Ala Ile Asp Lys Gly His Val Asn Lys Thr Thr Gly
        195                 200                 205

Asn Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Lys Thr Asn Thr Thr Thr Tyr Thr Phe Thr Asn Tyr Val
        275                 280                 285

Asp Gln Tyr Thr Asn Val Ser Gly Ser Phe Glu Gln Val Ala Phe Ala
    290                 295                 300

Lys Arg Glu Asn Ala Thr Thr Asp Lys Thr Ala Tyr Lys Met Glu Val
305                 310                 315                 320

Thr Leu Gly Asn Asp Thr Tyr Ser Lys Asp Val Ile Val Asp Tyr Gly
                325                 330                 335

Asn Gln Lys Gly Gln Gln Leu Ile Ser Ser Thr Asn Tyr Ile Asn Asn
```

-continued

```
                340                 345                 350
Glu Asp Leu Ser Arg Asn Met Thr Val Tyr Val Asn Gln Pro Lys Lys
            355                 360                 365

Thr Tyr Thr Lys Glu Thr Phe Val Thr Asn Leu Thr Gly Tyr Lys Phe
        370                 375                 380

Asn Pro Asp Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Gly Gln Phe Asp Val Ile Tyr Ser Asn Asp Asn Lys Thr Ala Thr
            420                 425                 430

Val Asp Leu Leu Asn Gly Gln Ser Ser Asp Lys Gln Tyr Ile Ile
        435                 440                 445

Gln Gln Val Ala Tyr Pro Asp Asn Ser Ser Thr Asp Asn Gly Lys Ile
    450                 455                 460

Asp Tyr Thr Leu Glu Thr Gln Asn Gly Lys Ser Ser Trp Ser Asn Ser
465                 470                 475                 480

Tyr Ser Asn Val Asn Gly Ser Ser Thr Ala Asn Gly Asp Gln Lys Lys
                485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
        515                 520                 525

Asp Ser Asn Gly Lys Glu Leu Asp Arg Thr Thr Thr Asp Glu Asn Gly
    530                 535                 540

Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Thr Ala Asn Ala Gly Thr Asp
                565                 570                 575

Asp Ala Val Asp Ser Asp Gly Leu Thr Thr Thr Gly Val Ile Lys Asp
            580                 585                 590

Ala Asp Asn Met Thr Leu Asp Ser Gly Phe Tyr Lys Thr Pro Lys Tyr
        595                 600                 605

Ser Leu Gly Asp Tyr Val Trp Tyr Asp Ser Asn Lys Asp Gly Lys Gln
    610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
        675                 680                 685

Lys Asp Ala Asp Gly Gly Glu Val Asp Val Thr Ile Thr Asp His Asp
    690                 695                 700

Asp Phe Thr Leu Asp Asn Gly Tyr Tyr Glu Glu Thr Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
        755                 760                 765
```

```
Asp Ser Asp Ser Glu Ser Asp Ser Asp Ser Asp Ser
        770             775             780

Asp Ser Asp Ser Asp Ser Asp Ser Asp Ser Asp Ser
785             790             795             800

Asp Ser Asp Ser Asp Ser Asp Ser Asp Ser Asp Ser
        805             810             815

Asp Ser Asp Ser Asp Ser Asn Ser Asp Ser Asp Ser
        820             825             830

Asp Ser Asp Ser Asp Ser Asp Ser Asp Ser Asp Ser
        835             840             845

Asp Ser Asp Ser Asp Ser Asp Ser Asp Ser Asp Ser
        850             855             860

Asp Ser Asp Ser Asp Ser Asp Ser Asp Ser Asp Ser
865             870             875             880

Asp Ser Asp Ser Asp Ser Asp Ser Asp Ser Asp Ala Gly Lys
        885             890             895

His Thr Pro Thr Lys Pro Met Ser Thr Val Lys Asp Gln His Lys Thr
                900             905             910

Ala Lys Ala Leu Pro Glu Thr Gly Ser Glu Asn Asn Asn Ser Asn Asn
        915             920             925

Gly Thr Leu Phe Gly Gly Leu Phe Ala Ala Leu Gly Ser Leu Leu Leu
        930             935             940

Phe Gly Arg Arg Lys Lys Gln Asn Lys
945             950
```

<210> SEQ ID NO 30
<211> LENGTH: 935
<212> TYPE: PRT
<213> ORGANISM: Staphylococcus aureus

<400> SEQUENCE: 30

```
Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190
```

-continued

```
Asn Thr Asp Ala Ser Asn Lys Asp Val Val Ser Gln Ala Val Asn Pro
            195                 200                 205
Ser Thr Pro Arg Met Arg Ala Phe Ser Leu Ala Ala Val Ala Ala Asp
        210                 215                 220
Ala Pro Ala Ala Gly Thr Asp Ile Thr Asn Gln Leu Thr Asp Val Lys
225                 230                 235                 240
Val Thr Ile Asp Ser Gly Thr Thr Val Tyr Pro His Gln Ala Gly Tyr
                245                 250                 255
Val Lys Leu Asn Tyr Gly Phe Ser Val Pro Asn Ser Ala Val Lys Gly
            260                 265                 270
Asp Thr Phe Lys Ile Thr Val Pro Lys Glu Leu Asn Leu Asn Gly Val
        275                 280                 285
Thr Ser Thr Ala Lys Val Pro Pro Ile Met Ala Gly Asp Gln Val Leu
290                 295                 300
Ala Asn Gly Val Ile Asp Ser Asp Gly Asn Val Ile Tyr Thr Phe Thr
305                 310                 315                 320
Asp Tyr Val Asp Asn Lys Glu Asn Val Thr Ala Asn Ile Thr Met Pro
                325                 330                 335
Ala Tyr Ile Asp Pro Glu Asn Val Thr Lys Thr Gly Asn Val Thr Leu
            340                 345                 350
Thr Thr Gly Ile Gly Thr Asn Thr Ala Ser Lys Thr Val Leu Ile Asp
        355                 360                 365
Tyr Glu Lys Tyr Gly Gln Phe His Asn Leu Ser Ile Lys Gly Thr Ile
370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Val Leu Pro Ala Leu Thr Gly Asn Leu
                405                 410                 415
Ile Pro Asn Thr Lys Ser Asn Ala Leu Ile Asp Ala Lys Asn Thr Asp
            420                 425                 430
Ile Lys Val Tyr Arg Val Asp Asn Ala Asn Asp Leu Ser Glu Ser Tyr
        435                 440                 445
Tyr Val Asn Pro Ser Asp Phe Glu Asp Val Thr Asn Gln Val Arg Ile
450                 455                 460
Ser Phe Pro Asn Ala Asn Gln Tyr Lys Val Glu Phe Pro Thr Asp Asp
465                 470                 475                 480
Asp Gln Ile Thr Thr Pro Tyr Ile Val Val Asn Gly His Ile Asp
                485                 490                 495
Pro Ala Ser Thr Gly Asp Leu Ala Leu Arg Ser Thr Phe Tyr Gly Tyr
            500                 505                 510
Asp Ser Asn Phe Ile Trp Arg Ser Met Ser Trp Asp Asn Glu Val Ala
        515                 520                 525
Phe Asn Asn Gly Ser Gly Ser Gly Asp Gly Ile Asp Lys Pro Val Val
530                 535                 540
Pro Glu Gln Pro Asp Glu Pro Gly Glu Ile Glu Pro Ile Pro Glu Asp
545                 550                 555                 560
Ser Asp Ser Asp Pro Gly Ser Asp Ser Gly Ser Asp Asn Ser Asp
                565                 570                 575
Ser Gly Ser Asp Ser Gly Ser Asp Ser Thr Ser Asp Ser Gly Ser Asp
            580                 585                 590
Ser Ala Ser Asp Ser Asp Ser Ala Ser Asp Asp Ser Ala Ser Asp
        595                 600                 605
Ser Asp Ser Ala Ser Asp Ser Ser Ala Ser Asp Ser Asp Ser Ala
            610                 615                 620
```

Ser Asp Ser Asp Ser Ala Ser Asp Ser Ala Ser Asp
625                 630                 635                 640

Ser Ala Ser Asp Ser Asp Ser Ala Ser Asp Ser Asp Ser Ala Ser Asp
            645                 650                 655

Ser Asp Ser Ala Ser Asp Ser Asp Ser Ala Ser Asp Ser Asp Ser Asp
                660                 665                 670

Ser Asp Ser Asp Ser Asp Ser Asp Ser Asp Ser Asp Ser Asp
        675                 680                 685

Ser Asp Ser Asp Ser Asp Ser Asp Ser Asp Ser Asp Ser Asp
690                 695                 700

Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp
                740                 745                 750

Ser Asp Ser Asp Ser Asp Ser Asp Ser Asp Ser Asp Ser Ala
        755                 760                 765

Ser Asp Ser Asp Ser Asp Ser Asp Ser Glu Ser Asp Ser Asp
770                 775                 780

Ser Asp Ser Asp Ser Asp Ser Asp Ser Asp Ser Asp Ser Asp
785                 790                 795                 800

Ser Glu Ser Asp Ser Asp Ser Asp Ser Asp Ser Glu Ser Asp
            805                 810                 815

Ser Asp Ser Asp Ser Asp Ser Asp Ser Ala Ser Asp Ser Asp
                820                 825                 830

Ser Gly Ser Asp Ser Asp Ser Ser Ser Asp Ser Asp Ser Thr
        835                 840                 845

Ser Asp Thr Gly Ser Asp Asn Asp Ser Asp Ser Asn Ser Asp
850                 855                 860

Ser Glu Ser Gly Ser Asn Asn Asn Val Val Pro Pro Asn Ser Pro Lys
865                 870                 875                 880

Asn Gly Thr Asn Ala Ser Asn Lys Asn Glu Ala Lys Asp Ser Lys Glu
                885                 890                 895

Pro Leu Pro Asp Thr Gly Ser Glu Asp Glu Ala Asn Thr Ser Leu Ile
                900                 905                 910

Trp Gly Leu Leu Ala Ser Leu Gly Ser Leu Leu Leu Phe Arg Arg Lys
            915                 920                 925

Lys Glu Asn Lys Asp Lys Lys
930                 935

<210> SEQ ID NO 31
<211> LENGTH: 1038
<212> TYPE: PRT
<213> ORGANISM: Staphylococcus aureus

<400> SEQUENCE: 31

Met Lys Asn Asn Leu Arg Tyr Gly Ile Arg Lys His Lys Leu Gly Ala
 1               5                  10                  15

Ala Ser Val Phe Leu Gly Thr Met Ile Val Val Gly Met Gly Gln Asp
            20                  25                  30

Lys Glu Ala Ala Ala Ser Glu Gln Lys Thr Thr Val Glu Glu Asn
        35                  40                  45

Gly Asn Ser Ala Thr Asp Asn Lys Thr Ser Glu Thr Gln Thr Thr Ala
    50                  55                  60

```
Thr Asn Val Asn His Ile Glu Glu Thr Gln Ser Tyr Asn Ala Thr Val
 65                  70                  75                  80

Thr Glu Gln Pro Ser Asn Ala Thr Gln Val Thr Thr Glu Glu Ala Pro
                 85                  90                  95

Lys Ala Val Gln Ala Pro Gln Thr Ala Gln Pro Ala Asn Val Glu Thr
            100                 105                 110

Val Lys Glu Glu Lys Pro Gln Val Lys Glu Thr Thr Gln Pro Gln
        115                 120                 125

Asp Asn Ser Gly Asn Gln Arg Gln Val Asp Leu Thr Pro Lys Lys Val
    130                 135                 140

Thr Gln Asn Gln Gly Thr Glu Thr Gln Val Glu Val Ala Gln Pro Arg
145                 150                 155                 160

Thr Ala Ser Glu Ser Lys Pro Arg Val Thr Arg Ser Ala Asp Val Ala
                165                 170                 175

Glu Ala Lys Glu Ala Ser Asp Val Ser Glu Val Lys Gly Thr Asp Val
            180                 185                 190

Thr Ser Lys Val Thr Val Glu Ser Gly Ser Ile Glu Ala Pro Gln Gly
        195                 200                 205

Asn Lys Val Glu Pro His Ala Gly Gln Arg Val Val Leu Lys Tyr Lys
    210                 215                 220

Leu Lys Phe Ala Asp Gly Leu Lys Arg Gly Asp Tyr Phe Asp Phe Thr
225                 230                 235                 240

Leu Ser Asn Asn Val Asn Thr Tyr Gly Val Ser Thr Ala Arg Lys Val
                245                 250                 255

Pro Glu Ile Lys Asn Gly Ser Val Val Met Ala Thr Gly Glu Ile Leu
            260                 265                 270

Gly Asn Gly Asn Ile Arg Tyr Thr Phe Thr Asn Glu Ile Glu His Lys
        275                 280                 285

Val Glu Val Thr Ala Asn Leu Glu Ile Asn Leu Phe Ile Asp Pro Lys
    290                 295                 300

Thr Val Gln Ser Asn Gly Glu Gln Lys Ile Thr Ser Lys Leu Asn Gly
305                 310                 315                 320

Glu Glu Thr Glu Lys Thr Ile Pro Val Tyr Asn Pro Gly Val Ser
                325                 330                 335

Asn Ser Tyr Thr Asn Val Asn Gly Ser Ile Glu Thr Phe Asn Lys Glu
                340                 345                 350

Ser Asn Lys Phe Thr His Ile Ala Tyr Ile Lys Pro Met Asn Gly Asn
        355                 360                 365

Gln Ser Asn Thr Val Ser Val Thr Gly Thr Leu Thr Glu Gly Ser Asn
    370                 375                 380

Leu Ala Gly Gly Gln Pro Thr Val Lys Val Tyr Glu Tyr Leu Gly Lys
385                 390                 395                 400

Lys Asp Glu Leu Pro Gln Ser Val Tyr Ala Asn Thr Ser Asp Thr Asn
                405                 410                 415

Lys Phe Lys Asp Val Thr Lys Glu Met Asn Gly Lys Leu Ser Val Gln
            420                 425                 430

Asp Asn Gly Ser Tyr Ser Leu Asn Leu Asp Lys Leu Asp Lys Thr Tyr
        435                 440                 445

Val Ile His Tyr Thr Gly Glu Tyr Leu Gln Gly Ser Asp Gln Val Asn
    450                 455                 460

Phe Arg Thr Glu Leu Tyr Gly Tyr Pro Glu Arg Ala Tyr Lys Ser Tyr
465                 470                 475                 480

Tyr Val Tyr Gly Gly Tyr Arg Leu Thr Trp Asp Asn Gly Leu Val Leu
```

```
                    485                 490                 495
Tyr Ser Asn Lys Ala Asp Gly Asn Gly Lys Asn Gly Gln Ile Ile Gln
                500                 505                 510

Asp Asn Asp Phe Glu Tyr Lys Glu Asp Thr Ala Lys Gly Thr Met Ser
            515                 520                 525

Gly Gln Tyr Asp Ala Lys Gln Ile Ile Glu Thr Glu Glu Asn Gln Asp
        530                 535                 540

Asn Thr Pro Leu Asp Ile Asp Tyr His Thr Ala Ile Asp Gly Glu Gly
545                 550                 555                 560

Gly Tyr Val Asp Gly Tyr Ile Glu Thr Ile Glu Glu Thr Asp Ser Ser
                565                 570                 575

Ala Ile Asp Ile Asp Tyr His Thr Ala Val Asp Ser Glu Val Gly His
            580                 585                 590

Val Gly Gly Tyr Thr Glu Ser Ser Glu Glu Ser Asn Pro Ile Asp Phe
        595                 600                 605

Glu Glu Ser Thr His Glu Asn Ser Lys His His Ala Asp Val Val Glu
    610                 615                 620

Tyr Glu Glu Asp Thr Asn Pro Gly Gly Gly Gln Val Thr Thr Glu Ser
625                 630                 635                 640

Asn Leu Val Glu Phe Asp Glu Glu Ser Thr Lys Gly Ile Val Thr Gly
                645                 650                 655

Ala Val Ser Asp His Thr Thr Ile Glu Asp Thr Lys Glu Tyr Thr Thr
            660                 665                 670

Glu Ser Asn Leu Ile Glu Leu Val Asp Glu Leu Pro Glu Glu His Gly
        675                 680                 685

Gln Ala Gln Gly Pro Ile Glu Glu Ile Thr Glu Asn Asn His His Ile
    690                 695                 700

Ser His Ser Gly Leu Gly Thr Glu Asn Gly His Gly Asn Tyr Gly Val
705                 710                 715                 720

Ile Glu Glu Ile Glu Glu Asn Ser His Val Asp Ile Lys Ser Glu Leu
                725                 730                 735

Gly Tyr Glu Gly Gly Gln Asn Ser Gly Asn Gln Ser Phe Glu Glu Asp
            740                 745                 750

Thr Glu Glu Asp Lys Pro Lys Tyr Glu Gln Gly Gly Asn Ile Val Asp
        755                 760                 765

Ile Asp Phe Asp Ser Val Pro Gln Ile His Gly Gln Asn Lys Gly Asp
    770                 775                 780

Gln Ser Phe Glu Glu Asp Thr Glu Lys Asp Lys Pro Lys Tyr Glu His
785                 790                 795                 800

Gly Gly Asn Ile Ile Asp Ile Asp Phe Asp Ser Val Pro Gln Ile His
                805                 810                 815

Gly Phe Asn Lys His Asn Glu Ile Ile Glu Glu Asp Thr Asn Lys Asp
            820                 825                 830

Lys Pro Asn Tyr Gln Phe Gly Gly His Asn Ser Val Asp Phe Glu Glu
        835                 840                 845

Asp Thr Leu Pro Lys Val Ser Gly Gln Asn Glu Gly Gln Gln Thr Ile
    850                 855                 860

Glu Glu Asp Thr Thr Pro Pro Thr Pro Pro Thr Pro Glu Val Pro Ser
865                 870                 875                 880

Glu Pro Glu Thr Pro Met Pro Pro Thr Pro Glu Val Pro Ser Glu Pro
                885                 890                 895

Glu Thr Pro Thr Pro Pro Thr Pro Glu Val Pro Ser Glu Pro Glu Thr
            900                 905                 910
```

```
Pro Thr Pro Pro Thr Pro Glu Val Pro Ser Glu Pro Glu Thr Pro Thr
            915                 920                 925
Pro Pro Thr Pro Glu Val Pro Ser Glu Pro Glu Thr Pro Thr Pro Pro
        930                 935                 940
Thr Pro Glu Val Pro Ala Glu Pro Gly Lys Pro Val Pro Pro Ala Lys
945                 950                 955                 960
Glu Glu Pro Lys Lys Pro Ser Lys Pro Val Glu Gln Gly Lys Val Val
                965                 970                 975
Thr Pro Val Ile Glu Ile Asn Glu Lys Val Lys Ala Val Ala Pro Thr
            980                 985                 990
Lys Lys Ala Gln Ser Lys Ser Glu Leu Pro Glu Thr Gly Gly Glu
            995                 1000                1005
Glu Ser Thr Asn Lys Gly Met Leu Phe Gly Gly Leu Phe Ser Ile Leu
        1010                1015                1020
Gly Leu Ala Leu Leu Arg Arg Asn Lys Lys Asn Asn Lys Ala
1025                1030                1035

<210> SEQ ID NO 32
<211> LENGTH: 877
<212> TYPE: PRT
<213> ORGANISM: Staphylococcus aureus

<400> SEQUENCE: 32

Met Lys Lys Arg Ile Asp Tyr Leu Ser Asn Lys Gln Asn Lys Tyr Ser
 1               5                  10                  15
Ile Arg Arg Phe Thr Val Gly Thr Thr Ser Val Ile Val Gly Ala Thr
            20                  25                  30
Ile Leu Phe Gly Ile Gly Asn His Gln Ala Gln Ala Ser Glu Gln Ser
        35                  40                  45
Asn Asp Thr Thr Gln Ser Ser Lys Asn Asn Ala Ser Ala Asp Ser Glu
50                  55                  60
Lys Asn Asn Met Ile Glu Thr Pro Gln Leu Asn Thr Thr Ala Asn Asp
65                  70                  75                  80
Thr Ser Asp Ile Ser Ala Asn Thr Asn Ser Ala Asn Val Asp Ser Thr
                85                  90                  95
Thr Lys Pro Met Ser Thr Gln Thr Ser Asn Thr Thr Thr Thr Glu Pro
            100                 105                 110
Ala Ser Thr Asn Glu Thr Pro Gln Pro Thr Ala Ile Lys Asn Gln Ala
        115                 120                 125
Thr Ala Ala Lys Met Gln Asp Gln Thr Val Pro Gln Glu Ala Asn Ser
130                 135                 140
Gln Val Asp Asn Lys Thr Thr Asn Asp Ala Asn Ser Ile Ala Thr Asn
145                 150                 155                 160
Ser Glu Leu Lys Asn Ser Gln Thr Leu Asp Leu Pro Gln Ser Ser Pro
                165                 170                 175
Gln Thr Ile Ser Asn Ala Gln Gly Thr Ser Lys Pro Ser Val Arg Thr
            180                 185                 190
Arg Ala Val Arg Ser Leu Ala Val Ala Glu Pro Val Val Asn Ala Ala
        195                 200                 205
Asp Ala Lys Gly Thr Asn Val Asn Asp Lys Val Thr Ala Ser Asn Phe
210                 215                 220
Lys Leu Glu Lys Thr Thr Phe Asp Pro Asn Gln Ser Gly Asn Thr Phe
225                 230                 235                 240
Met Ala Ala Asn Phe Thr Val Thr Asp Lys Val Lys Ser Gly Asp Tyr
                245                 250                 255
```

```
Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
                355                 360                 365

Pro Asn Gly Ala Asn Ile Ser Ser Gln Ile Ile Gly Val Asp Thr Ala
            370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
            435                 440                 445

Asp Pro Asn Asp Ser Asn Leu Lys Glu Val Thr Asp Gln Phe Lys Asn
        450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
            500                 505                 510

Thr Asn Arg Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn Pro Lys
530                 535                 540

Asp Pro Thr Pro Gly Pro Pro Val Asp Pro Glu Pro Ser Pro Asp Pro
545                 550                 555                 560

Glu Pro Glu Pro Thr Pro Asp Pro Glu Pro Ser Pro Asp Pro Glu Pro
                565                 570                 575

Glu Pro Ser Pro Asp Pro Asp Pro Asp Ser Asp Ser Asp Ser Asp Ser
            580                 585                 590

Gly Ser Asp Ser Asp Ser Gly Ser Asp Ser Asp Ser Glu Ser Asp Ser
            595                 600                 605

Asp Ser Asp Ser Asp Ser Asp Ser Asp Ser Asp Ser Asp Ser Glu Ser
        610                 615                 620

Asp Ser Asp Ser Glu Ser Asp Ser Asp Ser Asp Ser Asp Ser Asp Ser
625                 630                 635                 640

Asp Ser Asp Ser Asp Ser Glu Ser Asp Ser Asp Ser Asp Ser Asp Ser
                645                 650                 655

Asp Ser Asp Ser Asp Ser Asp Ser Glu Ser Asp Ser Asp Ser Glu Ser
            660                 665                 670

Asp Ser Glu Ser Asp Ser Asp Ser Asp Ser Asp Ser Asp Ser Asp Ser
            675                 680                 685
```

```
Asp Ser Asp Ser Asp Ser Asp Ser Asp Ser Asp Ser
    690                 695                 700

Asp Ser Asp Ser Asp Ser Glu Ser Asp Ser Asp Ser
705                 710                 715                 720

Asp Ser Asp Ser Asp Ser Asp Ser Asp Ser Asp Ser
            725                 730                 735

Asp Ser Asp Ser Asp Ser Asp Ser Asp Ser Asp Ser
        740                 745                 750

Asp Ser Asp Ser Asp Ser Asp Ser Asp Ser Asp Ser
    755                 760                 765

Asp Ser Asp Ser Asp Ser Asp Ser Asp Ser Asp Ser
770                 775                 780

Asp Ser Asp Ser Asp Ser Asp Ser Asp Ser Asp Ser
785                 790                 795                 800

Asp Ser Asp Ser Arg Val Thr Pro Pro Asn Glu Gln Lys Ala Pro
            805                 810                 815

Ser Asn Pro Lys Gly Glu Val Asn His Ser Asn Lys Val Ser Lys Gln
                820                 825                 830

His Lys Thr Asp Ala Leu Pro Glu Thr Gly Asp Lys Ser Glu Asn Thr
            835                 840                 845

Asn Ala Thr Leu Phe Gly Ala Met Met Ala Leu Leu Gly Ser Leu Leu
    850                 855                 860

Leu Phe Arg Lys Arg Lys Gln Asp His Lys Glu Lys Ala
865                 870                 875

<210> SEQ ID NO 33
<211> LENGTH: 658
<212> TYPE: PRT
<213> ORGANISM: Staphylococcus aureus

<400> SEQUENCE: 33

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Lys Ser Lys Lys Gly Ala Thr Val
        35                  40                  45

Ser Asp Tyr Tyr Tyr Trp Lys Ile Ile Asp Ser Leu Glu Ala Gln Phe
    50                  55                  60

Thr Gly Ala Ile Asp Leu Leu Glu Asp Tyr Lys Tyr Gly Asp Pro Ile
65                  70                  75                  80

Tyr Lys Glu Ala Lys Asp Arg Leu Met Thr Arg Val Leu Gly Glu Asp
                85                  90                  95

Gln Tyr Leu Leu Lys Lys Ile Asp Glu Tyr Glu Leu Tyr Lys Lys
            100                 105                 110

Trp Tyr Lys Ser Ser Asn Lys Asn Thr Asn Met Leu Thr Phe His Lys
        115                 120                 125

Tyr Asn Leu Tyr Asn Leu Thr Met Asn Glu Tyr Asn Asp Ile Phe Asn
    130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
            180                 185                 190
```

```
Val Val Thr Tyr Tyr Ala Asp Lys Asp Tyr Gly Glu His Ala Lys Glu
            195                 200                 205

Leu Arg Ala Lys Leu Asp Leu Ile Leu Gly Asp Thr Asp Asn Pro His
        210                 215                 220

Lys Ile Thr Asn Glu Arg Ile Lys Lys Glu Met Ile Asp Asp Leu Asn
225                 230                 235                 240

Ser Ile Ile Asp Asp Phe Phe Met Glu Thr Lys Gln Asn Arg Pro Asn
                245                 250                 255

Ser Ile Thr Lys Tyr Asp Pro Thr Lys His Asn Phe Lys Glu Lys Ser
            260                 265                 270

Glu Asn Lys Pro Asn Phe Asp Lys Leu Val Glu Thr Lys Lys Ala
        275                 280                 285

Val Lys Glu Ala Asp Glu Ser Trp Lys Asn Lys Thr Val Lys Lys Tyr
        290                 295                 300

Glu Glu Thr Val Thr Lys Ser Pro Val Val Lys Glu Lys Lys Val
305                 310                 315                 320

Glu Glu Pro Gln Leu Pro Lys Val Gly Asn Gln Glu Val Lys Thr
                325                 330                 335

Thr Ala Gly Lys Ala Glu Glu Thr Thr Gln Pro Val Ala Gln Pro Leu
            340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
        370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
            420                 425                 430

Leu Lys Gly Ile Gln Gly Glu Ser Ser Asp Ile Glu Val Lys Pro Gln
        435                 440                 445

Ala Thr Glu Thr Thr Glu Ala Ser Gln Tyr Gly Pro Arg Pro Gln Phe
        450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Asn Gln Asp
            500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
        530                 535                 540

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr His Ala
            580                 585                 590

Asn Gly Gln Val Ser Tyr Gly Ala Arg Pro Thr Tyr Lys Lys Pro Ser
        595                 600                 605

Glu Thr Asn Ala Tyr Asn Val Thr Thr His Ala Asn Gly Gln Val Ser
```

```
            610              615             620
Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys

<210> SEQ ID NO 34
<211> LENGTH: 1602
<212> TYPE: DNA
<213> ORGANISM: Staphylococcus aureus

<400> SEQUENCE: 34
atgttacaag taactgatgt gagtttacgt tttggagatc gtaaactatt tgaagatgta      60
aatattaaat ttacagaagg taattgttat ggattaattg gtgcgaatgg tgcaggtaaa     120
tcaacattct taaaaatatt atctggtgaa ttagattctc aaacaggaca tgtttcatta     180
ggtaaaaatg aacgtctagc tgttttaaaa caggaccact atgcttatga agatgaacgc     240
gtgcttgatt tgtaattaa aggtcacgaa cgtctttatg aggttatgaa agaaaaagat     300
gaaatctata tgaagccaga tttcagtgat gaagatggta tccgtgctgc tgaacttgaa     360
ggtgaatttg cagaaatgaa tggttggaat gctgaagctg atgctgctaa ccttttatct     420
ggtttaggta tcgatccaac tttacacgat aaaaaaatgg ctgaattaga aacaaccaa     480 aaaattaaag tattattagc gcaaagttta ttcggtgaac cagacgtact attactggat     540
gagcctacta acggtctcga tattccagca atcagttggt tagaagattt cttaattaac     600
tttgataata ctgttatcgt agtatcgcat gaccgtcatt tcttaaataa tgtatgtact     660
catatcgctg atttagactt cggtaaaatt aaagtttatg ttggtaacta tgatttttgg     720
tatcaatcta gtcagttagc tcaaaagatg gctcaagaac aaaacaagaa aaagaagaa     780 aaaatgaaag agttacagga ctttattgca cgtttctcag ctaacgcttc taaatctaaa     840
caagcaacaa gtcgtaaaaa acaacttgag aaaattgaat tagatgatat tcaaccatca     900
tcaagaagat atcctttcgt taaattcacg cctgagcgtg agattggtaa cgacttatta     960
atcgttcaaa atctttctaa acaattgac ggcgaaaaag tattagataa tgtatcattc     1020
acaatgaatc caaatgataa agcgatttta attggagata tgaaattgc aaaaacaaca     1080 ttacttaaaa tattagctgg cgaaatggaa ccagacgaag gttcatttaa atggggtgtt     1140
actacatcat taagttactt ccctaaagat aactcagagt tctttgaggg tgtaaatatg     1200
aatctcgttg attggttaag acaatatgct cctgaagatg aacaaacaga acattttta     1260 cgtggtttct taggtcgtat gttatttagt ggtgaagaag ttaagaaaaa agctagtgtg     1320
ctttcaggtg gagaaaaagt acgttgtatg ctaagtaaaa tgatgttatc aagtgcgaat     1380
gtacttttac ttgacgaacc tactaaccac ttagacttag aaagtattac tgctgtcaat     1440
gatggtctta atcatttaa aggttctatc atctttactt cttatgactt cgaatttatc     1500
aacacgattg caaccgtgt tatcgattta aataaacaag gcggcgtttc aaaagaaatt     1560
ccatatgaag aatacttgca agaaatcggc gttttaaaat aa                       1602

<210> SEQ ID NO 35
<211> LENGTH: 1608
<212> TYPE: DNA
<213> ORGANISM: Staphylococcus epidermidis

<400> SEQUENCE: 35
```

-continued

| | |
|---|---|
| atgttacaag taactgatgt aagtttacgt tttggtgatc gtaaactatt tgaagatgta | 60 |
| aatataaaat ttacagaggg taattgttat ggattaattg gtgcaaatgg tgctgggaaa | 120 |
| tctacattct tgaagatttt atcaggcgaa attgattcac agactggtca tgtatctcta | 180 |
| ggtaaagatg agcgtttggc tgtgttaaaa caagatcatt ttgcttatga agatgaacgt | 240 |
| gttttagatg ttgtgattaa aggacatgaa cgtttgtatc aagtgatgaa agagaaagat | 300 |
| gaaatttata tgaaacctga tttcagcgat gaggacggta ttcgcgctgc agaacttgaa | 360 |
| ggagaatttg cagaaatgaa cggttggaat gctgaagctg atgctgctaa cttattatca | 420 |
| ggattaggca tagaacctga cttacatgat aaaaatatgt ctgaacttga aaataatcaa | 480 |
| aaagttaagg tattgttagc tcaaagttta tttggtgatc ctgacgttct tttactagat | 540 |
| gagcctacca atggtttaga tataccagca ataagttggt tagaagactt tttaattaat | 600 |
| tttgaaaata ctgtcattgt cgtttcgcat gaccgtcact tcttaaataa tgtttgtact | 660 |
| catattgctg atttagactt tggcaaaatt aaacttatg ttggtaacta tgattttgg | 720 |
| tatcaatcaa gtcaattagc acaaaaaatg gcacaagaac aaaataagaa aaagaagaa | 780 |
| aaaatgaaag agttacagga tttcatcgca cgcttctcag caaatgcttc taaatctaaa | 840 |
| caggcaacaa gtcgtaagaa acaattagaa aaaattgaat tagatgatat ccagccatca | 900 |
| tctcgtagat accottacgt gaaatttact cctgaacgtg aaattggaaa tgatttactt | 960 |
| acagtagaaa atctttctaa aacaattgac ggcgaaaaag tactagacaa tgtttcattc | 1020 |
| actatgaatc ctaatgataa agctatttta gttggtgata gcgaaattgc taaaacaaca | 1080 |
| ttgttaaaaa ttttagctgg agaaatggaa ccagatgaag gtacatttaa atgggggtgta | 1140 |
| acgacatctt taagttactt ccctaaagat aactctgagt tctttgatgg tgtcgatatg | 1200 |
| aatttagttg aatggttacg tcaatacgct ccagaagatg aacaaactga acatttttta | 1260 |
| cgtggttct taggtcgcat gttatttagt ggtgaggaag ttaagaaaaa agcaagcgtg | 1320 |
| ctttcaggtg gagaaaaagt acgttgcatg ttaagtaaaa tgatgttatc aagtgctaac | 1380 |
| gtacttttac ttgatgagcc aacaaaccat ttagatttgg aaagtatcac tgctgtaaat | 1440 |
| gacggattaa aatcatttaa aggttctatc atcttcactt cttatgattt tgaatttatt | 1500 |
| aatacaatcg caaatcgagt gattgacttg aatcaagctg gtgcccttc taaagaagta | 1560 |
| ccttatgagg aatacttaca agaaattggt gtattacaaa ataattaa | 1608 |

<210> SEQ ID NO 36
<211> LENGTH: 1305
<212> TYPE: DNA
<213> ORGANISM: Staphylococcus aureus

<400> SEQUENCE: 36

| | |
|---|---|
| atgccaatta ttacagatgt ttacgctcgc gaagtcttag actctcgtgg taacccaact | 60 |
| gttgaagtag aagtattaac tgaaagtggc gcatttggtc gtgcattagt accatcaggt | 120 |
| gcttcaactg gtgaacacga agctgttgaa ttacgtgatg gagacaaatc acgttattta | 180 |
| ggtaaaggtg ttactaaagc agttgaaaac gttaatgaaa tcatcgcacc agaaattatt | 240 |
| gaaggtgaat tttcagtatt agatcaagta tctattgata aaatgatgat cgcattagac | 300 |
| ggtactccaa acaaaggtaa attaggtgca aatgctattt aggtgtatc tatcgcagta | 360 |
| gcacgtgcag cagctgactt attaggtcaa ccactttaca atatttagg tggatttaat | 420 |
| ggtaagcagt taccagtacc aatgatgaac atcgttaatg gtggttctca ctcagatgct | 480 |
| ccaattgcat tccaagaatt catgattta cctgtaggtg ctacaacgtt caaagaatca | 540 |

| ttacgttggg gtactgaaat tttccacaac ttaaaatcaa ttttaagcaa acgtggttta | 600 |
| gaaactgcag taggtgacga aggtggtttc gctcctaaat tgaaggtac tgaagatgct | 660 |
| gttgaaacaa ttatccaagc aatcgaagca gctggttaca aaccaggtga agaagtattc | 720 |
| ttaggatttg actgtgcatc atcagaattc tatgaaaatg gtgtatatga ctacagtaag | 780 |
| ttcgaaggcg aacacggtgc aaaacgtaca gctgcagaac aagttgacta cttagaacaa | 840 |
| ttagtagaca aatatcctat cattacaatt gaagacggta tggacgaaaa cgactgggat | 900 |
| ggttggaaac aacttacaga acgtatcggt gaccgtgtac aattagtagg tgacgattta | 960 |
| ttcgtaacaa acactgaaat tttagcaaaa ggtattgaaa acggaattgg taactcaatc | 1020 |
| ttaattaaag ttaaccaaat cggtacatta actgaaacat tgatgcaat cgaaatggct | 1080 |
| caaaaagctg gttacacagc agtagtttct caccgttcag gtgaaacaga agatacaaca | 1140 |
| attgctgata ttgctgttgc tacaaacgct ggtcaaatta aaactggttc attatcacgt | 1200 |
| actgaccgta ttgctaaata caatcaatta ttacgtatcg aagatgaatt atttgaaact | 1260 |
| gctaaatatg acggtatcaa atcattctat aacttagata aataa | 1305 |

<210> SEQ ID NO 37
<211> LENGTH: 1305
<212> TYPE: DNA
<213> ORGANISM: Staphylococcus epidermidis

<400> SEQUENCE: 37

| atgccaatta ttacagatgt ttacgctcgc gaagtcttag actcacgtgg taacccaaca | 60 |
| gttgaagttg aagtattaac tgaaagcggt gctttcggac gtgcattagt accttctggt | 120 |
| gcttctactg gtgaacatga agcagttgaa ttacgtgatg gagataaatc acgttattta | 180 |
| ggtaaaggtg tgactaaagc ggtagaaaat gttaacgaaa tgatcgcacc agaaatcgtt | 240 |
| gaaggtgaat tttcagtttt agatcaagta tctattgata aaatgatgat tcaattagac | 300 |
| ggtacacaca acaaaggtaa attaggtgca atgccatttt aggtgtttc tattgccgta | 360 |
| gctcgtgcag ctgctgactt attaggtcaa ccattatata aatatttagg tggatttaat | 420 |
| ggtaaacaat tgccagtacc tatgatgaat attgttaatg gtggttctca ctcagatgca | 480 |
| ccaattgctt tccaagagtt catgattttta cctgtaggtg ctgagtcatt caaagaatca | 540 |
| ttacgttggg gtgcagaaat cttccataac cttaaatcaa tcttaagtga acgtggttta | 600 |
| gaaactgcag taggtgatga aggtggtttc gctcctagat ttgaaggcac tgaagacgct | 660 |
| gtagaaacta ttattaaagc tatcgaaaaa gcaggataca aaccaggtga agatgtattc | 720 |
| ttaggatttg actgtgcttc ttctgaattc tatgaaaatg gtgtttatga ttacactaaa | 780 |
| ttcgaaggtg aacacggtgc taaacgtagt gcagcagagc aagttgacta cttagaagaa | 840 |
| ttaattggta aatatccaat catcactatt gaagatggta tggatgaaaa cgattgggaa | 900 |
| ggttggaaac aattaactga tcgtatcggt gataaagttc aattagttgg tgatgattta | 960 |
| ttcgtaacta acactgaaat tttatctaaa ggtatcgaac aaggtattgg taactcaatc | 1020 |
| ttaatcaaag taaaccaaat cggtacatta actgaaacat tcgatgctat tgaaatggct | 1080 |
| caaaaagctg gatatactgc ggttgtatct caccgttctg gtgaaactga agatactaca | 1140 |
| attgctgata tcgcagttgc tacaaatgca ggccaaatta aaacaggttc attatctaga | 1200 |
| actgaccgta ttgctaaata caatcaatta ttacgtattg aagatgaatt atacgaaaca | 1260 |
| gctaaatttg aaggaattaa atctttctac aatttagata aataa | 1305 |

<210> SEQ ID NO 38

-continued

```
<211> LENGTH: 768
<212> TYPE: DNA
<213> ORGANISM: Staphylococcus aureus

<400> SEQUENCE: 38
atgaaaaaaa tcgttacagc tacaatcgct acagcaggac ttgccactat cgcatttgca      60
ggacatgatg cacaagccgc agaacaaaat aacaatggat ataattctaa tgacgctcaa     120
tcatacagct atacgtatac aattgatgca caagtaatt atcattacac ttggacagga     180
aattggaatc caagtcaatt aacgcaaaac aacacatact actacaacaa ctacaatact     240
tatagttata acaatgcatc ttacaataac tactataatc attcatatca atacaataac     300
tatacaaaca atagccaaac agcaacaaat aactattata ctggtggttc aggtgcaagt     360
tatagcacaa caagtaataa tgttcatgtg actacaactg cagcgccatc ttcaaatggt     420
cgttcaattt ctaatggtta tgcatcagga gtaacttat atacttcagg acaatgtact     480
tattatgtat ttgatcgtgt tggtgggaaa attggttcaa catggggtaa cgcaagtaat     540
tgggctaacg cagctgcatc atctggctat acagtgaaca atacaccaaa agttggtgct     600
atcatgcaaa caacacaagg ctattacggt catgttgctt acgttgaagg cgttaacagc     660
aacggttctg ttcgtgtttc agaaatgaac tatggacatg gtgctggtgt ggttacgtct     720
cgtacaattt cagcaaacca agcaggttca tataatttca ttcattaa               768

<210> SEQ ID NO 39
<211> LENGTH: 804
<212> TYPE: DNA
<213> ORGANISM: Staphylococcus aureus

<400> SEQUENCE: 39
atgaagaaaa tcgctacagc tactatcgca actgcaggat tcgctacaat cgcaattgca      60
tcaggaaatc aagctcatgc ttctgagcaa gataactacg ttataatcc aaacgaccca     120 acatcatata gctatactta cactattgat gcacaaggta actaccatta cacatggaaa     180
ggtaactggc atccaagtca attaaaccaa gataatggct actacagcta ttactactac     240
aatggctaca ataactacaa caattacaac aatggttata gctacaataa ttacagccgt     300
tacaacaact actcaaataa taatcaatca tataactaca ataactataa tagttacaac     360
acaaacagct accgtactgg tggtttaggt gcaagctaca gcacttcaag caacaatgtt     420
caagtaacta caactatggc tccatcatca aatggccgtt caatctcaag tggttatact     480
tcaggacgta acttatacac ttctggtcaa tgtacatact acgtatttga tcgtgtaggt     540
ggtaaaatcg gttcaacttg gggcaatgca agtaactggg ctaacgcagc tgcaagagct     600
ggttacacag tgaacaatac accaaaagct ggtgcaatta tgcaaacaac tcaaggtgca     660
tacggtcacg ttgcatacgt tgaaagtgtt aacagcaatg gttcagtaag agtttcagaa     720
atgaactatg gttatggccc aggtgttgta acttcacgta caatctcagc tagccaagct     780
gctggttata acttcattca ctaa                                           804

<210> SEQ ID NO 40
<211> LENGTH: 774
<212> TYPE: DNA
<213> ORGANISM: Staphylococcus epidermidis

<400> SEQUENCE: 40
atgaaaaaaa tcgctacagc tacaattgca actgcaggaa tcgctacttt cgcatttgca      60
caccatgacg cacaagcagc agaacaaaat aatgatgggt acaatccaaa cgacccttat     120
```

-continued

```
tcatatagct acacttacac aatcgatgct gaaggtaact accactacac ttggaaaggt    180
aactggagtc cagatcgtgt aaatacttca tataactata ataattataa taactacaac    240
tactatggtt acaataacta tagcaactac aataactaca gtaattacaa caattacaac    300
aactatcaat caaacaacac gcaatcacaa agaacaactc aaccgactgg tggtttaggc    360
gcaagctatt caacatcaag tagtaatgtt cacgttacaa caacttctgc gccatcatca    420
aacggtgtat ctttatcaaa cgctcgctca gcatctggta acttatacac ttcaggtcaa    480
tgtacatatt atgtatttga cagagtaggt ggcaaaatcg gttcaacgtg ggtaacgca     540
aacaactggg caaacgctgc agcacgttct ggttacacag taaacaattc gcctgctaaa    600
ggtgcaatct tacaaacgtc acaaggtgca tacggacacg tagcatacgt tgaaggtgta    660
aacagcaatg gttcaatcag agtttcagaa atgaactacg gtcacggtgc aggtgttgtc    720
acttcacgta caatctctgc gagccaagct gcttcatata actatattca ctaa          774
```

<210> SEQ ID NO 41
<211> LENGTH: 930
<212> TYPE: DNA
<213> ORGANISM: Staphylococcus aureus

<400> SEQUENCE: 41

```
atgaaaaaat tagtaccttt attattagcc ttattacttc tagttgctgc atgtggtact     60
ggtggtaaac aaagcagtga taagtcaaat ggcaaattaa aagtagtaac gacgaattca    120
attttatatg atatggctaa aaatgttggt ggagacaacg tcgatattca tagtattgta    180
cctgttggtc aagatcctca tgaatatgaa gttaaaccta aagatattaa aaagttaact    240
gacgctgacg ttattttata caacggatta aatttagaga ctggtaacgg ttggtttgaa    300
aaagccttag aacaggctgg taaatcatta aaagataaaa aagttatcgc agtatcaaaa    360
gatgttaaac ctatctattt aaacggtgaa gaaggcaaca aagataaaca agatccacac    420
gcatggttaa gtttagataa tggtattaaa tacgtaaaaa caattcaaca aacatttatc    480
gataacgaca aaaaacataa agcagattat gaaaagcaag gtaacaaata cattgctcaa    540
ttggaaaaat taaataatga cagtaaagac aaatttaatg acattccaaa agaacaacgt    600
gccatgatta caagtgaagg tgccttcaag tacttctcaa aacaatacgg tattacacca    660
ggttatattt gggaaattaa cactgaaaaa caaggtacac ctgaacaaat gagacaagct    720
attgagtttg ttaaaaagca caaattaaaa cacttattag tagaaacaag tgttgataag    780
aaagcaatgg aaagtttatc tgaagaaacg aagaaagata tctttggtga agtgtacaca    840
gattcaatcg gtaaagaagg cactaaaggt gactcttact acaaaatgat gaaatcaaat    900
attgaaactg tacacggaag catgaaataa                                     930
```

<210> SEQ ID NO 42
<211> LENGTH: 930
<212> TYPE: DNA
<213> ORGANISM: Staphylococcus epidermidis

<400> SEQUENCE: 42

```
gtgaaaaaaa ttctcgcttt agcaatagca tttttaatta tccttgccgc atgtgggaat     60
cacagtaacc atgaacatca ctcacatgaa ggaaaattaa aagttgtaac tacaaactct    120
attctctatg acatggttaa acgtgtcggt ggaaataagg tcgatgttca tagcatcgtt    180
ccagtaggac aagacccaca tgaatatgag gttaaaccta aagatattaa agcattaaca    240
gatgctgacg ttgtatttta taacggttta aacctagaaa ctggaaatgg ttggtttgaa    300
```

```
aaagcacttg accaagcagg aaaatcaaca aaagataaaa atgtgatagc agcatcaaat      360
aatgttaaac caatatactt aaatggtgag gaaggtaaca aaaacaaaca agatccacat      420
gcatggttaa gtttagagaa tggaattaaa tacgtaaaaa caatacaaaa atcactagaa      480
catcatgata aaaagataa gtctacatat gaaaaacaag ggaatgcata tatatcaaaa       540
ttagaagaac ttaataaaga tagtaaaaat aaatttgatg acatacccaa aaatcaacgt      600
gccatgatga caagtgaagg tgcatttaaa tattttgctc aacaattcga tgttaaacca      660
ggttatattt gggagataaa cacagaaaaa caaggtacac ctggtcaaat gaaacaagcc      720
attaaatttg ttaaagataa tcatttaaaa catttattag tcgaaacaag cgtagataaa      780
aaagctatgc aaagtttatc agaagaaact aagaaagata tttatggtga agtatttacc      840
gactctatag gtaaggaagg tactaaaggt gactcatact ataaaatgat gaaatctaat      900
attgatacaa tacatggtag tatgaaataa                                       930

<210> SEQ ID NO 43
<211> LENGTH: 702
<212> TYPE: DNA
<213> ORGANISM: Staphylococcus aureus

<400> SEQUENCE: 43
atgaaaaaga caattatggc atcatcatta gcagtggcat taggtgtaac aggttacgca       60
gcaggtacag gacatcaagc acacgctgct gaagtaaacg ttgatcaagc acacttagtt      120
gacttagcgc ataatcacca agatcaatta aatgcagctc caatcaaaga tggtgcatat      180
gacatccact ttgtaaaaga tggtttccaa tataaccttta cttcaaatgg tactacatgg      240
tcatggagct atgaagcagc taatggtcaa actgctggtt tctcaaacgt tgcaggtgca      300
gactacacta cttcatacaa ccaaggttca gatgtacaat cagtaagcta caatgcacaa      360
tcaagtaact caaacgttga agctgtttca gctccaactt accataacta cagcacttca      420
actacttcaa gttcagtgag attaagcaat ggtaatactg caggtgctac tggttcatca      480
gcagctcaaa tcatggctca acgtactggt gtttcagctt ctacatgggc tgcaatcatc      540
gctcgtgaat caaatggtca gtaaatgct tacaacccat caggtgcttc aggtttattc      600
caaactatgc caggttgggg tccgacaaac actgttgacc aacaaatcaa cgcagctgtt      660
aaagcataca aagcacaagg tttaggtgct tggggattct aa                         702

<210> SEQ ID NO 44
<211> LENGTH: 708
<212> TYPE: DNA
<213> ORGANISM: Staphylococcus epidermidis

<400> SEQUENCE: 44
atgaaaaaaa cagttatcgc ttctacatta gcagtatctt taggaattgc aggttacggt       60
ttatcaggac atgaagcaca cgcttcagaa actacaaacg ttgataaagc acacttagta      120
gatttagcac aacataatcc tgaagaatta aatgctaaac cagttcaagc tggtgcttac      180
gatattcatt tcgtagacaa tggataccaa tacaacttca cttcaaatgg ttctgaatgg      240
tcatggagct acgctgtagc tggttcagat gctgattaca cagaatcatc atcaaaccaa      300
gaagtaagtg caaatacaca atctagtaac acaaatgtac aagctgtttc agctccaact      360
tcttcagaaa gtcgtagcta cagcacatca actacttcat actcagcacc aagccataac      420
tacagctctc acagtagttc agtaagatta tcaaatggta atactgctgg ttctgtaggt      480
tcatatgctg ctgctcaaat ggctgcacgt actggtgtat ctgcttcaac atgggaacac      540
```

-continued

| | |
|---|---|
| atcattgcta gagaatcaaa tggtcaatta catgcacgta atgcttcagg tgctgctgga | 600 |
| ttattccaaa ctatgccagg ttggggttca actggttcag taaatgatca aatcaatgcc | 660 |
| gcttataaag catataaagc acaaggttta tctgcttggg gtatgtaa | 708 |

<210> SEQ ID NO 45
<211> LENGTH: 11670
<212> TYPE: DNA
<213> ORGANISM: Staphylococcus aureus

<400> SEQUENCE: 45

| | |
|---|---|
| gtgaattatc gtgataaaat tcaaaagttt agtattcgta aatatacagt tggtacattt | 60 |
| tcaactgtca ttgcgacatt ggtattttta ggattcaata catcacaagc acatgctgct | 120 |
| gaaacaaatc aaccagcaag cgtggttaaa cagaaacaac aaagtaataa tgaacagact | 180 |
| gagaatcgag aatctcaagt acaaaattct caaaattcac aaaatagtca atcattatcc | 240 |
| gctactcatg aaaatgagca accaaataat agtcaagcta atttagtaaa tcaaaaagta | 300 |
| gcgcaatcat ctactactaa tgatgaacaa ccagcatctc aaaatgtaaa tacaaagaaa | 360 |
| gattcggcaa cggctgcgac aacacaacca gataaagaag aaagtaagca taaacaaaac | 420 |
| gaaagtcaat ctgctaataa aaatggaaac gacaatagag cggctcatgt agaaaatcat | 480 |
| gaagcaaatg tagtaacagc ttcagattca tctgataatg gtaacgtaca acatgaccga | 540 |
| aatgaattac aagcattttt tgatgcaaat tatcatgatt atcgctttat tgaccgtgaa | 600 |
| aatgcagatt ctggcacatt taactatgta aaaggcattt ttgacaagat taatacttta | 660 |
| ttaggcagta atgatccaat taacaataaa gacttgcaac ttgcatacaa agaattggaa | 720 |
| caagctgttg cttttaattcg tacaatgcct caacgtcaac aaaactagccg tcgatcaaac | 780 |
| agaattcaaa cgcgttctgt tgagtctaga gctgcagagc ctagatcagt atcagactat | 840 |
| caaaatgcaa attcatcata ttatgttgaa aatgctaatg atggttcagg atatcctgta | 900 |
| ggtacatata tcaatgcttc tagtaaaggg gcgccatata atttaccaac tacaccatgg | 960 |
| aatacattga aggcctctga ctcaaaggaa attgctctta tgacagcgaa acaaactgga | 1020 |
| gatggctacc aatgggttat taagtttaat aaaggacatg ctccacatca aaatatgatt | 1080 |
| ttctggtttg cattaccagc agaccaagtg ccagtaggaa gaactgactt tgtaacagtt | 1140 |
| aattcagatg gaacaaatgt acaatggagt catggagcag gagcaggtgc aaataaacca | 1200 |
| cttcaacaaa tgtgggaata tggagtaaat gatcctgatc gttcacatga ctttaaaata | 1260 |
| agaaatagaa gtggccaagt aatatatagc tggccaactg tccatgttta ttctttagaa | 1320 |
| gatttatcta gagcgagtga ttattttagt gaagctggag cgacacctgc tactaaagca | 1380 |
| tttggtagac aaaattttga atatattaat ggtcaaaaac ctgctgaatc accgggtgtt | 1440 |
| cctaaagttt atactttcat cggtcaaggt gatgcaagtt atacaatttc atttaaaaca | 1500 |
| caaggtccaa ctgttaataa attgtattat gcagcaggtg ggcgtgcttt agagtacaat | 1560 |
| caattattta tgtacagtca actatacgtc gaatcaacgc aagaccatca acaacgtctt | 1620 |
| aatggtttaa gacaagtggt taatcgtaca tatcgcatag gtacaactaa acgtgtagaa | 1680 |
| gtgagtcaag gaaatgtaca aacgaaaaag gtattagaaa gtacaaacct aaatatagat | 1740 |
| gattttgttg atgatccttt aagttatgtt aagacgccga gtaataaagt gttaggtttt | 1800 |
| tacccaacta atgcaaatac taacgctttt agaccggggg gcgttcaaga attaaatgaa | 1860 |
| tatcaattaa gtcaattatt tactgatcaa aaattacaag aagcagcaag aactagaaac | 1920 |
| ccaataagat taatgattgg tttcgactat cctgatggtt atggtaatag tgaaacttta | 1980 |

```
gttcctgtta acttaacggt attacctgaa atccaacata atattaaatt ctttaaaaat     2040
gacgatactc aaaatattgc tgaaaaacca ttttcaaaac aagctgggca tccagttttc     2100
tatgtatatg caggtaacca agggaatgct tccgtgaatt taggtggtag cgtaacatct     2160
attcaaccat tacgtattaa tttaacaagt aatgagaatt ttacagataa agattggcaa     2220
attacaggta ttccgcgtac attacacatt gaaaactcga caaatagaac taataatgct     2280
agagaacgta acattgaact tgttggtaat ttattaccag gggattactt tggtacgata     2340
cgttttggac gtaaagaaca attatttgaa attcgtgtta aaccacatac accaacaatt     2400
acaacgacag ctgagcaatt aagaggtaca gcattacaaa aagtgcctgt taatatttcg     2460
ggaataccgt tggatccatc ggcattggtt tatttagttg caccaacaaa tcaaactacg     2520
aatggtggta gtgaggcaga tcaaatacca tctggttata cgatacttgc gactggtaca     2580
cctgatgggg tgcataatac aattactata cgaccgcaag attatgttgt attcatacca     2640
cctgtaggta aacaaattag agcagtagtt tattataata aagtagttgc atctaatatg     2700
agtaatgctg ttactatttt gccagatgac attccaccaa caatcaataa tcctgttgga     2760
ataaatgcca aatactatcg aggcgacgaa gtcaacttta caatgggagt ctctgataga     2820
cattctggta taaaaaatac aactattact actttgccaa gtggttggac atcaaattta     2880
actaaatccg acaacaaaaa cggctcatta gctattacag gtagagtctc tatgaatcag     2940
gcatttaaca gtgatattac atttaaagta tcagcgacag acaatgtcaa taatacgaca     3000
aatgatagtc aatctaaaca tgtgtcaatt catgtaggta aaattagtga agatgctcat     3060
ccgattgtat taggaaatac tgagaaagtt gtagtagtca atccgactgc tgtatctaat     3120
gatgaaaagc aaagcataat tactgccttt atgaataaaa accaaaatat aagaggatat     3180
ttagcatcaa ctgatccagt aactgtcgat aataatggta acgtcacatt acattaccgt     3240
gatggctcat caacaacgct tgatgctaca aatgtgatga catacgaacc agttgtgaaa     3300
tctgaatatc aaactgccaa tgctgctaaa acagcaacgg taacgattgc taaaggacaa     3360
tcatttaata ttggtgatat taaacaatat tttactttaa gtaatggaca agctattcca     3420
aatggcacat ttacaaatat tacatctgat agaactattc caactgcaca agaagttagt     3480
caaatgaatg caggtacgca gttatatcat atagttgctt caaatgcata tcataaagac     3540
actgaagatt tctatattag tttaaaaatc gttgatgtga acaacctgaa aggcgatcaa     3600
cgtgtctatc gtacgtcaac atatgattta accactgatg aaatctcaaa agtaaaacaa     3660
gcttttatta atgcaaatag agatgtaatt acgcttgccg aaggtgatat ttcagttaca     3720
aatacaccta atggtgctaa tgtaagtact attacagtaa atattaataa aggtcgatta     3780
acgaaatcat tcgcgtctaa cctagctaat atgaatttct tgcgttgggt taatttccca     3840
caagattata cagtgacatg gacgaatgca aaaattgcaa acagaccaac agatggtggt     3900
ttatcatggt ccgatgacca taaatcttta atttatcgtt atgatgctac attaggcaca     3960
caaattacaa ctaatgatat tttaacgatg ctaaaagcga ctactacagt gcctggattg     4020
cgtaataata ttactggtaa tgaaaaagca aagcagaag caggtggaag accaaactat     4080
agaacaactg gttattcaca atcaaatgcg acaactgatg gtcaacgtca atttacgttg     4140
aatggtcaag tgattcaaat attagacatc atcaaccctt caaacggtta tggtgggcaa     4200
cctgttacaa attcaaatac tcgtgcaaac catagtaact caactgttgt taacgtaaac     4260
gaaccggcag ctaatggtgc tggcgcattt acaattgacc acgttgtaaa aagtaattct     4320
acacataatg caagtgatgc agtttataaa gcgcagttat acttaacgcc atatggtcca     4380
```

```
aaacaatatg ttgaacattt aaatcaaaat acaggaaata ctactgacgc tattaacatt    4440
tattttgtac caagtgactt agtgaatcca acaatttcag taggtaatta cactaatcat    4500
caagtgttct caggtgaaac atttacaaat acgattacag cgaatgataa ctttggtgtg    4560
caatcggtaa ctgtaccaaa tacatcacaa attacaggta ctgttgataa taaccatcaa    4620
catgtttctg caacggcacc aaatgtgaca tcagcaacta gtaagacaat caatttatta    4680
gcaactgata caagtggtaa tacagctaca acttcattca atgtaacagt gaaacctttg    4740
cgtgataaat atcgagttgg tacttcatca acggctgcta atcctgttag aattgccaat    4800
atttcgaata atgcgacagt atcacaagct gatcaaacga caattattaa ttcgttaacg    4860
tttacaagta atgcaccaaa tagaaactat gcaacagcaa gcgcaaatga aatcactagt    4920
aaaacagtta gtaatgtcag tcgtactgga aataatgcca atgtcacagt aactgttact    4980
catcaagatg gaacaacatc aacagtgact gtacctgtaa agcatgtcat tccagaaatc    5040
gttgcacatt cgcattacac tgtacaaggc caagacttcc cagcaggtaa tggttctagt    5100
gcagcagatt actttaagtt atctaatggt agtgccattc cagatgcaac gattacatgg    5160
gtaagtggac aagcgccaaa taaagataat acacgtattg gtgaagatat aacagtaact    5220
gcacatatct taattgatgg cgaaacaacg ccgattacga aaacagcaac atataaagta    5280
gtaagaactg taccgaaaca tgtctttgaa acagccagag gtgttttata cccaggtgtt    5340
tcagatatgt atgatgcgaa acaatatgtt aagccagtaa ataattcttg gtcgacaaat    5400
gcgcaacata tgaattttca atttgttgga acatatggtc ctaacaaaga tgttgtaggt    5460
atatcaacgc gtcttattag agtgacttat gataatagac aaactgaaga tttaactatt    5520
ttatctaaag ttaaacctga cccaccaaga attgacgcaa actctgtgac atataaagca    5580
ggtcttacaa accaagaaat taagttaat aacgtattaa ataactcgtc agtaaaatta    5640
tttaaagcag ataatacacc attaaatgtc acaatatta ctcatggtag tggttttagt    5700
tcggttgtga cagtaagtga cgcgttacca aatggcggaa ttaaagcaaa atcttcaatt    5760
tcaatgaaca atgtgacgta tacgacgcaa gacgaacatg gtcaagttgt tacagtaaca    5820
agaaatgaat ctgttgattc aaatgatagt gcttctgtta cagtaacacc acaattacaa    5880
gcaactactg aaggcgctgt atttattaaa ggtggcgacg ttttgatttc ggtcatgta    5940 gaacgattta ttcaaaatcc gccacatggg gcaacggtcg catggcatga tagtccagat    6000
acatggaaga atacagtcgg caacacacat aaaactgcgg ttgtaacatt acctagtggt    6060
caaggtacgc gtaatgttga agttccagtc aaagtttatc cagttgctaa tgctaaggcg    6120
ccatcacgtg atgtgaaagg tcaaaatttg acacatggta caaacgctat tgattacatt    6180
acatttgatc caaatactaa tacgaatggt attacagcag catgggcaaa tagacaacaa    6240
ccaaataacc agcaagcagg cgttcaacat ttaaatgtcg atgtcacata tccaggtatt    6300
tcagctgcta aacgagttcc tgtaactgtg aacgtatatc aatttgaatt ccctcaaact    6360
acttatacaa caacagttgg tggcactttta gcaagtggta cgcaagcatc aggatatgca    6420
catatgcaaa acgcttcagg tttaccaaca gatggattta cgtataaatg gaatcgtgat    6480
actacgggta caaacgatgc aaactgggca gcaatgaata accaaatac tgcacaagtc    6540 gttaatgcaa aatatgatgt catctataat ggacatacat ttgcaacatc tttaccagcg    6600
aaatttgtag taaaagatgt tcaaccagcg aaaccaactg tcactgaaac agcggcagga    6660
gcgattacaa ttgcacctgg tgcgaaccaa acagtcaata ctcatgctgg taatgttacg    6720
acatatgctg acaaattagt tattaaacgt aatggaaatg ttgtaacgac atttacacgt    6780
```

```
cgtaataata cgagcccatg ggtgaaagaa gcatcagcag ataatgtaac aggtattgtt    6840
ggaactaata atggtattac tgtggcagca ggtactttca atcctgctga tacaattcaa    6900
gttgttgcaa cacaaggtag tggcgaaaca atcagtgacg agcaacgtag tgatgatttc    6960
acagttgtcg caccacaacc gaaccaagcg actacgaaaa tttggcaaaa tggtcatatt    7020
gatatcacgc ctaataatcc atcaggacat ttaattaatc caacacaagc aatggatatt    7080
gcttacactg aaaaagtggg taatggtgca gaacatagta agacaattaa tgttgttcgt    7140
ggtcaaaata atcaatggac aattgcgaat aagcctgact atgtaacgtt agatgcacaa    7200
actggtaaag tgacgttcaa tgccaatact ataaaaccaa attcatcaat cacaattact    7260
ccgaaagcag gtacaggtca ctcagtaagt agtaatccaa gtacattaac tgcaccggca    7320
gctcatactg tcaacacaac tgaaattgtg aaagattatg gttcaaatgt aacagcagct    7380
gaaattaaca atgcagttca agttgctaat aaacgtactg caacgattaa aaatggcaca    7440
gcaatgccta ctaatttagc tggtggtagc acaacgacga ttcctgtgac agtaacttac    7500
aatgatggta gtactgaaga agtacaagag tccattttca caaaagcgga taaacgtgag    7560
ttaatcacag ctaaaaatca tttagatgat ccagtaagca ctgaaggtaa aaagccaggt    7620
acaattacgc agtacaataa tgcaatgcat aatgcgcaac aacaaatcaa taccgcgaaa    7680
acagaagcac aacaagtgat taataatgag cgtgcaacac cacaacaagt ttctgacgca    7740
ctaactaaag ttcgtgcagc acaaactaag attgatcaag ctaaagcatt acttcaaaat    7800
aaagaagata atagccaatt agtaacgtct aaaaataact acaaagttc tgtgaaccaa    7860 gtaccatcaa ctgctggtat gacgcaacaa agtattgata actataatgc gaagaagcgt    7920
gaagcagaaa ctgaaataac tgcagctcaa cgtgttattg acaatggcga tgcaactgca    7980
caacaaattt cagatgaaaa acatcgtgtc gataacgcat aacagcatt aaaccaagcg    8040 aaacatgatt taactgcaga tacacatgcc ttagagcaag cagtgcaaca attgaatcgc    8100
acaggtacaa cgactggtaa gaagccggca agtattactg cttacaataa ttcgattcgt    8160
gcacttcaaa gtgacttaac aagtgctaaa aatagcgcta atgctatcat tcagaagcca    8220
ataagaacag tgcaagaggt acaatctgcg ttaacaaatg taaatcgtgt caatgagcga    8280
ttaacgcaag caattaatca attagtacct ttagctgata atagtgcttt aagaactgct    8340
aagacgaaac ttgatgaaga aatcaataaa tcagtaacta ctgatggtat gacacaatca    8400
tcaatccaag catatgaaaa tgctaaacgt gcaggtcaaa cagaaacaac aaatgcacaa    8460
aatgttatta acaatggtga cgcgacagac caacaaattg ccgcagaaaa aacaaaagta    8520
gaagaaaaat ataatagctt aaaacaagca attgctggat taacaccaga cttggcacca    8580
ttacaaactg caaaaactca gttgcaaaat gatattgatc agccaacgag tacgactggt    8640
atgacaagcg catctgttgc tgcatttaat gacaaacttt cagcagctag aactaaaatt    8700
caagaaattg atcgcgtact agcatctcat ccagatgtag caacgattcg tcaaaacgtg    8760
acagcagcga atgctgctaa aacagcactt gatcaagcgc gcaatggctt aacagtcgat    8820
aaagcacctt tagaaaatgc gaaaaatcaa ctacaacata gtattgatac gcaaacaagt    8880
acaactggta tgacacaaga ctctataaat gcatacaatg cgaagttaac agctgcacgt    8940
aataaggttc aacaaatcaa tcaagtatta gcaggttcac ctactgtaga tcaaattaat    9000
acaaatacgt ctgcagcaaa tcaagcgaaa tctgatttag atcatgcacg tcaagcgtta    9060
acaccagata aagcgccgct tcaaaatgcg aaaacgcaat tagaacaaag cattaatcaa    9120
ccaacagata caacaggtat gacaaccgct tcgttaaatg catacaacca aaaattacaa    9180
```

```
gcagcacgtc aaaagttaac tgaaattaat caagtgttga atggcaaccc aactgtccaa    9240
aatatcaatg ataaagtggc agaggcaaac caagctaagg atcaattaaa tacagcacgt    9300
caaggtttaa cattagatag acagccagcg ttaacaacat tacatggtgc atctaactta    9360
aaccaagcac aacaaaataa tttcacgcaa caaattaatg ctgctcaaaa tcatgctgcg    9420
cttgaaacaa ttaagtctaa cattacggct ttaaatactg cgatgacgaa attaaaagac    9480
agtgttgcgg ataataatac aattaaatca ggtcaaaatt acactgacgc aacaccagct    9540
aataaacaag cctatgataa tgcagttaat gcggctaaag gtgtcattgg agaaacgact    9600
aatccaacga tggatgttaa cacagtgaac caaaaagcag catctgttaa atcgacgaaa    9660
gatgctttag atggtcaaca aaacttacaa cgtgcgaaaa cagaagcaac aaatgcgatt    9720
acgcatgcaa gtgatttaaa ccaagcacaa aagaatgcat taacacaaca agtgaatagt    9780
gcacaaaacg tgcaagcagt aaatgatatt aaacaaacga ctcaaagctt aaatactgct    9840
atgacaggtt taaacgtgg cgttgctaat cataaccaag tcgtacaaag tgataattat     9900
gtcaacgcag atactaataa gaaaaatgat tacaacaatg catcaaccaa tgcgaatgac    9960
attattaatg gtaatgcaca acatccagtt ataacaccaa gtgatgttaa caatgctttta  10020 tcaaatgtca caagtaaaga acatgcattg aatggtgaag ctaagttaaa tgctgcgaaa  10080
caagaagcga atactgcatt aggtcattta aacaatttaa ataatgtaca acgtcaaaac  10140
ttacaatcgc aaattaatgg tgcgcatcaa attgatgcag ttaatacaat taagcaaaat  10200
gcaacaaact tgaatagtgc aatgggtaac ttaagacaag ctgttgcaga taaagatcaa  10260
gtgaaacgta cagaagatta tgcggatgca gatacagcta aacaaaatgc atataacagt  10320
gcagtttcaa gtgctgaaac aattattaat caaacagcta atccgacaat gtctgttgat  10380
gatgttaatc gtgcaacttc agctgttact actaataaaa atgcattaaa tggtgatgaa  10440
aaattagtac aatctaaaac agatgctgca agagcaattg atgcattacc acatttaaat  10500
aatgcacaaa aagcagatgt taaatctaaa attaatgctg catcaaatat tgctggtgta  10560
aataccgtta acaacaagg tacagattta aatacagcga tgggtaactt gcagggtgca   10620
atcaatgatg aacaaacgac gcttaatagt caaaattatc aagatgcgac acctagtaag  10680
aaaacagcat acacaaatgc ggtgcaagct gcgaaagata ttttaaataa atcaaatggt  10740
caaaataaaa cgaaagatca agttactgaa gcgatgaatc aagtgaattc ggctaaaaat  10800
aacttagatg gtacgcgttt attagatcaa gcgaagcaaa cagcgaaaca gcagttaaat  10860
aatatgacgc atttaacaac tgcacaaaaa acgaatttaa caaatcaaat taatagtggt  10920
actactgttg ctggtgttca tacggttcaa tcaaatgcca acacattaga tcaagcgatg  10980
aatacgttaa gacaaagtat tgctaacaat gatgcgacta agcaagtgaa agattacgta  11040
gatgctaata atgataagca aacagcatat aacaacgcgg tagctgctgc tgaaacgatt  11100
attaatgcga atagtaatcc agaaatgaat ccaagtacga ttacacaaaa agcagagcaa  11160
gtgaatagtt ctaaaacggc acttaacggt gatgaaaact tagctacggc aaaacaaaat  11220
gcgaaaacgt acttaaacac attaacgagt attacagatg ctcaaaagaa caatttgatt  11280
agtcaaatta gtagtgcgac aagagtgagt ggtgttgata ctgtaaaaca aaatgcacaa  11340
catttagatc aagctatggc taacttacaa aatggtatta caacgaatc tcaagtgaaa   11400 tcatctgaga atatcgtga tgctgataca aataaacaac aagagtatga taatgctatt    11460
actgcagcga aagcgatttt aaataaatcg acaggtccaa acactgcgca aaatgcagtt  11520
gaagcagcat tgcaacgtgt taatactgcg aaagatgcat tgaatggtga tgcaaaatta  11580
```

```
attgcagctc aaaacgcagc gaaacaacat ttaggtactt taacgcatat cactacagca    11640
caacgcaatg atttaacaaa tcaaatttca                                     11670

<210> SEQ ID NO 46
<211> LENGTH: 20139
<212> TYPE: DNA
<213> ORGANISM: Staphylococcus aureus

<400> SEQUENCE: 46
atgggtaact tacaaacggc tatcaacgat aagtcaggaa cattagcgag ccaaaacttc      60
ttggatgctg atgagcaaaa acgtaatgct tacaatcaag ctatatcagc tgccgaaacc     120 atttaaata aacaaactgg accgaataca gcgaaaacag cggttgaaca agcacttaat      180
aatgttaata gtgcgaaaca tgcattaaat ggtacgcaaa acttaaataa tgcgaaacaa     240
gcagcgatta cagcaattaa tggcgcatct gatttaaatc aaaaacaaaa agatgcatta     300
aaagcacaag ctaatggtgc tcaacgcgta tctaatgcaa atgatgtaca acgtaatgcg     360
actgaactga acacggcaat gggtcaatta caacatgcca tcgcagataa gacgaatacg     420
ttagcaagca gtaaatatgt caacgccgat agcactaaac aaaatgctta cacaactaaa     480
gttaccaatg ctgaacatat tattagcggt acgccaacgg ttgttacaac accttcagaa     540
gtaacagctg cagctaatca gtaaacagc gcgaaacaag aattaaatgg tgacgaaaga      600
ttacgtgttg caaaacaaaa cgccaatact gctattgatg cattaacgca attaaatact     660
cctcaaaaag ctaattaaa agaacaagtg gacaagcca atagattaga agacgtacaa       720
tctgttcaaa caaatggaca atcattgaac aatgcaatga aaggcttaag agatagtatt     780
gctaacgaaa aacagtcaa agcaagtcaa aactatacag acgcaagtcc gaataaccaa     840
tcaacatata atagcgctgt gtcaaatgcg aaaggtatca ttaatcaaac taacaatcca     900
actatggata ctagtgcgat tacccaagct acaacacaag tgaataatgc taaaaatggt     960
ttaaacggtg ctgaaaactt aagaaatgca caaaacactg ctaagcaaaa cttaaatacg    1020
ttatcacact taacaaataa ccaaaaatct gcaatctcat cacaaattga tcgtgcaggt    1080
catgtgagtg aggtaacagc tgctaaaaat gcagcaactg agttaaacgc gcaaatgggc    1140
aacttggaac aagctatcca tgatcaaaac acagttaaac aaggtgttaa cttcactgat    1200
gcagataaag ctaacgtga tgcttataca atgcgggtaa gcagagcaga aacaattctg    1260
aataaaacgc aaggtgcaaa tacgtctaaa caagatgttg aagcggctat tcaaaatgtt    1320
acaagtgcta aaaatgcatt gaatggtgat caaaacgtta caaatgcgaa gaatgcagct    1380
aaaaatgcat taaataactt aacgtcaatt aataatgcac aaaaacgtga cttaacaact    1440
aaaattgatc aagcaacaac agtagctggt gttgaagcgg tatctaatac aggtacacaa    1500
ttgaatacag cgatggctaa cttgcaaaat ggtattaatg ataaagcgaa tactttagcg    1560
agcgaaaact atcatgatgc tgattcagat aagaaaactg cttatactca agccgttacg    1620
aacgcagaaa atatttaaa taaaaatagt ggatcaaatt tagataaagc tgccgttgaa    1680
aacgcgttgt cacaagtgac aaatgcgaaa ggtgccctaa atggtaacca taatttagag    1740
caagctaaat caaatgcaaa cactactata aacggccttc aacatttaac aacagcacaa    1800
aaagataaat tgaaacaaca agtgcaacaa gcacaaaatg ttgcaggtgt agatactgtt    1860
aaatcaagtg ccaacacatt aaatggtgct atgggtacgt taagaaatag catacaagat    1920
aacacagcta cgaaaatgg ccaaaactat cttgatgcta cagaacgtaa caaaacaaac    1980
tataacaatg ctgttgatag tgctaatggt gtcattaatg caacaagcaa tccaaatatg    2040
```

```
gatgctaatg caattaacca aatcgctaca caagtgacat caacgaaaaa tgcattagat    2100
ggtacacata atttaacgca agcgaaacaa acagcaacaa atgccatcga tggtgctact    2160
aacttaaata aagcgcaaaa agatgcgtta aaagcacaag ttacaagtgc gcaacgtgtt    2220
gcaaatgtaa caagtatcca acaaactgca atgaactta atacagctat gggtcaatta     2280
caacatggta ttgatgatga aaatgcaaca aaacaaactc aaaaatatcg tgacgctgaa    2340
caaagtaaga aaactgctta tgatcaagct gtagctgctg cgaaagcaat tttaaataaa    2400
caaacaggtt ccaattcaga taaagcagca gttgaccgtg cattacaaca agtaacaagt    2460
acgaaagatg cattgaatgg ggatgctaaa ctggcagaag cgaaagcggc agctagacaa    2520
aacttaggta ctttaaacca tattacgaat gcacaacgta ctgcgttaga aggtcaaatc    2580
aatcaagcga cgactgttga tggcgttaat actgtaaaaa caaatgccaa tacattagac    2640
ggcgctatga atagcttaca aggtgcaatc aatgataaag atgcgacatt aagaaatcaa    2700
aattatcttg atgcagatga atcaaaacga aatgcatata cgcaagctgt cacagcggct    2760
gaaggcattt taaataaaca aacaggtggt aacacatcta aagcagacgt tgataatgca    2820
ttaaatgcag ttacaagagc gaaagcggct taaatggtg ctgaaaactt aagaaatgcg     2880
aaaacttcag caacaaatac gattaatggt ttacctaact taacacaatt acaaaaagac    2940
aacttgaagc atcaagttga acaagcgcaa aatgtagttg gtgtaaatgg tgttaaagat    3000
aaaggtaata cattaaatac tgccatgggt gcattacgta caagtatcca aaatgataat    3060
acgacgaaaa caagtcaaaa ttatcttgat gcatctgata gcaacaaaaa taattacaat    3120
actgctgtaa ataatgcaaa tggtgttatt aatgcaacga acaatccaaa tatggatgct    3180
aatgcgatta tgacatggc aaatcaagtc aatacaacaa aagcagcgtt aaatggtgca     3240
caaaacttag ctcaagctaa acaaatgcg acgaacacaa ttaacaacgc gcaagactta     3300
aaccaaaaac aaaaagatgc attaaaaaca caagttaaca atgcacaacg tgtatctgat    3360
gcaaataacg ttcaacatac agctactgaa ttgaacggtg cgatgacagc acttaaagca    3420
gctattgcgg ataaagaaag aacaaaagca agcggtaatt atgtcaatgc tgatcaagaa    3480
aaacgtcaag cgtatgattc aaaagtgact aacgctgaaa atatcattaa tggtacacca    3540
aatgcgacat taacagtcaa tgacgtaaat agtgcggcat cacaagtcaa tgcggctaaa    3600
acagcattaa atggtgataa caacttacgt gtagcgaaag agcatgctaa caatacaatt    3660
gacggcttag cacaattgaa taatgtacaa aaagcaaaat taaagaaca agttcaaagt     3720 gcaactacat tagatggtgt tcaaactgtt aaaaatagtt ctcaaacgtt gaatacagcg    3780
atgaaaggct aagagatag tattgcgaat gaagcaacga ttaaagcagg tcaaaactac    3840
actgacgcaa gtccaaataa tcgtaacgag tacgacagcg cagttactgc agcaaaagca    3900
atcattaatc aaacatcgaa cccaacgatg gaaccaaata ctattacgca agcaacatca    3960
caagtgacaa ctaaagaaca tgcattaaat ggtgcgcaaa acttagctca agctaagaca    4020
acagcgaaaa acaacttgaa taacttaaca tcaattaaca atgcacaaaa agatgcgtta    4080
acgcgtaaca ttgatggtgc aactacagta gctggtgtaa atcaagaaac tgcaaaagca    4140
acagaattaa ataacgcaat gcacagttta caaaatggta tcaatgatga gacacaaaca    4200
aaacaaactc agaaataacct agatgctgag ccaagtaaga aatcagctta tgatcaagca    4260
gtaaatgcag caaaagcaat tttaacaaaa gctagtggtc aaaatgtaga caagcagca     4320 gttgaacaag cattacaaaa tgtgaacagt acgaagacgg cgttgaacgg tgatgcgaaa    4380
ttaaatgaag ctaaagctgc tgcgaaacaa acgttaggta cattaacaca cattaataat    4440
```

```
gcacaacgta atgcgttaga taatgaaatt acacaagcaa caaatgttga aggtgttaat    4500
acagttaaag ccaaagcgca acaattagat ggtgctatgg gtcaattaga acatcaatt    4560 cgtgataaag acacgacgtt acaaagtcaa aattatcaag atgctgatga tgctaaacga    4620
acggcttatt ctcaagcagt aaatgcagca gcaactattt taaataaaac agctggagga    4680
aatacaccta aagcagatgt cgaaagagca atgcaagctg ttacacaagc caatactgca    4740
ttaaacggta ttcaaaactt agaacgtgcg aaacaggctg cgaacacagc gattacaaat    4800
gcttcggact aaatacaaa acaaaagaa gcattgaaag cacaagtaac aagtgcagga    4860
cgcgtatctg cagcaaatgg tgttgaacat actgcgactg aattaaatac tgcgatgaca    4920 gcttttaaaac gtgccattgc tgataaagct gacacaaaag ctagtggtaa ttatgtcaat    4980
gctgatgcga ataaacgcca agcatatgat gaaaaagtga cagctgcaga acatatcgtt    5040
agtggtacac caacaccaac gttaacacca tcagatgtta caaatgcagc aacgcaagta    5100
acgaatgcga agacgcagtt aaacggtaat cataatttag aagtagcgaa acaaaatgct    5160
aacacagcaa ttgatggttt aacttcttta aatggtccgc aaaaagcaaa acttaaagaa    5220
caagtgggtc aagcgacgac gttgccaaat gttcaaactg ttcgtgataa tgcacaaaca    5280
ttaaacactg caatgaaagg tctacgagat agcattgcga atgaagcaac gattaaagca    5340
ggtcaaaact acacagatgc aagtcaaaac aaacaaaatg actacaacaa tgcagtcact    5400
gcagcaaaag caatcattgg tcaaacaact agtccatcaa tgattgcgca agaaattaat    5460
caagcgaaag accaagtgac agctaaacaa caagcgttaa acggtcaaga aaacttaaga    5520
actgcgcaaa caaatgcgaa gcaacatttg aatggcttaa gtgacttaac taatgcacaa    5580
aaagatgcag cgaaacgcca aatcgaaggt gcaacgcatg ttaatgaagt aacacaagcg    5640
caaaataatg cggacgcatt aaatacagct atgacgaact tgaaaaatgg tattcaagat    5700
caaaatacga ttaagcaagg tgttaacttc actgatgcag atgaagcgaa acgtaatgca    5760
tatacaaatg cagtgacgca agctgaacaa attttaaata aagcacaagg tccaaatact    5820 gcaaagacg gtgtcgaaac tgcgttacaa aatgtacaac gtgctaaaaa cgaattgaac    5880
ggtaatcaaa atgttgcgaa cgctaagaca actgcgaaaa atgcattgaa taaccttaca    5940
tcaattaata atgcacaaaa agcagcattg aaatcacaaa ttgaaggtgc gacaacagtt    6000
gcaggtgtaa atcaagtgtc tacaatggca tctgaattaa atactgcaat gagcaactta    6060
caacgtggta ttaatgacga agcagctaca aaagcagctc agaaatatac tgaagcagat    6120
agagataaac aaaactgcata caatgatgct gtaacagcag ctaaacgttt attagataaa    6180
acagctggtt caaatgacaa taaagtagcc gttgaacaag cattacaacg tgtgaatact    6240
gctaaaacag cattaaatgg tgacgcgcga ttaaatgaag cgaagaacac agctaaacaa    6300
caattagcga caatgtcaca tttaactaat gctcaaaaag caaacttaac agaacaaatt    6360
gaacgtggta caactgttgc tggtgttcaa ggcatccaag caaatgctgg tactttaaat    6420
caagcaatga atcaattaag acaaagtatt gcttctaaag atgcgactaa atcaagcgaa    6480
gattatcaag acgcgaatgc agatttacaa aatgcataca atgatgcggt aactaatgct    6540
gaaggtatta ttagtgcaac gaataaccct gaaatgaatc ctgatacaat taaccaaaaa    6600
gcgagccaag tgaacagtgc gaagtctgca ttgaacggtg atgaaaaatt agcagcagta    6660
aaacaaactg cgaaatcaga tatcggtcgt ttgacagact tgaacaatgc acaacgaact    6720
gcggcaaatg ctgaagtgga tcaagcacca aatcttgcag ctgtcacagc ggctaaaaat    6780
aaagcaacat cgttaaacac agcgatgggt aatttgaaac atgcacttgc tgaaaaggat    6840
```

-continued

```
aatacgaaac gtagtgtcaa ttacacagat gcggatcaac caaaacaaca agcgtatgat    6900
actgcagtta cacaagcaga agcaattact aatgcaaatg gcagtaacgc gaatgaaaca    6960
caagttcaag cagcgcttaa ccaattgaat caagctaaaa acgacttgaa tggtgataat    7020
aaagttgctc aagcgaaaga aacagcaaaa cgtgcattag cttcatatag taacttgaat    7080
aacgcgcaat caactgcagc aactagtcaa attgacaatg caacgacagt agcagacgta    7140
actgctgcac aaaatactgc taatgaatta aatacagcaa tgggtcaact tcaaaatggt    7200
attaatgacc aaaacactgt taaacaacaa gtgaaccttta cagatgctga ccaaggtaag    7260
aaagatgctt acacaaatgc tgttacgaat gctcaaggta ttttagataa agcaaacggt    7320
caaaatatga caaaagcaca agttgaagct gcattaaatc aagtaacgac tgctaagaat    7380
gctttaaacg gtgatgcaaa tgtaagacaa gcaaaatcag atgcgaaagc aaacttaggt    7440
acattaacac acttaaataa tgcacaaaaa caagatttaa catcacaaat cgaaggtgca    7500
acaacagtca acggtgtaaa tagtgttaaa acgaaagcac aagacttaga tggtgcaatg    7560
caacgattag agtcagcaat cgcaaataaa gatcaaacta aagcgagcga aaactacatt    7620
gacgcagatc caactaagaa aacagcattt gataatgcca tcacacaagc tgaatcttac    7680
ttaaataaag atcatggtac gaataaagat aagcaagctg ttgaacaagc aattcaaagt    7740
gtaacgtcta ctgaaaatgc tttgaacggt gacgcgaact acaatgcgc taaaactgaa    7800 gctacacaag ctatcgataa cttgacacaa ttgaatacac cgcaaaaaac agcattgaaa    7860
caacaagtga atgctgcaca acgcgtatca ggtgtaactg atctgaaaaa tagtgctaca    7920
tcacttaata atgcgatgga tcaattaaaa caagcaattg gtgatcatga cacaattgta    7980
gctggtggta attacactaa cgcaagtcct gataaacaag gtgcttacac tgatgcatat    8040
aatgctgcga agaatatcgt aaatggttca cctaatgtga ttacaaatgc agcagatgtt    8100
actgcggcaa cacaacgtgt caataatgct gaaacaagtt taaatggtga tacaaactta    8160
gcaactgcga agcaacaagc taaagatgca ttacgtcaaa tgacacattt atctgatgca    8220
caaaaacaaa gtattactgg tcaaattgat agcgcgacac aagtaactgg tgtacaaagt    8280
gtgaaagaca atgcaacaaa tcttgacaat gcaatgaatc aacttcgaaa tagtattgcg    8340
aataaagatg aagtaaaagc gagtcaacca tatgttgatg cagatacaga taaacaaaat    8400
gcatacaata cagcagttac aagtgctgaa aatatcatta atgcaacgag tcagccaaca    8460
cttgatccat ctgcagtaac acaagcagct aatcaagtga acactaacaa aactgcgctt    8520
aatggtgcgc aaaacttagc aaataaaaag caagaaacaa ctgctaacat caaccgatta    8580
agtcatttaa acaatgctca aaagcaagat ttaaatacac aagtgacaaa tgcaccaaat    8640
attagcacag taaatcaagt gaaaactaaa gctgaacaat tagatcaagc aatggaacgt    8700
ttaatcaacg gaatccaaga caaagatcaa gtgaaacaaa gtgttaactt tacagatgca    8760
gatccagaaa aacaaacagc atacaacaat gcggtaactg ctgctgaaaa tattattaat    8820
caagcaaatg gtacaaatgc gaaccaatca caagttgaag cagcactttc aactgtaaca    8880
actactaaac aagcgttgaa tggtgataga aaagtaacag atgctaaaaa caatgcaaac    8940
caaacattat ctacgttaga taacttaaac aatgcacaaa aaggtgctgt tactggaaac    9000
atcaatcaag cgcacactgt agctgaagta acgcaagcca ttcaaaccgc tcaggaactg    9060
aatacagcga tgggtaactt gaaaaatagc ttgaatgata agacactac acttggcagt    9120 caaaactttg cagatgcaga tccagagaag aaaaatgcat acaatgaagc ggttcgtaat    9180
gctgaaaata ttttaaataa atctacaggt acgaacgtgc ctaaagatca agttgaagca    9240
```

```
gctatgaatc aagtgaatac tacaaaagca gcgcttaatg gtactcaaaa ccttgaaaaa   9300
gcgaaacaac acgcaaatac agcaattgac ggtttaagcc atttaacaaa tgcacaaaaa   9360
gaggcattaa acaattggt acaacaatcg actactgttg cagaagcaca aggtaatgaa     9420
caaaaagcaa acaatgttga tgcagcaatg gacaaattac gtcaaagtat tgcagataat   9480
gcgacaacaa acaaaacca aaattatact gatgcaagtc cgaataaaaa ggatgcgtac    9540
aataatgctg tcacaactgc acaaggtatt attgatcaaa ctacaaaccc ttcattagat   9600
ccgactgtta tcaatcaagc tgctggacaa gtaagcacgt ctaaaaatgc tttaaatggt   9660
aatgaaaact tagaggcagc gaagcaacaa gcaacgcaat ctttaggttc attagacaac   9720
ttaaataatg cgcaaaaaca agctgttact aatcaaatta atggcgcgca tactgttgat   9780
gaagcaaatc aaattaagca aaatgcgcaa aacttaaata ctgcgatggg taacttgaaa   9840
caagcgatag ctgataaaga tgctacgaaa gcaacagtta acttcactga tgcagatcaa   9900
gcaaaacaac aagcatataa cactgcagtt acaaatgctg aaaatatcat ttcaaaagct   9960
aatggtggta atgcaacaca aactgaagtt gaacaagcaa tccaacaagt aaatgcagca   10020
aaacaagcat taaatggtaa tgccaacgtt caacatgcaa aagacgaagc aacagcatta   10080
attaataact ctaatgatct taaccaagca cagaaagatg cattaaaaca acaagtacaa   10140
aatgcaacta ctgtagctgg tgtaaacaat gttaaacaaa cggcgcaaga gttaaacaat   10200
gcgatgacac aattaaaaca aggcattgca gataaagaac aaacaaaagc tgatggtaac   10260
tttgtcaatg cagattctga caagcaaaat gcatataatc aagcagtagc gaaagctgaa   10320
gcattaatta gtggtacgcc tgatgttgtc gttacaccta gcgaaattac tgcagcgtta   10380 aataagtta cgcaagctaa aaatgattta atggtaata caaacttagc aacggcgaaa    10440
caaaatgttc aacatgctat tgatcaattg ccaaacttaa accaagcgca acgtgatgaa   10500
tacagcaaac aaatcacgca agcaacactt gtaccaaacg tcaatgctat tcaacaagcg   10560
gcaacaacgc ttaatgacgc gatgacacaa ttgaaacaag gtattgcgaa taaagcacaa   10620
attaaaggta gcgagaacta tcacgatgct gatactgaca agcaaacagc atatgataat   10680
gcagtaacaa aagcagaaga attgttaaaa caaacaacaa atccaacaat ggatccaaat   10740
acaattcaac aagcattaac taaagtgaat gacacaaatc aagcacttaa cggtaatcaa   10800
aaattagctg atgccaaaca agatgctaag acaaacttg gtacactaga tcatttaaat    10860
gatgctcaaa acaagcgct aacaactcaa gttgaacaag caccagatat tgcaacagtt    10920
aataatgtta agcaaaatgc tcaaaatctg aataatgcta tgactaactt aaacaatgca   10980
ttacaagata aaactgagac attaaatagc attaacttta ctgatgcaga tcaagctaag   11040
aaagatgatt atactaatgc ggtttcacat gcagaaggta tttttatctaa agcaaatggc   11100 agcaatgcaa gtcaaactga agtggaacaa gcgatgcaac gtgtgaacga agcgaaacaa   11160
gcattgaatg gtaatgacaa tgtacaacgt gcaaagatg cagcgaaaca agtaattaca     11220
aatgcaaatg atttaaatca agcgcaaaaa gatgcattaa acaacaagt cgatgctgcg    11280 caaactgttg caaatgtaaa cacgattaag caaacagcac aagatttaaa tcaagcaatg   11340
acacaattga acaaggtat tgcagataaa gaccaaacta agcaaatgg taactttgtc     11400 aatgctgata ctgataagca aaatgcatat aacaatgcgg tagcgcatgc tgaacaaatc   11460
attagtggta caccaaatgc aaacgtggat ccacaacaag tggctcaagc gttacaacaa   11520
gtgaatcaag ctagggtga tttaaacggt aaccacaact tacaagttgc taaagacaat    11580
gcaaatacag ccattgatca gttaccaaac ttaaatcaac cacaaaaaac agcattaaaa   11640
```

```
gaccaagtgt cgcatgcaga acttgttaca ggtgttaatg ctattaagca aaatgctgat   11700
gcgttaaata atgcaatggg tacgttgaaa caacaaattc aagcgaatag tcaagtacca   11760
caatcagttg actttacaca agcggatcaa gacaaacaac aagcttataa caatgcagct   11820
aaccaagcgc aacaaatcgc aaatggcaca ccaacacctg tattggcgcc tgatacagta   11880
acaaaagcag ttacaactat gaatcaagcg aaagatgcat taaacggtga tgaaaaatta   11940
gcgcaagcga acaagatgc tttagcaaat cttgatacgt tacgtgactt aaatcaacca   12000
caacgtgatg cattacgaaa ccaaatcaat caagcacaag ctttagctac agttgaacaa   12060
actaaacaaa atgcacaaaa tgtgaataca gcaatgggta acttgaaaca aggtattgca   12120
aataaagata ctgtgaaagc aagtgagaac taccacgatg ctgatgtcga taagcaaaca   12180
gcatatacaa atgcagtgtc tcaagcggaa ggtattatca atcaaacgac aaatccaacg   12240
cttaacccag atgacattac tcgtgcatta actcaagtga ctgatgctaa aaatagctta   12300
aacggtgaag ctaaattagc cactgaaaag caaaatgcta agatgccgt aagtggaatg   12360 acgcatttaa acgatgctca aaaacaagca ttaaaggtc aaatcgatca atcgcctgaa   12420
attgctacag tgaaccaagt taaacaaaca gcaacgagcc tagatcaagc aatggatcaa   12480
ttatcacaag ctattaatga taaagatcaa atattagcgg acggtaatta cttaaatgca   12540
gatcctgaca acaaaatgc gtataaacag gcagtagcaa aagctgaagc attattgaat   12600
aaacaaagtg gtactaatga agtacaagca caagttgaaa gcatcactaa tgaagtgaac   12660
gcagcgaaac aagcattaaa tggtaatgac aatttggcaa atgcaaaaca caagcaaaa   12720 caacaattgg cgaacttaac acacttaaat gatgcacaaa aacaatcatt tgaaagtcaa   12780
attacacaag cgccacttgt tacagatgtc actacgatta tcaaaaagc acaaacgtta   12840 gatcatgcga tggaattatt aagaaatagt gttgcggata tcaaacgac attagcgtct   12900 gaagattatc atgatgcaac tgcgcaaaga caaaatgact ataacaaagc tgtaacagct   12960
gctaataata tcattaatca aactacatcg cctacgatga tccagatga tgttaatggt   13020 gcaacgacac aagtgaataa tacgaaagtt gcattagatg gtgatgaaaa ccttgcagca   13080
gctaaacaac aagcaaacaa cagacttgat caattagatc atttgaataa tgcgcaaaag   13140
caacagttac aatcacaaat tacgcaatca tctgatattg ctgcagttaa tggtcacaaa   13200
caaacagcag aatctttaaa tactgcgatg ggtaacttaa ttaatgcgat tgcagatcat   13260
caagccgttg aacaacgtgg taacttcatc aatgctgata ctgataaaca aactgcttat   13320
aatacagcgg taaatgaagc agcagcaatg attaacaaac aaactggtca aaatgcgaac   13380
caaacagaag tagaacaagc tattactaaa gttcaaacaa cacttcaagc gttaaatgga   13440
gatcataatt tacaagttgc taaaacaaat gcgacgcaag caattgatgt tttaacaagc   13500
ttaaatgatc ctcaaaaaac agcattaaaa gaccaagtta cagctgcaac tttagtaact   13560
gcagttcatc aaattgaaca aaatgcgaat acgcttaacc aagcaatgca tggtttaaga   13620
cagagcattc aagataacgc agcaactaaa gcaaatagca atatatcaa cgaagatcaa   13680 ccagagcaac aaaactatga tcaagctgtt caagccgcaa ataatattat caatgaacaa   13740
actgcaacat tagataataa tgcgattaat caagtagcgg caactgtgaa tacaacgaaa   13800
gcagcattac atggtgatgt gaaattacaa aatgataaag atcatgctaa acaaacggtt   13860
agccaattag cacatctaaa caatgcacaa aaacatatgg aagatacgtt aattgatagt   13920
gaaacaacta gaacagcagt taagcaagat ttgactgaag tacaagcatt agatcaactt   13980
atggatgcat tacaacaaag tatttgctgac aaagatgcaa cacgtgcgag cagtgcatat   14040
```

```
gtcaatgcag aaccgaataa aaaacaagcc tatgatgaag cagttcaaaa tgctgagtct    14100
atcattgcag gattaaataa tccaactatc aataaaggta atgtatcaag tgcgactcaa    14160
gcagtaatat catctaaaaa tgcattagat ggtgttgaac gattagctca agataagcaa    14220
actgctggaa attctctaaa tcatttagat caattaacac cagctcaaca acaagcgcta    14280
gaaaatcaaa ttaataatgc aacaacttgt gataaagtgg ctgaaatcat tgcacaagcg    14340
caagcattaa atgaagcgat gaaagcatta aagaaagta ttaaggatca accacaaact    14400
gaagcaagta gtaaatttat taacgaggat caagcgcaaa aagatgcata tacgcaagca    14460
gtacaacacg cgaaagattt gattaacaaa acaactgatc ctacattagc taaatcaatc    14520
attgatcaag cgacacaggc agtgactgat gctaaaaaca atttacatgg tgatcaaaaa    14580
ctagctcaag ataagcaacg tgcaacgaaa acgttaaata acttgtctaa cttgaataca    14640
ccacaacgtc aagcacttga aaatcaaatc aataatgcag caactcgtgg tgaagtagca    14700
caaaaattaa ctgaagcaca agcacttaac caagcaatgg aagctttacg taatagcatt    14760
caagatcaac aacaaacaga atctggtagc aagtttatta atgaagataa accgcaaaaa    14820
gatgcttacc aagcagcagt tcaaaatgca aaagatttaa ttaaccaaac aggtaatcca    14880
acgcttgata aagcacaagt tgaacaattg acacatgctt ttaaacaagc taaagataac    14940
ctacacggtg atcaaaaact tgcagacgat aaacaacatg cggttactga tttaaatcaa    15000
ttaaatggtt tgaataatcc gcaacgtcaa gcacttgaaa gccaaataaa caacgcagca    15060
actcgtggcg aagtagcgca aaaattagct gaagcaaaag cgcttgatca agcaatgcaa    15120
gcattacgaa atagtattca agatcaacaa caaacggaag cgggtagcaa gtttatcaat    15180
gaagataaac cgcaaaaaga tgcttaccaa gcagcagttc aaaatgcaaa agatttaatt    15240
aaccaaacag gtaatccaac actcgacaaa tcacaagtag aacaattaac acaagcagta    15300
acaactgcaa aagataatct acatggtgat caaaaacttg ctcgtgatca acaacaagca    15360
gtaacaactg taaatgcatt gccaaactta aatcatgcac aacaacaaac attaactgat    15420
gctataaatg cagcgcctac aagaacagag gttgcacaac atgttcaaac tgctactgaa    15480
cttgatcacg cgatggaaac attgaaaaat aaagttgatc aagtgaatac agataaggct    15540
caaccaaatt acactgaagc gtcaactgat aaaaagaag cagtagatca agcgttacaa    15600
gctgcacaaa gcattacaga tccaactaat ggttcaaatg cgaataaaga cgctgtagaa    15660
caagcattaa ctaagcttca agaaaaagtg aatgagttaa atggtaatga gagagtcgct    15720
gaagctaaaa cacaagcgaa acaaactatt gaccaattaa cacatttaaa tgctgatcaa    15780
attgcaactg ctaaacaaaa tattgatcaa gcgacgaaac ttcaaccaat cgctgaatta    15840
gtagatcaag caacgcaatt gaaccaatca atggatcaat tacaacaagc agttaatgaa    15900
catgctaacg ttgagcaaac tatagattac acacaagcag attcagataa gcaaaaggct    15960
tataaacaag cgattgctga tgctgaaaat gtattgaaac aaaatgcgaa taagcaacaa    16020
gtggatcaag cacttcaaaa tatttttaaat gcaaaacaag cattaaatgg tgatgaacgt    16080
gtagcacttg ctaaaacaaa tggtaaacat gacatcgacc aattgaatgc attaaacaat    16140
gctcaacaag atggatttaa aggtcgcatc gatcaatcaa acgatttaaa tcaaatccaa    16200
caaattgtag atgaggctaa ggcacttaat cgtgcaatgg atcaattgtc acaagaaatc    16260
actggcaatg aaggacgcac gaaaggtagc acgaactatg tcaatgcaga tacacaagtc    16320
aaacaagtat atgatgaagc ggttgataaa gcgaaacaag cacttgataa atcgtctggg    16380
caaaacttaa ctgcagaaca agttatcaaa ttaaatgatg cagtcactgc agctaagaaa    16440
```

```
gcattaaatg gtgaagaaag acttaataat cgtaaagctg aagcattaca aagattggat    16500
caattaacac atctaaacaa tgctcaaaga caattagcaa tccaacaaat taataatgct    16560
gaaacgctaa ataaagcatc tcgagcaatt aatagagcaa ctaaattaga taatgcaatg    16620
ggtgcagtac aacaatatat tgacgaacag caccttggtg ttatcagcag cacaaattac    16680
atcaatgcag atgacaattt gaaagcaaat tatgataatg caattgcgaa tgcagcacat    16740
gagttagata aagtgcaagg taatgcaatt gcaaagctg aagcagagca attgaaacaa    16800
aatattatcg atgctcaaaa tgcattaaat ggagaccaaa accttgcaaa tgccaaagat    16860
aaagcaaatg cgtttgttaa ttcgttaaat ggattaaatc aacagcaaca agatcttgca    16920
cataaagcaa ttaacaatgc cgatactgta tcagatgtaa cagatattgt taataatcaa    16980
attgacttaa atgatgcaat ggaaacattg aaacatttag ttgacaatga aattccaaat    17040
gcagagcaaa ctgtcaatta ccaaaacgct gacgataatg ctaaaacaaa cttcgatgat    17100
gccaaacgtc tagcaaatac attgctaaat agtgataaca caaatgtgaa tgatatcaat    17160
ggcgcaatcc aagcagtcaa tgatgcaatc cataatctta atggtgatca acgactacaa    17220
gatgctaaag acaaggcaat tcaatcaatt aatcaagctt tagctaataa gctaaaagaa    17280
atcgaagctt caaatgcgac ggatcaagac aagcttattg cgaaaaataa agcagaagaa    17340
ttggcaaaca gcatcatcaa caacattaat aaagcaacaa gtaatcaggc tgtatctcaa    17400
gttcaaacag caggcaacca cgcgattgaa caagtgcatg ctaatgaaat accaaaagca    17460
aaaattgatg ccaataaaga cgttgataag caagttcaag cattaattga cgaaattgat    17520
cgaaatccaa atctaacaga taaggaaaaa caagcactta aagatcgtat taatcaaata    17580
cttcaacaag gtcataacga cattaacaat gcgctgacta agaagaaat tgaacaagct    17640 aaagcacaac ttgcgcaagc attacaagac atcaaagatt tagtgaaagc taagaagat    17700 gcgaaacaag atgttgataa acaagttcaa gcattaattg acgaaatcga tcaaaatcca    17760
aatctaacag ataaggaaaa acaagcactt aaagatcgta ttaatcaaat acttcaacaa    17820
ggtcataacg gcattaacaa tgcgatgact aaagaagaaa ttgaacaagc caaagcacaa    17880
cttgcacaag cattaaaaga aattaaagat ttagtgaaag ctaaagaaaa tgcgaaacaa    17940
gatgttgata aacaagttca agcattaatt gacgaaatcg atcaaaatcc aaatctaaca    18000
gataaggaaa acaagcgct taagatcga atcaatcaaa tactgcaaca aggtcataac    18060
gacattaaca atgcgatgac taaagaagaa attgaacaag ccaaagcaca acttgcacaa    18120
gcattacaag acatcaaaga tttagtgaaa gctaaagaag atgcgaaaaa tgcaataaaa    18180
gccttagcta atgcgaagcg tgatcaaatc aattcaaatc cagatttaac acctgagcaa    18240
aaagcaaaag cgctcaaaga aattgacgaa gctgaaaaac gagcactaca aaacgttgag    18300
aatgctcaaa ctatagatca attaaatcga ggattaaact taggtttaga tgacattaga    18360
aatacacatg tatgggaggt tgatgaacaa cctgctgtaa atgaaattt tgaagcaaca    18420 cctgagcaaa tcctagttaa tggtgaactc attgtacatc gtgatgacat cattacagaa    18480
caagatattc ttgcacacat aaacttaatt gatcagcttt cagcagaagt tattgataca    18540
ccatcaactg caacgatttc tgatagctta acagcaaaag ttgaagttac attgcttgat    18600
ggatcaaaag tgattgttaa tgttcctgta aaagttgtag aaaagaatt gtcagtagtc    18660 aaacaacagg caattgaatc aatcgaaaat gcggcacaac aaaagattga tgaaatcaat    18720
aatagtgtga cattaacact ggaacaaaaa gaagctgcaa ttgcagaagt taataagctt    18780
aaacaacaag caattgatca tgttaacaat gcacctgatg ttcattcagt tgaagaaatt    18840
```

| | | | | | |
|---|---|---|---|---|---|
| caacaacaag | aacaagcgta | tattgaacaa | tttaatccag | aacaatttac | gattgaacaa | 18900
| gcaaaatcaa | atgcaattaa | atcgattgaa | gatgcaattc | aacatatgat | tgatgaaatc | 18960
| aaagctcgta | ctgatctaac | agataaagag | aagcaagaag | ctattgctaa | gttaaatcaa | 19020
| ttaaaagaac | aagcaattca | agcgattcaa | cgtgcgcaaa | gcatcagtga | ataactgag | 19080
| caattggaac | aatttaaagc | tcaaatgaaa | gcagctaatc | aacagcaaa | agaactagct | 19140
| aaacgcaagc | aagaagctat | tagtagaatt | aaagactttt | caaatgaaaa | aataaatagt | 19200
| attcgaaata | gtgaaattgg | cacagctgat | gaaaacaag | cagcaatgaa | tcaaattaac | 19260
| gaaattgtgc | ttgaaacaat | tagagatatt | aataatgcgc | atacattaca | gcaagttgag | 19320
| gctgcattga | acaatggtat | tgctcgaatt | tcagcagtac | aaattgtaat | atctgatcgt | 19380
| gctaaacaat | cgtcaagtac | tggaaatgaa | tctaatagcc | atttaacaat | tggttatgga | 19440
| actgcaaatc | atccatttaa | cagttcgact | attggacata | aaagaaact | tgatgaagat | 19500
| gatgacattg | atccacttca | tatgcgtcac | tttagtaata | atttcggtaa | tgttattaaa | 19560
| aacgctattg | gtgtggtggg | tatctctggc | ttactagcta | gtttctggtt | cttcattgcc | 19620
| aaacgtcgtc | gtaaagaaga | tgaagaggaa | gaattagaaa | taagagataa | taataaagat | 19680
| tcaataaaag | agactttaga | cgatacaaaa | catttaccac | ttttatttgc | gaaacgtcgc | 19740
| agaaaagaag | atgaagaaga | tgttactgtt | gaagaaaaag | attcgctaaa | taatggcgag | 19800
| tcactcgata | aagttaaaca | tacgccgttc | ttcttaccaa | aacgtcgtcg | taaagaagat | 19860
| gaagaagatg | tggaagttac | aaatgaaaac | acagatgaaa | aagtgttgaa | agataacgaa | 19920
| cattcaccac | tcttattcgc | aaaacgacgc | aaagataaag | aggaagatgt | tgaaacaaca | 19980
| actagtattg | aatctaaaga | tgaggacgtt | cctttattat | tggctaaaaa | gaaaaatcaa | 20040
| aaagataacc | aatccaaaga | caaaaagtca | gcatcaaaaa | atacttctaa | aaaggtagca | 20100
| gctaaaaaga | agaaaaagaa | atctaagaaa | aataaaaaa | | | 20139

<210> SEQ ID NO 47
<211> LENGTH: 2103
<212> TYPE: DNA
<213> ORGANISM: Staphylococcus epidermidis

<400> SEQUENCE: 47

| | | | | | |
|---|---|---|---|---|---|
| ttgaataatc | gtgataaatt | acaaaaattt | agtattcgaa | aatacgcaat | tggaacattt | 60
| tctactgtga | ttgcaacact | tgtgttcatg | ggtatcaata | caaaccatgc | aagtgccgac | 120
| gagttgaatc | aaaatcaaaa | gttaattaaa | caattaaatc | aaacagatga | tgatgattcg | 180
| aatacgcata | gtcaagaaat | cgaaaataac | aaacaaaatt | ctagtgggca | gactgaatca | 240
| ttacgttcat | caactagtca | aaatcaagca | atgcacgac | tgtcggatca | attcaaagac | 300
| actaatgaaa | catcgcaaca | attacctaca | aatgtttcgg | atgatagtat | caatcaatcg | 360
| catagtgaag | caaatatgaa | taacgaacca | ttgaaagttg | ataatagtac | tatgcaagca | 420
| catagtaaaa | tagtaagcga | tagcgatggg | aatgcttctg | aaaataaaca | tcataaacta | 480
| acagaaaatg | tacttgcaga | aagccgagca | agtaaaaatg | acaagagaa | agagaatcta | 540
| caagagaaag | ataaatcgca | gcaagtacat | ccaccattag | ataaaaatgc | attcaagct | 600
| tttttttgacg | catcatatca | caattacaga | atgattgata | gagatcgtgc | ggatgcaaca | 660
| gaatatcaaa | aagtcaaatc | tacttttgac | tacgtcaatg | acttactagg | taataatcaa | 720
| aatattcctt | cagaacagct | tgtttcggca | tatcaacaat | tagagaaagc | attagaactt | 780
| gcacgtacgt | taccacaaca | atctactaca | gaaaaacgtg | gtagaagaag | tacgagaagt | 840

```
gttgttgaga atcgttcatc aagaagcgat tacttagatg ctagaactga atattatgtt      900
tcaaaagacg atgatgattc tggtttccct cctggtactt tcttccatgc ttcaaataga      960
agatggcctt ataatttacc aagatctagg aacatcttac gtgcttctga tgtacaaggt     1020
aatgcttata tcactacaaa acgacttaaa gatggtatat caatgggatat tttatttaat    1080 agtaatcata aagggcatga atatatgtac tattggtttg gacttccaag tgatcaaaca     1140
ccaactggtc cagtaacttt cactattatc aaccgtgatg gttcaagtac atctactggt    1200
ggcgttggat ttggatcagg tgcaccacta cctcaatttt ggagatcagc aggtgctatt     1260
aattctagcg tagcgaatga ttttaaacat ggctccgcta caaattatgc atttttatgat   1320 ggtgttaata atttttctga ctttgctaga gggggagaat tatacttcga cagagaaggc    1380
gctacacaaa ctaataaata ttatggcgat gaaaacttcg cattgctaaa tagtgagaaa    1440
ccagatcaaa taagaggatt agatacaata tatagtttta aaggtagtgg tgatgtaagt    1500
tatcgtattt catttaaaac tcaaggagct ccaactgcaa gattgtatta tgctgctggc    1560
gcgcgttctg gtgaatataa acaagcaacg aactataacc aactctatgt cgaaccttat    1620
aagaattatc gaaatcgagt acagtcaaat gtccaagtta aaaatcgtac acttcattta    1680
aaaagaacaa tcagacaatt cgatcctaca ttacagagaa ctactgatgt tcctattttg    1740
gatagtgacg gttccggaag tattgattcg gtatacgacc cattaagtta tgtaaagaat    1800
gtgactggta cagtcctagg tatttatcca tcttatcttc cttataatca ggaaagatgg    1860
cagggagcta atgcaatgaa tgcctatcaa attgaagaac ttttttcaca agaaaatctt    1920
caaaatgcag cacgttcagg ccgtccaatt caatttcttg taggttttga tgttgaagat    1980
agccatcata accctgaaac tcttttacca gtaaatttat atgtaaaacc tgagttaaaa    2040
catacaattg agttatatca cgataatgaa aacaagata gaaggaatt ttcagtatcg      2100 aaa                                                                  2103

<210> SEQ ID NO 48
<211> LENGTH: 28317
<212> TYPE: DNA
<213> ORGANISM: Staphylococcus epidermidis

<400> SEQUENCE: 48
atgagtggaa cgcttcataa cactgtagga tcaggaatat taccttatca acaagagata      60
cgtatcaaac ttactagtaa tgaaccaatt aaagatagtg aatggtctat tacaggatat     120
cctaacacgc ttacattaca aaacgctgtg ggtagaacaa ataatgctac tgaaaaaaac     180
ttagctcttg ttggtcatat tgatccagga aattatttca tcactgttaa gtttggtgat     240
aaagtagaac aatttgaaat tagatcaaaa ccaactccac caagaatcat tacaactgct     300
aatgaattac gtggaaatcc taaccataag cctgaaataa gagtaacaga tataccaaat     360
gatactactg ctaaaatcaa acttgtgatg gcggaaccg atggcgatca tgatccagaa     420
ataaatccat atactgtccc tgaaaactac acagtagttg cagaagcata ccatgataat    480
gatccaagta aaaatggggt cttaacattc cgttcatcag actaccttaa agatctacca    540
ttaagcggtg aattaaaggc aattgtttat tacaatcaat atgtacaatc aaactttagt    600
aaaagcgttc cgtttagtag cgatacaaca ccacctacaa ttaatgaacc ggcaggacta    660
gttcataagt attcagggg agatcatgta gaaattactc ttccagtcac tgataatact    720
ggcggttcag gttaagaga tgtaaacgtc aatttacctc aaggttggac aaaaaccttt    780
acaatcaatc ctaataataa tactgagggt acgcttaagt taattggtaa tataccagt    840
```

```
aatgaagcat ataatacgac atatcatttc aatattactg caaccgataa ttctggaaat    900
acaacaaatc cagctaaaac ctttatttta aatgttggta agttggctga tgatttaaat    960
ccagtcggat tatctagaga tcaactacaa ttagtgacag acccttcttc attatctaat   1020
tccgaacgag aagaggtaaa aagaaaaata agtgaagcaa atgctaatat aagatcatat   1080
ttattacaaa ataacccaat actcgctgga gtaaacggcg atgttacatt ttattataga   1140
gatggttctg tagatgttat tgatgctgaa atgtaatca catatgagcc cgaaagaaaa   1200
tccattttca gtgaaaatgg taatacaaat aaaaagaag cagtaatcac tattgctaga   1260
ggacaaaact ataccattgg tccaaactta agaaaatatt tctcattaag taatggttcg   1320
gatttaccta atagagattt cacctctata tcagctattg gatctttacc ttcatcgagt   1380
gaaattagtc gactcaatgt tggaaattat aactatagag ttaatgctaa aaatgcttat   1440
cataagactc aacaagaact taatttaaaa cttaaaatag tagaggttaa tgcacctact   1500
ggtaataatc gtgtatatag agttagtact tataatttaa ctaatgatga aatcaataaa   1560
atcaaacaag catttaaagc agctaattct ggacttaatt taaacgataa cgatatcact   1620
gtttcgaata actttgacca tagaaatgtt agtagtgtga cagtaactat acgtaagggc   1680
gatttgataa aagagttttc atcaaatctc aataatatga atttcttacg ttgggttaat   1740
ataagggatg attataccat ttcgtggact tctagtaaga ttcaaggtag aaatacagat   1800
ggtggattag aatggtcacc agatcataaa tcacttattt ataaatatga tgcaacatta   1860
ggtagacaaa taaatactaa tgacgtgtta actttacttc aagcaacagc taaaaactca   1920
aatttacgtt caaatatcaa tagtaatgaa aaacagttag cagaacgagg gtctaatggg   1980
tattctaaat ctataattag agatgatggc gagaaatctt atttacttaa ctcaaatcct   2040
attcaagtat tagacttagt agaaccagat aatggttacg gtggacgtca agtcagtcat   2100
tctaacgtta tatataatga aaaaaattct tctatcgtaa atggtcaagt tccagaagct   2160
aatggggcat ccgcttttaa tattgataaa gttgttaaag ctaatgcggc aaataatggt   2220
attatgggtg ttatctataa ggcacaatta tacttagcac catacagtcc aaaaggttac   2280
attgaaaaat taggccaaaa tttaagcaat accaataacg tgattaatgt ttattttgtg   2340
ccttctgata aagtaaatcc tagtataact gtaggtaatt acgaccatca tacggtatat   2400
tctggtgaaa catttaaaaa tactatcaat gtaaatgata attatggatt aaatacagta   2460
gcttctacaa gtgatagtgc aattactatg accagaaaca acaacgagtt agtaggtcag   2520
gctcctaatg ttactaatag cataaataaa attgtaaaag ttaaagccac agataaaagt   2580
ggaaatgaaa gtattgtttc tttcacagta aatataaaac cattaaacga gaaatataga   2640
ataacaactt catcaagtaa tcaaacacca gtgagaatta gtaatattca aaacaatgct   2700
aacctttcaa ttgaagatca aaatagagta aaatcttcac tcagcatgac taaaattta   2760 ggtacaagaa attatgtcaa tgagtcaaat aatgacgttc gtagtcaagt tgtaagtaaa   2820
gtaaatagaa gtgggaacaa tgctacagtt aatgttacaa ctacatttc tgatggtaca   2880 actaatacaa taaccgttcc agttaaacat gtgttattag aagttgtacc tactactaga   2940
acaacagtaa gaggacaaca atttccaacc ggcaaaggaa cttccccaaa tgatttcttt   3000
agtttaagaa cggaggtcc agttgatgcg agaatagttt gggttaataa tcagggaccc   3060
gatataaata gtaatcaaat tggtagagat ttaacattac acgctgaaat attctttgat   3120
ggtgaaacaa caccaattag aaaagatact acttacaaac ttagtcaatc tattccaaag   3180
caaatatatg aaacaactat caatggtcga tttaattcat caggtgatgc atatccagga   3240
```

```
aattttgttc aagcagtaaa tcaatattgg ccagaacata tggacttcag atgggcccaa   3300
ggatcaggca caccaagttc tcgtaatgca ggttcattta ctaaaacagt tacggtagtt   3360
tatcaaaacg gccaaactga aaacgttaat gtactattca aagtcaaacc aaataaacct   3420
gttattgata gtaatagtgt gatttcaaaa ggacaattaa atggtcaaca aattttagtt   3480
cgaaatgttc cacaaaatgc acaagtcact ctatatcaat caaatggaac tgttattcct   3540
aatacaaata caactataga ttctaatggt atagctactg taacaattca aggcactcta   3600
ccaaccggaa atattactgc taaaacctca atgacaaata atgtaacgta cactaaacaa   3660
aatagtagtg gaattgcttc aaatacaact gaagatataa gtgttttttc agaaaacagt   3720
gatcaagtaa atgttaccgc tggcatgcaa gctaaaaatg atggtattaa aataattaaa   3780
ggtacaaact ataattttaa tgacttcaat agtttcataa gtaatatacc agcccattct   3840
actcttacat ggaacgagga gcctaatagt tggaaaaaca acatcggtac tacaacaaaa   3900
actgttacag ttactctacc taatcatcaa ggtacgagaa ctgtagatat tccaataaca   3960
atctatccaa cagttacagc taagaatcca gtaagagatc aaaaaggacg aaacttaacc   4020
aatggtactg acgtttataa ttatattatt tttgaaaata ataaccgtct tggaggaaca   4080
gcttcttgga aagacaatcg tcaacctgat aaaaacatag ccggtgtaca aaatttaatt   4140
gcacttgtta attatcctgg catatctaca ccattagaag ttcctgttaa agtgtgggta   4200
tataattttg atttcactca acctatctac aaaattcaag taggagatac attccctaaa   4260
ggaacatggg caggctatta caaacatctt gaaaatggag agggattacc aatagatggt   4320
tggaaatttt attggaacca gcaaagtaca ggaactacta gtgatcaatg gcaatcatta   4380
gcatatacta gaactccttt tgttaaaact ggtacttatg atgtcgttaa tcctagcaac   4440
tggggtgttt ggcaaacatc acaatcagct aaatttatag ttacaaatgc taaacctaat   4500
caaccaacca taactcagtc taaaactggt gatgtaacag taacacctgg tgctgtgcgt   4560
aatatactaa taagtgggac aaaatgattat atccaagcat ctgcagataa gattgttatt   4620
aataaaaatg gaaataaatt aactacattt gttaaaaata atgatggtcg ttggactgtt   4680
gaaactgggt cacctgacat aaatggtatc ggaccaacaa ataacggaac tgctatatct   4740
ttaagtcgat tagcagttag acctggggat tcaatagaag caatagcgac tgaaggttcc   4800
ggagaaacta aagtacttc agcaactagt gaaattata ttgtcaaagc tccacaacct   4860
gaacaagtag caactcatac ttatgataat ggaacattcg atatattacc tgacaattca   4920
cgtaattctt taaatccaac tgaacgtgtc gaaattaatt acactgaaaa attaaatggc   4980
aatgaaacac aaaaatcatt cactattact aaaaataaca acggcaaatg gacgataaat   5040
aataaaccaa attatgtcga gttcaatcag gataatggta agttgtatt ttcggccaat   5100
acaattaaac ctaattctca aattacaata actcctaaag caggtcaggg taacactgaa   5160
aacacaaatc ctactgtaat tcaagcaccct gcgcaacata cttaacaat caatgaaatt   5220
gttaaagaac agggtcaaaa tgtgactaat gatgatatta ataatgcggt tcaagtgcca   5280
aataaaaata gagttgcgat taaacaagga aacgctcttc caacaaattt agctggtggt   5340
agtacatcac atattccagt agttatttat tacagtgatg gaagttctga agaagctact   5400
gagactgtta gaactaaagt taataaaacc gaattaatca atgctcgtcg tcgactagat   5460
gaagaaatta gtaaagagaa caaaacacca tcaagtatca gaaactttga tcaagctatg   5520
aatcgtgctc aatcacaaat taatacagct aaaagtgatg ctgaccaagt tataggcaca   5580
gaatttgcaa caccctcaaca agtaaattca gctttatcta aagttcaagc ggcacaaaat   5640
```

```
aaaataaatg aagctaaagc attattacaa aacaaggctg ataatagtca acttgtgaga    5700
gcaaaagaac aattacaaca atcgattcaa ccagccgctt caactgatgg tatgactcaa    5760
gatagcacaa ggaactacaa caataaacgc caagcagctg aacaagcaat acaacatgca    5820
aatagcgtta taaataatgg agatgcaaca tcccaacaaa ttaatgatgc taaaaacaca    5880
gttgaacagg cacagagaga ttatgttgaa gctaaaagca acttacgtgc tgataagtca    5940
cagttacaaa gcgcttatga tacgttaaat agagatgttt taacaaatga taaaaagcca    6000
gcatctgtaa gacgctataa tgaagccatt tcaaatatta gaaaagaatt agatacagct    6060
aaagcggatg caagtagtac tttgcgaaac accaatcctt ccgttgaaca agttagagac    6120
gctttaaata aaataaatac tgttcaacct aaagtgaatc aagcaattgc tttacttcaa    6180
ccaaaagaaa ataattcaga acttgtacaa gctaaaaaac gtttacaaga cgctgtaaat    6240
gacatacctc aaacacaagg tatgacacaa caaacaatta taattataa tgacaaacaa    6300 cgtgaagctg aaagagcact acatctgca caaagagtga ttgataatgg ggatgctaca    6360
actcaagaaa ttacttctga aaaatctaaa gtagagcaag caatgcaagc tttaactaat    6420
gctaaaagta atctgagagc tgataagaat gagttacaga ctgcatataa caaattaatt    6480
gagaacgtat ctaccaatgg taaaaaaccg gcgagtatac gtcaatacga aacagccaaa    6540
gccagaatac aaaatcaaat taatgatgct aaaaatgaag cggagcgaat tttaggtaat    6600
gataatccac aagtatcaca gtaactcaa gcattgaaca aaatcaaagc tattcaacca    6660
aaattaacag aagctatcaa catgcttcaa aacaagaaaa ataatacaga attagtcaat    6720
gctaaaaaca gacttgaaaa tgcagtaaat gatacagatc caacacacgg tatgactcaa    6780
gaaacaatta ataattacaa cgctaaaaag cgagaagctc aaaatgaaat acaaaaagcg    6840
aacatgatta ttaataatgg agatgctact gctcaagata tttcttctga aaaatctaaa    6900
gtagagcaag tattcaaagc attacaaaat gctaagaatg acttaagagc tgataaaaga    6960
gaattacaga ctgcatacaa taaacttata caaaatgtta ataccaatgg taaaaaacca    7020
tctagtattc aaaactataa gtctgcaaga cgaaatatcg aaaaccaata taataccgct    7080
aaaaatgaag cacataatgt tcttgaaaat acaaacccta ctgtaaatgc agtagaagat    7140
gctttacgta agataaatgc aattcaacca gaggttacaa aagctattaa tatacttcaa    7200
gataaagaag ataatagcga acttgttaga gcaaagaaaa aattagatca agcgattaat    7260
agtcaaccat cactaaatgg tatgactcaa gaatctatta ataattacac aacaaaacgt    7320
agagaagcac aaaatatagc aagttctgct gacactatta ttaataatgg ggatgcatct    7380
attgaacaaa taacagaaaa taaaattcga gttgaagagg caactaatgc acttaacgaa    7440 gcaaacaac atttaacggc agatacaact tctttaaaaa ctgaagtacg gaaattaagt    7500
aggagaggcg acacaaacaa caaaaagcct agcagtgtta gtgcttataa caatactatt    7560
cattcgctac aatctgaaat tacacagact gaaaatagag caaatactat catcaataag    7620
cctattcgtt ctgttgaaga agtaaataat gcattgcatg aagtaaacca attgaaccaa    7680
cgcttaacag atacaattaa cttattacaa ccttttagcga ataagaaag cttaaaagaa    7740 gctcgtaatc gacttgaaag taaaattaat gaaaccgttc aaacagacgg tatgactcaa    7800
caatctgttg agaattataa gcaagctaaa ataaagctc aaaatgaatc tagtattgca    7860
caaactctta ttaataatgg tgatgcatct gatcaagaag tttctacaga aatagaaaaa    7920
ttaaatcaaa agctgtctga attaacaaat tcaatcaatc acttaacagt taataaagaa    7980
cctttagaaa ctgccaaaaa tcagttacaa gcaaatattg accaaaaacc tagcactgat    8040
```

```
ggtatgacgc aacaatctgt acaaagctat gaacgtaaac tacaagaagc caaagataaa   8100
ataaactcaa ttaataatgt cttagctaac aatccagatg ttaatgctat cagaacaaac   8160
aaagttgaga cggaacaaat caataatgaa ttaacacagg cgaaacaagg tcttactgtt   8220
gataaacaac cattgattaa tgcaaaaact gctttgcaac aaagtctaga taatcaacca   8280
agtactactg gtatgactga agcaacaatt caaaattata acgctaaacg tcaaaaagca   8340
gagcaagtta tacaaaatgc aaataaaatt attgaaaacg ctcaacctag tgtacaacaa   8400
gtgtctgatg agaaatctaa ggtagagcaa gcactcagtg aattgaacaa cgccaaatca   8460
gcgcttagag ctgataaaca agaattacag caagcatata atcagttgat tcaaccaacg   8520
gatttaaata ataagaaacc agcttctatc actgcgtaca atcaaagata tcaacaattt   8580
agtaacgaat tgaacagcac taaaacaaat acagatcgca ttttaaaaga gcaaaatcca   8640
agtgtagctg atgtcaacaa tgcactaaat aaagtaagag aagtacaaca aaaattaaac   8700
gaagccagag cacttttaca aaataaagaa gataatagtg cactagttcg agccaaagaa   8760
caacttcaac aggcagttga ccaagtccct tcaacagaag gtatgacgca acaaactaaa   8820
gatgattaca attcaaaaca acaagctgct caacaagaaa tatcaaaagc acaacaagtt   8880
atcgataatg gcgatgcgac tacacaacaa atttctaacg ccaaaacaaa tgttgaacgc   8940
gctttagaag cattaaataa tgcaaaaact ggtttaagag cagataaaga ggaacttcaa   9000
aatgcatata atcaattaac tcaaaatatt gatacgagcg gtaaaacgcc tgcaagtatc   9060
aggaaataca atgaagctaa gtcacgtatt caaactcaaa ttgattcagc taaaaatgaa   9120
gcaaacagta ttttaacaaa tgacaatcct caagtatcac aagtgactgc tgcgttaaac   9180
aaaataaaag ctgttcaacc tgaattagat aaagcgatag caatgcttaa aaataaagag   9240
aataataatg cattggttca agcgaaacaa caacttcaac aaattgttaa tgaagtagat   9300
ccaacacaag gcatgacaac agatactgct aataactata atcaaaaaa acgtgaagct   9360
gaagatgaaa tacaaaaagc tcaacaaatc attaacaatg gcgatgccac tgagcaacaa   9420
attactaacg aaacaaatag agtaaatcaa gcgattaatg caataaacaa agccaaaaac   9480
gatttacgtg ctgataagtc tcaattggaa aatgcttata accaattaat acaaaatgtt   9540
gatacaaatg gtaaaaaacc tgctagtatt caacaatacc aagctgctcg acaagctatt   9600
gagacgcaat acaataacgc taaatcagaa gcacatcaaa ttcttgaaaa tagtaaccct   9660
tcagttaatg aagtagcaca agcattacaa aaagttgaag ctgtacaact taaagttaat   9720
gacgcgattc atatacttca aaataaagag aataatagtg cacttgtcac agctaaaaat   9780
caacttcagc aatcagttaa tgatcaacca ttaacaacag gtatgactca agattctatt   9840
aataactatg aagctaagag aaatgaggct caaagtgcta tcagaaatgc agaagctgtc   9900
atcaacaatg gcgatgcaac tgcaaaacaa atttcagacg agaaatctaa agttgaacaa   9960
gcactagcac atttgaatga tgctaaacag caattaactg cagatactac tgaattacaa  10020
acagcagttc aacaattaaa cagaagaggc gatacaaata taaaaagcc aagaagtatc  10080
aatgcatata ataagcaat tcaatcatta gaaacacaaa ttacttctgc taaagataat  10140
gccaacgctg tgatacaaaa acctatacgt actgttcaag aggtaaataa tgcattacaa  10200
caagtaaatc agttgaatca acaattaact gaagcaatta tcaacttcca accgctatca  10260
aataatgatg cattaaaagc tgcaagatta aatttagaaa ataaaattaa tcaaactgta  10320
caaactgatg gtatgacaca acaatctata gaggcttatc aaaacgctaa acgcgtagcc  10380
caaaatgaat ctaacactgc tttagcatta attaataacg gcgatgccga tgaacaacaa  10440
```

```
attacaactg aaacagaccg agtcaatcag caaactacaa acttaactca agcaattaac    10500
gggttaacag ttaataaaga accattagaa accgctaaaa cagcgttaca aaataacatc    10560
gaccaggtac ctagtacaga tggtatgact cagcaatctg ttgcaaatta taatcaaaaa    10620
ctacaaatag ctaaaaacga aattaacaca attaataacg ttttagcgaa caatccagat    10680
gttaatgcaa tcaaaacgaa taaagcagaa gcggaacgaa tcagtaacga tttaacacaa    10740
gctaagaata acttacaagt tgatactcaa cctttagaaa aaataaaaag acaacttcaa    10800
gatgaaattg atcaaggtac taacacagat ggaatgactc aagattcagt ggataattac    10860
aatgatagct taagtgcagc aattatagaa aaaggcaaag taaataaatt acttaaacgt    10920
aatccgacag tagaacaagt taaagagagc gttgctaatg cacaacaagt catacaagat    10980
ttacaaaatg ctcgaacttc acttgttcca gacaaaactc aacttcaaga agctaaaaat    11040
agattagaaa acagtattaa ccaacaaaca gatactgacg gcatgactca agattcgctt    11100
aacaattata atgataaatt agcaaaagct agacaaaacc ttgaaaaaat atctaaagtt    11160
ttaggtggtc aacctactgt agctgaaatt agacaaaata cagatgaagc aaatgcacat    11220
aaacaagcat tagacactgc acgttctcaa cttacattaa atagagagcc atatatcaat    11280
catattaata atgaaagtca tttaaataac gcgcaaaaag ataattttaa agctcaagtt    11340
aactcagcac ctaatcataa tactttagaa acgattaaaa ataaggctga tactttaaat    11400
caatctatga cagcattaag tgaaagtatt gcagattacg aaaatcaaaa acaacaagaa    11460
aattatttag atgcatctaa caataaacgt caagactatg acaatgcagt caatgcggct    11520
aaaggtattt taaccaaac tcaaagtccg acaatgagtg ctgatgtgat tgatcaaaaa    11580
gctgaagatg ttaaacgtac gaaaactgcg ttagatggaa atcaaagatt agaagttgct    11640
aaacaacaag cacttaatca tttaaatacc ttaaatgatt taaacgatgc tcagcgacaa    11700
actttaactg atactataaa tcactctcca aacatcaatt cagtgaatca agctaaagaa    11760
aaagctaata ctgttaacac agcaatgact caactgaaac aaaactattgc taactatgac    11820
gatgaattgc atgacggcaa ttacattaat gcagataaag acaaaaaaga tgcttataat    11880
aacgctgtta acaatgctaa acaactgatt aatcaatctg atgctaatca agcacaactt    11940
gatccagctg aaattaataa agttacacaa agagtcaata cgactaaaaa tgatctaaat    12000
ggtaatgaca aattggctga agctaaaaga gatgctaata caaccattga tggtttaact    12060
tatctaaatg aagctcaacg taacaaagct aaagaaaatg taggcaaagc ttctacaaaa    12120
acaaatatta cgagtcagtt acaagattac aatcaattga atattgctat gcaagcatta    12180
cgtaacagtg tgaacgacgt taacaatgtt aaagcaaata gcaattatat aaatgaagat    12240
aatggtccaa aagaagctta caatcaagcc gttactcatg ctcaaacatt gataaatgca    12300
caatctaacc ctgaaatgag ccgtgacgta gtaaatcaaa aaacacaagc agtaaatact    12360
gcccatcaga atttacatgg acaacaaaag ttagaacaag cacaaagtag tgctaataca    12420
gaaatcggta acttaccaaa cttaactaat actcaaaaag ctaaagaaaa ggaactggta    12480
aatagtaaac aaactcgtac ggaagtacaa gaacaactta accaagctaa gtcactagat    12540
agttctatgg gcacgttaaa atcattagtt gctaaacaac ctacagtaca aaaaacaagt    12600
gtttatatta acgaagatca acctgagcaa tctgcctaca atgattccat tacaatggga    12660
caaactataa ttaataaaac agctgatcca gtacttgata aaactttagt tgataacgca    12720
atcagtaaca tttcaactaa agagaatgca ctgcatggtg aacaaaaatt aacaactgct    12780
aaaacggaag caattaatgc acttaataca ttagctgatt taaacacacc tcagaaagag    12840
```

```
gctattaaaa cagctattaa cactgctcat acaagaactg atgtaactgc agagcaaagt    12900
aaggctaatc aaataaatag tgcaatgcac acgttgagac aaaacatttc tgacaacgaa    12960
tcagtaacaa acgaaagtaa ttatattaac gctgaacccg aaaaacaaca tgcctttact    13020
gaggctctaa ataatgctaa agaaatagtt aatgaacaac aagccactct tgatgccaat    13080
tcaattaacc aaaaagcaca agcgattctt actactaaaa atgctttaga tggtgaagaa    13140
caattacgtc gtgctaaaga aaatgccgat caagaaatca atacgttaaa tcaattgact    13200
gatgcgcaaa gaaatagtga aaaaggttta gtcaacagtt ctcaaactag aacagaagtt    13260
gcttctcaat tagcaaaagc taagaactaa aataaggtga tggaacaact gaatcacctt    13320
atcaatggta aaaccaaat gataaatagc agtaaattta tcaatgaaga tgcgaaccaa    13380
caacaagcat attcaaatgc gattgcaagt gcagaagcgc ttaaaaacaa atcacaaaac    13440
cctgaattag ataaagtaac aattgaacaa gcaattaata atattaattc tgcaattaac    13500
aatctaaacg gtgaagctaa actgactaaa gctaaagaag atgctgttgc ttcaataaac    13560
aacctaagcg gattaacaaa cgagcaaaaa acaaagaaa atcaagccgt taatggcgct    13620
caaactagag accaagttgc taataaatta cgtgatgctg aagcattaga tcaatcaatg    13680
caaacattac gtgacttagt taacaatcaa aatgcaatac attcaacaag taattatttt    13740
aacgaggatt caactcaaaa gaatacttat gataatgcaa ttgataatgg ctcgacatat    13800
ataactggtc aacacaatcc agaattaaat aaatctacta ttgatcaaac gattagccga    13860
attaacacag ctaaaaatga tttacatggt gtagaaaagt tacaaagaga taagggaact    13920
gctaatcaag aaattggaca attaggttat ttaaatgacc ctcaaaaatc tggtgaggaa    13980
tccttagtca acggttcaaa tacacgttct gaagtagaag agcatcttaa tgaagctaaa    14040
tcattaaata atgcaatgaa acaattaaga gataaagtag ctgaaaagac taatgtcaaa    14100
caaagtagcg attacattaa tgattcaact gaacatcaac gtgggtatga tcaagcactt    14160
caagaagcag aaaatattat taatgaaatc ggtaatccaa cattaaataa atcggaaatt    14220
gaacaaaagt tacaacaatt gactgacgct caaaatgcgt tacaaggttc acatctatta    14280
gaagaagcta aaataatgc gattactgga atcaataaac ttacagcatt aaatgatgca    14340
caacgtcaaa aagcaattga aaatgttcaa gcacagcaga caatcccagc agttaatcaa    14400
caattaactt tggatagaga aataaatact gcaatgcaag ctttacgaga taaagtaggc    14460
caacaaaata cgttcaccaa caaagtaatt tatttcaatg aagatgaaca accaaaacat    14520
aactatgata attctgtaca agccggtcaa actattattg ataaacttca agatccaatc    14580
atgaacaaaa atgaaattga gcaggctatt aatcaaatca atacgactca acagcgtta    14640 agtggagaaa ataaattaca cactgaccaa gaaagcacaa atagacaaat agaaggttta    14700
tctagtttga acacagctca aatcaacgcc gaaaaagatt tagtcaatca agctaaaaca    14760
agaacagatg ttgctcaaaa gttagctgca gctaaagaaa taaattctgc tatgagtaat    14820
ttaagagatg gcattcaaaa taaagaggac atcaaacgta gcagtgcata tatcaacgca    14880
gatccgacta agttacagc ttacgatcaa gcactacaga acgcagaaaa tatcatcaat    14940
gccacaccaa acgtagagct taataaagct acaattgaac aagcgctatc acgcgttcaa    15000
caagcacaac aagatcttga tggtgttcaa caattagcta atgctaaaca acaagctaca    15060
caaactgtca atgggttaaa tagcttaaat gacggtcaaa agcgtgaatt aaatctatta    15120
attaattcag ctaatacccg tacaaaagta caagaagaat taaacaaagc aactgaattg    15180
aaccatgcga tggaagcttt aagaaacagt gttcaaaacg ttgatcaagt aaaacaaagt    15240
```

```
agcaattatg tcaatgaaga tcaacctgaa cagcacaatt atgataatgc tgtcaatgaa    15300
gctcaagcta caatcaacaa caatgctcaa cctgttctag acaaattagc tatagaacgt    15360
ttaactcaaa ctgttaacac tacaaaagat gcattacatg gtgctcaaaa actgacacaa    15420
gaccaacaag ctgctgaaac tggaatacgt ggtttaacga gtctcaatga acctcagaaa    15480
aatgctgaag tagctaaagt aactgcagca acaacacgtg atgaagtgag aaatattcgt    15540
caagaagcaa caacattaga tactgcaatg cttggtttac gtaaaagcat taagagataaa    15600 aacgatacta aaaatagtag taaatatatt aatgaggatc atgaccaaca caagcttat     15660 gacaatgctg taaataatgc tcaacaagtt atcgatgaaa ctcaagcaac gttaagctca    15720
gatacaatca atcaattggc aaatgccgta actcaagcta atctaatct tcatggagat     15780 actaaactac aacacgataa agatagtgct aaacaaacga ttgctcaatt acagaatttg    15840
aattcagctc aaaaacatat ggaagattct ttaattgata atgaatctac acgtacgcaa    15900
gtccaacacg atttaacaga agctcaagct ttagatggtt taatgggtgc cttaaaagaa    15960
agtattaaag attatactaa tattgtttca acggtaatt acatcaatgc ggaaccatct     16020
aagaaacaag catatgatgc agctgtacaa aatgctcaaa atataataaa tggaacgaat    16080
caaccaacaa ttaataaagg taatgtcact acagcaacac aaaccgtgaa aaatactaaa    16140
gatgccttag acggtgatca tagattagag gaagctaaaa ataatgccaa tcaaacaatc    16200
agaaatctat ctaatttgaa caatgcccaa aaagatgcag agaaaaatct agttaatagc    16260
gcatcaacat tagaacaagt tcaacaaaac ttacaaaccg ctcaacaatt agataatgct    16320
atgggtgagt tacgacaaag tattgctaaa aaagatcaag tgaaagcaga tagtaaatat    16380
ctaaatgaag atcctcaaat taagcaaaac tatgatgatg cagttcaacg tgttgaaact    16440
attattaacg aaactcaaaa ccctgaatta cttaaagcaa acattgacca agcaactcaa    16500
tccgttcaaa atgcagaaca agctttacat ggtgctgaaa aattaaatca agacaaacaa    16560
acgtcttcga cagaactaga tggattaaca gatttaacag atgcacaacg tgaaaaactc    16620
agagaacaaa ttaacacttc taatagtaga gatgatatta gcaaaaaaat tgagcaagca    16680
aaagcactaa atgacgcaat gaaaaaactt aagaacaag ttgcgcaaaa agatggtgtt     16740
catgctaaca gtgattatac aaatgaagat tctgcacaaa aagatgcgta taataatgca    16800
cttaaacaag cggaagacat tattaataac agctcaaatc ctaacttaaa tgcacaagac    16860
attactaatg ctttaaataa tattaaacaa gcacaagata accttcatgg agctcaaaaa    16920
ttacagcaag acaaaaatac aactaatcaa gccattggta acttaaatca tcttaatcaa    16980
cctcaaaaag atgcgcttat acaagctatt aatggagcta catctaggga ccaagttgca    17040
gaaaaactta agaggccgaa agcgcttgat gaagctatga acaacttgaa agatcaagtg    17100
aatcaagatg atcaaatttc aaatagcagc ccattcataa atgaagactc agacaaacaa    17160
aaaacttata atgataaaat ccaagctgca aagaaaataa ttaatcaaac atctaatcca    17220
accttagata acaaaaaaat tgctgataca cttcaaaata ttaaagatgc agtgaataat    17280
ttacatggtg atcaaaaatt agctcaatct aaacaagatg ctaataatca attaaatcat    17340
ttagatgact taaccgaaga acaaaaaaac catttttaaac cgttaattaa taatgctgat    17400
actcgagatg aggtaaataa acaactagag attgctaaac aattaaatgg tgatatgagt    17460
acacttcata aagtcataaa tgataaagat caaattcaac atttaagcaa ttacattaat    17520
gctgataatg ataaaaaaca aaattatgat aatgctatta agaagctga ggatttaatt      17580 cataatcatc cagatacatt agatcataaa gcattacaag atttattaaa caagatagac    17640
```

```
caagcgcata acgaattaaa tggagaatcc agatttaaac aggctttaga caatgcttta    17700
aacgacatag atagcttaaa cagtctcaat gttccacaac gccaaactgt taaggataac    17760
atcaaccatg tgacaactct agaaagttta gctcaagaat tgcagaaagc aaaagagctt    17820
aatgatgcta tgaaagcaat gagagatagc attatgaatc aagagcaaat tcgtaaaaat    17880
agcaattata ctaatgaaga cttagctcaa caaaatgcct ataatcatgc agtagataaa    17940
ataaataaca ttattggtga agacaatgcg acgatggatc ctcaaataat caacaagca    18000 actcaagata taaatacagc tataaatgga ttaaatggag atcaaaaact tcaagatgca    18060
aagacagatg ctaaacaaca aattactaac tttactggtt taactgaacc acaaaaacaa    18120
gcattggaaa acatcattaa ccaacaaaca agcagagcaa atgttgctaa acagttaagt    18180
catgctaaat tcttaaatgg aaaaatgaa gaattaaaag ttgcagtagc caaagcgtca    18240
ttagtaagac aaaatagtaa ctatattaat gaagatgtct ctgaaaaaga agcatatgaa    18300
caagctatcg caaaggtca ggaaataatt aattcagaaa ataatccaac aataagtagt    18360
actgatatca atcgtaccat tcaagaaatt aatgatgctg aacaaaatct tcatggtgat    18420
aataaattaa gacaagcaca ggaaattgca aagaatgaaa tacaaaatct agacggatta    18480
aattcagctc aaataacaaa attaatccaa gatataggca gaacaacaac taaacctgca    18540
gtaactcaga aactagaaga agcaaaagca ataaaccaag ctatgcaaca acttaaacaa    18600
agtatagccg ataaggatgc tactctaaat tctagtaact atctcaatga agattctgag    18660
aaaaagttag cgtacgataa tgctgtaagc caagctgaac aactcataaa tcaacttaac    18720
gacccaacta tggatataag taatattcaa gctattactc aaaaggtcat tcaagcaaaa    18780
gattcattgc acggtgcgaa taaacttgca caaaatcaag cagattcaaa tttaataata    18840
aatcaatcaa caaatttaaa tgataaacaa aagcaagcat taaatgactt aattaatcat    18900
gctcaaacta acagcaagt ggcagaaata attgcacaag ctaataagtt aaataacgaa    18960
atgggcacac taaaaacact cgtagaagaa cagtcaaacg ttcatcaaca aagtaaatat    19020
attaatgaag atccgcaagt tcaaaatatt tataatgact ccattcaaaa aggtcgagaa    19080
atattaaacg gcactacaga tgatgtttta aacaacaata aaatagcaga tgccattcaa    19140
aacattcatt taactaaaaa cgatttacat ggtgatcaaa aattacaaaa agcacaacaa    19200
gatgcaacca atgaattaaa ctatttaaca aatctaaaca attctcaaag acaaagcgag    19260
catgatgaga ttaactctgc tccttcaaga actgaagttt ctaatgattt aaatcatgct    19320
aaagcactta atgaagctat gcgtcaactt gagaatgaag ttgctcttga aaacagtgtt    19380
aaaaaattaa gcgactttat caatgaagat gaagcggcac aaaatgaata tagtaatgca    19440
cttcaaaaag ctaaagacat tatcaacggc gttccaagta gcactttaga taaagctaca    19500
attgaagatg ctttattaga attgcaaaat gctagagaaa gtttacatgg tgagcaaaaa    19560
cttcaagagg ctaaaaatca agctgttgct gaaattgata atttacaagc attaaatcct    19620
ggacaggttc ttgctgaaaa acattagtt aaccaagcat caaccaaacc agaagttcaa    19680
gaagccttac aaaaagcaaa agaacttaat gaagctatga agcactgaa aactgaaata    19740 aataaaaaag aacaaatcaa ggctgatagt agatatgtaa atgctgacag tggtcttcaa    19800
gcaaattaca attctgcgtt aaattatggt tctcaaatta ttgcaactac ccaaccacca    19860
gagcttaata aagatgtaat aaatagagca actcaaacga ttaaaactgc tgaaaataat    19920
ttaaatgggc aatctaaatt agcagaggct aagtcagacg gaaatcaaag catcgaacat    19980
ttgcaaggat taacacaatc acaaaagat aaacaacatg atttaattaa tcaagctcaa    20040
```

```
actaaacaac aggtagatga tatcgtaaat aactctaaac aattagataa ctctatgaat    20100
caactacaac aaattgttaa caatgacaat acagtaaaac aaaatagtga tttcattaat    20160
gaagattcca gccaacagga tgcttataat catgcaattc aagcagcaaa agatttgata    20220
actgctcatc caactatcat ggataaaaat caaatagatc aagctattga aaatatcaaa    20280
caagcactta atgatttaca cggtagtaat aaactatcag aagataaaaa agaagcttca    20340
gaacaactac aaaaccttaa tagcttgacg aacgggcaaa aagatacgat tttaaatcat    20400
attttcagtg caccaacaag aagccaagta ggagaaaaaa ttgcaagtgc taaacaatta    20460
aataatacaa tgaaagcact tagagattct attgctgata ataatgaaat tttacaaagt    20520
agtaagtact tcaatgaaga ttctgaacaa caaaatgctt ataatcaagc cgtaaataaa    20580
gctaaaaata taattaatga tcaaccaaca ccagtaatgg caaatgatga gattcaaagt    20640
gtcctaaatg aagttaaaca aactaaagat aatttacatg gtgatcaaaa acttgctaac    20700
gacaagacag atgctcaagc aacattaaat gcgttaaatt acttaaatca agcgcaaaga    20760
ggtaatcttg aaactaaagt tcaaaactct aattctagac cagaagtaca aaaagtagtt    20820
caattagcaa atcaacttaa tgatgcgatg aaaaaattag atgatgcttt aactggtaat    20880
gacgcaataa aacaaacgag taattatatt aatgaagata cttctcaaca agttaacttt    20940
gatgagtata cagatagagg taaaaacata gttgctgaac aaacaaatcc aaatatgtct    21000
ccaactaata ttaacactat tgctgataaa attactgaag ctaaaaacga tttacatggc    21060
gtacaaaaac taaacaagc tcaacaacag tccatcaata ctattaatca aatgactggt    21120
ctaaaccaag ctcaaaaaga acaattaaat caagaaattc aacaaactca aacccgttct    21180
gaagtacatc aagtaattaa taaagcacaa gctttaaatg attcaatgaa tactttacgt    21240
caaagtatta ctgatgaaca tgaagttaaa caaacaagta actacatcaa tgaaactgtt    21300
ggtaatcaaa ctgcatataa caatgccgtt gatcgtgtaa aacaaataat caatcaaaca    21360
tctaatccaa ctatgaatcc tttagaggtg gaacgtgcaa catcaaatgt aaaaatttct    21420
aaagatgcac ttcatggtga acgtgaattg aatgacaata aaaattcaaa aacttttgca    21480
gtcaatcact tagataacct caatcaagct caaaaagaag cattaactca tgaaattgaa    21540
caagcaacta tagtttcaca agtaaataat atctataaca aagcgaaagc tttaaataat    21600
gatatgaaaa aacttaaaga tatcgttgct caacaagata atgtgagaca atcaaacaat    21660
tatataaacg aggatagtac acctcaaaat atgtacaacg atacaattaa tcatgcacaa    21720
tcaatcattg atcaagtagc aaaccctacg atgtctcatg acgaaataga gaatgcaatc    21780
aataacataa agcatgccat caatgcactc gatggagaac ataaattaca acaagcaaaa    21840
gaaaatgcaa acttattgat taatagttta aacgatttaa atgcaccaca aagagatgcc    21900
ataaatagat tggttaatga agctcaaaca agagaaaaag tagctgaaca acttcaaagt    21960
gctcaagctt taaatgacgc tatgaagcat ttaagaaaca gcattcaaaa tcaatcatcc    22020
gtaagacaag agagcaaata tattaatgca agtgatgcta aaaagagca atataatcac    22080 gcagttagag aagtcgaaaa tattatcaat gaacaacatc caacattgga taagaaaata    22140
attaagcaac taacggatgg tgtaaatcaa gcgaataatg acttaaatgg cgttgaatta    22200
ttagatgctg ataagcaaaa cgcacatcaa tcgatacccta cattgatgca cttaaatcaa    22260
gcacaacaaa acgcattaaa tgaaaaaatt aataacgcag ttaccagaac tgaagttgcg    22320
gctattattg gccaagcaaa actactcgat catgctatgg agaatttaga agaaagtatc    22380
aaagataaag agcaagtcaa acagtcaagt aactatatta atgaagattc tgatgttcaa    22440
```

```
gaaacatacg ataacgccgt tgatcatgtg acagaaatac ttaatcaaac agtaaatcca    22500
actttatcta ttgaagatat agagcatgct atcaacgaag ttaatcaagc gaaaaaacaa    22560
ctcagaggta aacaaaaact ttatcaaact atcgatttag ctgataaaga attaagtaaa    22620
ttggatgatt taacatcaca acaaagcagt tcaatatcta atcaaatata tactgctaaa    22680
acgagaacag aagttgccca agcaattgaa aaagcaaaat cattaaatca tgcaatgaaa    22740
gcacttaaca aagtatataa aaatgcagat aaagtgttag atagtagtcg attcattaac    22800
gaagatcaac ctgaaaaaaa ggcgtatcaa caagctataa atcatgttga ttcaatcatt    22860
catagacaaa caaatcctga aatggatcca acagtaatca atagcataac tcatgaactc    22920
gaaacagctc aaaataactt acatggtgat cagaaacttg ctcatgcaca acaagatgcc    22980
gctaatgtaa ttaatggtct aattcatctt aatgttgctc aacgtgaggt aatgataaat    23040
acgaatacaa atgctacaac acgcgaaaaa gttgcaaaga acttagataa tgctcaagct    23100
cttgataaag ctatggaaac actacaacaa gtagttgctc ataaaaataa tatattgaac    23160
gatagtaaat atttaaatga agattcaaaa tatcaacaac aatacgatcg agttattgct    23220
gatgccgaac aactacttaa tcagacaaca aatccaacat tagaacctta taaagtcgat    23280
attgttaagg ataatgtcct agctaacgaa aaaatactat ttggcgcaga aaaactatca    23340
tatgacaaat caaatgcaaa tgatgaaatt aaacatatga attatcttaa taatgcacaa    23400
aagcaatcta taaagatat gatttctcac gcagcattaa gaactgaagt taaacaactt    23460
ctgcaacaag ctaaaatcct tgatgaagcc atgaaatcac ttgaagataa aactcaagta    23520
gtgattacag atactacttt gcctaattac actgaagctt cagaggataa aaaggaaaaa    23580
gtagaccaaa ctgtatcaca tgctcaagcg attattgata aaataaatgg ctcaaatgta    23640
agtttagatc aagtacgaca agcactagaa caattaactc aagcatcaga aaacctcgat    23700
ggtgatcagc gagttgaaga agctaaagtt catgctaatc aaacaattga tcaattaaca    23760
catcttaatt cattacaaca acaaactgcg aaagaaagtg ttaaaaacgc aacaaaacta    23820
gaagaaatcg ctactgttag taacaatgct caggcattaa acaaagtaat gggtaaatta    23880
gaacaattca ttaatcatgc tgattctgtt gaaaatagtg ataattatag acaagccgac    23940
gacgacaaaa tcatcgctta tgatgaagca cttgaacatg gacaagatat acaaaaaact    24000
aacgcaaccc aaaatgaaac aaaacaagcg ttacaacaat taatatatgc agaaacatcg    24060
ttaaatggtt tcgaaagatt aaatcatgct agaccacgag ctttagaata tatcaaatca    24120
ctagaaaaaa taaacaatgc tcaaaagtct gctttagagg ataaagtaac gcaatcgcat    24180
gatttattag aattagaaca tattgtcaac gagggcacaa acctcaatga cattatgggt    24240
gaattagcta acgcaatcgt taataactat gctccaacca aagcaagtat aaattatatt    24300
aacgccgata acctacgcaa agataacttt actcaagcta tcaacaatgc acgtgatgca    24360
ctcaacaaaa ctcaaggtca gaacttagat ttcaatgcaa ttgatacatt taagatgat    24420 atattcaaaa ctaaagatgc acttaacggt attgaacgtt taacagctgc aaaatcaaaa    24480
gcagaaaaac taattgatag tttaaaattt attaataaag ctcaattcac acatgcaaat    24540
gatgaaatta tgaatactaa ttctattgca caattgtcta gaatcgtgaa tcaagcattt    24600
gatttaaatg atgcaatgaa atctttaaga gatgaactta ataatcaagc ttttcctgtc    24660
caagcaagct caaattatat aaattcagat gaagatttaa acaacaatt tgaccatgct    24720 ttaagtaatg ctcgaaaagt tcttgcaaaa gaaaatggta aaaatttaga tgaaaaacaa    24780
attcagggac tcaaacaagt gattgaggat actaaagatg ctttaaatgg tatccaacgt    24840
```

```
ttatcaaaag ctaaagctaa agcaattcaa tacgtacaat ctttatctta tatcaatgat    24900
gcacagcgtc atattgctga aaataatatt cacaactctg atgatttatc atctttagca    24960
aatacattat ctaaagctag tgatttagat aatgcaatga aagacttacg agatactata    25020
gaaagtaatt caacttctgt tccaaatagt gtgaattata ttaatgctga taagaattta    25080
caaattgaat ttgatgaggc gctacaacaa gcaagtgcaa caagttctaa aacttcagaa    25140
aatccagcaa cgattgaaga agtattaggt cttagtcaag ccatttacga tacaaaaaat    25200
gcattaaatg gtgaacaacg acttgcaact gagaagagca aagatctaaa attaataaaa    25260
ggattaaaag atttaaataa agcacaactt gaagatgtca caaacaaggt aaattcagca    25320
aatactttaa cagagttatc tcagctcact caatcaacgt tagaattaaa cgataaaatg    25380
aaattattga gagataagct taaaacttta gtaaatcctg ttaaagcaag tttaaattat    25440
agaaacgctg attataattt aaaacgtcaa tttaacaaag cttttaaaaga agctaaaggc    25500 gtattaaata aaaatagcgg tacaaatgtc aatatcaatg acattcaaca tcttttaaca    25560
caaatagata atgctaaaga ccaattaaat ggtgaacgac gtctaaaaga acatcaacaa    25620
aaatctgaag tatttattat taagaattta gatatactta ataatgctca aaaagctgca    25680
ataattaatc agattagagc gtctaaagac attaaaataa ttaatcaaat cgttgataat    25740
gcaatagaat taaatgatgc tatgcaaggt ttaaagaac atgtagctca attaacagca    25800
actacaaaag acaacattga atatttaaat gctgatgaag accataaatt acaatatgat    25860
tacgctatca acttagcgaa taatgttctt gacaaagaaa acggtacaaa taaagacgct    25920
aatatcataa ttggaatgat tcaaaacatg gatgatgcta gagcacttct aaatggaatt    25980
gaaagactta aagatgctca aacaaaagca cataatgaca ttaaagatac gctcaaacgt    26040
caacttgatg aaattgaaca cgctaatgca acatcaaatt ctaaagctca agctaaacaa    26100
atggtaaatg aggaagctag aaaagcgctt tctaatatta atgacgcaac atcaaatgat    26160
ttagttaatc aagcaaaaga tgaagggcaa tctgcaattg aacacataca tgcagatgaa    26220
ttacctaaag caaaactaga tgctaatcaa atgattgacc aaaaagttga agatataaat    26280
cacttaatta gtcaaaatcc aaacttatca aatgaagaaa aaataaaact aatatctcaa    26340
attaataagt tagtaaatgg aattaagaat gaaattcaac aagctataaa caaacaacaa    26400
atagaaaatg ctacaacaaa actagatgaa gtcattgaaa ctactaaaaa attaattatc    26460
gccaaagcag aagctaaaca aatgataaaa gagttatcac aaaagaaacg agatgcaata    26520
aataacaaca ctgatttaac accttctcaa aaggcacatg ctttagcaga tattgataaa    26580
acagaaaaag atgcacttca acatatcgaa aattctaatt caattgatga tatcaataac    26640
aataaagagc atgcatttaa tacttttagct catatcatta tttgggatac tgatcagcaa    26700
ccattagttt ttgaactacc tgaattgagc cttcaaaatg ctctagtaac aagtgaggtg    26760
gttgttcaca gagatgaaac tatttcatta gaatctataa ttggagctat gactttaact    26820
gatgaactta aagtcaatat tgtttcatta ccgaacactg ataaagtagc tgatcaccta    26880
accgctaaag ttaaggttat tttagctgat ggctcatatg tcactgtaaa tgttccagtc    26940
aaagttgtag aaaaagaatt acaaatagct aaaaaggatg ctataaaaac aattgatgtt    27000
ctggtaaaac aaaaaatcaa agatatagat tctaataacg aattaacgtc tactcaacgt    27060
gaagatgcaa aagctgaaat tgaaagattg aaaaagcaag ccatcgataa agtgaatcat    27120
tcaaaatcga ttaaagatat tgaaacagta aaacgaactg attttgaaga aatagatcag    27180
tttgatccta aacgctttac gctaaataaa gctaaaaagg atatcattac tgatgttaat    27240
```

| | |
|---|---|
| actcaaatcc aaaatggttt caaagaaatt gaaacaataa aaggtttaac ttctaatgaa | 27300 |
| aaaactcagt ttgataaaca attaactgca ctacaaaaag aatttttaga aaaagtcgag | 27360 |
| catgctcata atttagtaga attaaatcaa ttcaacaag agtttaataa tagatataaa | 27420 |
| catattttaa accaagcaca tttactaggt gaaaaacata tagcagaaca taaattagga | 27480 |
| tatgttgtag taaacaaaac tcagcaaata ctaataatc aatctgcttc ttactttata | 27540 |
| aaacaatggg cacttgatag aattaaacaa attcaactag aaacgatgaa ttcaattcgt | 27600 |
| ggtgcgcata ccgtacaaga tgtacacaaa gcattattac aaggtataga gcaaatcttg | 27660 |
| aaagtaaatg taagtattat aaatcaatct ttcaacgatt ccttgcataa ctttaattat | 27720 |
| cttcattcaa aatttgatgc tagattaaga gaaaaggatg ttgcaaacca tatcgtacaa | 27780 |
| actgaaacat tcaaagaagt tctaaaagga acgggtgttg aaccaggtaa atcaacaaa | 27840 |
| gaaacacagc aaccaaaact tcataagaat gataatgata gcctattcaa acatttagtt | 27900 |
| gataatttcg gcaaaactgt aggtgttatt acattaactg gttactttc tagtttctgg | 27960 |
| ttagttttgg ctaaaagacg taaaaaagaa gaagaagaaa aacaatcgat aaaaaatcat | 28020 |
| cacaaagata ttcgtctttc agatactgat aaaatagatc caattgtaat aactaagcgt | 28080 |
| aaaatagata agaagaaca aattcaaaac gatgacaaac attcaattcc agttgctaaa | 28140 |
| cataagaaat ctaagaaaa gcaattgagt gaagaggata ttcattcaat ccccgtcgtt | 28200 |
| aagcgtaaac aaaacagtga taacaaagat acaaacaga gaaagttac ttctaaaaag | 28260 |
| aagaaaacgc tcagtcaac taaaaaagtt gtaaaaacca aaaagcgttc taaaaag | 28317 |

<210> SEQ ID NO 49
<211> LENGTH: 3348
<212> TYPE: DNA
<213> ORGANISM: Staphylococcus aureus

<400> SEQUENCE: 49

| | |
|---|---|
| atgagagata agaaaggacc ggtaaataaa agagtagatt ttctatcaaa taaattgaat | 60 |
| aaatattcaa taagaaaatt tacagttgga acagcatcta tttaattgg ctcactaatg | 120 |
| tatttgggaa ctcaacaaga agcagaagca gctgaaaaca atattgagaa tccaactaca | 180 |
| ttaaaagata tgtccaatc aaaagaagtg aagattgaag aagtaacaaa caaagacact | 240 |
| gcaccacaag gtgtagaagc taaatctgaa gtaacttcaa acaaagacac aatcgaacat | 300 |
| gaagcatcag taaaagctga agatatatca aaaaaggagg atacaccaaa agaagtagct | 360 |
| aatgttgctg aagttcagcc gaaatcgtca gtcactcata acgcagaggc acctaaggtt | 420 |
| agaaaagctc gttctgttga tgaaggctct tttgatatta caagagattc taaaaatgta | 480 |
| gttgaatcta ccccaattac aattcaaggt aaagaacatt ttgaaggtta cggaagtgtt | 540 |
| gatatacaaa aaaacccaac agatttaggg gtatcagagg taaccaggtt taatgttggt | 600 |
| aatgaaagta atggttttgat aggagcttta caattaaaaa ataaaataga ttttagtaag | 660 |
| gatttcaatt ttaaagttag agtggcaaat aaccatcaat caaataccac aggtgctgat | 720 |
| ggttgggggt tcttatttag taaggaaat gcagaagaat attaactaa tggtggaatc | 780 |
| cttgggata aaggtctggt aaattcaggc ggatttaaaa ttgatactgg atacattat | 840 |
| acaagttcca tggacaaaac tgaaaagcaa gctggacaag ttatagagg atacggagct | 900 |
| tttgtgaaaa atgacagttc tggtaattca caatggttg gagaaaatat tgataaatca | 960 |
| aaaactaatt ttttaaacta tgcggacaat tcaactaata catcagatgg aaagtttcat | 1020 |
| gggcaacgtt taaatgatgt catcttaact tatgttgctt caactggtaa aatgagagca | 1080 |

```
gaatatgctg gtaaaacttg ggagacttca ataacagatt taggtttatc taaaaatcag   1140 gcataataatt tcttaattac atctagtcaa agatggggcc ttaatcaagg gataaatgca   1200
aatggctgga tgagaactga cttgaaaggt tcagagtttta cttttacacc agaagcgcca   1260
aaaacaataa cagaattaga aaaaaaagtt gaagagattc cattcaagaa agaacgtaaa   1320
tttaatccgg atttagcacc agggacagaa aaagtaacaa gagaaggaca aaaggtgag   1380 aagcacaataa caacaccaac actaaaaaat ccattaactg gagaaattat tagtaaaggt   1440
gaatcgaaag aagagatcac aaaagatccg attaatgaat taacagaata cggaccagaa   1500
acgatagcac caggtcatcg agacgaattt gatccgaagt taccaacagg agagaaagaa   1560
gaagttccag gtaaaccagg aattaagaat ccagaaacag gagacgtagt tagaccaccg   1620
gtcgatagtg taacaaaata tggacctgta aaaggagact cgattgtaga aaagaagaa   1680 attccattcg agaaagaacg taaatttaat cctgatttag caccaggaac agaaaaagta   1740
acaagagaag gacaaaaagg tgagaagaca ataacgacac caacactaaa aaatccatta   1800
actggagaaa ttattagtaa aggtgaatcg aaagaagaga tcacaaaaga tccgattaat   1860
gaattaacag aatacggacc tgaaacaata gcgccaggtc atcgagacga atttgatccg   1920
aagttaccaa caggagagaa agaagaagtt ccaggtaaac caggaattaa gaatccagaa   1980
acaggagacg tagttagacc gccggtcgat agcgtaacaa aatatggacc tgtaaaagga   2040
gactcgattg tagaaaaaga gaaaattcca ttcaagaaag aacgtaaatt taatcctgat   2100
ttagcaccag gacagaaaaa agtaacaaga aggacaaa aagtgagaa gacaataacg   2160 acgccaacac taaaaaatcc attaactgga gaaattatta gtaaaggtga atcgaaagaa   2220
gaaatcacaa aagatccgat taatgaatta acagaatacg gaccgaaaac gataacacca   2280
ggtcatcgag acgaatttga tccgaagtta ccaacaggag agaaagagga agttccaggt   2340
aaaccaggaa ttaagaatcc agaaacagga gatgtagtta gaccaccggt cgatagcgta   2400
acaaaatatg gacctgtaaa aggagactcg attgtagaaa agaagaaat tccattcgag   2460 aaagaacgta aatttaatcc tgatttagca ccagggacag aaaaagtaac aagagaagga   2520
caaaaaggtg agaagacaat aacgacgcca acactaaaaa atccattaac tggagaaatt   2580
attagtaaag gtgaatcgaa agaagaaatc acaaaagatc cagttaatga attaacagaa   2640
ttcggtggcg agaaaatacc gcaaggtcat aaagatatct ttgatccaaa cttaccaaca   2700
gatcaaacgg aaaaagtacc aggtaaacca ggaatcaaga atccagacac aggaaaagtg   2760
atcgaagagc cagtggatga tgtgattaaa cacggaccaa aaacgggtac accagaaaca   2820
aaaacagtag agataccgtt tgaaacaaaa cgtgagtttta atccaaaatt acaacctggt   2880
gaagagcgag tgaaacaaga aggacaacca ggaagtaaga caatcacaac accaatcaca   2940
gtgaacccat taacaggtga aaaagttggc gagggtcaac caacagaaga gatcacaaaa   3000
caaccagtag ataagattgt agagttcggt ggagagaaac caaagatcc aaaggacct   3060 gaaacccag agaagccgag cagaccaact catccaagtg gcccagtaaa tcctaacaat   3120
ccaggattat cgaaagacag agcaaaacca aatggcccag ttcattcaat ggataaaaat   3180
gataaagtta aaaaatctaa aattgctaaa gaatcagtag ctaatcaaga gaaaaaacga   3240
gcagaattac caaaaacagg tttagaaagc acgcaaaaag gtttgatctt tagtagtata   3300
attggaattg ctggattaat gttattggct cgtagaagaa agaattaa               3348
```

<210> SEQ ID NO 50
<211> LENGTH: 4410
<212> TYPE: DNA

<213> ORGANISM: Staphylococcus epidermidis

<400> SEQUENCE: 50

```
atgggcaaac gtagacaagg tcctattaat aaaaaagtgg attttttacc taacaaatta      60
aacaagtatt ctataagaaa attcactgtt ggtacggcct caatattact tggttcgaca     120
cttattttg gaagtagtag ccatgaagcg aaagctgcag aagaaaaaca agttgatcca      180
attacacaag ctaatcaaaa tgatagtagt gaaagatcac ttgaaaacac aaatcaacct     240
actgtaaaca atgaagcacc acagatgtct tctacattgc aagcagaaga aggaagcaat     300
gcagaagcac cgaatgttcc aactatcaaa gctaattcag ataatgatac acaaacacaa     360
ttttcagaag cccctacaag aaatgaccta gctagaaaag aagatatccc tgctgtttct     420
aaaaacgagg aattacaatc atcacaacca aacactgaca gtaaaataga acctacaact     480
tcagaacctg tgaatttaaa ttatagttct ccgtttatgt ccttattaag catgcctgct     540
gatagttcat ccaataacac taaaaataca atagatatac cgccaactac ggttaaaggt     600
agagataatt acgatttta cggtagagta gatatccaaa gtaatcctac agatttaaat      660
gcgacaaatt taacgagata taattatgga cagccacctg gtacaacaac agctggtgca     720
gttcaattta aaaatcaagt tagttttgat aaagatttcg actttaacat tagagtagca     780
aacaatcgtc aaagtaatac aactggtgca gatggttggg gctttatgtt cagcaagaaa     840
gatggggatg atttcctaaa aaacggtggt atcttacgtg aaaaaggtac acctagtgca     900
gctggtttca gaattgatac aggatattat aataacgatc cattagataa aatacagaaa     960
caagctggtc aaggctatag agggtatggg acatttgtta aaaatgactc ccaaggtaat    1020
acttctaaag taggatcagg tactccatca acagattttc ttaactacgc agataatact    1080
actaatgatt tagatggtaa attccatggt caaaaattaa ataatgttaa tttgaaatat    1140
aatgcttcaa atcaaacttt tacagctact tatgctggta aaacttggac ggctacgtta    1200
tctgaattag gattgagtcc aactgatagt tacaatttt tagttacatc aagtcaatat    1260
ggaaatggta atagtggtac atacgcagat ggcgttatga gagctgattt agatggtgca    1320
acattgacat atactcctaa agcagtcgat ggagacccaa ttcatcaac taaggaaata    1380
ccatttaata aaaaacgcga atttgatcca aacttagcgc caggtacaga aaaagtcgtt    1440
caaaaaggtg aaccaggaat tgaaacaaca acaacaccaa cttatgtcaa tcctaatact    1500
ggagaaaaag taggtgaagg cacacctaca acaaagatca ctaaacaacc agtggatgaa    1560
atcgttcatt atggtggcga agaaatcaag ccaggacata agatgaatt tgatccaaat    1620
gcaccgaaag gtagtcaaac aacgcaacca ggtaagccag gagttaaaaa tcctgataca    1680
ggcgaagtag tcacaccacc agtggatgat gtgacaaaat atggtccagt tgatggagat    1740
ccgattacgt caacggaaga aattccattc gacaagaaac gtgaattcaa tcctgattta    1800
aaaccaggtg aagagcgtgt taaacaaaaa ggtgaaccag gaacaaaaac aattacaaca    1860
ccaacaacta gaacccatt aacaggggaa aaagttggcg aaggtgaacc aacagaaaaa    1920
ataacaaaac aaccagtaga tgaaatcaca gaatatggtg gcgaagaaat caagccaggc    1980
cataaggatg aatttgatcc gaacgcaccg aaaggtagcc aagaggacgt tccaggtaaa    2040
ccaggagtta aaaatcctga tacaggcgaa gtagtcacac caccagtgga tgatgtgaca    2100
aaatatggtc cagttgatgg agatccgatt acgtcaacgg aagaaattcc gtttgataaa    2160
aaacgcgaat ttgatccaaa cttagcgcca ggtacagaga agtcgttca aaaggtgaa    2220
ccaggaacaa aaacaattac aacaccaaca actaagaacc cattaacagg agaaaaagtt    2280
```

```
ggcgaaggtg aaccaacaga aaaaataaca aaacaaccag tgatgaaat cgttcattat    2340
ggtggcgaag aaatcaagcc aggccataag gatgaatttg atccgaacgc accgaaaggt    2400
agccaagagg acgttccagg taagccagga gttaaaaatc ctgatacagg cgaagtagtc    2460
acaccaccag tggatgatgt gacaaaatat ggtccagttg atggagatcc gattacgtca    2520
acggaagaaa ttccattcga caagaaacgt gaattcaatc ctgatttaaa accaggtgaa    2580
gagcgtgtta acaaaaaagg tgaaccagga acaaaaacaa ttacaacacc aacaactaag    2640
aacccattaa caggggaaaa agttggcgaa ggtgaaccaa cagaaaaagt aacaaaacaa    2700
ccagtggatg aaatcgttca ttatggtggc gaagaaatca agccaggcca taaggatgaa    2760
tttgatccaa atgcaccgaa aggtagccaa gaagacgttc caggtaaacc aggagttaaa    2820
aaccctgata caggcgaagt agttactcca ccagtggatg atgtgacaaa atatggtcca    2880
gttgatggag atccgattac gtcaacggaa gaaattccgt ttgataaaaa acgcgaattt    2940
gatccaaact agcgccagg tacagagaaa gtcgttcaaa aaggtgaacc aggaacaaaa    3000
acaattacaa caccaacaac taagaaccca ttaacaggag aaaaagttgg cgaaggtgaa    3060
ccaacagaaa aaataacaaa acaaccagtg gatgagatcg ttcattatgg tggcgaagaa    3120
atcaagccag gccataagga tgaatttgat ccgaacgcac cgaaaggtag tcaaacaacg    3180
caaccaggta agccaggagt taaaaatcct gatacaggcg aagtagtcac accaccagtg    3240
gatgatgtga caaatatgg tccagttgat ggagatccga ttacgtcaac ggaagaaatt    3300
ccgtttgata aaaacgcga atttgatcca aacttagcgc caggtacaga aagtcgtt     3360
caaaaaggtg aaccaggaac aaaaacaatt acaacgccaa caactaagaa cccattaaca    3420
ggagaaaaag ttggcgaagg tgaaccaaca gaaaaaataa caaaacaacc agtggatgag    3480
attgttcatt atggtggtga acaaatacca caaggtcata agatgaatt tgatccaaat    3540
gcacctgtag atagtaaaac tgaagttcca ggtaaaccag gagttaaaaa tcctgataca    3600
ggtgaagttg ttaccccacc agtggatgat gtgacaaaat atggtccgaa agttggtaat    3660
ccaatcacat caacggaaga gattccattt gataagaaac gtgtatttaa tcctgattta    3720
aaaccaggtg aagagcgcgt taaacaaaaa ggtgaaccag aacaaaaac aattacaaca    3780
ccaatattag ttaatcctat tacaggagaa aaagttggcg aaggtaaatc aacagaaaaa    3840
gtcactaaac aacctgttga cgaaattgtt gagtatggtc aacaaaaagc agaaccaggt    3900
aaaccagcgg aaccaggtaa accagcggaa ccaggtaaac cagcggaacc aggtaaacca    3960
gcggaaccag gtacgccagc agaaccaggt aaaccagcgg aaccaggtaa accagcgaaa    4020
ccaggtaaac cagcggaacc aggtaaacca gcggaaccag gtaaaccagc ggaaccaggt    4080
acgccagcag aaccaggtaa accagcggaa ccaggtaaac cagcggaacc aggtaaacca    4140
gcggaaccag gtacgccagc agaaccaggt aaaccagcgg aaccaggtac gccagcagaa    4200
ccagtaaac cagcggaacc aggtacgcca acacaatcag gtgcaccaga caaccaaat    4260
agatcaatgc attcaacaga taataaaaat caattacctg atacaggtga aaatcgtcaa    4320
gctaatgagg gaactttagt cggatctcta ttagcaattg tcggatcatt gttcatattt    4380
ggtcgtcgta aaaaggtaa tgaaaaataa                                      4410
```

<210> SEQ ID NO 51
<211> LENGTH: 504
<212> TYPE: DNA
<213> ORGANISM: Staphylococcus aureus

<400> SEQUENCE: 51

| | |
|---|---|
| atgaagaaac tatatacatc ttatggcact tatggatttt tacatcaaat aaaaatcaat | 60 |
| aacccgaccc atcaactatt ccaatttttca gcatcagata cttcagttat ttttgaagaa | 120 |
| actgatggtg agactgtttt aaaatcacct tcaatatatg aagttattaa agaaattggt | 180 |
| gaattcagtg aacatcattt ctattgtgca atcttcattc cttcaacaga agatcatgca | 240 |
| tatcaacttg aaaagaaact gattagtgta gacgataatt tcagaaactt tggtggcttt | 300 |
| aaaagctatc gtttgttaag acctgctaaa ggtacaacat ataaaattta tttcggatttt | 360 |
| gctgatcgac atgcatacga agactttaag caatctgatg cctttaatga ccattttttca | 420 |
| aaagacgcat taagtcatta ctttggttca agcggacaac attcaagtta ttttgaaaga | 480 |
| tatctatacc caataaaaga atag | 504 |

<210> SEQ ID NO 52
<211> LENGTH: 504
<212> TYPE: DNA
<213> ORGANISM: Staphylococcus epidermidis

<400> SEQUENCE: 52

| | |
|---|---|
| atgtatttat atacatctta tgggacttac caatttttaa atcaaattaa acttaatcat | 60 |
| caagaacgta gtttatttca attttccact aatgattcct caataatctt agaagagtct | 120 |
| gagggaaaat caatcttaaa acatcctagt gcatatcaag tgattgatag cacaggtgaa | 180 |
| tttaacgaac atcatttta tagtgctatt tttgtcccta catctgaaga tcatcgtcaa | 240 |
| cagctagaga aaaaattatt actcgtagac gtacctttaa gaaattttgg tggttttaaa | 300 |
| agctatcgtt tattaaaacc cactgagggg tctacctaca aaatttactt tggttttgca | 360 |
| aatcgaacag catatgaaga tttcaaagct tctgatatat ttaatgaaaa cttttcaaaa | 420 |
| gatgcattga gccaatactt tggtgctagt ggtcaacatt ctagctactt tgaaagatat | 480 |
| ttatatccaa tagaagatca ttaa | 504 |

<210> SEQ ID NO 53
<211> LENGTH: 3426
<212> TYPE: DNA
<213> ORGANISM: Staphylococcus aureus

<400> SEQUENCE: 53

| | |
|---|---|
| atgattaaca gggataataa aaaggcaata acaaaaaagg gtatgatttc aaatcgctta | 60 |
| aacaaatttt cgattagaaa gtatactgta ggaactgcat cgattttagt aggtacgaca | 120 |
| ttgattttg gtctagggaa ccaagaagct aaagctgctg aaaacactag tacagaaaat | 180 |
| gcgaaacaag atgatgcaac gactagtgat aataagaag tagtgtcgga actgaaaat | 240 |
| aattcgacaa cagaaaatga ttcaacaaat ccaattaaga agaaacaaa tactgattca | 300 |
| caaccagaag ctaaagaaga atcaactaca tcaagtactc aacaacagca aaataacgtt | 360 |
| acagctacaa ctgaaactaa gcctcaaaac attgaaaaag aaaatgttaa accttcaact | 420 |
| gataaaactg cgacagaaga tacatctgtt attttagaag agaagaaagc accaaattat | 480 |
| acaaataacg atgtaactac aaaaccatct caagtgaaaa ttcaaacaaa accaactaca | 540 |
| cctcaagaat ctacaaatat tgaaaattca caaccgcaac caacgccttc aaaagtagac | 600 |
| aatcaagtta cagatgcaac taatccaaaa gaaccagtaa atgtgtcaaa agaagaactt | 660 |
| aaaaataatc ctgagaaatt aaaagaatta gttagaaatg ataacaatac agatcgttca | 720 |
| actaaaccag ttgctacagc tccaacaagt gttgcaccaa aacgattaaa tgcgaaaatg | 780 |
| cgttttgcag ttgcacaacc agcagcagtt gcttcaaata atgtaaatga cttaattaca | 840 |

```
gttacgaaac agacgatcaa agttggcgat ggtaaagata atgtggcagc agcgcatgac    900
ggtaaagata ttgaatatga tacagagttt acaattgaca ataaagtcaa aaaaggcgat    960
acaatgacga ttaattatga taagaatgta attccttcgg atttaacaga taaaaatgat   1020
cctatcgata ttactgatcc atcaggagag gtcattgcca aaggaacatt tgataaagcg   1080
actaagcaaa tcacatatac atttacagat tatgtagata aatatgaaga tataaaagca   1140
cgtttaactt tatactcata tattgataag caagcagtac ctaatgaaac tagtttgaat   1200
ttaacgtttg caacagcagg taaagaaact agccaaaacg tttctgttga ttatcaagac   1260
ccaatggttc atggtgattc aaacattcaa tctatcttta caaagttaga tgaaaacaaa   1320
caaactattg aacaacaaat ttatgttaat cctttgaaaa aaacagcaac taacactaaa   1380
gttgatatag ctggtagtca agtagatgat tatggaaata ttaaactagg aaatggtagt   1440
accattattg accaaaatac agaaataaaa gtttataaag ttaaccctaa tcaacaattg   1500
cctcaaagta atagaatcta tgattttagt caatacgaag atgtaacaag tcaatttgat   1560
aataaaaaat catttagtaa taatgtagca acattggatt ttggtgatat taattcagcc   1620
tatattatca aagttgttag taaatataca cctacatcag atggcgaact agatattgct   1680
caaggtacta gtatgagaac aactgataaa tatggttatt ataattatgc aggatattca   1740
aacttcatcg taacttctaa tgacactggc ggtggcgacg gtactgttaa acctgaagaa   1800
aagttataca aaattggtga ctatgtatgg gaagacgttg ataaagacgg tgtccaaggt   1860
acagattcga aagaaaagcc aatggcaaac gttttagtta cattaactta cccgacggt    1920
actacaaaat cagtaagaac agatgctaac ggtcattatg aattcggtgg tttgaaagac   1980
ggagaaactt atacagttaa attcgaaacg ccagctggat atcttccaac aaaagtaaat   2040
ggaacaactg atggtgaaaa agactcaaat ggtagttcta taactgttaa aattaatggt   2100
aaagatgata tgtctttaga cactggtttt tataaagaac taaatataa tcttggtgac   2160
tatgtatggg aagatacaaa taagatggt atccaagatg ctaatgaacc tggtatcaaa   2220
gatgttaagg ttacattaaa agatagtact ggaaaagtta ttggtacaac tactactgat   2280
gcctcgggta aatataaatt tacagattta gataatggta actatacagt agaatttgaa   2340
acaccagcag gttacacgcc aacggttaaa aatactacag ctgaagataa agattctaat   2400
ggtttaacaa caacaggtgt cattaaagat gcagataata tgacattaga cagtggtttc   2460
tataaaacac caaaatacag tttaggtgat tatgtttggt acgacagtaa taaagacggt   2520
aaacaagatt caactgaaaa aggtatcaaa gatgttaaag ttactttatt aaatgaaaaa   2580
ggcgaagtaa ttggaacaac taaaacagat gaaaatggta atatcgtttt cgataattta   2640
gatagcggta aatacaaagt tatttttgaa aagcctgctg gcttaacaca aacagttaca   2700
aatacaactg aagatgataa agatgccgat ggtggcgaag ttgacgtaac aattacggat   2760
catgatgatt tcatacttga taacggatac ttcgaagaag atacatcaga cagtgattca   2820
gactcagaca gtgattcaga ctcagacagc gactcagatt cagacagtga ttcagactca   2880
gatagcgatt cagattcaga cagcgactca gactcagata gcgactcaga ctcagacagc   2940
gactcagact cagatagcga ctcagattcg gacagcgatt cagactcaga tagcgactca   3000
gattcagaca gcgattcaga ctcagatagc gactcagatt cagacagtga ctcagactca   3060
gatagcgact cagactcaga cagtgactca gactcagaca gcgattcaga ttcagatagc   3120
gactcagatt cggacagtga ttcagactca gatagcgact cagattcaga cagcgactca   3180
gactcagata gcgactcaga ctcagacagt gattcagact cagatagcga ttcggactcg   3240
```

```
gatgcaggaa acatacacc tgttaaacca atgagtacta ctaaagacca tcacaataaa    3300
gcaaaagcat taccagaaac aggtagtgaa ataacggct caaataacgc aacgttattt    3360
ggtggattat ttgcagcatt aggttcatta ttgttattcg gtcgtcgcaa aaaacaaaac    3420
aaataa                                                              3426

<210> SEQ ID NO 54
<211> LENGTH: 3171
<212> TYPE: DNA
<213> ORGANISM: Staphylococcus epidermidis

<400> SEQUENCE: 54
atgattaata aaaaaaataa tttactaact aaaaagaaac ctatagcaaa taaatccaat     60
aaatatgcaa ttagaaaatt cacagtaggt acagcgtcta ttgtaatagg tgcaacatta    120
ttgtttggtt taggtcataa tgaggccaaa gccgaggaga attcagtaca agacgttaaa    180
gattcgaata cggatgatga attatcgac agcaatgatc agtctagtga tgaagaaaag    240
aatgatgtga tcaataataa tcagtcaata aacaccgacg ataataacca ataattaaa    300 aaagaagaaa cgaataacta cgatggcata gaaaaacgct cagaagatag aacagagtca    360
acaacaaatg tagatgaaaa cgaagcaaca ttttttacaaa agacccctca agataatact    420
catcttacag aagaagaggt aaaagaatcc tcatcagtcg aatcctcaaa ttcatcaatt    480
gatactgccc aacaaccatc tcacacaaca ataaatagag aagaatctgt tcaaacaagt    540
gataatgtag aagattcaca cgtatcagat tttgctaact ctaaaataaa agagagtaac    600
actgaatctg gtaaagaaga gaatactata gagcaaccta ataaagtaaa agaagattca    660
acaacaagtc agccgtctgg ctatacaaat atagatgaaa aaatttcaaa tcaagatgag    720
ttattaaatt taccaataaa tgaatatgaa ataaggcta gaccattatc tacaacatct    780
gcccaaccat cgattaaacg tgtaaccgta aatcaattag cggcggaaca aggttcgaat    840
gttaatcatt taattaaagt tactgatcaa gtattactg aaggatatga tgatagtgaa    900
ggtgttatta agcacatga tgctgaaaac ttaatctatg atgtaacttt tgaagtagat    960
gataaggtga atctggtga tacgatgaca gtggatatag ataagaatac agttccatca   1020
gatttaaccg atagctttac aataccaaaa ataaaagata attctggaga aatcatcgct   1080
acaggtactt atgataacaa aaataaacaa atcaccctata cttttacaga ttatgtagat   1140
aagtatgaaa atattaaagc acaccttaaa ttaacgtcat acattgataa atcaaaggtt   1200
ccaaataata ataccaagtt agatgtgaaa tataaaacgg cccttttcatc agtaaataaa   1260 acaattacgg ttgaatatca aagacctaac gaaaatcgga ctgctaacct tcaaagtatg   1320
tttacaaaca tagatacgaa aaatcataca gttgagcaaa cgatttatat taaccctctt   1380
cgttattcag ccaaggaaac aaatgtaaat atttcaggga atggtgatga aggttcaaca   1440
attatagacg atagcacaat aattaaagtt tataaggttg gagataatca aaatttacca   1500
gatagtaaca gaatttatga ttacagtgaa tatgaagatg tcacaaatga tgattatgcc   1560
caattaggaa ataataatga tgtgaatatt aattttggta atatagattc accatatatt   1620
attaaagtta ttagtaaata tgaccctaat aaggatgatt acacgactat acagcaaact   1680
gtgacaatgc agacgactat aaatgagtat actggtgagt ttagaacagc atcctatgat   1740
aatacaattg ctttctctac aagttcaggt caaggacaag gtgacttgcc tcctgaaaaa   1800
acttataaaa tcggagatta cgtatgggaa gatgtagata agatggtat tcaaaataca   1860 aatgataatg aaaaaccgct tagtaatgta ttggtaactt tgacgtatcc tgatggaact   1920
```

| | |
|---|---:|
| tcaaaatcag tcagaacaga tgaagatggg aaatatcaat ttgatggatt gaaaaacgga | 1980 |
| ttgacttata aaattacatt cgaaacacct gaaggatata cgccgacgct aaacattca | 2040 |
| ggaacaaatc ctgcactaga ctcagaaggt aattctgtat gggtaactat taatggacaa | 2100 |
| gacgatatga cgattgatag tggattttat caaacaccta aatacagctt agggaactat | 2160 |
| gtatggtatg acactaataa agatggtatt caaggtgatg atgaaaaagg aatctctgga | 2220 |
| gttaaagtga cgttaaaaga tgaaaacgga aatatcatta gtacaactac aaccgatgaa | 2280 |
| aatggaaagt atcaatttga taatttaaat agtggtaatt atattgttca ttttgataaa | 2340 |
| ccttcaggta tgactcaaac aacaacagat tctggtgatg atgacgaaca ggatgctgat | 2400 |
| ggggaagaag ttcatgtaac aattactgat catgatgact ttagtataga taacggatac | 2460 |
| tatgatgacg aatcggattc cgatagtgac tcagacagcg actcagattc cgatagtgat | 2520 |
| tcagactccg atagcgactc ggattcagac agcgactcag attcagacag cgactcggat | 2580 |
| tctgatagcg actcggattc agacagcgac tcagactcag acagtgattc agattcagac | 2640 |
| agcgactcag attccgatag tgattcagac tcagacagcg actcagattc tgatagtgat | 2700 |
| tcagactcag acagtgattc agattcagac agcgactcag attccgatag tgattcagac | 2760 |
| tcagacagcg actcagattc cgatagtgat tcagactcag acagcgactc agattctgat | 2820 |
| agtgattcag actcagacag tgattcagat tccgatagtg attcagactc cgatagcgac | 2880 |
| tcagactcgg atagtgactc agattctgat agtgattcag actcagacag tgattcggat | 2940 |
| tccgatagtg attcagactc agacagcgac tcagattctg atagtgattc agactcagac | 3000 |
| aacgactcag atttaggcaa tagctcagat aagagtacaa aagataaatt acctgataca | 3060 |
| ggagctaatg aagattatgg ctctaaaggc acgttacttg gaactctgtt tgcaggttta | 3120 |
| ggagcgttat tatagggaa acgtcgcaaa aatagaaaaa ataaaaatta a | 3171 |

<210> SEQ ID NO 55
<211> LENGTH: 1461
<212> TYPE: DNA
<213> ORGANISM: Staphylococcus aureus

<400> SEQUENCE: 55

| | |
|---|---:|
| atgtctaata tttttaaaga tgactttgaa aaaaatcgtc aatcgataga cacaaattca | 60 |
| catcaagacc atacggaaga tgttgaaaaa gaccaatcag aattagaaca tcaggataca | 120 |
| atagagaata cggagcaaca gtttccgcca agaaatgccc aaagaagaaa aagacgccgt | 180 |
| gatttagcaa cgaatcataa taaacaagtt cacaatgaat cacaaacatc tgaagacaat | 240 |
| gttcaaaatg aggctggcac aatagatgat cgtcaagtcg aatcatcaca cagtactgaa | 300 |
| agtcaagaac ctagccatca agacagtaca cctcaacatg aagaggaata ttataataag | 360 |
| aatgcttttg caatggataa atcacatcca gaaccaatcg aagacaatga taaacacgag | 420 |
| actattaaag atgcagaaaa taacactgag cattcaacag tttctgataa gagtatagct | 480 |
| gaacaatctc agcaacctaa accatatttt gcaacaggtg ctaaccaagc aaatacatca | 540 |
| aaagataaac atgatgatgt aactgttaag caagacaaag atgaatctaa agatcatcat | 600 |
| agtggtaaaa aaggcgcagc aattggtgct ggaacagcgg gtgttgcagg tgcagctggt | 660 |
| gcaatgggtg tttctaaagc taagaaacat tcaaatgacg ctcaaaacaa agtaattct | 720 |
| gacaagtcga taactcgac tgaggataaa gcgtctcaag ataagtctaa agatcatcat | 780 |
| aatggcaaaa aaggtgcagc gatcggtgct ggaacagcag gtttggctgg aggcgcagca | 840 |
| agtaaaagtg cttctgccgc ttcaaaacca catgcctcta ataatgcaag ccaaaaccat | 900 |

```
gatgaacatg acaatcatga cagagataaa gaacgtaaaa aaggtggcat ggccaaagta      960
ttgttaccat taattgcagc tgtactaatt atcggtgcat tagcgatatt tggaggcatg     1020
gcattaaaca atcataataa tggtacaaaa gaaaataaaa tcgcgaatac aaataaaaat     1080
aatgctgatg aaagtaaaga caaagacaca tctaaagacg cttctaaaga taaatcaaaa     1140
tctacagaca gtgataaatc aaaagaggat caagacaaag cgactaaaga tgaatctgat     1200
aatgatcaaa acaacgctaa tcaagcgaac aatcaagcac aaaataatca aaatcaacaa     1260
caagctaatc aaaatcaaca acagcaacaa caacgtcaag gtggtggcca aagacataca     1320
gtgaatggtc aagaaaactt ataccgtatc gcaattcaat actacggttc aggttcaccg     1380
gaaaatgttg aaaaaattag acgtgccaat ggtttaagtg gtaacaatat tagaaacggt     1440
caacaaatcg ttattccata a                                               1461

<210> SEQ ID NO 56
<211> LENGTH: 1419
<212> TYPE: DNA
<213> ORGANISM: Staphylococcus epidermidis

<400> SEQUENCE: 56
gtgattgaat taattaaaat ggaagggatg atagttgtgt ctaataataa ttttaaagat       60
gatttcgaaa agaatcgtca atctattaat ccagacgaac agcaaacaga attaaaagaa      120
gatgataaaa caaatgaaaa taaaaaagaa gctgactctc aaaacagttt atctaataac      180
tcaaatcaac aatttcctcc gagaaatgcc aacgacgaa aaagacgtag agagacagca       240
actaatcaaa gcaaacaaca agacgacaaa catcaaaaaa atagtgacgc taaaactaca      300
gaaggttcat tagatgaccg ttatgacgaa gcacagttac agcaacaaca tgataaatcg      360
caacaacaaa ataaaactga aaaacaatca aagataata gaatgaaaga tggaaaagat      420
gcagctattg taaatggaac atctgagtca ccagaacata atcaaaatc aacacaaaat      480 agacccggcc ctaaagctca acaacaaaag cgtaaatcag aaagtacgca atcaaaaccg     540
tcaacaaaca aagataaaaa agcagctaca ggtgctggaa tagctggtgc agctggtgtt     600
gctggtgcag cagaaacatc caaacgtcat cataataaaa aagataaaca agattctaaa     660
cactcaaacc atgagaatga cgaaaaatct gttaaaaatg atgaccaaaa gcaatctaaa     720
aaaggcaaaa aagcagcagt cggtgctggc gcagctgcag gagttggtgc ggctggtgtt     780
gcgcatcata taatcaaaa taaacatcat aatgaggaaa aaattctaa tcaaaacaat       840 cagtacaatg accaatcaga aggtaagaaa aaaggtggtt tcatgaaaat cttgttacca     900
cttatagcag ccattcttat tctaggtgca atagcaatat tcggtggtat ggctctaaat     960
aatcacaacg atagtaaag tgatgaccaa aaaatagcga atcaaagtaa gaaagactca     1020
gataaaaaag atggtgcgca atccgaagat aacaaagaca aaaatctga tagtaacaaa      1080 gacaaaaaat ctgattctga taagaacgca gatgatgact ctgataatag ttcctcaaat     1140
cctaacgcta cttcaactaa taataacgat aatgtagcca ataataactc aaattataca     1200
aaccaaaatc aacaagataa tgcaaccaa aatagcaata tcaacaggc aactcaaggt       1260 caacaatcac atacagtata cggtcaagaa aacttatatc gtatcgccat acaatattat     1320
ggagaaggaa ctcaagctaa cgtagataaa attaaacgtg cgaatggatt aagcagtaat     1380
aatattcata atggtcaaac attagttatt cctcaataa                            1419

<210> SEQ ID NO 57
<211> LENGTH: 498
<212> TYPE: DNA
```

-continued

<213> ORGANISM: Staphylococcus aureus

<400> SEQUENCE: 57

| atgaaaaata aattgatagc aaaatcttta ttaacaatag cggcaattgg tattactaca | 60 |
| actacaattg cgtcaacagc agatgcgagc gaaggatacg gtccaagaga aagaaacca | 120 |
| gtgagtatta atcacaatat cgtagagtac aatgatggta cttttaaata tcaatctaga | 180 |
| ccaaaattta actcaacacc taaatatatt aaattcaaac atgactataa tattttagaa | 240 |
| tttaacgatg gtacattcga atatggtgca cgtccacaat ttaataaacc agcagcgaaa | 300 |
| actgatgcaa ctattaaaaa agaacaaaaa ttgattcaag ctcaaaatct tgtgagagaa | 360 |
| tttgaaaaaa cacatactgt cagtgcacac agaaaagcac aaaaggcagt caacttagtt | 420 |
| tcgtttgaat acaaagtgaa gaaaatggtc ttacaagagc gaattgataa tgtattaaaa | 480 |
| caaggattag tgagataa | 498 |

<210> SEQ ID NO 58
<211> LENGTH: 960
<212> TYPE: DNA
<213> ORGANISM: Staphylococcus aureus

<400> SEQUENCE: 58

| atgaaaacac gtatagtcag ctcagtaaca acaacactat tgctaggttc catattaatg | 60 |
| aatcctgtcg ctaatgccgc agattctgat attaatatta aaccggtac tacagatatt | 120 |
| ggaagcaata ctacagtaaa aacaggtgat ttagtcactt atgataaaga aaatggcatg | 180 |
| cacaaaaaag tattttatag ttttatcgat gataaaaatc acaataaaaa actgctagtt | 240 |
| attagaacga aaggtaccat tgctggtcaa tatagagttt atagcgaaga aggtgctaac | 300 |
| aaaagtggtt tagcctggcc ttcagccttt aaggtacagt tgcaactacc tgataatgaa | 360 |
| gtagctcaaa tatctgatta ctatccaaga aattcgattg atacaaaaga gtatatgagt | 420 |
| actttaactt atggattcaa cggtaatgtt actggtgatg atacaggaaa aattggcggc | 480 |
| cttattggtg caaatgtttc gattggtcat acactgaaat atgttcaacc tgatttcaaa | 540 |
| acaattttag agagcccaac tgataaaaaa gtaggctgga aagtgatatt taacaatatg | 600 |
| gtgaatcaaa attggggacc atatgataga gattcttgga acccggtata tggcaatcaa | 660 |
| cttttcatga aaactagaaa tggttctatg aaagcagcag agaacttcct tgatcctaac | 720 |
| aaagcaagtt ctctattatc ttcagggttt tcaccagact tcgctacagt tattactatg | 780 |
| gatagaaaag catccaaaca acaaacaaat atagatgtaa tatacgaacg agttcgtgat | 840 |
| gactaccaat tgcattggac ttcaacaaat tggaaggta ccaatactaa agataaatgg | 900 |
| acagatcgtt cttcagaaag atataaaatc gattgggaaa agaagaaat gacaaattaa | 960 |

<210> SEQ ID NO 59
<211> LENGTH: 1287
<212> TYPE: DNA
<213> ORGANISM: Staphylococcus aureus

<400> SEQUENCE: 59

| atacacatga aaaataaata tatctcgaag ttgctagttg gggcagcaac aattacttta | 60 |
| gctacaatga tttcaaatgg ggaagcaaaa gcgagtgaaa acacgcaaca aacttcaact | 120 |
| aagcaccaaa caactcaaaa caactacgta acagatcaac aaaaagcttt ttatcaagta | 180 |
| ttacatctaa aaggtatcac agaagaacaa cgtaaccaat acatcaaaac attacgcgaa | 240 |
| cacccagaac gtgcacaaga agtattctct gaatcactta aagacagcaa gaacccagac | 300 |

```
cgacgtgttg cacaacaaaa cgcttttac aatgttctta aaaatgataa cttaactgaa      360
caagaaaaaa ataattacat tgcacaaatt aaagaaaacc ctgatagaag ccaacaagtt      420
tgggtagaat cagtacaatc ttctaaagct aaagaacgtc aaaatattga aaatgcggat      480
aaagcaatta aagatttcca agataacaaa gcaccacacg ataaatcagc agcatatgaa      540
gctaactcaa aattacctaa agatttacgc gataaaaata accgctttgt agaaaaagtt      600
tcaattgaaa aagcaatcgt tcgtcatgat gagcgtgtga aatcagcaaa tgatgcaatc      660
tcaaaattaa atgaaaaga ttcaattgaa acagacgtt tagcacaacg tgaagttaac       720
aaagcaccta tggatgtaaa agagcattta cagaaacaat tagacgcatt agtagctcaa      780
aaagatgctg aaaagaaagt ggcgccaaaa gttgaggctc ctcaaattca atcaccacaa      840
attgaaaaac ctaaagcaga atcaccaaaa gttgaagtcc ctcaatctaa attattaggt      900
tactaccaat cattaaaaga ttcatttaac tatggttaca agtatttaac agatacttat      960
aaaagctata aagaaaaata tgatacagca aagtactact ataatacgta ctataaatac     1020
aaaggtgcga ttgatcaaac agtattaaca gtactaggta gtggttctaa atcttacatc     1080
caaccattga aagttgatga taaaaacggc tacttagcta aatcatatgc acaagtaaga     1140
aactatgtaa ctgagtcaat caatactggt aaagtattat atactttcta ccaaaaccca    1200
acattagtaa aaacagctat taaagctcaa gaaactgcat catcaatcaa aaatacatta    1260
agtaatttat tatcattctg gaaataa                                         1287

<210> SEQ ID NO 60
<211> LENGTH: 1053
<212> TYPE: DNA
<213> ORGANISM: Staphylococcus aureus

<400> SEQUENCE: 60
atgacaaaac attatttaaa cagtaagtat caatcagaac aacgttcatc agctatgaaa       60
aagattacaa tgggtacagc atctatcatt ttaggttccc ttgtatacat aggcgcagac     120
agccaacaag tcaatgcggc aacagaagct acgaacgcaa ctaataatca aagcacacaa     180
gtttctcaag caacatcaca accaattaat ttccaagtgc aaaaagatgg ctcttcagag     240
aagtcacaca tggatgacta tatgcaacac cctggtaaag taattaaaca aaataataaa     300
tattatttcc aaaccgtgtt aaacaatgca tcattctgga agaatacaa attttacaat     360 gcaaacaatc aagaattagc aacaactgtt gttaacgata taaaaaagc ggatactaga     420 acaatcaatg ttgcagttga acctggatat aagagcttaa ctactaaagt acatattgtc     480
gtgccacaaa ttaattacaa tcatagatat actacgcatt tggaatttga aaaagcaatt    540
cctacattag ctgacgcagc aaaaccaaac aatgttaaac cggttcaacc aaaaccagct    600
caacctaaaa cacctactga gcaaactaaa ccagttcaac ctaaagttga aaaagttaaa    660
cctactgtaa ctcaacaag caaagttgaa gacaatcact ctactaaagt tgtaagtact    720
gacacaacaa aagatcaaac taaaacacaa actgctcata cagttaaaac agcacaaact    780
gctcaagaac aaaataaagt tcaaacacct gttaaagatg ttgcaacagc gaaatctgaa    840
agcaacaatc aagctgtaag tgataataaa tcacaacaaa ctaacaaagt tacaaaacat    900
aacgaaacgc taaacaagc atctaaagct aagaattac caaaaactgg tttaacttca    960
gttgataact ttattagcac agttgccttc gcaacacttg ccctttagg ttcattatct  1020 ttattacttt tcaaaagaaa agaatctaaa taa                                 1053

<210> SEQ ID NO 61
```

<211> LENGTH: 1938
<212> TYPE: DNA
<213> ORGANISM: Staphylococcus aureus

<400> SEQUENCE: 61

| | | | | | |
|---|---|---|---|---|---|
| atgaacaaac | agcaaaaaga | atttaaatca | ttttattcaa | ttagaaagtc | atcactaggc | 60 |
| gttgcatctg | tagcgattag | tacacttta | ttattaatgt | caaatggcga | agcacaagca | 120 |
| gcagctgaag | aaacaggtgg | tacaaataca | gaagcacaac | caaaaactga | agcagttgca | 180 |
| agtccaacaa | caacatctga | aaaagctcca | gaaactaaac | cagtagctaa | tgctgtctca | 240 |
| gtatctaata | aagaagttga | ggccctact | tctgaaacaa | agaagctaa | agaagttaaa | 300 |
| gaagttaaag | cccctaagga | aacaaaagca | gttaaaccag | cagcaaaagc | cactaacaat | 360 |
| acatatccta | ttttgaatca | ggaacttaga | gaagcgatta | aaaccctgc | aataaaagat | 420 |
| aaagatcata | gcgcaccaaa | ctctcgtcca | attgattttg | aaatgaaaaa | agaaatggt | 480 |
| gagcaacaat | tttatcatta | tgccagctct | gttaaacctg | ctagagttat | tttcactgat | 540 |
| tcaaaaccag | aaattgaatt | aggattacaa | tcaggtcaat | tttggagaaa | atttgaagtt | 600 |
| tatgaaggtg | acaaaaagtt | gccaattaaa | ttagtatcat | acgatactgt | taaagattac | 660 |
| gcttacattc | gcttctctgt | ttcaaatgga | acaaaagccg | ttaaaattgt | aagttcaact | 720 |
| cacttcaata | caaagaaga | aaatacgat | tacacattaa | tggaattcgc | acaaccaatt | 780 |
| tataacagtg | cagataaatt | caaaactgaa | gaagattata | agctgaaaaa | attattagcg | 840 |
| ccatataaaa | aagcgaaaac | actagaaaga | caagtttatg | aattaaataa | aattcaagat | 900 |
| aaacttcctg | aaaaattaaa | ggctgagtac | aagaagaaat | tagaggatac | aaagaaagct | 960 |
| ttagatgagc | aagtgaaatc | agctattact | gaattccaaa | atgtacaacc | aacaaatgaa | 1020 |
| aaaatgactg | atttacaaga | tacaaaatat | gttgtttatg | aaagtgttga | gaataacgaa | 1080 |
| tctatgatgg | atacttttgt | taaacaccct | attaaaacag | gtatgcttaa | cggcaaaaaa | 1140 |
| tatatggtca | tggaaactac | taatgacgat | tactggaaag | atttcatggt | tgaaggtcaa | 1200 |
| cgtgttagaa | ctataagcaa | agatgctaaa | ataatacta | gaacaattat | tttcccatat | 1260 |
| gttgaaggta | aaactctata | tgatgctatc | gttaaagttc | acgtaaaaac | gattgattat | 1320 |
| gatggacaat | accatgtcag | aatcgttgat | aaagaagcat | ttacaaaagc | caataccgat | 1380 |
| aaatctaaca | aaaagaaca | acaagataac | tcagctaaga | aggaagctac | tccagctacg | 1440 |
| cctagcaaac | caacaccatc | acctgttgaa | aagaatcac | aaaaacaaga | cagccaaaaa | 1500 |
| gatgacaata | acaattacc | aagtgttgaa | aagaaaatg | acgcatctag | tgagtcaggt | 1560 |
| aaagacaaaa | cgcctgctac | aaaaccaact | aaaggtgaag | tagaatcaag | tagtacaact | 1620 |
| ccaactaagg | tagtatctac | gactcaaaat | gttgcaaaac | caacaactgc | ttcatcaaaa | 1680 |
| acaacaaaag | atgttgttca | aacttcagca | ggttctagcg | aagcaaaaga | tagtgctcca | 1740 |
| ttacaaaaag | caaacattaa | aaacacaaat | gatggacaca | ctcaaagcca | aaacaataaa | 1800 |
| aatacacaag | aaaataaagc | aaaatcatta | ccacaaactg | gtgaagaatc | aaataaagat | 1860 |
| atgcacattac | cattaatggc | attactagct | ttaagtagca | tcgttgcatt | cgtattacct | 1920 |
| agaaaacgta | aaaactaa | | | | | 1938 |

<210> SEQ ID NO 62
<211> LENGTH: 2862
<212> TYPE: DNA
<213> ORGANISM: Staphylococcus aureus

<400> SEQUENCE: 62

```
atgaataata aaaagacagc aacaaataga aaaggcatga taccaaatcg attaaacaaa        60
ttttcgataa gaaagtattc tgtaggtact gcttcaattt tagtagggac aacattgatt       120
tttgggttaa gtggtcatga agctaaagcg gcagaacata cgaatggaga attaaatcaa       180
tcaaaaaatg aaacgacagc cccaagtgag aataaaacaa ctgaaaaagt tgatagtcgt       240
caactaaaag acaatacgca aactgcaact gcagatcagc ctaaagtgac aatgagtgat       300
agtgcaacag ttaagaaaac tagtagtaac atgcaatcac cacaaaacgc tacagctagt       360
caatctacta cacaaactag caatgtaaca acaaatgata aatcatcaac tacatatagt       420
aatgaaactg ataaaagtaa tttaacacaa gcaaaaaacg tttcaactac acctaaaaca       480
acgactatta aacaagagc tttaaatcgc atggcagtga atactgttgc agctccacaa       540
caaggaacaa atgttaatga taaagtacat tttacgaaca ttgatattgc gattgataaa       600
ggacatgtta ataaaacaac aggaaatact gaattttggg caacttcaag tgatgtttta       660
aaattaaaag cgaattacac aatcgatgat tctgttaaag agggcgatac atttactttt       720
aaatatggtc aatatttccg tccaggttct gtaagattac cttcacaaac tcaaaattta       780
tataatgccc aaggtaatat tattgcaaaa ggtatttacg atagtaaaac aaatacaaca       840
acgtatactt ttacgaatta tgtagatcaa tacacaaatg ttagcggtag ctttgaacaa       900
gtcgcatttg cgaaacgtga aaatgcaaca actgataaaa ctgcttataa aatgaagta       960 actttaggta atgatacata tagtaaagat gtcattgtcg attatggtaa tcaaaaaggt      1020
caacaactta tttcgagtac aaattatatt aataatgaag atttgtcacg taatatgact      1080
gtttatgtaa atcaacctaa aaagacctat acaaaagaaa catttgtaac aaatttaact      1140
ggttataaat ttaatccaga tgctaaaaac ttcaaaattt acgaagtgac agatcaaaat      1200
caatttgtgg atagtttcac cccagatact tcaaaactta agatgttac tggtcaattc      1260 gatgttattt atagtaatga taataagacg gcgacagtag atttattgaa tggtcaatct      1320
agtagtgata aacagtacat cattcaacaa gttgcttatc cagataatag ttcaacagat      1380
aatgggaaaa ttgattatac tttagaaaca caaaatggaa aaagtagttg gtcaaacagt      1440
tattcaaatg tgaatggctc atcaactgca aatggcgacc aaaagaaata taatctaggt      1500
gactatgtat gggaagatac aaataaagat ggtaaacaag atgccaatga aaaagggatt      1560
aaaggtgttt atgtcattct taaagatagt aacggtaaag aattagatcg tacgacaaca      1620
gatgaaaatg gtaaatatca gttcactggt ttaagcaatg gaacttatag tgtagagttt      1680
tcaacaccag ccggttatac accgacaact gcaaatgcag gtacagatga tgctgtagat      1740
tctgatggac taactacaac aggtgtcatt aaagacgctg acaacatgac attagatagt      1800
ggattctaca aaacaccaaa atatagttta ggtgattatg tttggtacga cagtaataaa      1860
gatggtaaac aagattcgac tgaaaaagga attaaaggtg ttaaagttac tttgcaaaac      1920
gaaaaaggcg aagtaattgg tacaactgaa acagatgaaa atggtaaaata ccgctttgat      1980 aatttagata gtggtaaata caaagttatc tttgaaaagc ctgctggttt aactcaaaca      2040
ggtacaaata caactgaaga tgataaagat gccgatggtg cgaagttga tgtaacaatt      2100 acggatcatg atgatttcac acttgataat ggctactacg aagaagaaac atcagatagt      2160
gactcagatt cggacagcga ttcagactca gatagcgact cagattcaga tagtgactca      2220
gactcagata gcgactcaga ctcagatagc gactcagaca gcgactcaga ctcagatagt      2280
gattcagatt cggacagcga ctcagattca gacagcgaat cagattcgga tagcgactca      2340
gactcagata gcgactcaga cagcgactca gattcagaca gtgactcaga ctcagacagc      2400
```

```
gactcagatt cagacagcga ttcagattcg gatagcgact cagattcaga tagcgattcg    2460
gactcagaca acgactcaga ttctgacagc gattcagact cagatagcga ctcagattca    2520
gacagcgact cagattcaga cagcgattca gattcagata gcgattcaga ttcagacagc    2580
gactcagatt cagatagcga ctcagactca gacagcgatt cagactcaga tagcgactca    2640
gacagcgatt cagattcgga tagcgattca gattcagatg caggtaaaca tactccgact    2700
aaaccaatga gtacggttaa agatcagcat aaaacagcta aagcattacc agaaacaggt    2760
agtgaaaata ataattcaaa taatggcaca ttattcggtg gattattcgc ggcattagga    2820
tcattattgt tattcggtcg tcgtaaaaaa caaaataaat aa                       2862
```

<210> SEQ ID NO 63
<211> LENGTH: 2808
<212> TYPE: DNA
<213> ORGANISM: Staphylococcus aureus

<400> SEQUENCE: 63

```
atgaatatga agaaaaaga aaaacacgca attcggaaaa aatcgattgg cgtggcttca      60
gtgcttgtag gtacgttaat cggttttgga ctactcagca gtaaagaagc agatgcaagt    120
gaaaatagtg ttacgcaatc tgatagcgca agtaacgaaa gcaaaagtaa tgattcaagt    180
agcgttagtc ctgcacctaa aacagacgac acaaacgtga gtgatactaa acatcgtca    240 aacactaata atggcgaaac gagtgtggcg caaaatccag cacaacagga aacgacacaa    300
tcatcatcaa caaatgcaac tacgaagaa acgccggtaa ctggtgaagc tactactacg    360
acaacgaatc aagctaatac accggcaaca actcaatcaa gcaatacaaa tgcggaggaa    420
ttagtgaatc aaacaagtaa tgaaacgact tctaatgata ctaatacagt atcatctgta    480
aattcacctc aaaattctac aaatgcggaa atgtttcaa caacgcaaga tacttcaact    540
gaagcaacac cttcaaacaa tgaatcagct ccacagaata cagatgcaag taataaagat    600
gtagttagtc aagcggttaa tccaagtacg cctagaatga gagcatttag tttagcggca    660
gtagctgcag atgcaccggc agctggcaca gatattacga atcagttgac agatgtgaaa    720
gttactattg actctggtac gactgtgtat ccgcaccaag caggttatgt caaactgaat    780
tatggttttt cagtgcctaa ttctgctgtt aaaggtgaca cattcaaaat aactgtacct    840
aaagaattaa acttaaatgg tgtaacttca actgctaaag tgccaccaat tatggctgga    900
gatcaagtat tggcaaatgg tgtaatcgat agtgatggta atgttattta tacatttaca    960
gactatgttg taataaaga aaatgtaaca gctaatatta ctatgccagc ttatattgac   1020
cctgaaaatg ttacaaagac aggtaatgtg acattgacaa ctggcatagg aaccaatact   1080
gctagtaaga cagtattaat cgactatgag aaatatggac aattccataa tttatcaatt   1140
aaaggtacga ttgatcaaat cgataaaaca aataatacgt atcgccaaac aatttatgtc   1200
aatccaagcg gagataacgt tgtgttacct gccttaacag taatttaat tcctaataca   1260 aagagtaatg cgttaataga tgcaaaaaac actgatatta agtttatag agtcgataat   1320 gctaatgatt tatctgaaag ttattatgtg aatcctagcg atttttgaaga tgtaactaat   1380 caagttagaa tttcatttcc aaatgctaat caatacaaag tagaatttcc tacggacgat   1440
gaccaaatta caacaccgta tattgtagtt gttaatggcc atattgatcc tgctagtaca   1500
ggtgatttag cactacgttc gacattttat ggttatgatt ctaattttat atggagatct   1560
atgtcatggg acaacgaagt agcatttaat aacggatcag gttctggtga cggtatcgat   1620
aaaccagttg ttcctgaaca acctgatgag cctggtgaaa ttgaaccaat tccagaggat   1680
```

```
tcagattctg acccaggttc agattctggc agcgattcta attcagatag cggttcagat   1740
tctggcagtg attctacatc agatagtggt tcagattcag cgagtgattc agattcagca   1800
agtgattcag actcagcgag tgattcagat tcagcaagtg attcagattc agcaagtgat   1860
tcagattcag caagtgattc agactcagca agtgattcag attcagcaag tgattcagat   1920
tcagcaagcg attcagattc agcgagcgat tcagattcag cgagcgattc agattcagcg   1980
agtgattccg actcagcgag cgattcagac tcagatagtg actcagattc cgatagcgat   2040
tccgactcag atagcgactc agattcagac agcgattctg actcagacag cgattctgac   2100
tcagacagtg actcagattc cgatagcgat tctgactcag acagtgactc agattccgat   2160
agcgattcag attcagacag tgattcagac tcagatagcg attcagattc cgacagtgac   2220
tcagactcag acagcgattc agattccgat agcgattcag attccgacag tgactcagat   2280
tccgatagtg actcggattc agcgagtgat tcagattcag atagcgattc agaatcagat   2340
agtgactcag actcagacag tgattcagat tcagatagtg actcagactc agacagcgat   2400
tcagaatcag atagtgactc cgattcagac agcgattcag aatcagatag tgactccgat   2460
tcagatagcg attcggattc agcgagtgat tcagactcag gtagtgactc cgattcatca   2520
agtgattcag attccgattc aacgagtgac acaggatcag acaacgactc agacagtgat   2580
tcaaatagcg attccgagtc aggttctaac aataatgtag ttccgcctaa ttcacctaaa   2640
aatggtacta atgcttctaa taaaaatgag gctaaagata gtaaagaacc attaccagat   2700
acaggttctg aagatgaagc gaatacgtca ctaatttggg gattattagc atcattaggt   2760
tcattactac ttttcagaag aaaaaaagaa aataaagata gaaaataa              2808
```

<210> SEQ ID NO 64
<211> LENGTH: 3117
<212> TYPE: DNA
<213> ORGANISM: Staphylococcus aureus

<400> SEQUENCE: 64

```
gtgaaaaaca atcttaggta cggcattaga aaacataaat tgggagcagc atcagtattc     60
ttaggaacaa tgatcgttgt tgggatggga caagataaag aagctgcagc atcagaacaa    120
aagacaacta cagtagaaga aaatgggaat tcagctactg ataataaaac aagtgaaaca    180
caaacaactg ctactaacgt taatcatata gaagaaactc aatcatataa cgcaacagta    240
acagaacaac cgtcaaacgc aacacaagta acaactgaag aagcaccaaa agcagtacaa    300
gcaccacaaa ctgcacaacc agcaaatgta gaaacagtta agaagaaga gaaacctcaa    360 gttaaggaaa cgacacaacc tcaagacaat agcggaaatc aaagacaagt agatttaaca    420
cctaaaaagg ttacacaaaa tcaagggaca gaaacacaag ttgaagtggc acagccaaga    480
acggcatcag aaagtaagcc acgtgtgaca agatcagcag atgtagcgga agctaaggaa    540
gctagtgacg tttcagaagt taaaggcaca gatgttacaa gtaaagttac agtagaaagt    600
ggttctattg aggcacctca aggaaataaa gtagagccac atgctggtca acgtgtcgta    660
ttgaaataca aattgaaatt cgcagatgga ttaaaaagag gagattattt tgattttaca    720
ttatcaaata atgtaaatac ttatgggggtt tcaacagcta gaaaggtacc agagattaaa    780
aatggctcag ttgtaatggc tacaggtgag atcttaggga atggtaacat aagatataca    840
tttactaacg aaattgaaca caaggtagag gtaacagcta atttagaaat caacttatt    900 attgacccta aaactgtaca aagcaatgga gaacaaaaga ttacttctaa attaaatggt    960
gaagaaacag aaaaaacaat accagttgtt tataatccag gtgttagcaa tagttataca   1020
```

-continued

```
aatgtaaatg gatcaattga acatttaat aaagaatcta ataaatttac acatatagct   1080
tatattaagc caatgaatgg aaaccagtca aacactgtat cagtaacagg gacgttgact   1140
gaaggtagta atttagctgg tggacaacct actgttaaag tatatgaata tctagggaaa   1200
aaagatgaat tgccacaaag tgtttatgca aatacatcag atactaacaa attcaaagat   1260
gtaacaaagg aaatgaatgg aaaattgagt gtgcaagaca atggtagtta ctcattgaat   1320
ttagataagt tggataaaac gtatgtcatt cattatacag gtgaatattt gcaagggtca   1380
gatcaggtta attttagaac tgaattatat gggtatccag aacgagcata taaatcttac   1440
tatgtttatg ggggatatcg tttaacttgg gataatggtt tagttttata tagcaataaa   1500
gctgacggca atggtaaaaa tggacaaatt attcaagata tgattttga atataaagaa     1560
gatactgcaa aaggaactat gagcgggcag tacgatgcca agcaaattat tgaaacagaa   1620
gaaaatcaag acaatacacc gcttgacatt gattaccaca cagctataga tggtgagggt   1680
ggttatgttg atgggtatat tgaaacaata gaagaaacgg attcatcagc tattgatatc   1740
gattaccata ctgctgtgga tagtgaagtg ggtcacgttg gaggatacac tgagtcctct   1800
gaggaatcaa atccaattga ctttgaagaa tcgacacatg aaaattcaaa acatcacgct   1860
gatgttgttg aatatgaaga ggatacaaat ccaggtggtg gccaagtaac aactgagtct   1920
aacttagttg aatttgacga agagtctaca aaaggtattg taactggcgc agtgagcgac   1980
catacaacaa ttgaagatac gaaagaatat acgactgaaa gtaatctgat tgaactagta   2040
gatgaactac ctgaagaaca tggtcaagca caaggaccaa tcgaggaaat tactgaaaac   2100
aatcatcata tttctcattc tggtttagga actgaaaatg gtcacggtaa ttatggcgtg   2160
attgaagaaa tcgaagaaaa tagccacgtt gatattaaga gtgaattagg ttacgaaggt   2220
ggccaaaata gcggtaacca gtcattcgag gaagacacag aagaagacaa acctaaatat   2280
gaacaaggtg gcaatatcgt agatatcgat ttcgacagtg tacctcaaat tcatggtcaa   2340
aataaaggtg accagtcatt cgaagaagat acagagaaag acaagcctaa atatgaacat   2400
ggcggtaata tcattgatat cgacttcgac agtgtgccac aaattcatgg attcaataag   2460
cataatgaaa ttattgaaga agatacaaac aaagataaac ctaattatca attcggtgga   2520
cacaatagtg ttgactttga agaagataca cttccaaaag taagcggcca aaatgaaggt   2580
caacaaacga ttgaagaaga tacaacgccg ccaacgccac cgacaccaga gtaccgagt   2640
gagccggaaa caccaatgcc accgacacca gaagtaccga gtgagccgga acaccaacg   2700
ccaccaacac cagaggtacc aagtgagccg gaaacaccaa caccaccgac tccggaagta   2760
ccaagtgagc cggaaacacc aacaccaccg acaccagaag tgccgagtga gccagaaaca   2820
ccaacaccgc caacaccaga ggtaccagct gaacctggta accagtacc acccgcaaaa   2880
gaagaaccta aaagccttc taaccagtg gaacaaggta agtagtaac acctgttatt   2940
gaaatcaatg aaaggttaa agcagtggca ccaactaaaa agcacaatc taagaaatct   3000
gaactacctg aaacaggtgg agaagaatca acaaacaaag gtatgttgtt cggcggatta   3060
ttcagcattc taggtttagc attattacgc agaaataaaa agaataacaa agcataa     3117
```

<210> SEQ ID NO 65
<211> LENGTH: 2634
<212> TYPE: DNA
<213> ORGANISM: Staphylococcus aureus

<400> SEQUENCE: 65

```
ttgaaaaaaa gaattgatta tttgtcgaat aagcagaata agtattcgat tagacgtttt     60
```

```
acagtaggta ccacatcagt aatagtaggg gcaactatac tatttgggat aggcaatcat    120
caagcacaag cttcagaaca atcgaacgat acaacgcaat cttcgaaaaa taatgcaagt    180
gcagattccg aaaaaaacaa tatgatagaa acacctcaat taaatacaac ggctaatgat    240
acatctgata ttagtgcaaa cacaaacagt gcgaatgtag atagcacaac aaaaccaatg    300
tctacacaaa cgagcaatac cactacaaca gagccagctt caacaaatga aacacctcaa    360
ccgacggcaa ttaaaaatca agcaactgct gcaaaaatgc aagatcaaac tgttcctcaa    420
gaagcaaatt ctcaagtaga taataaaaca acgaatgatg ctaatagcat agcaacaaac    480
agtgagctta aaaattctca aacattagat ttaccacaat catcaccaca aacgatttcc    540
aatgcgcaag gaactagtaa accaagtgtt agaacgagag ctgtacgtag tttagctgtt    600
gctgaaccgg tagtaaatgc tgctgatgct aaaggtacaa atgtaaatga taagttacg     660 gcaagtaatt tcaagttaga aaagactaca tttgacccta atcaaagtgg taacacattt    720
atggcggcaa attttacagt gacagataaa gtgaaatcag gggattattt tacagcgaag    780
ttaccagata gtttaactgg taatggagac gtggattatt ctaattcaaa taatacgatg    840
ccaattgcag acattaaaag tacgaatggc gatgttgtag ctaaagcaac atatgatatc    900
ttgactaaga cgtatacatt tgtctttaca gattatgtaa ataataaaga aaatattaac    960
ggacaatttt cattaccttt atttacagac cgagcaaagg cacctaaatc aggaacatat   1020
gatgcgaata ttaatattgc ggatgaaatg tttaataata aaattactta taactatagt   1080
tcgccaattg caggaattga taaaccaaat ggcgcgaaca tttcttctca aattattggt   1140
gtagatacag cttcaggtca aaacacatac aagcaaacag tatttgttaa ccctaagcaa   1200
cgagttttag gtaatacgtg ggtgtatatt aaaggctacc aagataaaat cgaagaaagt   1260
agcggtaaag taagtgctac agatacaaaa ctgagaattt ttgaagtgaa tgatacatct   1320
aaattatcag atagctacta tgcagatcca aatgactcta accttaaaga agtaacagac   1380
caatttaaaa atagaatcta ttatgagcat ccaaatgtag ctagtattaa atttggtgat   1440
attactaaaa catatgtagt attagtagaa gggcattacg acaatacagg taagaactta   1500
aaaactcagg ttattcaaga aaatgttgat cctgtaacaa atagagacta cagtattttc   1560
ggttggaata tgagaatgt tgtacgttat ggtggtggaa gtgctgatgg tgattcagca   1620
gtaaatccga aagacccaac tccagggccg ccggttgacc cagaaccaag tccagaccca   1680
gaaccagaac caacgccaga tccagaacca agtccagacc cagaaccgga accaagccca   1740
gacccggatc cggattcgga ttcagacagt gactcaggct cagacagcga ctcaggttca   1800
gatagcgact cagaatcaga tagcgattcg gattcagaca gtgattcaga ttcagacagc   1860
gactcagaat cagatagcga ttcagaatca gatagcgact cagattcaga tagcgattca   1920
gattcagata gcgattcaga atcagatagc gattcggatt cagacagtga ttcagattca   1980
gacagcgact cagaatcaga tagcgactca gaatcagata gtgagtcaga ttcagacagt   2040
gactcggact cagacagtga ttcagactca gatagcgatt cagactcaga tagcgattca   2100
gactcagaca gcgattcaga ttcagacagc gactcagaat cagacagcga ctcagactca   2160
gatagcgact cagactcaga cagcgactca gattcagata gcgattcaga ctcagacagc   2220
gactcagact cagacagcga ctcagactca gatagcgatt cagactcaga cagcgactca   2280
gattcagata gcgattcgga ctcagacagc gattcagatt cagacagcga ctcagactcg   2340
gatagcgatt cagattcaga cagcgactca gactcggata gcgactcgga ttcagatagt   2400
gactccgatt caagagttac accaccaaat aatgaacaga aagcaccatc aaatcctaaa   2460
```

-continued

| | |
|---|---:|
| ggtgaagtaa accattctaa taaggtatca aaacaacaca aaactgatgc tttaccagaa | 2520 |
| acaggagata agagcgaaaa cacaaatgca actttatttg gtgcaatgat ggcattatta | 2580 |
| ggatcattac tattgtttag aaaacgcaag caagatcata agaaaaagc gtaa | 2634 |

<210> SEQ ID NO 66
<211> LENGTH: 1977
<212> TYPE: DNA
<213> ORGANISM: Staphylococcus aureus

<400> SEQUENCE: 66

| | |
|---|---:|
| atgaaaaagc aaataatttc gctaggcgca ttagcagttg catctagctt atttacatgg | 60 |
| gataacaaag cagatgcgat agtaacaaag gattatagta agaatcaag agtgaatgag | 120 |
| aaaagtaaaa agggagctac tgtttcagat tattactatt ggaaaataat tgatagttta | 180 |
| gaggcacaat ttactggagc aatagactta ttggaagatt ataaatatgg agatcctatc | 240 |
| tataaagaag cgaaagatag attgatgaca agagtattag gagaagacca gtatttatta | 300 |
| aagaaaaaga ttgatgaata tgagctttat aaaaagtggt ataaaagttc aaataagaac | 360 |
| actaatatgc ttactttcca taaatataat ctttacaatt taacaatgaa tgaatataac | 420 |
| gatattttta actctttgaa agatgcagtt tatcaattta ataaagaagt taaagaaata | 480 |
| gagcataaaa atgttgactt gaagcagttt gataaagatg gagaagacaa ggcaactaaa | 540 |
| gaagtttatg accttgtttc tgaaattgat acattagttg taacttatta tgctgataag | 600 |
| gattatgggg agcatgcgaa agagttacga gcaaaactgg acttaatcct tggagataca | 660 |
| gacaatccac ataaaattac aaatgagcgt ataaaaaaag aaatgatcga tgacttaaat | 720 |
| tcaattatag atgatttctt tatggagact aaacaaaata gaccgaattc tataacaaaa | 780 |
| tatgatccaa caaaacacaa ttttaaagag aagagtgaaa ataaacctaa ttttgataaa | 840 |
| ttagttgaag aaacaaaaaa agcagttaaa gaagcagacg aatcttggaa aaataaaact | 900 |
| gtcaaaaaat acgaggaaac tgtaacaaaa tctcctgttg taaagaaga gaagaaagtt | 960 |
| gaagaacctc aattacctaa agttggaaac cagcaagagg ttaaaactac ggctggtaaa | 1020 |
| gctgaagaaa caacacaacc agtggcacag ccattagtaa aaattccaca agaaacaatc | 1080 |
| tatggtgaaa ctgtaaaagg tccagaatat ccaacgatgg aaaataaaac gttacaaggt | 1140 |
| gaaatcgttc aaggtcccga ttttctaaca atggaacaaa acagaccatc tttaagcgat | 1200 |
| aattatactc aaccgacgac accgaaccct attttagaag gtcttgaagg tagctcatct | 1260 |
| aaacttgaaa taaaccaca aggtactgaa tcaacgttga aggtattca aggagaatca | 1320 |
| agtgatattg aagttaaacc tcaagcaact gaaacaacag aagcttctca atatggtccg | 1380 |
| agaccgcaat ttaacaaaac acctaagtat gtgaaatata gagatgctgg tacaggtatc | 1440 |
| cgtgaataca acgatggaac atttggatat gaagcgagac caagattcaa caagccaagt | 1500 |
| gaaacaaatg catacaacgt aacgacaaat caagatggca cagtatcata cggagctcgc | 1560 |
| ccaacacaaa acaagccaag tgaaacaaac gcatataacg taacaacaca tgcaaatggt | 1620 |
| caagtatcat acggtgctcg cccaacacaa aaaagccaa gcaaacaaa tgcatacaac | 1680 |
| gtaacaacac atgcaaatgg tcaagtatca tatggcgctc gcccgacaca aaaaaagcca | 1740 |
| agcaaaacaa atgcatataa cgtaacaaca catgcaaatg gtcaagtatc atacggagct | 1800 |
| cgcccgacat acaagaagcc aagcgaaaca aatgcataca acgtaacaac acatgcaaat | 1860 |
| ggtcaagtat catatggcgc tcgcccgaca caaaaaaagc caagcgaaac aaacgcatat | 1920 |
| aacgtaacaa cacatgcaga tggtactgcg acatatgggc ctagagtaac aaaataa | 1977 |

<210> SEQ ID NO 67
<211> LENGTH: 961
<212> TYPE: PRT
<213> ORGANISM: Staphylococcus aureus

<400> SEQUENCE: 67

Met Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
            20                  25                  30

Lys Glu Ala Ala Ser Glu Gln Asn Asn Thr Thr Val Glu Glu Ser
        35                  40                  45

Gly Ser Ser Ala Thr Glu Ser Lys Ala Ser Glu Thr Gln Thr Thr Thr
    50                  55                  60

Asn Asn Val Asn Thr Ile Asp Glu Thr Gln Ser Tyr Ser Ala Thr Ser
65                  70                  75                  80

Thr Glu Gln Pro Ser Lys Ser Thr Gln Val Thr Thr Glu Glu Ala Pro
                85                  90                  95

Thr Thr Val Gln Ala Pro Lys Val Glu Thr Glu Met Lys Ser Gln Glu
            100                 105                 110

Asp Leu Pro Ser Glu Lys Val Ala Asp Lys Glu Thr Thr Gly Thr Gln
        115                 120                 125

Val Asp Ile Ala Gln Pro Ser Asn Val Ser Glu Ile Lys Pro Arg Met
    130                 135                 140

Lys Arg Ser Ala Asp Val Thr Ala Val Ser Glu Lys Glu Val Ala Glu
145                 150                 155                 160

Glu Ala Lys Ala Thr Gly Thr Asp Val Thr Asn Lys Val Glu Val Thr
                165                 170                 175

Glu Ser Ser Leu Glu Gly His Asn Lys Asp Ser Asn Ile Val Asn Pro
            180                 185                 190

His Asn Ala Gln Arg Val Thr Leu Lys Tyr Lys Trp Lys Phe Gly Glu
        195                 200                 205

Gly Ile Lys Ala Gly Asp Tyr Phe Asp Phe Thr Leu Ser Asp Asn Val
    210                 215                 220

Glu Thr His Gly Ile Ser Thr Leu Arg Lys Val Pro Glu Ile Lys Ser
225                 230                 235                 240

Ser Thr Glu Asp Lys Val Met Ala Asn Gly Gln Val Ile Asn Glu Arg
                245                 250                 255

Thr Ile Arg Tyr Thr Phe Thr Asp Tyr Ile Asn Asn Lys Lys Asp Leu
            260                 265                 270

Thr Ala Glu Leu Asn Leu Asn Leu Phe Ile Asp Pro Thr Thr Val Thr
        275                 280                 285

Lys Gln Gly Ser Gln Lys Val Glu Val Thr Leu Gly Gln Asn Lys Val
    290                 295                 300

Ser Lys Glu Phe Asp Ile Lys Tyr Leu Asp Gly Val Lys Asp Arg Met
305                 310                 315                 320

Gly Val Thr Val Asn Gly Arg Ile Asp Thr Leu Asn Lys Glu Glu Gly
                325                 330                 335

Lys Phe Ser His Phe Ala Tyr Val Lys Pro Asn Asn Gln Ser Leu Thr
            340                 345                 350

Ser Val Thr Val Thr Gly Gln Val Thr Ser Gly Tyr Lys Gln Ser Ala
        355                 360                 365

Asn Asn Pro Thr Val Lys Val Tyr Lys His Ile Gly Ser Asp Glu Leu
    370                 375                 380

-continued

```
Ala Glu Ser Val Tyr Ala Lys Leu Asp Asp Thr Ser Lys Phe Glu Asp
385                 390                 395                 400

Val Thr Glu Lys Val Asn Leu Ser Tyr Thr Ser Asn Gly Gly Tyr Thr
                405                 410                 415

Leu Asn Leu Gly Asp Leu Asp Asn Ser Lys Asp Tyr Val Ile Lys Tyr
            420                 425                 430

Glu Gly Glu Tyr Asp Gln Asn Ala Lys Asp Leu Asn Phe Arg Thr His
        435                 440                 445

Leu Ser Gly Tyr His Lys Tyr Tyr Pro Tyr Tyr Pro Tyr Tyr Pro Tyr
    450                 455                 460

Tyr Pro Val Gln Leu Thr Trp Asn Asn Gly Val Ala Phe Tyr Ser Asn
465                 470                 475                 480

Asn Ala Lys Gly Asp Gly Lys Asp Lys Pro Asn Asp Pro Ile Ile Glu
                485                 490                 495

Lys Ser Glu Pro Ile Asp Leu Asp Ile Lys Ser Glu Pro Pro Val Glu
                500                 505                 510

Lys His Glu Leu Thr Gly Thr Ile Glu Glu Ser Asn Asp Ser Lys Pro
            515                 520                 525

Ile Asp Phe Glu Tyr His Thr Ala Val Glu Gly Ala Glu Gly His Ala
530                 535                 540

Glu Gly Ile Ile Glu Thr Glu Asp Ser Ile His Val Asp Phe Glu
545                 550                 555                 560

Glu Ser Thr His Glu Asn Ser Lys His His Ala Asp Val Val Glu Tyr
                565                 570                 575

Glu Glu Asp Thr Asn Pro Gly Gly Gly Gln Val Thr Thr Glu Ser Asn
            580                 585                 590

Leu Val Glu Phe Asp Glu Glu Ser Thr Lys Gly Ile Val Thr Gly Ala
        595                 600                 605

Val Ser Asp His Thr Thr Val Glu Asp Thr Lys Glu Tyr Thr Thr Glu
    610                 615                 620

Ser Asn Leu Ile Glu Leu Val Asp Glu Leu Pro Glu Glu His Gly Gln
625                 630                 635                 640

Ala Gln Gly Pro Ile Glu Glu Ile Thr Glu Asn Asn His His Ile Ser
                645                 650                 655

His Ser Gly Leu Gly Thr Glu Asn Gly His Gly Asn Tyr Gly Val Ile
                660                 665                 670

Asp Glu Ile Glu Glu Asn Ser His Val Asp Ile Lys Ser Glu Leu Gly
            675                 680                 685

Tyr Glu Gly Gly Gln Asn Ser Gly Asn Gln Ser Phe Glu Glu Asp Thr
        690                 695                 700

Glu Glu Asp Lys Pro Lys Tyr Glu Gln Gly Gly Asn Ile Val Asp Ile
705                 710                 715                 720

Asp Phe Asp Ser Val Pro Gln Ile His Gly Gln Asn Gly Asn Gln
                725                 730                 735

Ser Phe Glu Glu Asp Thr Glu Asp Lys Pro Lys Tyr Glu Gln Gly
            740                 745                 750

Gly Asn Ile Ile Asp Ile Asp Phe Asp Ser Val Pro Gln Ile His Gly
        755                 760                 765

Phe Asn Lys His Asn Glu Ile Ile Glu Glu Asp Thr Asn Lys Asp Lys
770                 775                 780

Pro Asn Tyr Gln Phe Gly Gly His Asn Ser Val Asp Phe Glu Glu Asp
785                 790                 795                 800

Thr Leu Pro Lys Val Ser Gly Gln Asn Glu Gly Gln Gln Thr Ile Glu
                805                 810                 815
```

```
Glu Asp Thr Thr Pro Pro Thr Pro Thr Pro Glu Val Pro Ser Glu
                820                 825                 830

Pro Glu Thr Pro Thr Pro Pro Thr Pro Glu Val Pro Ser Glu Pro Gly
            835                 840                 845

Glu Pro Thr Pro Pro Lys Pro Glu Val Pro Ser Glu Pro Glu Thr Pro
    850                 855                 860

Val Pro Pro Thr Pro Glu Val Pro Ser Glu Pro Gly Lys Pro Val Pro
865                 870                 875                 880

Pro Ala Lys Glu Glu Pro Lys Lys Pro Ser Lys Pro Val Glu Gln Gly
                885                 890                 895

Lys Val Val Thr Pro Val Ile Glu Ile Asn Glu Lys Val Lys Ala Val
                900                 905                 910

Ala Pro Thr Lys Gln Lys Gln Ser Lys Lys Ser Glu Leu Pro Glu Thr
                915                 920                 925

Gly Gly Glu Glu Ser Thr Asn Lys Gly Met Leu Phe Gly Gly Leu Phe
            930                 935                 940

Ser Ile Leu Gly Leu Val Leu Leu Arg Arg Asn Lys Lys Asn Asn Lys
945                 950                 955                 960

Ala

<210> SEQ ID NO 68
<211> LENGTH: 578
<212> TYPE: PRT
<213> ORGANISM: Staphylococcus aureus

<400> SEQUENCE: 68

Met Lys Phe Lys Ser Leu Ile Thr Thr Thr Leu Ala Leu Gly Val Ile
1               5                   10                  15

Ala Ser Thr Gly Ala Asn Phe Asn Thr Asn Glu Ala Ser Ala Ala Ala
                20                  25                  30

Lys Pro Leu Asp Lys Ser Ser Thr Leu His His Gly His Ser Asn
        35                  40                  45

Ile Gln Ile Pro Tyr Thr Ile Thr Val Asn Gly Thr Ser Gln Asn Ile
    50                  55                  60

Leu Ser Ser Leu Thr Phe Asn Lys Asn Gln Asn Ile Ser Tyr Lys Asp
65                  70                  75                  80

Ile Glu Asn Lys Val Lys Ser Val Leu Tyr Phe Asn Arg Gly Ile Ser
                85                  90                  95

Asp Ile Asp Leu Arg Leu Ser Lys Gln Ala Glu Tyr Thr Val His Phe
            100                 105                 110

Lys Asn Gly Thr Lys Arg Val Ile Asp Leu Lys Ser Gly Ile Tyr Thr
        115                 120                 125

Ala Asp Leu Ile Asn Thr Ser Asp Ile Lys Ala Ile Ser Val Asn Val
    130                 135                 140

Asp Thr Lys Lys Gln Pro Lys Asp Lys Ala Lys Ala Asn Val Gln Val
145                 150                 155                 160

Pro Tyr Thr Ile Thr Val Asn Gly Thr Ser Gln Asn Ile Leu Ser Asn
                165                 170                 175

Leu Thr Phe Asn Lys Asn Gln Asn Ile Ser Tyr Lys Asp Leu Glu Gly
            180                 185                 190

Lys Val Lys Ser Val Leu Glu Ser Asn Arg Gly Ile Thr Asp Val Asp
        195                 200                 205

Leu Arg Leu Ser Lys Gln Ala Lys Tyr Thr Val Asn Phe Lys Asn Gly
    210                 215                 220
```

```
Thr Lys Lys Val Ile Asp Leu Lys Ser Gly Ile Tyr Thr Ala Asn Leu
225                 230                 235                 240

Ile Asn Ser Ser Asp Ile Lys Ser Ile Asn Ile Asn Val Asp Thr Lys
            245                 250                 255

Lys His Ile Glu Asn Lys Ala Lys Arg Asn Tyr Gln Val Pro Tyr Ser
        260                 265                 270

Ile Asn Leu Asn Gly Thr Ser Thr Asn Ile Leu Ser Asn Leu Ser Phe
    275                 280                 285

Ser Asn Lys Pro Trp Thr Asn Tyr Lys Asn Leu Thr Ser Gln Ile Lys
290                 295                 300

Ser Val Leu Lys His Asp Arg Gly Ile Ser Glu Gln Asp Leu Lys Tyr
305                 310                 315                 320

Ala Lys Lys Ala Tyr Tyr Thr Val Tyr Phe Lys Asn Gly Gly Lys Arg
                325                 330                 335

Ile Leu Gln Leu Asn Ser Lys Asn Tyr Thr Ala Asn Leu Val His Ala
            340                 345                 350

Lys Asp Val Lys Arg Ile Glu Ile Thr Val Lys Thr Gly Thr Lys Ala
        355                 360                 365

Lys Ala Asp Arg Tyr Val Pro Tyr Thr Ile Ala Val Asn Gly Thr Ser
    370                 375                 380

Thr Pro Ile Leu Ser Lys Leu Lys Ile Ser Asn Lys Gln Leu Ile Ser
385                 390                 395                 400

Tyr Lys Tyr Leu Asn Asp Lys Val Lys Ser Val Leu Lys Ser Glu Arg
                405                 410                 415

Gly Ile Ser Asp Leu Asp Leu Lys Phe Ala Lys Gln Ala Lys Tyr Thr
            420                 425                 430

Val Tyr Phe Lys Asn Gly Lys Lys Gln Val Val Asn Leu Lys Ser Asp
        435                 440                 445

Ile Phe Thr Pro Asn Leu Phe Ser Ala Lys Asp Ile Lys Lys Ile Asp
    450                 455                 460

Ile Asp Val Lys Gln Tyr Thr Lys Ser Lys Lys Ile Asn Lys Ser
465                 470                 475                 480

Asn Asn Val Lys Phe Pro Val Thr Ile Asn Lys Phe Glu Asn Ile Val
                485                 490                 495

Ser Asn Glu Phe Val Phe Tyr Asn Ala Ser Lys Ile Thr Ile Asn Asp
            500                 505                 510

Leu Ser Ile Lys Leu Lys Ser Ala Met Ala Asn Asp Gln Gly Ile Thr
        515                 520                 525

Lys His Asp Ile Gly Leu Ala Glu Arg Ala Val Tyr Lys Val Tyr Phe
    530                 535                 540

Lys Asn Gly Ser Ser Lys Tyr Val Asp Leu Lys Thr Glu Tyr Lys Asp
545                 550                 555                 560

Glu Arg Val Phe Lys Ala Thr Asp Ile Lys Lys Val Asp Ile Glu Leu
                565                 570                 575

Lys Phe

<210> SEQ ID NO 69
<211> LENGTH: 895
<212> TYPE: PRT
<213> ORGANISM: Staphylococcus aureus

<400> SEQUENCE: 69

Met Asn Lys His His Pro Lys Leu Arg Ser Phe Tyr Ser Ile Arg Lys
1               5                   10                  15

Ser Thr Leu Gly Val Ala Ser Val Ile Val Ser Thr Leu Phe Leu Ile
```

-continued

```
                20                  25                  30
Thr Ser Gln His Gln Ala Gln Ala Ala Glu Asn Thr Asn Thr Ser Asp
            35                  40                  45
Lys Ile Ser Glu Asn Gln Asn Asn Ala Thr Thr Thr Gln Pro Pro
50                  55                  60
Lys Asp Thr Asn Gln Thr Gln Pro Ala Thr Gln Pro Ala Asn Thr Ala
65                  70                  75                  80
Lys Asn Tyr Pro Ala Ala Asp Glu Ser Leu Lys Asp Ala Ile Lys Asp
                85                  90                  95
Pro Ala Leu Glu Asn Lys Glu His Asp Ile Gly Pro Arg Glu Gln Val
                100                 105                 110
Asn Phe Gln Leu Leu Asp Lys Asn Asn Glu Thr Gln Tyr Tyr His Phe
            115                 120                 125
Phe Ser Ile Lys Asp Pro Ala Asp Val Tyr Tyr Thr Lys Lys Lys Ala
130                 135                 140
Glu Val Glu Leu Asp Ile Asn Thr Ala Ser Thr Trp Lys Lys Phe Glu
145                 150                 155                 160
Val Tyr Glu Asn Asn Gln Lys Leu Pro Val Arg Leu Val Ser Tyr Ser
                165                 170                 175
Pro Val Pro Glu Asp His Ala Tyr Ile Arg Phe Pro Val Ser Asp Gly
                180                 185                 190
Thr Gln Glu Leu Lys Ile Val Ser Ser Thr Gln Ile Asp Asp Gly Glu
            195                 200                 205
Glu Thr Asn Tyr Asp Tyr Thr Lys Leu Val Phe Ala Lys Pro Ile Tyr
            210                 215                 220
Asn Asp Pro Ser Leu Val Lys Ser Asp Thr Asn Asp Ala Val Val Thr
225                 230                 235                 240
Asn Asp Gln Ser Ser Ser Val Ala Ser Asn Gln Thr Asn Thr Asn Thr
                245                 250                 255
Ser Asn Gln Asn Ile Ser Thr Ile Asn Asn Ala Asn Asn Gln Pro Gln
                260                 265                 270
Ala Thr Thr Asn Met Ser Gln Pro Ala Gln Pro Lys Ser Ser Thr Asn
            275                 280                 285
Ala Asp Gln Ala Ser Ser Gln Pro Ala His Glu Thr Asn Ser Asn Gly
            290                 295                 300
Asn Thr Asn Asp Lys Thr Asn Glu Ser Ser Asn Gln Ser Asp Val Asn
305                 310                 315                 320
Gln Gln Tyr Pro Pro Ala Asp Glu Ser Leu Gln Asp Ala Ile Lys Asn
                325                 330                 335
Pro Ala Ile Ile Asp Lys Glu His Thr Ala Asp Asn Trp Arg Pro Ile
                340                 345                 350
Asp Phe Gln Met Lys Asn Asp Lys Gly Glu Arg Gln Phe Tyr His Tyr
            355                 360                 365
Ala Ser Thr Val Glu Pro Ala Thr Val Ile Phe Thr Lys Thr Gly Pro
            370                 375                 380
Ile Ile Glu Leu Gly Leu Lys Thr Ala Ser Thr Trp Lys Lys Phe Glu
385                 390                 395                 400
Val Tyr Glu Gly Asp Lys Lys Leu Pro Val Glu Leu Val Ser Tyr Asp
                405                 410                 415
Ser Asp Lys Asp Tyr Ala Tyr Ile Arg Phe Pro Val Ser Asn Gly Thr
                420                 425                 430
Arg Glu Val Lys Ile Val Ser Ser Ile Glu Tyr Gly Glu Asn Ile His
            435                 440                 445
```

-continued

Glu Asp Tyr Asp Tyr Thr Leu Met Val Phe Ala Gln Pro Ile Thr Asn
450                     455                     460

Asn Pro Asp Asp Tyr Val Asp Glu Glu Thr Tyr Asn Leu Gln Lys Leu
465                     470                     475                 480

Leu Ala Pro Tyr His Lys Ala Lys Thr Leu Glu Arg Gln Val Tyr Glu
                485                     490                     495

Leu Glu Lys Leu Gln Glu Lys Leu Pro Glu Lys Tyr Lys Ala Glu Tyr
                500                     505                     510

Lys Lys Lys Leu Asp Gln Thr Arg Val Glu Leu Ala Asp Gln Val Lys
                515                     520                     525

Ser Ala Val Thr Glu Phe Glu Asn Val Thr Pro Thr Asn Asp Gln Leu
530                     535                     540

Thr Asp Leu Gln Glu Ala His Phe Val Phe Glu Ser Glu Glu Asn
545                     550                     555                 560

Ser Glu Ser Val Met Asp Gly Phe Val Glu His Pro Phe Tyr Thr Ala
                565                     570                     575

Thr Leu Asn Gly Gln Lys Tyr Val Met Lys Thr Lys Asp Asp Ser
                580                     585                     590

Tyr Trp Lys Asp Leu Ile Val Glu Gly Lys Arg Val Thr Thr Val Ser
                595                     600                     605

Lys Asp Pro Lys Asn Asn Ser Arg Thr Leu Ile Phe Pro Tyr Ile Pro
610                     615                     620

Asp Lys Ala Val Tyr Asn Ala Ile Val Lys Val Val Ala Asn Ile
625                     630                     635                 640

Gly Tyr Glu Gly Gln Tyr His Val Arg Ile Ile Asn Gln Asp Ile Asn
                645                     650                     655

Thr Lys Asp Asp Asp Thr Ser Gln Asn Asn Thr Ser Glu Pro Leu Asn
                660                     665                     670

Val Gln Thr Gly Gln Glu Gly Lys Val Ala Asp Thr Asp Val Ala Glu
                675                     680                     685

Asn Ser Ser Thr Ala Thr Asn Pro Lys Asp Ala Ser Asp Lys Ala Asp
690                     695                     700

Val Ile Glu Pro Glu Ser Asp Val Val Lys Asp Ala Asp Asn Asn Ile
705                     710                     715                 720

Asp Lys Asp Val Gln His Asp Val Asp His Leu Ser Asp Met Ser Asp
                725                     730                     735

Asn Asn His Phe Asp Lys Tyr Asp Leu Lys Glu Met Asp Thr Gln Ile
                740                     745                     750

Ala Lys Asp Thr Asp Arg Asn Val Asp Lys Asp Ala Asp Asn Ser Val
                755                     760                     765

Gly Met Ser Ser Asn Val Asp Thr Asp Lys Asp Ser Asn Lys Asn Lys
                770                     775                     780

Asp Lys Val Ile Gln Leu Asn His Ile Ala Asp Lys Asn Asn His Thr
785                     790                     795                 800

Gly Lys Ala Ala Lys Leu Asp Val Val Lys Gln Asn Tyr Asn Asn Thr
                805                     810                     815

Asp Lys Val Thr Asp Lys Thr Thr Glu His Leu Pro Ser Asp Ile
                820                     825                     830

His Lys Thr Val Asp Lys Thr Val Lys Thr Lys Glu Lys Ala Gly Thr
                835                     840                     845

Pro Ser Lys Glu Asn Lys Leu Ser Gln Ser Lys Met Leu Pro Lys Thr
850                     855                     860

Gly Glu Thr Thr Ser Ser Gln Ser Trp Trp Gly Leu Tyr Ala Leu Leu
865                     870                     875                 880

```
Gly Met Leu Ala Leu Phe Ile Pro Lys Phe Arg Lys Glu Ser Lys
            885                 890                 895

<210> SEQ ID NO 70
<211> LENGTH: 747
<212> TYPE: PRT
<213> ORGANISM: Staphylococcus aureus

<400> SEQUENCE: 70

Met Ala Glu Thr Thr Gln Asp Gln Thr Thr Asn Lys Asn Val Leu Asp
  1               5                  10                  15

Ser Asn Lys Val Lys Ala Thr Thr Glu Gln Ala Lys Ala Glu Val Lys
             20                  25                  30

Asn Pro Thr Gln Asn Ile Ser Gly Thr Gln Val Tyr Gln Asp Pro Ala
         35                  40                  45

Ile Val Gln Pro Lys Thr Ala Asn Asn Lys Thr Gly Asn Ala Gln Val
     50                  55                  60

Ser Gln Lys Val Asp Thr Ala Gln Val Asn Gly Asp Thr Arg Ala Asn
 65                  70                  75                  80

Gln Ser Ala Thr Thr Asn Asn Thr Gln Pro Val Ala Lys Ser Thr Ser
                 85                  90                  95

Thr Thr Ala Pro Lys Thr Asn Thr Asn Val Thr Asn Ala Gly Tyr Ser
            100                 105                 110

Leu Val Asp Asp Glu Asp Asp Asn Ser Glu Asn Gln Ile Asn Pro Glu
        115                 120                 125

Leu Ile Lys Ser Ala Ala Lys Pro Ala Ala Leu Glu Thr Gln Tyr Lys
    130                 135                 140

Thr Ala Pro Lys Ala Ala Thr Thr Ser Ala Pro Lys Ala Lys Thr
145                 150                 155                 160

Glu Ala Thr Pro Lys Val Thr Thr Phe Ser Ala Ser Ala Gln Pro Arg
                165                 170                 175

Ser Val Ala Ala Thr Pro Lys Thr Ser Leu Pro Lys Tyr Lys Pro Gln
            180                 185                 190

Val Asn Ser Ser Ile Asn Asp Tyr Ile Cys Lys Asn Asn Leu Lys Ala
        195                 200                 205

Pro Lys Ile Glu Glu Asp Tyr Thr Ser Tyr Phe Pro Lys Tyr Ala Tyr
    210                 215                 220

Arg Asn Gly Val Gly Arg Pro Glu Gly Ile Val Val His Asp Thr Ala
225                 230                 235                 240

Asn Asp Arg Ser Thr Ile Asn Gly Glu Ile Ser Tyr Met Lys Asn Asn
                245                 250                 255

Tyr Gln Asn Ala Phe Val His Ala Phe Val Asp Gly Asp Arg Ile Ile
            260                 265                 270

Glu Thr Ala Pro Thr Asp Tyr Leu Ser Trp Gly Val Gly Ala Val Gly
        275                 280                 285

Asn Pro Arg Phe Ile Asn Val Glu Ile Val His Thr His Asp Tyr Ala
    290                 295                 300

Ser Phe Ala Arg Ser Met Asn Asn Tyr Ala Asp Tyr Ala Ala Thr Gln
305                 310                 315                 320

Leu Gln Tyr Tyr Gly Leu Lys Pro Asp Ser Ala Glu Tyr Asp Gly Asn
                325                 330                 335

Gly Thr Val Trp Thr His Tyr Ala Val Ser Lys Tyr Leu Gly Gly Thr
            340                 345                 350

Asp His Ala Asp Pro His Gly Tyr Leu Arg Ser His Asn Tyr Ser Tyr
        355                 360                 365
```

Asp Gln Leu Tyr Asp Leu Ile Asn Glu Lys Tyr Leu Ile Lys Met Gly
        370                 375                 380

Lys Val Ala Pro Trp Gly Thr Gln Ser Thr Thr Pro Thr Thr Pro
385                 390                 395                 400

Ser Lys Pro Thr Thr Pro Ser Lys Pro Ser Thr Gly Lys Leu Thr Val
                405                 410                 415

Ala Ala Asn Asn Gly Val Ala Gln Ile Lys Pro Thr Asn Ser Gly Leu
            420                 425                 430

Tyr Thr Thr Val Tyr Asp Lys Thr Gly Lys Ala Thr Asn Glu Val Gln
            435                 440                 445

Lys Thr Phe Ala Val Ser Lys Thr Ala Thr Leu Gly Asn Gln Lys Phe
450                 455                 460

Tyr Leu Val Gln Asp Tyr Asn Ser Gly Asn Lys Phe Gly Trp Val Lys
465                 470                 475                 480

Glu Gly Asp Val Val Tyr Asn Thr Ala Lys Ser Pro Val Asn Val Asn
                485                 490                 495

Gln Ser Tyr Ser Ile Lys Pro Gly Thr Lys Leu Tyr Thr Val Pro Trp
            500                 505                 510

Gly Thr Ser Lys Gln Val Ala Gly Ser Val Ser Gly Ser Gly Asn Gln
            515                 520                 525

Thr Phe Lys Ala Ser Lys Gln Gln Gln Ile Asp Lys Ser Ile Tyr Leu
            530                 535                 540

Tyr Gly Ser Val Asn Gly Lys Ser Gly Trp Val Ser Lys Ala Tyr Leu
545                 550                 555                 560

Val Asp Thr Ala Lys Pro Thr Pro Thr Pro Thr Pro Lys Pro Ser Thr
                565                 570                 575

Pro Thr Thr Asn Asn Lys Leu Thr Val Ser Ser Leu Asn Gly Val Ala
            580                 585                 590

Gln Ile Asn Ala Lys Asn Asn Gly Leu Phe Thr Thr Val Tyr Asp Lys
            595                 600                 605

Thr Gly Lys Pro Thr Lys Glu Val Gln Lys Thr Phe Ala Val Thr Lys
            610                 615                 620

Glu Ala Ser Leu Gly Gly Asn Lys Phe Tyr Leu Val Lys Asp Tyr Asn
625                 630                 635                 640

Ser Pro Thr Leu Ile Gly Trp Val Lys Gln Gly Asp Val Ile Tyr Asn
                645                 650                 655

Asn Ala Lys Ser Pro Val Asn Val Met Gln Thr Tyr Thr Val Lys Pro
            660                 665                 670

Gly Thr Lys Leu Tyr Ser Val Pro Trp Gly Thr Tyr Lys Gln Glu Ala
            675                 680                 685

Gly Ala Val Ser Gly Thr Gly Asn Gln Thr Phe Lys Ala Thr Lys Gln
            690                 695                 700

Gln Gln Ile Asp Lys Ser Ile Tyr Leu Phe Gly Thr Val Asn Gly Lys
705                 710                 715                 720

Ser Gly Trp Val Ser Lys Ala Tyr Leu Ala Val Pro Ala Ala Pro Lys
                725                 730                 735

Lys Ala Val Ala Gln Pro Lys Thr Ala Val Lys
            740                 745

<210> SEQ ID NO 71
<211> LENGTH: 482
<212> TYPE: PRT
<213> ORGANISM: Staphylococcus aureus

<400> SEQUENCE: 71

```
Met Ala Tyr Thr Val Thr Lys Pro Gln Thr Thr Gln Thr Val Ser Lys
 1               5                  10                  15

Ile Ala Gln Val Lys Pro Asn Asn Thr Gly Ile Arg Ala Ser Val Tyr
             20                  25                  30

Glu Lys Thr Ala Lys Asn Gly Ala Lys Tyr Ala Asp Arg Thr Phe Tyr
         35                  40                  45

Val Thr Lys Glu Arg Ala His Gly Asn Glu Thr Tyr Val Leu Leu Asn
     50                  55                  60

Asn Thr Ser His Asn Ile Pro Leu Gly Trp Phe Asn Val Lys Asp Leu
65                   70                  75                  80

Asn Val Gln Asn Leu Gly Lys Glu Val Lys Thr Thr Gln Lys Tyr Thr
                 85                  90                  95

Val Asn Lys Ser Asn Asn Gly Leu Ser Met Val Pro Trp Gly Thr Lys
             100                 105                 110

Asn Gln Val Ile Leu Thr Gly Asn Asn Ile Ala Gln Gly Thr Phe Asn
         115                 120                 125

Ala Thr Lys Gln Val Ser Val Gly Lys Asp Val Tyr Leu Tyr Gly Thr
     130                 135                 140

Ile Asn Asn Arg Thr Gly Trp Val Asn Ala Lys Asp Leu Thr Ala Pro
145                 150                 155                 160

Thr Ala Val Lys Pro Thr Thr Ser Ala Ala Lys Asp Tyr Asn Tyr Thr
                 165                 170                 175

Tyr Val Ile Lys Asn Gly Asn Gly Tyr Tyr Tyr Val Thr Pro Asn Ser
             180                 185                 190

Asp Thr Ala Lys Tyr Ser Leu Lys Ala Phe Asn Glu Gln Pro Phe Ala
     195                 200                 205

Val Val Lys Glu Gln Val Ile Asn Gly Gln Thr Trp Tyr Tyr Gly Lys
         210                 215                 220

Leu Ser Asn Gly Lys Leu Ala Trp Ile Lys Ser Thr Asp Leu Ala Lys
225                 230                 235                 240

Glu Leu Ile Lys Tyr Asn Gln Thr Gly Met Thr Leu Asn Gln Val Ala
                 245                 250                 255

Gln Ile Gln Ala Gly Leu Gln Tyr Lys Pro Gln Val Gln Arg Val Pro
             260                 265                 270

Gly Lys Trp Thr Asp Ala Lys Phe Asn Asp Val Lys His Ala Met Asp
     275                 280                 285

Thr Lys Arg Leu Ala Gln Asp Pro Ala Leu Lys Tyr Gln Phe Leu Arg
     290                 295                 300

Leu Asp Gln Pro Gln Asn Ile Ser Ile Asp Lys Ile Asn Gln Phe Leu
305                 310                 315                 320

Lys Gly Lys Gly Val Leu Glu Asn Gln Gly Ala Ala Phe Asn Lys Ala
                 325                 330                 335

Ala Gln Met Tyr Gly Ile Asn Glu Val Tyr Leu Ile Ser His Ala Leu
             340                 345                 350

Leu Glu Thr Gly Asn Gly Thr Ser Gln Leu Ala Lys Gly Ala Asp Val
         355                 360                 365

Val Asn Asn Lys Val Val Thr Asn Ser Asn Thr Lys Tyr His Asn Val
     370                 375                 380

Phe Gly Ile Ala Ala Tyr Asp Asn Asp Pro Leu Arg Glu Gly Ile Lys
385                 390                 395                 400

Tyr Ala Lys Gln Ala Gly Trp Asp Thr Val Ser Lys Ala Ile Val Gly
                 405                 410                 415

Gly Ala Lys Phe Ile Gly Asn Ser Tyr Val Lys Ala Gly Gln Asn Thr
```

-continued

```
                    420                 425                 430
Leu Tyr Lys Met Arg Trp Asn Pro Ala His Pro Gly Thr His Gln Tyr
        435                 440                 445

Ala Thr Asp Val Asp Trp Ala Asn Ile Asn Ala Lys Ile Ile Lys Gly
450                 455                 460

Tyr Tyr Asp Lys Ile Gly Glu Val Gly Lys Tyr Phe Asp Ile Pro Gln
465                 470                 475                 480

Tyr Lys

<210> SEQ ID NO 72
<211> LENGTH: 706
<212> TYPE: PRT
<213> ORGANISM: Staphylococcus aureus

<400> SEQUENCE: 72

Asp Arg Val Leu Ala Ser His Pro Asp Val Ala Thr Ile Arg Gln Asn
  1               5                  10                  15

Val Thr Ala Ala Asn Ala Ala Lys Ser Ala Leu Asp Gln Ala Arg Asn
                 20                  25                  30

Gly Leu Thr Val Asp Lys Ala Pro Leu Glu Asn Ala Lys Asn Gln Leu
             35                  40                  45

Gln His Ser Ile Asp Thr Gln Thr Ser Thr Gly Met Thr Gln Asp
         50                  55                  60

Ser Ile Asn Ala Tyr Asn Ala Lys Leu Thr Ala Ala Arg Asn Lys Ile
 65                  70                  75                  80

Gln Gln Ile Asn Gln Val Leu Ala Gly Ser Pro Thr Val Glu Gln Ile
                 85                  90                  95

Asn Thr Asn Thr Ser Thr Ala Asn Gln Ala Lys Ser Asp Leu Asp His
                100                 105                 110

Ala Arg Gln Ala Leu Thr Pro Asp Lys Ala Pro Leu Gln Thr Ala Lys
            115                 120                 125

Thr Gln Leu Glu Gln Ser Ile Asn Gln Pro Thr Asp Thr Thr Gly Met
        130                 135                 140

Thr Thr Ala Ser Leu Asn Ala Tyr Asn Gln Lys Leu Gln Ala Ala Arg
145                 150                 155                 160

Gln Lys Leu Thr Glu Ile Asn Gln Val Leu Asn Gly Asn Pro Thr Val
                165                 170                 175

Gln Asn Ile Asn Asp Lys Val Thr Glu Ala Asn Gln Ala Lys Asp Gln
            180                 185                 190

Leu Asn Thr Ala Arg Gln Gly Leu Thr Leu Asp Arg Gln Pro Ala Leu
        195                 200                 205

Thr Thr Leu His Gly Ala Ser Asn Leu Asn Gln Ala Gln Gln Asn Asn
    210                 215                 220

Phe Thr Gln Gln Ile Asn Ala Ala Gln Asn His Ala Ala Leu Glu Thr
225                 230                 235                 240

Ile Lys Ser Asn Ile Thr Ala Leu Asn Thr Ala Met Thr Lys Leu Lys
                245                 250                 255

Asp Ser Val Ala Asp Asn Asn Thr Ile Lys Ser Asp Gln Asn Tyr Thr
            260                 265                 270

Asp Ala Thr Pro Ala Asn Lys Gln Ala Tyr Asp Asn Ala Val Asn Ala
        275                 280                 285

Ala Lys Gly Val Ile Gly Glu Thr Thr Asn Pro Thr Met Asp Val Asn
    290                 295                 300

Thr Val Asn Gln Lys Ala Ala Ser Val Lys Ser Thr Lys Asp Ala Leu
305                 310                 315                 320
```

```
Asp Gly Gln Gln Asn Leu Gln Arg Ala Lys Thr Glu Ala Thr Asn Ala
            325                 330                 335

Ile Thr His Ala Ser Asp Leu Asn Gln Ala Gln Lys Asn Ala Leu Thr
            340                 345                 350

Gln Gln Val Asn Ser Ala Gln Asn Val Gln Ala Val Asn Asp Ile Lys
            355                 360                 365

Gln Thr Thr Gln Ser Leu Asn Thr Ala Met Thr Gly Leu Lys Arg Gly
            370                 375                 380

Val Ala Asn His Asn Gln Val Val Gln Ser Asp Asn Tyr Val Asn Ala
385                 390                 395                 400

Asp Thr Asn Lys Lys Asn Asp Tyr Asn Asn Ala Tyr Asn His Ala Asn
            405                 410                 415

Asp Ile Ile Asn Gly Asn Ala Gln His Pro Val Ile Thr Pro Ser Asp
            420                 425                 430

Val Asn Asn Ala Leu Ser Asn Val Thr Ser Lys Glu His Ala Leu Asn
            435                 440                 445

Gly Glu Ala Lys Leu Asn Ala Ala Lys Gln Glu Ala Asn Thr Ala Leu
450                 455                 460

Gly His Leu Asn Asn Leu Asn Asn Ala Gln Arg Gln Asn Leu Gln Ser
465                 470                 475                 480

Gln Ile Asn Gly Ala His Gln Ile Asp Ala Val Asn Thr Ile Lys Gln
            485                 490                 495

Asn Ala Thr Asn Leu Asn Ser Ala Met Gly Asn Leu Arg Gln Ala Val
            500                 505                 510

Ala Asp Lys Asp Gln Val Lys Arg Thr Glu Asp Tyr Ala Asp Ala Asp
            515                 520                 525

Thr Ala Lys Gln Asn Ala Tyr Asn Ser Ala Val Ser Ser Ala Glu Thr
            530                 535                 540

Ile Ile Asn Gln Thr Thr Asn Pro Thr Met Ser Val Asp Val Asn
545                 550                 555                 560

Arg Ala Thr Ser Ala Val Thr Ser Asn Lys Asn Ala Leu Asn Gly Tyr
            565                 570                 575

Glu Lys Leu Ala Gln Ser Lys Thr Asp Ala Ala Arg Ala Ile Asp Ala
            580                 585                 590

Leu Pro His Leu Asn Asn Ala Gln Lys Ala Asp Val Lys Ser Lys Ile
            595                 600                 605

Asn Ala Ala Ser Asn Ile Ala Gly Val Asn Thr Val Lys Gln Gln Gly
            610                 615                 620

Thr Asp Leu Asn Thr Ala Met Gly Asn Leu Gln Gly Ala Ile Asn Asp
625                 630                 635                 640

Glu Gln Thr Thr Leu Asn Ser Gln Asn Tyr Gln Asp Ala Thr Pro Ser
            645                 650                 655

Lys Lys Thr Ala Tyr Thr Asn Ala Val Gln Ala Ala Lys Asp Ile Leu
            660                 665                 670

Asn Lys Ser Asn Gly Gln Asn Lys Thr Lys Asp Gln Val Thr Glu Ala
            675                 680                 685

Met Asn Gln Val Asn Ser Ala Lys Asn Asn Leu Asp Gly Thr Arg Leu
            690                 695                 700

Leu Asp
705

<210> SEQ ID NO 73
<211> LENGTH: 241
<212> TYPE: PRT
```

<213> ORGANISM: Staphylococcus aureus

<400> SEQUENCE: 73

```
Ala Ser Thr Gln His Thr Val Gln Ser Gly Glu Ser Leu Trp Ser Ile
1               5                   10                  15
Ala Gln Lys Tyr Asn Thr Ser Val Glu Ser Ile Lys Gln Asn Asn Gln
            20                  25                  30
Leu Asp Asn Asn Leu Val Phe Pro Gly Gln Val Ile Ser Val Gly Gly
        35                  40                  45
Ser Asp Ala Gln Asn Thr Ser Asn Thr Ser Pro Gln Ala Gly Ser Ala
50                  55                  60
Ser Ser His Thr Val Gln Ala Gly Glu Ser Leu Asn Ile Ile Ala Ser
65                  70                  75                  80
Arg Tyr Gly Val Ser Val Asp Gln Leu Met Ala Ala Asn Asn Leu Arg
                85                  90                  95
Gly Tyr Leu Ile Met Pro Asn Gln Thr Leu Gln Ile Pro Asn Gly Gly
            100                 105                 110
Ser Gly Gly Thr Thr Pro Thr Ala Thr Thr Gly Ser Asn Gly Asn Ala
        115                 120                 125
Ser Ser Phe Asn His Gln Asn Leu Tyr Thr Ala Gly Gln Cys Thr Trp
130                 135                 140
Tyr Val Phe Asp Arg Arg Ala Gln Ala Gly Ser Pro Ile Ser Thr Tyr
145                 150                 155                 160
Trp Ser Asp Ala Lys Tyr Trp Ala Gly Asn Ala Ala Asn Asp Gly Tyr
                165                 170                 175
Gln Val Asn Asn Thr Pro Ser Val Gly Ser Ile Met Gln Ser Thr Pro
            180                 185                 190
Gly Pro Tyr Gly His Val Ala Tyr Val Glu Arg Val Asn Gly Asp Gly
        195                 200                 205
Ser Ile Leu Ile Ser Glu Met Asn Tyr Thr Tyr Gly Pro Tyr Asn Met
210                 215                 220
Asn Tyr Arg Thr Ile Pro Ala Ser Glu Val Ser Ser Tyr Ala Phe Ile
225                 230                 235                 240
His
```

<210> SEQ ID NO 74
<211> LENGTH: 995
<212> TYPE: PRT
<213> ORGANISM: Staphylococcus aureus

<400> SEQUENCE: 74

```
Met Asn Asn Lys Lys Thr Ala Thr Asn Arg Lys Gly Met Ile Pro Asn
1               5                   10                  15
Arg Leu Asn Lys Phe Ser Ile Arg Lys Tyr Ser Val Gly Thr Ala Ser
            20                  25                  30
Ile Leu Val Gly Thr Thr Leu Ile Phe Gly Leu Ser Gly His Glu Ala
        35                  40                  45
Lys Ala Ala Glu His Thr Asn Gly Glu Leu Asn Gln Ser Lys Asn Glu
50                  55                  60
Thr Thr Ala Pro Ser Glu Asn Lys Thr Thr Lys Val Asp Ser Arg
65                  70                  75                  80
Gln Leu Lys Asp Asn Thr Gln Thr Ala Thr Ala Asp Gln Pro Lys Val
                85                  90                  95
Thr Met Ser Asp Ser Ala Thr Val Lys Glu Thr Ser Ser Asn Met Gln
            100                 105                 110
```

```
Ser Pro Gln Asn Ala Thr Ala Asn Gln Ser Thr Thr Lys Thr Ser Asn
        115                 120                 125

Val Thr Thr Asn Asp Lys Ser Thr Thr Tyr Ser Asn Glu Thr Asp
    130                 135                 140

Lys Ser Asn Leu Thr Gln Ala Lys Asp Val Ser Thr Thr Pro Lys Thr
145                 150                 155                 160

Thr Thr Ile Lys Pro Arg Thr Leu Asn Arg Met Ala Val Asn Thr Val
            165                 170                 175

Ala Ala Pro Gln Gln Gly Thr Asn Val Asn Asp Lys Val His Phe Ser
            180                 185                 190

Asn Ile Asp Ile Ala Ile Asp Lys Gly His Val Asn Gln Thr Thr Gly
            195                 200                 205

Lys Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Thr Thr Asn Thr Thr Tyr Thr Phe Thr Asn Tyr Val
    275                 280                 285

Asp Gln Tyr Thr Asn Val Arg Gly Ser Phe Glu Gln Val Ala Phe Ala
    290                 295                 300

Lys Arg Lys Asn Ala Thr Thr Asp Lys Thr Ala Tyr Lys Met Glu Val
305                 310                 315                 320

Thr Leu Gly Asn Asp Thr Tyr Ser Glu Glu Ile Ile Val Asp Tyr Gly
                325                 330                 335

Asn Lys Lys Ala Gln Pro Leu Ile Ser Ser Thr Asn Tyr Ile Asn Asn
            340                 345                 350

Glu Asp Leu Ser Arg Asn Met Thr Ala Tyr Val Asn Gln Pro Lys Asn
            355                 360                 365

Thr Tyr Thr Lys Gln Thr Phe Val Thr Asn Leu Thr Gly Tyr Lys Phe
    370                 375                 380

Asn Pro Asn Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Asp Gln Phe Asp Val Ile Tyr Ser Asn Asp Asn Lys Thr Ala Thr
            420                 425                 430

Val Asp Leu Met Lys Gly Gln Thr Ser Ser Asn Lys Gln Tyr Ile Ile
            435                 440                 445

Gln Gln Val Ala Tyr Pro Asp Asn Ser Ser Thr Asp Asn Gly Lys Ile
    450                 455                 460

Asp Tyr Thr Leu Asp Thr Asp Lys Thr Lys Tyr Ser Trp Ser Asn Ser
465                 470                 475                 480

Tyr Ser Asn Val Asn Gly Ser Ser Thr Ala Asn Gly Asp Gln Lys Lys
                485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
            515                 520                 525

Asp Ser Asn Gly Lys Glu Leu Asp Arg Thr Thr Thr Asp Glu Asn Gly
530                 535                 540
```

-continued

```
Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Thr Ala Asn Val Gly Thr Asp
                565                 570                 575

Asp Ala Val Asp Ser Asp Gly Leu Thr Thr Gly Val Ile Lys Asp
                580                 585                 590

Ala Asp Asn Met Thr Leu Asp Ser Gly Phe Tyr Lys Thr Pro Lys Tyr
                595                 600                 605

Ser Leu Gly Asp Tyr Val Trp Tyr Asp Ser Asn Lys Asp Gly Lys Gln
                610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
                660                 665                 670

Lys Pro Ala Gly Leu Thr Gln Thr Gly Thr Asn Thr Thr Glu Asp Asp
                675                 680                 685

Lys Asp Ala Asp Gly Gly Glu Val Asp Val Thr Ile Thr Asp His Asp
                690                 695                 700

Asp Phe Thr Leu Asp Asn Gly Tyr Tyr Glu Glu Thr Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
                740                 745                 750

Asp Ser Asp Ser Asp Ser Asp Ser Asp Ser Asp Ser Asp Ser Asp Ser
                755                 760                 765

Asp Ser Asp Ser Asp Ser Asp Ser Asp Ser Asp Ser Asp Ser Asp Ser
                770                 775                 780

Asp Ser Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser Asp Ser
                805                 810                 815

Asp Ser Asp Ser Asp Ser Asp Ser Asp Ser Asp Ser Asp Ser Asp Ser
                820                 825                 830

Asp Ser Asp Ser Asp Ser Asp Ser Asp Ser Asp Ser Asp Ser Asp Ser
                835                 840                 845

Asp Ser Asp Ser Asp Ser Asp Ser Asn Asp Ser Asp Ser Asp Ser
850                 855                 860

Asp Ser Asp Ser Asp Ser Asp Ser Asp Ser Asp Ser Asp Ser Asp Ser
865                 870                 875                 880

Asp Ser Asp Ser Asp Ser Asp Ser Asp Ser Asp Ser Asp Ser Asp Ser
                885                 890                 895

Asp Ser Asp Ser Asp Ser Asp Ser Asp Ser Asp Ser Asp Ser Asp Ser
                900                 905                 910

Asp Ser Asp Ser Asp Ser Asp Ser Asp Ser Asp Asn Asp Ser Asp Ser
                915                 920                 925

Asp Ser Asp Ser Asp Ser Asp Ala Gly Lys His Thr Pro Ala Lys Pro
                930                 935                 940

Met Ser Thr Val Lys Asp Gln His Lys Thr Ala Lys Ala Leu Pro Glu
945                 950                 955                 960

Thr Gly Ser Glu Asn Asn Asn Ser Asn Asn Gly Thr Leu Phe Gly Gly
```

-continued

```
                                 965                 970                 975
Leu Phe Ala Ala Leu Gly Ser Leu Leu Leu Phe Gly Arg Arg Lys Lys
                980                 985                 990

Gln Asn Lys
        995

<210> SEQ ID NO 75
<211> LENGTH: 2186
<212> TYPE: PRT
<213> ORGANISM: Staphylococcus aureus

<400> SEQUENCE: 75

Met Asn Leu Leu Lys Lys Asn Lys Tyr Ser Ile Arg Lys Tyr Lys Val
1               5                   10                  15

Gly Ile Phe Ser Thr Leu Ile Gly Thr Val Leu Leu Leu Ser Asn Pro
            20                  25                  30

Asn Gly Ala Gln Ala Leu Thr Thr Asp Asn Asn Val Gln Ser Asp Thr
        35                  40                  45

Asn Gln Ala Thr Pro Val Asn Ser Gln Asp Lys Asp Val Ala Asn Asn
    50                  55                  60

Arg Gly Leu Ala Asn Ser Ala Gln Asn Thr Pro Asn Gln Ser Ala Thr
65                  70                  75                  80

Thr Asn Gln Ala Thr Asn Gln Ala Leu Val Asn His Asn Asn Gly Ser
                85                  90                  95

Ile Val Asn Gln Ala Thr Pro Thr Ser Val Gln Ser Ser Thr Pro Ser
            100                 105                 110

Ala Gln Asn Asn Asn His Thr Asp Gly Asn Thr Thr Ala Thr Glu Thr
        115                 120                 125

Val Ser Asn Ala Asn Asn Asp Val Val Ser Asn Thr Ala Leu
    130                 135                 140

Asn Val Pro Thr Lys Thr Asn Glu Asn Gly Ser Gly His Leu Thr
145                 150                 155                 160

Leu Lys Glu Ile Gln Glu Asp Val Arg His Ser Ser Asn Lys Pro Glu
                165                 170                 175

Leu Val Ala Ile Ala Glu Pro Ala Ser Asn Arg Pro Lys Lys Arg Ser
            180                 185                 190

Arg Arg Ala Ala Pro Ala Asp Pro Asn Ala Thr Pro Ala Asp Pro Ala
        195                 200                 205

Ala Ala Val Gly Asn Gly Gly Ala Pro Val Ala Ile Thr Ala Pro
    210                 215                 220

Tyr Thr Pro Thr Thr Asp Pro Asn Ala Asn Asn Ala Gly Gln Asn Ala
225                 230                 235                 240

Pro Asn Glu Val Leu Ser Phe Asp Asp Asn Gly Ile Arg Pro Ser Thr
                245                 250                 255

Asn Arg Ser Val Pro Thr Val Asn Val Val Asn Asn Leu Pro Gly Phe
            260                 265                 270

Thr Leu Ile Asn Gly Gly Lys Val Gly Val Phe Ser His Ala Met Val
        275                 280                 285

Arg Thr Ser Met Phe Asp Ser Gly Asp Asn Lys Asn Tyr Gln Ala Gln
    290                 295                 300

Gly Asn Val Ile Ala Leu Gly Arg Ile His Gly Thr Asp Thr Asn Asp
305                 310                 315                 320

His Gly Asp Phe Asn Gly Ile Glu Lys Ala Leu Thr Val Asn Pro Asn
                325                 330                 335

Ser Glu Leu Ile Phe Glu Phe Asn Thr Met Thr Thr Lys Asn Gly Gln
```

```
                340             345                 350
Gly Ala Thr Asn Val Ile Ile Lys Asn Ala Asp Thr Asn Asp Thr Ile
            355                 360             365

Ala Glu Lys Thr Val Glu Gly Pro Thr Leu Arg Leu Phe Lys Val
370                 375                 380

Pro Asp Asn Val Arg Asn Leu Lys Ile Gln Phe Val Pro Lys Asn Asp
385                 390                 395                 400

Ala Ile Thr Asp Ala Arg Gly Ile Tyr Gln Leu Lys Asp Gly Tyr Lys
            405                 410                 415

Tyr Tyr Ser Phe Val Asp Ser Ile Gly Leu His Ser Gly Ser His Val
            420                 425                 430

Phe Val Glu Arg Arg Thr Met Asp Pro Thr Ala Thr Asn Asn Lys Glu
            435                 440                 445

Phe Thr Val Thr Thr Ser Leu Lys Asn Asn Gly Asn Ser Gly Ala Ser
            450                 455                 460

Leu Asp Thr Asn Asp Phe Val Tyr Gln Val Gln Leu Pro Glu Gly Val
465                 470                 475                 480

Glu Tyr Val Asn Asn Ser Leu Thr Lys Asp Phe Pro Ser Asn Asn Ser
            485                 490                 495

Gly Val Asp Val Asn Asp Met Asn Val Thr Tyr Asp Ala Ala Asn Arg
            500                 505                 510

Val Ile Thr Ile Lys Ser Thr Gly Gly Thr Ala Asn Ser Pro Ala
            515                 520                 525

Arg Leu Met Pro Asp Lys Ile Leu Asp Leu Arg Tyr Lys Leu Arg Val
            530                 535                 540

Asn Asn Val Pro Thr Pro Arg Thr Val Thr Phe Asn Glu Thr Leu Thr
545                 550                 555                 560

Tyr Lys Thr Tyr Thr Gln Asp Phe Ile Asn Ser Ala Ala Glu Ser His
                565                 570                 575

Thr Val Ser Thr Asn Pro Tyr Thr Ile Asp Ile Met Asn Lys Asp
                580                 585                 590

Ala Leu Gln Ala Glu Val Asp Arg Arg Ile Gln Gln Ala Asp Tyr Thr
            595                 600                 605

Phe Ala Ser Leu Asp Ile Phe Asn Gly Leu Lys Arg Arg Ala Gln Thr
            610                 615                 620

Ile Leu Asp Glu Asn Arg Asn Asn Val Pro Leu Asn Lys Arg Val Ser
625                 630                 635                 640

Gln Ala Tyr Ile Asp Ser Leu Thr Asn Gln Met Gln His Thr Leu Ile
                645                 650                 655

Arg Ser Val Asp Ala Glu Asn Ala Val Asn Lys Lys Val Asp Gln Met
                660                 665                 670

Glu Asp Leu Val Asn Gln Asn Asp Glu Leu Thr Asp Glu Lys Gln
            675                 680                 685

Ala Ala Ile Gln Val Ile Glu Glu His Lys Asn Glu Ile Ile Gly Asn
            690                 695                 700

Ile Gly Asp Gln Thr Thr Asp Asp Gly Val Thr Arg Ile Lys Asp Gln
705                 710                 715                 720

Gly Ile Gln Thr Leu Ser Gly Asp Thr Ala Thr Pro Val Val Lys Pro
                725                 730                 735

Asn Ala Lys Lys Ala Ile Arg Asp Lys Ala Thr Lys Gln Arg Glu Ile
                740                 745                 750

Ile Asn Ala Thr Pro Asp Ala Thr Glu Asp Glu Ile Gln Asp Ala Leu
                755                 760                 765
```

-continued

```
Asn Gln Leu Ala Thr Asp Glu Thr Asp Ala Ile Asp Asn Val Thr Asn
            770                 775                 780

Ala Thr Thr Asn Ala Asp Val Glu Thr Ala Lys Asn Asn Gly Ile Asn
785                 790                 795                 800

Thr Ile Gly Ala Val Val Pro Gln Val Thr His Lys Lys Ala Ala Arg
                805                 810                 815

Asp Ala Ile Asn Gln Ala Thr Ala Thr Lys Arg Gln Gln Ile Asn Ser
            820                 825                 830

Asn Arg Glu Ala Thr Gln Glu Glu Lys Asn Ala Ala Leu Asn Glu Leu
        835                 840                 845

Thr Gln Ala Thr Asn His Ala Leu Glu Gln Ile Asn Gln Ala Thr Thr
    850                 855                 860

Asn Ala Asn Val Asp Asn Ala Lys Gly Asp Gly Leu Asn Ala Ile Asn
865                 870                 875                 880

Pro Ile Ala Pro Val Thr Val Lys Gln Ala Ala Arg Asp Ala Val
                885                 890                 895

Ser His Asp Ala Gln Gln His Ile Ala Glu Ile Asn Ala Asn Pro Asp
            900                 905                 910

Ala Thr Gln Glu Glu Arg Gln Ala Ala Ile Asp Lys Val Asn Ala Ala
        915                 920                 925

Val Thr Ala Ala Asn Thr Asn Ile Leu Asn Ala Asn Thr Asn Ala Asp
    930                 935                 940

Val Glu Gln Val Lys Thr Asn Ala Ile Gln Gly Ile Gln Ala Ile Thr
945                 950                 955                 960

Pro Ala Thr Lys Val Lys Thr Asp Ala Lys Asn Ala Ile Asp Lys Ser
                965                 970                 975

Ala Glu Thr Gln His Asn Thr Ile Phe Asn Asn Asp Ala Thr Leu
            980                 985                 990

Glu Glu Gln Gln Ala Ala Gln Gln Leu Leu Asp Gln Ala Val Ala Thr
        995                 1000                1005

Ala Lys Gln Asn Ile Asn Ala Ala Asp Thr Asn Gln Glu Val Ala Gln
    1010                1015                1020

Ala Lys Asp Gln Gly Thr Gln Asn Ile Val Val Ile Gln Pro Ala Thr
1025                1030                1035                1040

Gln Val Lys Thr Asp Thr Arg Asn Val Val Asn Asp Lys Ala Arg Glu
                1045                1050                1055

Ala Ile Thr Asn Ile Asn Ala Thr Thr Gly Ala Thr Arg Glu Glu Lys
            1060                1065                1070

Gln Glu Ala Ile Asn Arg Val Asn Thr Leu Lys Asn Arg Ala Leu Thr
        1075                1080                1085

Asp Ile Gly Val Thr Ser Thr Thr Ala Met Val Asn Ser Ile Arg Asp
    1090                1095                1100

Asp Ala Val Asn Gln Ile Gly Ala Val Gln Pro His Val Thr Lys Lys
1105                1110                1115                1120

Gln Thr Ala Thr Gly Val Leu Asn Asp Leu Ala Thr Ala Lys Lys Gln
                1125                1130                1135

Glu Ile Asn Gln Asn Thr Asn Ala Thr Thr Glu Glu Lys Gln Val Ala
            1140                1145                1150

Leu Asn Gln Val Asp Gln Glu Leu Ala Thr Ala Ile Asn Asn Ile Asn
        1155                1160                1165

Gln Ala Asp Thr Asn Ala Glu Val Asp Gln Ala Gln Gln Leu Gly Thr
    1170                1175                1180

Lys Ala Ile Asn Ala Ile Gln Pro Asn Ile Val Lys Lys Pro Ala Ala
1185                1190                1195                1200
```

Leu Ala Gln Ile Asn Gln His Tyr Asn Ala Lys Leu Ala Glu Ile Asn
                1205                1210                1215

Ala Thr Pro Asp Ala Thr Asn Asp Glu Lys Asn Ala Ala Ile Asn Thr
            1220                1225                1230

Leu Asn Gln Asp Arg Gln Gln Ala Ile Glu Ser Ile Lys Gln Ala Asn
                1235                1240                1245

Thr Asn Ala Glu Val Asp Gln Ala Ala Thr Val Ala Glu Asn Asn Ile
        1250                1255                1260

Asp Ala Val Gln Val Asp Val Val Lys Lys Gln Ala Ala Arg Asp Lys
1265                1270                1275                1280

Ile Thr Ala Glu Val Ala Lys Arg Ile Glu Ala Val Lys Gln Thr Pro
                1285                1290                1295

Asn Ala Thr Asp Glu Glu Lys Gln Ala Ala Val Asn Gln Ile Asn Gln
            1300                1305                1310

Leu Lys Asp Gln Ala Ile Asn Gln Ile Asn Gln Asn Gln Thr Asn Asp
                1315                1320                1325

Gln Val Asp Thr Thr Thr Asn Gln Ala Val Asn Ala Ile Asp Asn Val
        1330                1335                1340

Glu Ala Glu Val Val Ile Lys Thr Lys Ala Ile Ala Asp Ile Glu Lys
1345                1350                1355                1360

Ala Val Lys Glu Lys Gln Gln Gln Ile Asp Asn Ser Leu Asp Ser Thr
            1365                1370                1375

Asp Asn Glu Lys Glu Val Ala Ser Gln Ala Leu Ala Lys Glu Lys Glu
            1380                1385                1390

Lys Ala Leu Ala Ala Ile Asp Gln Ala Gln Thr Asn Ser Gln Val Asn
                1395                1400                1405

Gln Ala Ala Thr Asn Gly Val Ser Ala Ile Lys Ile Ile Gln Pro Glu
        1410                1415                1420

Thr Lys Val Lys Pro Ala Ala Arg Glu Lys Ile Asn Gln Lys Ala Asn
1425                1430                1435                1440

Glu Leu Arg Ala Lys Ile Asn Gln Asp Lys Glu Ala Thr Ala Glu Glu
            1445                1450                1455

Arg Gln Val Ala Leu Asp Lys Ile Asn Glu Phe Val Asn Gln Ala Met
                1460                1465                1470

Thr Asp Ile Thr Asn Asn Arg Thr Asn Gln Gln Val Asp Asp Thr Thr
        1475                1480                1485

Ser Gln Ala Leu Asp Ser Ile Ala Leu Val Thr Pro Asp His Ile Val
        1490                1495                1500

Arg Ala Ala Ala Arg Asp Ala Val Lys Gln Gln Tyr Glu Ala Lys Lys
1505                1510                1515                1520

Arg Glu Ile Glu Gln Ala Glu His Ala Thr Asp Glu Glu Lys Gln Val
                1525                1530                1535

Ala Leu Asn Gln Leu Ala Asn Asn Glu Lys Arg Ala Leu Gln Asn Ile
            1540                1545                1550

Asp Gln Ala Ile Ala Asn Asn Asp Val Lys Arg Val Glu Thr Asn Gly
                1555                1560                1565

Ile Ala Thr Leu Lys Gly Val Gln Pro His Ile Val Ile Lys Pro Glu
        1570                1575                1580

Ala Gln Gln Ala Ile Lys Ala Ser Ala Glu Asn Gln Val Glu Ser Ile
1585                1590                1595                1600

Lys Asp Thr Pro His Ala Thr Val Asp Glu Leu Asp Glu Ala Asn Gln
            1605                1610                1615

Leu Ile Ser Asp Thr Leu Lys Gln Ala Gln Gln Glu Ile Glu Asn Thr

-continued

```
                1620            1625            1630

Asn Gln Asp Ala Ala Val Thr Asp Val Arg Asn Gln Thr Ile Lys Ala
        1635            1640            1645

Ile Glu Gln Ile Lys Pro Lys Val Arg Arg Lys Arg Ala Ala Leu Asp
        1650            1655            1660

Ser Ile Glu Glu Asn Asn Lys Asn Gln Leu Asp Ala Ile Arg Asn Thr
1665            1670            1675            1680

Leu Asp Thr Thr Gln Asp Glu Arg Asp Val Ala Ile Asp Thr Leu Asn
            1685            1690            1695

Lys Ile Val Asn Thr Ile Lys Asn Asp Ile Ala Gln Asn Lys Thr Asn
            1700            1705            1710

Ala Glu Val Asp Arg Thr Glu Thr Asp Gly Asn Asp Asn Ile Lys Val
            1715            1720            1725

Ile Leu Pro Lys Val Gln Val Lys Pro Ala Ala Arg Gln Ser Val Gly
            1730            1735            1740

Val Lys Ala Glu Ala Gln Asn Ala Leu Ile Asp Gln Ser Asp Leu Ser
1745            1750            1755            1760

Thr Glu Glu Glu Arg Leu Ala Ala Lys His Leu Val Glu Gln Ala Leu
            1765            1770            1775

Asn Gln Ala Ile Asp Gln Ile Asn His Ala Asp Lys Thr Ala Gln Val
            1780            1785            1790

Asn Gln Asp Ser Ile Asn Ala Gln Asn Ile Ile Ser Lys Ile Lys Pro
            1795            1800            1805

Ala Thr Thr Val Lys Ala Thr Ala Leu Gln Gln Ile Gln Asn Ile Ala
            1810            1815            1820

Thr Asn Lys Ile Asn Leu Ile Lys Ala Asn Asn Glu Ala Thr Asp Glu
1825            1830            1835            1840

Glu Gln Asn Ile Ala Ile Ala Gln Val Glu Lys Leu Ile Lys Ala
            1845            1850            1855

Lys Gln Gln Ile Ala Ser Ala Val Thr Asn Ala Asp Val Ala Tyr Leu
            1860            1865            1870

Leu His Asp Glu Lys Asn Glu Ile Arg Glu Ile Glu Pro Val Ile Asn
            1875            1880            1885

Arg Lys Ala Ser Ala Arg Glu Gln Leu Thr Thr Leu Phe Asn Asp Lys
            1890            1895            1900

Lys Gln Ala Ile Glu Ala Asn Ile Gln Ala Thr Val Glu Glu Arg Asn
1905            1910            1915            1920

Ser Ile Leu Ala Gln Leu Gln Asn Ile Tyr Asp Thr Ala Ile Gly Gln
            1925            1930            1935

Ile Asp Gln Asp Arg Ser Asn Ala Gln Val Asp Lys Thr Ala Ser Leu
            1940            1945            1950

Asn Leu Gln Thr Ile His Asp Leu Asp Val His Pro Ile Lys Lys Pro
            1955            1960            1965

Asp Ala Glu Lys Thr Ile Asn Asp Asp Leu Ala Arg Val Thr Ala Leu
            1970            1975            1980

Val Gln Asn Tyr Arg Lys Val Ser Asn Arg Asn Lys Ala Asp Ala Leu
1985            1990            1995            2000

Lys Ala Ile Thr Ala Leu Lys Leu Gln Met Asp Glu Glu Leu Lys Thr
            2005            2010            2015

Ala Arg Thr Asn Ala Asp Val Asp Ala Val Leu Lys Arg Phe Asn Val
            2020            2025            2030

Ala Leu Ser Asp Ile Glu Ala Val Ile Thr Glu Lys Glu Asn Ser Leu
            2035            2040            2045
```

```
Leu Arg Ile Asp Asn Ile Ala Gln Gln Thr Tyr Ala Lys Phe Lys Ala
        2050                2055                2060

Ile Ala Thr Pro Glu Gln Leu Ala Lys Val Lys Val Leu Ile Asp Gln
2065                2070                2075                2080

Tyr Val Ala Asp Gly Asn Arg Met Ile Asp Glu Asp Ala Thr Leu Asn
                2085                2090                2095

Asp Ile Lys Gln His Thr Gln Phe Ile Val Asp Glu Ile Leu Ala Ile
            2100                2105                2110

Lys Leu Pro Ala Glu Ala Thr Lys Val Ser Pro Lys Glu Ile Gln Pro
        2115                2120                2125

Ala Pro Lys Val Cys Thr Pro Ile Lys Lys Glu Thr His Glu Ser
        2130                2135                2140

Arg Lys Val Glu Lys Glu Leu Pro Asn Thr Gly Ser Glu Gly Met Asp
2145                2150                2155                2160

Leu Pro Leu Lys Glu Phe Ala Leu Ile Thr Gly Ala Ala Leu Leu Ala
                2165                2170                2175

Arg Arg Arg Thr Lys Asn Glu Lys Glu Ser
            2180                2185

<210> SEQ ID NO 76
<211> LENGTH: 773
<212> TYPE: PRT
<213> ORGANISM: Staphylococcus aureus

<400> SEQUENCE: 76

Glu Glu Asn Ser Val Gln Asp Val Lys Asp Ser Asn Thr Asp Asp Glu
 1               5                  10                  15

Leu Ser Asp Ser Asn Asp Gln Ser Ser Asp Glu Glu Lys Asn Asp Val
            20                  25                  30

Ile Asn Asn Asn Gln Ser Ile Asn Thr Asp Asp Asn Gln Ile Ile
        35                  40                  45

Lys Lys Glu Glu Thr Asn Asn Tyr Asp Gly Ile Glu Lys Arg Ser Glu
50                  55                  60

Asp Arg Thr Glu Ser Thr Thr Asn Val Asp Glu Asn Glu Ala Thr Phe
65                  70                  75                  80

Leu Gln Lys Thr Pro Gln Asp Asn Thr His Leu Thr Glu Glu Val
                85                  90                  95

Lys Glu Ser Ser Ser Val Glu Ser Ser Asn Ser Ser Ile Asp Thr Ala
            100                 105                 110

Gln Gln Pro Ser His Thr Thr Ile Asn Arg Glu Glu Ser Val Gln Thr
        115                 120                 125

Ser Asp Asn Val Glu Asp Ser His Val Ser Asp Phe Ala Asn Ser Lys
130                 135                 140

Ile Lys Glu Ser Asn Thr Glu Ser Gly Lys Glu Glu Asn Thr Ile Glu
145                 150                 155                 160

Gln Pro Asn Lys Val Lys Glu Asp Ser Thr Thr Ser Gln Pro Ser Gly
                165                 170                 175

Tyr Thr Asn Ile Asp Glu Lys Ile Ser Asn Gln Asp Glu Leu Leu Asn
            180                 185                 190

Leu Pro Ile Asn Glu Tyr Glu Asn Lys Ala Arg Pro Leu Ser Thr Thr
        195                 200                 205

Ser Ala Gln Pro Ser Ile Lys Arg Val Thr Val Asn Gln Leu Ala Ala
210                 215                 220

Glu Gln Gly Ser Asn Val Asn His Leu Ile Lys Val Thr Asp Gln Ser
225                 230                 235                 240
```

```
Ile Thr Glu Gly Tyr Asp Asp Ser Glu Gly Val Ile Lys Ala His Asp
            245                 250                 255

Ala Glu Asn Leu Ile Tyr Asp Val Thr Phe Glu Val Asp Asp Lys Val
            260                 265                 270

Lys Ser Gly Asp Thr Met Thr Val Asp Ile Asp Lys Asn Thr Val Pro
        275                 280                 285

Ser Asp Leu Thr Asp Ser Phe Thr Ile Pro Lys Ile Lys Asp Asn Ser
        290                 295                 300

Gly Glu Ile Ile Ala Thr Gly Thr Tyr Asp Asn Lys Asn Lys Gln Ile
305                 310                 315                 320

Thr Tyr Thr Phe Thr Asp Tyr Val Asp Lys Tyr Glu Asn Ile Lys Ala
            325                 330                 335

His Leu Lys Leu Thr Ser Tyr Ile Asp Lys Ser Lys Val Pro Asn Asn
            340                 345                 350

Asn Thr Lys Leu Asp Val Glu Tyr Lys Thr Ala Leu Ser Ser Val Asn
        355                 360                 365

Lys Thr Ile Thr Val Glu Tyr Gln Arg Pro Asn Glu Asn Arg Thr Ala
        370                 375                 380

Asn Leu Gln Ser Met Phe Thr Asn Ile Asp Thr Lys Asn His Thr Val
385                 390                 395                 400

Glu Gln Thr Ile Tyr Ile Asn Pro Leu Arg Tyr Ser Ala Lys Glu Thr
            405                 410                 415

Asn Val Asn Ile Ser Gly Asn Gly Asp Glu Gly Ser Thr Ile Ile Asp
            420                 425                 430

Asp Ser Thr Ile Ile Lys Val Tyr Lys Val Gly Asp Asn Gln Asn Leu
        435                 440                 445

Pro Asp Ser Asn Arg Ile Tyr Asp Tyr Ser Glu Tyr Glu Asp Val Thr
        450                 455                 460

Asn Asp Asp Tyr Ala Gln Leu Gly Asn Asn Asn Asp Val Asn Ile Asn
465                 470                 475                 480

Phe Gly Asn Ile Asp Ser Pro Tyr Ile Ile Lys Val Ile Ser Lys Tyr
            485                 490                 495

Asp Pro Asn Lys Asp Asp Tyr Thr Thr Ile Gln Gln Thr Val Thr Met
        500                 505                 510

Gln Thr Thr Ile Asn Glu Tyr Thr Gly Glu Phe Arg Thr Ala Ser Tyr
        515                 520                 525

Asp Asn Thr Ile Ala Phe Ser Thr Ser Ser Gly Gln Gly Gln Gly Asp
        530                 535                 540

Leu Pro Pro Glu Lys Thr Tyr Lys Ile Gly Asp Tyr Val Trp Glu Asp
545                 550                 555                 560

Val Asp Lys Asp Gly Ile Gln Asn Thr Asn Asp Asn Glu Lys Pro Leu
            565                 570                 575

Ser Asn Val Leu Val Thr Leu Thr Tyr Pro Asp Gly Thr Ser Lys Ser
            580                 585                 590

Val Arg Thr Asp Glu Asp Gly Lys Tyr Gln Phe Asp Gly Leu Lys Asn
        595                 600                 605

Gly Leu Thr Tyr Lys Ile Thr Phe Glu Thr Pro Glu Gly Tyr Thr Pro
        610                 615                 620

Thr Leu Lys His Ser Gly Thr Asn Pro Ala Leu Asp Ser Glu Gly Asn
625                 630                 635                 640

Ser Val Trp Val Thr Ile Asn Gly Gln Asp Asp Met Thr Ile Asp Ser
            645                 650                 655

Gly Phe Tyr Gln Thr Pro Lys Tyr Ser Leu Gly Asn Tyr Val Trp Tyr
            660                 665                 670
```

```
Asp Thr Asn Lys Asp Gly Ile Gln Gly Asp Asp Glu Lys Gly Ile Ser
            675                 680                 685
Gly Val Lys Val Thr Leu Lys Asp Glu Asn Gly Asn Ile Ile Ser Thr
        690                 695                 700
Thr Thr Thr Asp Glu Asn Gly Lys Tyr Gln Phe Asp Asn Leu Asn Ser
705                 710                 715                 720
Gly Asn Tyr Ile Val His Phe Asp Lys Pro Ser Gly Met Thr Gln Thr
                725                 730                 735
Thr Thr Asp Ser Gly Asp Asp Glu Gln Asp Ala Asp Gly Glu Glu
            740                 745                 750
Val His Val Thr Ile Thr Asp His Asp Asp Phe Ser Ile Asp Asn Gly
            755                 760                 765
Tyr Tyr Asp Asp Glu
    770

<210> SEQ ID NO 77
<211> LENGTH: 2886
<212> TYPE: DNA
<213> ORGANISM: Staphylococcus aureus

<400> SEQUENCE: 77
gtgaaaagca atcttagata cggcataaga aaacacaaat tgggagcggc ctcagtattc    60
ttaggaacaa tgatcgttgt tggaatggga caagaaaaag aagctgcagc atcggaacaa   120
aacaatacta cagtagagga aagtgggagt tcagctactg aaagtaaagc aagcgaaaca   180
caaacaacta caaataacgt taatacaata gatgaaacac aatcatacag cgcgacatca   240
actgagcaac catcaaaatc aactcaagta acaacagaag aagcaccaac aactgtgcaa   300
gcaccaaaag tagaaaccga atgaaatca caagaagatt taccatcaga aaaagttgct   360
gataaggaaa ctacaggaac tcaagttgac atagctcaac caagtaacgt ctcagaaatt   420
aaaccaagaa tgaaagatc agctgacgtt acagcagttt cagagaaaga agtagcggaa   480
gaagctaaag cgacaggtac agatgtaaca aataaagtgg aagttactga aagctcttta   540
gaaggacata ataaagattc gaatattgtt aatccgcata tgctcaaag agtaacttta   600 aaatacaaat ggaaatttgg agaaggaatt aaggcaggag attattttga tttcacatta   660
agtgataatg ttgaaacaca tggtatatca acactgcgta aagttccgga gataaaaagt   720
tcaacagaag ataagttat ggcaaatggt caagttataa atgaacgtac aattcgctat   780
acatttactg attatataaa taacaaaaaa gatttaactg ctgaattaaa cttaaaccta   840
ttcattgacc caacaacagt gacaaagcaa gggagtcaaa agttgaagt aacactaggt   900 caaaataaag tctcaaaaga atttgatatc aaatatttag acggcgttaa agatagaatg   960
ggtgttactg ttaatggtcg tattgatact ttgaataaag aagagggtaa atttagccat  1020
tttgcatatg tgaagcctaa caaccagtcg ttaacttctg tcacagtaac tggtcaagta  1080
acatctggat ataaacaaag tgctaataat ccaacagtca agtatataa acacattggt  1140 tcagatgaat tagctgaaag tgtttatgca aagcttgatg ataccagtaa atttgaagat  1200
gtgactgaaa aagtaaatct atcttacaca agtaatggtg ggtacacatt gaaccttggc  1260
gatttagata ttcgaaaga ctatgtaatt aaatatgaag gtgaatatga tcaaaatgct  1320
aaggatctaa atttccgaac acatctttca ggatatcata atactacccc atactatcct  1380
tattacccgt attatccagt tcaattaact tggaacaacg tgttgcatt ttactctaat  1440 aatgctaaag gcgatggtaa agataaacca atgatcctat cattgagaa gagtgaacca  1500
```

```
attgatttag acattaaatc agagccacca gtggagaagc atgaattgac tggtacaatc      1560
gaagaaagta acgattctaa gccaattgat tttgaatatc atacagctgt tgaaggtgca      1620
gaaggtcatg cagaaggtat tattgaaact gaagaagatt ctattcatgt ggattttgaa      1680
gaatctacac atgaaaattc aaaacatcac gctgatgttg ttgaatatga agaggataca      1740
aacccaggtg gtggccaagt aacaactgag tctaacttag ttgaatttga cgaagagtct      1800
acaaaaggta ttgtaactgg cgcagtgagc gaccatacaa cagttgaaga tacgaaagaa      1860
tatacaactg aaagtaatct gattgaatta gtggatgaat tacctgaaga catggtcaa       1920 gcacaagggc caatcgagga aattactgaa acaatcatc atatttctca ttctggttta       1980
ggaactgaaa atggtcacgg taattatggc gtgattgatg aaatcgaaga aaatagccac      2040
gttgatatta agagtgaatt aggttatgaa ggtggccaaa atagcggtaa tcagtcattc      2100
gaggaagaca cagaagaaga taaacctaaa tatgaacaag gtggtaatat cgtagatatc      2160
gatttcgaca gtgtacctca aattcatggt caaaataatg gtaaccagtc attcgaggaa      2220
gacacagaag aagacaagcc taagtatgaa caaggtggta acatcattga tatcgacttc      2280
gacagtgtgc cacaaattca tggattcaat aagcataatg aaattattga agaagataca      2340
aacaaagata aacctaatta tcaatttggt ggacacaaca gtgttgattt tgaagaagat      2400
acacttccaa aagtaagtgg tcaaaatgaa ggtcaacaaa cgattgaaga agatacaacg      2460
ccgccaacac cgccaacacc agaggtacca agtgagccgg aaacaccaac accaccaaca      2520
ccagaagtac cgagtgagcc aggcgaacca acgccaccaa accggaagt accaagtgag       2580 ccggaaacac cagtaccacc aacaccagag gtaccatctg aacctggtaa accagtacca      2640
cctgctaaag aagaacctaa aaaaccttct aaaccagtgg aacaaggtaa ggtagtaaca      2700
cctgttattg aaatcaatga aaaggttaaa gcagtggcac caactaaaca aaaacaatct      2760
aagaaatctg aactacctga aacaggtgga gaagaatcaa caaacaaagg tatgttgttc      2820
ggcggattat tcagcattct aggtttagta ttattacgca gaaataaaaa gaataacaaa      2880
gcataa                                                                2886
```

<210> SEQ ID NO 78
<211> LENGTH: 1737
<212> TYPE: DNA
<213> ORGANISM: Staphylococcus aureus

<400> SEQUENCE: 78

```
atgaaattta gtcattgat tacaacaaca ttagcattag gcgttatagc atcaacagga       60
gcaaacttta atactaacga agcatctgcc gcagctaagc cattagataa atcatcaagt      120
acattacacc atggacattc taacatccag attccatata caattactgt gaacggtaca      180
agccaaaaca ttttatcaag cttaacattt aataagaatc aaaatattag ttataaagat      240
atagagaata aagttaaatc agttttatac tttaatagag gtattagtga tatcgattta      300
agactttcaa agcaagcgga atatacggtt catttttaaaa atggaacaaa aagagttatc      360
gatttgaaat caggtatcta cacagctgac ttaatcaata caagtgacat taaagctatc      420
agtgttaacg tagatactaa aaaagcaacct aaagataaag ctaaagcaaa tgttcaagtg      480
ccatatacaa tcacagtgaa cggcacaagc caaaacattt tatcaaacct aacatttaat      540
aaaaatcaaa atattagtta caagatttta gagggtaaag ttaaatcagt tttagaatca      600
aatagaggta ttactgatgt tgatttaaga cttttcgaagc aagcgaaata tacagttaat      660
tttaaaaatg gaacgaagaa agttatcgat ttgaaatcag gtatttacac agcgaattta      720
```

```
atcaattcaa gtgatattaa aagtatcaat attaacgtag atacaaaaaa acatatcgaa      780
aataaagcta aaagaaacta tcaagttcca tattcaatta atctaaatgg tacatctaca      840
aacattttat cgaatctttc attttcaaat aaaccttgga caaattacaa aaatttaact      900
agtcaaataa aatcagtact gaagcatgat agaggtatta gtgaacaaga tttaaaatat      960
gctaagaaag cttattatac tgtttatttt aaaaatggtg taaaagaat cttacagtta     1020 aattcaaaaa attacacagc aaacttagtt catgcgaaag atgttaagag aattgaaatt     1080
actgttaaaa caggaactaa agcgaaagca gacagatatg taccatacac aattgcagta     1140
aatggcacat caacaccaat tttatcaaaa ctaaaaattt cgaataaaca attaattagt     1200
tacaaatatt taaacgacaa agtgaaatct gtattaaaaa gtgaaagagg tatcagtgat     1260
cttgacttaa aatttgcgaa acaagcaaaa tatacagtat atttcaaaaa tggaaagaaa     1320
caagtagtga atttaaaatc agacatcttt acacctaatt tatttagtgc caaagatatt     1380
aaaaagattg atattgatgt aaaacaatac actaaatcaa aaaaaaaat aaataaatct     1440 aataatgtga aattcccagt aacaataaat aaatttgaaa acatagtttc aaatgaattt     1500
gtgttctata atgcaagcaa aattacaatt aatgatttaa gtataaaact taaatcagca     1560
atggcaaatg atcaagggat aactaaacat gacataggac ttgctgaacg cgcagtgtat     1620
aaagtgtatt ttaaaaatgg ttcgtcaaaa tatgtagact taaaaactga gtataaagat     1680
gaaagagtat ttaaagcaac tgacattaaa aaggtagata ttgaacttaa attctaa       1737

<210> SEQ ID NO 79
<211> LENGTH: 2688
<212> TYPE: DNA
<213> ORGANISM: Staphylococcus aureus

<400> SEQUENCE: 79
atgaacaaac atcacccaaa attaaggtct ttctattcta ttagaaaatc aactctaggc       60
gttgcatcgg tcattgtcag tacactattt ttaattactt ctcaacatca agcacaagca      120
gcagaaaata caaatacttc agataaaatc tcggaaaatc aaaataataa tgcaactaca      180
actcagccac ctaaggatac aaatcaaaca caacctgcta cgcaaccagc aaacactgcg      240
aaaaactatc ctgcagcgga tgaatcactt aaagatgcaa ttaaagatcc tgcattagaa      300 aataagaac atgatatagg tccaagagaa caagtcaatt tccagttatt agataaaaac      360
aatgaaacgc agtactatca ctttttcagc atcaaagatc cagcagatgt gtattacact      420
aaaaagaaag cagaagttga attagacatc aatactgctt caacatggaa gaagtttgaa      480
gtctatgaaa acaatcaaaa attgccagtg agacttgtat catatagtcc tgtaccagaa      540
gaccatgcct atattcgatt cccagtttca gatggcacac aagaattgaa attgtttct      600 tcgactcaaa ttgatgatgg agaagaaaca aattatgatt atactaaatt agtatttgct      660
aaacctattt ataacgatcc ttcacttgta aaatcagata caaatgatgc agtagtaacg      720
aatgatcaat caagttcagt cgcaagtaat caaacaaaca cgaatacatc taatcaaaat      780
atatcaacga tcaacaatgc taataatcaa ccgcaggcaa cgaccaatat gagtcaacct      840
gcacaaccaa aatcgtcaac gaatgcagat caagcgtcaa gccaaccagc tcatgaaaca      900
aattctaatg gtaatactaa cgataaaacg aatgagtcaa gtaatcagtc ggatgttaat      960
caacagtatc caccagcaga tgaatcacta caagatgcaa ttaaaacccc ggctatcatc     1020
gataaagaac atacagctga taattggcga ccaattgatt ttcaaatgaa aaatgataaa     1080
ggtgaaagac agttctatca ttatgctagt actgttgaac cagcaactgt cattttttaca     1140
```

```
aaaacaggac caataattga attaggttta agacagctt caacatggaa gaaatttgaa    1200
gtttatgaag gtgacaaaaa gttaccagtc gaattagtat catatgattc tgataaagat    1260
tatgcctata ttcgtttccc agtatctaat ggtacgagag aagttaaaat tgtgtcatct    1320
attgaatatg tgagaacat  ccatgaagac tatgattata cgctaatggt ctttgcacag    1380
cctattacta ataacccaga cgactatgtg gatgaagaaa catacaattt acaaaaatta    1440
ttagctccgt atcacaaagc taaaacgtta gaaagacaag tttatgaatt agaaaaatta    1500
caagagaaat tgccagaaaa atataaggcg aatataaaa  agaaattaga tcaaactaga    1560
gtagagttag ctgatcaagt taaatcagca gtgacggaat ttgaaaatgt tacacctaca    1620
aatgatcaat taacagattt acaagaagcg cattttgttg tttttgaaag tgaagaaaat    1680
agtgagtcag ttatggacgg ctttgttgaa catccattct atacagcaac tttaaatggt    1740
caaaaatatg tagtgatgaa acaaaggat  gacagttact ggaaagattt aattgtagaa    1800
ggtaaacgtg tcactactgt ttctaaagat cctaaaaata attctagaac gctgattttc    1860
ccatatatac ctgacaaagc agtttacaat gcgattgtta agtcgttgt  ggcaaacatt    1920 ggttatgaag gtcaatatca tgtcagaatt ataaatcagg atatcaatac aaaagatgat    1980
gatacatcac aaaataacac gagtgaaccg ctaaatgtac aaacaggaca agaaggtaag    2040
gttgctgata cagatgtagc tgaaaatagc agcactgcaa caaatcctaa agatgcgtct    2100
gataaagcag atgtgataga accagagtct gacgtggtta agatgctga  taataatatt    2160 gataaagatg tgcaacatga tgttgatcat ttatccgata tgtcggataa taatcacttc    2220
gataaatatg atttaaaaga aatggatact caaattgcca agatactga  tagaaatgtg    2280 gataaagatg ccgataatag cgttggtatg tcatctaatg tcgatactga taaagactct    2340
aataaaaata aagacaaagt catacagctg aatcatattg ccgataaaaa taatcatact    2400
ggaaaagcag caaagcttga cgtagtgaaa caaaattata ataatacaga caaagttact    2460
gacaaaaaaa caactgaaca tctgccgagt gatattcata aaactgtaga taaaacagtg    2520
aaaacaaaag aaaaagccgg cacaccatcg aaagaaaaca aacttagtca atctaaaatg    2580
ctaccaaaaa ctggagaaac aacttcaagc caatcatggt ggggcttata tgcgttatta    2640
ggtatgttag ctttattcat tcctaaattc agaaaagaat ctaaataa                 2688
```

<210> SEQ ID NO 80
<211> LENGTH: 2238
<212> TYPE: DNA
<213> ORGANISM: Staphylococcus aureus

<400> SEQUENCE: 80

```
gctgagacga cacaagatca aactactaat aaaaacgttt tagatagtaa taaagttaaa     60
gcaactactg aacaagcaaa agctgaggta aaaaatccaa cgcaaaacat ttctggcact    120
caagtatatc aagaccctgc tattgtccaa ccaaaaacag caataacaa  acaggcaat     180 gctcaagtaa gtcaaaagt  tgatactgca caagtaaatg gtgacactcg tgctaatcaa    240
tcagcgacta caaataatac gcagcctgtt gcaaagtcaa caagcactac agcacctaaa    300
actaacacta atgttacaaa tgctggttat agtttagttg atgatgaaga tgataattca    360
gaaaatcaaa ttaatccaga attaattaaa tcagctgcta aacctgcagc tcttgaaacg    420
caatataaaa ccgcagcacc taaagctgca actacatcag cacctaaagc taaaactgaa    480
gcgacaccta agtaactac ttttagcgct tcagcacaac caagatcagt tgctgcaaca    540
ccaaaaacga gtttgccaaa atataaacca caagtaaact cttcaattaa cgattacatt    600
```

-continued

```
tgtaaaaata acttaaaagc acctaaaatt gaagaagatt atacatctta cttccctaaa      660
tacgcatacc gtaacggcgt aggtcgtcct gaaggtatcg tagttcatga tacagctaat      720
gatcgttcga cgataaatgg tgaaattagt tatatgaaaa ataactatca aaacgcattc      780
gtacatgcat tgttgatgg ggatcgtata atcgaaacag caccaacgga ttacttatct       840
tggggtgtcg gtgcagtcgg taaccctaga ttcatcaatg ttgaaatcgt acacacacac      900
gactatgctt catttgcacg ttcaatgaat aactatgctg actatgcagc tacacaatta      960
caatattatg gtttaaaacc agacagtgct gagtatgatg aaatggtac agtatggact      1020 cactacgctg taagtaaata tttaggtggt actgaccatg ccgatccaca tggatattta     1080
agaagtcata attatagtta tgatcaatta tatgacttaa ttaatgaaaa atatttaata     1140
aaaatgggta aagtggcgcc atggggtacg caatctacaa ctaccccta tacaccatca      1200 aaaccaacaa caccgtcgaa accatcaact ggtaaattaa cagttgctgc aaacaatggt     1260
gtcgcacaaa tcaaaccaac aaatagtggt ttatatacta ctgtatacga caaaactggt     1320
aaagcaacta atgaagttca aaaaacattt gctgtatcta aaacagctac attaggtaat     1380
caaaaattct atcttgttca agattacaat tctggtaata aatttggttg ggttaaagaa     1440
ggcgatgtgg tttacaacac agctaaatca cctgtaaatg taaatcaatc atattcaatc     1500
aaacctggta cgaaacttta tacagtacct tggggtacat ctaaacaagt tgctggtagt     1560
gtgtctggct ctggaaacca acatttaag gcttcaaagc aacaacaaat tgataaatca      1620
atttatttat atggctctgt gaatggtaaa tctggttggg taagtaaagc atatttagtt     1680
gatactgcta aacctacgcc tacaccaaca cctaagccat caacacctac aacaaataat     1740
aaattaacag tttcatcatt aaacggtgtt gctcaaatta atgctaaaaa caatggctta     1800
ttcactacag tttatgacaa aactggtaag ccaacgaaag aagttcaaaa acatttgct     1860 gtaacaaaag aagcaagttt aggtggaaac aaattctact tagttaaaga ttacaatagt     1920
ccaactttaa ttggttgggt taaacaaggt gacgttattt ataacaatgc aaaatcacct     1980
gtaaatgtaa tgcaaacata tacagtaaaa ccaggcacta aattatattc agtaccttgg     2040
ggcacttata aacaagaagc tggtgcagtt tctggtacag gtaaccaaac ttttaaagcg     2100
actaagcaac aacaaattga taaatctatc tatttatttg gaactgtaaa tggtaaatct     2160
ggttgggtaa gtaagcata tttagctgta cctgctgcac ctaaaaaagc agtagcacaa      2220
ccaaaaacag ctgtaaaa                                                   2238
```

<210> SEQ ID NO 81
<211> LENGTH: 1443
<212> TYPE: DNA
<213> ORGANISM: Staphylococcus aureus

<400> SEQUENCE: 81

```
gcttatactg ttactaaacc acaaacgact caaacagtta gcaagattgc tcaagttaaa       60
ccaaacaaca ctggtattcg tgcttctgtt tatgaaaaa cagcgaaaaa cggtgcgaaa      120
tatgcagacc gtacgttcta tgtaacaaaa gagcgtgctc atggtaatga aacgtatgta     180
ttattaaaca atacaagcca taacatccca ttaggttggt tcaatgtaaa agacttaaat    240
gttcaaaact taggcaaaga agttaaaacg actcaaaaat atactgttaa taaatcaaat    300
aacggcttat caatggttcc ttggggtact aaaaaccaag tcattttaac aggcaataac    360
attgctcaag gtcatttaa tgcaacgaaa caagtatctg taggcaaaga tgtttattta    420
tacggtacta ttaataaccg cactggttgg gtaaatgcaa aagatttaac tgcaccaact    480
```

```
gctgtgaaac caactacatc agctgccaaa gattataact acacttatgt aattaaaaat    540
ggtaatggtt attactatgt aacaccaaat tctgatacag ctaaatactc attaaaagca    600
tttaatgaac aaccattcgc agttgttaaa gaacaagtca ttaatggaca aacttggtac    660
tatggtaaat tatctaacgg taaattagca tggattaaat caactgattt agctaaagaa    720
ttaattaagt ataatcaaac aggtatgaca ttaaaccaag ttgctcaaat acaagctggt    780
ttacaatata aaccacaagt acaacgtgta ccaggtaagt ggacagatgc taaatttaat    840
gatgttaagc atgcaatgga tacgaagcgt ttagctcaag atccagcatt aaaatatcaa    900
ttcttacgct tagaccaacc acaaaatatt tctattgata aaattaatca attcttaaaa    960
ggtaaaggtg tattagaaaa ccaaggtgct gcatttaaca aagctgctca aatgtatggc   1020
attaatgaag tttatcttat ctcacatgcc ctattagaaa caggtaacgg tacttctcaa   1080
ttagcgaaag gtgcagatgt agtgaacaac aaagttgtaa ctaactcaaa cacgaaatac   1140
cataacgtat ttggtattgc tgcatatgat aacgatcctt acgtgaagg tattaaatat   1200 gctaaacaag ctggttggga cacagtatca aaagcaatcg ttggtggtgc taaattcatc   1260
ggcaactcat atgtaaaagc tggtcaaaat acactttaca aaatgagatg gaatcctgca   1320
catccaggaa cacaccaata tgctacagat gtagattggg ctaacatcaa tgctaaaatc   1380
atcaaaggct actatgataa aattggcgaa gtcggcaaat acttcgacat cccacaatat   1440
aaa                                                                1443

<210> SEQ ID NO 82
<211> LENGTH: 2118
<212> TYPE: DNA
<213> ORGANISM: Staphylococcus aureus

<400> SEQUENCE: 82
gatcgtgtat tagcctcaca tccagatgtt gcgacaatac gtcaaaacgt gacagcagcg     60
aatgccgcta aatcagcact tgatcaagca cgtaatggct aacagtcga taaagcgcct    120 ttagaaaatg cgaaaaatca actacaacat agtattgaca cgcaaacaag tacaactggt    180
atgacacaag actctataaa tgcatacaat gcgaagttaa cagctgcacg taataagatt    240
caacaaatca atcaagtatt agcaggttca ccgactgtag aacaaattaa tacaaatacg    300
tctacagcaa atcaagctaa atctgattta gatcatgcac gtcaagcttt aacaccagat    360
aaagcgccgc ttcaaactgc gaaaacgcaa ttagaacaaa gcattaatca accaacggat    420
acaacaggta tgacgaccgc ttcgttaaat gcgtacaacc aaaaattaca agcagcgcgt    480
caaaagttaa ctgaaattaa tcaagtgttg aatggcaacc caactgtcca aaatatcaat    540
gataaagtga cagaggcaaa ccaagctaag gatcaattaa atacagcacg tcaaggttta    600
acattagata gacagccagc gttaacaaca ttacatggtg catctaactt aaaccaagca    660
caacaaaata atttcacgca acaaattaat gctgctcaaa atcatgctgc gcttgaaaca    720
attaagtcta acattacggc tttaaatact gcgatgacga aattaaaaga cagtgttgcg    780
gataataata caattaaatc agatcaaaat tacactgacg caacaccagc taataaacaa    840
gcgtatgata atgcagttaa tgcggctaaa ggtgtcattg gagaaacgac taatccaacg    900
atggatgtta acagtgtgaa ccaaaaagca gcatctgtta atcgacgaa agatgcttta    960 gatggtcaac aaaacttaca acgtgcgaaa acagaagcaa caaatgcgat tacgcatgca   1020
agtgatttaa accaagcaca aaagaatgca ttaacacaac aagtgaatag tgcacaaaac   1080
gtgcaagcag taaatgatat taaacaaacg actcaaagct taaatactgc tatgacaggt   1140
```

```
ttaaaacgtg gcgttgctaa tcataaccaa gtcgtacaaa gtgataatta tgtcaacgca    1200
gatactaata agaaaaatga ttacaacaat gcatacaacc atgcgaatga cattattaat    1260
ggtaatgcac aacatccagt tataacacca agtgatgtta acaatgcttt atcaaatgtc    1320
acaagtaaag aacatgcatt gaatggtgaa gctaagttaa atgctgcgaa acaagaagcg    1380
aatactgcat taggtcattt aaacaattta ataatgcac aacgtcaaaa cttacaatcg    1440
caaattaatg gtgcgcatca aattgatgca gttaatacaa ttaagcaaaa tgcaacaaac    1500
ttgaatagtg caatgggtaa cttaagacaa gctgttgcag ataaagatca agtgaaacgt    1560
acagaagatt atgcggatgc agatacagct aaacaaaatg catataacag tgcagtttca    1620
agtgccgaaa caatcattaa tcaaacaaca aatccaacga tgtctgttga tgatgttaat    1680
cgtgcaactt cagctgttac ttctaataaa aatgcattaa atggttatga aaaattagca    1740
caatctaaaa cagatgctgc aagagcaatt gatgcattac cacatttaaa taatgcacaa    1800
aaagcagatg ttaaatctaa aattaatgct gcatcaaata ttgctggcgt aaatactgtt    1860
aaacaacaag gtacagattt aaatacagcg atgggtaact tgcaaggtgc aatcaatgat    1920
gaacaaacga cgcttaatag tcaaaactat caagatgcga cacctagtaa gaaaacagca    1980
tacacaaatg cggtacaagc tgcgaaagat attttaaata aatcaaatgg tcaaaataaa    2040
acgaaagatc aagttactga agcgatgaat caagtgaatt ctgctaaaaa taacttagat    2100
ggtacgcgtt tattagat                                                  2118

<210> SEQ ID NO 83
<211> LENGTH: 726
<212> TYPE: DNA
<213> ORGANISM: Staphylococcus aureus

<400> SEQUENCE: 83
gcttctacac aacatacagt acaatctggt gaatcattat ggagtattgc tcaaaaatac      60
aacacttcag tagagagtat taaacaaaat aaccaattag ataacaactt ggtattccct     120
ggtcaagtta tctcagtagg tggaagtgat gcacaaaata cgtcaaacac ttctccacaa     180
gctggttcag catcatctca tactgtacaa gctggtgaat cattaaatat cattgctagc     240
agatatggtg tttcagttga tcaattaatg gcagccaata acttacgtgg ttatttaatt     300
atgcctaacc aaacattaca aattcctaat ggtggatcag gtggtacaac accaacagct     360
acaacaggta gcaatggcaa tgcatcatct tttaatcacc aaaatttata cactgctggt     420
caatgtacat ggtacgtatt tgaccgtcgt gctcaagctg gtagtccaat tagcacatat     480
tggtcagacg ctaagtattg ggctggtaac gcagctaatg atggttacca agtaaacaac     540
acaccatcag ttggttcaat tatgcaaagc acacctggtc catatggtca tgttgcttat     600
gttgaacgtg tcaatggtga tggtagtatc ttgatttctg aaatgaatta cacatatggt     660
ccatacaata tgaactaccg tacaattcca gcttcagaag tttctagcta tgcattcatc     720
cattaa                                                               726

<210> SEQ ID NO 84
<211> LENGTH: 2988
<212> TYPE: DNA
<213> ORGANISM: Staphylococcus aureus

<400> SEQUENCE: 84
atgaataata aaaagacagc aacaaataga aaaggcatga taccaaatcg attaaacaaa      60
ttttcgataa gaaagtattc tgtaggtact gcttcaattt tagtagggac aacattgatt     120
```

```
tttgggttaa gtggtcatga agctaaagcg gcagaacata cgaatggaga attaaatcaa    180
tcaaaaaatg aaacgacagc cccaagtgag aataaaacaa ctaaaaaagt tgatagtcgt    240
caactaaaag acaatacgca aactgcaact gcagatcagc ctaaagtgac aatgagtgat    300
agtgcaacag ttaagaaaac tagtagtaac atgcaatcac cacaaaacgc tacagctaat    360
caatctacta caaaaactag caatgtaaca acaaatgata aatcatcaac tacatatagt    420
aatgaaactg ataaaagtaa tttaacacaa gcaaagatg tttcaactac acctaaaaca     480
acgactatta aaccaagaac tttaaatcgc atggcagtga atactgttgc agctccacaa    540
caaggaacaa atgttaatga taaagtacat ttttcaaata ttgacattgc gattgataaa    600
ggacatgtta atcagactac tggtaaaact gaattttggg caacttcaag tgatgtttta    660
aaattaaaag caaattacac aatcgatgat tctgttaaag agggcgatac atttactttt    720
aaatatggtc aatatttccg tccaggatca gtaagattac cttcacaaac tcaaaattta    780
tataatgccc aaggtaatat tattgcaaaa ggtatttatg atagtacaac aaacacaaca    840
acatatactt ttacgaacta tgtagatcaa tatacaaatg ttagaggtag ctttgaacaa    900
gttgcatttg cgaaacgtaa aaatgcaaca actgataaaa cagcttataa aatgaagta    960 actttaggta atgatacata tagcgaagaa atcattgtcg attatggtaa taaaaagca   1020 caaccgctta tttcaagtac aaactatatt aacaatgaag atttatcgcg taatatgact   1080
gcatatgtaa atcaacctaa aaatacatat actaaacaaa cgtttgttac taatttaact   1140
ggatataaat ttaatccaaa tgcaaaaaac ttcaaaattt acgaagtgac agatcaaaat   1200
caatttgtgg atagtttcac ccctgatact tcaaaactta agatgttac tgatcaattc   1260 gatgttattt atagtaatga taataaaaca gctacagtcg atttaatgaa aggccaaaca   1320
agcagcaata acaatacat cattcaacaa gttgcttatc cagataatag ttcaacagat   1380 aatgaaaaa ttgattatac tttagacact gacaaaacta aatatagttg gtcaaatagt    1440
tattcaaatg tgaatggctc atcaactgct aatggcgacc aaaagaaata taatctaggt   1500
gactatgtat gggaagatac aaataaagat ggtaaacaag atgccaatga aaaagggatt   1560
aaaggtgttt atgtcattct taaagatagt aacggtaaag aattagatcg tacgacaaca   1620
gatgaaaatg gtaaatatca gttcactggt ttaagcaatg gaacttatag tgtagagttt   1680
tcaacaccag ccggttatac accgacaact gcaaatgtag gtacagatga tgctgtagat   1740
tctgatggac taactacaac aggtgtcatt aaagacgctg acaacatgac attagatagt   1800
ggattctaca aaacaccaaa atatagttta ggtgattatg tttggtacga cagtaataaa   1860
gatggtaaac aagattcgac tgaaaaagga attaaaggtg ttaaagttac tttgcaaaac   1920
gaaaaaggcg aagtaattgg tacaactgaa acagatgaaa atggtaaaata ccgctttgat   1980 aatttagata gtggtaaaata caaagttatc tttgaaaaac ctgctggctt aactcaaaca   2040
ggtacaaata caactgaaga tgataaagat gccgatggtg gcgaagttga tgtaacaatt   2100
acggatcatg atgatttcac acttgataat ggctactacg aagaagaaac atcagatagc   2160
gactcagatt ctgacagcga ttcagactca gatagcgact cagattcaga tagcgactca   2220
gattcagaca gcgattcaga cagcgactca gactcagata gcgattcaga ttcagacagc   2280
gactcagact cagacagcga ttcagactcg gatagcgact cagactcaga tagcgactca   2340
gattcggata gcgactcaga ctcagatagc gattcagatt cagatagcga ttcggactca   2400
gacagtgatt cagattcaga ctcagatagc gactcagatt ctgacagcga ttcagactca   2460
gacagcgact cagactcaga cagtgattca gattcagaca gcgactcaga ttcagatagc   2520
```

```
gactcagact cagatagcga ctcagattca gatagcgatt cggactcaga caacgactca   2580
gattcagata gcgattcaga ttcagatagc gactcagatt cggacagcga ttcagactca   2640
gatagcgatt cagactcaga cagcgattca gattcagata gcgactcaga ctcagatagc   2700
gactcagact cggatagcga ttcagattca gacagcgact cagattcaga tagcgattcg   2760
gactcagaca acgactcaga ttcagatagc gattcagatt cagatgcagg taaacatact   2820
ccggctaaac caatgagtac ggttaaagat cagcataaaa cagctaaagc attaccagaa   2880
acaggtagtg aaaataataa ttcaaataat ggcacattat tcggtggatt attcgcggca   2940
ttaggatcat tattgttatt cggtcgtcgt aaaaaacaaa ataaataa                2988

<210> SEQ ID NO 85
<211> LENGTH: 6561
<212> TYPE: DNA
<213> ORGANISM: Staphylococcus aureus

<400> SEQUENCE: 85
atgaatttgt taagaaaaaa taaatatagt attaggaagt ataaagtagg catattctct     60
actttaatcg gaacagtttt attactttca aacccaaatg gtgcacaagc cttaactacg    120
gataataatg tacaaagcga tactaatcaa gcaacacctg taaattcaca agataaagat    180
gttgctaata atagaggttt agcaaatagt gcgcagaata cacctaatca atctgcaaca    240
accaatcaag caacgaatca agcattggtt aatcataata atggtagtat agtaaatcaa    300
gctacgccaa catcagtgca atcaagtacg ccttcagcac aaaacaataa tcatacagat    360
ggcaatacaa cagcaactga gacagtgtca aacgctaata ataatgatgt agtgtcgaat    420
aataccgcat taaatgtacc aactaaaaca aatgaaaatg gttcaggagg acatctaact    480
ttaaaggaaa ttcaagaaga tgttcgtcat tcttcaaata accagagct agttgcaatt    540 gctgaaccag catctaatag accgaaaaag agaagtagac gtgcggcacc ggcagatcct    600
aatgcaactc cagcagatcc agcggctgca gcggtaggaa acggtggtgc accagttgca    660
attacagcgc catatacgcc aacaactgat cctaatgcca ataatgcagg acaaaatgca    720
cctaacgaag tgctgtcatt tgatgacaat ggtattagca caagtaccaa ccgttctgtg    780
ccaacagtaa acgttgttaa taacttgccg ggcttcacac taatcaatgg tggcaaagta    840
ggggtgttta gtcatgcaat ggtaagaacg agcatgtttg attcaggaga taataagaac    900
tatcaagcac aaggaaatgt aattgcatta ggtcgtatac atggaactga tacgaatgac    960
catggcgatt taatggtat cgagaaagca ttaacagtaa atccgaattc tgaattaatc    1020
tttgaattta atacaatgac tactaaaaac ggtcaaggcg caacaaatgt tattatcaaa    1080
aatgctgata ctaatgatac gattgctgaa aagactgttg aaggcggtcc aactttgcgt    1140
ttatttaaag tacctgataa tgtgagaaat ctcaaaattc aatttgtacc taaaaatgac    1200
gcaataacag atgcgcgtgg catttatcaa ctaaagatg gttacaaata ctatagctt    1260 gttgactcta tcggacttca ttctgggtca catgttttg ttgaaagacg aacaatggat    1320
ccaacagcaa caaataataa agagtttact gtaacaacat cattaaagaa taatggtaat    1380
tctggtgctt ctctagatac aaatgacttt gtatatcaag ttcaattacc tgaaggtgtt    1440
gaatatgtga acaattcatt gactaaagat tttccaagta caattcagg cgttgatgtt    1500 aatgatatga atgttacata tgatgcagca atcgtgtga taacaattaa aagtactgga    1560
ggaggtacag caaactctcc ggcacgactt atgcctgata aaatactcga tttaagatat    1620
aaattacgtg taaataatgt gccgacacca agaacagtaa catttaacga gacattaacg    1680
```

```
tataaaacat atacacaaga tttcattaat tcagctgcag aaagtcatac tgtaagtaca    1740
aatccatata ctatcgatat catcatgaat aaagatgcat tacaagccga agttgacaga    1800
cgtattcaac aagctgatta tacatttgcg tcattagata tctttaatgg tctgaaacga    1860
cgcgcacaaa cgattttaga tgaaaatcgt aacaatgtac cattaaataa aagagtttct    1920
caagcatata ttgattcatt aactaatcaa atgcaacata cgttaattcg aagtgttgat    1980
gctgaaaatg cagttaataa aaagttgac caaatggaag atttagttaa tcaaaatgat    2040
gaattgacag atgaagaaaa acaagcagca atacaagtta tcgaggaaca taaaaatgaa    2100
ataattggta atattggtga ccaaacgact gatgatggcg ttactagaat caagatcaa    2160 ggtatacaga ccttaagtgg ggatactgca acaccggttg ttaaaccaaa tgctaaaaaa    2220
gcaatacgtg ataaagcaac gaaacaaagg gaaattatca atgcaacacc agatgctact    2280
gaagacgaga ttcaagatgc actaaatcaa ttagctacgg atgaaacaga tgctattgat    2340
aatgttacga atgctactac aaatgctgac gttgaaacag ctaaaaataa tggcatcaat    2400
actattggag cagttgttcc tcaagtaact cataaaaaag ctgcaagaga tgcaattaac    2460
caagcaacag caacgaaaag acaacaaata aatagtaata gagaagcaac tcaggaagag    2520
aaaaatgcag cattgaacga attaactcaa gcaaccaacc atgctttaga acaaatcaat    2580
caagcaacaa caaatgctaa tgttgataac gccaaaggag atggtctaaa tgccattaat    2640
ccaattgctc ctgtaactgt tgttaagcaa gctgcaaggg atgccgtatc acatgatgca    2700
caacaacata tcgcagagat caatgctaat cctgatgcga ctcaagaaga aagacaagca    2760
gcaattgaca aagtgaatgc tgctgtaact gcagcaaaca caaacatttt aaacgctaat    2820
accaatgctg atgttgaaca agtaaagaca aatgcgattc aaggaataca agcaattaca    2880
ccagctacaa aagtaaaaac agatgcaaaa aatgccatcg ataaaagtgc ggaaacgcaa    2940
cataatacga tatttaataa taatgatgcg acgctcgaag aacaacaagc agcacaacaa    3000
ttacttgatc aagctgtagc cacagcgaag caaaatatta atgcagcaga tacgaatcaa    3060
gaagttgcac aagcaaaaga tcagggcaca caaaatatag tagtgattca accggcaaca    3120
caagttaaaa cggatactcg caatgttgta aatgataaag cgcgagaggc gataacaaat    3180
atcaatgcta caactggcgc gactcgagaa gagaaacaag aagcgataaa tcgtgtcaat    3240
acacttaaaa atagagcatt aactgatatt ggtgtgacgt ctactactgc gatggtcaat    3300
agtattagag acgatgcagt caatcaaatc ggcgcagttc aaccgcatgt aacgaagaaa    3360
caaactgcta caggtgtatt aaatgattta gcaactgcta aaaagcaaga aattaatcaa    3420
aacacaaatg caacaactga agaaaagcaa gtggctttaa atcaagtgga tcaagagtta    3480
gcaacggcaa ttaataatat aaatcaagct gatacaaatg cggaagtaga tcaagcgcaa    3540
caattaggta caaaagcaat taatgcgatt cagccaaata ttgttaaaaa acctgcagca    3600
ttagcacaaa tcaatcagca ttataatgct aaattagctg aaatcaatgc tacaccagat    3660
gcaacgaatg atgagaaaaa tgctgcgatc aatactttaa atcaagacag acaacaagct    3720
attgaaagta ttaaacaagc taacacaaat gcagaagtag accaagctgc gacagtagca    3780
gagaataata tcgatgctgt tcaagttgat gtagtaaaaa aacaagcagc gcgagataaa    3840
atcactgctg aagtggcgaa gcgtattgaa gcggttaaac aaacacctaa tgcaactgac    3900
gaagaaaagc aggctgctgt taatcaaatc aatcaactta aagatcaagc aattaatcaa    3960
attaatcaaa accaaacaaa tgatcaggta gacacaacta caaatcaagc ggtaaatgct    4020
atagataatg ttgaagctga agtagtaatt aaaacaaagg caattgcaga tattgaaaaa    4080
```

```
gctgttaaag aaaagcaaca gcaaattgat aatagtcttg attcaacaga taatgagaaa    4140
gaagttgctt cacaagcatt agctaaagaa aaagaaaaag cacttgcagc tattgaccaa    4200
gctcaaacga atagtcaggt gaatcaagca gcaacaaatg gtgtatcagc gattaaaatt    4260
attcaacctg aaacaaaagt taaaccagct gcacgtgaaa aaatcaatca aaaagcgaat    4320
gaattacgtg ctaagattaa tcaggataaa gaagcaacag cagaagaaag acaagtagca    4380
ctagataaaa tcaatgaatt tgtaaatcaa gccatgacag atattacgaa taatagaaca    4440
aatcaacaag ttgatgatac aacaagtcaa gcgcttgata gcattgcttt agtgacgcct    4500
gaccatattg ttagagcagc tgctagagat gcagttaagc aacaatatga agctaaaaag    4560
cgcgaaattg agcaagcgga acatgcgact gatgaagaaa acaagttgc tttaaatcaa     4620
ttagcgaata atgaaaaacg tgcattacaa aacatcgatc aagcaatagc gaataatgat    4680
gtgaaacgtg ttgaaacaaa tggcattgct acactaaaag gtgtacaacc tcatattgta    4740
attaagcctg aagcacaaca agcaataaaa gcaagtgcag aaaatcaagt agaatcaata    4800
aaagatacac cacatgcaac agttgatgaa ttagatgaag cgaatcaatt aattagcgac    4860
acactcaaac aagcgcaaca agaaatagaa aatacaaatc aagatgctgc tgttactgat    4920
gttagaaatc aaacaatcaa ggcaatagag caaataaaac ctaaagtaag acgtaaacga    4980
gctgcgcttg atagcattga agaaaataat aaaaatcaac tcgatgcaat ccgaaatacg    5040
ttggatacta ctcaagatga agagatgtt gctattgata ctttaaataa aattgtaaat     5100
acaattaaaa atgacattgc acaaaacaaa acgaatgcag aagtggatcg aactgagact    5160
gatggcaacg acaacatcaa agtgattta cctaaagttc aagttaaacc agcagcgcgt     5220
caatctgttg gtgtaaaagc cgaagctcaa atgcactaa tcgatcaaag cgatttatca     5280
actgaagaag aaagactagc tgctaaacat ttagtagaac aagcacttaa tcaggctatt    5340
gatcagatca atcatgcaga taagactgcc caagttaatc aagatagtat aaatgctcaa    5400
aatattattt caaaaattaa accagcgaca acagttaaag caacagcatt acaacaaatt    5460
caaaatatcg ctacaaataa aattaattta attaaagcaa ataacgaagc gacagatgaa    5520
gaacaaaata ttgcaatagc acaagttgaa aaagagttaa ttaaagctaa acaacaaatt    5580
gctagtgcag tgactaatgc agatgtggca tatttattgc atgatgagaa aaacgaaatt    5640
cgtgaaatcg aacctgttat taacagaaag gcgtctgctc gagaacaatt gacaacatta    5700
ttcaacgata aaaacaagc aattgaagcg aatattcaag caacggtaga agaaagaaat     5760
agtatattag cacagttaca aaatatttat gacactgcta ttggacaaat tgatcaagat    5820
cgtagcaatg cacaagttga taaaacagca tcattaaatc tacaaacaat acatgattta    5880
gatgtacatc ctattaaaaa gccagatgct gaaaaaacga ttaatgatga tcttgcacgc    5940
gtcactgctt tagtgcaaaa ttatcgaaaa gtaagtaatc gtaataaggc tgatgcatta    6000
aaagctataa ctgctttaaa attacaaatg gatgaagaat taaaacagc acgcactaat     6060
gctgatgttg atgcagtttt aaaacgattt aatgttgcat aagcgatat agaagcagta     6120
attactgaaa aagaaaatag cttactgcga attgataaca ttgctcaaca acatatgcg     6180
aaattcaaag cgatcgcaac accagaacaa ttagctaaag taaagtatt aattgatcaa    6240
tatgttgcag atggcaatag aatgattgat gaagatgcga cattaaatga catcaaacaa    6300
cacacgcaat tcattgttga tgaaatttta gcaattaaat taccagctga agcgacgaaa    6360
gtatcaccaa agaaattca gccagctcca aaagtttgta cgcctattaa aaaagaagag     6420
acacatgaat cgcgcaaagt tgaaaagaa cttccaaata caggttctga aggaatggat     6480
```
ttaccattga aagaatttgc actgattaca ggtgcggctt tgttagctag aagacgtact    6540
aaaaacgaaa aagaatcata a    6561

<210> SEQ ID NO 86
<211> LENGTH: 2319
<212> TYPE: DNA
<213> ORGANISM: Staphylococcus aureus

<400> SEQUENCE: 86
gaggagaatt cagtacaaga cgttaaagat tcgaatacgg atgatgaatt atcagacagc      60
aatgatcagt ctagtgatga agaaaagaat gatgtgatca ataataatca gtcaataaac     120
accgacgata taaccaaat aattaaaaaa gaagaaacga ataactacga tggcatagaa     180
aaacgctcag aagatagaac agagtcaaca acaaatgtag atgaaaacga agcaacattt     240
ttacaaaaga cccctcaaga taatactcat cttacagaag aagaggtaaa agaatcctca     300
tcagtcgaat cctcaaattc atcaattgat actgcccaac aaccatctca cacaacaata     360
aatagagaag aatctgttca acaagtgat aatgtagaag attcacacgt atcagatttt     420
gctaactcta aaataaaaga gagtaacact gaatctggta agaagagaa tactatagag     480 caacctaata aagtaaaaga agattcaaca acaagtcagc cgtctggcta tacaaatata     540
gatgaaaaaa tttcaaatca agtgagtta ttaaatttac caataaatga atatgaaaat     600
aaggctagac cattatctac aacatctgcc caaccatcga ttaaacgtgt aaccgtaaat     660
caattagcgg cggaacaagg ttcgaatgtt aatcatttaa ttaaagttac tgatcaaagt     720
attactgaag gatatgatga tagtgaaggt gttattaaag cacatgatgc tgaaaactta     780
atctatgatg taactttga gtagatgat aaggtgaaat ctggtgatac gatgacagtg     840
gatatagata agaatacagt tccatcagat ttaaccgata gctttacaat accaaaaata     900
aaagataatt ctggagaaat catcgctaca ggtacttatg ataacaaaaa taaacaaatc     960
acctatactt ttacagatta tgtagataag tatgaaaata ttaaagcaca ccttaaatta    1020
acgtcataca ttgataaatc aaaggttcca aataataata ccaagttaga tgtagaatat    1080
aaaacggccc tttcatcagt aaataaaaca attacggttg aatatcaaag acctaacgaa    1140
aatcggactg ctaaccttca agtatgtttt acaaacatag atacgaaaaa tcatacagtt    1200
gagcaaacga tttatattaa ccctcttcgt tattcagcca aggaaacaaa tgtaaatatt    1260
tcagggaatg gtgatgaagg ttcaacaatt atagacgata gcacaataat taaagtttat    1320
aaggttggag ataatcaaaa tttaccagat agtaacagaa tttatgatta cagtgaatat    1380
gaagatgtca caaatgatga ttatgcccaa ttaggaaata ataatgatgt gaatattaat    1440
tttggtaata tagattcacc atatattatt aaagttatta gtaaatatga ccctaataag    1500
gatgattaca cgactataca gcaaactgtg acaatgcaga cgactataaa tgagtatact    1560
ggtgagttta aacagcatc ctatgataat acaattgctt tctctacaag ttcaggtcaa    1620
ggacaaggtg acttgcctcc tgaaaaaact tataaaatcg gagattacgt atgggaagat    1680
gtagataaag atggtattca aaatacaaat gataatgaaa accgcttag taatgtattg    1740 gtaactttga cgtatcctga tggaacttca aaatcagtca gaacagatga agatgggaaa    1800
tatcaatttg atggattgaa aaacggattg acttataaaa ttacattcga aacacctgaa    1860
ggatatacgc cgacgcttaa acattcagga acaaatcctg cactagactc agaaggtaat    1920
tctgtatggg taactattaa tggacaagac gatatgacga ttgatagtgg attttatcaa    1980
acacctaaat acagcttagg gaactatgta tggtatgaca ctaataaaga tggtattcaa    2040

```
ggtgatgatg aaaaaggaat ctctggagtt aaagtgacgt taaaagatga aaacggaaat  2100
atcattagta caactacaac cgatgaaaat ggaaagtatc aatttgataa tttaaatagt  2160
ggtaattata ttgttcattt tgataaacct tcaggtatga ctcaaacaac aacagattct  2220
ggtgatgatg acgaacagga tgctgatggg gaagaagttc atgtaacaat tactgatcat  2280
gatgacttta gtatagataa cggatactat gatgacgaa                         2319
```

<210> SEQ ID NO 87
<211> LENGTH: 1141
<212> TYPE: PRT
<213> ORGANISM: Staphylococcus aureus

<400> SEQUENCE: 87

| Met | Ile | Asn | Arg | Asp | Asn | Lys | Lys | Ala | Ile | Thr | Lys | Lys | Gly | Met | Ile |
| 1   |     |     |     | 5   |     |     |     |     | 10  |     |     |     |     | 15  |     |

| Ser | Asn | Arg | Leu | Asn | Lys | Phe | Ser | Ile | Arg | Lys | Tyr | Thr | Val | Gly | Thr |
|     |     |     | 20  |     |     |     |     | 25  |     |     |     |     | 30  |     |     |

| Ala | Ser | Ile | Leu | Val | Gly | Thr | Thr | Leu | Ile | Phe | Gly | Leu | Gly | Asn | Gln |
|     |     | 35  |     |     |     |     | 40  |     |     |     |     | 45  |     |     |     |

| Glu | Ala | Lys | Ala | Ala | Glu | Asn | Thr | Ser | Thr | Glu | Asn | Ala | Lys | Gln | Asp |
|     | 50  |     |     |     |     |     | 55  |     |     |     |     | 60  |     |     |     |

| Asp | Ala | Thr | Thr | Ser | Asp | Asn | Lys | Glu | Val | Val | Ser | Glu | Thr | Glu | Asn |
| 65  |     |     |     |     | 70  |     |     |     |     | 75  |     |     |     |     | 80  |

| Asn | Ser | Thr | Thr | Glu | Asn | Asp | Ser | Thr | Asn | Pro | Ile | Lys | Lys | Glu | Thr |
|     |     |     |     | 85  |     |     |     |     | 90  |     |     |     |     | 95  |     |

| Asn | Thr | Asp | Ser | Gln | Pro | Glu | Ala | Lys | Glu | Ser | Thr | Thr | Ser | Ser |     |
|     |     |     | 100 |     |     |     |     | 105 |     |     |     |     | 110 |     |     |

| Thr | Gln | Gln | Gln | Gln | Asn | Asn | Val | Thr | Ala | Thr | Thr | Glu | Thr | Lys | Pro |
|     |     | 115 |     |     |     |     | 120 |     |     |     |     | 125 |     |     |     |

| Gln | Asn | Ile | Glu | Lys | Glu | Asn | Val | Lys | Pro | Ser | Thr | Asp | Lys | Thr | Ala |
|     | 130 |     |     |     |     | 135 |     |     |     |     | 140 |     |     |     |     |

| Thr | Glu | Asp | Thr | Ser | Val | Ile | Leu | Glu | Glu | Lys | Lys | Ala | Pro | Asn | Tyr |
| 145 |     |     |     |     | 150 |     |     |     |     | 155 |     |     |     |     | 160 |

| Thr | Asn | Asn | Asp | Val | Thr | Thr | Lys | Pro | Ser | Thr | Ser | Glu | Ile | Gln | Thr |
|     |     |     |     | 165 |     |     |     |     | 170 |     |     |     |     | 175 |     |

| Lys | Pro | Thr | Thr | Pro | Gln | Glu | Ser | Thr | Asn | Ile | Glu | Asn | Ser | Gln | Pro |
|     |     |     | 180 |     |     |     |     | 185 |     |     |     |     | 190 |     |     |

| Gln | Pro | Thr | Pro | Ser | Lys | Val | Asp | Asn | Gln | Val | Thr | Asp | Ala | Thr | Asn |
|     |     | 195 |     |     |     |     | 200 |     |     |     |     | 205 |     |     |     |

| Pro | Lys | Glu | Pro | Val | Asn | Val | Ser | Lys | Glu | Glu | Leu | Lys | Asn | Asn | Pro |
|     | 210 |     |     |     |     | 215 |     |     |     |     | 220 |     |     |     |     |

| Glu | Lys | Leu | Lys | Glu | Leu | Val | Arg | Asn | Asp | Asn | Asn | Thr | Asp | Arg | Ser |
| 225 |     |     |     |     | 230 |     |     |     |     | 235 |     |     |     |     | 240 |

| Thr | Lys | Pro | Val | Ala | Thr | Ala | Pro | Thr | Ser | Val | Ala | Pro | Lys | Arg | Leu |
|     |     |     |     | 245 |     |     |     |     | 250 |     |     |     |     | 255 |     |

| Asn | Ala | Lys | Met | Arg | Phe | Ala | Val | Ala | Gln | Pro | Ala | Ala | Val | Ala | Ser |
|     |     |     | 260 |     |     |     |     | 265 |     |     |     |     | 270 |     |     |

| Asn | Asn | Val | Asn | Asp | Leu | Ile | Thr | Val | Thr | Lys | Gln | Thr | Ile | Lys | Val |
|     |     | 275 |     |     |     |     | 280 |     |     |     |     | 285 |     |     |     |

| Gly | Asp | Gly | Lys | Asp | Asn | Val | Ala | Ala | Ala | His | Asp | Gly | Lys | Asp | Ile |
|     | 290 |     |     |     |     | 295 |     |     |     |     | 300 |     |     |     |     |

| Glu | Tyr | Asp | Thr | Glu | Phe | Thr | Ile | Asp | Asn | Lys | Val | Lys | Lys | Gly | Asp |
| 305 |     |     |     |     | 310 |     |     |     |     | 315 |     |     |     |     | 320 |

| Thr | Met | Thr | Ile | Asn | Tyr | Asp | Lys | Asn | Val | Ile | Pro | Ser | Asp | Leu | Thr |
|     |     |     |     | 325 |     |     |     |     | 330 |     |     |     |     | 335 |     |

```
Asp Lys Asn Asp Pro Ile Asp Ile Thr Asp Pro Ser Gly Glu Val Ile
            340                 345                 350
Ala Lys Gly Thr Phe Asp Lys Ala Thr Lys Gln Ile Thr Tyr Thr Phe
            355                 360                 365
Thr Asp Tyr Val Asp Lys Tyr Glu Asp Ile Lys Ala Arg Leu Thr Leu
370                 375                 380
Tyr Ser Tyr Ile Asp Lys Gln Ala Val Pro Asn Glu Thr Ser Leu Asn
385                 390                 395                 400
Leu Thr Phe Ala Thr Ala Gly Lys Glu Thr Ser Gln Asn Val Ser Val
                405                 410                 415
Asp Tyr Gln Asp Pro Met Val His Gly Asp Ser Asn Ile Gln Ser Ile
            420                 425                 430
Phe Thr Lys Leu Asp Glu Asn Lys Gln Thr Ile Glu Gln Gln Ile Tyr
            435                 440                 445
Val Asn Pro Leu Lys Lys Thr Ala Thr Asn Thr Lys Val Asp Ile Ala
450                 455                 460
Gly Ser Gln Val Asp Asp Tyr Gly Asn Ile Lys Leu Gly Asn Gly Ser
465                 470                 475                 480
Thr Ile Ile Asp Gln Asn Thr Glu Ile Lys Val Tyr Lys Val Asn Pro
                485                 490                 495
Asn Gln Gln Leu Pro Gln Ser Asn Arg Ile Tyr Asp Phe Ser Gln Tyr
            500                 505                 510
Glu Asp Val Thr Ser Gln Phe Asp Asn Lys Lys Ser Phe Ser Asn Asn
            515                 520                 525
Val Ala Thr Leu Asp Phe Gly Asp Ile Asn Ser Ala Tyr Ile Ile Lys
530                 535                 540
Val Val Ser Lys Tyr Thr Pro Thr Ser Asp Gly Glu Leu Asp Ile Ala
545                 550                 555                 560
Gln Gly Thr Ser Met Arg Thr Thr Asp Lys Tyr Gly Tyr Tyr Asn Tyr
                565                 570                 575
Ala Gly Tyr Ser Asn Phe Ile Val Thr Ser Asn Asp Thr Gly Gly Gly
            580                 585                 590
Asp Gly Thr Val Lys Pro Glu Glu Lys Leu Tyr Lys Ile Gly Asp Tyr
            595                 600                 605
Val Trp Glu Asp Val Asp Lys Asp Gly Val Gln Gly Thr Asp Ser Lys
610                 615                 620
Glu Lys Pro Met Ala Asn Val Leu Val Thr Leu Thr Tyr Pro Asp Gly
625                 630                 635                 640
Thr Thr Lys Ser Val Arg Thr Asp Ala Asn Gly His Tyr Glu Phe Gly
                645                 650                 655
Gly Leu Lys Asp Gly Glu Thr Tyr Thr Val Lys Phe Glu Thr Pro Ala
            660                 665                 670
Gly Tyr Leu Pro Thr Lys Val Asn Gly Thr Thr Asp Gly Glu Lys Asp
            675                 680                 685
Ser Asn Gly Ser Ser Ile Thr Val Lys Ile Asn Gly Lys Asp Asp Met
690                 695                 700
Ser Leu Asp Thr Gly Phe Tyr Lys Glu Pro Lys Tyr Asn Leu Gly Asp
705                 710                 715                 720
Tyr Val Trp Glu Asp Thr Asn Lys Asp Gly Ile Gln Asp Ala Asn Glu
                725                 730                 735
Pro Gly Ile Lys Asp Val Lys Val Thr Leu Lys Asp Ser Thr Gly Lys
            740                 745                 750
Val Ile Gly Thr Thr Thr Thr Asp Ala Ser Gly Lys Tyr Lys Phe Thr
```

```
                755                 760                 765
Asp Leu Asp Asn Gly Asn Tyr Thr Val Glu Phe Glu Thr Pro Ala Gly
770                 775                 780

Tyr Thr Pro Thr Val Lys Asn Thr Thr Ala Glu Asp Lys Asp Ser Asn
785                 790                 795                 800

Gly Leu Thr Thr Thr Gly Val Ile Lys Asp Ala Asp Asn Met Thr Leu
                805                 810                 815

Asp Ser Gly Phe Tyr Lys Thr Pro Lys Tyr Ser Leu Gly Asp Tyr Val
                820                 825                 830

Trp Tyr Asp Ser Asn Lys Asp Gly Lys Gln Asp Ser Thr Glu Lys Gly
                835                 840                 845

Ile Lys Asp Val Lys Val Thr Leu Leu Asn Glu Lys Gly Glu Val Ile
850                 855                 860

Gly Thr Thr Lys Thr Asp Glu Asn Gly Lys Tyr Arg Phe Asp Asn Leu
865                 870                 875                 880

Asp Ser Gly Lys Tyr Lys Val Ile Phe Glu Lys Pro Ala Gly Leu Thr
                885                 890                 895

Gln Thr Val Thr Asn Thr Thr Glu Asp Asp Lys Asp Ala Asp Gly Gly
                900                 905                 910

Glu Val Asp Val Thr Ile Thr Asp His Asp Asp Phe Ile Leu Asp Asn
                915                 920                 925

Gly Tyr Phe Glu Glu Asp Thr Ser Asp Ser Asp Ser Asp Ser Asp Ser
                930                 935                 940

Asp Ser Asp Ser Asp Ser Asp Ser Asp Ser Asp Ser Asp Ser Asp Ser
945                 950                 955                 960

Asp Ser Asp Ser Asp Ser Asp Ser Asp Ser Asp Ser Asp Ser Asp Ser
                965                 970                 975

Asp Ser Asp Ser Asp Ser Asp Ser Asp Ser Asp Ser Asp Ser Asp Ser
                980                 985                 990

Asp Ser Asp Ser Asp Ser Asp Ser Asp Ser Asp Ser Asp Ser Asp Ser
                995                 1000                1005

Asp Ser Asp Ser Asp Ser Asp Ser Asp Ser Asp Ser Asp Ser Asp Ser
1010                1015                1020

Asp Ser Asp Ser Asp Ser Asp Ser Asp Ser Asp Ser Asp Ser Asp Ser
1025                1030                1035                1040

Asp Ser Asp Ser Asp Ser Asp Ser Asp Ser Asp Ser Asp Ser Asp Ser
                1045                1050                1055

Asp Ser Asp Ser Asp Ser Asp Ser Asp Ser Asp Ser Asp Ser Asp Ser
                1060                1065                1070

Asp Ser Asp Ser Asp Ser Asp Ser Asp Ala Gly Lys His Thr Pro Val
                1075                1080                1085

Lys Pro Met Ser Thr Thr Lys Asp His His Asn Lys Ala Lys Ala Leu
1090                1095                1100

Pro Glu Thr Gly Ser Glu Asn Asn Gly Ser Asn Asn Ala Thr Leu Phe
1105                1110                1115                1120

Gly Gly Leu Phe Ala Ala Leu Gly Ser Leu Leu Leu Phe Gly Arg Arg
                1125                1130                1135

Lys Lys Gln Asn Lys
                1140

<210> SEQ ID NO 88
<211> LENGTH: 3426
<212> TYPE: DNA
<213> ORGANISM: Staphylococcus aureus
```

<400> SEQUENCE: 88

```
atgattaaca gggataataa aaaggcaata acaaaaaagg gtatgatttc aaatcgctta    60
aacaaatttt cgattagaaa gtatactgta ggaactgcat cgattttagt aggtacgaca   120
ttgattttg gtctagggaa ccaagaagct aaagctgctg aaaacactag tacagaaaat   180
gcgaaacaag atgatgcaac gactagtgat aataagaag tagtgtcgga aactgaaaat   240
aattcgacaa cagaaaatga ttcaacaaat ccaattaaga agaaacaaa tactgattca   300
caaccagaag ctaaagaaga atcaactaca tcaagtactc aacaacagca aaataacgtt   360
acagctacaa ctgaaactaa gcctcaaaac attgaaaaag aaatgttaa accttcaact   420
gataaaactg cgacagaaga tacatctgtt attttagaag agaagaaagc accaaattat   480
acaaataacg atgtaactac aaaaccatct acaagtgaaa ttcaaacaaa accaactaca   540
cctcaagaat ctacaaatat tgaaaattca caaccgcaac caacgccttc aaaagtagac   600
aatcaagtta cagatgcaac taatccaaaa gaaccagtaa atgtgtcaaa agaagaactt   660
aaaaataatc ctgagaaatt aaaagaatta gttagaaatg ataacaatac agatcgttca   720
actaaaccag ttgctacagc tccaacaagt gttgcaccaa acgattaaa tgcgaaaatg   780
cgttttgcag ttgcacaacc agcagcagtt gcttcaaata atgtaaatga cttaattaca   840
gttacgaaac agacgatcaa agttggcgat ggtaaagata atgtggcagc agcgcatgac   900
ggtaaagata ttgaatatga tacagagttt acaattgaca ataaagtcaa aaaaggcgat   960
acaatgacga ttaattatga taagaatgta attccttcgg atttaacaga taaaaatgat  1020
cctatcgata ttactgatcc atcaggagag gtcattgcca aaggaacatt tgataaagcg  1080
actaagcaaa tcacatatac atttacagat tatgtagata aatatgaaga tataaaagca  1140
cgtttaactt tatactcata tattgataag caagcagtac ctaatgaaac tagtttgaat  1200
ttaacgtttg caacagcagg taagaaaact agccaaaacg tttctgttga ttatcaagac  1260
ccaatggttc atggtgattc aaacattcaa tctatcttta caaagttaga tgaaaacaaa  1320
caaactattg aacaacaaat ttatgttaat ccttgaaaa aaacagcaac taacactaaa  1380
gttgatatag ctggtagtca agtagatgat tatggaaata ttaaactagg aaatggtagt  1440
accattattg accaaaatac agaaataaaa gtttataaag ttaaccctaa tcaacaattg  1500
cctcaaagta atagaatcta tgattttagt caatacgaag atgtaacaag tcaatttgat  1560
aataaaaaat catttagtaa taatgtagca acattggatt ttggtgatat taattcagcc  1620
tatattatca aagttgttag taaatataca cctacatcag atggcgaact agatattgct  1680
caaggtacta gtatgagaac aactgataaa tatggttatt ataattatgc aggatattca  1740
aacttcatcg taacttctaa tgacactggc ggtggcgacg gtactgttaa acctgaagaa  1800
aagttataca aaattggtga ctatgtatgg gaagacgttg ataaagacgg tgtccaaggt  1860
acagattcga agaaaagcc aatggcaaac gttttagtta cattaactta cccgacggt   1920
actacaaaat cagtaagaac agatgctaac ggtcattatg aattcggtgg tttgaaagac  1980
ggagaaactt atacagttaa attcgaaacg ccagctggat atcttccaac aaaagtaaat  2040
ggaacaactg atggtgaaaa agactcaaat ggtagttcta aactgttaa aattaatggt  2100
aaagatgata tgtctttaga cactggtttt tataaagaac ctaaatataa tcttggtgac  2160
tatgtatggg aagatacaaa taagatggt atccaagatg ctaatgaacc tggtatcaaa  2220
gatgttaagg ttacattaaa agatagtact ggaaaagtta ttggtacaac tactactgat  2280
gcctcgggta atataaaatt tacagattta gataatggta actatacagt agaatttgaa  2340
```

-continued

```
acaccagcag gttacacgcc aacggttaaa aatactacag ctgaagataa agattctaat   2400
ggtttaacaa caacaggtgt cattaaagat gcagataata tgacattaga cagtggtttc   2460
tataaaacac caaaatacag tttaggtgat tatgtttggt acgacagtaa taaagacggt   2520
aaacaagatt caactgaaaa aggtatcaaa gatgttaaag ttactttatt aaatgaaaaa   2580
ggcgaagtaa ttggaacaac taaaacagat gaaaatggta aatatcgttt cgataattta   2640
gatagcggta aatacaaagt tattttttgaa aagcctgctg gcttaacaca aacagttaca   2700
aatacaactg aagatgataa agatgccgat ggtggcgaag ttgacgtaac aattacggat   2760
catgatgatt tcatacttga taacggatac ttcgaagaag atacatcaga cagtgattca   2820
gactcagaca gtgattcaga ctcagacagc gactcagatt cagacagtga ttcagactca   2880
gatagcgatt cagattcaga cagcgactca gactcagata gcgactcaga ctcagacagc   2940
gactcagact cagatagcga ctcagattcg gacagcgatt cagactcaga tagcgactca   3000
gattcagaca gcgattcaga ctcagatagc gactcagatt cagacagtga ctcagactca   3060
gatagcgact cagactcaga cagtgactca gactcagaca gcgattcaga ttcagatagc   3120
gactcagatt cggacagtga ttcagactca gatagcgact cagattcaga cagcgactca   3180
gactcagata gcgactcaga ctcagacagt gattcagact cagatagcga ttcggactcg   3240
gatgcaggaa acatacacc tgttaaacca atgagtacta ctaaagacca tcacaataaa    3300
gcaaaagcat taccagaaac aggtagtgaa ataacggct caaataacgc aacgttattt    3360
ggtggattat ttgcagcatt aggttcatta ttgttattcg gtcgtcgcaa aaaacaaaac   3420
aaataa                                                               3426
```

<210> SEQ ID NO 89
<211> LENGTH: 1349
<212> TYPE: PRT
<213> ORGANISM: Staphylococcus aureus

<400> SEQUENCE: 89

```
Met Leu Asn Arg Glu Asn Lys Thr Ala Ile Thr Arg Lys Gly Met Val
 1               5                  10                  15

Ser Asn Arg Leu Asn Lys Phe Ser Ile Arg Lys Tyr Thr Val Gly Thr
                20                  25                  30

Ala Ser Ile Leu Val Gly Thr Thr Leu Ile Phe Gly Leu Gly Asn Gln
            35                  40                  45

Glu Ala Lys Ala Ala Glu Ser Thr Asn Lys Glu Leu Asn Glu Ala Thr
        50                  55                  60

Thr Ser Ala Ser Asp Asn Gln Ser Ser Asp Lys Val Asp Met Gln Gln
 65                  70                  75                  80

Leu Asn Gln Glu Asp Asn Thr Lys Asn Asp Gln Lys Glu Met Val
                85                  90                  95

Ser Ser Gln Gly Asn Glu Thr Thr Ser Asn Gly Asn Lys Leu Ile Glu
                100                 105                 110

Lys Glu Ser Val Gln Ser Thr Thr Gly Asn Lys Val Glu Val Ser Thr
            115                 120                 125

Ala Lys Ser Asp Glu Gln Ala Ser Pro Lys Ser Thr Asn Glu Asp Leu
        130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
```

```
                180                 185                 190
Asp Ala Ile Lys Ser Asn Asp Glu Thr Leu Val Asp Asn Asn Ser Asn
            195                 200                 205
Ser Asn Asn Glu Asn Asn Ala Asp Ile Ile Leu Pro Lys Ser Thr Ala
        210                 215                 220
Pro Lys Arg Leu Asn Thr Arg Met Arg Ile Ala Ala Val Gln Pro Ser
225                 230                 235                 240
Ser Thr Glu Ala Lys Asn Val Asn Asp Leu Ile Thr Ser Asn Thr Thr
                245                 250                 255
Leu Thr Val Val Asp Ala Asp Lys Asn Asn Lys Ile Val Pro Ala Gln
            260                 265                 270
Asp Tyr Leu Ser Leu Lys Ser Gln Ile Thr Val Asp Asp Lys Val Lys
        275                 280                 285
Ser Gly Asp Tyr Phe Thr Ile Lys Tyr Ser Asp Thr Val Gln Val Tyr
        290                 295                 300
Gly Leu Asn Pro Glu Asp Ile Lys Asn Ile Gly Asp Ile Lys Asp Pro
305                 310                 315                 320
Asn Asn Gly Glu Thr Ile Ala Thr Ala Lys His Asp Thr Ala Asn Asn
                325                 330                 335
Leu Ile Thr Tyr Thr Phe Thr Asp Tyr Val Asp Arg Phe Asn Ser Val
            340                 345                 350
Gln Met Gly Ile Asn Tyr Ser Ile Tyr Met Asp Ala Asp Thr Ile Pro
        355                 360                 365
Val Ser Lys Asn Asp Val Glu Phe Asn Val Thr Ile Gly Asn Thr Thr
        370                 375                 380
Thr Lys Thr Thr Ala Asn Ile Gln Tyr Pro Asp Tyr Val Val Asn Glu
385                 390                 395                 400
Lys Asn Ser Ile Gly Ser Ala Phe Thr Glu Thr Val Ser His Val Gly
                405                 410                 415
Asn Lys Glu Asn Pro Gly Tyr Tyr Lys Gln Thr Ile Tyr Val Asn Pro
            420                 425                 430
Ser Glu Asn Ser Leu Thr Asn Ala Lys Leu Lys Val Gln Ala Tyr His
        435                 440                 445
Ser Ser Tyr Pro Asn Asn Ile Gly Gln Ile Asn Lys Asp Val Thr Asp
        450                 455                 460
Ile Lys Ile Tyr Gln Val Pro Lys Gly Tyr Thr Leu Asn Lys Gly Tyr
465                 470                 475                 480
Asp Val Asn Thr Lys Glu Leu Thr Asp Val Thr Asn Gln Tyr Leu Gln
                485                 490                 495
Lys Ile Thr Tyr Gly Asp Asn Asn Ser Ala Val Ile Asp Phe Gly Asn
            500                 505                 510
Ala Asp Ser Ala Tyr Val Val Met Val Asn Thr Lys Phe Gln Tyr Thr
        515                 520                 525
Asn Ser Glu Ser Pro Thr Leu Val Gln Met Ala Thr Leu Ser Ser Thr
        530                 535                 540
Gly Asn Lys Ser Val Ser Thr Gly Asn Ala Leu Gly Phe Thr Asn Asn
545                 550                 555                 560
Gln Ser Gly Gly Ala Gly Gln Glu Val Tyr Lys Ile Gly Asn Tyr Val
                565                 570                 575
Trp Glu Asp Thr Asn Lys Asn Gly Val Gln Glu Leu Gly Glu Lys Gly
            580                 585                 590
Val Gly Asn Val Thr Val Thr Val Phe Asp Asn Asn Thr Asn Thr Lys
        595                 600                 605
```

-continued

```
Val Gly Glu Ala Val Thr Lys Glu Asp Gly Ser Tyr Leu Ile Pro Asn
610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
                660                 665                 670

Ala Asp Leu Gly Ile Tyr Lys Pro Lys Tyr Asn Leu Gly Asp Tyr Val
            675                 680                 685

Trp Glu Asp Thr Asn Lys Asn Gly Ile Gln Asp Gln Asp Glu Lys Gly
690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
                740                 745                 750

Pro Thr Thr Val Thr Ser Gly Ser Asp Ile Glu Lys Asp Ser Asn Gly
            755                 760                 765

Leu Thr Thr Thr Gly Val Ile Asn Gly Ala Asp Asn Met Thr Leu Asp
770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
                820                 825                 830

Thr Thr Lys Thr Asp Lys Asp Gly Lys Tyr Gln Phe Thr Gly Leu Glu
            835                 840                 845

Asn Gly Thr Tyr Lys Val Glu Phe Glu Thr Pro Ser Gly Tyr Thr Pro
850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
                885                 890                 895

Gly Phe Tyr Lys Pro Thr Tyr Asn Leu Gly Asp Tyr Val Trp Glu Asp
                900                 905                 910

Thr Asn Lys Asn Gly Val Gln Asp Lys Asp Glu Lys Gly Ile Ser Gly
            915                 920                 925

Val Thr Val Thr Leu Lys Asp Glu Asn Asp Lys Val Leu Lys Thr Val
930                 935                 940

Thr Thr Asp Glu Asn Gly Lys Tyr Gln Phe Thr Asp Leu Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
            980                 985                 990

Thr Gly Val Ile Lys Asp Ala Asp Asn Met Thr Leu Asp Ser Gly Phe
            995                 1000                1005

Tyr Lys Thr Pro Lys Tyr Ser Leu Gly Asp Tyr Val Trp Tyr Asp Ser
    1010                1015                1020

Asn Lys Asp Gly Lys Gln Asp Ser Thr Glu Lys Gly Ile Lys Asp Val
1025                1030                1035                1040
```

Lys Val Thr Leu Leu Asn Glu Lys Gly Glu Val Ile Gly Thr Thr Lys
            1045                1050                1055

Thr Asp Glu Asn Gly Lys Tyr Cys Phe Asp Asn Leu Asp Ser Gly Lys
        1060                1065                1070

Tyr Lys Val Ile Phe Glu Lys Pro Ala Gly Leu Thr Gln Thr Val Thr
    1075                1080                1085

Asn Thr Thr Glu Asp Asp Lys Asp Ala Asp Gly Gly Glu Val Asp Val
    1090                1095                1100

Thr Ile Thr Asp His Asp Asp Phe Thr Leu Asp Asn Gly Tyr Phe Glu
1105                1110                1115                1120

Glu Asp Thr Ser Asp Ser Asp Ser Asp Ser Asp Ser Asp Ser Asp Ser
                1125                1130                1135

Asp Ser Asp Ser Asp Ser Asp Ser Asp Ser Asp Ser Asp Ser Asp Ser
            1140                1145                1150

Asp Ser Asp Ser Asp Ser Asp Ser Asp Ser Asp Ser Asp Ser Asp Ser
            1155                1160                1165

Asp Ser Asp Ser Asp Ser Asp Ser Asp Ser Asp Ser Asp Ser Asp Ser
        1170                1175                1180

Asp Ser Asp Ser Asp Ser Asp Ser Asp Ser Asp Ser Asp Ser Asp Ser
1185                1190                1195                1200

Asp Ser Asp Ser Asp Ser Asp Ser Asp Ser Asp Ser Asp Ser Asp Ser
            1205                1210                1215

Asp Ser Asp Ser Asp Ser Asp Ser Asp Ser Asp Ser Asp Ser Asp Ser
            1220                1225                1230

Asp Ser Asp Ser Asp Ser Asp Ser Asp Ser Asp Ser Asp Ser Asp Ser
        1235                1240                1245

Asp Ser Asp Ser Asp Ser Asp Ser Asp Ser Asp Ser Asp Ser Asp Ser
    1250                1255                1260

Asp Ser Asp Ser Asp Ser Asp Ser Asp Ser Asp Ser Asp Ser Asp Ser
1265                1270                1275                1280

Asp Ser Asp Ser Asp Ser Asp Ser Asp Ala Gly Lys His Thr Pro Val
            1285                1290                1295

Lys Pro Met Ser Thr Thr Lys Asp His His Asn Lys Ala Lys Ala Leu
        1300                1305                1310

Pro Glu Thr Gly Ser Glu Asn Asn Gly Ser Asn Ala Thr Leu Phe
    1315                1320                1325

Gly Gly Leu Phe Ala Ala Leu Gly Ser Leu Leu Leu Phe Gly Arg Arg
    1330                1335                1340

Lys Lys Gln Asn Lys
1345

<210> SEQ ID NO 90
<211> LENGTH: 4050
<212> TYPE: DNA
<213> ORGANISM: Staphylococcus aureus

<400> SEQUENCE: 90
atgctaaaca gagaaaataa aacggcaata acaaggaaag gcatggtatc caatcgatta      60
aataaatttt cgattagaaa gtacacagtg ggaacagcat caattttagt aggtacaaca     120
ttaatttttg gtctggggaa ccaagaagca aaggctgcag aaagtactaa taagaattg      180 aacgaagcga caacttcagc aagtgataat caatcgagtg ataaagttga tatgcagcaa     240
ctaaatcaag aagacaatac taaaaatgat aatcaaaaag aaatggtatc atctcaaggt     300
aatgaaacga cttcaaatgg gaataaatta atagaaaaag aaagtgtaca atctaccact     360

```
ggaaataaag ttgaagtttc aactgccaaa tcagatgagc aagcttcacc aaaatctacg      420
aatgaagatt taaacactaa acaaactata agtaatcaag aagcgttaca acctgatttg      480
caagagaata aatcagtggt aaatgttcaa ccaactaatg aggaaaacaa aaaggtagat      540
gccaaaactg aatcaactac attaaatgtt aaaagtgatg ctatcaagag taatgatgaa      600
actcttgttg ataacaatag taattcaaat aatgaaaata atgcagatat cattttgcca      660
aaaagtacag cacctaaacg tttgaataca agaatgcgta tagcagcagt acagccatca      720
tcaacagagg ctaaaaatgt taatgattta atcacatcaa atacaacatt aactgtcgtt      780
gatgcagata aaacaataa aatcgtacca gcccaagatt atttatcatt aaaatcacaa       840
attacagttg atgacaaagt taaatcaggt gattatttca caattaaata ctcagataca      900
gtacaagtat atggattgaa tccggaagat attaaaaata ttggtgatat aaagatcca       960 aataatggtg aaacaattgc gactgcaaaa catgatactg caaataattt aattacatat     1020
acatttacag attatgttga tcgatttaat tctgtacaaa tgggaattaa ttattcaatt     1080
tatatggatg ctgatacaat tcctgttagt aaaaacgatg ttgagtttaa tgttacgata     1140
ggtaatacta caacaaaaac aactgctaac attcaatatc cagattatgt tgtaaatgag     1200
aaaaattcaa ttggatcagc gttcactgaa acagtttcac atgttggaaa taagaaaat      1260 ccagggtact ataaacaaac gatttatgta atccatcgg aaaattcttt aacaaatgcc      1320
aaactaaaag ttcaagctta ccactcaagt tatcctaata atatcgggca ataaataaa      1380 gatgtaacag atataaaaat atatcaagtt cctaaaggtt atacattaaa taaggatac      1440 gatgtgaata ctaaagagct tacagatgta acaaatcaat acttgcagaa aattacatat     1500
ggcgacaaca atagcgctgt tattgatttt ggaaatgcag attctgctta tgttgtaatg     1560
gttaatacaa aattccaata tacaaatagc gaaagcccaa cacttgttca aatggctact     1620
ttatcttcaa caggtaataa atccgtttct actggcaatg ctttaggatt tactaataac     1680
caaagtggcg gagctggtca agaagtatat aaaattggta actacgtatg ggaagatact     1740
aataaaaacg gtgttcaaga attaggagaa aaaggcgttg gcaatgtaac tgtaactgta     1800
tttgataata atacaaatac aaaagtagga gaagcagtta ctaaagaaga tgggtcatac     1860
ttgattccaa acttacctaa tggagattac cgtgtagaat tttcaaactt accaaaaggt     1920
tatgaagtaa ccccttcaaa acaaggtaat aacgaagaat tagattcaaa cggcttatct     1980
tcagttatta cagttaatgg caaagataac ttatctgcag acttaggtat ttacaaacct     2040
aaatacaact taggtgacta tgtctgggaa gatacaaata aaaatggtat ccaagaccaa     2100
gatgaaaaag gtatatctgg cgtaacggta acattaaaag atgaaaacgg taacgtgtta     2160
aaaacagtta caacagacgc tgatggcaaa tataaattta ctgatttaga taatggtaat     2220
tataaagttg aatttactac accagaaggc tatacaccga ctacagtaac atctggtagc     2280
gacattgaaa aagactctaa tggtttaaca caacaggtg ttattaatgg tgctgataac      2340
atgacattag atagtggatt ctacaaaaca ccaaaatata atttaggtaa ttatgtatgg     2400
gaagatacaa ataaagatgg taagcaggat tcaactgaaa aaggtatttc aggcgtaaca     2460
gttacattga aaaatgaaaa cggtgaagtt ttacaaacaa ctaaaacaga taaagatggt     2520
aaatatcaat ttactggatt agaaaatgga acttataaag ttgaattcga acaccatca      2580 ggttacacac caacacaagt aggttcagga actgatgaag gtatagattc aaatggtaca     2640
tcaacaacag gtgtcattaa agataaagat aacgatacta ttgactctgg tttctacaaa     2700
ccgacttaca acttaggtga ctatgtatgg gaagatacaa ataaaaacgg tgttcaagat     2760
```

```
aaagatgaaa agggcatttc aggtgtaaca gttacgttaa aagatgaaaa cgacaaagtt    2820
ttaaaaacag ttacaacaga tgaaaatggt aaatatcaat tcactgattt aaacaatgga    2880
acttataaag ttgaattcga gacaccatca ggttatacac caacttcagt aacttctgga    2940
aatgatactg aaaaagattc taatggttta acaacaacag gtgtcattaa agatgcagat    3000
aacatgacat tagacagtgg tttctataaa acaccaaaat atagtttagg tgattatgtt    3060
tggtacgaca gtaataaaga cggcaaacaa gattcaactg aaaaaggtat caaagatgtt    3120
aaagttactt tattaaatga aaaggcgaaa gtaattggaa caactaaaac agatgaaaat    3180
ggtaaatact gctttgataa tttagatagc ggtaaataca aagttatttt tgaaaagcct    3240
gctggcttaa cacaaacagt tacaaataca actgaagatg ataaagatgc agatggtggc    3300
gaagttgacg taacaattac ggatcatgat gatttcacac ttgataacgg atacttcgaa    3360
gaagatacat cagacagcga ttcagactca gatagtgact cagacagcga ctcagactca    3420
gacagcgact cagactcaga cagtgattca gattcagaca gcgactcaga ttcagatagc    3480
gactcagatt cggacagcga ttcagactca gatagcgact cagattcaga tagcgattca    3540
gactcagaca gcgactcaga ttcagatagc gattcggact cagacagcga ttcagactca    3600
gatagcgact cagactcaga cagcgactca gattcagata gcgattcgga ctcagatagc    3660
gactcagatt cagacagcga ttcagactca gatagcgact cagattcaga cagcgattca    3720
gactcagata gcgactcaga ctcagacagt gattcagatt cagacagcga ctcagactca    3780
gatagcgact cagattcgga cagcgactca gactctgata gcgactcaga ctcagacagt    3840
gattcagaca gcgattcaga ctcggatgca ggaaaacata cacctgttaa accaatgagt    3900
actactaaag accatcacaa taaagcaaaa gcattaccag aaacaggtag tgaaaataac    3960
ggctcaaata acgcaacgtt atttggtgga ttatttgcag cattaggttc attattgtta    4020
ttcggtcgtc gcaaaaaaca aaacaaataa                                    4050
```

<210> SEQ ID NO 91
<211> LENGTH: 635
<212> TYPE: PRT
<213> ORGANISM: Staphylococcus aureus

<400> SEQUENCE: 91

```
Met Ala Lys Tyr Arg Gly Lys Pro Phe Gln Leu Tyr Val Lys Leu Ser
 1               5                  10                  15

Cys Ser Thr Met Met Ala Thr Ser Ile Ile Leu Thr Asn Ile Leu Pro
             20                  25                  30

Tyr Asp Ala Gln Ala Ala Ser Glu Lys Asp Thr Glu Ile Thr Lys Glu
         35                  40                  45

Ile Leu Ser Lys Gln Asp Leu Leu Asp Lys Val Asp Lys Ala Ile Arg
     50                  55                  60

Gln Ile Glu Gln Leu Lys Gln Leu Ser Ala Ser Lys Glu His Tyr
 65                  70                  75                  80

Lys Ala Gln Leu Asn Glu Ala Lys Thr Ala Ser Gln Ile Asp Glu Ile
                 85                  90                  95

Ile Lys Arg Ala Asn Glu Leu Asp Ser Lys Asp Lys Ser Ser His
            100                 105                 110

Thr Glu Met Asn Gly Gln Ser Asp Ile Asp Ser Lys Leu Asp Gln Leu
        115                 120                 125

Leu Lys Asp Leu Asn Glu Val Ser Ser Asn Val Asp Arg Gly Gln Gln
    130                 135                 140
```

```
Ser Gly Glu Asp Asp Leu Asn Ala Met Lys Asn Asp Met Ser Gln Thr
145                 150                 155                 160

Ala Thr Thr Lys His Gly Glu Lys Asp Asp Lys Asn Asp Glu Ala Met
            165                 170                 175

Val Asn Lys Ala Leu Glu Asp Leu Asp His Leu Asn Gln Gln Ile His
        180                 185                 190

Lys Ser Lys Asp Ala Ser Lys Asp Thr Ser Glu Asp Pro Ala Val Ser
    195                 200                 205

Thr Thr Asp Asn Asn His Glu Val Ala Lys Thr Pro Asn Asn Asp Gly
210                 215                 220

Ser Gly His Val Val Leu Asn Lys Phe Leu Ser Asn Glu Glu Asn Gln
225                 230                 235                 240

Ser His Ser Asn Arg Leu Thr Asp Lys Leu Gln Gly Ser Asp Lys Ile
            245                 250                 255

Asn His Ala Met Ile Glu Lys Leu Ala Lys Ser Asn Ala Ser Thr Gln
        260                 265                 270

His Tyr Thr Tyr His Lys Leu Asn Thr Leu Gln Ser Leu Asp Gln Arg
    275                 280                 285

Ile Ala Asn Thr Gln Leu Pro Lys Asn Gln Lys Ser Asp Leu Met Ser
290                 295                 300

Glu Val Asn Lys Thr Lys Glu Arg Ile Lys Ser Gln Arg Asn Ile Ile
305                 310                 315                 320

Leu Glu Glu Leu Ala Arg Thr Asp Asp Lys Lys Tyr Ala Thr Gln Ser
            325                 330                 335

Ile Leu Glu Ser Ile Phe Asn Lys Asp Glu Ala Val Lys Ile Leu Lys
        340                 345                 350

Asp Ile Arg Val Asp Gly Lys Thr Asp Gln Gln Ile Ala Asp Gln Ile
    355                 360                 365

Thr Arg His Ile Asp Gln Leu Ser Leu Thr Thr Ser Asp Asp Leu Leu
370                 375                 380

Thr Ser Leu Ile Asp Gln Ser Gln Asp Lys Ser Leu Leu Ile Ser Gln
385                 390                 395                 400

Ile Leu Gln Thr Lys Leu Gly Lys Ala Glu Ala Asp Lys Leu Ala Lys
            405                 410                 415

Asp Trp Thr Asn Lys Gly Leu Ser Asn Arg Gln Ile Val Asp Gln Leu
        420                 425                 430

Lys Lys His Phe Ala Ser Thr Gly Asp Thr Ser Ser Asp Asp Ile Leu
    435                 440                 445

Lys Ala Ile Leu Asn Asn Ala Lys Asp Lys Gln Ala Ile Glu Thr
450                 455                 460

Ile Leu Ala Thr Arg Ile Glu Arg Gln Lys Ala Lys Leu Leu Ala Asp
465                 470                 475                 480

Leu Ile Thr Lys Ile Glu Thr Asp Gln Asn Lys Ile Phe Asn Leu Val
            485                 490                 495

Lys Ser Ala Leu Asn Gly Lys Ala Asp Asp Leu Leu Asn Leu Gln Lys
        500                 505                 510

Arg Leu Asn Gln Thr Lys Lys Asp Ile Asp Tyr Ile Leu Ser Pro Ile
    515                 520                 525

Val Asn Arg Pro Ser Leu Leu Asp Arg Leu Asn Lys Asn Gly Lys Thr
530                 535                 540

Thr Asp Leu Asn Lys Leu Ala Asn Leu Met Asn Gln Gly Ser Asp Leu
545                 550                 555                 560

Leu Asp Ser Ile Pro Asp Ile Pro Thr Pro Lys Pro Glu Lys Thr Leu
            565                 570                 575
```

```
Thr Leu Gly Lys Gly Asn Gly Leu Leu Ser Gly Leu Leu Asn Ala Asp
            580                 585                 590
Gly Asn Val Ser Leu Pro Lys Ala Gly Glu Thr Ile Lys Glu His Trp
        595                 600                 605
Leu Pro Ile Ser Val Ile Val Gly Ala Met Gly Val Leu Met Ile Trp
    610                 615                 620
Leu Ser Arg Arg Asn Lys Leu Lys Asn Lys Ala
625                 630                 635

<210> SEQ ID NO 92
<211> LENGTH: 1908
<212> TYPE: DNA
<213> ORGANISM: Staphylococcus aureus

<400> SEQUENCE: 92
atggctaaat atcgagggaa accgtttcaa ttatatgtaa agttatcgtg ttcgacaatg      60
atggcgacaa gtatcatttt aacgaatatc ttgccgtacg atgcccaagc tgcatctgaa     120
aaggatactg aaattacaaa agagatatta tctaagcaag atttattaga caaagttgac     180
aaggcaattc gtcaaattga gcaattaaaa cagttatcgg cttcatctaa agaacattat     240
aaagcacaac taaatgaagc gaaaacagca tcgcaaatag atgaaatcat aaaacgagct     300
aatgagttgg atagcaaaga caataaaagt tctcacactg aaatgaacgg tcaaagtgat     360
atagacagta aattagatca attgcttaaa gatttaaatg aggtttcttc aaatgttgat     420
aggggtcaac aaagtggcga ggacgatctt aatgcaatga aaatgatat gtcacaaacg     480 gctacaacaa acatggaga aaaagatgat aaaaatgatg aagcaatggt aaataaggcg     540
ttagaagacc tagaccattt gaatcagcaa atacacaaat cgaaagatgc atcgaaagat     600
acatcggaag atccagcagt gtctacaaca gataataatc atgaagtagc taaaacgcca     660
aataatgatg gttctggaca tgttgtgtta aataaattcc tttcaaatga agagaatcaa     720
agccatagta atcgactcac tgataaatta caaggaagcg ataaaattaa tcatgctatg     780
attgaaaaat tagctaaaag taatgcctca acgcaacatt acacatatca taaactgaat     840
acgttacaat ctttagatca acgtattgca aatacgcaac ttcctaaaaa tcaaaaatca     900
gacttaatga gcgaagtaaa taagacgaaa gagcgtataa aaagtcaacg aaatattatt     960
ttggaagaac ttgcacgtac tgatgataaa aagtatgcta cacaaagcat tttagaaagt    1020
atatttaata aagacgaggc agttaaaatt ctaaaagata tacgtgttga tggtaaaaca    1080
gatcaacaaa ttgcagatca aattactcgt catattgatc aattatctct gacaacgagt    1140
gatgatttat taacgtcatt gattgatcaa tcacaagata agtcgctatt gatttctcaa    1200 atttttacaaa cgaaattagg aaaagctgaa gcagataaat tggctaaaga ttggacgaat    1260
aaaggattat caaatcgcca aatcgttgac caattgaaga acatttttgc atcaactggc    1320
gacacgtctt cagatgatat attaaaagca attttgaata atgccaaaga taaaaaacaa    1380
gcaattgaaa cgattttagc aacacgtata gaaagacaaa aggcaaaatt actggcagat    1440
ttaattacta aaatagaaac agatcaaaat aaaattttta atttagttaa atcggcattg    1500
aatggtaaag cggatgattt attgaattta caaaagagac tcaatcaaac gaaaaaagat    1560
atagattata ttttatcacc aatagtaaat cgtccaagtt tactagatcg attgaataaa    1620
aatgggaaaa cgacagattt aaataagtta gcaaatttaa tgaatcaagg atcagattta    1680
ttagacagta ttccagatat acccacacca aagccagaaa agacgttaac acttggtaaa    1740
ggtaatggat tgttaagtgg attattaaat gctgatggta atgtatcttt gcctaaagcg    1800
```

```
ggggaaacga taaagaaaca ttggttgccg atatctgtaa ttgttggtgc aatgggtgta    1860
ctaatgattt ggttatcacg acgcaataag ttgaaaaata aagcataa                 1908

<210> SEQ ID NO 93
<211> LENGTH: 241
<212> TYPE: PRT
<213> ORGANISM: Staphylococcus aureus

<400> SEQUENCE: 93

Met Lys Lys Leu Ala Thr Val Gly Ser Leu Ile Val Thr Ser Thr Leu
 1               5                  10                  15

Val Phe Ser Ser Met Pro Phe Gln Asn Ala His Ala Asp Thr Thr Ser
             20                  25                  30

Met Asn Val Ser Asn Lys Gln Ser Gln Asn Val Gln Asn His Arg Pro
         35                  40                  45

Tyr Gly Gly Val Val Pro Gln Gly Met Thr Gln Ala Gln Tyr Thr Glu
     50                  55                  60

Leu Glu Lys Ala Leu Pro Gln Leu Ser Ala Gly Ser Asn Met Gln Asp
 65                  70                  75                  80

Tyr Asn Met Lys Leu Tyr Asp Ala Thr Gln Asn Ile Ala Asp Lys Tyr
                 85                  90                  95

Asn Val Ile Ile Thr Thr Asn Val Gly Val Phe Lys Pro His Ala Val
            100                 105                 110

Arg Asp Met Asn Gly His Ala Leu Pro Leu Thr Lys Asp Gly Asn Phe
        115                 120                 125

Tyr Gln Thr Asn Val Asp Ala Asn Gly Val Asn His Gly Gly Ser Glu
    130                 135                 140

Met Val Gln Asn Lys Thr Gly His Met Ser Gln Gln Gly His Met Asn
145                 150                 155                 160

Gln Asn Thr His Met Asn Gln Gln Pro His Met Gln Gln Gly His Met
                165                 170                 175

Gln Ser Ser Asn His Gln Met Met Ser Pro Lys Ala Asn Met His Ser
            180                 185                 190

Ser Asn His Gln Met Asn Gln Ser Asn Lys Lys Val Leu Pro Ala Ala
        195                 200                 205

Gly Glu Ser Met Thr Ser Ser Ile Leu Thr Ala Ser Ile Ala Ala Leu
    210                 215                 220

Leu Leu Val Ser Gly Leu Phe Leu Ala Phe Arg Arg Ser Thr Asn
225                 230                 235                 240

Lys

<210> SEQ ID NO 94
<211> LENGTH: 726
<212> TYPE: DNA
<213> ORGANISM: Staphylococcus aureus

<400> SEQUENCE: 94
atgaaaaaat tagcaacagt aggttcttta attgtaacaa gcactttagt attctcaagt      60
atgccttttc aaaatgcgca tgccgacaca acttcaatga atgtgtcgaa taaacaaagc     120
caaaatgtac aaaatcatcg tccttatggc ggagtagtac cacaaggaat gacgcaagca     180
caatatactg aattagagaa agctttaccc caattaagcg ctggcagtaa tatgcaagac     240
tataatatga attgtatga tgcgacgcaa aatattgctg ataaatacaa tgtgataatt     300
acaactaatg tagggggtatt taaaccacat gctgttagag atatgaatgg ccatgcgtta     360
```

```
cctttaacaa aagatggcaa tttttatcaa acgaatgtag atgcaaatgg tgttaatcat    420
ggtggtagtg aaatggtgca aaataaaaca ggtcatatga gtcaacaagg ccatatgaat    480
cagaacacac acatgaacca acagccacac atgcaacaag gtcatatgca atcatcaaac    540
catcaaatga tgagtccaaa agcaaatatg cattcatcaa atcatcaaat gaaccaaagt    600
aacaaaaaag ttttaccagc tgctggtgaa agtatgacat caagtattct tactgcaagt    660
attgccgcac tactattagt atctgggtta ttcttagcat ttagacgacg ttcaacaaat    720
aaataa                                                              726
```

<210> SEQ ID NO 95
<211> LENGTH: 5
<212> TYPE: PRT
<213> ORGANISM: Artificial Sequence
<220> FEATURE:
<221> NAME/KEY: VARIANT
<222> LOCATION: (1)...(5)
<223> OTHER INFORMATION: Xaa = Any Amino Acid
<220> FEATURE:
<223> OTHER INFORMATION: in silico derived motif

<400> SEQUENCE: 95

```
Leu Pro Xaa Thr Gly
 1               5
```

<210> SEQ ID NO 96
<211> LENGTH: 774
<212> TYPE: PRT
<213> ORGANISM: Staphylococcus epidermidis

<400> SEQUENCE: 96

```
Met Glu Glu Asn Ser Val Gln Asp Val Lys Asp Ser Asn Thr Asp Asp
 1               5                  10                  15

Glu Leu Ser Asp Ser Asn Asp Gln Ser Ser Asp Glu Glu Lys Asn Asp
                20                  25                  30

Val Ile Asn Asn Asn Gln Ser Ile Asn Thr Asp Asp Asn Asn Gln Ile
            35                  40                  45

Ile Lys Lys Glu Glu Thr Asn Asn Tyr Asp Gly Ile Glu Lys Arg Ser
    50                  55                  60

Glu Asp Arg Thr Glu Ser Thr Thr Asn Val Asp Glu Asn Glu Ala Thr
65                  70                  75                  80

Phe Leu Gln Lys Thr Pro Gln Asp Asn Thr His Leu Thr Glu Glu Glu
                85                  90                  95

Val Lys Glu Ser Ser Ser Val Glu Ser Ser Asn Ser Ser Ile Asp Thr
            100                 105                 110

Ala Gln Gln Pro Ser His Thr Thr Ile Asn Arg Glu Glu Ser Val Gln
        115                 120                 125

Thr Ser Asp Asn Val Glu Asp Ser His Val Ser Asp Phe Ala Asn Ser
130                 135                 140

Lys Ile Lys Glu Ser Asn Thr Glu Ser Gly Lys Glu Glu Asn Thr Ile
                145                 150                 155                 160

Glu Gln Pro Asn Lys Val Lys Glu Asp Ser Thr Thr Ser Gln Pro Ser
                165                 170                 175

Gly Tyr Thr Asn Ile Asp Glu Lys Ile Ser Asn Gln Asp Glu Leu Leu
            180                 185                 190

Asn Leu Pro Ile Asn Glu Tyr Glu Asn Lys Ala Arg Pro Leu Ser Thr
        195                 200                 205

Thr Ser Ala Gln Pro Ser Ile Lys Arg Val Thr Val Asn Gln Leu Ala
    210                 215                 220
```

```
Ala Glu Gln Gly Ser Asn Val Asn His Leu Ile Lys Val Thr Asp Gln
225                 230                 235                 240

Ser Ile Thr Glu Gly Tyr Asp Asp Ser Glu Gly Val Ile Lys Ala His
            245                 250                 255

Asp Ala Glu Asn Leu Ile Tyr Asp Val Thr Phe Glu Val Asp Asp Lys
                260                 265                 270

Val Lys Ser Gly Asp Thr Met Thr Val Asp Ile Asp Lys Asn Thr Val
        275                 280                 285

Pro Ser Asp Leu Thr Asp Ser Phe Thr Ile Pro Lys Ile Lys Asp Asn
    290                 295                 300

Ser Gly Glu Ile Ile Ala Thr Gly Thr Tyr Asp Asn Lys Asn Lys Gln
305                 310                 315                 320

Ile Thr Tyr Thr Phe Thr Asp Tyr Val Asp Lys Tyr Glu Asn Ile Lys
                325                 330                 335

Ala His Leu Lys Leu Thr Ser Tyr Ile Asp Lys Ser Lys Val Pro Asn
                340                 345                 350

Asn Asn Thr Lys Leu Asp Val Glu Tyr Lys Thr Ala Leu Ser Ser Val
            355                 360                 365

Asn Lys Thr Ile Thr Val Glu Tyr Gln Arg Pro Asn Glu Asn Arg Thr
    370                 375                 380

Ala Asn Leu Gln Ser Met Phe Thr Asn Ile Asp Thr Lys Asn His Thr
385                 390                 395                 400

Val Glu Gln Thr Ile Tyr Ile Asn Pro Leu Arg Tyr Ser Ala Lys Glu
                405                 410                 415

Thr Asn Val Asn Ile Ser Gly Asn Gly Asp Glu Gly Ser Thr Ile Ile
                420                 425                 430

Asp Asp Ser Thr Ile Ile Lys Val Tyr Lys Val Gly Asp Asn Gln Asn
            435                 440                 445

Leu Pro Asp Ser Asn Arg Ile Tyr Asp Tyr Ser Glu Tyr Glu Asp Val
    450                 455                 460

Thr Asn Asp Asp Tyr Ala Gln Leu Gly Asn Asn Asn Asp Val Asn Ile
465                 470                 475                 480

Asn Phe Gly Asn Ile Asp Ser Pro Tyr Ile Ile Lys Val Ile Ser Lys
                485                 490                 495

Tyr Asp Pro Asn Lys Asp Asp Tyr Thr Thr Ile Gln Gln Thr Val Thr
            500                 505                 510

Met Gln Thr Thr Ile Asn Glu Tyr Thr Gly Glu Phe Arg Thr Ala Ser
    515                 520                 525

Tyr Asp Asn Thr Ile Ala Phe Ser Thr Ser Ser Gly Gln Gly Gln Gly
    530                 535                 540

Asp Leu Pro Pro Glu Lys Thr Tyr Lys Ile Gly Asp Tyr Val Trp Glu
545                 550                 555                 560

Asp Val Asp Lys Asp Gly Ile Gln Asn Thr Asn Asp Asn Glu Lys Pro
                565                 570                 575

Leu Ser Asn Val Leu Val Thr Leu Thr Tyr Pro Asp Gly Thr Ser Lys
            580                 585                 590

Ser Val Arg Thr Asp Glu Asp Gly Lys Tyr Gln Phe Asp Gly Leu Lys
        595                 600                 605

Asn Gly Leu Thr Tyr Lys Ile Thr Phe Glu Thr Pro Glu Gly Tyr Thr
    610                 615                 620

Pro Thr Leu Lys His Ser Gly Thr Asn Pro Ala Leu Asp Ser Glu Gly
625                 630                 635                 640

Asn Ser Val Trp Val Thr Ile Asn Gly Gln Asp Asp Met Thr Ile Asp
```

```
                    645                 650                 655
Ser Gly Phe Tyr Gln Thr Pro Lys Tyr Ser Leu Gly Asn Tyr Val Trp
                660                 665                 670

Tyr Asp Thr Asn Lys Asp Gly Ile Gln Gly Asp Glu Lys Gly Ile
            675                 680                 685

Ser Gly Val Lys Val Thr Leu Lys Asp Glu Asn Gly Asn Ile Ile Ser
        690                 695                 700

Thr Thr Thr Thr Asp Glu Asn Gly Lys Tyr Gln Phe Asp Asn Leu Asn
705                 710                 715                 720

Ser Gly Asn Tyr Ile Val His Phe Asp Lys Pro Ser Gly Met Thr Gln
            725                 730                 735

Thr Thr Thr Asp Ser Gly Asp Asp Glu Gln Asp Ala Asp Gly Glu
        740                 745                 750

Glu Val His Val Thr Ile Thr Asp His Asp Phe Ser Ile Asp Asn
            755                 760                 765

Gly Tyr Tyr Asp Asp Glu
        770
```

<210> SEQ ID NO 97
<211> LENGTH: 128
<212> TYPE: PRT
<213> ORGANISM: Staphylococcus aureus

<400> SEQUENCE: 97

```
Met Asp Val Asn Thr Val Asn Gln Lys Ala Ala Ser Val Lys Ser Thr
1               5                   10                  15

Lys Asp Ala Leu Asp Gly Gln Gln Asn Leu Gln Arg Ala Lys Thr Glu
            20                  25                  30

Ala Thr Asn Ala Ile Thr His Ala Ser Asp Leu Asn Gln Ala Gln Lys
        35                  40                  45

Asn Ala Leu Thr Gln Gln Val Asn Ser Ala Gln Asn Val His Ala Val
    50                  55                  60

Asn Asp Ile Lys Gln Thr Thr Gln Ser Leu Asn Thr Ala Met Thr Gly
65                  70                  75                  80

Leu Lys Arg Gly Val Ala Asn His Asn Gln Val Val Gln Ser Asp Asn
                85                  90                  95

Tyr Val Asn Ala Asp Thr Asn Lys Lys Asn Asp Tyr Asn Asn Ala Tyr
            100                 105                 110

Asn His Ala Asn Asp Ile Ile Asn Gly Asn Ala Gln His Pro Val Ile
        115                 120                 125
```

<210> SEQ ID NO 98
<211> LENGTH: 128
<212> TYPE: PRT
<213> ORGANISM: Staphylococcus aureus

<400> SEQUENCE: 98

```
Met Asp Val Asn Thr Val Asn Gln Lys Ala Ala Ser Val Lys Ser Thr
1               5                   10                  15

Lys Asp Ala Leu Asp Gly Gln Gln Asn Leu Gln Arg Ala Lys Thr Glu
            20                  25                  30

Ala Thr Asn Ala Ile Thr His Ala Ser Asp Leu Asn Gln Ala Gln Lys
        35                  40                  45

Asn Ala Leu Thr Gln Gln Val Asn Ser Ala Gln Asn Val His Ala Val
    50                  55                  60

Asn Asp Ile Lys Gln Thr Thr Gln Ser Leu Asn Thr Ala Met Thr Gly
65                  70                  75                  80
```

```
Leu Lys Arg Gly Val Ala Asn His Asn Gln Val Val Gln Ser Asp Asn
                85                  90                  95

Tyr Val Asn Ala Asp Thr Asn Lys Lys Asn Asp Tyr Asn Asn Ala Tyr
            100                 105                 110

Asn His Ala Asn Asp Ile Ile Asn Gly Asn Ala Gln His Pro Val Ile
        115                 120                 125

<210> SEQ ID NO 99
<211> LENGTH: 52
<212> TYPE: PRT
<213> ORGANISM: Staphylococcus aureus

<400> SEQUENCE: 99

Gln Thr Thr Gln Asn Asn Tyr Val Thr Asp Gln Gln Lys Ala Phe Tyr
1               5                   10                  15

Gln Val Leu His Leu Lys Gly Ile Thr Glu Glu Gln Arg Asn Gln Tyr
            20                  25                  30

Ile Lys Thr Leu Arg Glu His Pro Glu Arg Ala Gln Glu Val Phe Ser
        35                  40                  45

Glu Ser Leu Lys
    50

<210> SEQ ID NO 100
<211> LENGTH: 36
<212> TYPE: PRT
<213> ORGANISM: Staphylococcus aureus

<400> SEQUENCE: 100

Val Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala
        35

<210> SEQ ID NO 101
<211> LENGTH: 6
<212> TYPE: PRT
<213> ORGANISM: Staphylococcus aureus

<400> SEQUENCE: 101

Asp Arg His Phe Leu Asn
1               5

<210> SEQ ID NO 102
<211> LENGTH: 4
<212> TYPE: PRT
<213> ORGANISM: Staphylococcus aureus

<400> SEQUENCE: 102

Gly Asn Tyr Asp
1

<210> SEQ ID NO 103
<211> LENGTH: 5
<212> TYPE: PRT
<213> ORGANISM: Staphylococcus aureus

<400> SEQUENCE: 103

Arg Arg Tyr Pro Phe
1               5
```

<210> SEQ ID NO 104
<211> LENGTH: 6
<212> TYPE: PRT
<213> ORGANISM: Staphylococcus aureus

<400> SEQUENCE: 104

Lys Thr Thr Leu Leu Lys
 1               5

<210> SEQ ID NO 105
<211> LENGTH: 7
<212> TYPE: PRT
<213> ORGANISM: Staphylococcus aureus

<400> SEQUENCE: 105

Gly Val Thr Thr Ser Leu Ser
 1               5

<210> SEQ ID NO 106
<211> LENGTH: 5
<212> TYPE: PRT
<213> ORGANISM: Staphylococcus aureus

<400> SEQUENCE: 106

Val Asp Trp Leu Arg
 1               5

<210> SEQ ID NO 107
<211> LENGTH: 4
<212> TYPE: PRT
<213> ORGANISM: Staphylococcus aureus

<400> SEQUENCE: 107

Arg Gly Phe Leu
 1

<210> SEQ ID NO 108
<211> LENGTH: 15
<212> TYPE: PRT
<213> ORGANISM: Staphylococcus aureus

<400> SEQUENCE: 108

Lys Ile Lys Val Tyr Val Gly Asn Tyr Asp Phe Trp Tyr Gln Ser
 1               5                   10                  15

<210> SEQ ID NO 109
<211> LENGTH: 16
<212> TYPE: PRT
<213> ORGANISM: Staphylococcus aureus

<400> SEQUENCE: 109

Thr Val Ile Val Val Ser His Asp Arg His Phe Leu Tyr Asn Asn Val
 1               5                   10                  15

<210> SEQ ID NO 110
<211> LENGTH: 15
<212> TYPE: PRT
<213> ORGANISM: Staphylococcus aureus

<400> SEQUENCE: 110

Thr Glu Thr Phe Leu Arg Gly Phe Leu Gly Arg Met Leu Phe Ser
 1               5                   10                  15

<210> SEQ ID NO 111
<211> LENGTH: 35

```
<212> TYPE: DNA
<213> ORGANISM: Staphylococcus aureus

<400> SEQUENCE: 111
cgcggatccg cagattctga tattaatatt aaaac                         35

<210> SEQ ID NO 112
<211> LENGTH: 33
<212> TYPE: DNA
<213> ORGANISM: Staphylococcus aureus

<400> SEQUENCE: 112
cccaagcttt taatttgtca tttcttcttt ttc                           33

<210> SEQ ID NO 113
<211> LENGTH: 34
<212> TYPE: DNA
<213> ORGANISM: Staphylococcus aureus

<400> SEQUENCE: 113
cgcggatccg ctgggtctaa taattttaaa gatg                          34

<210> SEQ ID NO 114
<211> LENGTH: 30
<212> TYPE: DNA
<213> ORGANISM: Staphylococcus aureus

<400> SEQUENCE: 114
cccaagcttt tatggaataa cgatttgttg                               30

<210> SEQ ID NO 115
<211> LENGTH: 32
<212> TYPE: DNA
<213> ORGANISM: Staphylococcus aureus

<400> SEQUENCE: 115
cgcggatcca gtgaaaatag tgttacgcaa tc                            32

<210> SEQ ID NO 116
<211> LENGTH: 33
<212> TYPE: DNA
<213> ORGANISM: Staphylococcus aureus

<400> SEQUENCE: 116
cccaagcttt tactctggaa ttggttcaat ttc                           33

<210> SEQ ID NO 117
<211> LENGTH: 31
<212> TYPE: DNA
<213> ORGANISM: Staphylococcus aureus

<400> SEQUENCE: 117
cgcggatcca cacaaacaac tgcaactaac g                             31

<210> SEQ ID NO 118
<211> LENGTH: 35
<212> TYPE: DNA
<213> ORGANISM: Staphylococcus aureus

<400> SEQUENCE: 118
cccaagcttt tatgctttgt gattcttttt caaac                         35

<210> SEQ ID NO 119
<211> LENGTH: 26
```

```
<212> TYPE: DNA
<213> ORGANISM: Staphylococcus aureus

<400> SEQUENCE: 119
cgcggatcca acacgcaaca aacttc                                          26

<210> SEQ ID NO 120
<211> LENGTH: 36
<212> TYPE: DNA
<213> ORGANISM: Staphylococcus aureus

<400> SEQUENCE: 120
ggaactgcag ttatttccag aatgataata aattac                               36

<210> SEQ ID NO 121
<211> LENGTH: 28
<212> TYPE: DNA
<213> ORGANISM: Staphylococcus aureus

<400> SEQUENCE: 121
cgcggatccg cagaacatac gaatggag                                        28

<210> SEQ ID NO 122
<211> LENGTH: 32
<212> TYPE: DNA
<213> ORGANISM: Staphylococcus aureus

<400> SEQUENCE: 122
cccaagcttt tatgtttctt cttcgtagta gc                                   32

<210> SEQ ID NO 123
<211> LENGTH: 28
<212> TYPE: DNA
<213> ORGANISM: Staphylococcus epidermidis

<400> SEQUENCE: 123
cgcggatccg aggagaattc agtacaag                                        28

<210> SEQ ID NO 124
<211> LENGTH: 31
<212> TYPE: DNA
<213> ORGANISM: Staphylococcus aureus

<400> SEQUENCE: 124
cccaagcttt tattcgtcat catagtatcc g                                    31

<210> SEQ ID NO 125
<211> LENGTH: 25
<212> TYPE: DNA
<213> ORGANISM: Staphylococcus aureus

<400> SEQUENCE: 125
aaaagtactc accaccacca ccacc                                           25

<210> SEQ ID NO 126
<211> LENGTH: 29
<212> TYPE: DNA
<213> ORGANISM: Staphylococcus aureus

<400> SEQUENCE: 126
aaaagtactc acttgattca tcgcttcag                                       29

<210> SEQ ID NO 127
<211> LENGTH: 33
```

<212> TYPE: DNA
<213> ORGANISM: Staphylococcus aureus

<400> SEQUENCE: 127
gcgcgccatg gcacaagctt ctacacaaca tac                          33

<210> SEQ ID NO 128
<211> LENGTH: 32
<212> TYPE: DNA
<213> ORGANISM: Staphylococcus aureus

<400> SEQUENCE: 128
gcgcgctcga gatggatgaa tgcatagcta ga                           32

<210> SEQ ID NO 129
<211> LENGTH: 48
<212> TYPE: DNA
<213> ORGANISM: Staphylococcus aureus

<400> SEQUENCE: 129
gcatccatgg caccatcacc atcaccacga agtaaacgtt gatcaagc           48

<210> SEQ ID NO 130
<211> LENGTH: 34
<212> TYPE: DNA
<213> ORGANISM: Staphylococcus aureus

<400> SEQUENCE: 130
agcactcgag ttagaatccc caagcaccta aacc                         34

<210> SEQ ID NO 131
<211> LENGTH: 29
<212> TYPE: DNA
<213> ORGANISM: Staphylococcus aureus

<400> SEQUENCE: 131
gcacccatgg cagaaaatac aaatacttc                               29

<210> SEQ ID NO 132
<211> LENGTH: 31
<212> TYPE: DNA
<213> ORGANISM: Staphylococcus aureus

<400> SEQUENCE: 132
ttttctcgag cattttagat tgactaagtt g                            31

<210> SEQ ID NO 133
<211> LENGTH: 33
<212> TYPE: DNA
<213> ORGANISM: Staphylococcus aureus

<400> SEQUENCE: 133
caagtcccat ggctgagacg acacaagatc aac                          33

<210> SEQ ID NO 134
<211> LENGTH: 31
<212> TYPE: DNA
<213> ORGANISM: Staphylococcus aureus

<400> SEQUENCE: 134
cagtctcgag tttacagct gtttttggtt g                             31

<210> SEQ ID NO 135
<211> LENGTH: 30

-continued

```
<212> TYPE: DNA
<213> ORGANISM: Staphylococcus aureus

<400> SEQUENCE: 135
agctcatatg gcttatactg ttactaaacc                                   30

<210> SEQ ID NO 136
<211> LENGTH: 29
<212> TYPE: DNA
<213> ORGANISM: Staphylococcus aureus

<400> SEQUENCE: 136
gcgcctcgag tttatattgt gggatgtcg                                    29

<210> SEQ ID NO 137
<211> LENGTH: 34
<212> TYPE: DNA
<213> ORGANISM: Staphylococcus aureus

<400> SEQUENCE: 137
caagtcccat ggcaacagaa gctacgaacg caac                              34

<210> SEQ ID NO 138
<211> LENGTH: 35
<212> TYPE: DNA
<213> ORGANISM: Staphylococcus aureus

<400> SEQUENCE: 138
accagtctcg agtaattctt tagctttaga gcttg                             35

<210> SEQ ID NO 139
<211> LENGTH: 33
<212> TYPE: DNA
<213> ORGANISM: Staphylococcus aureus

<400> SEQUENCE: 139
tattctcgag gctttgagtg tgtccatcat ttg                               33

<210> SEQ ID NO 140
<211> LENGTH: 32
<212> TYPE: DNA
<213> ORGANISM: Staphylococcus aureus

<400> SEQUENCE: 140
gaagccatgg cagcagctga agaaacaggt gg                                32

<210> SEQ ID NO 141
<211> LENGTH: 30
<212> TYPE: DNA
<213> ORGANISM: Staphylococcus aureus

<400> SEQUENCE: 141
gattacacca tggttaaacc tcaagcgaaa                                   30

<210> SEQ ID NO 142
<211> LENGTH: 30
<212> TYPE: DNA
<213> ORGANISM: Staphylococcus aureus

<400> SEQUENCE: 142
aggtgtctcg agtgcgattg tagcttcatt                                   30
```